United States Patent
Brister et al.

(10) Patent No.: US 10,264,995 B2
(45) Date of Patent: Apr. 23, 2019

(54) SYSTEMS AND METHODS FOR LOCATING AND/OR CHARACTERIZING INTRAGASTRIC DEVICES

(71) Applicant: Obalon Therapeutics, Inc., Carlsbad, CA (US)

(72) Inventors: Mark C. Brister, Carlsbad, CA (US); Neil R. Drake, Carlsbad, CA (US); Sheldon Nelson, Carlsbad, CA (US); Daniel J. Proctor, Carlsbad, CA (US)

(73) Assignee: Obalon Therapeutics, Inc., Carlsbad, CA (US)

( * ) Notice: Subject to any disclaimer, the term of this patent is extended or adjusted under 35 U.S.C. 154(b) by 0 days.

(21) Appl. No.: 14/407,923

(22) PCT Filed: Dec. 3, 2014

(86) PCT No.: PCT/US2014/068458
§ 371 (c)(1),
(2) Date: Dec. 12, 2014

(87) PCT Pub. No.: WO2015/085011
PCT Pub. Date: Jun. 11, 2015

(65) Prior Publication Data
US 2016/0278662 A1    Sep. 29, 2016

Related U.S. Application Data

(60) Provisional application No. 62/062,081, filed on Oct. 9, 2014, provisional application No. 61/911,958, filed on Dec. 4, 2013.

(51) Int. Cl.
*A61B 1/04* (2006.01)
*A61B 5/06* (2006.01)
(Continued)

(52) U.S. Cl.
CPC .............. *A61B 5/062* (2013.01); *A61B 1/041* (2013.01); *A61B 5/0024* (2013.01);
(Continued)

(58) Field of Classification Search
CPC ... A61B 5/062; A61B 5/14507; A61B 5/6852; A61B 50/13; A61B 5/742; A61B 8/0833;
(Continued)

(56) References Cited

U.S. PATENT DOCUMENTS 2,183,900 A   12/1939   Voit et al.
3,788,322 A   1/1974    Michaels
(Continued)

FOREIGN PATENT DOCUMENTS

DE   3540936   10/1986
EP   0103481   3/1984
(Continued)

OTHER PUBLICATIONS

Mackay, 2.9. Power Sources, in Bio-Medical Telemetry: Sensing and Transmitting Biological Information from Animals and Man, 2d ed., IEEE Press, New York, 1993, pp. 62-70.
(Continued)

*Primary Examiner* — Amanda Lauritzen Moher
(74) *Attorney, Agent, or Firm* — Knobbe Martens Olson & Bear, LLP

(57) ABSTRACT

Devices and methods for treating obesity are provided. More particularly, intragastric devices and methods of fabricating, deploying, inflating, locating, tracking, monitoring, deflating, and retrieving the same are provided.

41 Claims, 79 Drawing Sheets

(51) Int. Cl.
*A61B 5/00* (2006.01)
*A61B 5/07* (2006.01)
*A61B 5/145* (2006.01)
*A61B 8/08* (2006.01)
*A61B 8/00* (2006.01)
*A61F 5/00* (2006.01)
*A61B 50/13* (2016.01)
*A61B 34/20* (2016.01)
*A61B 90/00* (2016.01)
*A61M 25/10* (2013.01)

(52) U.S. Cl.
CPC .......... *A61B 5/0028* (2013.01); *A61B 5/065* (2013.01); *A61B 5/073* (2013.01); *A61B 5/14507* (2013.01); *A61B 5/14539* (2013.01); *A61B 5/4238* (2013.01); *A61B 5/6852* (2013.01); *A61B 5/6853* (2013.01); *A61B 5/6861* (2013.01); *A61B 5/742* (2013.01); *A61B 8/0833* (2013.01); *A61B 8/461* (2013.01); *A61B 8/56* (2013.01); *A61B 50/13* (2016.02); *A61F 5/003* (2013.01); *A61F 5/0046* (2013.01); *A61B 2034/2051* (2016.02); *A61B 2034/2063* (2016.02); *A61B 2034/2072* (2016.02); *A61B 2090/3929* (2016.02); *A61B 2090/3966* (2016.02); *A61B 2562/162* (2013.01); *A61B 2562/168* (2013.01); *A61F 5/0036* (2013.01); *A61M 2025/1054* (2013.01)

(58) Field of Classification Search
CPC .......... A61B 8/461; A61B 8/56; A61B 1/041; A61B 5/0028; A61B 5/14539; A61B 5/6853; A61B 5/6861; A61F 5/0046; A61F 5/003
See application file for complete search history.

(56) References Cited

U.S. PATENT DOCUMENTS

| | | | |
|---|---|---|---|
| 3,797,492 A | 3/1974 | Place |
| 4,133,315 A | 1/1979 | Berman et al. |
| 4,234,454 A | 11/1980 | Strope |
| 4,236,521 A | 12/1980 | Lauterjung |
| 4,246,893 A | 1/1981 | Berson |
| 4,340,626 A | 7/1982 | Rudy |
| 4,416,267 A | 11/1983 | Garren et al. |
| 4,485,805 A | 12/1984 | Foster, Jr. |
| 4,489,440 A | 12/1984 | Chaoui |
| 4,517,979 A | 5/1985 | Pecenka |
| 4,545,367 A | 10/1985 | Tucci |
| 4,560,392 A | 12/1985 | Basevi |
| 4,607,618 A | 8/1986 | Angelchik |
| 4,694,827 A | 9/1987 | Weiner et al. |
| 4,718,639 A | 1/1988 | Sherwood et al. |
| 4,723,547 A | 2/1988 | Kullas et al. |
| 4,739,758 A | 4/1988 | Lai et al. |
| 4,748,562 A | 5/1988 | Miller et al. |
| 4,812,315 A | 3/1989 | Tarabishi |
| 4,813,934 A | 3/1989 | Engelson et al. |
| 4,819,637 A | 4/1989 | Dormandy et al. |
| 4,857,029 A | 8/1989 | Dierick et al. |
| 4,899,747 A | 2/1990 | Garren et al. |
| 4,917,885 A | 4/1990 | Chiba et al. |
| 4,925,446 A | 5/1990 | Garay et al. |
| 4,929,214 A | 5/1990 | Liebermann |
| 5,049,106 A | 9/1991 | Kim et al. |
| 5,084,061 A | 1/1992 | Gau et al. |
| 5,129,915 A | 7/1992 | Cantenys et al. |
| 5,234,454 A | 8/1993 | Bangs |
| 5,259,399 A | 11/1993 | Brown |
| 5,308,326 A | 5/1994 | Zimmon |
| 5,425,382 A | 6/1995 | Golden et al. |
| 5,431,917 A | 7/1995 | Yamamoto et al. |
| 5,622,169 A | 4/1997 | Golden et al. |
| 5,713,141 A | 2/1998 | Mitchell et al. |
| 5,728,119 A | 3/1998 | Smith et al. |
| 5,852,889 A | 12/1998 | Rinaldi |
| 5,868,141 A | 2/1999 | Ellias |
| 5,879,297 A | 3/1999 | Haynor et al. |
| 5,897,205 A | 4/1999 | Sinsteden |
| 5,910,128 A | 6/1999 | Quinn |
| 5,948,227 A | 9/1999 | Dubrow |
| 6,042,710 A | 3/2000 | Dubrow |
| 6,129,668 A | 10/2000 | Haynor et al. |
| 6,216,028 B1 | 4/2001 | Haynor et al. |
| 6,263,230 B1 | 7/2001 | Haynor et al. |
| 6,427,089 B1 | 7/2002 | Knowlton |
| 6,454,785 B2 * | 9/2002 | De Hoyos Garza .... A61F 5/003 606/191 |
| 6,579,301 B1 | 6/2003 | Bales et al. |
| 6,682,473 B1 | 1/2004 | Matsuura et al. |
| 6,733,512 B2 | 5/2004 | McGhan et al. |
| 6,981,980 B2 | 1/2006 | Sampson et al. |
| 6,988,983 B2 | 1/2006 | Connors et al. |
| 7,031,946 B1 | 4/2006 | Tamai et al. |
| 7,032,822 B2 | 4/2006 | Waters |
| 7,035,818 B1 | 4/2006 | Bandy et al. |
| 7,035,877 B2 | 4/2006 | Markham et al. |
| 7,192,397 B2 | 3/2007 | Lewkowicz et al. |
| 7,682,306 B2 | 3/2010 | Shah |
| 7,699,863 B2 | 4/2010 | Marco et al. |
| 7,854,745 B2 | 12/2010 | Brister et al. |
| 8,105,247 B2 | 1/2012 | Buchwald |
| 8,162,969 B2 | 4/2012 | Brister et al. |
| 8,202,291 B1 | 6/2012 | Brister et al. |
| 8,226,602 B2 | 7/2012 | Quijana et al. |
| 8,282,666 B2 | 10/2012 | Birk |
| 8,292,911 B2 | 10/2012 | Brister et al. |
| 8,428,691 B2 | 4/2013 | Byrd et al. |
| 8,491,464 B2 | 7/2013 | Yokoi et al. |
| 8,535,230 B2 | 9/2013 | Maschke |
| 8,562,589 B2 | 10/2013 | Imran |
| 8,721,620 B2 | 5/2014 | Imran |
| 8,734,429 B2 | 5/2014 | Imran et al. |
| 8,764,733 B2 | 7/2014 | Imran |
| 8,809,269 B2 | 8/2014 | Imran |
| 8,809,271 B2 | 8/2014 | Imran |
| 8,836,513 B2 | 9/2014 | Hafezi et al. |
| 8,847,766 B2 | 9/2014 | Zdeblick et al. |
| 8,858,432 B2 | 10/2014 | Robertson et al. |
| 8,870,966 B2 | 10/2014 | Schwab et al. |
| 2003/0021822 A1 | 1/2003 | Lloyd |
| 2003/0171768 A1 | 9/2003 | McGhan |
| 2004/0044351 A1 | 3/2004 | Searle |
| 2004/0102677 A1 | 5/2004 | Frering |
| 2004/0133095 A1 | 7/2004 | Dunki-Jacobs et al. |
| 2004/0186502 A1 | 9/2004 | Sampson |
| 2005/0033331 A1 | 2/2005 | Burnett et al. |
| 2005/0131281 A1 | 6/2005 | Ayer et al. |
| 2005/0192614 A1 | 9/2005 | Binmoeller |
| 2005/0222329 A1 | 10/2005 | Shah et al. |
| 2005/0245814 A1 | 11/2005 | Anderson et al. |
| 2005/0266109 A1 | 12/2005 | Chin et al. |
| 2005/0267405 A1 | 12/2005 | Shah |
| 2005/0267595 A1 | 12/2005 | Chen et al. |
| 2006/0058829 A1 | 3/2006 | Sampson et al. |
| 2006/0178691 A1 | 8/2006 | Binmoeller |
| 2006/0224145 A1 | 10/2006 | Gillis et al. |
| 2006/0247530 A1 | 11/2006 | Hardin et al. |
| 2007/0078476 A1 | 4/2007 | Hull et al. |
| 2007/0100208 A1 | 5/2007 | Lewkowicz et al. |
| 2007/0100367 A1 | 5/2007 | Quijano et al. |
| 2007/0100369 A1 | 5/2007 | Cragg et al. |
| 2007/0104754 A1 | 5/2007 | Sterling et al. |
| 2007/0104755 A1 | 5/2007 | Sterling et al. |
| 2007/0110934 A1 | 5/2007 | Goldman |
| 2007/0129735 A1 | 6/2007 | Filipi et al. |
| 2007/0149994 A1 | 6/2007 | Sosnowski et al. |
| 2007/0156248 A1 | 7/2007 | Marco et al. |
| 2007/0173881 A1 | 7/2007 | Birk et al. |
| 2007/0207199 A1 | 9/2007 | Sogin et al. |
| 2007/0212559 A1 | 9/2007 | Shah |

(56) References Cited

U.S. PATENT DOCUMENTS

| | | |
|---|---|---|
| 2007/0250101 A1 | 10/2007 | Horn et al. |
| 2007/0288033 A1 | 12/2007 | Murature et al. |
| 2007/0293885 A1 | 12/2007 | Binmoeller |
| 2008/0051866 A1 | 2/2008 | Chen et al. |
| 2008/0172079 A1 | 7/2008 | Birk |
| 2008/0255601 A1 | 10/2008 | Birk |
| 2008/0306506 A1 | 12/2008 | Leatherman et al. |
| 2009/0058575 A1* | 3/2009 | Pizzuto .............. H03K 17/9517 335/78 |
| 2009/0082644 A1 | 3/2009 | Li |
| 2009/0118756 A1 | 5/2009 | Valencon et al. |
| 2009/0182368 A1 | 7/2009 | Lunsford et al. |
| 2009/0182424 A1 | 7/2009 | Marco et al. |
| 2009/0187206 A1 | 7/2009 | Binmoeller et al. |
| 2009/0192535 A1 | 7/2009 | Kasic, II et al. |
| 2009/0222065 A1 | 9/2009 | Dlugos et al. |
| 2009/0259246 A1 | 10/2009 | Eskaros et al. |
| 2010/0063530 A1 | 3/2010 | Valencon |
| 2010/0094116 A1* | 4/2010 | Silverstein ............... A61B 5/06 600/409 |
| 2010/0100115 A1 | 4/2010 | Soetermans et al. |
| 2010/0100116 A1 | 4/2010 | Brister et al. |
| 2010/0100117 A1 | 4/2010 | Brister et al. |
| 2010/0137897 A1 | 6/2010 | Brister et al. |
| 2010/0168782 A1 | 7/2010 | Hancock |
| 2010/0198249 A1 | 8/2010 | Sabliere |
| 2010/0222802 A1 | 9/2010 | Gillespie et al. |
| 2011/0021881 A1 | 1/2011 | Wenchell et al. |
| 2011/0125007 A1* | 5/2011 | Steinberg ........... A61B 1/00158 600/424 |
| 2011/0152639 A1* | 6/2011 | Matott .................... A61B 5/062 600/302 |
| 2011/0184279 A1 | 7/2011 | Massonneau |
| 2011/0202127 A1 | 8/2011 | Mauch et al. |
| 2011/0295300 A1 | 12/2011 | Verd et al. |
| 2011/0301497 A1* | 12/2011 | Shachar ............. A61B 1/00158 600/567 |
| 2012/0010590 A1 | 1/2012 | Imran |
| 2012/0191123 A1* | 7/2012 | Brister .................. A61F 5/0043 606/191 |
| 2012/0191124 A1 | 7/2012 | Brister et al. |
| 2012/0232576 A1 | 9/2012 | Brister et al. |
| 2012/0296365 A1 | 11/2012 | Nguyen |
| 2013/0012980 A1 | 1/2013 | Brister et al. |
| 2013/0165859 A1 | 6/2013 | Imran |
| 2013/0190796 A1 | 7/2013 | Tilson et al. |
| 2013/0226219 A1 | 8/2013 | Brister et al. |
| 2013/0267983 A1 | 10/2013 | Pavlovic et al. |
| 2013/0289604 A1 | 10/2013 | Brister et al. |
| 2014/0066968 A1 | 3/2014 | Pavlovic et al. |
| 2014/0221912 A1 | 8/2014 | Imran |
| 2014/0221927 A1 | 8/2014 | Imran et al. |
| 2016/0029998 A1 | 2/2016 | Brister et al. |
| 2016/0058322 A1 | 3/2016 | Brister et al. |
| 2016/0100970 A1 | 4/2016 | Brister et al. |
| 2016/0278662 A1 | 9/2016 | Brister et al. |
| 2018/0049901 A1 | 2/2018 | Brister et al. |
| 2018/0290693 A1 | 10/2018 | Nelson et al. |

FOREIGN PATENT DOCUMENTS

| | | |
|---|---|---|
| EP | 0246999 | 11/1987 |
| JP | 62286470 | 12/1987 |
| JP | 2007-500538 | 1/2007 |
| JP | 2008-178686 | 8/2008 |
| JP | 2009-519086 | 5/2009 |
| WO | WO 1987/00034 | 1/1987 |
| WO | WO 1999/25418 | 5/1999 |
| WO | WO 2001/068007 | 9/2001 |
| WO | WO 2002/016001 | 2/2002 |
| WO | WO 2002/040081 | 5/2002 |
| WO | WO 2002/091961 | 11/2002 |
| WO | WO 2003/055420 | 7/2003 |
| WO | WO 04/045374 | 6/2004 |
| WO | WO 04/091361 | 10/2004 |
| WO | WO 2004/084763 | 10/2004 |
| WO | WO 2006/020929 | 2/2006 |
| WO | WO 2006/116718 A2 | 11/2006 |
| WO | WO 07/053556 | 5/2007 |
| WO | WO 2007/074445 | 7/2007 |
| WO | WO 2007/136735 | 11/2007 |
| WO | WO 2008/052136 A2 | 5/2008 |
| WO | WO 2009/055386 | 4/2009 |
| WO | WO 2009/059803 | 5/2009 |
| WO | WO 2009/086119 | 7/2009 |
| WO | WO 2010/045477 | 4/2010 |
| WO | WO 2010/045482 | 4/2010 |
| WO | WO 10/097774 | 8/2010 |
| WO | WO 2011/136745 | 11/2011 |
| WO | WO 12/099610 | 7/2012 |
| WO | WO 13/120184 | 8/2013 |
| WO | WO 14/081725 | 5/2014 |
| WO | WO 2014/081725 A2 | 5/2014 |

OTHER PUBLICATIONS

Remington's Pharmaceutical Sciences, Mace Publishing Company, Philadelphia, PA, 17th ed. (1985).
Bar-Shalom et al., Tracking and Data Association, Academic Press, Inc., Boston, 1988.
Almeida, N. et al., "Capsule endoscopy assisted by traditional upper endoscopy" Revista Espãnola De Enfermedades Digestives, 2008, pp. 758-763, vol. 100, No. 12.
Ambe, Peter et al., "Swallowed Foreign Bodies in Adults" Dtsch Arztebl Int, 2012, pp. 869-875, vol. 109, No. 50.
Sherlock II Tip Location System, Bard Access Systems, Imaging Technologies http://www.bardaccess.com/loc-sherlock.php.
Torres, Fernanda et al., "Management of contact dermatitis due to nickel allergy: an update" Clinical, Cosmetic and Investigational Dermatology, 2009, pp. 39-48, vol. 2.
Vălean, Simona et al., "Pill Esophagitis: Two Cases Reports" Romanian Journal of Gastroenterology, Jun. 2005, pp. 159-163, vol. 14, No. 2.
Vijaysadan, Viju et al., "Revisiting Swallowed Troubles: Intestinal Complications Caused by Two Magnets—A Case Report, Review and Proposed Revision to the Algorithm for the Management of Foreign Body Ingestion" JABFM, Sep.-Oct. 2006, pp. 511-516, vol. 19, No. 5.
Yoshihisa, Yoko et al., "Metal Allergy and Systemic Contact Dermatitis: An Overview" Dermatology Research and Practice, 2012, pp. 1-5, vol. 2012, Article ID 749250.
U.S. Food and Drug Administration. Jul. 29, 2009. 510(k) substantial equivalence clearance, Given PillCam Platform with PillCam SB Capsules with PillCam SensorBelt http://www.accessdata.fda.gov/scripts/cdrh/cfdocs/cfpmn/pmn.cfm?id=k091405.
U.S. Food and Drug Administration. Jun. 2, 2006. 510(k) substantial equivalence clearance, Sherlock tip location system (TLS) detector and accessories. http://www.accessdata.fda.gov/scripts/cdrh/cfdocs/cfpmn/pmn.cfm?id=k061240.
U.S. Food and Drug Administration. Sep. 7, 2000. 510(k) substantial equivalence clearance, Zotran Detector. http://www.accessdata.fda.gov/scripts/cdrh/cfdocs/cfpmn/pmn.cfm?id=k000997.
U.S. Appl. No. 60/807,060, filed Jul. 11, 2006, titled: Acoustic Pharma-Informatic System.
U.S. Appl. No. 60/866,581, filed Nov. 20, 2006, titled: "In-Vivo Transmission Decoder".
U.S. Appl. No. 60/889,868, filed Feb. 14, 2007, titled: "Pharma Informatics System Power Source".
U.S. Appl. No. 60/889,871, filed Feb. 14, 2007, titled: "Pharma Informatics System Having Short Resistant Series Battery".
Al Kahtani et al., Bio-Enteric Intragastric Balloon in Obese Patients: A Retrospective Analysis of King Faisal Specialist Hospital Experience; Obes Surg; Aug. 28, 2008.
Al-Momen et al., Intragastric Balloon for Obesity: A Retrospective Evaluation of Tolerance and Efficacy; Obes Surg; 2005; 15(1):101-5.

(56) References Cited

OTHER PUBLICATIONS

Benjamin et al., Double-Blind Controlled Trial of the Garren-Edwards Gastric Bubble: An Adjunctive Treatment for Exogenous Obesity, Gastroenterology, vol. 95, No. 3, pp. 581-588, Sep. 1988.
Carvalho et al., An Improved Intragastric Balloon Procedure Using A New Balloon: Preliminary Analysis of Safety and Efficacy, Obes Surg, 2008.
Coskun et al., Bioenterics Intragastric Balloon: Clinical Outcomes of the First 100 Patients—A Turkish Experience, Obes Surg, Sep. 2008; 18(9):1154-6, published online Jun. 3, 2008.
Dastis et al., Intragastric Balloon for Weight Loss: Results in 100 Individuals Followed for At Least 2.5 Years; Endoscopy. Jul. 2009; 41(7):575-80; published online Jul. 8, 2009.
De Waele et al., Endoscopic Volume Adjustment of Intragastric Balloons for Intolerance, Obes Surg; Apr. 2001; 11(2):223-4.
Doldi et al., Treatment of Morbid Obesity With Intragastric Balloon in Association With Diet; Obes Surg; 2002; 12(4):583-7.
Dumonceau, Evidence-Based Review of the Bioenterics Intragastric Balloon for Weight Loss, Obes Surg. Dec. 2008; 18(12):1611-7, published online Jun. 21, 2008.
Durrans et al., Comparison of Weight Loss With Short Term Dietary and Intragastric Balloon Treatment; Gut 1989, 30, 565-568.
Eckhauser et al., Hydrostatic Balloon Dilation for Stomal Stenosis after Gastric Partitioning, Surgical Gastroenterology, vol. 3, No. 1, pp. 43-50, 1984.
Evans et al., Intragastric Balloon in the Treatment of Patients With Morbid Obesity, British Journal of Surgery; 2001; 88:1245-1248.
Fernandes et al., Intragastric Balloon for Obesity (Review); Cochrane Review; Jan. 24, 2007; Issue 1.
Forestieri et al., Heliosphere Bag in the Treatment of Severe Obesity: Preliminary Experience, Obes Surg; May 2006; 16(5):635-7.
Gaggiotti et al., Adjustable Totally Implanted Intragastric Prosthesis (ATIIP). Endogast for Treatment of Morbid Obesity: One Year Follow-Up of a Multicenter Prospective Clinical Survey; Obesity Surgery. 2007: 17, 949-956.
Geliebter et al., Gastric balloon to treat obesity: a double-blind study in nondieting subjects, The American Journal of Clinical Nutrition, vol. 51, pp. 584-588, 1990.
Genco et al., Bioenterics Intragastric Balloon (BIB): A Short-Term, Double-Blind, Randomized, Controlled, Crossover Study on Weight Reduction In Morbidly Obese Patients; International Journal of Obesity (Lond); Jan. 2006; 30(1):129-33; published online Sep. 27, 2005.
Genco et al., Bioenterics Intragastric Balloon: The Italian Experience With 2,515 Patients; Obes Surg; 2005: 15(8):1161-4.
Genco et al., Intragastric Balloon or Diet Alone? A Retrospective Evaluation, Obes Surg, Aug. 2008; 18(8):989-92, published online May 16, 2008.
Genco et al., Laparoscopic Sleeve Gastrectomy Versus Intragastric Balloon: A Case-Control Study, Surg Endosc. Springer Science & Business Media, published online Jan. 24, 2009.
Gottig et al., Analysis of Safety and Efficacy of Intragastric Balloon in Extremely Obese Patients, Obes Surg, Jun. 2009; 19(6):677-83, published online Mar. 17, 2009.
Imaz et al., Safety and Effectiveness of the Intragastric Balloon for Obesity. A Meta-Analysis; Obes Surg; Jul. 2008; 18(7):841-6; published online May 6, 2008.
Langer, R., Drug delivery and targeting, Nature, Supplement to vol. 392, No. 6679, pp. 5-10, Apr. 1998.
Malik; Endoluminal and Transluminal Surgery: Current Status and Future Possibilities; Surgical Endoscopy; 2006; 20(8):1179-92.
Martin et al., Safety of the Ullorex Oral Intragastric Balloon for the Treatment of Obesity, Journal of Diabetic Science and Technology, vol. 1, Issue 4, pp. 574-581, Jul. 2007.
Mathus-Vliegen et al., Intragastric Ballon in the Treatment of Super-morbid Obesity-Double-Blind, Sham-Controlled, Crossover Evaluation of 500-Milliliter Balloon, Gastroenterology, vol. 99, No. 2, pp. 362-369, Aug. 1990.
Melissas et al., The Intragastric Balloon—Smoothing the Path to Bariatric Surgery, Obes Surg 2006; 16:897-902.
Mion et al., Tolerance and Efficacy of an Air-Filled Balloon in Non-Morbidly Obese Patients: Results of a Prospective Multicenter Study; Obes Surg; Jul. 2007; 17(7):764-769.
Nieben et al., Ingtragastric Balloon as an Artificial Bezoar for Treatment of Obesity, The Lancet, vol. 1, No. 8265, pp. 198-199, Jan. 1982.
Ramhamadany et al, Effect of the Gastric Balloon Versus Sham Procedure on Weight Loss in Obese Subjects; Gut 1989; 30; 1054-1057.
Rodriguez-Hermosa et al., Gastric Necrosis: A Possible Complication of the Use of the Intragastric Balloon in a Patient Previously Submitted to Nissen Fundoplication; Obes Surg; 19:1456-1459; published online Jun. 9, 2009.
Roman et al., Intragastric Balloon for "Non-Morbid" Obesity: A Retrospective Evaluation of Tolerance and Efficacy; Obes Surg; Apr. 2004; 14(4):539-44.
Sallet et al. Brazilian Multicenter Study of the Intragastric Balloon; Obesity Surgery; Aug. 2004; 14(7); 991-998.
Totte et al., Weight Reduction by Means of Intragastric Device: Experience With the Bioenterics Intragastric Balloon; Obes Surg; Aug. 2001; 11(4):519-23.
Trande et al., Efficacy, Tolerance and Safety of New Intragastric Air-Filled Balloon (Heliosphere Bag) for Obesity: The Experience of 17 Cases; Obes Surg; Dec. 10, 2008.
Vansonnenberg et al., Percutaneous Gastrostomy: Use of Intragastric Ballon Support, Radiology, vol. 152, No. 2, pp. 531-532, Aug. 1984.
Wahlen et al., The Bioenterics Intragastric Balloon (BIB): How to Use It; OBES SURG; 2001; 11(4):524-7.

* cited by examiner

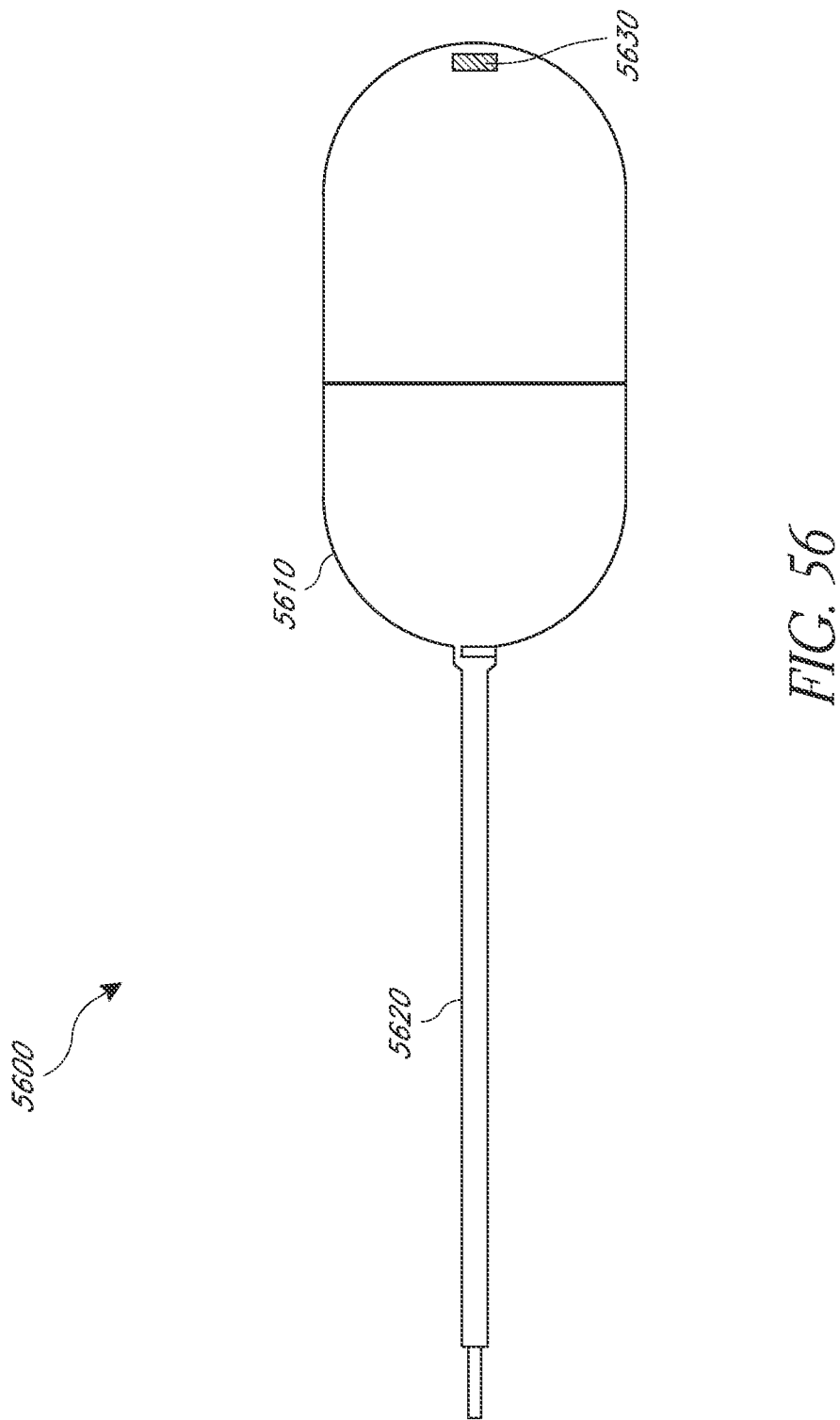

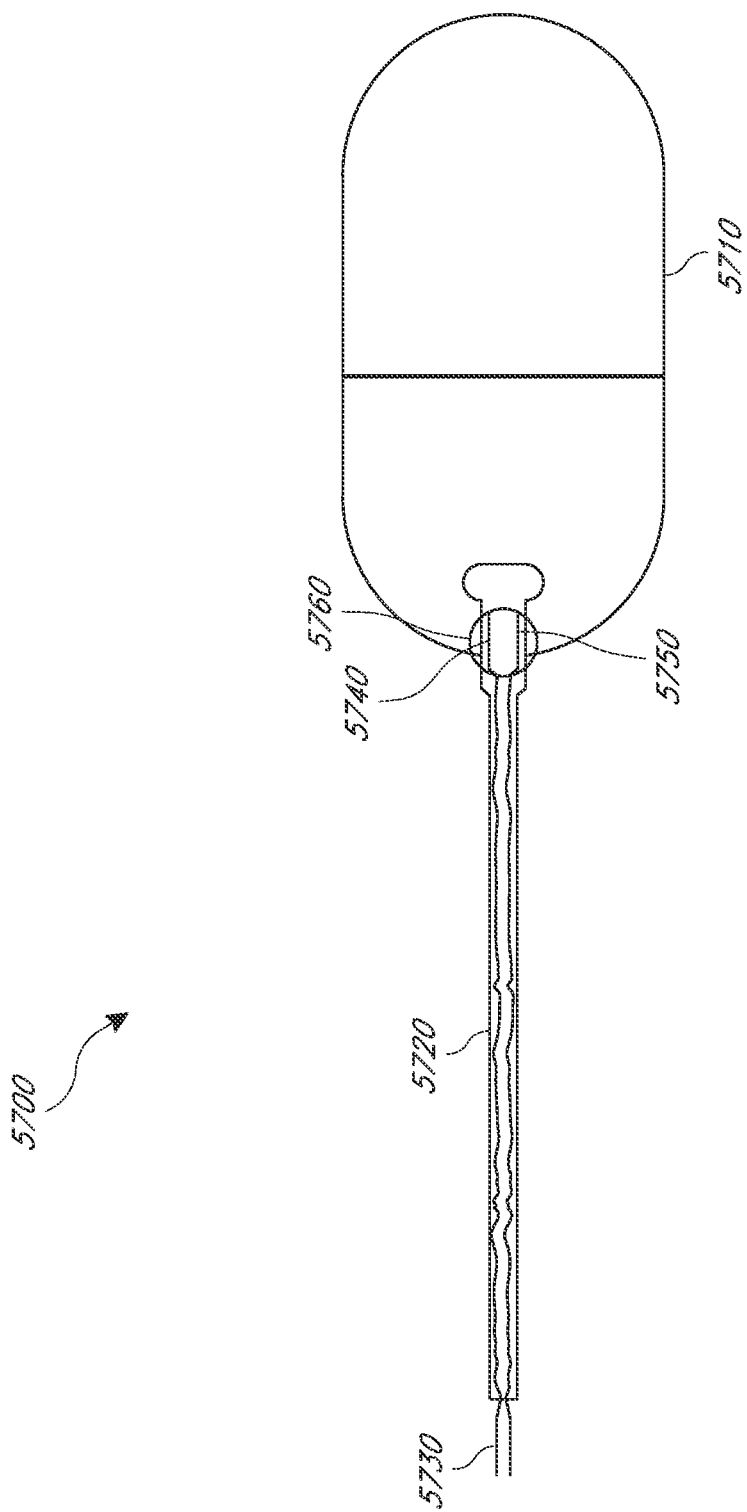

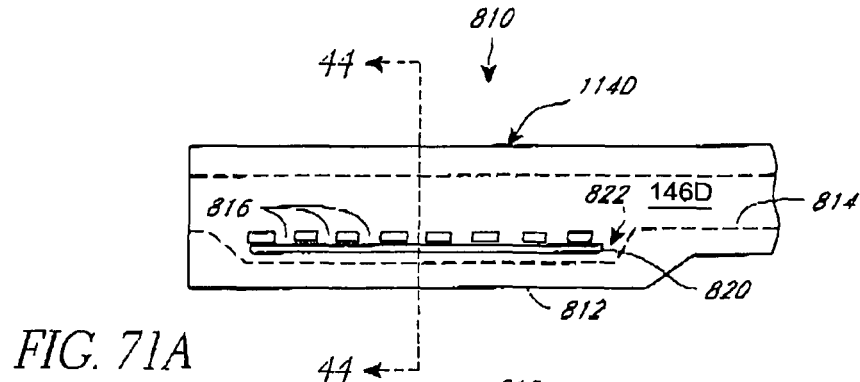
FIG. 71A
FIG. 71B
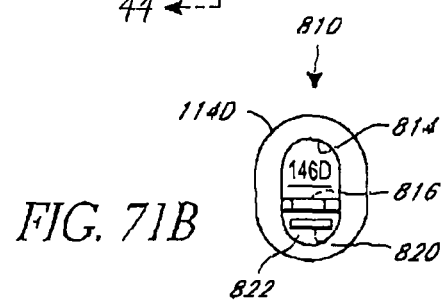
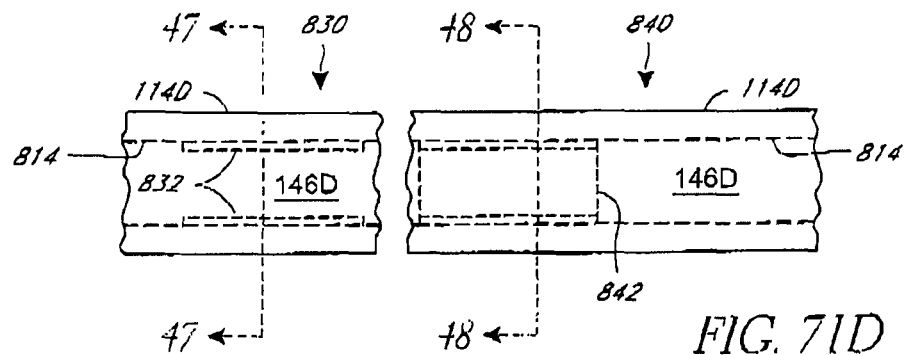
FIG. 71C
FIG. 71D
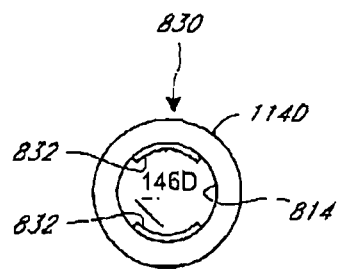
FIG. 71E
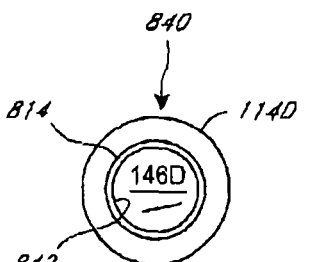
FIG. 71F

SYSTEMS AND METHODS FOR LOCATING AND/OR CHARACTERIZING INTRAGASTRIC DEVICES

INCORPORATION BY REFERENCE TO RELATED APPLICATIONS

Any and all priority claims identified in the Application Data Sheet, or any correction thereto, are hereby incorporated by reference under 37 CFR 1.57. This application is the national stage of PCT International Application No. PCT/US14/68458, filed Dec. 3, 2014, which claims priority to U.S. Provisional Application No. 61/911,958, filed Dec. 4, 2013, and to U.S. Provisional Application No. 62/062,081, filed Oct. 9, 2014. Each of the aforementioned applications is incorporated by reference herein in its entirety, and each is hereby expressly made a part of this specification.

FIELD

Devices and methods for treating obesity are provided. More particularly, intragastric devices and methods of fabricating, deploying, inflating, locating, tracking, monitoring, deflating, and retrieving the same are provided.

BACKGROUND

Obesity is a major health problem in developed countries. Obesity puts you at greater risk of developing high blood pressure, diabetes and many other serious health problems. In the United States, the complications of being overweight or obese are estimated to affect nearly one in three American adults, with an annual medical cost of over $80 billion and, including indirect costs such as lost wages, a total annual economic cost of over $120 billion. Except for rare pathological conditions, weight gain is directly correlated to overeating.

Noninvasive methods for reducing weight include increasing metabolic activity to burn calories and/or reducing caloric intake, either by modifying behavior or with pharmacological intervention to reduce the desire to eat. Other methods include surgery to reduce the stomach's volume, banding to limit the size of the stoma, and intragastric devices that reduce the desire to eat by occupying space in the stomach.

Intragastric volume-occupying devices provide the patient a feeling of satiety after having eaten only small amounts of food. Thus, the caloric intake is diminished while the person is satisfied with a feeling of fullness. Currently available volume-occupying devices have many shortcomings. For example, complex gastric procedures are required to insert some devices.

U.S. Pat. No. 4,133,315, the contents of which are incorporated herein by reference in their entirety, discloses an apparatus for reducing obesity comprising an inflatable, elastomeric bag and tube combination. The bag can be inserted into the patient's stomach by swallowing. The end of the attached tube distal to the bag remains in the patient's mouth. A second tube is snaked through the nasal cavity and into the patient's mouth. The tube ends located in the patient's mouth are connected to form a continuous tube for fluid communication through the patient's nose to the bag. Alternatively, the bag can be implanted by a gastric procedure. The bag is inflated through the tube to a desired degree before the patient eats so that the desire for food is reduced. After the patient has eaten, the bag is deflated. The tube extends out of the patient's nose or abdominal cavity throughout the course of treatment.

U.S. Pat. Nos. 5,259,399, 5,234,454 and 6,454,785, the contents of which are incorporated herein by reference in their entirety, disclose intragastric volume-occupying devices for weight control that must be implanted surgically.

U.S. Pat. Nos. 4,416,267, 4,485,805, 4,607,618, 4,694,827, 4,723,547, 4,739,758, and 4,899,747 and European Patent No. 246,999, the contents of which are incorporated herein by reference in their entirety, relate to intragastric, volume-occupying devices for weight control that can be inserted endoscopically. Of these, U.S. Pat. Nos. 4,416,267, 4,694,827, 4,739,758 and 4,899,747, the contents of which are incorporated herein by reference in their entirety relate to balloons whose surface is contoured in a certain way to achieve a desired end. In U.S. Pat. Nos. 4,416,267 and 4,694,827, the contents of which are incorporated herein by reference in their entirety, the balloon is torus-shaped with a flared central opening to facilitate passage of solids and liquids through the stomach cavity. The balloon of U.S. Pat. No. 4,694,827, the contents of which are incorporated herein by reference in their entirety, has a plurality of smooth-surfaced convex protrusions. The protrusions reduce the amount of surface area which contacts the stomach wall, thereby reducing the deleterious effects resulting from excessive contact with the gastric mucosa. The protrusions also define channels between the balloon and stomach wall through which solids and liquids may pass. The balloon of U.S. Pat. No. 4,739,758, the contents of which are incorporated herein by reference in their entirety, has blisters on its periphery that prevent it from seating tightly against the cardia or pylorus.

The balloons of U.S. Pat. Nos. 4,899,747 and 4,694,827, the contents of which are incorporated herein by reference in their entirety, are inserted by pushing the deflated balloon and releasably attached tubing down a gastric tube. U.S. Pat. No. 4,723,547, the contents of which are incorporated herein by reference in their entirety discloses a specially adapted insertion catheter for positioning its balloon. In U.S. Pat. No. 4,739,758, the contents of which are incorporated herein by reference in their entirety, the filler tube effects insertion of the balloon. In U.S. Pat. No. 4,485,805, the contents of which are incorporated herein by reference in their entirety, the balloon is inserted into a finger cot that is attached by string to the end of a conventional gastric tube that is inserted down the patient's throat. The balloon of European Patent No. 246,999 is inserted using a gastroscope with integral forceps.

In U.S. Pat. Nos. 4,416,267, 4,485,805, 4,694,827, 4,739,758, and 4,899,747 and European Patent No. 246,999, the contents of which are incorporated herein by reference in their entirety, the balloon is inflated with a fluid from a tube extending down from the patient's mouth. In these patents, the balloon also is provided with a self-sealing hole (U.S. Pat. No. 4,694,827, the contents of which are incorporated herein by reference in their entirety), injection site (U.S. Pat. Nos. 4,416,267 and 4,899,747, the contents of which are incorporated herein by reference in their entirety), self-sealing fill valve (U.S. Pat. No. 4,485,805, the contents of which are incorporated herein by reference in their entirety), self-closing valve (European Patent No. 246,999, the contents of which are incorporated herein by reference in their entirety) or duck-billed valve (U.S. Pat. No. 4,739,758, the contents of which are incorporated herein by reference in their entirety). U.S. Pat. No. 4,723,547, the contents of which are incorporated herein by reference in their entirety, uses an elongated thick plug and the balloon is filled by inserting a needle attached to an air source through the plug.

U.S. Pat. No. 4,607,618, the contents of which are incorporated herein by reference in their entirety, describes a collapsible appliance formed of semi-rigid skeleton members joined to form a collapsible hollow structure. The appliance is not inflatable. It is endoscopically inserted into the stomach using an especially adapted bougie having an ejector rod to release the collapsed appliance. Once released, the appliance returns to its greater relaxed size and shape.

U.S. Pat. No. 5,129,915, the contents of which are incorporated herein by reference in their entirety, relates to an intragastric balloon that is intended to be swallowed and that inflates automatically under the effect of temperature. Three ways that an intragastric balloon might be inflated by a change in temperature are discussed. A composition comprising a solid acid and non-toxic carbonate or bicarbonate is separated from water by a coating of chocolate, cocoa paste or cocoa butter that melts at body temperature. Alternatively, citric acid and an alkaline bicarbonate coated with non-toxic vegetable or animal fat melting at body temperature and which placed in the presence of water, can produce the same result. Lastly, the solid acid and non-toxic carbonate or bicarbonate are isolated from water by an isolation pouch of low-strength synthetic material which it will suffice to break immediately before swallowing the bladder. Breaking the isolation pouches causes the acid, carbonate or bicarbonate and water to mix and the balloon to begin to expand immediately. A drawback of thermal triggering of inflation is that it does not afford the degree of control and reproducibility of the timing of inflation that is desirable and necessary in a safe self-inflating intragastric balloon.

After swallowing, food and oral medicaments typically reach a patient's stomach in under a minute. Food is retained in the stomach on average from one to three hours. However, the residence time is highly variable and dependent upon such factors as the fasting or fed state of the patient. Accordingly, proper timing of inflation of an intragastric balloon is a factor in successful deployment of the intragastric devices of various embodiments. Timing is selected to avoid premature inflation in the esophagus that could lead to an esophageal obstruction or belated inflation that could lead to intestinal obstruction.

Methods for verifying that the intragastric device is in the stomach are useful in that they do not rely on mere timing after administration of the intragastric device. Verification of location can be done with radiography. After a patient swallows an encapsulated balloon, radiography can be done to ensure the balloon is in the stomach after swallowing, with the encapsulated balloon visualized by a radio-opaque marker. Radiographic techniques include x-ray or fluoroscopy techniques that provide real-time images of the balloon using radiation. However, radiation may be harmful to the body if prolonged or administered in high doses. While fluoroscopy typically uses low doses of radiation, repeated use may create a risk of harm to a patient. Further, there is the risk of accidental administration of too high of a dose to a patient.

Electromagnetic-based systems and methods provide advantages over, e.g., radiography. Electromagnetism refers generally to the magnetic fields corresponding to electric currents. A current may be induced in a conducting material by the presence of a magnetic field. A magnetic field may also be induced by the presence of a current running through a conductive material. Electromagnetism has been used in many different contexts, and it presents advantages when used in the intragastric device locating and characterizing context.

Voltage-based systems and methods also provide advantages over e.g., radiography. Voltages are created when the electric potential of one point is different from that of another point. Voltage has been used in many different contexts, and it presents advantages when used in the intragastric device locating and characterizing context.

U.S. Pat. No. 8,858,432, the contents of which are incorporated herein by reference in their entirety, discloses ingestible markers incorporating a signal generating circuit. The ingestible event marker systems include an ingestible event marker (IEM) and a personal signal receiver. The IEM includes an identifier, such as a physiologically acceptable carrier, that is activated upon contact with a target internal physiological site of a body, such as digestive tract internal target site. The personal signal receiver is configured to be associated with a physiological location, e.g., inside of or on the body, and to receive a signal the IEM. During use, the IEM broadcasts a signal which is received by the personal signal receiver.

U.S. Pat. No. 8,836,513, the contents of which are incorporated herein by reference in their entirety, describes a system having an ingestible product indicating that it has been consumed. The system includes a conductive element, an electronic component, and a partial power source in the form of dissimilar materials. Upon contact with a conducting fluid, a voltage potential is created and the power source is completed, which activates the system. The electronic component controls the conductance between the dissimilar materials to produce a unique current signature. The system can be associated with food and communicate data about ingestion of food material to a receiver.

U.S. Pat. No. 8,847,766, the contents of which are incorporated herein by reference in their entirety, describes a system for physical delivery of a pharmaceutical agent. The system includes an identifier that transmits a conductive signal and consumable electrodes formed of dissimilar materials. The electrodes are configured to both generate a voltage to energize the identifier and transmit the conductive signal to the body when the first and second electrodes contact the bodily fluid.

Ultrasound-based systems and methods also provide advantages over, e.g., radiology. Ultrasound is an oscillating sound pressure wave with a frequency greater than the upper limit of the human hearing range. Ultrasound is thus not separated from 'normal' (audible) sound based on differences in physical properties, only the fact that humans cannot hear it. Although this limit varies from person to person, it is approximately 20 kilohertz (20,000 hertz) in healthy, young adults. Ultrasound devices operate with frequencies from 20 kHz up to several gigahertz.

Ultrasonic devices may be used to detect objects and measure distances. Ultrasonic imaging (sonography) is used in both veterinary medicine and human medicine. In the nondestructive testing of products and structures, ultrasound is used to detect invisible flaws. Industrially, ultrasound is used for cleaning and for mixing, and to accelerate chemical processes. Animals such as bats and porpoises use ultrasound for locating prey and obstacles.

Ultrasonics is the application of ultrasound. Ultrasound can be used for medical imaging, detection, measurement and cleaning. At higher power levels, ultrasonics is useful for changing the chemical properties of substances.

Medical sonography (ultrasonography) is an ultrasound-based diagnostic medical imaging technique used to visualize muscles, tendons, and many internal organs, to capture their size, structure and any pathological lesions with real time tomographic images. Ultrasound has been used by radiologists and sonographers to image the human body for at least 50 years and has become a widely used diagnostic tool. The technology is relatively inexpensive and portable, especially when compared with other techniques, such as magnetic resonance imaging (MRI) and computed tomography (CT). Ultrasound is also used to visualize fetuses during routine and emergency prenatal care. Such diagnostic applications used during pregnancy are referred to as obstetric sonography. As currently applied in the medical field, properly performed ultrasound poses no known risks to the patient. Sonography does not use ionizing radiation, and the power levels used for imaging are too low to cause adverse heating or pressure effects in tissue.

Ultrasound is also increasingly being used in trauma and first aid cases, with emergency ultrasound becoming a staple of most EMT response teams. Furthermore, ultrasound is used in remote diagnosis cases where teleconsultation is required, such as scientific experiments in space or mobile sports team diagnosis. Ultrasounds are also useful in the detection of pelvic abnormalities and can involve techniques known as abdominal (transabdominal) ultrasound, vaginal (transvaginal or endovaginal) ultrasound in women, and also rectal (transrectal) ultrasound in men.

Ultrasound has been used in many different contexts, and it presents advantages when used in the intragastric device locating and characterizing context.

Medical imaging is employed to diagnose a large number of diseases. The oldest method, dye X-ray technology, delivers high-resolution images within a short examination time; however, it has the disadvantage of exposing the patient to X-rays. Ultrasound imaging is a method of image acquisition that works without using radiation. With said ultrasound imaging, ultrasound signals are sent via an ultrasound transducer into the object to be examined and a corresponding control device receives the reflected ultrasound signals and processes the receive signals for imaging purposes.

U.S. Pat. No. 8,535,230, the contents of which are incorporated herein by reference in their entirety, describes an ultrasound device including an ultrasound transducer on a robotic arm to track an object as it moves. However, such a system is incompatible with tracking a device inside the body.

U.S. Pat. No. 8,105,247, the contents of which are incorporated herein by reference in their entirety, describes use of ultrasonic transceivers to measure the size of a gastric banding device. However, that system is intended for a stationary gastric banding device and is not directly applicable to locating and characterizing a translating, rotating and transforming intragastric device.

SUMMARY

There remains a need for an intragastric balloon device and method of locating such a device in vivo that avoids the aforementioned drawbacks of radiography.

A free-floating or tethered intragastric volume-occupying device or devices that maintain volume and/or internal pressure within a predetermined range over time, or which undergoes a predetermined adjustment in volume and/or internal pressure over time, is disclosed. By maintaining a predetermined volume and/or internal pressure, stresses on the device leading to a breach in structural integrity can be minimized, which prevents premature and/or uncontrolled deflation or other device failure. By undergoing a predetermined adjustment in volume and/or internal pressure over time, a preselected volume profile can be obtained to accommodate changes in stomach size over the course of treatment with the device. The devices can be self-inflating (also referred to as automatic inflating) or inflatable (also referred to as manually inflating via a tether).

Volume-occupying devices and methods for manufacturing, deploying, inflating, tracking, locating, deflating and retrieving of such devices are provided. The devices and methods of the preferred embodiments may be employed for treating over weight and obese individuals. Methods employing the device of the preferred embodiments need not utilize invasive procedures, but rather the device may simply be swallowed by a patient, with or without a catheter attached. Once in the stomach of the patient, the device is inflated with a preselected fluid, e.g., a gas, liquid, vapor or mixtures thereof, to a preselected volume. Therefore, the use of one fluid, such as a "gas", e.g., an initial fill gas, to describe the various embodiments herein, does not preclude the use of other fluids as well. Further, a "fluid," such as an initial fill fluid, also includes a material or materials in the solid, liquid, vapor, or gas phase that are incorporated within, mixed within, carried within or otherwise entrained in a fluid such as a gas or liquid. A fluid can comprise one substance, or mixtures of different substances, and may be or include saline, physiologically acceptable fluids or substances, etc. as further described herein. The wall of the device is preselected for its particular fluid, e.g. gas, diffusion properties. Once in the in vivo environment, the gas(es) within the device diffuse out through the wall of the device, and gases diffuse into the device from the in vivo environment. By preselecting the device wall and gas(es) initially employed to inflate the device, taking into account diffusion properties of gases into the device from the in vivo environment, the volume and/or internal pressure of the device can be maintained within a preselected range, or can follow a preselected profile of volume and/or pressure changes. After a predetermined time period, the device can be removed using endoscopic tools or will decrease in volume or deflate so as to pass through the remainder of the patient's digestive tract.

Inflation may be achieved by use of a removable catheter that initially remains in fluid contact with the device after it has been swallowed by the patient. Alternatively, inflation may be achieved by a self-inflation process, e.g., generation of gas in the device once it reaches the stomach by reaction of gas-generating components contained within the device upon swallowing, or by introduction of one or more components in the gas generating process into the device by use of a removable catheter.

The volume-occupying subcomponent of devices may be formed by injection, blow or rotational molding of a flexible, gas-impermeable, biocompatible material, such as, for example, polyurethane, nylon or polyethylene terephthalate. Materials that may be used to control the gas permeability/impermeability of the volume-occupying subcomponent include, but are not limited to, silicon oxide (SiOx), gold or any noble metal, saran, conformal coatings and the like, when it is desired to reduce permeability. To enhance gas-impermeable characteristics of the wall of the device, if desirable, the volume-occupying subcomponent may be further coated with one or more gas-barrier compounds, or be formed of a Mylar polyester film coating or kelvalite, silver or aluminum as a metalized surface to provide a gas impermeable barrier.

In further embodiments, the device employs a delivery state in which the device is packaged such that the device may be swallowed while producing minimal discomfort to the patient. In a delivery state, the device may be packaged into a capsule. Alternatively, the device may be coated with a material operable to confine the device and facilitate swallowing. Various techniques may also be employed to ease swallowing of the device including, for example, wetting, temperature treating, lubricating, and treating with pharmaceuticals such as anesthetics.

The devices incorporate a tracking or visualization component or components that enable physicians to determine the location and/or orientation and/or state of the device within the patient's body using electromagnetic, magnetic, voltaic, pH, and/or acoustic (e.g., ultrasonic) methods. The tracking or visualization component can be the balloon or a component thereof or therein, or an additional component added to or affixed to the balloon or a component thereof or therein, or an additional component having a property indicative of placement of the balloon.

In some embodiments, tracking subcomponents may incorporate materials that emit electromagnetic energy. The device may be tracked and located using a complementary electromagnetic energy sensor that is responsive to the electromagnetic properties of the device. Such techniques may also be used to obtain certain device specific information and specifications while the device remains inside the patient's body, including but not limited to device location, orientation, size or state as it travels inside the body. The electromagnetic-responsive sensor outside the body can detect and process information related to the electromagnetic energy relayed by the internal device, which energy may be reflected off, created by, or otherwise propagated from the intragastric device or materials or objects in or on the intragastric device. This information can then be interpreted to identify the device's location, orientation, size and other attributes while still inside the body. An electromagnetic system provides a simple, non-invasive and less harmful method of tracking, locating and characterizing intragastric devices.

In some embodiments, tracking subcomponents may incorporate materials that are responsive to ultrasonic or other acoustic energy. The device may be tracked and located using a complementary ultrasonic energy sensor that is responsive to the acoustic properties of the device. Such techniques may also be used to obtain certain device specific information and specifications while the device remains inside the patient's body, including but not limited to device location, orientation, size or state as it travels inside the body. The acoustically-responsive sensor outside the body can detect and process information related to the acoustic energy relayed by the internal device, which energy may be reflected off, created by, or otherwise propagated from the intragastric device or materials or objects in or on the intragastric device. This information can then be interpreted to identify the device's location, orientation, size and other attributes while still inside the body. An ultrasound system provides a simple, non-invasive and less harmful method of tracking, locating and characterizing intragastric devices.

In some embodiments, an electromagnetic system or portions thereof may be combined with an acoustic system or potions thereof. The combination of the systems or portions thereof may be implemented for further enhancing the locating and/or characterizing of the intragastric device in vivo.

Such techniques may also be used to obtain certain device specific information and specifications while the device remains inside the patient's body, including but not limited to device location, orientation, size or state as it travels inside the body. The magnetically-responsive sensor, e.g., a sensor outside of the body, can detect and relay information related to the magnetic field of the internal device. This information can then be interpreted to identify the device's location, orientation, size and other attributes while still inside the body. A magnetic field detecting system provides a simple, non-invasive and less harmful method of tracking, locating and characterizing intragastric devices.

In a first aspect, an electromagnetic system is provided for locating an intragastric device inside the body, the system comprising: an electromagnetic field generator configured to generate an electromagnetic field; a swallowable electromagnetic sensor configured to couple with the system and further configured to produce an electric current when exposed to the electromagnetic field in an in vivo gastric environment; and a valve system configured for introducing an initial fill fluid into a volume occupying intragastric device when the intragastric device is in the in vivo gastric environment, the valve system comprising a swallowable catheter configured to releasably couple with the intragastric device.

In an embodiment of the first aspect, the electromagnetic sensor is configured to couple with the swallowable catheter.

In an embodiment of the first aspect, the electromagnetic sensor is configured to couple with a distal end of the swallowable catheter.

In an embodiment of the first aspect, the electromagnetic sensor is configured to couple with the intragastric device.

In an embodiment of the first aspect, the system further comprises at least one external reference sensor configured to be placed outside the body and to produce an electric current when exposed to the magnetic field.

In an embodiment of the first aspect, the system further comprises three external reference sensors configured to be placed outside the body and to produce an electric current when exposed to the magnetic field.

In an embodiment of the first aspect, the system further comprises a sensor interface unit configured to electrically communicate with the electromagnetic sensor and the at least one external reference sensor.

In an embodiment of the first aspect, the system further comprises a system control unit configured to electrically communicate with the sensor interface unit and with the electromagnetic field generator.

In an embodiment of the first aspect, the system further comprises a computer configured to electrically communicate with the system control unit and to display an identifier indicating the location of the electromagnetic sensor inside the body.

In an embodiment of the first aspect, the system further comprises at least one external reference sensor configured to be placed outside the body and to produce an electric current when exposed to the magnetic field, wherein the computer is further configured to display at least one second identifier indicating the location of the at least one external reference sensor.

In an embodiment of the first aspect, the computer is further configured to display a trace indicating a path traveled by the electromagnetic sensor inside the body.

In an embodiment of the first aspect, the system further comprises the intragastric device, wherein the intragastric device is a balloon.

In an embodiment of the first aspect, the system further comprises the initial fill fluid, wherein the intragastric device comprises a polymeric wall configured to have, under conditions of the in vivo gastric environment, a permeability to $CO_2$ of more than 10 cc/m²/day, such that a rate and an amount of diffusion of $CO_2$ from the in vivo gastric environment into a lumen of the intragastric device through the polymeric wall is controlled, at least in part, by a concentration of an inert gas in the initial fill fluid.

In an embodiment of the first aspect, the polymeric wall comprises a $CO_2$ barrier material comprising an ethylene vinyl alcohol layer.

In an embodiment of the first aspect, the polymeric wall comprises a two layer $CO_2$ barrier material comprising a nylon layer and a polyethylene layer.

In an embodiment of the first aspect, the polymeric wall comprises a three layer $CO_2$ barrier material comprising a nylon layer, a polyvinylidene chloride layer, and a polyethylene layer.

In an embodiment of the first aspect, the polymeric wall comprises a three layer $CO_2$ barrier material comprising a nylon layer, an ethylene vinyl alcohol layer, and a polyethylene layer.

In an embodiment of the first aspect, the initial fill fluid consists essentially of gaseous $N_2$.

In an embodiment of the first aspect, the initial fill fluid consists essentially of gaseous $N_2$ and gaseous $CO_2$.

In an embodiment of the first aspect, the initial fill fluid consists essentially of gaseous $N_2$ and gaseous $CO_2$, and wherein the gaseous $N_2$ is excess in concentration to the gaseous $CO_2$ in the initial fill fluid.

In an embodiment of the first aspect, the initial fill fluid comprises $SF_6$ in one or more of liquid form, vapor form, or gaseous form.

In an embodiment of the first aspect, the initial fill fluid comprises gaseous $N_2$ and gaseous $SF_6$.

In an embodiment of the first aspect, the polymeric wall is configured to have, under conditions of an in vivo gastric environment, a permeability to $CO_2$ of more than 50 cc/m²/day.

In a second aspect, a method is provided for electromagnetically locating an intragastric device inside the body of a patient, the method comprising: generating an electromagnetic field with an electromagnetic field generator situated outside of the body of the patient; introducing into the body of the patient, via swallowing, the intragastric device comprising an uninflated gastric balloon, the intragastric device releasably coupled with a catheter and coupled with an electromagnetic sensor, the electromagnetic sensor configured to produce an electrical current in the presence of the electromagnetic field generated by the magnetic field generator; sensing a current induced in the electromagnetic sensor by the electromagnetic field; and confirming a location of the uninflated gastric balloon inside the patient based on sensing the current induced in the electromagnetic sensor.

In an embodiment of the second aspect, the location of the uninflated gastric balloon inside the patient is the patient's stomach.

In an embodiment of the second aspect, the method further comprises: introducing an initial fill fluid into a lumen of the uninflated gastric balloon through the catheter, the intragastric balloon comprising a polymeric wall configured to have, under conditions of an in vivo gastric environment, a permeability to $CO_2$ of more than 10 cc/m²/day; and exposing the inflated intragastric balloon to the in vivo intragastric environment for a useful life of at least 30 days, wherein a rate and an amount of diffusion of $CO_2$ from the in vivo gastric environment into the lumen of the balloon through the polymeric wall is controlled, at least in part, by a concentration of an inert gas in the initial fill fluid.

In an embodiment of the second aspect, the polymeric wall comprises a three layer $CO_2$ barrier material comprising a nylon layer, a polyvinylidene chloride layer and a polyethylene layer.

In an embodiment of the second aspect, the polymeric wall comprises a three layer $CO_2$ barrier material comprising a nylon layer, an ethylene vinyl alcohol layer, and a polyethylene layer.

In an embodiment of the second aspect, the polymeric wall comprises a two layer $CO_2$ barrier material comprising a nylon layer and a polyethylene layer.

In an embodiment of the second aspect, the polymeric wall comprises a $CO_2$ barrier material comprising an ethylene vinyl alcohol layer.

In an embodiment of the second aspect, the initial fill fluid consists essentially of gaseous $N_2$.

In an embodiment of the second aspect, the first gas consists essentially of gaseous $N_2$ and gaseous $CO_2$.

In an embodiment of the second aspect, the first gas consists essentially of gaseous $N_2$ and gaseous $CO_2$, and wherein the gaseous $N_2$ is excess in concentration to the gaseous $CO_2$ in the first gas.

In an embodiment of the second aspect, the first gas comprises $SF_6$ in one or more of liquid form, vapor form, or gaseous form.

In an embodiment of the second aspect, the first gas comprises gaseous $N_2$ and gaseous $SF_6$.

In an embodiment of the second aspect, the polymeric wall is configured to have, under conditions of an in vivo gastric environment, a permeability to $CO_2$ of more than 50 cc/m²/day.

In an embodiment of the second aspect, confirming a location of the uninflated gastric balloon inside the patient based on sensing the current induced in the electromagnetic sensor comprises displaying on a computer an identifier indicating the location of the electromagnetic sensor.

In an embodiment of the second aspect, the method further comprises placing at least one external reference sensor outside the body of the patient, the at least one external reference sensor configured to produce an electric current when exposed to the electromagnetic field, and sensing a current induced in the at least one external reference sensor by the electromagnetic field.

In an embodiment of the second aspect, confirming a location of the uninflated gastric balloon inside the patient based on sensing the current induced in the electromagnetic sensor comprises displaying on a computer at least one second identifier indicating the location of the at least one external reference sensor.

In an embodiment of the second aspect, the electromagnetic sensor is coupled with the catheter.

In an embodiment of the second aspect, the electromagnetic sensor is coupled with the intragastric device.

In a third aspect, a magnetic system is provided for locating an intragastric device inside the body, the system comprising: a magnetic field sensor configured to sense a magnetic field; a swallowable magnetic marker configured to couple with the system and further configured to produce a local magnetic field in an in vivo gastric environment; and a valve system configured for introducing an initial fill fluid into a volume occupying intragastric device when the intragastric device is in the in vivo gastric environment, the valve system comprising a swallowable catheter configured to releasably couple with the intragastric device.

In an embodiment of the third aspect, the magnetic marker is configured to couple with the swallowable catheter.

In an embodiment of the third aspect, the magnetic marker is configured to couple with a distal end of the swallowable catheter.

In an embodiment of the third aspect, the magnetic marker is configured to couple with the intragastric device.

In an embodiment of the third aspect, the system further comprises at least one external reference sensor configured to be placed outside the body and to sense a local magnetic field.

In an embodiment of the third aspect, the system further comprises a sensor interface unit configured to electrically communicate with the magnetic marker.

In an embodiment of the third aspect, the system further comprises a system control unit configured to electrically communicate with the sensor interface unit and with the magnetic field sensor.

In an embodiment of the third aspect, the system further comprises a computer configured to electrically communicate with the system control unit and to display an identifier indicating the location of the magnetic marker inside the body.

In an embodiment of the third aspect, the computer is further configured to display a trace indicating a path traveled by the magnetic marker inside the body.

In an embodiment of the third aspect, the system further comprises the intragastric device, wherein the intragastric device is a balloon.

In an embodiment of the third aspect, the system further comprises the initial fill fluid, wherein the intragastric device comprises a polymeric wall configured to have, under conditions of the in vivo gastric environment, a permeability to $CO_2$ of more than 10 $cc/m^2/day$, such that a rate and an amount of diffusion of $CO_2$ from the in vivo gastric environment into a lumen of the intragastric device through the polymeric wall is controlled, at least in part, by a concentration of an inert gas in the initial fill fluid.

In an embodiment of the third aspect, the polymeric wall comprises a $CO_2$ barrier material comprising an ethylene vinyl alcohol layer.

In an embodiment of the third aspect, the polymeric wall comprises a two layer $CO_2$ barrier material comprising a nylon layer and a polyethylene layer.

In an embodiment of the third aspect, the polymeric wall comprises a three layer $CO_2$ barrier material comprising a nylon layer, a polyvinylidene chloride layer, and a polyethylene layer.

In an embodiment of the third aspect, the polymeric wall comprises a three layer $CO_2$ barrier material comprising a nylon layer, an ethylene vinyl alcohol layer, and a polyethylene layer In an embodiment of the third aspect, the initial fill fluid consists essentially of gaseous $N_2$.

In an embodiment of the third aspect, the initial fill fluid consists essentially of gaseous $N_2$ and gaseous $CO_2$.

In an embodiment of the third aspect, the initial fill fluid consists essentially of gaseous $N_2$ and gaseous $CO_2$, and wherein the gaseous $N_2$ is excess in concentration to the gaseous $CO_2$ in the initial fill fluid.

In an embodiment of the third aspect, the initial fill fluid comprises $SF_6$ in one or more of liquid form, vapor form, or gaseous form.

In an embodiment of the third aspect, the initial fill fluid comprises gaseous $N_2$ and gaseous $SF_6$.

In an embodiment of the third aspect, the polymeric wall is configured to have, under conditions of an in vivo gastric environment, a permeability to $CO_2$ of more than 50 $cc/m^2/day$.

In a fourth aspect, a method is provided for magnetically locating an intragastric device inside the body of a patient, the method comprising: introducing into the body of the patient, via swallowing, the intragastric device comprising an uninflated gastric balloon, the intragastric device releasably coupled with a catheter and coupled with a magnetic marker, the magnetic marker configured to be sensed by the magnetic field sensor; sensing the magnetic field with the magnetic field sensor; and confirming a location of the uninflated gastric balloon inside the patient based on sensing the magnetic field.

In an embodiment of the fourth aspect, the location of the uninflated gastric balloon inside the patient is the patient's stomach.

In an embodiment of the fourth aspect, the method further comprises: introducing an initial fill fluid into a lumen of the uninflated gastric balloon through the catheter, the intragastric balloon comprising a polymeric wall configured to have, under conditions of an in vivo gastric environment, a permeability to $CO_2$ of more than 10 $cc/m^2/day$; and exposing the inflated intragastric balloon to the in vivo intragastric environment for a useful life of at least 30 days, wherein a rate and an amount of diffusion of $CO_2$ from the in vivo gastric environment into the lumen of the balloon through the polymeric wall is controlled, at least in part, by a concentration of an inert gas in an initial fill fluid.

In an embodiment of the fourth aspect, the polymeric wall comprises a three layer $CO_2$ barrier material comprising a nylon layer, a polyvinylidene chloride layer, and a polyethylene layer.

In an embodiment of the fourth aspect, the polymeric wall comprises a three layer $CO_2$ barrier material comprising a nylon layer, an ethylene vinyl alcohol layer, and a polyethylene layer.

In an embodiment of the fourth aspect, the polymeric wall comprises a two layer $CO_2$ barrier material comprising a nylon layer and a polyethylene layer.

In an embodiment of the fourth aspect, the polymeric wall comprises a $CO_2$ barrier material comprising an ethylene vinyl alcohol layer.

In an embodiment of the fourth aspect, the initial fill fluid consists essentially of gaseous $N_2$.

In an embodiment of the fourth aspect, the first gas consists essentially of gaseous $N_2$ and gaseous $CO_2$.

In an embodiment of the fourth aspect, the initial fill fluid consists essentially of gaseous $N_2$ and gaseous $CO_2$, and wherein the gaseous $N_2$ is excess in concentration to the gaseous $CO_2$ in the first gas.

In an embodiment of the fourth aspect, the initial fill fluid comprises $SF_6$ in one or more of liquid form, vapor form, or gaseous form.

In an embodiment of the fourth aspect, the initial fill fluid comprises gaseous $N_2$ and gaseous $SF_6$.

In an embodiment of the fourth aspect, the polymeric wall is configured to have, under conditions of an in vivo gastric environment, a permeability to $CO_2$ of more than 50 $cc/m^2/day$.

In an embodiment of the fourth aspect, confirming a location of the uninflated gastric balloon inside the patient based on sensing the magnetic field generated by the magnetic marker comprises displaying on a computer an identifier indicating the location of the magnetic marker.

In an embodiment of the fourth aspect, the magnetic marker is coupled with the catheter.

In an embodiment of the fourth aspect, the electromagnetic sensor is coupled with the intragastric device.

In a fifth aspect, a voltaic system is provided for locating an intragastric device inside the body, the system comprising: a swallowable voltaic sensor configured to couple with the system and further configured to produce a voltage in an in vivo gastric environment; and a valve system configured for introducing an initial fill fluid into a volume occupying intragastric device when the intragastric device is in the in vivo gastric environment, the valve system comprising a swallowable catheter configured to releasably couple with the intragastric device.

In an embodiment of the fifth aspect, the voltaic sensor is configured to couple with the swallowable catheter.

In an embodiment of the fifth aspect, the voltaic sensor is configured to couple with a distal end of the swallowable catheter.

In an embodiment of the fifth aspect, the voltaic sensor is configured to couple with the intragastric device.

In an embodiment of the fifth aspect, the system further comprises at least one receiver configured to be placed outside the body and to receive a signal related to the voltage produced by the voltaic sensor.

In an embodiment of the fifth aspect, the system further comprises a sensor interface unit configured to electrically communicate with the voltaic sensor.

In an embodiment of the fifth aspect, the system further comprises a system control unit configured to electrically communicate with the sensor interface unit and with the voltaic sensor.

In an embodiment of the fifth aspect, the system further comprises a computer configured to electrically communicate with the system control unit and to display an identifier indicating the location of the voltaic sensor inside the body.

In an embodiment of the fifth aspect, the system further comprises the intragastric device, wherein the intragastric device is a balloon.

In an embodiment of the fifth aspect, the system further comprises the initial fill fluid, wherein the intragastric device comprises a polymeric wall configured to have, under conditions of the in vivo gastric environment, a permeability to $CO_2$ of more than 10 $cc/m^2/day$, such that a rate and an amount of diffusion of $CO_2$ from the in vivo gastric environment into a lumen of the intragastric device through the polymeric wall is controlled, at least in part, by a concentration of an inert gas in the initial fill fluid.

In an embodiment of the fifth aspect, the polymeric wall comprises a $CO_2$ barrier material comprising an ethylene vinyl alcohol layer.

In an embodiment of the fifth aspect, the polymeric wall comprises a two layer $CO_2$ barrier material comprising a nylon layer and a polyethylene layer.

In an embodiment of the fifth aspect, the polymeric wall comprises a three layer $CO_2$ barrier material comprising a nylon layer, an ethylene vinyl alcohol layer, and a polyethylene layer.

In an embodiment of the fifth aspect, the polymeric wall comprises a three layer $CO_2$ barrier material comprising a nylon layer, a polyvinylidene chloride layer, and a polyethylene layer.

In an embodiment of the fifth aspect, the initial fill fluid consists essentially of gaseous $N_2$.

In an embodiment of the fifth aspect, the initial fill fluid consists essentially of gaseous $N_2$ and gaseous $CO_2$.

In an embodiment of the fifth aspect, the initial fill fluid consists essentially of gaseous $N_2$ and gaseous $CO_2$, and wherein the gaseous $N_2$ is excess in concentration to the gaseous $CO_2$ in the initial fill fluid.

In an embodiment of the fifth aspect, the initial fill fluid comprises $SF_6$ in one or more of liquid form, vapor form, or gaseous form.

In an embodiment of the fifth aspect, the initial fill fluid comprises gaseous $N_2$ and gaseous $SF_6$.

In an embodiment of the fifth aspect, the polymeric wall is configured to have, under conditions of an in vivo gastric environment, a permeability to $CO_2$ of more than 50 $cc/m^2/day$.

In a sixth aspect, a method is provided for voltaically locating an intragastric device inside the body of a patient, the method comprising: introducing into the body of the patient, via swallowing, the intragastric device comprising an uninflated gastric balloon, the intragastric device releasably coupled with a catheter and coupled with a voltaic sensor, the voltaic sensor configured to produce a voltage in the presence of a gastric environment; producing a voltage with the voltaic sensor in response to contact with the gastric environment; and confirming a location of the uninflated gastric balloon inside the patient based on sensing the produced voltage.

In an embodiment of the sixth aspect, the location of the uninflated gastric balloon inside the patient is the patient's stomach.

In an embodiment of the sixth aspect, the method further comprises: introducing an initial fill fluid into a lumen of the uninflated gastric balloon through the catheter, the intragastric balloon comprising a polymeric wall configured to have, under conditions of an in vivo gastric environment, a permeability to $CO_2$ of more than 10 $cc/m^2/day$; and exposing the inflated intragastric balloon to the in vivo intragastric environment for a useful life of at least 30 days, wherein a rate and an amount of diffusion of $CO_2$ from the in vivo gastric environment into the lumen of the balloon through the polymeric wall is controlled, at least in part, by a concentration of an inert gas in the initial fill fluid.

In an embodiment of the sixth aspect, the polymeric wall comprises a three layer $CO_2$ barrier material comprising a nylon layer, a polyvinylidene chloride layer and a polyethylene layer.

In an embodiment of the sixth aspect, the polymeric wall comprises a three layer $CO_2$ barrier material comprising a nylon layer, an ethylene vinyl alcohol layer, and a polyethylene layer.

In an embodiment of the sixth aspect, the polymeric wall comprises a two layer $CO_2$ barrier material comprising a nylon layer and a polyethylene layer.

In an embodiment of the sixth aspect, the polymeric wall comprises a $CO_2$ barrier material comprising an ethylene vinyl alcohol layer.

In an embodiment of the sixth aspect, the initial fill fluid consists essentially of gaseous $N_2$ and gaseous $CO_2$.

In an embodiment of the sixth aspect, the initial fill fluid consists essentially of gaseous $N_2$.

In an embodiment of the sixth aspect, the first gas consists essentially of gaseous $N_2$ and gaseous $CO_2$, and wherein the gaseous $N_2$ is excess in concentration to the gaseous $CO_2$ in the initial fill fluid.

In an embodiment of the sixth aspect, the initial fill fluid comprises $SF_6$ in one or more of liquid form, vapor form, or gaseous form.

In an embodiment of the sixth aspect, the initial fill fluid comprises gaseous $N_2$ and gaseous $SF_6$.

In an embodiment of the sixth aspect, the polymeric wall is configured to have, under conditions of an in vivo gastric environment, a permeability to $CO_2$ of more than 50 $cc/m^2/day$.

In an embodiment of the sixth aspect, the voltaic sensor is coupled with the catheter.

In an embodiment of the sixth aspect, the voltaic sensor is coupled with the intragastric device.

In a seventh aspect, a pH based system is provided for locating an intragastric device inside the body, the system comprising: a swallowable pH sensor configured to couple with the system and further configured to sense the pH level of fluid in an in vivo gastric environment; and a valve system configured for introducing an initial fill fluid into a volume occupying intragastric device when the intragastric device is in the in vivo gastric environment, the valve system comprising a swallowable catheter configured to releasably couple with the intragastric device.

In an embodiment of the seventh aspect, the pH sensor is configured to couple with the swallowable catheter.

In an embodiment of the seventh aspect, the pH sensor is configured to couple with a distal end of the swallowable catheter.

In an embodiment of the seventh aspect, the pH sensor is configured to couple with the intragastric device.

In an embodiment of the seventh aspect, the system further comprises at least one receiver configured to be placed outside the body and to receive a signal related to the pH level sensed by the pH sensor.

In an embodiment of the seventh aspect, the system further comprises a sensor interface unit configured to electrically communicate with the pH sensor.

In an embodiment of the seventh aspect, the system further comprises a system control unit configured to electrically communicate with the sensor interface unit and with the pH sensor.

In an embodiment of the seventh aspect, the system further comprises a computer configured to electrically communicate with the system control unit and to display an identifier indicating the location of the pH sensor inside the body.

In an embodiment of the seventh aspect, the system further comprises the intragastric device, wherein the intragastric device is a balloon.

In an embodiment of the seventh aspect, the system further comprises the initial fill fluid, wherein the intragastric device comprises a polymeric wall configured to have, under conditions of an in vivo gastric environment, a permeability to $CO_2$ of more than 10 $cc/m^2/day$, such that a rate and an amount of diffusion of $CO_2$ from the in vivo gastric environment into a lumen of the intragastric device through the polymeric wall is controlled, at least in part, by a concentration of an inert gas in the initial fill fluid.

In an embodiment of the seventh aspect, the polymeric wall comprises a $CO_2$ barrier material comprising an ethylene vinyl alcohol layer.

In an embodiment of the seventh aspect, the polymeric wall comprises a two layer $CO_2$ barrier material comprising a nylon layer and a polyethylene layer.

In an embodiment of the seventh aspect, the polymeric wall comprises a three layer $CO_2$ barrier material comprising a nylon layer, a polyvinylidene chloride layer, and a polyethylene layer.

In an embodiment of the seventh aspect, the polymeric wall comprises a three layer $CO_2$ barrier material comprising a nylon layer, an ethylene vinyl alcohol layer, and a polyethylene layer.

In an embodiment of the seventh aspect, the initial fill fluid consists essentially of gaseous $N_2$.

In an embodiment of the seventh aspect, the initial fill fluid consists essentially of gaseous $N_2$ and gaseous $CO_2$.

In an embodiment of the seventh aspect, the initial fill fluid consists essentially of gaseous $N_2$ and gaseous $CO_2$, and wherein the gaseous $N_2$ is excess in concentration to the gaseous $CO_2$ in the initial fill fluid.

In an embodiment of the seventh aspect, the initial fill fluid comprises $SF_6$ in one or more of liquid form, vapor form, or gaseous form.

In an embodiment of the seventh aspect, the initial fill fluid comprises gaseous $N_2$ and gaseous $SF_6$.

In an embodiment of the seventh aspect, the polymeric wall is configured to have, under conditions of an in vivo gastric environment, a permeability to $CO_2$ of more than 50 $cc/m^2/day$.

In an eighth aspect, a method is provided for locating an intragastric device inside the body of a patient based on sensing a pH level of fluid inside the body, the method comprising: introducing into the body of the patient, via swallowing, the intragastric device comprising an uninflated gastric balloon, the intragastric device releasably coupled with a catheter and coupled with a pH sensor, the pH sensor configured to sense the pH level of the fluid in a gastric environment inside the body; sensing the pH level of the fluid in response to contact of the pH sensor with the gastric environment; and confirming a location of the uninflated gastric balloon inside the patient based on sensing the pH level.

In an embodiment of the eighth aspect, the location of the uninflated gastric balloon inside the patient is the patient's stomach.

In an embodiment of the eighth aspect, the method further comprises: introducing an initial fill fluid into a lumen of the uninflated gastric balloon through the catheter, the intragastric balloon comprising a polymeric wall configured to have, under conditions of an in vivo gastric environment, a permeability to $CO_2$ of more than 10 $cc/m^2/day$; and exposing the inflated intragastric balloon to the in vivo intragastric environment for a useful life of at least 30 days, wherein a rate and an amount of diffusion of $CO_2$ from the in vivo gastric environment into the lumen of the balloon through the polymeric wall is controlled, at least in part, by a concentration of an inert gas in an initial fill fluid.

In an embodiment of the eighth aspect, the polymeric wall comprises a three layer $CO_2$ barrier material comprising a nylon layer, a polyvinylidene chloride layer and a polyethylene layer.

In an embodiment of the eighth aspect, the polymeric wall comprises a three layer $CO_2$ barrier material comprising a nylon layer, an ethylene vinyl alcohol layer, and a polyethylene layer.

In an embodiment of the eighth aspect, the polymeric wall comprises a two layer $CO_2$ barrier material comprising a nylon layer and a polyethylene layer.

In an embodiment of the eighth aspect, the polymeric wall comprises a $CO_2$ barrier material comprising an ethylene vinyl alcohol layer.

In an embodiment of the eighth aspect, the initial fill fluid consists essentially of gaseous $N_2$.

In an embodiment of the eighth aspect, the initial fill fluid consists essentially of gaseous $N_2$ and gaseous $CO_2$.

In an embodiment of the eighth aspect, the initial fill fluid consists essentially of gaseous $N_2$ and gaseous $CO_2$, and wherein the gaseous $N_2$ is excess in concentration to the gaseous $CO_2$ in the first gas.

In an embodiment of the eighth aspect, the initial fill fluid comprises $SF_6$ in one or more of liquid form, vapor form, or gaseous form.

In an embodiment of the eighth aspect, the initial fill fluid comprises gaseous $N_2$ and gaseous $SF_6$.

In an embodiment of the eighth aspect, the polymeric wall is configured to have, under conditions of an in vivo gastric environment, a permeability to $CO_2$ of more than 50 $cc/m^2$/day.

In an embodiment of the eighth aspect, the pH sensor is coupled with the catheter.

In an embodiment of the eighth aspect, the pH sensor is coupled with the intragastric device.

In a ninth aspect, an acoustic system is provided for locating an intragastric device inside the body, the system comprising: an acoustic signal generator configured to generate an acoustic signal; a swallowable acoustic marker configured to couple with the system and further configured to produce an acoustic response in an in vivo gastric environment in response to the generated acoustic signal; and a valve system configured for introducing an initial fill fluid into a volume occupying intragastric device when the intragastric device is in the in vivo gastric environment, the valve system comprising a swallowable catheter configured to releasably couple with the intragastric device.

In an embodiment of the ninth aspect, the acoustic marker is configured to couple with the swallowable catheter.

In an embodiment of the ninth aspect, the acoustic marker is configured to couple with a distal end of the swallowable catheter.

In an embodiment of the ninth aspect, the acoustic marker is configured to couple with the intragastric device.

In an embodiment of the ninth aspect, the system further comprises at least one external acoustic sensor configured to be placed outside the body and to sense the acoustic response of the acoustic marker.

In an embodiment of the ninth aspect, the system further comprises a sensor interface unit configured to electrically communicate with the acoustic marker and with the acoustic sensor.

In an embodiment of the ninth aspect, the system further comprises a system control unit configured to electrically communicate with the sensor interface unit In an embodiment of the ninth aspect, the system further comprises a computer configured to electrically communicate with the system control unit and the acoustic sensor and to display an identifier indicating the location of the acoustic marker inside the body.

In an embodiment of the ninth aspect, the computer is further configured to display a trace indicating a path traveled by the magnetic marker inside the body.

In an embodiment of the ninth aspect, the system further comprises the intragastric device, wherein the intragastric device is a balloon.

In an embodiment of the ninth aspect, the system further comprises the initial fill fluid, wherein the intragastric device comprises a polymeric wall configured to have, under conditions of the in vivo gastric environment, a permeability to $CO_2$ of more than 10 $cc/m^2/day$, such that a rate and an amount of diffusion of $CO_2$ from the in vivo gastric environment into a lumen of the intragastric device through the polymeric wall is controlled, at least in part, by a concentration of an inert gas in the initial fill fluid.

In an embodiment of the ninth aspect, the polymeric wall comprises a $CO_2$ barrier material comprising an ethylene vinyl alcohol layer.

In an embodiment of the ninth aspect, the polymeric wall comprises a two layer $CO_2$ barrier material comprising a nylon layer and a polyethylene layer.

In an embodiment of the ninth aspect, the polymeric wall comprises a three layer $CO_2$ barrier material comprising a nylon layer, a polyvinylidene chloride layer, and a polyethylene layer.

In an embodiment of the ninth aspect, the polymeric wall comprises a three layer $CO_2$ barrier material comprising a nylon layer, an ethylene vinyl alcohol layer, and a polyethylene layer.

In an embodiment of the ninth aspect, the initial fill fluid consists essentially of $N_2$.

In an embodiment of the ninth aspect, the initial fill fluid consists essentially of gaseous $N_2$ and gaseous $CO_2$.

In an embodiment of the ninth aspect, the initial fill fluid consists essentially of gaseous $N_2$ and gaseous $CO_2$, and wherein the gaseous $N_2$ is excess in concentration to the gaseous $CO_2$ in the initial fill fluid.

In an embodiment of the ninth aspect, the initial fill fluid comprises $SF_6$ in one or more of liquid form, vapor form, or gaseous form.

In an embodiment of the ninth aspect, the initial fill fluid comprises $N_2$ and $SF_6$.

In an embodiment of the ninth aspect, the polymeric wall is configured to have, under conditions of an in vivo gastric environment, a permeability to $CO_2$ of more than 50 $cc/m^2$/day.

In an embodiment of the ninth aspect, the acoustic signal is an ultrasound signal.

In a tenth aspect, a method is provided for acoustically locating an intragastric device inside the body of a patient, the method comprising: introducing into the body of the patient, via swallowing, the intragastric device comprising an uninflated gastric balloon, the intragastric device releasably coupled with a catheter and coupled with an acoustic marker, the acoustic marker configured to produce an acoustic response in response to an acoustic signal; generating an acoustic signal; and confirming a location of the uninflated gastric balloon inside the patient based on the acoustic response produced in response to the acoustic signal.

In an embodiment of the tenth aspect, the location of the uninflated gastric balloon inside the patient is the patient's stomach.

In an embodiment of the tenth aspect, the method further comprises: introducing an initial fill fluid into a lumen of the uninflated gastric balloon through the catheter, the intragastric balloon comprising a polymeric wall configured to have, under conditions of an in vivo gastric environment, a permeability to $CO_2$ of more than 10 $cc/m^2/day$; and exposing the inflated intragastric balloon to the in vivo intragastric environment for a useful life of at least 30 days, wherein a rate and an amount of diffusion of $CO_2$ from the in vivo gastric environment into the lumen of the balloon through the polymeric wall is controlled, at least in part, by a concentration of an inert gas in an initial fill fluid.

In an embodiment of the tenth aspect, the polymeric wall comprises a three layer $CO_2$ barrier material comprising a nylon layer, a polyvinylidene chloride layer and a polyethylene layer.

In an embodiment of the tenth aspect, the polymeric wall comprises a three layer $CO_2$ barrier material comprising a nylon layer, an ethylene vinyl alcohol layer, and a polyethylene layer.

In an embodiment of the tenth aspect, the polymeric wall comprises a two layer $CO_2$ barrier material comprising a nylon layer and a polyethylene layer.

In an embodiment of the tenth aspect, the polymeric wall comprises a $CO_2$ barrier material comprising an ethylene vinyl alcohol layer.

In an embodiment of the tenth aspect, the initial fill fluid consists essentially of gaseous $N_2$.

In an embodiment of the tenth aspect, the first gas consists essentially of $N_2$ and $CO_2$.

In an embodiment of the tenth aspect, the initial fill fluid consists essentially of gaseous $N_2$ and gaseous $CO_2$, and wherein the gaseous $N_2$ is excess in concentration to the gaseous $CO_2$ in the first gas.

In an embodiment of the tenth aspect, the initial fill fluid comprises $SF_6$ in one or more of liquid form, vapor form, or gaseous form.

In an embodiment of the tenth aspect, the initial fill fluid comprises gaseous $N_2$ and gaseous $SF_6$.

In an embodiment of the tenth aspect, the polymeric wall is configured to have, under conditions of an in vivo gastric environment, a permeability to $CO_2$ of more than 50 $cc/m^2$/day.

In an embodiment of the tenth aspect, confirming a location of the uninflated gastric balloon inside the patient based on sensing the acoustic response comprises displaying on a computer an identifier indicating the location of the acoustic marker.

In an embodiment of the tenth aspect, the acoustic marker is coupled with the catheter.

In an embodiment of the tenth aspect, the acoustic marker is coupled with the intragastric device.

In an embodiment of the tenth aspect, the acoustic sensor is an ultrasound sensor and the acoustic marker is an ultrasound marker.

In an eleventh aspect, a system is provided substantially as described in the specification and/or drawings.

In a twelfth aspect, a method is provided substantially as described in the specification and/or drawings.

Any of the aforementioned embodiments can be combined with other embodiments or with other aspects and associated embodiments. For example, any of the methods of the second aspect can be employed in association with the system of the first aspect, any of the methods of the fourth aspect can be employed in association with the system of the third aspect, any of the methods of the sixth aspect can be employed in association with the system of the fifth aspect, any of the methods of the eighth aspect can be employed in association with the system of the seventh aspect, or any of the methods of the tenth aspect can be employed in association with the system of the ninth aspect, etc. Similarly, any embodiment of any of the aspects can be employed in combination with one or more other embodiments of any of the aspects. Further, any or all of the embodiments may use a gas or liquid phase material as the "fluid." Thus, recitation of "gas" in any embodiment is not meant to limit it to just a gaseous material, but may also include liquid phase materials as well, as is described in further detail herein.

BRIEF DESCRIPTION OF THE DRAWINGS

FIG. 56 is a side view of an embodiment of an intragastric balloon capsule attached to a delivery/inflation catheter where the balloon has a voltaic sensor therein.

FIG. 57 is a side view of an embodiment of an intragastric balloon system having an anode and a cathode with pH coating.

FIG. 71A is a side view of a proximal end section of an embodiment of an intragastric tube showing a chemical-property indicating element thereof for pH level detection.

FIG. 71B is a cross section view of the alternate embodiment of the intragastric tube of FIG. 71A, taken along the section lines 44-44 of FIG. 71A;

FIG. 71C is a side view of the proximal end section of a further embodiment of an intragastric tube showing a chemical-property indicating medium thereof for pH level detection in a first example configuration.

FIG. 71D is a side view of the proximal end section of a further embodiment of an intragastric tube showing a chemical-property indicating medium thereof for pH level detection in a second example configuration.

FIG. 71E is a cross section view of the alternate embodiment of the intragastric tube of FIG. 71C, taken along the section lines 47-47 of FIG. 71C;

FIG. 71F is a cross section view of the alternate embodiment of the intragastric tube of FIG. 71D, taken along the section lines 48-48 of FIG. 71D;

DETAILED DESCRIPTION

Figure 1:
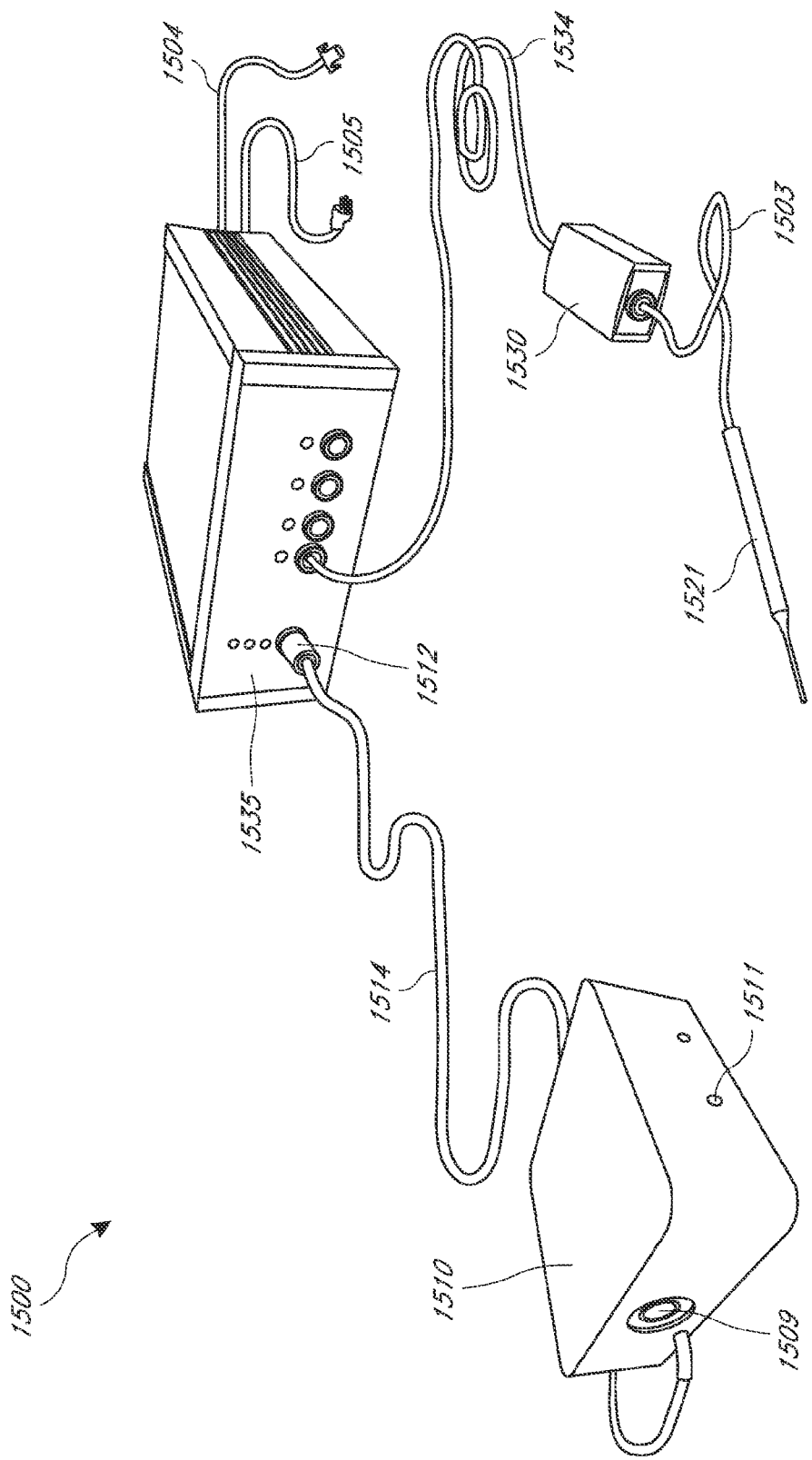
FIG. 1 depicts an embodiment of an electromagnetic tracking system for locating a sensor.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

The term "degradable" as used herein is a broad term, and is to be given its ordinary and customary meaning to a person of ordinary skill in the art (and is not to be limited to a special or customized meaning), and refers without limitation to a process by which structural integrity of the balloon is compromised (e.g., by chemical, mechanical, or other means (e.g., light, radiation, heat, etc.) such that deflation occurs. The degradation process can include erosion, dissolution, separation, digestion, disintegration, delamination, comminution, and other such processes. Degradation after a predetermined time, or within a predetermined window of time, after ingestion is particularly preferred.

The term "$CO_2$ barrier material" as used herein is a broad term, and is to be given its ordinary and customary meaning to a person of ordinary skill in the art (and is not to be limited to a special or customized meaning), and refers without limitation to a material having a permeability to $CO_2$ of 10 $cc/m^2/day$ or less under simulated in vivo conditions (100% humidity and body temperature of 37° C.). As used herein, the term "in vivo conditions" as used herein refers to both actual in vivo conditions, such as in vivo intragastric conditions, and simulated in vivo conditions. The permeability of a material to $CO_2$ may vary depending upon the conditions under which it is measured.

The term "swallowable" as used herein is a broad term, and is to be given its ordinary and customary meaning to a person of ordinary skill in the art (and is not to be limited to a special or customized meaning), and refers without limitation to ingestion of a balloon by a patient such that the outer capsule and its constituents are delivered to the stomach via normal peristalsis movement. While the systems of preferred embodiments are swallowable, they are also configured by ingestion by methods other than swallowing. The swallowability of the system is derived, at least in part, by the outer container size for the self-inflating system and the catheter and outer container size for the manual inflation system. For the self-inflating system, the outer capsule is sufficient to contain the inner container and its constituents, an amount of activation agent injected prior to administration, the balloon size, and the balloon material thickness. The system is preferably of a size less than the average normal esophagus diameter.

Described herein is a system for an orally ingestible device with magnetic, electromagnetic and/or ultrasonic locating, tracking, and/or otherwise sensing of the device or state of the device. In preferred embodiments, the device is able to traverse the alimentary canal. The device may be useful, for example, as an intragastric volume-occupying device. The device overcomes one or more of the above-described problems and shortcomings found in current intragastric volume-occupying devices. While in certain embodiments specific devices are described, it is understood that the materials and methods can also be applied to other devices.

In order to more clearly describe the subject matter of the preferred embodiments, different embodiments of the same subcomponent will be described under a single relevantly-titled subheading. This organization is not intended to limit the manner in which embodiments of different subcomponents may be combined in accordance with the present invention. The various subcomponents for use in the presently disclosed magnetic, electromagnetic and ultrasonic systems may be discussed under their respective subheaded sections or in any other section, including any section or sections discussing various tracking and visualization subcomponents.

Swallowable Intragastric Balloon System

A swallowable, self-inflating or inflatable intragastric balloon system according to selected preferred embodiments includes the following components: self-sealing valve system for addition of fluid to the lumen of the balloon or to the inner container ("valve system"), a balloon in a deflated and compacted state ("balloon") and an outer capsule, container, or coating ("outer container") that contains the balloon. For self-inflating balloons, an inner capsule or other container ("inner container") that contains one or more $CO_2$ generating components is present inside the lumen of the balloon. The system may also include various components for facilitating delivery ("delivery components") of the balloon to the mouth and/or through the esophagus.

For inflatable balloons, an inflation fluid source, a catheter, and tubing ("inflation assembly") are provided for inflating the balloon after ingestion or placement in the stomach. In the self-inflating balloon configuration, the valve is preferably attached to the inner surface of the balloon by an adhesive or other means (e.g., welding), and provided with an inoculation spacer to prevent puncture of the wall of the balloon and inner container by a needle or other means for injecting an liquid activation agent into the lumen of the balloon via the self-sealing valve. A valve providing releasable attachment of the tubing to the balloon is provided in the inflatable balloon configuration. Preferably, the self-sealing valve system attached to the balloon (e.g., on its inside surface) in the inflatable configuration is "universal" or compatible with a swallowable catheter or a physician-assisted catheter. The valve system serves to allow for balloon inflation using a miniature catheter that includes a needle assembly and also provides a mechanism for detachment of the catheter after inflation has been completed.

The outer container preferably incorporates the balloon in a compacted state (e.g., folded and rolled), preferably with sufficient space to allow for activation liquid to be injected into the balloon in the self-inflating balloon configuration, wherein the liquid activation agent initiates separation, erosion, degradation, and/or dissolution of the inner container and generation of $CO_2$ upon contact with the inflation agent contained within the inner container, which subsequently causes outer container separation, erosion, degradation, and/or dissolution due to $CO_2$ gas pressure. In the inflatable balloon configuration, the outer container need only incorporate the balloon in a compacted state.

Selected components of a swallowable intragastric balloon system of a preferred embodiment can include a silicone head with radioopacity ring, trimmed 30 D silicone septum, Nylon 6 inoculation spacer, compacted balloon, inner container (if self-inflating), and outer container as constituents of the system in unassembled form. A fully assembled outer container can include a vent hole aligned with a septum for puncture to inject liquid activation agent (if self-inflating) or a port for connection of tubing (if inflatable). As discussed further below, the components of particularly preferred systems possess the attributes described herein; however, in certain embodiments systems can be employed which utilize components having other attributes and/or values.

Devices according to the preferred embodiments are intended for ingestion by a patient and deployment without the need to resort to invasive methods. It is therefore desirable that the device of the preferred embodiments be operable to conform to a compact delivery state which can be swallowed by a patient with minimal discomfort. Once in the stomach, it is desirable for the device to assume a substantially larger deployed state. In order to achieve the transition from a delivery state to a deployed state the device is subjected to inflation.

Inner Container

In order to initiate inflation in the self-inflating configuration, the inflation subcomponent may require outside inputs such as an activation agent. The activation agent is preferably injected using a syringe having a needle with a gauge diameter of from 25 to 32. The needle length is preferably from about 0.25 inches (0.6 cm) to 1 inches (2.54 cm) in length so as to create a flow rate that allows for delivery of the full volume of inflation agent within 30 seconds, but in a manner/stream/flow that does not physically damage the inner container, thereby causing premature $CO_2$ generation and inflation. The activation agent is preferably pure water, or a solution containing up to 50% concentration of anhydrous citric acid at 20° C., or the equivalent thereof at varying solution temperatures based on solubility of anhydrous citric acid. Preferably, the system is configured to have an occupyable void space in the central lumen of the balloon when in compacted form in the outer container of from about 0.3 ml to about 4.5 ml, such that a corresponding volume of activation agent can be injected into the void space.

In one embodiment, prior to folding, the free-floating inner container with inflation agent for $CO_2$ generation is preferably vertically aligned with the self-sealing valve system such that the septum/inoculation spacer is placed directly above the tip of the capsule. The balloon contains an inner container. A self-sealing valve system is adhesively adhered to the interior of the wall of the balloon, and the inverted configuration of the balloon is provided by inversion through a hole sealed with a patch. The top approximate ¼ of the balloon wall is folded over the inner capsule, and the pleats where the capsule is are creased similar to the pleats formed in the second step of making a paper airplane, then folded over to the left or to the right. The bottom approximate ¾ of the sphere is then accordioned using no more than 2 creases and folded over the capsule. The left half is then folded over the right half of the capsule or vice versa so that the wings touch. Then the material is rolled over until it creates a tight roll. The device is then placed inside the outer container.

In a self-inflating configuration, the balloon is folded so as to form a pocket around the inner capsule, to insure that the liquid injected through the self-sealing valve system is contained in an area less than 10% of the entire balloon surface area. It is not necessary to provide a pocket in the inflatable configuration, as no inner capsule is provided. The balloon is folded such that the number of total folds is minimized so as to minimize possible damage to the outer material or compromise of barrier properties. The number of total folds is preferably less than 10 folds. The balloon material is rolled when at all possible such that the number of creases required to fit the balloon in an outer container is minimized. This is done in effort to also to prevent lumen material damage. The self-sealing valve is also preferably constructed off-center of the balloon so as to minimize the number of folds that layer on top of each other.

In the self-inflating configuration, the material forming the wall of the balloon is processed and folded to maximize reaction efficiency by localizing the initiation agent injected into the balloon so that it is maintained proximal to the reactants within the inner container. The balloon is folded such that once the reaction initiates and the outer container separates, the balloon unfolds in a manner that creates the largest possible surface area, which prohibits the balloon from readily passing through the pyloric sphincter. The ratio of reactants in the inflation agent and activation agent are selected such that the pH of any remnant liquid inside the lumen of the balloon is acidic, with a pH of less than 6, such that any balloon leakage or breach that allows stomach acid to enter does not cause additional $CO_2$ generation and resulting unintentional re-inflation.

In a self-inflating configuration, an inflation agent is compressed, formed or otherwise held in a shape which provides good surface area availability for the reactants for $CO_2$ generation, while minimizing the space and/or volume sufficient to hold the inner container. Preferably, the inner container has a length (longest dimension) of from about 0.748 inches (1.9 cm) to 1.06 inches (2.7 cm) and a diameter or width of from about 0.239 inches (0.6 cm) to about 0.376 inches (1 cm). The volume of the inner container is preferably from about 0.41 ml to about 1.37 ml. The inner container is preferably in the form of a standard push-fit gelatin capsule but a gelatin tape may be used in lieu of a push-fit capsule. The container is preferably relied upon for containing the inflation agent; however, additional sealing or other encapsulation can be employed to control timing of inflation. Gelatin is particularly preferred for use as the inner container; however other materials can also be suitable for use, e.g., cellulose. In order to minimize the internal volume of the system, it is generally preferred to include only a single inner container; however, in certain embodiments two or more internal containers can advantageously be employed. Timing of self-inflation is selected based on a normal esophageal transit time and a normal time of gastric emptying of large food particles, such that the balloon does not inflate to a size that can block the esophageal passageway or prematurely pass through the pyloric sphincter. Timing is also controlled by compacting the balloon such that the activation agent is substantially localized in the balloon next to the inner capsule, creating an efficient $CO_2$ self-inflation method. Balloon inflation is initiated by the liquid activation agent causing degradation of the inner container, such that the inflation agent in the inner container contacts the liquid activation agent, thereby initiating the gas generation reaction.

The inner container for the self-inflating balloon is contained within the lumen of the balloon and contains the $CO_2$ generator for balloon self-inflation. The $CO_2$ generator comprises an inflation agent mixture housed within the container. Preferably, from about 10% to about 80% of the total inflation agent used comprises powdered citric acid, with the remainder comprising powdered sodium bicarbonate. Sufficient inflation agent is provided such that upon completion of the $CO_2$ generating reaction, the balloon achieves inflation at the nominal inflation pressure described above. Preferably, a total of from about 0.28 to 4 grams inflation agent mixture is employed, depending upon the balloon size to be inflated; preferably up to 1.15 grams of sodium bicarbonate is used with the remainder being powdered citric acid to generate 300 cm$^3$ of $CO_2$ at nominal pressure.

Outer Container

The balloon is preferably provided in a deflated and folded state in a capsule or other retaining, containing or coating structure ("outer container"). The outer container is preferably in the form of a standard push-fit gelatin capsule, with the push-fit relied upon for containing the deflated/folded balloon; however, a gelatin wrap can advantageously be employed in certain embodiments. Gelatin is particularly preferred for use as the outer container; however other materials can also be suitable for use, e.g., cellulose, collagen, and the like. Preferably, the outer container has a length (longest dimension) of from about 0.95 inches (2.4 cm) to 2.5 inches (6.3 cm) and a diameter or width of from about 0.35 inches (0.9 cm) to about 0.9 inches (2.4 cm). The volume of the inner container is preferably from about 1.2 ml to about 8.25 ml. In the self-inflating configuration, the outer container is preferably configured with one or more holes, slits, passageways or other egresses, preferably on each end, which act as vents such that any gas created due to inflation agent exposure to condensation or other ambient moisture present during processing does not cause premature separation or degradation of the inner container prior to 30 seconds after inoculation of the liquid activation agent, which may have an undesirable effect on reaction efficiency. Such egresses can also expedite dissolution of the outer container to prepare the balloon for inflation in the inflatable configuration. The process of the outer capsule degrading (e.g., separates, dissolves, or otherwise opens) is expedited by pressure build up caused by inflation (self-inflation or inflation via catheter) of the balloon. The outer capsule can be dipped in water for a brief time to soften the materials but not release the balloon prior to swallowing to minimize the time lapse between swallowing and balloon inflation. In the inflatable configuration, the outer container is provided with a hole to house the inflation tube needle assembly, wherein the diameter of the catheter needle housing is mechanically compatible with the diameter of the outer container hole such that the needle can be inserted into the self-sealing valve while maintaining therein the housed balloon to facilitate pushing or swallowing of the balloon assembly. In a preferred embodiment, the outer container is a capsule. The distal half of the capsule may be flared to prevent abrasion of the balloon materials by the leading edge of the capsule as the compacted balloon is inserted into the capsule. The capsule can also comprise two parts held together with a gel band and encompassing the folded balloon that allows for quicker separation of the capsule so that inflation can take place more expeditiously. The outer capsule degrades (e.g., separates, dissolves, or otherwise opens) due to contact with ingested fluid ingestion (e.g., water intake) and preferably degrades within 5 minutes or less, more preferably within 2 minutes or less, so as not to cause discomfort to the patient while the balloon/catheter tube is in place.

In a preferred embodiment, the device is fitted into a standard sized gelatin capsule. The capsule may be formed of a material that has a known rate of degradation such that the device will not be released from the capsule or otherwise deployed prior to entry into the stomach. For example, the capsule materials may include one or more polysaccharide and/or one or more polyhydric alcohols.

Alternatively, the device, in its delivery state, may be coated in a substance that confines the device in its delivery state while also facilitating swallowing. The coating may be applied by a dipping, sputtering, vapor deposition, or spraying process which may be conducted at an ambient or positive pressure.

In certain preferred embodiments, the encapsulated or coated device is lubricated or otherwise treated so as to facilitate swallowing. For example, the encapsulated or coated device may be wetted, heated, or cooled, prior to swallowing by the patient. Alternatively, the encapsulated or coated device may be dipped in a viscous substance that will serve to lubricate the device's passage through the esophagus. Examples of possible coatings can be any substances with lubricious and/or hydrophilic properties and include glycerine, polyvinylpyrrolidone (PVP), petroleum jelly, aloe vera, silicon-based materials (e.g. Dow 360) and tetrafluoroethylene (TFE). The coating may also be applied by a sputtering, vapor deposition or spraying process.

In additional embodiments the coating or capsule is impregnated or treated with one or more local anesthetics or analgesics to ease swallowing. Such anesthetics may include anesthetics in the amino amide group, such as articaine, lidocaine and trimecaine, and anesthetics in the amino ester group, such as benzocaine, procaine and tetracaine. Such analgesics may include chloraseptic.

In certain embodiments, the capsule may be weighted at a certain end in order for it to be oriented appropriately when it is administered, as it travels down the esophagus, and/or when it is in the stomach. The weighting components may include polymer materials or inflation reactants.

The swallowable, self-inflating intragastric balloon is provided with mechanisms to reliably control timing of self-inflation such that premature inflation while in the esophagus during swallowing is avoided and sufficient inflation once in the stomach so as to prevent passage through the pyloric sphincter is ensured. Normal esophageal transit time for large food particles has been documented as 4-8 seconds, and gastric emptying of large food particles through the pylorus does not occur for at least 15-20 minutes. The outer container is preferably configured to separate, dissolve, degrade, erode, and/or otherwise allow the deflated/folded balloon to begin unfolding not less than 60 seconds but not more than 15 minutes after inoculation with liquid activation agent. The inner container is preferably configured chemically, mechanically or a combination thereof to retard the initial $CO_2$ generating chemical reaction such that sufficient $CO_2$ to begin inflating the balloon is not available earlier than 30 seconds after inoculation with the liquid activation agent, but to permit generation of sufficient $CO_2$ such that at least 10% of the occupyable volume of the balloon is filled within 30 minutes, at least 60% of the occupyable volume of the balloon is filled within 12 hours, and at least 90% of the occupyable volume of the balloon is filled within 24 hours. This timing allows for injection of the activation agent into the outer container by the medical professional, passing the device to the patient, and swallowing by normal peristaltic means by the patient. This timing also prohibits potential passing of an uninflated balloon into the duodenum by the balloon being inflated to a sufficient size such that gastric emptying of the balloon cannot be easy, as objects more than 7 mm in diameter do not readily pass.

Delivery Components

It certain embodiments, it may advantageous for an administrator of the device to use a delivery tool for delivering the device to the mouth or facilitating its passage through the esophagus in the optimal orientation. A delivery tool may enable the device administrator to inject the device with one or more inflation agents or inflation gases as part of administering the device to the patient. In a preferred embodiment, such injection may be accomplished in the same mechanical action(s) of the administrator that are employed to release the device from the delivery tool into the mouth or esophagus. For example, the delivery tool may include a plunger, a reservoir containing a fluid, and an injection needle. The administrator pushes the plunger which, either in sequence or approximately simultaneously, forces the injection needle into the device and thereby injects the liquid contained in reservoir into the device. Subsequent application of force to the plunger pushes the device out of the delivery tool and into the desired location within the patient. Furthermore, the delivery tool may also include a subcomponent that administers an anesthetic or lubricant into the patient's mouth or esophagus to ease the swallowability of the device.

Balloon

The volume-occupying subcomponent ("balloon") of the preferred embodiments is generally formed of a flexible material forming a wall which defines an exterior surface and an interior cavity. Various of the above-described subcomponents may be either incorporated into the wall or interior cavity of the volume-occupying subcomponent. The volume-occupying subcomponent can vary in size and shape according to the patient's internal dimensions and the desired outcome. The volume-occupying subcomponent may be engineered to be semi-compliant, allowing the volume-occupying subcomponent to stretch or expand with increases in pressure and/or temperature. Alternatively, in some embodiments, a compliant wall offering little resistance to increases in volume may be desirable.

Spherical volume-occupying subcomponents are preferred in certain embodiments. Alternatively, the volume-occupying subcomponent may be constructed to be donut-shaped, with a hole in the middle of it, and may be weighted and shaped in such a way that it orients in the stomach to cover all or part of the pyloric sphincter, similar to a check valve. The hole in the middle of the volume-occupying subcomponent can then serve as the primary passage for the contents of the stomach to enter the small intestine, limiting the passage of food out of the stomach and inducing satiety by reducing gastric emptying. Volume-occupying subcomponents may be manufactured with different-sized donut-holes according to the degree that gastric emptying is desired to be reduced. Delivery, inflation and deflation of the volume-occupying subcomponent may be accomplished by any of the methods described above.

It is advantageous for the volume-occupying subcomponent wall to be both high in strength and thin, so as to minimize the compacted volume of the device as it travels the esophagus of the patient. In certain embodiments, the volume-occupying subcomponent wall materials are manufactured with a biaxial orientation that imparts a high modulus value to the volume-occupying subcomponent.

In one embodiment, the volume-occupying subcomponent is constructed of a polymeric substance such as polyurethane, polyethylene terephthalate, polyethylene naphthalate, polyvinyl chloride (PVC), Nylon 6, Nylon 12, or polyether block amide (PEBA). The volume-occupying subcomponent may be coated with one or more layers of substances that modify (increase, reduce, or change over time) gas-barrier characteristics, such as a thermoplastic substance.

Preferably, the gas-barrier materials have a low permeability to carbon dioxide or other fluids that may be used to inflate the volume-occupying subcomponent. The barrier layers should have good adherence to the base material. Preferred barrier coating materials include biocompatible poly(hydroxyamino ethers), polyethylene naphthalate, polyvinylidene chloride (PVDC), saran, ethylene vinyl alcohol copolymers, polyvinyl acetate, silicon oxide (SiOx), acrylonitrile copolymers or copolymers of terephthalic acid and isophthalic acid with ethylene glycol and at least one diol. Alternative gas-barrier materials may include polyamine-polyepoxides. These materials are commonly acquired as a solvent or aqueous based thermosetting composition and are generally spray-coated onto a preform and then heat-cured to form the finished barrier coating. Alternative gas-barrier materials which may be applied as coatings to the volume-occupying subcomponent include metals such as silver or aluminum. Other materials that may be used to improve the gas impermeability of the volume-occupying subcomponent include, but are not limited to, gold or any noble metal, PET coated with saran, conformal coatings and the like, as listed, for example, in Tables 1a-b.

In certain preferred embodiments, the volume-occupying subcomponent is injection, blow or rotational molded. Either immediately following such molding, or after a period of curing, the gas-barrier coating may be applied if not already applied within the composite wall.

In another embodiment, the intragastric volume-occupying subcomponent is formed using a Mylar polyester film coating silver, aluminum or kelvalite as a metalized surface, to improve the gas impermeability of the volume-occupying subcomponent.

In the event that the volume-occupying subcomponent's wall is composed of multiple layers of materials, it may be necessary to use certain substances or methods to connect, attach or hold together such multiple layers. Such substances can include a solvent or an ether-based adhesive. Such multiple layers may also be heat-bonded together. Once such layers are attached together to form (for example) a sheet of material to be made into a volume-occupying subcomponent, it may also be necessary to apply additional treatment steps to such material to allow it to seal together (for example, by application of a certain degree of heat and pressure) in order to be made into a volume-occupying subcomponent. Accordingly, it may be advantageous to include as an additional layer in the volume-occupying subcomponent certain materials that seal. For example, a volume-occupying subcomponent comprised of a combination of PET and SiOx layers, which impart favorable mechanical and gas impermeability characteristics to the volume-occupying subcomponent, may be sealed by including a layer of sealable polyethylene in such volume-occupying subcomponent.

According to another embodiment of the preferred embodiments, the functionality of the volume-occupying subcomponent and the deflation component is combined either in part or in whole. For example, the volume-occupying subcomponent may be formed of a substance that is degraded within the stomach over a desired period of time. Once the degradation process has formed a breach in the wall of the volume-occupying subcomponent, the volume-occupying subcomponent deflates, continues to degrade and passes through the remainder of the digestive tract.

Preferably, an automated process is employed that takes a fully constructed volume-occupying subcomponent, evacuates all of the air within the interior cavity and folds or compresses the volume-occupying subcomponent into the desired delivery state. For example, the evacuation of air from the volume-occupying subcomponent may be actuated by vacuum or mechanical pressure (e.g. rolling the volume-occupying subcomponent). In certain embodiments, it is desirable to minimize the number of creases produced in the volume-occupying subcomponent when in the delivery state.

Deflation and/or inflation of the volume-occupying subcomponent may be achieved through one or more injection sites within the wall of the volume-occupying subcomponent. For example, two self-sealing injection sites can be incorporated at opposite sides of the volume-occupying subcomponent. The volume-occupying subcomponent may be positioned within a fixture that employs two small-gauge needles to evacuate the air from the volume-occupying subcomponent.

In one embodiment, the self-sealing injection sites may further be used to insert chemical elements of the inflation subcomponent into the interior of the volume-occupying subcomponent. After injection of the chemical elements into the volume-occupying subcomponent, the same needles may be used to perform evacuation of the volume-occupying subcomponent.

It may be desirable that the volume-occupying subcomponent is packed into the delivery state under, for example, a negative vacuum pressure or under a positive external pressure.

The volume-occupying subcomponent wall materials may also be engineered to, once they are initially punctured or torn, tear relatively easily from the point of such puncture or tear. Such properties can, for example, be advantageous if deflation of the volume-occupying subcomponent were initiated by a tearing or puncturing of the volume-occupying subcomponent wall, since such initial tear or puncture may then increase in scope, hastening and/or maximizing the deflation process.

The volume-occupying subcomponent may also be coated by a lubricious substance that facilitates its passage out of the body following its deflation. Examples of possible coatings can be any substances with lubricious and/or hydrophilic properties and include glycerine, polyvinylpyrrolidone (PVP), petroleum jelly, aloe vera, silicon-based materials (e.g. Dow 360) and tetrafluoroethylene (TFE). The coating may be applied by a dipping, sputtering, vapor deposition or spraying process which may be conducted at an ambient or positive pressure.

The balloon composite wall materials can be of similar construction and composition as those described in U.S. Patent Publication No. 2010-0100116-A1, the contents of which is hereby incorporated by reference in its entirety. The materials are able to contain a fluid, preferably in compressed or non-compressed gas form, such as, e.g., $N_2$, Ar, $O_2$, $CO_2$, or mixture(s) thereof, or atmospheric air (composed of a mixture of $N_2$, $O_2$, Ar, $CO_2$, Ne, $CH_4$, He, Kr, $H_2$, and Xe) that simulate gastric space concentrations. In certain embodiments, the balloon is able to hold the fluid (gas) and maintain an acceptable volume for up to 6 months, preferably for at least 1 to 3 months after inflation. Particularly preferred fill gases include non-polar, large molecule gases that can be compressed for delivery.

Prior to placement in the outer container, the balloon is deflated and folded. In the inverted configuration in a deflated state, the balloon is flat, with the inverted seam extending around the perimeter of the balloon. The self-sealing valve system is affixed to the inner wall of the lumen close to the center of the deflated balloon, with the inner container positioned adjacent to the self-sealing valve system. The walls of the balloon are then folded. As part of the balloon design, the self-sealing valve system is manufactured in a manner such that it is placed "off center" to minimize the number of folds upon themselves (e.g., doubling or tripling up) required to fit the balloon in the outer container. For example, the self-sealing valve system can advantageously be placed ½r±¼ r from the center of the balloon, wherein r is the radius of the balloon along a line extending from the center of the balloon through the septum.

In a preferred embodiment, a self-inflating balloon is fully sealed 360 degrees around. In the self-inflating configuration, with injection of an inflation agent by needle syringe, there are preferably no external openings or orifices to the central lumen. In the inflatable configuration, a valve structure (either protruding, recessed, or flush with the surface of the balloon) is provided for providing an inflation fluid to the central lumen. The balloon can have a "noninverted," "inverted," or "overlapped" configuration. In a "noninverted" configuration, the seams or welds and seam allowance, if any, are on the outside of the inflated balloon. In an "overlapped" configuration, layers are overlapped, optionally with one or more folds, and secured to each other via welds, a seam, adhesive, or the like, resulting in a smooth external surface. In an "inverted" configuration, the balloon has a smooth external surface with seams, welds, adhesive bead, or the like inside the inflated balloon. In order to create a balloon with an inverted configuration, e.g., a balloon with no external seam allowance (no wall material between the edge of the balloon and the weld, seam, or other feature joining the sides together), two balloon halves are joined together in some fashion (e.g., adhered using adhesive or heat or the like based on the balloon material used). One of the balloon halves encompasses an opening to allow for the balloon to be pulled through itself after adherence of the two halves and to have the seams of the balloon on the inside. The opening created is preferably circular but can be any similar shape, and the diameter of the opening preferably does not exceed 3.8 cm; however, in certain embodiments a larger diameter may be acceptable. A patch of material is adhered (adhesively, heat welded, or the like, based on the material used) to cover the original balloon-half opening. The inversion hole thus created that is subsequently patched is small enough that the forces exerted during inflation do not compromise the material used to maintain fluid in the balloon.

The preferred shape for the inflated balloon in final assembly is ellipsoid, preferably spheroid or oblate spheroid, with nominal radii of from 1 inch (2.5 cm) to 3 inches (7.6 cm), a nominal height of from 0.25 inches (0.6 cm) to 3 inches (7.6 cm), a volume of from 90 $cm^3$ to 350 $cm^3$ (at 37° C. and at internal nominal pressure and/or full inflation), an internal nominal pressure (at 37° C.) of 0 psi (0 Pa) to 15 psi (103421 Pa), and a weight of less than 15 g. The self-inflating balloon is configured for self-inflation with $CO_2$ and is configured to retain more than 75% of the original nominal volume for at least 25 days, preferably for at least 90 days when residing in the stomach. The inflatable balloon is configured for inflation with an appropriate mixture of gases so as to deliver a preselected volume profile over a preselected time period (including one or more of volume increase periods, volume decrease periods, or steady state volume periods).

In certain embodiments wherein a stable volume over the useful life of the device is preferred, the balloon is configured to maintain a volume of at least 90% to 110% of its original nominal volume. In other embodiments, it can be desirable for the balloon to increase and/or decrease in volume over its useful life (e.g., in a linear fashion, in a stepwise fashion, or in another non-linear fashion). In other embodiments, the balloon maintains a volume of 75% to 125% of its original nominal volume, or 75% to 150%

The intragastric device can be a single free-floating or tethered device. In some embodiments, it can be desirable to provide multiple devices (2, 3, 4, 5, 6, or more), either free-floating or tethered to each other, e.g., in a similar configuration to a cluster of grapes. The individual devices can be simultaneously inflated with one inflation system connected to all of the devices, or each device can be provided with a separate inflation system.

Valve System

In preferred embodiments, a self-sealing valve system which contains a self-sealing septum housed within a metallic concentric cylinder is provided. In the inflatable configuration, the self-sealing valve system is preferably adhered to the underside of the balloon material such that only a portion of the valve protrudes slightly outside of the balloon surface to ensure a smooth surface. The valve system for the inflatable configuration can utilize the same self-sealing septum designed for the self-inflating configuration. The septum preferably consists of a material possessing a durometer of 20 Shore A to 60 Shore D. The septum is inserted or otherwise fabricated into the smaller cylinder of the concentric metallic retaining structure that is preferably cylindrical in shape. The smaller cylinder within the larger cylinder controls alignment of the catheter needle sleeve/needle assembly with the septum, provides a hard barrier so that the catheter needle does not pierce the balloon material (needle stop mechanism), and provides compression such that the valve/septum re-seals after inflation and subsequent needle withdrawal.

The concentric valve system can also provide radio opacity during implantation and is preferably titanium, gold, stainless steel, MP35N (nonmagnetic, nickel-cobalt-chromium-molybdenum alloy) or the like. Non-metallic polymeric materials can also be used, e.g., an acrylic, epoxy, polycarbonate, nylon, polyethylene, PEEK, ABS, or PVC or any thermoplastic elastomer or thermoplastic polyurethane that is fabricated to be visible under x-ray (e.g., embedded with barium).

The septum is preferably cone shaped, so that the compressive forces are maximized for self-sealing after inflation. The self-sealing septum allows air to be evacuated from the balloon for processing/compacting and insertion into the outer container, and allows for piercing by an inflation agent syringe needle (self-inflating configuration) or inflation catheter needle (inflatable configuration), and then subsequent withdrawal of the inflation agent syringe needle or detachment of the inflation catheter and withdrawal of the catheter needle significantly limiting gas leakage outside of the balloon during the inflation process and needle withdrawal/catheter detachment. The septum is inserted into the valve using a mechanical fit mechanism to provide compression. An additional ring can be placed at the distal end of the inner cylinder to provide additional compression to ensure the septum material is dense enough to re-seal itself. The ring is preferably metallic in nature, but can also be a non-metallic polymeric material such as an acrylic, epoxy, or thermoplastic elastomer or thermoplastic polyurethane. The ring material is preferably the same material as the cylinder, titanium, but can also be gold, stainless steel, MP35N or the like.

In the inflatable configuration, a larger, outer cylinder of the concentric valve housing contains a slightly harder durometer material than the inner cylinder (50 Shore A or greater), but is also preferably silicone. The purpose of using a harder durometer material is to ensure sealing when connected to the needle sleeve for inflation. The silicone located in the outer ring of the concentric valve is adhered to the balloon from the inside surface. The entire outer cylinder is filled and a small circular lip of this same material is provided that is slightly larger than the diameter of the inner cylinder and extends to the outside surface of the balloon. The lip is compatible with the bell shaped needle sleeve and provides sealing to enhance connection of the valve to the catheter to withstand the inflation pressures applied and also increases the tensile force of the catheter. This silicone lip preferably does not protrude past the balloon surface more than 2 mm to ensure that the balloon surface remains relatively smooth and does not cause abrasion or ulcerations of the mucosa. It is designed to provide compressive forces against the needle sleeve of the catheter for inflation and detachment whereby when connected to the needle sleeve of the inflation catheters, the connection force during the inflation process can withstand up to 35 PSI. The seal is then broken during detachment using hydrostatic pressure that is more than 40 PSI less than 200 PSI to break the connection force. Two additional retaining rings, preferably made of the same material as concentric valve, are included in the valve system to further enhance the seal between the metal and the valve silicone and provide additional mechanical support to ensure proper mechanical fit and are intended to disrupt slippage of the silicone material from the hard (metallic) valve system (causing an increase in tensile force).

The valve structure for the inflatable configuration uses a mechanical fit mechanism to provide the functions of the self-sealable valve for inflation by the catheter and subsequent catheter detachment; however, primer and/or adhesive may be used to provide additional support in maintaining the assembly. The configuration can be modified by modifying the surfaces of the metal components, making them more sticky or slippery to provide the desired mechanical/interference fit. The interference fit between the valve and the catheter can be modified to change the pressure requirements for inflation and/or detachment. Additional assemblies can include overmolding the metallic portions or the concentric system in silicone such that additional support rings to ensure the mechanical fit and the tensile strength and forces required to sustain the assembly during catheter inflation and detachment can be omitted.

The total valve diameter in the inflatable configuration is designed to fit a miniature catheter system that does not exceed 8 French (2.7 mm, 0.105 inches) in diameter. The total diameter does not exceed 1 inch (2.54 cm) and is preferably less than 0.5 inches (1.27 cm), to facilitate swallowing. Additional valves can be added, if desired; however, it is generally preferred to employ a single valve so as to maintain the volume of the deflated/folded balloon (and thus the outer container dimensions) as small as possible. The valve system is preferably attached to the inner surface of the balloon such that a shear force greater than 9 lbs (40 N) is required to dislodge the valve system.

In a self-inflating configuration, the valve system can be attached to the balloon (e.g., on its inside surface) without the use of an opening, orifice, or other conduit in the wall of the balloon. The valve system can utilize a septum with a durometer of 20 Shore A to 60 Shore D. The valve can be inserted or otherwise fabricated into a retaining structure that has a higher durometer, e.g., 40 Shore D to 70 Shore D or more. The retaining structure can be fabricated from a silicone, rubber, soft plastic or any suitable non-metallic polymeric material such as an acrylic, an epoxy, a thermoplastic elastomer, or thermoplastic polyurethane. Preferably, a structure, such as a ring, that can be metallic or non-metallic but radioopaque (e.g., barium) and visible under X-ray, or magnetic or magnetizable and detectable by sensing of a magnetic field, can be embedded in the retaining structure. Using a mechanical fit mechanism of two structures of different durometers, one softer (septum) with a large diameter, can be inserted into a snug, more rigid durometer structure creates compressive forces in the once open orifice to enable $CO_2$ retention and reduce susceptibility for $CO_2$ gas leaks. The metallic ring for radio-opacity also helps to create compressive forces on the septum. The self-sealing septum allows air to be evacuated from the balloon for processing/compacting and inserting in the outer container, and also allows for the inflation agent to be injected into the outer container for inflation initiation. Additional septums can be provided, if desired; however, it is generally preferred to employ a single septum so as to maintain the volume of the deflated/folded balloon (and thus the outer capsule) as small as possible. The valve system is preferably attached to the inner surface of the balloon such that a shear force greater than 9 lbs (40 N) is required to dislodge the valve system. A silicone head and opacity ring of a self-sealing valve system can be employed, as can a wedge-shaped septum.

In the self-inflating configuration, an inoculation spacer is preferably incorporated to guide a needle into the self-sealing valve for injection of liquid activation agent into the lumen of the balloon and to prevent the needle from penetrating the wall of the deflated/folded balloon elsewhere such that pressure within the lumen of the balloon cannot be maintained. The inoculation spacer also facilitates preventing liquid activation agent from penetrating the inner container or the folded balloon material, thereby focusing the activation agent in an appropriate manner to properly mix the reactants for $CO_2$ generation according to the criteria described above. The inoculation spacer is generally in the form of a tube or cylinder. The inoculation spacer is preferably attached to the inner container and/or the self-sealing valve system with an adhesive or other fixing means; however, in certain embodiments the inoculation spacer can be "free-floating" and maintained in position by the folding or rolling of the walls of the balloon. The inoculation spacer can comprise any suitable material that can be passed after separation, erosion, degradation, digestion, and/or dissolution of the outer container; however, preferable materials include non-metallic materials with a minimum Shore D durometer of 40 or more, any metallic material, or a combination thereof. A cupped needle stop (inoculation spacer) can be employed in preferred embodiments.

Inflation Assembly

In certain preferred embodiments, the volume-occupying subcomponent is filled with a fluid using tubing which is subsequently detached and pulled away from the volume-occupying subcomponent. One end of the volume-occupying subcomponent has a port connected to tubing of sufficient length that when unwound can span the entire length of the esophagus, from mouth to stomach. This tubing is connected to the volume-occupying subcomponent with a self-sealable valve or septum that can tear away from the volume-occupying subcomponent and self-seal once the volume-occupying subcomponent is inflated. A physician or other health care professional secures one end of the tubing as the patient swallows the device. Once the device is residing within the stomach, the physician uses the tube to transmit a fluid, such as air, nitrogen, $SF_6$, other gas(es), vapors, saline solution, pure water, a liquid or vapor under external ambient conditions (e.g., room temperature) that forms a vapor or gas, respectively, at in vivo temperatures (e.g., $SF_6$), or the like, into the volume-occupying subcomponent and thereby inflate it. The fluid may be or include a variety of other fluid or non-fluid materials as well, including physiologically acceptable fluids, such as aqueous fluids, e.g., water, water with one or more additives (e.g., electrolytes, nutrients, flavorants, colorants, sodium chloride, glucose, etc.), saline solution, or the like. After the volume-occupying subcomponent is fully inflated, the tubing is released and can be pulled out from inside the patient.

The tube may be released in a number of manners. For example, the tubing may be detached by applying a gentle force, or tug, on the tubing. Alternatively, the tubing may be detached by actuating a remote release, such as a magnetic or electronic release. Additionally, the tubing may be released from the volume-occupying subcomponent by an automatic ejection mechanism. Such an ejection mechanism may be actuated by the internal pressure of the inflated volume-occupying subcomponent. For example, the ejection mechanism may be sensitive to a specific pressure beyond which it will open so as to release any excess pressure and simultaneously release the tube. This embodiment provides a desirable feature through combining release of the tubing with a safety valve that serves to avert accidental over inflation of the volume-occupying subcomponent in the patient's stomach.

This automatic release embodiment also provides the benefit that the device inflation step may be more closely monitored and controlled. Current technology allows for a self-inflating intragastric volume-occupying subcomponent which generally begins to inflate in a four minute timeframe after injection with an activation agent such as citric acid. In this approach, the volume-occupying subcomponent may, in some instances, begin to inflate prior to residing within the stomach (e.g., in the esophagus), or, in patients with gastric dumping syndrome or rapid gastric emptying, the volume-occupying subcomponent may end up in the small intestine prior to the time that inflation occurs. Accordingly, in certain embodiments it can be desirable to inflate the volume-occupying subcomponent on command, once it is ascertained that the volume-occupying subcomponent is residing in the correct location.

In certain embodiments, it may also be advantageous for the volume-occupying subcomponent to inflate gradually or in several steps over time, or for the volume-occupying subcomponent to maintain a volume and/or internal pressure within a preselected range. For example, if gas escapes the volume-occupying subcomponent prior to the desired deflation time, it can be beneficial for the device to re-inflate in order to preserve it in its expanded state.

An intragastric balloon system that is manually inflated by a miniature catheter can be employed in certain embodiments. The system preferably remains "swallowable." The balloon for delivery is in a compacted state and is attached to a flexible, miniature catheter, preferably no larger than 4 French (1.35 mm) in diameter. The catheter is designed such that a portion of the catheter can be bundled or wrapped upon itself for delivery with the encapsulated balloon, allowing the patient to swallow both catheter and balloon for delivery to the stomach. The balloon can contain a self-sealable valve system for attachment of the catheter and inflation of the balloon once it reaches the stomach cavity. The proximal end of the catheter can be left just outside of the patient's mouth, permitting connection to an inflation fluid container that can house the preferred inflation fluid (gas or liquid). After inflation the catheter can be detached from the balloon valve and pulled back through the mouth. This method allows for the intragastric balloon to maintain its swallowability but allow for inflation by a fluid source or a mixture of fluid sources via the catheter. Alternatively, a more rigid, pushable system can be employed wherein the balloon valve is compatible with either the swallowable, flexible catheter or the pushable, rigid catheter assembly.

The inflation catheters (swallowable or administrator-assisted pushable) described herein are configured to deliver the balloon device orally and without any additional tools. The administration procedure does not require conscious sedation or other similar sedation procedures or require endoscopy tools for delivery. However, other versions of the device can be used in conjunction with endoscopy tools for visualization or can be adapted such that the balloon device can be delivered nasogastrically as well.

In operation, the proximal end of the inflation catheter is connected to a valve or connector that allows for connection to the inflation source or the disconnect source, this is preferably a Y-arm connector or inflation valve. The connector materials may consist of polycarbonate or the like and can connect to a single or multi-lumen catheter tube. The distal end of the inflation catheter is connected to the universal balloon valve of the balloon that has been compacted and housed within a gelatin capsule or compacted using gelatin bands. The catheter tube is preferably from 1 French (0.33 mm) to 6 French (2 mm) in diameter. The catheter is preferably long enough to extend out past the mouth (connected to the inflation connector or valve) and transverse the esophagus down to at least the middle of the stomach—approximately 50-60 cm. Measurement ticks can be added to the tubing or catheter to aid in identifying where the end of the tube is located. Timing for inflation can be initiated by having the tube contain a pH sensor that determines a location difference between the esophagus (pH 5-7) and the stomach (pH 1-4) based on the different pH between the two anatomical sources, or can be derived or verified from the expected pressure in a contained (i.e., esophagus) versus a less-constrained space (i.e., stomach). The tube can also contain nitinol that has a tunable transmission to the body temperature, taking into account the timing for swallowing. The tube can also be connected to a series of encapsulated or compacted balloons on a single catheter. Each can be inflated and released separately. The number of balloons released can be tune-able to the patient's needs and desired weight loss. In certain embodiments, the intragastric balloon or catheter is located or tracked in the body by sensing a magnetic field of a magnetizable component of both or either devices, as discussed in detail below.

In certain embodiments, a catheter with the balloon at the distal end (inflated with air) is employed to temporarily and firmly hold the balloon in place. A small deflated balloon catheter can be positioned through the head of the gastric balloon (e.g., a "balloon within the balloon"), and then inflated with air during delivery to firmly hold the capsule and balloon in place and prevent spontaneous detachment of balloon from the catheter. This balloon catheter can incorporate a dual channel that can also allow the bigger gastric balloon to be inflated (by gas or liquid). Once the gastric balloon has been satisfactorily inflated, the small air balloon catheter can be deflated and pulled out of the valve (allowing the valve to self seal), and out of the body, leaving the inflated gastric balloon in the stomach.

In other embodiments, the catheter may be coated to enhance swallowability or is impregnated or treated with one or more local anesthetics or analgesics to ease swallowing. Such anesthetics may include anesthetics in the amino amide group, such as articaine, lidocaine and trimecaine, and anesthetics in the amino ester group, such as benzocaine, procaine and tetracaine. Such analgesics may include chloraseptic.

Dual Lumen Catheter

In a preferred embodiment, a swallowable dual lumen catheter is provided. The dual lumen catheter has two lumens with a diameter of the complete assembly no larger than 5 French (1.67 mm), preferably no larger than 4 French (1.35 mm). The inner lumen preferably does not exceed 3 French (1 mm) and functions as the inflation tube, and the outer lumen preferably does not exceed 5 French (1.67 mm) and functions as the disconnection tube; the inner and outer lumen do not exceed 2 French (0.66 mm) and 4 French (1.35 mm), in diameter, respectively. The catheter assembly is connected to a needle assembly, described in more detail below, at the distal end and to a dual port inflation connector at the proximal end. The tubing that the catheter assembly employs is flexible for swallowability, is kink resistant, can withstand body temperature, is resistant to acid, and is biocompatible as the tube transverses the alimentary canal into the stomach cavity. The tube materials are preferably soft and flexible and have moderate tensile strength and a significant amount of hoop strength to handle applied pressures. The lumens are preferably round and co-axial and free-floating so as to provide flexibility. The dual lumen assembly also preferably requires no adhesive or glue. Alternative lumen configurations can include two D-lumens or a combination of a D-lumen and round lumen, and can be used in stiffer configurations of the final catheter assembly. Preferred materials for the tubing include a thermo-resistant polyethylene tubing such as PEBAX® or a thermo-resistant polyurethane tubing such as PELLETHANE™, PEEK or Nylon. The tubing can also be manufactured out of bioresorbable materials such as polylactic acid (PLA), poly-L-aspartic acid (PLAA), polylactic/glycolic acid (PLG), polycaprolactone (PCL), DL-lactide-co-ε-caprolactone (DL-PLCL) or the like, wherein the tube can be released after inflation and detachment and swallowed as normal.

At the distal end of the catheter assembly, the inner lumen or inflation tube is attached to the needle assembly that is used to puncture the balloon's self-sealing valve, preferably located at one of the apexes of the balloon housed inside of a gelatin capsule as outer container. The outer lumen is connected to the needle sleeve and provides connection force between the catheter assembly and balloon providing the tensile strength to withstand balloon inflation pressures, e.g., pressures of up to 10 psi or higher, while maintaining the assembly together. The needle sleeve is configured to mechanically couple with the balloon valve assembly. The needle is preferably made of metal, preferably stainless steel or the like, with a maximum size of 25 gauge (0.455 mm), preferably no smaller than 30 gauge (0.255 mm) for inflation timing purposes. The needle sleeve is preferably a soft material such as nylon or the like, or can also be polycarbonate, polyethylene, PEEK, ABS or PVC. The needle sleeve covers the length of the needle in its entirety, such that the body is protected from the needle and the needle can only pierce the balloon septum. Preferably the needle sleeve is flush or extends out slightly more than the needle length. The needle is inserted into the balloon septum prior to swallowing and maintains a retention force of approximately 0.33 lb (0.15 kg) when coupled to the silicone area of the balloon valve. The needle sleeve is preferably slightly bell shaped or contains a circular relief or lip so that when inserted into the silicone area of the valve a lock and key mechanism is created to increase the tensile strength of the assembly and enhance the sealing for inflation.

At the proximal end, the catheter assembly is connected to a Y-adapter assembly preferably made of polycarbonate. The y-adapter is "keyed" so that the inflation gas and connection fluid are connected to the catheter assembly appropriately and travel down the correct lumen.

Prior to inflation, priming of the disconnection lumen may be employed using a liquid. For example, the outer lumen is first flushed with 2 cc of water, saline, DI water or the like prior to balloon inflation. Thereafter, the inflation source container is attached to the connector leading to the inner lumen. The inflation source container works on the premise of the ideal gas law and a pressure decay model. For a given compressed gas formulation, the device is designed to equalize such that a higher starting pressure is used to inflate the balloon than is the resulting end pressure of the balloon. The starting pressure and volume are dependent upon the gas formulation selected, as well as the length of the catheter and the starting temperature (typically ambient temperature) and ending temperature (typically body temperature).

After inflation, the balloon is detached from the catheter assembly using hydraulic pressure. A syringe filled with water, DI water, or preferably saline is attached to the female end of the Y-assembly. The syringe contains 2 cc of liquid and when the syringe plunger is pushed in, enough hydraulic pressure is exerted such that the needle is ejected from the balloon valve.

Single Lumen Catheter

To further reduce the diameter of the inflation catheter, thereby increasing swallowability comfort, a single lumen catheter can be employed that does not exceed 2 French (0.66 mm) in diameter.

The needle/needle sleeve assembly is similar in design to that of the dual lumen catheter described herein. However, with the single lumen system, the distal end of the catheter lumen connects to the needle sleeve only and there is no second catheter inside. Instead, a single thread attached to a needle hub runs co-axially the length of the catheter to aid in tensile strength for detachment and overall flexibility.

The needle sleeve is slightly bell shaped or contains a circular relief or lip so that when inserted into the silicone area of the valve a lock and key mechanism is created to increase the tensile strength of the assembly, enhance the sealing for inflation, and since this is a single lumen assembly, the lip increases the force required to remove the needle from the valve so this does not occur haphazardly during the inflation process.

The proximal end of the catheter is connected to a 3-way valve and uses a method of exclusion for inflation and detachment of the balloon. The distal end of the catheter contains the needle sleeve, which is made of nylon or other similar source. The needle is metallic and preferably stainless steel.

The tubing that the catheter assembly employs is flexible for swallowability, is kink resistant, can withstand body temperature, is resistant to acid, and is biocompatible as the tube transverses the alimentary canal into the stomach cavity. The tube materials are preferably soft and flexible, preferably co-axial, and resistant to necking or buckling or kinking. For a single lumen system, the catheter tubing is preferably made of PEBAX®, but can also comprise bioresorbable materials such as PLA, PLAA, PLG, PCL, DL-PLCL or the like, wherein the tube can be released after inflation and detachment and swallowed as normal. The wire inside the catheter tubing attached to the needle is preferably a nylon monofilament, but Kevlar or nitinol wire or other suitable materials can also be used.

To inflate the balloon, the distal end of the catheter is attached to the balloon capsule where the needle protrudes through the self-sealable valve. The container is swallowed and a portion of the inflation catheter remains outside of the mouth. The inflation source container is connected to the proximal 3-way valve, where the port for inflation gas is chosen by excluding the other ports. The inflation fluid (preferably compressed nitrogen gas or a mixture of gases) travels down the single catheter lumen, whereby the inflation gas selects the path of least resistance, or more specifically through the needle cavity and into the balloon. The balloon is preferably inflated in less than 3 minutes.

To detach and withdraw the needle from the balloon valve, 2 cc or other suitable volume of water or other liquid is injected into the catheter at a high pressure. Since water has a high surface tension and viscosity, it occludes the needle pathway and the pressure is transferred to the outside needle sleeve, thereby breaking the fit between the needle sleeve and the balloon valve.

If it is desired to place a substance inside the balloon, such as water or acid or any alternative liquid, it can be done by using a lower pressure to inject the liquid.

Miniature Stiff-Bodied Inflation Catheter

In certain embodiments, a stiff-bodied inflation catheter can be employed, which can be placed orally or transnasally. This system can be from 1 French (0.33 mm) to 10 French (3.3 mm), preferably 8 French (2.7 mm) in diameter. A larger diameter is typically preferred to enhance pushability, with wall thickness also contributing to pushability and kink resistance. The length of the tube can be approximately 50-60 cm. As discussed above, measurement ticks can be added to the tubing to identify where the end of the tube is located, or a pH or pressure sensor on the catheter can be employed to detect location of the balloon.

This system for inflation/detachment is similar to the dual lumen system described above, but with a larger needle sleeve to accommodate the larger diameter tube. Materials that can be used in the lumen include, e.g., expanded polytetrafluoroethylene (EPTFE) for the outer lumen and polyetheretherketone (PEEK) for the inner lumen. To also enhance pushability, a strain relief device can be added to the distal and proximal ends. It is particularly preferred to have strain relief at the distal end, e.g., 1 to 8 inches, preferably 6 inches, to ensure the catheter bypasses the larynx and follows into the esophagus. The proximal end can have strain relief as well, e.g., to ensure fit of the Y-arm. The preferred material for the strain relief is a polyolefin. The method for inflation/detachment is the same method as for the dual lumen configuration where the outer lumen connects to the needle sleeve and the inner lumen connects to the needle. As part of the procedure, the patient can swallow water or other suitable liquid so as to distend esophageal tissue for smooth passage down of the device. Patients can also be administered an anesthetic at the back of the throat to numb the area and lessen the gag reflex.

The tube can also be connected to a series of encapsulated or compacted balloons on a single catheter such that a total volume of up to 1000 cc or more can be administered, as necessary. Each can be inflated and released separately. The number of balloons released can be tunable to the patient's needs and desired weight loss.

In addition, a catheter can be used for administering a gastric balloon that is similar to balloon catheters used in angioplasty termed "over-the-wire" or rapid exchange catheters. In this case where the patients attempts to swallow the catheter but fails so the stiff catheter—or physician assisted catheter can slide over the flexible catheter and the balloon can be pushed down in the same manner as the physician-assisted catheter. Different materials can be used to provide the varying degrees of flexibility or one material that is fabricated with different diameters across the length to vary the degree of stiffness can be used.

The swallowable self-inflating balloon construction method and the swallowable inflation tube construction method both remove the requirement for endoscopy to place the balloon and make the balloon administration process less invasive. This also allows for the total volume to be placed in a patient to be "titratable," or adjustable. When a balloon is placed for 30 days, a patient may report that over time they lose their feeling of fullness without eating. To compensate, another balloon can be placed easily without sedation and endoscopy. When a non-deflatable balloon is to be removed endoscopically, it is desirable to color-code the balloon composite walls with different colors so that the physician has a visual marker for removing the balloon at the end of its useful life while keeping the balloon that has remaining useful life in the patient's stomach.

In addition, the balloon wall can be marked approximately 180° from the self-sealing valve such that when the balloon is punctured endoscopically it folds more efficiently on itself so as to facilitate removal of the thin-walled structure without causing esophageal perforations and/or other damage by the balloon due to its shape, stiffness, and/or thickness of the wall material.

Inflation Fluid Container

The inflation fluid container is employed to control the amount or volume of fluid placed inside of the balloon. This can be in the form of a canister of, e.g., PVC, stainless steel, or other suitable material. The container can also be in syringe form. The materials employed are able contain a fluid, preferably in gas form, e.g., compressed or non-compressed $N_2$, Ar, $O_2$, $CO_2$, or mixture(s) thereof, or compressed or non-compressed atmospheric air (a mixture of $N_2$, $O_2$, Ar, $CO_2$, Ne, $CH_4$, He, Kr, $H_2$, and Xe). The balloon composite wall materials and respective diffusion gradients and gas permeability characteristics are used to select a fluid for inflation of the intragastric balloon, so as to provide a desired volume profile over time for the inflated balloon. The inflation fluid container materials are selected to ensure no or minimal diffusion or leakage of the fluid before it is connected to the y-arm connector or valve of the inflation catheter. The inflation fluid container preferably incorporates a pressure gauge and a connector. It can also contain a smart chip that notifies the healthcare professional of whether inflation is successful or if the balloon should be detached due to an error in the system.

To maintain "swallowability" of the balloon and to ensure comfort of the patient during the procedure, it is preferred to minimize the amount of time the catheter is placed in the mouth/esophagus. Timing of inflation is can be selected so as to minimize time in place. The outer container-catheter assembly, once swallowed, takes approximately 4-8 seconds to reach the stomach. Once in the stomach, the Inflation source container can be attached to the valve or port of catheter system. Inflation timing can be controlled by selecting the length of catheter, diameter of the catheter tube, the starting temperature, and the starting pressure. Using the Ideal Gas Law for nitrogen and Boyle's Law ($P_1V_1=P_2V_2$) the amount of starting volume/pressure can be derived, where temperature is controlled inside the inflation source container to match that of the body. It is desired to have an inflation time after swallow of less than 5 minutes, and preferably 2-3 minutes, before balloon detachment and catheter withdrawal. The inputs use to derive inflation of the balloon (preferably in less than 3 minutes) include inflation container volume, type of inflation fluid (preferably a compressed gas or compressed gas mixture), starting pressure, catheter length and diameter, and desired end volume and pressure of the balloon. Thus, due to differences in diameter, a 2 French catheter system requires a higher starting pressure to achieve the same target balloon volume and pressure in the same time frame, assuming use of the same compressed gas formulation. In general, it is understood that starting with a higher pressure with the same flow rate/volume can decrease the inflation time.

The inflation source container provides feedback to the end user based on a pressure decay system. Where there is an expected starting pressure and expected ending pressure to indicate whether the balloon is inflated properly, there is no need for endoscopic visualization. Each scenario of expected pressure outputs can have its own tolerances around it to reduce possibilities of false positives, and the inflation fluid container can provide feedback based on these tolerances as to the status of balloon inflation and detachment. This is derived based on the Ideal Gas Law, where there is an expected end pressure based on the fixed volume of the balloon. If the pressure remains high and doesn't decay as expected, this can indicate a failure in the system (e.g., the balloon container did not dissolve, the balloon is expanding in the esophagus because there is, e.g., a kink in the tube or other failure in the catheter system). For example, for a successful decay using nitrogen only as the inflation fluid, the starting pressure is 22 PSI to inflate a balloon to 250 cc and 1.7 psi (0.120 $kg/cm^2$) for a nylon-based material. To indicate successful balloon inflation, a math chip can be added to the inflation source container that provides at least one of a visual, audible, or tactile notification, or otherwise transmits a notification to a healthcare professional or administrator of whether inflation is successful or if there is an error in the system based on the pressure curve and a set of predetermined pressure tolerances and expected timing of inflation.

Another method for detection of any degree of constraint that the balloon may be experiencing (e.g., capsule dissolved but balloon is in the esophagus or duodenum, or balloon is in the stomach and the capsule has not dissolved by reading the gauge output is to employ an inflation canister that has at least two reservoirs (one large and one small) and at least two gauges, with one or more valves that allow for selection of gas release into the second reservoir or into the balloon itself. With two reservoirs, the larger reservoir can contain the total amount of fluid required to fill the balloon. A small amount of fluid can be released from the larger reservoir into the smaller reservoir first to determine the location of the balloon and its readiness for full inflation. If the small amount of fluid in the smaller reservoir is released into the balloon catheter and the feedback on the gauge of the smaller reservoir indicates that the pressure is high, this indicates that the balloon is still contained in the capsule and it is not ready to be inflated. When the gauge reads back a medium pressure level (e.g., 1-4 psi), this indicates that the balloon is in a constrained space, such as the esophagus or duodenum, and should not be inflated. When the balloon catheter's feedback as read on the gauge is approximately 1 psi, this indicates that the balloon is in the stomach and ready to be inflated. If the feedback is at 0 psi, this indicates is a leak in the balloon valve catheter system and that the device should be retrieved. Once the balloon is detected in the stomach space, then the larger reservoir is opened and the balloon is inflated to its desired pressure.

Alternatively, the balloon can be filled based on a starting pressure by using a spring mechanism, a balloon-within-balloon mechanism, or other pressure source. These mechanisms can potentially result in more predictable/consistent pressure decay curves, and again can have accompanying, predetermined tolerances for feedback back to the end user.

Composite Wall

The materials selected for the composite wall of the balloon may be optimized to maintain the original inflation gas without significant diffusion, or may also allow for diffusion of the gases located in the gastric environment, e.g., $CO_2$, $O_2$, argon, or $N_2$ to diffuse through the wall of the balloon to inflate, partially or wholly, once the balloon is placed in the stomach. A fluid (a liquid or gas) can also be added inside of the balloon using the inflation catheter(s) described herein to change diffusion direction of the balloon composite wall and when it reaches stasis based on the internal and external environment.

A gastric balloon inflated by nitrogen, $CO_2$ gas, a single fluid (gas) or a mixture of gasses employs a composite wall that provides barrier properties (fluid retention), properties imparting resistance to pH and moisture conditions in the gastric environment or the environment within the central lumen of the balloon, and structural properties to resist gastric motility forces, abrasion of the balloon wall in vivo, and damage during manufacturing and folding of the balloon. Certain materials employed in the balloon materials are able to withstand a hostile gastric environment designed to break down foreign objects (e.g., food particles). Some of the variables that the gastric environment encompasses are as follows: gastric liquid pH of from 1.5-5; temperature of approx. 37° C.; a relative humidity of 90-100%; ingress of gastric space gas content; and constant gastric motility external pressures of from 0-4 psi at variable frequencies and cycle times based on the fed state of the stomach. The external pressure imparted by gastric motility can also cause abrasions on the surface of the balloon. The inside of the balloon lumen may contain moisture from a solution injected in the balloon for timing of auto-deflation or any moisture that has transferred across the membrane due to the external humid environment. In addition to these environmental stresses the wall materials meet biocompatibility requirements and are constructed such that the total thickness of the wall (barrier material) is thin enough to be compacted and placed inside of a swallowable-sized container ("outer container") without significant damage or lodging. The outer container is small enough to transcend the esophagus (which has a diameter of approximately 2.5 cm). The wall or barrier material is also heat formable and sealable for balloon construct and maintains a bond strength that can contain internal gas pressures of up to 10 psi generated by the initial inflation pressure as well as pressure due to the ingress of gas molecules from the stomach cavity until the system's gas environment reaches stasis. The film properties that are evaluated to determine suitability for use in the composite wall of the balloon include pH resistance, water vapor transmission rate, gas barrier properties, mechanical strength/abrasion properties, temperature resistance, formability, flex-crack (Gelbo) resistance, surface energy (wettability) compliance, and heat bond potential.

The various layers in the composite wall can impart one or more desirable properties to the balloon (e.g., $CO_2$ retention, resistance to moisture, resistance to acidic environment, wettability for processing, and structural strength). A list of polymer resins and coatings that can be combined into a multi-layer preformed system ("composite wall") is provided in Tables 1a-b. These films can be adhesively bonded together, co-extruded, or adhered via tie layers or a combination thereof to obtain the desired combination of properties for the composite wall, as discussed below. The materials identified as film coatings in Tables 1a-b are provided as coatings applied to a base polymer film, e.g., PET, Nylon, or other structural layer.

TABLE 1a

Film Resins

| | Characteristics | | |
|---|---|---|---|
| | Good Structural/ Behavior/ Mechanical Strength/ Compliance | Good Fluid Retention Barrier Properties | Good Manu-facturability/ Surface Energy Properties |
| FILM RESINS | | | |
| Polyethylene Terephthalate (PET) | X | X | |
| Polytrimethylene Terephthalate (PTT) | | | |
| Liquid Crystal Polymer (LCP) | X | X | |
| Polytrimethylene naphthalate (PTN) | X | X | |
| Polyethylene naphthalate (PEN) | X | X | |
| Polyimide (PI) | X | X | |
| Linear Low Density Polyethylene (LLDPE) | | | X |
| Ethylene Vinyl Alcohol (EVOH) | | X | |

TABLE 1a-continued

Film Resins

| | Characteristics | | |
|---|---|---|---|
| | Good Structural/ Behavior/ Mechanical Strength/ Compliance | Good Fluid Retention Barrier Properties | Good Manu-facturability/ Surface Energy Properties |
| Polyamide: Nylon (PA) and Nylon-6 (PAG)/Nylon 12 | | X | X |
| High Density Polyethylene (HDPE) | | | X |
| Polypropylene (PP) | | | X |
| Polyurethane | | | X |
| PVDC (Saran) | | X | X |
| Polyether Block Amide (Pebax) | | | X |
| Polyvinyl Alcohol (PVOH) | | X | |
| Silicone | X | | X |

TABLE 1b

Film Coatings

| | Characteristics | | |
|---|---|---|---|
| | Good Structural/Behavior/ Mechanical Strength/Compliance | Good Fluid Retention Barrier Properties | Good Manufacturability/ Surface Energy Properties |
| FILM COATINGS | | | |
| Silicon Dioxide (SiO2) | | X | |
| Aluminum Oxide ($Al_2O_3$) | | X | |
| Nanopolymers (Nano/Clay) | | X | |
| External Organic Coatings (e.g., epoxy amine) | | X | |
| Inorganic Coatings (e.g., Amorphous Carbon) | | X | |
| Oxygen Scavengers | | X | |
| Parylene C | | X | |

Fluid Retention Layers

In preferred embodiments, a blended polymer resin using multiple layers is employed to maintain the inflated balloon's shape and volume by retaining the inflation fluid for the duration of the intended use. Certain barrier films, widely used in the food packaging and plastic bottling industries, can advantageously be employed for this purpose in the composite wall of the balloon. Preferably, the barrier materials have a low permeability to carbon dioxide (or other gases, liquids, or fluids that are alternatively or additionally used to inflate the volume-occupying subcomponent). These barrier layers preferably have good adherence to the base material. Preferred barrier coating materials and films include polyethylene terephthalate (PET), linear low density polyethylene (LLDPE), ethylene vinyl alcohol (EVOH), polyamides such as Nylon (PA) and Nylon-6 (PA-6), polyimide (PI), liquid crystal polymer (LCP), high density polyethylene (HDPE), polypropylene (PP), biocompatible poly(hydroxyamino ethers), polyethylene naphthalate, polyvinylidene chloride (PVDC), saran, ethylene vinyl alcohol copolymers, polyvinyl acetate, silicon oxide (SiOx), silicon dioxide ($SiO_2$), aluminum oxide ($Al_2O_3$), polyvinyl alcohol (PVOH), nanopolymers (e.g., nanoclay), polyimide thermoset film, EVALCA EVAL EF-XL, Hostaphan GN, Hostaphan RHBY, RHB MI, Techbarrier HX (SiOx-coated PET), Triad Silver (silver metalized PET), Oxyshield 2454, Bicor 84 AOH, acrylonitrile copolymers, and copolymers of terephthalic acid and isophthalic acid with ethylene glycol and at least one diol. Alternative gas-barrier materials include polyamine-polyepoxides. These materials are typically provided as a solvent-based or aqueous-based thermosetting composition and are typically spray-coated onto a preform and then heat-cured to form the finished barrier coating. Alternative gas barrier materials that can be applied as coatings to the volume-occupying subcomponent include metals such as silver or aluminum. Other materials that may be used to improve the gas impermeability of the volume occupying subcomponent include, but are not limited to, gold or any noble metal, PET coated with saran, and conformal coatings.

One method that is used in the packaging industry to delay diffusion of the inflation fluid is to thicken the material. Thickening the material is generally not preferred, as the total composite wall thickness preferably does not exceed 0.004 inches (0.010 cm) in order for the balloon to be foldable into the desired delivery container size for swallowing by a patient.

A multilayer polymer film that is able to withstand the gastric environment over the course of the usable life of the balloon includes linear low density polyethylene (LLDPE) adhesively bonded to a Nylon 12 film. Alternatively, an additional film layer with barrier properties, such as PVDC can be added to the composite wall.

The layers providing gas barrier properties are preferably situated as inner layers in the composite wall as they are less mechanically robust than resins that are considered "structural" such as Nylon and the like.

Structural Layers

Layers such as polyurethane, Nylon, or polyethylene terephthalate (PET) can be added to the composite wall for structural purposes, and are preferably placed as outermost (proximal to the gastric environment or proximal to the central lumen of the balloon) layers, provided that the pH resistance of such layers can withstand the acidic environment of the stomach or the central lumen of the balloon. Other layers may in addition or alternatively be included, including but not limited to those described in the following "Layer Chemistry" subsections.

Layer Chemistry

Polyethylene Terephthalate (PET)

Polyethylene terephthalate is a thermoplastic polymer resin of the polyester family. Polyethylene terephthalate may exist as an amorphous (transparent) or as a semi-crystalline material. The semi-crystalline material can appear transparent (spherulites<500 nm) or opaque and white (spherulites up to a size of some µm) depending on its crystal structure and spherulite size. Its monomer (bis-β-hydroxyterephthalate) can be synthesized by the esterification reaction between terephthalic acid and ethylene glycol with water as a byproduct, or by transesterification reaction between ethylene glycol and dimethyl terephthalate with methanol as a byproduct. Polymerization is through a polycondensation reaction of the monomers (done immediately after esterification/transesterification) with ethylene glycol as the byproduct (the ethylene glycol is directly recycled in production). Some of the trade names of PET products are Dacron, Diolen, Tergal, Terylene, and Trevira fibers, Cleartuf, Eastman PET and Polyclear bottle resins, Hostaphan, Melinex, and Mylar films, and Arnite, Ertalyte, Impet, Rynite and Valox injection molding resins.

PET consists of polymerized units of the monomer ethylene terephthalate, with repeating C10H8O4 units. PET can be semi-rigid to rigid, depending on its thickness, and is very lightweight. It makes a good gas and fair moisture barrier, as well as a good barrier to alcohol and solvents. It is strong and impact-resistant. It is naturally colorless with high transparency.

When produced as a thin film (biaxially oriented PET film, often known by one of its trade names, "Mylar"), PET can be aluminized by evaporating a thin film of metal onto it to reduce its permeability, and to make it reflective and opaque (MPET). These properties are useful in many applications, including flexible food packaging. When filled with glass particles or fibers, it becomes significantly stiffer and more durable. This glass-filled plastic, in a semi-crystalline formulation, is sold under the trade name Rynite, Amite, Hostadur, and Crastin.

One of the most important characteristics of PET is intrinsic viscosity. The intrinsic viscosity of the material, measured in deciliters per gram (dl/g) is dependent upon the length of its polymer chains. The longer the chains, the stiffer the material, and therefore the higher the intrinsic viscosity. The average chain length of a particular batch of resin can be controlled during polymerization. An intrinsic viscosity of about: 0.65 dl/g-0.84 dl/g is preferred for use in a composite wall.

In addition to pure (homopolymer) PET, PET modified by copolymerization is also available. In some cases, the modified properties of copolymer are more desirable for a particular application. For example, cyclohexane dimethanol (CHDM) can be added to the polymer backbone in place of ethylene glycol. Since this building block is much larger (6 additional carbon atoms) than the ethylene glycol unit it replaces, it does not fit in with the neighboring chains the way an ethylene glycol unit can. This interferes with crystallization and lowers the polymer's melting temperature. Such PET is generally known as PETG (Eastman Chemical and SK Chemicals are the only two manufacturers). PETG is a clear amorphous thermoplastic that can be injection molded or sheet extruded. It can be colored during processing. Another common modifier is isophthalic acid, replacing some of the 1,4-(para-) linked terephthalate units. The 1,2-(ortho-) or 1,3-(meta-) linkage produces an angle in the chain, which also disturbs crystallinity. Such copolymers are advantageous for certain molding applications, such as thermoforming. On the other hand, crystallization is important in other applications where mechanical and dimensional stability are important. For PET bottles, the use of small amounts of CHDM or other comonomers can be useful: if only small amounts of comonomers are used, crystallization is slowed but not prevented entirely. As a result, bottles are obtainable via stretch blow molding ("SBM"), which are both clear and crystalline enough to be an adequate barrier to aromas and gases such as carbon dioxide in carbonated beverages.

Crystallization occurs when polymer chains fold up on themselves in a repeating, symmetrical pattern. Long polymer chains tend to become entangled on themselves, which prevents full crystallization in all but the most carefully controlled circumstances. 60% crystallization is the upper limit for commercial products, with the exception of polyester fibers.

PET in its natural state is a crystalline resin. Clear products can be produced by rapidly cooling molten polymer to form an amorphous solid. Like glass, amorphous PET forms when its molecules are not given enough time to arrange themselves in an orderly fashion as the melt is cooled. At room temperature the molecules are frozen in place, but if enough heat energy is put back into them, they begin to move again, allowing crystals to nucleate and grow. This procedure is known as solid-state crystallization.

Like most materials, PET tends to produce many small crystallites when crystallized from an amorphous solid, rather than forming one large single crystal. Light tends to scatter as it crosses the boundaries between crystallites and the amorphous regions between them. This scattering means that crystalline PET is opaque and white in most cases. Fiber drawing is among the few industrial processes that produces a nearly single-crystal product.

Comonomers such as CHDM or isophthalic acid lower the melting temperature and reduces the degree of crystallinity of PET (especially important when the material is used for bottle manufacturing). Thus the resin can be plastically formed at lower temperatures and/or with lower force. This helps to prevent degradation, reducing the acetaldehyde content of the finished product to an acceptable (that is, unnoticeable) level. Other ways to improve the stability of the polymer is by using stabilizers, mainly antioxidants such as phosphites. Recently, molecular level stabilization of the material using nanostructured chemicals has also been considered.

Unreinforced PET has the following properties: Bulk Density 0.800-0.931 g/cc; Density 1.10-1.20 g/cc @Temperature 285-285° C.; 1.25-1.91 g/cc; Apparent Bulk Density 0.000850 g/cc; Water Absorption 0.0500-0.800%; Moisture Absorption at Equilibrium 0.200-0.300%; Water Absorption at Saturation 0.400-0.500%; Particle Size 2500 μm; Water Vapor Transmission 0.490-6.00 g/m$^2$/day; Oxygen Transmission 5.10-23.0 cc-mm/m$^2$-24 hr-atm; Viscosity Measurement 0.550-0.980; Viscosity Test 74.0-86.0 cm$^3$/g; Thickness 250-254 microns; Linear Mold Shrinkage 0.00100-0.0200 cm/cm; Linear Mold Shrinkage, Transverse 0.00200-0.0110 cm/cm; Hardness, Rockwell M 80.0-95.0; Hardness, Rockwell R 105-120 105-120; Ball Indentation Hardness 160-170 MPa; Tensile Strength, Ultimate 22.0-207 MPa; Film Tensile Strength at Yield, MD 55.0-59.0 MPa; Film Tensile Strength at Yield, TD 53.0-57.0 MPa; Film Elongation at Break, MD 40.0-600%; Film Elongation at Break, TD 200-600%; Film Elongation at Yield, MD 4.00-6.00%; Film Elongation at Yield, TD 4.00-6.00%; Tensile Strength, Yield 47.0-90.0 MPa; Elongation at Break 1.50-600%; Elongation at Yield 3.50-30.0%; Modulus of Elasticity 1.83-14.0 GPa; Flexural Modulus 1.90-15.2 GPa; Flexural Yield Strength 55.0-240 MPa; Compressive Yield Strength 20.0-123 MPa; Izod Impact, Unnotched 2.67 J/cm-NB; Izod Impact, Unnotched Low Temp (ISO) 160-181 kJ/m$^2$; Izod Impact, Notched, Low Temp (ISO) 3.10-4.20 kJ/m$^2$; Charpy Impact Unnotched 3.00 J/cm$^2$-NB; Charpy Impact, Notched, Low Temp 0.270-0.500 J/cm$^2$; Charpy Impact, Notched 0.200-1.40 J/cm$^2$; Impact Test 0.800-8.20 J @Temperature −40.0° C.; Coefficient of Friction 0.190-0.250; Tear Strength, Total 15.0-120 N; Elmendorf Tear Strength, MD 3.14-4.00 g/micron; Elmendorf Tear Strength, TD 3.24-5.20 g/micron; Dart Drop 1.08-2.00 g/micron; Taber Abrasion, mg/1000 Cycles; Film Tensile Strength at Break, MD 13.8-60.0 MPa; Film Tensile Strength at Break, TD 39.0-48.0 MPa; Izod Impact, Notched @−40° C. 0.270-0.630 J/cm; Izod Impact, Notched 0.139-100 J/cm; Izod Impact, Notched (ISO) 2.00-10.0 kJ/m$^2$; Electrical Resistivity 5.00e+6-1.00e+16 ohm-cm; Surface Resistance 1.00e+14-1.00e+16 ohm; Dielectric Constant 2.40-3.90; Dielectric Strength 15.7-60.0 kV/mm; Dissipation Factor 0.00100-0.0250; Arc Resistance 80.0-181 sec; Comparative Tracking Index 175-600 V; Heat of Fusion 56.0-65.0 J/g; CTE, linear 25.0-92.0 μm/m-° C.; CTE, linear, Transverse to Flow 48.0-80.0 μm/m-° C.; Specific Heat Capacity 1.10-1.20 J/g-° C.; 1.30-2.30 J/g-° C. @Temperature 60.0-280° C.; Thermal Conductivity 0.190-0.290 W/m-K; Melting Point 200-255° C.; Maximum Service Temperature, Air 100-225° C.; Deflection Temperature at 0.46 MPa (66 psi) 66.0-245° C.; Deflection Temperature at 1.8 MPa (264 psi) 60.0-240° C.; Vicat Softening Point 74.0-85.0° C.; Minimum Service Temperature, Air −20.0° C.; Glass Temperature 70.0-78.0° C.; UL RTI, Electrical 75.0-175° C.; Haze 0.300-10.0%; Gloss 108-166%; Transmission, Visible 67.0-99.0%; Gardner Color Number—3.00-85.0; Processing Temperature 120-295° C.; Mold Temperature 10.0-163° C.; Drying Temperature 70.0-160° C.; Dry Time 3.00-8.00 hour; Moisture Content 0.0100-0.400%; Injection Pressure 68.9-120 MPa; Back Pressure 8.00-18.0 MPa.

Polyethylene terephthalate films are available from Mitsubishi Polyester Film of Wiesbaden, Germany under the trade name Hostaphan®. Hostaphan® GN is a glass clear biaxially oriented film, made of polyethylene terephthalate (PET) and is characterized by its high transparency and surface gloss and its low haze accompanied by its excellent mechanical strength and dimensional stability. Hostaphan® GN is one or two side chemically treated for improved slip and processability as well as for improvement of the adhesion of coatings, printing inks or metallic layers. Hostaphan® RHBY is a biaxially oriented film made of polyethylene terephthalate (PET) with a structure optimized to offer previously unattainable barrier properties against oxygen, water vapor and other gases as well as aroma substances after vacuum coating with aluminum, Al2O3 or SiOx.

Linear Low-Density Polyethylene (LLDPE)

Linear low-density polyethylene (LLDPE) is a substantially linear polymer (polyethylene), with significant numbers of short branches, commonly made by copolymerization of ethylene with longer-chain olefins. Linear low-density polyethylene differs structurally from conventional low-density polyethylene because of the absence of long chain branching. The linearity of LLDPE results from the different manufacturing processes of LLDPE and LDPE. In general, LLDPE is produced at lower temperatures and pressures by copolymerization of ethylene and such higher alpha olefins as butene, hexene, or octene. The copolymerization process produces an LLDPE polymer that has a narrower molecular weight distribution than conventional LDPE and in combination with the linear structure, significantly different rheological properties.

The production of LLDPE is initiated by transition metal catalysts, particularly Ziegler or Philips type of catalyst. The actual polymerization process can be done in either solution phase or gas phase reactors. Usually, octene is the copolymer in solution phase while butene and hexene are copolymerized with ethylene in a gas phase reactor. The LLDPE resin produced in a gas phase reactor is in granular form and may be sold as granules or processed into pellets. LLDPE has higher tensile strength and higher impact and puncture resistance than LDPE. It is very flexible and elongates under stress. It can be used to make thinner films, with better environmental stress cracking resistance. It has good resistance to chemicals and to ultraviolet radiation. It has good electrical properties. However it is not as easy to process as LDPE, has lower gloss, and narrower range for heat sealing.

LDPE and LLDPE have unique theoretical or melt flow properties. LLDPE is less shear sensitive because of its narrower molecular weight distribution and shorter chain branching. During a shear process, such as extrusion, LLDPE remains more viscous, therefore harder to process than an LDPE of equivalent melt index. The lower shear sensitivity of LLDPE allows for a faster stress relaxation of the polymer chains during extrusion and therefore the physical properties are susceptible to changes in blow-up ratios. In melt extension, LLDPE has lower viscosity at all strain rates. This means it will not strain harden the way LDPE does when elongated. As the deformation rate of the polyethylene increases, LDPE demonstrates a dramatic rise in viscosity because of chain entanglement. This phenomena is not observed with LLDPE because of the lack of long-chain branching in LLDPE allows the chains to "slide by" one another upon elongation without becoming entangled. This characteristic is important for film applications because LLDPE films can be downgauged easily while maintaining high strength and toughness.

Properties of film grade LLDPE include: Density 0.902-0.960 g/cc; Moisture Vapor Transmission 0.240-0.470 cc-mm/m$^2$-24 hr-atm; Water Vapor Transmission 6.00-8.00 g/m$^2$/day; Oxygen Transmission 0.720-236 cc-mm/m$^2$-24 hr-atm; Oxygen Transmission Rate 3500-5000 cc/m$^2$/day; Viscosity 37000-79000 cP @Temperature 190-190° C.; 37000-79000 cP @Shear Rate 300-5000 l/s; 37000-79000 cP @Shear Rate 300-5000 l/s; Thickness 12.7-76.2 microns; Melt Flow 0.200-40.0 g/10 min; Base Resin Melt Index 0.700-3.50 g/10 min; Antiblock Level 3500-9000 ppm; Slip Level 0.000-1700 ppm; Tensile Strength, Ultimate 9.80-26.2 MPa; Film Tensile Strength at Yield, MD 7.38-74.0 MPa; Film Tensile Strength at Yield, TD 6.90-77.0 MPa; Film Elongation at Break, MD 80.0-1460%; Film Elongation at Break, TD 460-1710%; Film Elongation at Yield, MD 435-640%; Film Elongation at Yield, TD 670-890%; Tensile Strength, Yield 9.70-22.1 MPa; Elongation at Break 8.00-1000%; Modulus of Elasticity 0.0110-0.413 GPa; Secant Modulus, MD 0.0103-0.717 GPa; Secant Modulus, TD 0.0106-0.869 GPa; Impact 48.0-65.0; Impact Test 0.452-5.00 J; Coefficient of Friction 0.100-2.00; Coefficient of Friction, Static 0.170-1.00; Elmendorf Tear Strength MD 25.0-1080 g 2; Elmendorf Tear Strength TD 180-1470 g; Elmendorf Tear Strength, MD 0.0750-20.9 g/micron; Elmendorf Tear Strength, TD 0.275-37.8 g/micron; Dart Drop 1.57-42.5 g/micron; Dart Drop Test 30.0-1350 g; Seal Strength 1800-2400 g/25 mm; Film Tensile Strength at Break, MD 9.65-82.7 MPa; Film Tensile Strength at Break, TD 7.24-55.1 MPa; Heat Seal Strength Initiation Temperature 72.0-100° C.; Melting Point 120-128° C.; Crystallization Temperature 104-115° C.; Vicat Softening Point 93.0-123° C.; Haze 0.700-80.0%; Gloss 3.00-140%; Processing Temperature 90.0-310° C.; Die Opening 0.0810-0.254 cm; Blow-up Ratio (BUR) 1.50-4.00.

Ethylene Vinyl Alcohol (EVOH)

Ethylene Vinyl Alcohol is a formal copolymer of ethylene and vinyl alcohol. Because the latter monomer mainly exists as its tautomer acetaldehyde, the copolymer is prepared by polymerization of ethylene and vinyl acetate followed by hydrolysis. The plastic resin is commonly used in food applications, and in plastic gasoline tanks for automobiles. Its primary purpose is to provide barrier properties, primarily as an oxygen barrier for improved food packaging shelf life and as a hydrocarbon barrier for fuel tanks. EVOH is typically coextruded or laminated as a thin layer between cardboard, foil, or other plastics. EVOH copolymer is defined by the mole % ethylene content: lower ethylene content grades have higher barrier properties; higher ethylene content grades have lower temperatures for extrusion.

Ethylene Vinyl Alcohol (EVOH) is one of the most common clear high barrier films used today. It is applied as a discrete layer in a coextrusion. EVOH provides excellent oxygen barrier properties (0.006-0.12 cc-mil/100 in2-day). The barrier that a particular EVOH film provides is dependent upon a number of factors: mole percent—as the ethylene mole percent increases, the barrier decreases; degree of crystallinity—as the degree of crystallinity increases, the barrier properties improve; thickness—as with all films, as the thickness increases, the barrier increases; temperature—as the temperature increases, the barrier decreases; humidity—at high humidity levels, the barrier provided by EVOH drops rapidly (it is the humidity level at the EVOH interface rather than ambient humidity that is critical). In addition to providing an excellent oxygen barrier, EVOH is also an excellent odor and aroma barrier. It has the added advantage of being thermoformable making it popular for 3D applications.

EVALCA EVAL® EF-XL Ethylene Vinyl Alcohol Copolymer Film has the following properties: Moisture Vapor Transmission 0.600 cc-mm/m$^2$-24 hr-atm 40° C., 90% RH; Oxygen Transmission 0.00400 cc-mm/m$^2$-24 hr-atm 20° C.; 65% RH (permeability increases significantly at higher moisture content); thickness 15.2 microns; Film Elongation at Break, MD 100% 10%/min.; ASTM D638 Film Elongation at Break, TD 100% 10%/min.; ASTM D638 Secant Modulus, MD 3.50 GPa; Youngs Modulus, ASTM D638, 10%/min.; Secant Modulus, TD 3.50 GPa; Youngs Modulus, ASTM D638, 10%/min.; Elmendorf Tear Strength MD 260 g; ASTM D638 Elmendorf Tear Strength TD 330 g; ASTM D638 Elmendorf Tear Strength, MD 17.0 g/micron; ASTM D638 Elmendorf Tear Strength, TD 21.7 g/micron; ASTM D638 Film Tensile Strength at Break, MD 205 MPa 10%/min.; ASTM D638 Film Tensile Strength at Break, TD 195 MPa 10%/min.; Surface Resistance 2.70e+15 ohm; Dielectric Constant 5.00; Dissipation Factor 0.220; Specific Heat Capacity 2.40 J/g-° C.; Thermal Conductivity 0.340 W/m-K; Melting Point 181° C. DSC; Haze 0.500% 65% RH; Gloss 95.0% 65% RH. EVAL® ethylene vinyl alcohol films are available from Kuraray America, Inc. of Houston, Tex.

Nylon

Nylon is a generic designation for a family of synthetic polymers known generically as polyamides. Nylon is a thermoplastic silky material. There are two common methods of making nylon for fiber applications. In one approach, molecules with an acid (COOH) group on each end are reacted with molecules containing amine (NH2) groups on each end. The resulting nylon is named on the basis of the number of carbon atoms separating the two acid groups and the two amines. These are formed into monomers of intermediate molecular weight, which are then reacted to form long polymer chains.

Solid nylon is used for mechanical parts such as machine screws, gears and other low- to medium-stress components previously cast in metal. Engineering-grade nylon is processed by extrusion, casting, and injection molding. Solid nylon is used in hair combs. Type 6/6 Nylon 101 is the most common commercial grade of nylon, and Nylon 6 is the most common commercial grade of molded nylon. Nylon is available in glass-filled variants which increase structural and impact strength and rigidity, and molybdenum sulfide-filled variants which increase lubricity.

Aramids are another type of polyamide with quite different chain structures which include aromatic groups in the main chain. Such polymers make excellent ballistic fibers.

Nylons are condensation copolymers formed by reacting equal parts of a diamine and a dicarboxylic acid, so that peptide bonds form at both ends of each monomer in a process analogous to polypeptide biopolymers. The numerical suffix specifies the numbers of carbons donated by the monomers; the diamine first and the diced second. The most common variant is nylon 6-6 which refers to the fact that the diamine (hexamethylene diamine) and the diacid (adipic acid) each donate 6 carbons to the polymer chain. As with other regular copolymers like polyesters and polyurethanes, the "repeating unit" consists of one of each monomer, so that they alternate in the chain. Since each monomer in this copolymer has the same reactive group on both ends, the direction of the amide bond reverses between each monomer, unlike natural polyamide proteins which have overall directionality. In the laboratory, nylon 6-6 can also be made using adipoyl chloride instead of adipic. It is difficult to get the proportions exactly correct, and deviations can lead to chain termination at molecular weights less than a desirable 10,000 daltons. To overcome this problem, a crystalline, solid "nylon salt" can be formed at room temperature, using an exact 1:1 ratio of the acid and the base to neutralize each other. Heated to 285° C., the salt reacts to form nylon polymer. Above 20,000 daltons, it is impossible to spin the chains into yarn, so to combat this some acetic acid is added to react with a free amine end group during polymer elongation to limit the molecular weight. In practice, and especially for nylon 6,6, the monomers are often combined in a water solution. The water used to make the solution is evaporated under controlled conditions, and the increasing concentration of "salt" is polymerized to the final molecular weight.

Homopolymer nylon 6, or polycaprolactam, is not a condensation polymer, but formed by a ring-opening polymerization (alternatively made by polymerizing aminocaproic acid). The peptide bond within the caprolactam is broken with the exposed active groups on each side being incorporated into two new bonds as the monomer becomes part of the polymer backbone. In this case, all amide bonds lie in the same direction, but the properties of nylon 6 are sometimes indistinguishable from those of nylon 6,6-except for melt temperature (N6 is lower) and some fiber properties in products like carpets and textiles. There is also nylon 9.

Nylon 5,10, made from pentamethylene diamine and sebacic acid has superior properties, but is more expensive to make. In keeping with this naming convention, "nylon 6,12" (N-6,12) or "PA-6,12" is a copolymer of a 6C diamine and a 12C diacid. Similarly for N-5,10 N-6,11; N-10,12, etc. Other nylons include copolymerized dicarboxylic acid/diamine products that are not based upon the monomers listed above. For example, some aromatic nylons are polymerized with the addition of diacids like terephthalic acid (Kevlar) or isophthalic acid (Nomex), more commonly associated with polyesters. There are copolymers of N-6,6/N6; copolymers of N-6,6/N-6/N-12; and others. Because of the way polyamides are formed, nylon can seem to be limited to unbranched, straight chains. But "star" branched nylon can be produced by the condensation of dicarboxylic acids with polyamines having three or more amino groups.

Above their melting temperatures, Tm, thermoplastics like nylon are amorphous solids or viscous fluids in which the chains approximate random coils. Below Tm, amorphous regions alternate with regions which are lamellar crystals. The amorphous regions contribute elasticity and the crystalline regions contribute strength and rigidity. The planar amide (—CO—NH—) groups are very polar, so nylon forms multiple hydrogen bonds among adjacent strands. Because the nylon backbone is so regular and symmetrical, especially if all the amide bonds are in the trans configuration, nylons often have high crystallinity and make excellent fibers. The amount of crystallinity depends on the details of formation, as well as on the kind of nylon. Apparently it can never be quenched from a melt as a completely amorphous solid.

Nylon 6,6 can have multiple parallel strands aligned with their neighboring peptide bonds at coordinated separations of exactly 6 and 4 carbons for considerable lengths, so the carbonyl oxygens and amide hydrogens can line up to form interchain hydrogen bonds repeatedly, without interruption. Nylon 5,10 can have coordinated runs of 5 and 8 carbons. Thus parallel (but not antiparallel) strands can participate in extended, unbroken, multi-chain β-pleated sheets, a strong and tough supermolecular structure similar to that found in natural silk fibroin and the β-keratins in feathers (proteins have only an amino acid a-carbon separating sequential —CO—NH— groups). Nylon 6 will form uninterrupted H-bonded sheets with mixed directionalities, but the β-sheet wrinkling is somewhat different. The three-dimensional disposition of each alkane hydrocarbon chain depends on rotations about the 109.47° tetrahedral bonds of singly-bonded carbon atoms.

Block nylon tends to be less crystalline, except near the surfaces due to shearing stresses during formation. Nylon is clear and colorless, or milky, but is easily dyed. Multistranded nylon cord and rope is slippery and tends to unravel. The ends can be melted and fused with a heat source such as a flame or electrode to prevent this.

When dry, polyamide is a good electrical insulator. However, polyamide is hygroscopic. The absorption of water will change some of the material's properties such as its electrical resistance. Nylon is less absorbent than wool or cotton.

Nylon can be used as the matrix material in composite materials, with reinforcing fibers like glass or carbon fiber, and has a higher density than pure nylon. Such thermoplastic composites (25% glass fiber) are frequently used in car components next to the engine, such as intake manifolds, where the good heat resistance of such materials makes them feasible competitors to metals.

All nylons are susceptible to hydrolysis, especially by strong acids, a reaction essentially the reverse of the synthetic reaction shown above. The molecular weight of nylon products so attacked drops fast, and cracks form quickly at the affected zones. Lower members of the nylons (such as nylon 6) are affected more than higher members such as nylon 12. This means that nylon parts cannot be used in contact with sulfuric acid for example, such as the electrolyte used in lead-acid batteries. When being molded, nylon must be dried to prevent hydrolysis in the molding machine barrel since water at high temperatures can also degrade the polymer.

Polyimide (PI)

Polyimide is a polymer of imide monomers. Thermosetting polyimides are commercially available as uncured resins, stock shapes, thin sheets, laminates and machines parts. Thermoplastic polyim ides are very often called pseudothermoplastic. There are two general types of polyimides. One type, so-called linear polyimides, is made by combining imides into long chains. Aromatic heterocyclic polyimides are the other usual kind. Examples of polyimide films include Apical, Kapton, UPILEX, VTEC PI, Norton TH and Kaptrex. Polyimide parts and shapes include VTEC PI, Meldin, Vespel and typical monomers include pyromellitic dianhydride and 4,4'-oxydianiline.

Thermosetting polyimides are known for thermal stability, good chemical resistance, excellent mechanical properties, and characteristic orange/yellow color. Polyimides compounded with graphite or glass fiber reinforcements have flexural strengths of up to 50,000 psi and flexural moduli of 3,000,000 psi. Thermoset polyimides exhibit very low creep and high tensile strength. These properties are maintained during continuous use to temperatures of 232° C. and for short excursions, as high as 482° C. Molded polyimide parts and laminates have very good heat resistance. Normal operating temperatures for such parts and laminates range from cryogenic to those exceeding 260° C. Polyimides are also inherently resistant to flame combustion and do not usually need to be mixed with flame retardants. Most carry a UL rating of VTM-0. Polyimide laminates have a flexural strength half-life at 249° C. of 400 hours.

Typical polyimide parts are not affected by commonly used solvents and oils including hydrocarbons, esters, ethers, alcohols and freons. They also resist weak acids but are not recommended for use in environments that contain alkalis or inorganic acids. Some polyimides, such as CP1 and CORIN XLS, are solvent-soluble and exhibit high optical clarity. The solubility properties lend them towards spray and low temperature cure applications.

The polyimide materials are lightweight, flexible, resistant to heat and chemicals. Therefore, they are used in the electronics industry for flexible cables, as an insulating film on magnet wire and for medical tubing. For example, in a laptop computer, the cable that connects the main logic board to the display (which must flex every time the laptop is opened or closed) is often a polyimide base with copper conductors. The semiconductor industry uses polyimide as a high-temperature adhesive; it is also used as a mechanical stress buffer. Some polyimide can be used like a photoresist; both "positive" and "negative" types of photoresist-like polyimide exist in the market.

Thermoset film polyimide has the following properties: Density 1.40-1.67 g/cc; Water Absorption 1.40-3.00%; Moisture Absorption at Equilibrium 0.400-1.80%; Water Absorption at Saturation 1.20-2.50%; Moisture Vapor Transmission 2.40-17.5 cc-mm/m$^2$-24 hr-atm; Oxygen Transmission 9.90 cc-mm/m$^2$-24 hr-atm; Thickness 22.0-187 microns; Film Tensile Strength at Yield, MD 49.0-255 MPa; Film Tensile Strength at Yield, TD 100-160 MPa; Film Elongation at Break, MD 10.0-85.0%; Film Elongation at Yield, MD 40.0-50.0%; Film Elongation at Yield, TD 45.0-55.0%; Tensile Strength, Yield 73.3-160 MPa; Elongation at Yield 10.0-45.0%; Poissons Ratio 0.340; Secant Modulus 2.28-5.20 GPa; Secant Modulus, MD 1.76-9.12 GPa; Impact Test 0.686-1.56 J; Coefficient of Friction 0.400-0.480; Coefficient of Friction, Static 0.630; Tear Strength Test 7.20-430; Peel Strength 0.240 kN/m; Elmendorf Tear Strength MD 8.20-270 g; Film Tensile Strength at Break, MD 98.1-736 MPa; Electrical Resistivity 1.00e+10-2.30e+17 ohm-cm; 1.00e+15-1.00e+16 ohm-cm @Temperature 200° C.; Surface Resistance 10000-1.00e+17 ohm; 1.00e+15-1.00e+15 ohm @Temperature 200° C.; Dielectric Constant 2.70-4.00; Dielectric Strength 48.0-272 kV/mm @Temperature 200° C.; Dissipation Factor 0.00130-0.0100; CTE, linear 12.0-20.0 μm/m-° C.; 32.0-40.0 μm/m-° C. @Temperature 100-300° C.; Specific Heat Capacity 1.09-1.13 J/g-° C.; Thermal Conductivity 0.120-0.289 W/m-K; Maximum Service Temperature, Air 180-400° C.; Minimum Service Temperature, Air −269° C.; Glass Temperature 360-500° C.; Oxygen Index 37.0-66.0%; Shrinkage 0.0100-0.200%; Refractive Index 1.70.

Liquid Crystal Polymer (LCP)

Liquid-crystal polymers (LCPs) are a class of aromatic polyester polymers. They are extremely unreactive and inert, and highly resistant to fire. Liquid crystallinity in polymers may occur either by dissolving a polymer in a solvent (lyotropic liquid-crystal polymers) or by heating a polymer above its glass or melting transition point (thermotropic liquid-crystal polymers). Liquid-crystal polymers are present in melted/liquid or solid form. In liquid form liquid-crystal polymers have primarily applications in liquid-crystal displays (LCDs). In solid form the main example of lyotropic LCPs is the commercial aramid known as Kevlar. The chemical structure of this aramid consists of linearly substituted aromatic rings linked by amide groups. In a similar way, several series of thermotropic LCPs have been commercially produced by several companies (e.g., Vectra). A high number of LCPs, produced in the 1980s, displayed order in the melt phase analogous to that exhibited by nonpolymeric liquid crystals. Processing of LCPs from liquid-crystal phases (or mesophases) gives rise to fibers and injected materials having high mechanical properties as a consequence of the self-reinforcing properties derived from the macromolecular orientation in the mesophase. Today, LCPs can be melt-processed on conventional equipment at high speeds with excellent replication of mold details.

A unique class of partially crystalline aromatic polyesters based on p-hydroxybenzoic acid and related monomers, liquid-crystal polymers is capable of forming regions of highly ordered structure while in the liquid phase. However, the degree of order is somewhat less than that of a regular solid crystal. Typically LCPs have a high mechanical strength at high temperatures, extreme chemical resistance, inherent flame retardancy, and good weatherability. Liquid-crystal polymers come in a variety of forms from sinterable high temperature to injection moldable compounds. LCP can be welded, though the lines created by welding are a weak point in the resulting product. LCP has a high Z-axis coefficient of thermal expansion.

LCPs are exceptionally inert. They resist stress cracking in the presence of most chemicals at elevated temperatures, including aromatic or halogenated hydrocarbons, strong acids, bases, ketones, and other aggressive industrial substances. Hydrolytic stability in boiling water is excellent. Environments that deteriorate the polymers are high-temperature steam, concentrated sulfuric acid, and boiling caustic materials. Because of their various properties, LCPs are useful for electrical and mechanical parts, food containers, and any other applications requiring chemical inertness and high strength.

High-Density Polyethylene (HDPE)

High-density polyethylene (HDPE) or polyethylene high-density (PEHD) is a polyethylene thermoplastic made from petroleum. HDPE has little branching, giving it stronger intermolecular forces and tensile strength than lower-density polyethylene. It is also harder and more opaque and can withstand somewhat higher temperatures (120° C. for short periods, 110° C. continuously). High-density polyethylene, unlike polypropylene, cannot withstand normally-required autoclaving conditions. The lack of branching is ensured by an appropriate choice of catalyst (e.g., Ziegler-Natta catalysts) and reaction conditions. HDPE contains the chemical elements carbon and hydrogen. Hollow goods manufactured through blow molding are the most common application area for HDPE.

Polypropylene (PP)

Polypropylene or polypropene (PP) is a thermoplastic polymer, made by the chemical industry and used in a wide variety of applications, including packaging, textiles (e.g. ropes, thermal underwear and carpets), stationery, plastic parts and reusable containers of various types, laboratory equipment, loudspeakers, automotive components, and polymer banknotes. An addition polymer made from the monomer propylene, it is rugged and unusually resistant to many chemical solvents, bases and acids.

Most commercial polypropylene is isotactic and has an intermediate level of crystallinity between that of low density polyethylene (LDPE) and high density polyethylene (HDPE); its Young's modulus is also intermediate. PP is normally tough and flexible, especially when copolymerized with ethylene. This allows polypropylene to be used as an engineering plastic, competing with materials such as ABS. Polypropylene is reasonably economical, and can be made translucent when uncolored but is not as readily made transparent as polystyrene, acrylic or certain other plastics. It is often opaque and/or colored using pigments. Polypropylene has good resistance to fatigue.

Polypropylene has a melting point of ~160° C. (320° F.), as determined by Differential scanning calorimetry (DSC). The MFR (Melt Flow Rate) or MFI (Melt Flow Index) is a measure of PP's molecular weight. This helps to determine how easily the molten raw material will flow during processing. Higher MFR PPs fill the plastic mold more easily during the injection or blow molding production process. As the melt flow increases, however, some physical properties, like impact strength, will decrease.

There are three general types of PP: homopolymer, random copolymer and block copolymer. The comonomer used is typically ethylene. Ethylene-propylene rubber or EPDM added to PP homopolymer increases its low temperature impact strength. Randomly polymerized ethylene monomer added to PP homopolymer decreases the polymer crystallinity and makes the polymer more transparent.

Polypropylene is liable to chain degradation from exposure to UV radiation such as that present in sunlight. For external applications, UV-absorbing additives must be used. Carbon black also provides some protection from UV attack. The polymer can also be oxidized at high temperatures, a common problem during molding operations. Anti-oxidants are normally added to prevent polymer degradation.

The relative orientation of each methyl group relative to the methyl groups on neighboring monomers has a strong effect on the finished polymer's ability to form crystals, because each methyl group takes up space and constrains backbone bending.

Like most other vinyl polymers, useful polypropylene cannot be made by radical polymerization due to the higher reactivity of the allylic hydrogen (leading to dimerization) during polymerization. Moreover, the material that can result from such a process can have methyl groups arranged randomly, so called atactic PP. The lack of long-range order prevents any crystallinity in such a material, giving an amorphous material with very little strength and only specialized qualities suitable for niche end uses.

A Ziegler-Natta catalyst is able to limit incoming monomers to a specific orientation, only adding them to the polymer chain if they face the right direction. Most commercially available polypropylene is made with such Ziegler-Natta catalysts, which produce mostly isotactic polypropylene. With the methyl group consistently on one side, such molecules tend to coil into a helical shape; these helices then line up next to one another to form the crystals that give commercial polypropylene many of its desirable properties.

More precisely engineered Kaminsky catalysts have been made, which offer a much greater level of control. Based on metallocene molecules, these catalysts use organic groups to control the monomers being added, so that a proper choice of catalyst can produce isotactic, syndiotactic, or atactic polypropylene, or even a combination of these. Aside from this qualitative control, they allow better quantitative control, with a much greater ratio of the desired tacticity than previous Ziegler-Natta techniques. They also produce narrower molecular weight distributions than traditional Ziegler-Natta catalysts, which can further improve properties.

To produce a rubbery polypropylene, a catalyst can be made which yields isotactic polypropylene, but with the organic groups that influence tacticity held in place by a relatively weak bond. After the catalyst has produced a short length of polymer which is capable of crystallization, light of the proper frequency is used to break this weak bond, and remove the selectivity of the catalyst so that the remaining length of the chain is atactic. The result is a mostly amorphous material with small crystals embedded in it. Since each chain has one end in a crystal but most of its length in the soft, amorphous bulk, the crystalline regions serve the same purpose as vulcanization.

Melt processing of polypropylene can be achieved via extrusion and molding. Common extrusion methods include production of melt blown and spun bond fibers to form long rolls for future conversion into a wide range of useful products such as face masks, filters, nappies and wipes. The most common shaping technique is injection molding, which is used for parts such as cups, cutlery, vials, caps, containers, housewares and automotive parts such as batteries. The related techniques of blow molding and injection-stretch blow molding are also used, which involve both extrusion and molding.

The large number of end use applications for PP is often possible because of the ability to tailor grades with specific molecular properties and additives during its manufacture. For example, antistatic additives can be added to help PP surfaces resist dust and dirt. Many physical finishing techniques can also be used on PP, such as machining. Surface treatments can be applied to PP parts in order to promote adhesion of printing ink and paints.

Since polypropylene is resistant to fatigue, most plastic living hinges, such as those on flip-top bottles, are made from this material. However, it is important to ensure that chain molecules are oriented across the hinge to maximize strength. Very thin sheets of polypropylene are used as a dielectric within certain high performance pulse and low loss RF capacitors.

High-purity piping systems are built using polypropylene. Stronger, more rigid piping systems, intended for use in potable plumbing, hydronic heating and cooling, and reclaimed water applications, are also manufactured using polypropylene. This material is often chosen for its resistance to corrosion and chemical leaching, its resilience against most forms of physical damage, including impact and freezing, and its ability to be joined by heat fusion rather than gluing.

Many plastic items for medical or laboratory use can be made from polypropylene because it can withstand the heat in an autoclave. Its heat resistance also enables it to be used as the manufacturing material of consumer-grade kettles. Food containers made from it will not melt in the dishwasher, and do not melt during industrial hot filling processes. For this reason, most plastic tubs for dairy products are polypropylene sealed with aluminum foil (both heat-resistant materials). After the product has cooled, the tubs are often given lids made of a less heat-resistant material, such as LDPE or polystyrene. Such containers provide a good hands-on example of the difference in modulus, since the rubbery (softer, more flexible) feeling of LDPE with respect to PP of the same thickness is readily apparent. Rugged, translucent, reusable plastic containers made in a wide variety of shapes and sizes for consumers from various companies such as Rubbermaid and Sterilite are commonly made of polypropylene, although the lids are often made of somewhat more flexible LDPE so they can snap on to the container to close it. Polypropylene can also be made into disposable bottles to contain liquid, powdered or similar consumer products, although HDPE and polyethylene terephthalate are commonly also used to make bottles. Plastic pails, car batteries, wastebaskets, cooler containers, dishes and pitchers are often made of polypropylene or HDPE, both of which commonly have rather similar appearance, feel, and properties at ambient temperature.

Polypropylene is a major polymer used in nonwovens, with over 50% used for diapers or sanitary products where it is treated to absorb water (hydrophilic) rather than naturally repelling water (hydrophobic). Other interesting nonwoven uses include filters for air, gas and liquids where the fibers can be formed into sheets or webs that can be pleated to form cartridges or layers that filter in various efficiencies in the 0.5 to 30 micron range. Such applications can be seen in the house as water filters or air conditioning type filters. The high surface area and naturally hydrophobic polypropylene nonwovens are ideal absorbers of oil spills with the familiar floating barriers near oil spills on rivers.

A common application for polypropylene is as Biaxially Oriented polypropylene (BOPP). These BOPP sheets are used to make a wide variety of materials including clear bags. When polypropylene is biaxially oriented, it becomes crystal clear and serves as an excellent packaging material for artistic and retail products.

Polypropylene's most common medical use is in the synthetic, nonabsorbable suture Prolene, manufactured by Ethicon Inc.

Polypropylene is most commonly used for plastic moldings where it is injected into a mold while molten, forming complex shapes at relatively low cost and high volume, examples include bottle tops, bottles and fittings.

Recently it has been produced in sheet form and this has been widely used for the production of stationary folders, packaging and storage boxes. The wide color range, durability and resistance to dirt make it ideal as a protective cover for papers and other materials. It is used in Rubik's cube stickers because of these characteristics.

Expanded Polypropylene (EPP) is a foam form of polypropylene. EPP has very good impact characteristics due to its low stiffness; this allows EPP to resume its shape after impacts. EPP is extensively used in model aircraft and other radio controlled vehicles by hobbyists. This is mainly due to its ability to absorb impacts, making this an ideal material for RC aircraft for beginners and amateurs.

Silicon Dioxide (SiO2)

The chemical compound silicon dioxide, also known as silica, is an oxide of silicon with a chemical formula of $SiO_2$. Oxides of silicon, commonly referred to as "SiOx," include silicon dioxide. Silica is most commonly found in nature as sand or quartz, as well as in the cell walls of diatoms. It is a principal component of most types of glass and substances such as concrete. Silica is the most abundant mineral in the Earth's crust.

$SiO_2$ has a number of distinct crystalline forms in addition to amorphous forms. With the exception of stishovite and fibrous silica, all of the crystalline forms involve tetrahedral $SiO_4$ units linked together by shared vertices in different arrangements. Silicon-oxygen bond lengths vary between the different crystal forms. In a-quartz the Si—O—Si angle is 144°. The only stable form under normal conditions is a-quartz and this is the form in which crystalline silicon dioxide is usually encountered.

Silicon dioxide is formed when silicon is exposed to oxygen (or air). A very thin layer (approximately 1 nm or 10 Å) of so-called 'native oxide' is formed on the surface when silicon is exposed to air under ambient conditions. Higher temperatures and alternative environments are used to grow well-controlled layers of silicon dioxide on silicon, for example at temperatures between 600 and 1200° C., using the so-called "dry" or "wet" oxidation with $O_2$ or $H_2O$, respectively. The thickness of the layer of silicon replaced by the dioxide is 44% of the thickness of the silicon dioxide layer produced. Alternative methods used to deposit a layer of $SiO_2$ include: Low temperature oxidation (400-450° C.) of silane; Decomposition of tetraethyl orthosilicate (TEOS) at 680-730° C.; Plasma enhanced chemical vapor deposition using TEOS at about 400° C.; Polymerization of tetraethyl orthosilicate (TEOS) at below 100° C. using amino acid as catalyst.

Pyrogenic silica (sometimes called fumed silica or silica fume), which is a very fine particulate form of silicon dioxide, is prepared by burning $SiCl_4$ in an oxygen rich hydrocarbon flame to produce a "smoke" of $SiO_2$. Amorphous silica, silica gel, is produced by the acidification of solutions of sodium silicate to produce a gelatinous precipitate that is then washed and then dehydrated to produce colorless microporous silica.

Aluminum Oxide ($Al_2O_3$)

Aluminum oxide is an amphoteric oxide of aluminum with the chemical formula $Al_2O_3$. It is also commonly referred to as alumina, corundum, sapphire, ruby or aloxite. Aluminum oxide is an electrical insulator but has a relatively high thermal conductivity (40 Wm-1K-1) for a ceramic material. In its most commonly occurring crystalline form, called corundum or a-aluminum oxide, its hardness makes it suitable for use as an abrasive and as a component in cutting tools. Aluminum oxide is responsible for resistance of metallic aluminum to weathering. Metallic aluminum is very reactive with atmospheric oxygen, and a thin passivation layer of alumina (4 nm thickness) forms in about 100 picoseconds on any exposed aluminum surface. This layer protects the metal from further oxidation. The thickness and properties of this oxide layer can be enhanced using a process called anodizing. A number of alloys, such as aluminum bronzes, exploit this property by including a proportion of aluminum in the alloy to enhance corrosion resistance. The alumina generated by anodizing is typically amorphous, but discharge assisted oxidation processes such as plasma electrolytic oxidation result in a significant proportion of crystalline alumina in the coating, enhancing its hardness. The most common form of crystalline alumina, a-aluminum oxide, is known as corundum. Alumina also exists in other phases. Each has a unique crystal structure and properties. Aluminum hydroxide minerals are the main component of bauxite, the principal ore of aluminum. Alumina tends to be multi-phase; e.g., constituting several of the alumina phases rather than solely corundum.

Polyvinyl Alcohol (PVOH, PVA, or PVAL)

Polyvinyl alcohol (PVOH, PVA, or PVAL) is a water-soluble synthetic polymer. Polyvinyl alcohol has excellent film forming, emulsifying, and adhesive properties. It is also resistant to oil, grease and solvent. It is odorless and non-toxic. It has high tensile strength and flexibility, as well as high oxygen and aroma barrier properties. However these properties are dependent on humidity, in other words, with higher humidity more water is absorbed. The water, which acts as a plasticizer, will then reduce its tensile strength, but increase its elongation and tear strength. PVA is fully degradable and is a quick dissolver. PVA has a melting point of 230° C. and 180–190° C. for the fully hydrolyzed and partially hydrolyzed grades, respectively. It decomposes rapidly above 200° C. as it can undergo pyrolysis at high temperatures.

PVA is an atactic material but exhibits crystallinity as the hydroxyl groups are small enough to fit into the lattice without disrupting it. Unlike most vinyl polymers, PVA is not prepared by polymerization of the corresponding monomer. The monomer, vinyl alcohol, almost exclusively exists as the tautomeric form, acetaldehyde. PVA instead is prepared by partial or complete hydrolysis of polyvinyl acetate to remove acetate groups.

Nanopolymers

Polymer nanocomposite (PNC) is a polymer or copolymer having dispersed in its nanoparticles. These may be of different shape (e.g., platelets, fibers, spheroids), but at least one dimension is in the range of 1 to 50 nm. The transition from micro- to nano-particles leads to changes in physical as well as chemical properties. Two of the major factors in this are the increase in the ratio of the surface area to volume, and the size of the particle. The increase in surface area-to-volume ratio, which increases as the particles get smaller, leads to an increasing dominance of the behavior of atoms on the surface area of particle over that of those interior of the particle. This affects the properties of the particles when they are reacting with other particles. Because of the higher surface area of the nano-particles the interaction with the other particles within the mixture is more and this increases the strength, heat resistance etc. and many factors do change for the mixture.

An example of a nanopolymer is silicon nanospheres which show quite different characteristics. The particle size is 40-100 nm and it is much harder than silicon (a hardness between that of sapphire and diamond). Many technical applications of biological objects like proteins, viruses or bacteria such as chromatography, optical information technology, sensors, catalysis and drug delivery require their immobilization. Carbon nanotubes, gold particles and synthetic polymers are used for this purpose. This immobilization has been achieved predominantly by adsorption or by chemical binding and to a lesser extent by incorporating these objects as guests in host matrices. In the guest host systems, an ideal method for the immobilization of biological objects and their integration into hierarchical architectures should be structured on a nanoscale to facilitate the interactions of biological nano-objects with their environment. Due to the large number of natural or synthetic polymers available and the advanced techniques developed to process such systems to nanofibers, rods, tubes etc. make polymers a good platform for the immobilization of biological objects.

Polymer fibers are, in general, produced on a technical scale by extrusion, e.g., a polymer melt or a polymer solution is pumped through cylindrical dies and spun/drawn by a take-up device. The resulting fibers have diameters typically on the 10-µm scale or above. To come down in diameter into the range of several hundreds of nanometers or even down to a few nanometers, electrospinning is today still the leading polymer processing technique available. A strong electric field of the order of 103 V/cm is applied to the polymer solution droplets emerging from a cylindrical die. The electric charges, which are accumulated on the surface of the droplet, cause droplet deformation along the field direction, even though the surface tension counteracts droplet evolution. In supercritical electric fields, the field strength overbears the surface tension and a fluid jet emanates from the droplet tip. The jet is accelerated towards the counter electrode. During this transport phase, the jet is subjected to strong electrically driven circular bending motions that cause a strong elongation and thinning of the jet, a solvent evaporation until, finally, the solid nanofiber is deposited on the counter electrode.

Electro spinning, co-electrospinning, and the template methods based on nanofibers yield nano-objects which are, in principle, infinitively long. For a broad range of applications including catalysis, tissue engineering, and surface modification of implants this infinite length is an advantage. But in some applications like inhalation therapy or systemic drug delivery, a well-defined length is required. The template method to be described in the following has the advantage such that it allows the preparation of nanotubes and nanorods with very high precision. The method is based on the use of well-defined porous templates, such as porous aluminum or silicon. The basic concept of this method is to exploit wetting processes. A polymer melt or solution is brought into contact with the pores located in materials characterized by high energy surfaces such as aluminum or silicon. Wetting sets in and covers the walls of the pores with a thin film with a thickness of the order of a few tens of nanometers. This process happens typically within a minute for temperatures about 50 K above the melting temperature or glass transition temperature, even for highly viscous polymers, such as, for instance, polytetrafluoroethylene, and this holds even for pores with an aspect ratio as large as 10,000. To obtain nanotubes, the polymer/template system is cooled down to room temperature or the solvent is evaporated, yielding pores covered with solid layers. The resulting tubes can be removed by mechanical forces for tubes up to 10 µm in length, e.g., by just drawing them out from the pores or by selectively dissolving the template. The diameter of the nanotubes, the distribution of the diameter, the homogeneity along the tubes, and the lengths can be controlled.

The size-dependent and pressure-dependent glass transition temperatures of free-standing films or supported films having weak interactions with substrates decreases with decreasing of pressure and size. However, the glass transition temperature of supported films having strong interaction with substrates increases of pressure and the decrease of size.

Nanocomposites are polymer structures that contain fillers, typically silicate nanoclays, with at least one dimension in the nanometer range. The fillers separate into tiny platelets that disperse into a matrix of layers. Because the matrix of layers creates a tortuous path for gasses trying to permeate through the film, the barrier properties of the modified polymer are improved. However, the challenge is to ensure that that the filler dispersion is consistent. In addition to better barrier properties, nanocomposites modified films also have improved dimensional stability and stiffness and, because crystallinity is increased, enhanced clarity. Nanocomposite masterbatches are commercially available for nylon and polyolefins. The oxygen barrier of nylon nanocomposite films can be as much as 50 percent higher than a nonmodified nylon. Polyethylene and polypropylene nanocomposite structures have shown improvement in gas barrier of 25 to 50 percent and in water vapor of 10 to 15 percent in laboratory settings. Achieving consistent barrier properties on a commercial scale remains challenging. Nanocomposite technology is very much an emerging science. It shows a great deal of promise and as more options become available for film applications it will have a significant impact on barrier material options.

Saran

Saran is the trade name for a number of polymers made from vinylidene chloride (especially polyvinylidene chloride or PVDC), along with other monomers. Saran film has a very low permeability to water vapor, flavor and aroma molecules, and oxygen compared to other plastics. The barrier to oxygen prevents food spoilage, and the barrier to flavor and aroma molecules helps food retain its flavor and aroma. Saran also possesses gas barrier properties.

Polytrimethylene Terephthalate (PTT)

Polytrimethylene Terephthalate (PTT) is a semi crystalline polymer that has many of the same advantages as PET. PTT exhibits good tensile strength, flexural strength, and stiffness. It has excellent flow and surface finish. PTT can have more uniform shrinkage and better dimensional stability in some applications than competing semicrystalline materials. PTT has excellent resistance to a broad range of chemicals at room temperature, including aliphatic hydrocarbons, gasoline, carbon tetrachloride, perchloroethylene, oils, fats, alcohols, glycols, esters, ethers and dilute acids and bases. Strong bases may attack PTT compounds. Impact modifiers and reinforcing fibers (long glass, short glass, or carbon) can be used to increase the impact properties, as well as the strength and stiffness of PTT.

Polytrimethylene Naphthalate (PTN)

Poly(trimethylene phthalates or naphthalate) and copolymers are aromatic polyesters made by polycondensation of 1,3-propanediol (PDO) and terephthalic acid (PTT), isophthalic acid (PTI) or naphthalic acid (PTN) and/or with comonomers (isophthalic acid, 1,4-butanediol, etc.). Films of PTN possess good barrier properties.

Polyethylene Naphthalate (PEN)

Polyethylene naphthalate (PEN) is a polyester with good barrier properties (even better than polyethylene terephthalate). Because it provides a very good oxygen barrier, it is particularly well-suited for bottling beverages that are susceptible to oxidation, such as beer. It is prepared from ethylene glycol and one or more naphthalene dicarboxylic acids by condensation polymerization.

Polyurethane

A polyurethane is any polymer consisting of a chain of organic units joined by urethane (carbamate) links. Polyurethane polymers are formed through step-growth polymerization by reacting a monomer containing at least two isocyanate functional groups with another monomer containing at least two hydroxyl (alcohol) groups in the presence of a catalyst. Polyurethane formulations cover an extremely wide range of stiffness, hardness, and densities. Though the properties of the polyurethane are determined mainly by the choice of polyol, the diisocyanate exerts some influence, and must be suited to the application. The cure rate is influenced by the functional group reactivity and the number of functional isocyanate groups. The mechanical properties are influenced by the functionality and the molecular shape. The choice of diisocyanate also affects the stability of the polyurethane upon exposure to light. Polyurethanes made with aromatic diisocyanates yellow with exposure to light, whereas those made with aliphatic diisocyanates are stable. Softer, elastic, and more flexible polyurethanes result when linear difunctional polyethylene glycol segments, commonly called polyether polyols, are used to create the urethane links. This strategy is used to make spandex elastomeric fibers and soft rubber parts, as well as foam rubber. More rigid products result if polyfunctional polyols are used, as these create a three-dimensional cross-linked structure which, again, can be in the form of a low-density foam.

Polyether Block Amide (PEBAX®)

Polyether block amide is a thermoplastic elastomer or a flexible polyamide without plasticizer consisting of a regular linear chain of rigid polyamide segments and flexible polyether segments.

Parylene C

Parylene is the trade name for a variety of chemical vapor deposited poly(p-xylylene) polymers used as moisture barriers and electrical insulators. Among them, Parylene C is the most popular due to its combination of barrier properties, cost, and other manufacturing advantages.

Silicone

Silicones, also referred to as polymerized siloxanes or polysiloxanes, are mixed inorganic-organic polymers with the chemical formula [R2SiO]n, where R is an organic group such as methyl, ethyl, or phenyl. These materials consist of an inorganic silicon-oxygen backbone ( . . . —Si—O—Si—O—Si—O— . . . ) with organic side groups attached to the silicon atoms, which are four-coordinate. In some cases organic side groups can be used to link two or more of these —Si—O— backbones together. By varying the —Si—O— chain lengths, side groups, and crosslinking, silicones can be synthesized with a wide variety of properties and compositions. They can vary in consistency from liquid to gel to rubber to hard plastic. The most common siloxane is linear polydimethylsiloxane (PDMS), a silicone oil. The second largest group of silicone materials is based on silicone resins, which are formed by branched and cage-like oligosiloxanes.

Fabrication of the Composite Wall

The various layers of the composite wall, including the gas barrier layers, need not be situated in any particular order, but those of superior resistance to acidity, temperature, mechanical abrasion, and superior biocompatibility profile are preferably employed as layers contacting the gastric environment. Those with superior resistance to, e.g., acidity and temperature, are preferably employed as layers contacting the central lumen of the balloon.

The various layers of the wall can include a single layer or up to 10 or more different monolayers; however, a film thickness of from 0.001 inches (0.0254 cm) to 0.004 inches (0.010 cm) thick is desirable such that the resulting balloon compacted to fit into a swallowable capsule. The resulting composite wall preferably has good performance specifications with respect to each category listed in Tables 1a-b.

Films that are co-extruded are advantageously employed, as some adhesives may contain leachables that are undesirable from a biocompatibility perspective. In addition, coextrusion allows for better blending such that the materials maintain their original properties when combined in this fashion and are less likely to be subject to delamination when exposed to gastric motility forces.

Combining films with similar properties, e.g., two film layers with excellent gas barrier properties, in a composite wall is advantageous for use in a gastric balloon containing nitrogen, oxygen, $CO_2$ or a mixture thereof as the inflation gas or where the external environment the product is to be placed in, contains a mixture of gases including $CO_2$, e.g., the stomach. A primary advantage of such composite films is that restrictions on film thickness can be observed without sacrifice of gas barrier properties. Such a configuration also contributes to reducing the effects of processing damage (e.g., manufacturing and compacting) and damage due to exposure to in vivo conditions (e.g., gastric motility forces).

In a particularly preferred embodiment, the composite wall includes a plurality of layers. The first layer is an outer protective layer that is configured for exposure to the gastric environment. This layer is resistant to mechanical forces, exposure to water (vapor), abrasion, and high acidity levels. Nylon or more specifically, Nylon 12 is particularly preferred for the layer exposed to the gastric environment, and is especially resistant to mechanical forces.

In an alternative embodiment, polyurethane is RF welded to saran to yield a 6-7 mil thick composite wall. In another embodiment, a five layer system is provided comprising a layer of saran sandwiched between two polyurethane layers. Between the saran layer and each of the polyurethane layers is a tie layer. The layers can be welded together, co-extruded or adhered using an adhesive. This tri-layer is then co-extruded to Nylon on each side, and then a final sealing layer (polyethylene or the like) is added to one of the nylon layers for the total composite wall. A representative example of material combinations that are commercially available or manufacturable is provided in Table 2. The orientation of the layers (innermost—in contact with the central balloon lumen, or outermost—in contact with the gastric environment) is also indicated if more than two layers are described to support a suggested composite wall.

Most of the film resins listed in Table 2 provide some degree of gas barrier properties. Therefore, many can be used solely to form the balloon wall as a monolayer film; however they can also be used in conjunction with other film resins to meet the desired gas retention and mechanical specifications for the useful life of the balloon based on the inflation gas and external environment the balloon is to be placed in. These film resins can also be coated with gas barrier coatings listed in Tables 1a-b. Additional film layers can be added to form the total composite wall. While such additional layers may not impart substantial barrier properties, they can provide structural and/or mechanical properties, protection for the other layers of the composite wall that are susceptible to water vapor, humidity, pH, or the like, or other desirable properties. The film layers can be assembled using various adhesives, via co-extrusion, via lamination, and/or using tie layers and such to create a composite wall that meets the requirements of an intragastric balloon suitable for use for at least 25 days, or up to 90 days or more, with the specified gas retention properties. Table 2 provides a list of layers and layer combinations suitable for use in composite walls for an intragastric balloon. The composite description, resin abbreviation, configuration (single layer, bilayer, trilayer, or the like) and trade name of commercially available combinations are listed. The number of layers indicated does not include any adhesive layers or tie layers used to fabricate the composite wall, such that a 6-layer composite wall may, for example, have two or three adhesive layers and/or tie layers that make up the total composite wall, and therefore the total number of layers can be eight or nine in final form. The term "layer" as used herein is a broad term, and is to be given its ordinary and customary meaning to a person of ordinary skill in the art (and is not to be limited to a special or customized meaning), and refers without limitation to a single thickness of a homogenous substance (e.g., a coating such as SiOx, or a layer such as PET, or a uniform polymeric blend), as well as to a supporting layer having a coating thereon (wherein a "coating" is, e.g., a material typically employed in conjunction with substrate that provides structural support to the coating layer). For example, a PET-SiOx "layer" is referred to herein, wherein a layer of Si-Ox is provided on a supporting PET layer. In the following table, as well as other tables referring to composite walls, a forward slash ("/") is used to indicate a boundary between layers of the specified chemistries. The boundary can be a discontinuity, or can be a tie layer, adhesive layer, or other layer separating the layers of recited chemistry.

TABLE 2

| Example Film Composite Walls* | Abbreviation | Trade name |
|---|---|---|
| polyethylene terephthalate | PET | Mylar |
| metalized oriented polyethylene terephthalate | metalized OPET | Custom |
| polyvinyl alcohol coated oriented polypropylene | PVOH coated OPP | Bicor |
| metalized biaxially oriented nylon 6 | metalized OPA6 | Custom |
| Biaxally oriented Nylon/ethylene vinyl alcohol/biaxially oriented Nylon | OPA/EVOH/OPA | Honeywell Oxyshield Plus |
| Nylon/ethylene vinyl alcohol/Low Density Polyethylene | Nylon/EVOH/LDPE | Custom |
| polyvinylidene chloride coated oriented polyethylene terephthalate | PVDC/OPET | Mylar |
| polyvinylidene chloride coated oriented polypropylene | PVCD/OPP | Custom |
| polyvinylidene chloride coated biaxially oriented Nylon 6 | PVCD/OPA6 | Honeywell Oxyshield |
| high density polyethylene/ethylene vinyl alcohol | HDPE/EVOH | Custom |
| polypropylene/ethylene vinyl alcohol laminate | PP/EVOH | Custom |
| polyethylene terephthalate/ethylene vinyl alcohol | PET/EVOH | Custom |
| metalized oriented polypropylene | metalized OPP | Custom |
| sealable PVDC coated oriented polypropylene | PVDC coated PP | Custom |
| polyvinylidene fluoride | PVDF | Custom |
| Polyvinyl chloride | PVC | Custom |
| polyvinyl fluoride | PVF | Tedlar |
| polychlorofluoroethylene | PCTFE | ACLAR UltRx, SupRx, Rx |
| amine-based epoxy coated Nylon | epoxy coated PA6 | Bairocade |
| polyvinyl chloride-polyvinylidene chloride copolymer | PVC-PVDC | Custom |
| medium density polyethylene | MDPE | Custom |
| Nylon/Polypropylene | Nylon/PP laminate | Custom |
| Nylon-High Density Polyethylene | Nylon-HDPE laminate | Custom |
| Nylon 12/Ethyl Methyl Acrylate/Polyvinylidene Chloride/Ethyl Methyl Acrylate/Nylon 12/Linear Low Density Polyethylene + Low Density Polyethylene | Co-extruded Nylon 12-encapsulated PVDC-Nylon 12-LLDPE + LDPE | Custom Co-extruded blend |
| Multi-layer Nylon 12/ Linear Low Density Polyethylene + Low Density Polyethylene | Co-extruded multi-layer Nylon 12-LLDPE + LDPE | Custom Co-Extruded Blend |
| acetylene plasma coating on polyester | PET/A | Custom |
| difluoroethylene coating on polyethylene terephthalate | PET/DA | Custom |
| oriented polypropylene | OPP | Custom |
| cast propylene | CPP | Custom |
| high density polyethylene | HDPE | Custom |
| cyclic olefin copolymer | COC | Custom |
| oriented polystyrene | OPS | Custom |
| Fluorinated Ethylene Propylene | FEP | Custom |
| difluoroethylene coating on low density polyethylene | LDPE/D | Custom |
| difluoroethylene coating on polypropylene | PP/D | Custom |

TABLE 2-continued

| Example Film Composite Walls* | Abbreviation | Trade name |
|---|---|---|
| acetylene plasma coating on polypropylene | PP/A | Custom |
| acetylene plasma coating on low density polyethylene | LDPE/A | Custom |
| polybutylene terephthalate polyether polyether glycol copolymer | TPC-ET | Hytrel |
| polyether block amide TPE | PEBA | Pebax |
| oxide coated biaxially oriented Nylon | oxide coated PA | Honeywell Oxyshield Ultra |
| Nanoclay/nylon | MXD6/Nanoclay | Imperm/Aegis OXCE |
| Polyethylene Terephthalate/Silicone Dioxide | PET/SiOx | BestPET/TechBarrier |
| Polyethylene Terephthalate/Oxygen scavengers | PET + 02 Scavengers | MonoxBar |
| Modified Polyethylene Terephthalate | Modified PET | DiamondClear |
| Polyethylene Terephthalate/Nylon 6 | PET/MXD6 | HP867 |
| Amorphous polyvinyl alcohol | Amorphous PVOH | Nichigo G-Polymer |
| Nylon 6/Ethyl vinyl alcohol/Linear Low Density Polyethylene | Nylon 6/EVOH/LLDPE | Custom |
| Ethyl vinyl alcohol/Poly-Propylene/Ethyl vinyl alcohol | EVOH/PP/EVOH | Custom |
| Ethyl vinyl alcohol/Nylon | EVOH/Nylon | Custom |
| Polyethylene/Ethyl vinyl alcohol/Polyethylene | PE/EVOH/PE | Custom |
| Polyethylene/Ethyl vinyl alcohol/Polyethylene Terephthalate | PE/EVOH/PET | Custom |
| Silicon dioxide-coated Polyethylene Terephthalate/Linear Low Density Polyethylene/Ethyl vinyl alcohol/Linear Low Density Polyethylene | PET-SiOx/LLDPE/EVOH/LLDPE | Custom |
| Aluminum Oxide-coated Polyethylene Terephthalate/Polyethylene | PET-Al$_2$O$_3$/LLDPE | Custom |
| Polyethylene/Ethyl vinyl alcohol/Linear Low Density Polyethylene | PE/EVOH/LLDPE | Custom |
| Polyethylene Terephthalate/Polyethylene/Polyethylene/Bi-axially oriented Ethyl vinyl alcohol | PET/PE/OEVOH/PE | Custom |
| Polyethylene Terephthalate/Polyethylene/Ethyl vinyl alcohol/Ethyl vinyl alcohol/Polyethylene | PET/PE/EVOH/EVOH/EVOH/PE | Custom |
| Polyethylene Terephthalate/Polyethylene/Nylon 6/Ethyl vinyl alcohol/Nylon 6/Polyethylene | PET/PE/Nylon 6/EVOH/Nylon 6/PE | Custom |
| Silicon dioxide-coated Polyethylene Terephthalate/Polyethylene/Ethyl vinyl alcohol/Polyethylene | PET-SiOx/PE/EVOH/PE | Custom |
| Polyethylene/Ethyl vinyl alcohol/polyvinylchloride | PE/EVOH/PVDC | Custom |
| Polyethylene Terephthalate/Linear Low Density Polyethylene/Ethyl vinyl alcohol/Linear Low Density Polyethylene | PET/LLDPE/EVOH/LLDPE | Custom |
| Kurrarister C-coated Polyethylene Terephthalate/Polyethylene/Ethyl vinyl alcohol/Polyethylene | PET-Kurrarister-C/PE/EVOH/PE | Custom |
| Polyethylene Terephthalate/Polyethylene/Nylon 6/Ethyl vinyl alcohol/Nylon 6/Polyethylene | PET/PE/Nylon 6/EVOH/Nylon 6/PE | Custom |
| Nylon 6/Ethyl vinyl alcohol/Polyvinylchloride/Low Density Polyethylene | Nylon 6/EVOH/PVDC/Nylon 6/LDPE | Custom |
| Polyimide | PI | Custom |
| Polyimide/Linear Low Density Polyethylene | PI/LLDPE | Custom |
| Polyimide/Polyvinylchloride | PI/PVdC | Custom |
| Polyimide/Polyvinylchloride/Linear Low Density Polyethylene | PI/PVdC/LLDPE | Custom |

In particularly preferred embodiments, the composite wall has a thickness of 0.005 inches or less (5.0 mil or less); however, in certain embodiments a thicker composite wall may be acceptable. Generally it is preferred that the composite wall have a thickness of no more than 0.004 inches (4.0 mil).

Fabrication of the Balloon

To ensure good mechanical strength of the balloon, the balloon is preferably thermoformed and sealed such that the edges of the pieces used to form the balloon are overlapping. This can be accomplished by any suitable method. For example, two flat sheets of material can be placed in a frame with magnetized edges to hold the two sheets in place. Slack can be added to the piece of film to orient the material such that it maintains its properties after the thermoforming process. The frame can be placed over a mold that represents a hemisphere the balloon. A heater (e.g., a 4520 watt infrared heater) can be used to form the material, and a vacuum can be pulled. The material, with slack put in it prior to vacuum being applied, re-orients the material such that it is more evenly distributed around the hemisphere shape. The material is preferably thickest in the middle and is made thinner on the sides where it will be welded to a second piece to create a sphere or ellipsoid having a substantially uniform wall thickness. For example, starting with a 0.0295" film, the middle of the film or subsequent apex has an ending film thickness of 0.0045" and the edges have an ending thickness of 0.0265" for subsequent overlapping during the welding process.

The valve can be adhered to the (e.g., polyethylene, PE) side of one of the hemispheres and protrude out of the opposite (e.g., nylon) side. One hemisphere typically consists of Nylon as the outermost layer and the second hemisphere typically has polyethylene (sealing web) as the outermost layer. The edges of the two hemispheres are preferably aligned such that they overlap by at least 1 mm and no more than 5 mm. Alignment and overlay of the two hemispheres is done to compensate for the thinning at the edges during the thermoforming process, which in turn inhibits seam bursts in vivo. Each half of the spheroid is placed on a fixture and the excess from the thermoforming process is trimmed. On a multi-layer film, the sealing layer, a PE or similar layer is bonded to the sealing layer of the second film half To do this the film of the hemisphere that has the nylon exposed to the external environment is folded up along the edges of the sphere on one half such that it can be bonded to the hemisphere with the polyethylene on the outermost layer.

The two film pieces are then sealed using a roller bonder or a band heater. In the roller bonder, the air provides the compression, the heater provides the sealing heat, and a motor that moves the bonder around the area controls the time that is required to ensure proper sealing. In the band heater, there is a heating element, an expandable plug that provides the compression, and a timer. The band is a metal, preferably copper and a spool-like fixture provides the compression needed. Using film layers of different melt temperatures helps ensure integrity of the barrier layers of the final balloon configuration. If two similar materials are welded, then an insulator can be employed. In a preferred embodiment, one sphere is provided with the Nylon layer facing out and the second sphere has a PE layer facing out.

Balloons with Resistance to Spontaneous Deflation

The largest percentage of intragastric balloon malfunctions is due to spontaneous deflations. Spontaneous deflations can occur due to (1) external puncture of the intragastric balloon due to gastric motility forces, (2) over inflation of the balloon due to increased internal pressure of the balloon from uptake of the gastric environment of the gasses and water vapor and (3) under inflation of the balloon that leads to fatiguing of the excess material and subsequent puncture of the balloon. By managing these two variables and tuning these variables to withstand the dynamic gastric environment, the balloon system can be tailored to ensure it remains inflated throughout its useful life. Instances of spontaneous deflation in this intragastric balloon can be minimized by selection of the starting inflation gas in conjunction with selection of the composite wall materials and construction. Selection of the permeability characteristics with respect to water vapor transmission and gas permeability of the composite wall so as to take advantage of the properties of the gastric space contents can enable the rate of diffusion of gases into and out of the balloon to be controlled. This method allows for a tunable method for prevention of under inflation and over inflation.

Another phenomenon seen with gastric balloons and obesity in general is stomach accommodation. In the process of stomach accommodation, the stomach grows to accommodate the space occupying device or excess food that is ingested. In the process of stomach accommodation, the volume of a stomach containing an intragastric balloon grows over time, such that the patient becomes hungrier. However, by controlling gas diffusion and water vapor transmission across the balloon wall over time, the balloon size can also be increased over time by selecting the starting inflation gas(es) and water and other in vivo gas permeability characteristics of the film so as to maintain weight loss. In addition to spontaneous deflations, selecting the permeability characteristics of the composite wall in conjunction with the starting gases and utilizing the transfer of gases and water inside of the balloon from the gastric environment, the balloon can be designed to grow over its useful life in response to stomach accommodation.

Experiments were performed wherein various starting inflation gases were selected in conjunction with varying external gas environments that mimic the stomach gas and water environment in vivo. The stomach environment consists of water, acid (hydrochloric acid), a mixture of gases, and chyme (the semifluid mass of partly digested food expelled by the stomach into the duodenum). Stomach gas usually arises from swallowing air during eating. The composition of air is nitrogen ($N_2$) 78.084%; oxygen ($O_2$) 20.9476%; argon (Ar) 0.934%; carbon dioxide ($CO_2$) 0.0314%; neon (Ne) 0.001818%; methane ($CH_4$) 0.0002%; helium (He) 0.000524%; krypton (Kr) 0.000114%; hydrogen ($H_2$) 0.00005%; and xenon (Xe) 0.0000087%.

Five gases constitute greater than 99% of the gases in gastrointestinal system: $N_2$, $O_2$, $CO_2$, $H_2$ and methane, with nitrogen predominating. Gastric $pCO_2$ closely parallels local (splanchnic) arterial and draining venous blood $pCO_2$ values. Neutralization of stomach acid can also generate gas. For example, when the stomach acid reacts with bicarbonates (e.g., as are present in certain antacids) in the digestive juices, the chemical process creates $CO_2$, which is normally absorbed into the blood stream. Digestion of food in the intestines, mainly through fermentation by colonic bacteria, generates $CO_2$, $H_2$, and methane. Microbes appear to be the sole source of all of the hydrogen and methane produced in the intestine. These arise from fermentation and digestion of nutrients (polysaccharides from fruits and vegetables are not digested in the small intestines). Small quantities of a few other gases, including hydrogen sulfide, indoles, and ammonia can also be generated.

In certain embodiments, it is preferred that the composition of the initial fill gas is substantially characteristic of the composition of the mixture of gases in the in vivo gastric environment. Such an initial fill gas can include only $N_2$ and $CO_2$, or can include only $N_2$, $CO_2$, and $O_2$, or can include $N_2$ and $CO_2$ as well as one or more other gases present in the in vivo environment (e.g., water vapor, $H_2$, $CH_4$, Ar, $H_2S$, or $NH_3$). Argon or another inert gas (or inert gases) can be substituted in part or in whole for $N_2$, which is considered an inert gas in the context of the preferred embodiments. In those embodiments wherein the fill gas includes only $N_2$ or $CO_2$, it is preferred that the initial fill gas comprises from about 75% v/v to about 96% v/v $N_2$, from about 5% v/v to about 15% (vol.) $O_2$, and from about 1% v/v to about 10% v/v $CO_2$, more preferably from about 80% (vol.) to about 85% (vol.) $N_2$, from about 5% (vol.) to about 13% (vol.) $O_2$, and from about 4% (vol.) to about 8% (vol.) $CO_2$. In those embodiments wherein the fill gas includes only $N_2$ or $CO_2$, it is preferred that the initial fill gas comprises from about 4% (vol.) to about 8% (vol.) $CO_2$, with the remainder $N_2$ or another inert gas. In embodiments wherein the initial fill gas comprises other gases in addition to $CO_2$ and the inert gas(es), it is preferred that the initial fill gas comprises from about 4% (vol.) to about 8% (vol.) $CO_2$.

Controlled self-inflation of the intragastric balloon in the in vivo environment can be achieved by using a semi-permeable or permeable composite wall in the balloon and initially filling the balloon with a preselected single gas, such as $N_2$ or $O_2$. The balloon utilizes differences in concentrations of gases and water concentration differences between the internal balloon environment and the external environment in vivo (GI/stomach) to increase and/or decrease the volume and/or pressure over time. To achieve a controlled decrease in volume and/or pressure, a wall can be employed that has a relatively higher permeability to the single gas used to inflate the balloon than to other gases present in the in vivo gastrointestinal environment. For example, if nitrogen gas is employed as the inflation gas, over time in the in vivo environment, the volume and/or pressure in the balloon will decrease as nitrogen diffuses out into the in vivo environment through the oxygen permeable wall. Similarly, if oxygen gas is employed as the inflation gas, over time in the in vivo environment, the volume and/or pressure in the balloon will decrease as oxygen diffuses out into the in vivo environment through the oxygen permeable wall. The differential in partial pressure of the single gas in the balloon (higher) versus the in vivo environment (lower) will drive the process until equilibrium or homeostasis is reached. To achieve a controlled increase in volume and/or pressure, a wall can be employed that has a relatively lower permeability to the single gas used to inflate the balloon than to other gases present in the in vivo gastrointestinal environment. For example, if nitrogen gas is employed as the inflation gas, over time in the in vivo environment, the volume and/or pressure in the balloon will increase as $CO_2$, and all of the other gases present in the gastric environment, diffuse into the balloon through the $CO_2$ permeable wall. The differential in partial pressure of the permeable gas in the balloon (lower) versus the in vivo environment (higher) will drive the process until equilibrium is reached.

In addition, maintaining and/or controlling inflation of the balloon can also be done using the differences in concentrations between the internal balloon environment and external gastric environment in which the balloon volume/pressure can be increased or decreased as needed to extend the useful life of the product. One reason to decrease the pressure can be to first inflate the balloon with a large, but highly diffusible/soluble gas molecule such as $CO_2$ in addition to a more inert gas like nitrogen to pre-stretch the balloon, with the soluble gas diffusing out of the balloon and other gases not originally present in the balloon migrating in to fill the balloon.

Inflation gases can be selected to start with the majority of the gas in the balloon comprising a large, inert gas or a gas that has low diffusivity through the selected composite wall. Examples of inert gases include but are not limited to nitrogen, as well as $SF_6$, $C_2F_6$, $C_3F_8$, $C_4F_{10}$, $C_4F_8$, $C_4F_8$, $C_3F_6$, $CF_4$, and $CClF_2$—$CF_3$. An inert gas in conjunction with a less inert gas(es) that are more soluble in the gastric environment, can be combined to comprise the starting balloon inflation gas composition where the inert gas would be in excess to the more soluble/diffusible gas. In certain embodiments, it is preferred to combine nitrogen as a more soluble/diffusible gas with a gas of lower diffusivity/solubility such as $SF_6$, $C_2F_6$, $C_3F_8$, $C_4F_{10}$, $C_4F_8$, $C_4F_8$, $C_3F_6$, $CF_4$, and $CClF_2$—$CF_3$. For example, a fill gas of certain embodiments can comprise 5% (vol.) of the more soluble/diffusible inert gas in combination with 95% (vol.) of the less soluble/diffusible inert gas (e.g., 5% $N_2$ in combination with 95% $SF_6$); or 10% of the more soluble/diffusible inert gas in combination with 90% of the less soluble/diffusible inert gas (e.g., 10% $N_2$ in combination with 90% $SF_6$); or 15% of the more soluble/diffusible inert gas in combination with 85% of the less soluble/diffusible inert gas (e.g., 15% $N_2$ in combination with 85% $SF_6$); or 20% of the more soluble/diffusible inert gas in combination with 80% of the less soluble/diffusible inert gas (e.g., 20% $N_2$ in combination with 80% $SF_6$); or 25% of the more soluble/diffusible inert gas in combination with 75% of the less soluble/diffusible inert gas (e.g., 25% $N_2$ in combination with 75% $SF_6$); or 30% of the more soluble/diffusible inert gas in combination with 70% of the less soluble/diffusible inert gas (e.g., 30% $N_2$ in combination with 70% $SF_6$); or 35% of the more soluble/diffusible inert gas in combination with 65% of the less soluble/diffusible inert gas (e.g., 35% $N_2$ in combination with 65% $SF_6$); or 40% of the more soluble/diffusible inert gas in combination with 60% of the less soluble/diffusible inert gas (e.g., 40% $N_2$ in combination with 60% $SF_6$); or 45% of the more soluble/diffusible inert gas in combination with 55% of the less soluble/diffusible inert gas (e.g., 45% $N_2$ in combination with 55% $SF_6$); or 50% of the more soluble/diffusible inert gas in combination with 50% of the less soluble/diffusible inert gas (e.g., 50% $N_2$ in combination with 50% $SF_6$). In certain embodiments, an initial fill gas consisting of 20% of the less soluble/diffusible inert gas with the remainder a more soluble/diffusible inert gas is employed; or an initial fill gas consisting of 19-21% of the less soluble/diffusible inert gas with the remainder a more soluble/diffusible inert gas is employed; or an initial fill gas consisting of 18-22% of the less soluble/diffusible inert gas with the remainder a more soluble/diffusible inert gas is employed; or an initial fill gas consisting of 17-23% of the less soluble/diffusible inert gas with the remainder a more soluble/diffusible inert gas is employed; or an initial fill gas consisting of 16-24% of the less soluble/diffusible inert gas with the remainder a more soluble/diffusible inert gas is employed; or an initial fill gas consisting of 15-25% of the less soluble/diffusible inert gas with the remainder a more soluble/diffusible inert gas is employed. For example, an initial fill gas comprising 18-20% $SF_6$ with the remainder as nitrogen can be employed, or 19-21% $SF_6$ with the remainder as nitrogen; or 18-22% $SF_6$ with the remainder as nitrogen; or 17-23% $SF_6$ with the remainder as nitrogen; or 16-24% $SF_6$ with the remainder as nitrogen; or 15-25% $SF_6$ with the remainder as nitrogen.

Patient diet and medications can also affect/control balloon inflation status—primarily by $CO_2$ concentration effects produced in the gastric environment. In addition, gastric pH also affects $CO_2$ concentration. This particular method can also allow for a greater degree of tuning of the device's useful life based on the composite wall material, e.g., barrier/non-barrier and whether the gas that diffuses in is maintained longer in the balloon if it has a barrier wall versus a non-barrier wall. This particular form of self-inflation can be employed using a self-inflating gastric balloon (e.g., initially inflated by a gas generating reaction in the balloon initiated after swallowing), or an inflatable gastric balloon (e.g., inflated using a catheter, with or without endoscopic assistance, delivered nasogastrically or any other delivery method). The method can be used with any gastric balloon, including swallowable balloons and balloons placed in the stomach by, e.g., endoscopic methods. The method is particularly preferred for use in connection with intragastric devices; however, it can also be applied to use in, e.g., pulmonary wedge catheters and urinary incontinence balloon devices. The advantages to this technology include the ability to compensate for stomach accommodation, allowing the balloon to adapt to a stomach that may increase in volume over time, thereby maintaining patient satiety. It also permits starting with a smaller amount of inflation gas constituents for a self-inflating balloon. It can prevent spontaneous deflations by utilizing diffusion gradients between gastric balloon systems and the in vivo gastric environment.

In a particularly preferred embodiment, used in connection with a suitable inert gas such as $SF_6$ and/or $N_2$ (with or without $CO_2$ as an additional inflation gas) as the inflation agent, a multi-layer co-extruded blend for the wall layers is employed. A particularly preferred configuration is Nylon 12/Ethyl Methyl Acrylate/Polyvinylidene Chloride/Ethyl Methyl Acrylate/Nylon 12/Linear Low Density Polyethylene+Low Density Polyethylene (also referred to as co-extruded Nylon 12-encapsulated PVDC-Nylon 12-LLDPE+LDPE multilayer). Another particularly preferred configuration is a co-extruded multi-layer Nylon 12/Linear Low Density Polyethylene+Low Density Polyethylene. Selection of the resins for the composite wall construction (as well as selection of using a coextrusion method or adhesives) can be varied to control compliance (stretchiness), puncture resistance, thickness, adhesion, sealing bond strength, orientation, acid resistance, and permeability characteristics to gasses and water vapor to achieve a particular effect.

Automatic Deflation of Intragastric Balloon Systems

The self-inflating (also referred to as automatic inflating) or inflatable (also referred to as manually inflating) intragastric balloon is provided with mechanisms to reliably control timing of deflation. In preferred embodiments, the balloon auto-deflates and passes through the stomach, through the lower gastrointestinal tract, and out of the body at the end of its pre-determined useful life (non-spontaneous), preferably between 30 and 90 days but can be timed to deflate within 6 months. In the preferred embodiments described below, the timing of deflation can be accomplished via the external gastric environment (by conditions of temperature, humidity, solubility, and/or pH, for example) or via the environment within the lumen of the inflated balloon. It is preferable for consistency to control the initiation of the self-deflation process by manipulating the internal balloon environment.

In other embodiments, the patch applied to allow for inverted seams as described above and/or one or more additional patches or other structures added to the balloon construction are made out of an erodible, degradable, or dissolvable material (natural or synthetic) and are incorporated into the wall of the balloon. The patch(es) are of sufficient size to ensure opening of a sufficient surface area to cause rapid deflation, and to prevent re-inflation by seepage of stomach fluid into the balloon. The balloon patch(es) comprise materials that can be applied to the balloon such that a substantially smooth surface is maintained, and preferably comprise a single layer or multi-layered material. The patch(es) are constructed using an erodible, disintegrable, degradable or other such material that is preferably tissue-compatible and degrades into non-toxic products or is a material that slowly hydrolyzes and/or dissolves over time (e.g., poly(lactic-co-glycolic acid) (PLGA), poly(lactide-co-glycolide) (PLG), polyglycolic acid (PGA), polycaprolactone (PCL), polyesteramide (PEA), polyhydroxyalkanoate (PHBV), polybutylene succinate adipate (PBSA), aromatic copolyesters (PBAT), poly (lactide-co-caprolactone) (PLCL), polyvinyl alcohol (PVOH), polylactic acid (PLA), poly-L-lactic acid PLAA, pullulan, polyethylene glycol (PEG), polyanhydrides, polyorthoesters, polyaryletherketones (PEEK), multi-block polyetheresters, poliglecaprone, polydioxanone, polytrimethylene carbonate, and other similar materials). These erodible, disintegrable, or degradable materials can be used alone, or in combination with other materials, or can be cast into/co-extruded, laminated, and/or dip coated in conjunction with non-erodible polymers (e.g., PET or the like) and employed in the construction of the balloon. Degradation/erosion occurs, is initiated by, and/or is controlled by the gastric environment (e.g., by conditions of temperature, humidity, solubility, and/or pH, for example), or is controlled within the lumen of the balloon (e.g., by conditions of humidity and/or derived pH, for example) based on what the patch is exposed to. Thickness of the polymer as well as environment which affects degradation and time of exposure can also facilitate degradation timing. Degradation/erosion are timed such that they occur once the pre-determined balloon useful life is completed (e.g., inflation is maintained for from 25 to 90 days in vivo in the stomach before degradation/erosion results in formation of an opening permitting deflation). As an alternative to (or in connection with) using an degradable material for the patch, the patch can comprise a similar fluid retention barrier film or the same film as the remaining wall of the balloon which is adhered to the balloon using a weak adhesive, or welded or adhered such that after a specified amount of time the patch delaminates from the applied area and allows for an opening for inflation fluid release for deflation. Or if deemed necessary for rapid deflation the entire balloon composite wall can be made of the erodible material. The mechanism of using an erodible material or a material that mechanically fails after a pre-specified time is be similar for all embodiments for deflation mechanisms described below as well. The timing of degradation or erosion can be controlled using the external gastric environment (e.g., by conditions of temperature, humidity, solubility, and/or pH, for example) and/or can be controlled by conditions within the lumen of the balloon (e.g., by conditions of humidity and/or pH of residual liquid in the balloon).

In other embodiments, a plug or plugs (optionally in conjunction another degradable retaining structure) can be incorporated into the balloon construction and can consist, all or in part, of an erodible, disintegrable, or otherwise degradable synthetic or natural polymer similar to those described above (e.g., PLGA, PLAA, PEG, or the like). The plug can be formed into various shapes (e.g., cylinder shape) to achieve various surface-to-volume ratios so as to provide a preselected and predictable bulk degradation pattern for the erodible polymer. The plug can incorporate a releasing mechanism that can be chemically initiated after degradation/erosion begins, such that the septum or plug material pops out of the balloon or falls inside of the balloon, thereby creating a passageway for fluid release and subsequent deflation of the balloon. Mechanical additions that can be used in conjunction with a plug include a degradable/erodible/disintegrable material that holds a plug (e.g., of a non-degradable or degradable material) in place or a compressed spring housed within the retaining structure or plug structure. More specifically one preferred embodiment to achieve deflation can comprise a housing, a radial seal, a solid eroding core, and a protective film attached to the external surface of the eroding core. The inside of the eroding core is exposed to the internal balloon liquid. The core creates a compressive force that holds the seal against the housing. As the core erodes, the compression between the housing and the radial seal is reduced until there is clearance between the housing and the seal. Once there is clearance, gas can move freely from the inside of the balloon to the outside environment. The seal can fall out of the housing and into the balloon. The diameter, length, and material types can be adjusted in order to create the deflation at a desired time point. Example materials for each component used to achieve this deflation mechanism can be as follows: Housing: Biocompatible structural material, capable of withstanding enough radial force to form an air tight seal. Possible materials include: polyethylene, polypropylene, polyurethane, UHMWPE, titanium, stainless steel, cobalt chrome, PEEK, or nylon; Radial Seal: The radial seal needs to be composed of a biocompatible elastic material, capable of providing liquid and gas barrier to acidic environments. Possible materials include: silicon, polyurethane, and latex; Eroding Core: The eroding core needs to be a material capable of breaking down at a predictable rate at given environmental conditions. Possible materials include: PLGA, PLA, or other polyanhydrides that are capable of losing integrity over time or any materials listed above that provide erodible characteristics.

For the spring mechanism, once the material degrades, the spring is released and/or the plug/septum is pulled into the balloon or pushed out of the balloon, thus releasing fluid once an orifice has been created by release of the spring mechanism and pushing out or pulling in of the plug.

Another preferred embodiment is comprised of a septum, moisture eroding material inside an inlet port, and moisture absorbing expansion material. The eroding materials slowly erode away when exposed to moisture, eventually exposing the moisture absorbing expansion material. When the moisture expanding material begins to absorb moisture, the expansion pulls the septum out of position in the head by pushing against a septum lip or a ring attached to the septum. Pulling the septum out of position causes an immediate deflation of the balloon. In order to protect the expanding material from moisture until a desired timepoint, the expanding material can be sheathed in water blocking materials, such as parylene, as well as slowly water degrading materials. The moisture contact can be controlled by small inlet ports. The inlet ports can be small holes, or a wick material that draws moisture in a controlled manner. The desired deflation time is achieved through a combination of eroding materials, blocking materials, and inlet port sizing.

In certain embodiments, the balloon can incorporate one or more plugs in the wall of the balloon that contain a compressed pellet or gas releasing pellet. The pellet can be comprised of any combination of constituents that, when activated, emit $CO_2$ gas (e.g., sodium bicarbonate and citric acid, or potassium bicarbonate and citric acid, or the like). The pellet can be in tablet or rod form protected by an erodible, disintegrable, or degradable material that is preferably tissue-compatible and degrades into non-toxic products or that slowly hydrolyzes and/or dissolves similarly to the plugs and patches described above (e.g., poly(lactic-co-glycolic acid) (PLGA), polyvinyl alcohol (PVOH), polylactic acid (PLA), poly-L-lactic acid PLAA, Pullulan, Polyethylene Glycol, polyanhydrides, polyorthoesters, polyaryletherketones (PEEK), multi-block polyetheresters, poliglecaprone, polydioxanone, polytrimethylene carbonate, and other like materials). Degradation/erosion of the plug initiates the reaction of the two chemicals in the pellet and subsequently leads to formation of gas (e.g., $CO_2$). As sufficient gas is trapped or built up, sufficient pressure is eventually generated to push out the softened polymer material and create a larger channel for the $CO_2$ gas in the balloon to escape. External pressure applied by the stomach to the balloon (e.g., squeezing) can contribute to the process of creating a larger channel. Dimensions and properties of the plug (diameter, thickness, composition, molecular weight, etc.) comprised of the polymer drives the timing of degradation.

In other embodiments, plugs or patches of different shapes or sizes similar to those of the plugs described above can be employed within the balloon lumen in a multi-layer configuration including a semi-permeable membrane to facilitate balloon deflation. The plug or patch is made of similar degradable/erodible/dissolvable material as described above (e.g., poly(lactic-co-glycolic acid) (PLGA), polyvinyl alcohol (PVOH), polylactic acid (PLA), PLAA, pullulan, and other like materials) and contains a compartment enclosed by a semi-permeable membrane (impermeable to an osmolyte) that contains a concentrated solution of a solute or osmolyte (such as glucose, sucrose, other sugars, salts, or combination thereof). Once the plug or patch begins to degrade or erode, the water molecules move by osmosis down the water gradient from the region of greater water concentration to the region of lower water concentration across the semi-permeable membrane into the hypertonic solution in the compartment. The compartment containing the osmolyte swells and eventually bursts, pushing the membranes and the degraded plug or patch out, thereby allowing rapid gas loss through the newly created channels or areas.

In certain embodiments, a balloon composed of a septum, moisture eroding material inside an inlet port, and moisture absorbing expansion material is employed. The eroding materials slowly erode away when exposed to moisture, eventually exposing the moisture absorbing expansion material. When the moisture expanding material begins to absorb moisture, the expansion pulls the septum out of position in the head by pushing against a septum lip or a ring attached to the septum. Pulling the septum out of position causes an immediate deflation of the balloon. In order to protect the expanding material from moisture until a desired time point has been reached, the expanding material can be sheathed in water blocking materials, such as parylene, as well as slowly water degrading materials. The moisture contact can be controlled by small inlet ports. The inlet ports can be small holes, or a wick material that draws moisture in a controlled manner. The desired deflation time is achieved through a combination of eroding materials, blocking materials, and inlet port sizing.

Another mechanism for self-deflation is to create a forced de-lamination scheme, which can provide a larger surface area to ensure rapid deflation. In, e.g., a balloon having a tri-layer wall, the outermost layer is substantially strong enough to hold the inflation fluid (e.g., polyethylene terephthalate (PET) or the like), the middle layer is comprised entirely of an erodible material (e.g., PVOH or the like) while the inner layer is comprised of a weaker material (e.g., polyethylene (PE) or the like). The PET or outermost layer is "scored" or hatched with erodible material to create small channels that erode over time. This creates channels such that the gastric fluid seeps into the balloon layers and starts degrading the fully erodible material. When the erodible layer degrades or dissolves, the material that composes the innermost layer also erodes, degrades or dissolves since it is not strong enough to withstand the gastric forces/environment on its own. The balloon then collapses on itself and eventually passes through the lower gastrointestinal tract. Having an erodible layer sandwiched between a strong and weak layer facilitates timing of erosion by creating a longer path length than an erodible plug or patch affected by the gastric environment. The distance between scores or openings can also be selected so as to provide a desired deflation rate.

In another embodiment providing abrupt deflation of the balloon after a desired period of time has elapsed, the composite wall of the entire balloon or a section of the composite wall (patch) includes several material layers that are slowly penetrated by water that has been injected inside the balloon during the manufacturing process or during the inflation process. This water penetrates through the layers, eventually reaching a material that substantially expands, rupturing a thin external protective later, and creating a large hole for gas to escape and the balloon to deflate. The water expanding material is protected from liquid via a coating or sheath, such as parylene, which allows a controllable amount of moisture exposure. Once water reaches the expansion material, it exerts a force on the protective outer layer, causing it to rupture. The outer layer may be created with a weakened bonding area, a partially scored area, or other methods of ensuring a desired rupture location and to facilitate desired timing for auto-deflation to take place. There can be any number of layers between the moist environment and the moisture expanding center. Each material layer can have different erosion rates (e.g., fast or slow) and can be selected by the predetermined time deflation is desired to occur (e.g., after 30 days, 60 days, or more). By varying the number, thickness, and rate of each of the circumferential layers, the time to deflation can be accurately controlled.

Alternatively a pressure sealing button that is adhesively bonded over a perforation in the balloon material can be provided for deflation. The adhesive bonding the button erodes over time when it comes into contact with moisture derived from the gastric fluid or that has been injected inside the balloon. Once the adhesive can no longer bond and create an airtight seal between the adhesive and the button, the balloon will rapidly deflate. By controlling the hole size and moisture exposure of the adhesive, the erosion time can be accurately predicted.

Deflation can also be facilitated by creating a series of connecting ports within the septum or on another similar structure attached to the balloon composite wall. The ports can be constructed using a water- or acid-dissolving, biologically compatible, low permeability substance, such as gelatin. The diameter of the hole, number of holes, channel width, and channel length can all be adjusted to control the dissolving parameters. Once the material in the ports and channel is dissolved, there is a clear path for gas trapped in the balloon to escape, eventually resulting in a deflated balloon. The water can be gastric fluid or controlled internally by including water inside the balloon at assembly or during the inflation process. There can be a plurality of port openings to guarantee gas transmits. Additionally, there are several variables that can be adjusted to control dissolution time: size of the port openings; number of port openings; the length of the internal channel; the width of the internal channel; and the rate of material dissolution. The port/channel layout design can ensure that only a small amount of surface area is exposed to moisture at any particular time, thereby controlling the rate of erosion and ultimately deflation.

A mechanism to facilitate passing involves an erosion mechanism that allows for the balloon to be broken down into a size that has a higher probability of predictably passing through the lower gastrointestinal system. Preferably, the size of the balloon as deflated is less than 5 cm long and 2 cm thick (similar to various foreign objects of similar size that have been shown to pass predictably and easily through the pyloric sphincter). This can be accomplished by providing the balloon with "erodible seams." One seam that breaks the balloon open into (at a minimum) two halves, or more seams are provided so that a plurality of smaller balloon pieces is produced in the dissociation reaction. The number of seams used can be selected based on the original surface area of the balloon and what is required to dissociate the balloon into pieces that are of a size that can predictably pass through the gastrointestinal tract more easily. The rate of seam erosion can be controlled by using a material affected by, e.g., the external gastric environment pH, liquid, humidity, temperature, or a combination thereof. Seams can be single layer consisting of only erodible material, or multi-layer. The timing of self-deflation can be further controlled by the design of the seam layers, e.g., making the reaction and/or degradation of the seam material dependent on the internal environment of the balloon instead of the external environment. By manipulating the reaction such that erosion or degradation is initiated by the internal environment (e.g., the balloon's internal pH, humidity, or other factors), any impact of person-to-person gastric variability (pH, etc.) that can affect erosion timing is minimized. The internal balloon environment can be manipulated by adding excess water at injection to create a more humid internal environment, or the amount of constituents added can be varied to manipulate the pH, etc.

Confirmation of Deflation of Intragastric Balloon Systems

Whether the balloon is self-deflating or non self-deflating, various mechanisms may be implemented to confirm deflation of the balloon. In preferred embodiments, the balloon deflates and emits a sensory stimulant that is configured to trigger a response by one of the patient's senses. In some embodiments, the device may emit an odor that is smelled by the patient. In some embodiments, the device may emit a taste that is tasted by the patient. In some embodiments, the device may emit a coloring agent that the patient can visually see after passing the agent, for example in a toilet. In some embodiments, the sensory stimulant may cause a physiological response indicative of deflation. For example, the deflated balloon may emit a substance that encourages passage through the bowels.

In some embodiments, flavorants may be used to indicate deflation to the patient. Theses may be the same or different as the flavoring agents that may be used in some embodiments, for example with the ingestible event markers for a voltaic or pH based locating system. Thus, flavorants such as peppermint, oil of wintergreen, cherry flavoring or the like can also be used. Additionally, it may be desirable to add a coloring agent to make the dosage form more attractive in appearance or to help identify the product.

Electromagnetic and Magnetic Tracking and Visualization Subcomponents

Tracking and visualization functionality can be incorporated into devices and systems described above. As used herein, "visualization" is used broadly to refer to identifying an item of interest in the body in a number of ways, including by magnetic field data such as field strength, field orientation, temporal characteristics of the field, the effects of the field on a magnetic sensor, and other attributes of a magnetic field that may be used to facilitate tracking, locating, identifying, and characterizing a magnetic or magnetized item of interest, as well as audio, visual, tactile, or other output based on the magnetic data that characterizes the magnetized item of interest. Due to the non-invasive nature of the present device, physicians may desire to determine, or confirm, the location and orientation of the device prior to inflation, during the course of treatment, or after deflation. Accordingly, intragastric devices are provided that incorporate magnetic components configured for enabling determining and confirming the location, orientation and state of an intragastric device at all phases of administration.

This section discusses magnetic components that may be implemented in the electromagnetic and/or the magnetic embodiments described herein. Although the terms "electromagnetic" and "magnetic" may be used interchangeably in this disclosure, it is understood that the electromagnetic embodiments include an "active" sensor that generates a current in response to a magnetic field, and that magnetic embodiments include a "passive" sensor that generates a magnetic field. Particular embodiments of electromagnetic and magnetic systems are described herein, for example in the "Electromagnetic Real-Time Confirmation of Placement" and the "Magnetic Real-Time Confirmation of Placement" sections, respectively.

Markers

An electromagnetic or magnetic marker component may comprise a variety of materials or objects that produce and/or are responsive to a magnetic field. A magnetic field is a force that attracts other ferromagnetic materials, such as iron, and attracts or repels other magnets.

Magnetism is a class of physical phenomena that includes forces exerted by magnets on other magnets. It has its origin in electric currents and the fundamental magnetic moments of elementary particles. These give rise to a magnetic field that acts on other currents and moments. All materials are influenced to some extent by a magnetic field. The strongest effect is on permanent magnets, which have persistent magnetic moments caused by ferromagnetism. Most materials do not have permanent moments. Some are attracted to a magnetic field (paramagnetism); others are repulsed by a magnetic field (diamagnetism); others have a much more complex relationship with an applied magnetic field (spin glass behavior and antiferromagnetism). Substances that are negligibly affected by magnetic fields are known as non-magnetic substances. They include copper, aluminum, gases, and plastic. Pure oxygen exhibits magnetic properties when cooled to a liquid state Magnetic behavior including that exhibited by permanent magnets, ferromagnetic and ferrimagnetic materials, paramagnetic substances, and diamagnetic substances, can be employed in various embodiments of a magnetic locating system to be used with intragastric devices.

In some embodiments, the magnetic locating system may use ferromagnetic or ferrimagnetic materials. Ferromagnetic and ferrimagnetic materials are the ones normally thought of as magnetic; they are attracted to a magnet strongly enough that the attraction can be felt. These materials are the only ones that can retain magnetization and become magnets. Ferrimagnetic materials, which include ferrites and the oldest magnetic materials magnetite and lodestone, are similar to but weaker than ferromagnetics. The difference between ferro- and ferrimagnetic materials is related to their microscopic structure.

In some embodiments, the magnetic locating system may use paramagnetic substances. Paramagnetic substances, such as platinum, aluminum, and oxygen, are weakly attracted to either pole of a magnet. This attraction is hundreds of thousands of times weaker than that of ferromagnetic materials, so it can only be detected by using sensitive instruments or using extremely strong magnets. Magnetic ferrofluids, although they are made of tiny ferromagnetic particles suspended in liquid, are sometimes considered paramagnetic since they cannot be magnetized.

In some embodiments, the magnetic locating system may use diamagnetic substances. Diamagnetic materials are those repelled by both poles of a magnet. Compared to paramagnetic and ferromagnetic substances, diamagnetic substances, such as carbon, copper, water, and plastic, are even more weakly repelled by a magnet. The permeability of diamagnetic materials is less than the permeability of a vacuum. All substances not possessing one of the other types of magnetism are diamagnetic; this includes most substances. Although force on a diamagnetic object from an ordinary magnet is far too weak to be felt, using extremely strong superconducting magnets, diamagnetic objects such as pieces of lead can be levitated. Superconductors repel magnetic fields from their interior and are strongly diamagnetic.

There are various other types of magnetism, such as spin glass, superparamagnetism, superdiamagnetism, and metamagnetism, each of which may be employed in various embodiments of the magnetic locating system.

An electromagnet is made from a coil of wire that acts as a magnet when an electric current passes through it but stops being a magnet when the current stops. Often, the coil is wrapped around a core of "soft" ferromagnetic material such as steel, which greatly enhances the magnetic field produced by the coil.

Various properties of magnets and magnetized objects may be used in embodiments of the magnetic locating system for intragastric devices. These properties include, but are not limited to, the magnetic field, magnetic moment, and magnetization.

The magnetic flux density (also called magnetic B field or just magnetic field, usually denoted B) is a vector field. The magnetic B field vector at a given point in space is specified by two properties: 1) Its direction, which is along the orientation of a compass needle, and 2) Its magnitude (also called strength), which is proportional to how strongly the compass needle orients along that direction. In SI units, the strength of the magnetic B field is given in teslas.

A magnet's magnetic moment (also called magnetic dipole moment and usually denoted $\mu$) is a vector that characterizes the magnet's overall magnetic properties. For a bar magnet, the direction of the magnetic moment points from the magnet's south pole to its north pole, and the magnitude relates to how strong and how far apart these poles are. In SI units, the magnetic moment is specified in terms of $A \cdot m^2$ (amperes times meters squared).

A magnet both produces its own magnetic field and responds to magnetic fields. The strength of the magnetic field it produces is at any given point proportional to the magnitude of its magnetic moment. In addition, when the magnet is put into an external magnetic field, produced by a different source, it is subject to a torque tending to orient the magnetic moment parallel to the field. The amount of this torque is proportional both to the magnetic moment and the external field. A magnet may also be subject to a force driving it in one direction or another, according to the positions and orientations of the magnet and source. If the field is uniform in space, the magnet is subject to no net force, although it is subject to a torque.

A wire in the shape of a circle with area A and carrying current I is a magnet, with a magnetic moment of magnitude equal to IA.

The magnetization of a magnetized material is the local value of its magnetic moment per unit volume, usually denoted M, with units A/m. It is a vector field, rather than just a vector (like the magnetic moment), because different areas in a magnet can be magnetized with different directions and strengths. A good bar magnet may have a magnetic moment of magnitude $0.1 \ A \cdot m^2$ and a volume of $1 \ cm^3$, or $1 \times 10^{-6} \ m^3$, and therefore an average magnetization magnitude is 100,000 A/m. Iron can have a magnetization of around a million amperes per meter. Such a large value explains why iron magnets are so effective at producing magnetic fields.

The various magnets and their magnetic properties may be implemented in the magnetic intragastric device locating system with magnetic markers and magnetic sensors or detectors. The magnetic markers comprise any magnetic or magnetized substance, material, or object, to which the sensors or detectors are responsive.

Flexible magnetic materials can also be employed in various embodiments. Such materials typically comprise a ferromagnetic compound (e.g., ferric oxide) mixed with a polymeric binder. Magnetic materials suitable for use in the various embodiments include magnetic tape, magnetic sheeting, magnetic rolls, inkjet-printed magnets, and the like. Magnetic tape typically comprises a layer of magnetic material with an adhesive on one side. Magnetic sheeting can include a layer of magnetic material that can be adhered to another layer, or incorporated between other polymeric layers. Magnetic rolls typically comprise a magnetic layer with one or more supporting or barrier layers incorporated therein, e.g., prepared by extrusion, lamination, or other techniques as are known in polymer processing and thin film formation. Such flexible magnetic materials can be isotropic or anisotropic in magnetic response.

Inkjet-printed magnets include a liquid comprising magnetic particles that can be deposited on a substrate using inkjet or bubblejet technology. Alternatively, magnetic particles can be printed on a substrate using laser jet technology.

While ferric oxide can offer advantages of low cost, in certain embodiments it may be desirable to employ other magnetic materials, e.g., strontium, barium, neodymium, e.g., NdFeB, samarium cobalt, platinum cobalt, and platinum iron.

In certain embodiments, the magnetic material is provided as one or more flexible layers in the device. A flexible magnetic layer can be incorporated into the composite wall as one of the layers comprising the wall, e.g., as a supporting layer. The magnetic layer can comprise an entire area of the composite wall, or a partial area of the composite wall. For example, one or more narrow strips or one or more patterns of dots, rings, squares, circles, or similar structures can be inserted between layers in the composite wall, or affixed or otherwise adhered to an interior or exterior surface of the composite wall. The magnetic material can be in sheet or roll form, as described above, or can be printed onto one or more of the layers of the composite wall using any suitable printing technology (inkjet, bubblejet, laser jet, screen printing, lithography, etc.)

In certain embodiments, the magnetic component can be provided as any of the rigid components incorporated into the intragastric balloon, e.g., as a retaining ring, or as a weight component configured to orient the balloon in the intragastric space (e.g., a plug, button, pellet, or other solid shape affixed to or incorporated into the materials of the balloon), or as a free-moving or "loose" component in the interior volume of the balloon.

A magnetic marker may be applied to the volume-occupying subcomponent when the volume-occupying subcomponent is in a creased or folded state such that when the volume-occupying subcomponent is in its deflated state the magnetic field appears concentrated (more localized), and when the volume-occupying subcomponent is inflated the magnetic field appears more diffuse. Alternatively, the magnetic marker may be applied or incorporated into the volume-occupying subcomponent so as to facilitate identification and location of the various subcomponents of the device, such as a valve, head, or weight. The magnetic marker may be printed or painted onto a surface of the volume-occupying subcomponent or between layers of the material forming the volume-occupying subcomponent. Alternatively, a magnetic coating as described below may be used as a magnetic marker to identify and/or locate the volume-occupying subcomponent. Magnetic coatings for visualizing the volume-occupying subcomponent may include iron or any suitable magnetized metallic material as described above. Alternatively, the magnetic marker may be applied to an elastomeric sleeve that covers all or part of the volume-occupying subcomponent.

In another embodiment, the volume-occupying subcomponent incorporates a subcomponent that changes mechanically upon inflation of the volume-occupying subcomponent, which mechanical change can be visualized using magnetic field detection equipment. For example, a mechanical portion of the volume-occupying subcomponent containing a magnetic marker may elongate upon an increase in pressure in the volume-occupying subcomponent, resulting in a more diffuse magnetic field.

Alternatively, a magnetized marker may be formed using a metallized mesh or other pattern located between layers of the material from which the volume-occupying subcomponent is constructed. The pattern or patterns formed by the imbedded magnetized marker will be locatable when the volume-occupying subcomponent is in an inflated, deployed state.

Electromagnetic Detection

It is envisioned that magnetic marker materials may be incorporated into the volume-occupying subcomponent to facilitate various magnetic locating and visualization systems comprising a variety of methods and apparatuses for sensing and detecting a magnetic marker.

In some embodiments, a magnetic locating system comprises a magnetic field proximity sensor. The sensor detects the strength and orientation of the magnetic field generated by the magnetic marker.

In some embodiments, the magnetic detector can be of similar configuration to commercially available magnetic stud detectors that use a small stationary magnet to detect the nails or screws placed into studs during the manufacturing of the wall. Handheld stationary magnetic detectors use a small (stationary) magnet to detect the magnetic marker placed with devices. It is the "pull" of the magnetic marker on the magnet that alerts the user holding the device to the presence of a magnetic marker. The amount of "pull" is proportional to the distance of the stationary magnet from the magnetic marker. For example, a weaker pull indicates a deeper depth in the body while a stronger pull indicates a shallower depth, relative to the stationary magnetic detector.

In another embodiment, the magnetic locating system uses a moving magnet to detect the magnetized portion of the device. Moving magnet detectors are an enhancement involving a neodymium magnet that is suspended such that it is free to move in response to magnetic markers. The strength of this rare earth magnet, along with the ease of movement of the magnet, allows the moving magnetic finder to extend its range of detection to include various sizes of patients (e.g., capable of accommodating morbidly obese patients). Accordingly, magnetic markers far from a detector can be located with this type of device. The magnet is suspended in such a way that it always sits in its "home" position until it is moved directly over a magnetic marker. Once the magnet is in the vicinity of the marker, it is pulled towards the body at a rate of acceleration that is proportional to the distance between the magnet and the metal. For markers located in shallow positions, the magnet moves towards the body with such velocity that it makes a distinct thud sound. For magnetic markers deeper in the body, the thud becomes more of a click since the speed of movement is reduced. The tissues of the body are not expected to exhibit an "insulating" effect as to the magnetic field. Instead, the strength of the field is expected to be a function of the distance of the detector to the locating device, and the strength of the magnetic field generated by the locating device. The stationary magnetic detector can be precalibrated to accurately identify the position of the device. The tissues of the body are not expected to exhibit an "insulating" effect as to the magnetic field. Accordingly, the device can be calibrated (e.g., experimentally, or by calculation) to output a value for distance and direction.

In some embodiments, the magnetic locating system uses an internal capacitor to detect changes in the dielectric constant of a person's body as the sensor is moved over the body. A change in the dielectric constant indicates a dense object in the body.

Some embodiments using an internal capacitor may be edge sensors, center sensors, or instant metal finders. In some embodiments, a magnetic locating system further comprises a track near the body on which the sensor passively travels as it follows a magnetic marker that is progressing through the body.

In some embodiments, the sensor comprises a large magnetic sheet placed near the body that remains stationary and passively detects the location of the magnetic marker as it progresses through the body.

In various embodiments a passive magnetic system can be employed or an active electromagnetic system can be employed. In the passive system, a magnetic component in the intragastric space is detected using a suitable detector. The magnetic component can passively generate a magnetic field, e.g., as a permanent magnet or by a magnetic field induced in the magnetic component by an ex vivo device configured to induce a magnetic field in the magnetic component. In contrast, in an active system, an electromagnetic field is generated and an electromagnetic component is brought within the presence of the field, and a current through or voltage across the in vivo electromagnetic component is thereby generated due to interaction with the electromagnetic field. The electromagnetic component is in electrical communication with an ex vivo current or voltage source, e.g, via a conductive wire or a conductive trace.

Types of Magnetometers

In preferred embodiments, a magnetometer (also referred to as a magnetic sensor or magnetic field sensing device) is employed to locate and/or track the intragastric device. Magnetometers can be divided into scalar devices which only measure the intensity of the field and vector devices which also measure the direction of the field.

Magnetometers can detect magnetic (ferrous) metals at large distances, e.g., at tens of meters. In recent years magnetometers have been miniaturized to the extent that they can be incorporated in integrated circuits at very low cost.

Scalar magnetometers measure the total strength of the magnetic field to which they are subjected, but not its direction. Proton precession magnetometers, also known as proton magnetometers, PPMs or simply mags, measure the resonance frequency of protons (hydrogen nuclei) in the magnetic field to be measured, due to nuclear magnetic resonance (NMR). Because the precession frequency depends only on atomic constants and the strength of the ambient magnetic field, the accuracy of this type of magnetometer can reach 1 ppm. A direct current flowing in a solenoid creates a strong magnetic field around a hydrogen-rich fluid, causing some of the protons to align themselves with that field. The current is then interrupted, and as protons realign themselves with ambient magnetic field, they precess at a frequency that is directly proportional to the magnetic field. This produces a weak rotating magnetic field that is picked up by a (sometimes separate) inductor, amplified electronically, and fed to a digital frequency counter whose output is typically scaled and displayed directly as field strength or output as digital data.

The Overhauser effect magnetometer or Overhauser magnetometer uses the same fundamental effect as the proton precession magnetometer to take measurements. By adding free radicals to the measurement fluid, the nuclear Overhauser effect can be exploited to significantly improve upon the proton precession magnetometer. Rather than aligning the protons using a solenoid, a low power radio-frequency field is used to align (polarize) the electron spin of the free radicals, which then couples to the protons via the Overhauser effect. This has two main advantages: driving the RF field takes a fraction of the energy (allowing lighter-weight batteries for portable units), and faster sampling as the electron-proton coupling can happen even as measurements are being taken. An Overhauser magnetometer produces readings with a 0.01 nT to 0.02 nT standard deviation while sampling once per second.

The optically pumped cesium vapor magnetometer is a highly sensitive (300 fT/Hz$^{0.5}$) and accurate device used in a wide range of applications. It is one of a number of alkali vapors (including rubidium and potassium) that are used in this way, as well as helium.

Vector magnetometers have the capability to measure the component of the magnetic field in a particular direction, relative to the spatial orientation of the device. Vector magnetometers can advantageously be employed to locate the intragastric device. A vector is a mathematical entity with both magnitude and direction. The Earth's magnetic field at a given point is a vector. A vector magnetometer measures both the magnitude and direction of the total magnetic field. Three orthogonal magnetometers can be employed measure the components of the magnetic field in all three dimensions, providing precise location of the medical device. Magnetometers are also classified as "absolute" if the strength of the field can be calibrated from their own known internal constants or "relative" if they need to be calibrated by reference to a known field. Magnetometers can also be classified as "AC" if they measure fields that vary relatively rapidly in time (>100 Hz), and "DC" if they measure fields that vary only slowly (quasi-static) or are static.

Vector magnetometers measure one or more components of the magnetic field electronically. Using three orthogonal magnetometers, both azimuth and dip (inclination) can be measured. By taking the square root of the sum of the squares of the components the total magnetic field strength (also called total magnetic intensity, TMI) can be calculated by Pythagoras's theorem. Vector magnetometers are subject to temperature drift and the dimensional instability of the ferrite cores. They also require leveling to obtain component information, unlike total field (scalar) instruments. For these reasons they are no longer used for mineral exploration.

In a rotating coil magnetometer, the magnetic field induces a sine wave in a rotating coil. The amplitude of the signal is proportional to the strength of the field, provided it is uniform, and to the sine of the angle between the rotation axis of the coil and the field lines. This type of magnetometer is obsolete.

In a Hall effect magnetometer, a voltage proportional to the applied magnetic field is generated and polarity is detected. Magnetoresistive devices are made of thin strips of permalloy (NiFe magnetic film) whose electrical resistance varies with a change in magnetic field. They have a well-defined axis of sensitivity, can be produced in 3-D versions and can be mass-produced as an integrated circuit. They have a response time of less than 1 microsecond and can be sampled in moving vehicles up to 1,000 times/second. They can be used in compasses that read within 1°, for which the underlying sensor must reliably resolve 0.1°. A fluxgate magnetometer consists of a small, magnetically susceptible core wrapped by two coils of wire. An alternating electrical current is passed through one coil, driving the core through an alternating cycle of magnetic saturation; i.e., magnetized, unmagnetized, inversely magnetized, and so forth. This constantly changing field induces an electrical current in the second coil, and this output current is measured by a detector. In a magnetically neutral background, the input and output currents will match. However, when the core is exposed to a background field, it will be more easily saturated in alignment with that field and less easily saturated in opposition to it. Hence the alternating magnetic field, and the induced output current, will be out of step with the input current. The extent to which this is the case will depend on the strength of the background magnetic field. Often, the current in the output coil is integrated, yielding an output analog voltage, proportional to the magnetic field.

A wide variety of sensors is currently available and used to measure magnetic fields. Fluxgate compasses and gradiometers measure the direction and magnitude of magnetic fields. Fluxgates are affordable, rugged and compact. This, plus their typically low power consumption makes them ideal for a variety of sensing applications.

The typical fluxgate magnetometer consists of a "sense" (secondary) coil surrounding an inner "drive" (primary) coil that is wound around permeable core material. Each sensor has magnetic core elements that can be viewed as two carefully matched halves. An alternating current is applied to the drive winding, which drives the core into plus and minus saturation. The instantaneous drive current in each core half is driven in opposite polarity with respect to any external magnetic field. In the absence of any external magnetic field, the flux in one core half cancels that in the other, and so the total flux seen by the sense coil is zero. If an external magnetic field is now applied, it will, at a given instance in time, aid the flux in one core half and oppose flux in the other. This causes a net flux imbalance between the halves, so that they no longer cancel one another. Current pulses are now induced in the sense coil winding on every drive current phase reversal (or at the 2nd, and all even harmonics). This results in a signal that is dependent on both the external field magnitude and polarity.

There are additional factors that affect the size of the resultant signal. These factors include the number of turns in the sense winding, magnetic permeability of the core, sensor geometry and the gated flux rate of change with respect to time. Phase synchronous detection is used to convert these harmonic signals to a DC voltage proportional to the external magnetic field.

SQUIDs, or superconducting quantum interference devices, measure extremely small magnetic fields. They are very sensitive vector magnetometers, with noise levels as low as 3 fT $Hz^{-1/2}$ in commercial instruments and 0.4 fT $Hz^{-1/2}$ in experimental devices. Many liquid-helium-cooled commercial SQUIDs achieve a flat noise spectrum from near DC (less than 1 Hz) to tens of kilohertz, making such devices ideal for time-domain biomagnetic signal measurements. SERF atomic magnetometers demonstrated in laboratories so far reach competitive noise floor but in relatively small frequency ranges.

SQUID magnetometers require cooling with liquid helium (4.2 K) or liquid nitrogen (77 K) to operate, hence the packaging requirements to use them are rather stringent both from a thermal-mechanical as well as magnetic standpoint. SQUID magnetometers are most commonly used to measure the magnetic fields produced by brain or heart activity (magnetoencephalography and magnetocardiography, respectively). Geophysical surveys use SQUIDS from time to time, but the logistics are much more complicated than coil-based magnetometers.

At sufficiently high atomic density, extremely high sensitivity can be achieved. Spin-exchange-relaxation-free (SERF) atomic magnetometers containing potassium, cesium or rubidium vapor operate similarly to the cesium magnetometers described above, yet can reach sensitivities lower than 1 fT $Hz^{-1/2}$. The SERF magnetometers only operate in small magnetic fields. The Earth's field is about 50 µT; SERF magnetometers operate in fields less than 0.5 µT.

Large volume detectors have achieved a sensitivity of 200 aT $Hz^{-1/2}$. This technology has greater sensitivity per unit volume than SQUID detectors. The technology can also produce very small magnetometers that may in the future replace coils for detecting changing magnetic fields. This technology may produce a magnetic sensor that has all of its input and output signals in the form of light on fiber-optic cables. This would allow the magnetic measurement to be made in places where high electrical voltages exist.

A computing system may be implemented in the magnetic locating system. The computing system comprises hardware and software that receives data from the magnetic sensor and calculates information related to the location, orientation, and/or state of an intragastric device according to certain algorithms.

In some embodiments, the hardware may comprise a central processing unit, memory, an analog to digital converter, analog circuitry, a display.

In some embodiments, the software proceeds through a number of steps including calibration, initialization, prediction, estimation, measuring magnetic sensor data, calculating various desired outputs including location, orientation, size, and configuration.

In some embodiments, the computing system predicts or estimates a location, position, orientation, state, or configuration of a magnetic marker, determines a corresponding estimated or predicted magnetic field, takes an actual measurement of the magnetic field generated by the magnetic marker, and determines the actual location, position, orientation, state, or configuration of a magnetic marker based on a difference between the values of the predicted field and actual field.

In embodiments using estimation or prediction, the computation may be done using iterative calculations and/or neural networks, and the hardware may further include an estimation processor.

The processor's output relating to the location, orientation and/or state of an intragastric device may be communicated to a user in a number of manners. In some embodiments, the output is shown visually on a display.

In some embodiments, the processor's output related to an intragastric device's location, orientation, and/or state is audibly communicated to a user through a speaker.

In some embodiments, the processor's output related to an intragastric device's location, orientation, and/or state is communicated to a user through a combination of methods. For instance, the system may employ a visual graphical display with audible alerts sent through speakers.

In some embodiments, the magnetic locating system is calibrated before use. The magnetic marker and the sensor are positioned in pre-planned locations and orientations to verify the output signal is within an expected range In some embodiments, the magnetic locating systems are calibrated or otherwise verified using a human patient simulator, or dummy, to test the magnetic locating system as a magnetic marker travels through the simulators In some embodiments, the magnetic locating system is checked for stray signals from nearby magnetic interferences.

The intragastric devices once ingested may be located using the magnetic intragastric locating system.

The orientation of the devices once ingested may be ascertained using the magnetic intragastric locating system.

Further, the various sizes and configurations of the devices once ingested may be characterized using the magnetic intragastric locating system. For instance, inflation of a balloon, or the inflation or configuration of multiple balloons, may be characterized and assessed.

The magnetic locating system may also be used in conjunction with a deflating system to characterize the deflation process.

The timing and other attributes of the various methods of administration can be characterized using the disclosed magnetic intragastric locating system. Whether the device is administered using endoscopic techniques or orally, the progress of the device as it makes its way to the stomach can be tracked with the magnetic locating system. For instance, the effects of swallowing the device with hard gelatin or water or other consumables may be characterized by tracking the location and orientation as it is ingested.

Electromagnetic Real-Time Confirmation of Placement

In certain embodiments, an electromagnetic tracking technology as is commercially available is employed. Suitable systems include, but are not limited to, the Sherlock* II Tip Location System as manufactured by Bard Access Systems of Salt Lake City, Utah, or the Aurora Electromagnetic Tracking System manufactured by NDI Medical, Inc. of Ontario, Canada.

The Aurora System

In some embodiments, a catheter is adapted to integrate the Aurora System sensors by situating the sensors inside the catheter. In other embodiments, the sensors may be situated in other components of the system, such as the balloon or intragastric device, or other features as described herein. The compatible NDI Aurora System Hardware components allow for tracking of the sensors placed inside the swallowable catheter using real time electromagnetic tracking system that delivers sub-millimetric, sub-degree accuracy. The software was modified to make the graphic user interface appropriate for GE use and detection of the capsule in the alimentary canal.

FIG. 1 depicts an embodiment of an electromagnetic tracking system 1500 for locating a sensor 1521. The system 1500 includes a field generator 1510, a system control unit 1535, the sensor interface unit 1530, and a catheter 1503 having a distal sensor 1521. In the embodiment shown, the field generator 1510 generates an electromagnetic field. In other embodiments described herein, the field generator 1510 may generate a pressure wave for use, for example, in an ultrasound-based system (see FIGS. 27-40). As shown in FIG. 1, the field generator 1510 may include one or more mounting holes 1511. The mounting holes 1511 allow the generator 1510 to be mounted to a wall, support, or other attachments. A field generator connector 1512 connects a field generator cable 1514 to the system control unit 1535. The field generator connector 1512 is a nineteen pin circular metal connector, however other connectors maybe used.

As shown, the field generator 1510 may be planar. A planar field generator 1510 emits a low-intensity, varying electromagnetic field and establishes the position of a tracking volume (see FIG. 6). The planar field generator 1510 contains a number of large coils (not shown) that generate known electromagnetic fields. The field generator 1510 produces a series of varying magnetic fields, creating a known volume of varying magnetic flux. This volume is referred to as the characterized measurement volume. The shape of the characterized measurement volume is dependent on the field generator type and how it was characterized. The characterized measurement volume is the volume where data was collected and used to characterize the field generator 1510. It is a subset of the detection region. The detection region is the total volume in which the field generator can detect a sensor, regardless of accuracy. The measurement volumes for the generated magnetic fields are discussed in further detail herein, for example with respect to FIG. 6. The volume is projected outwards from the field generator's 1510 front face, offset by 50 mm from the field generator 1510.

Figure 4:
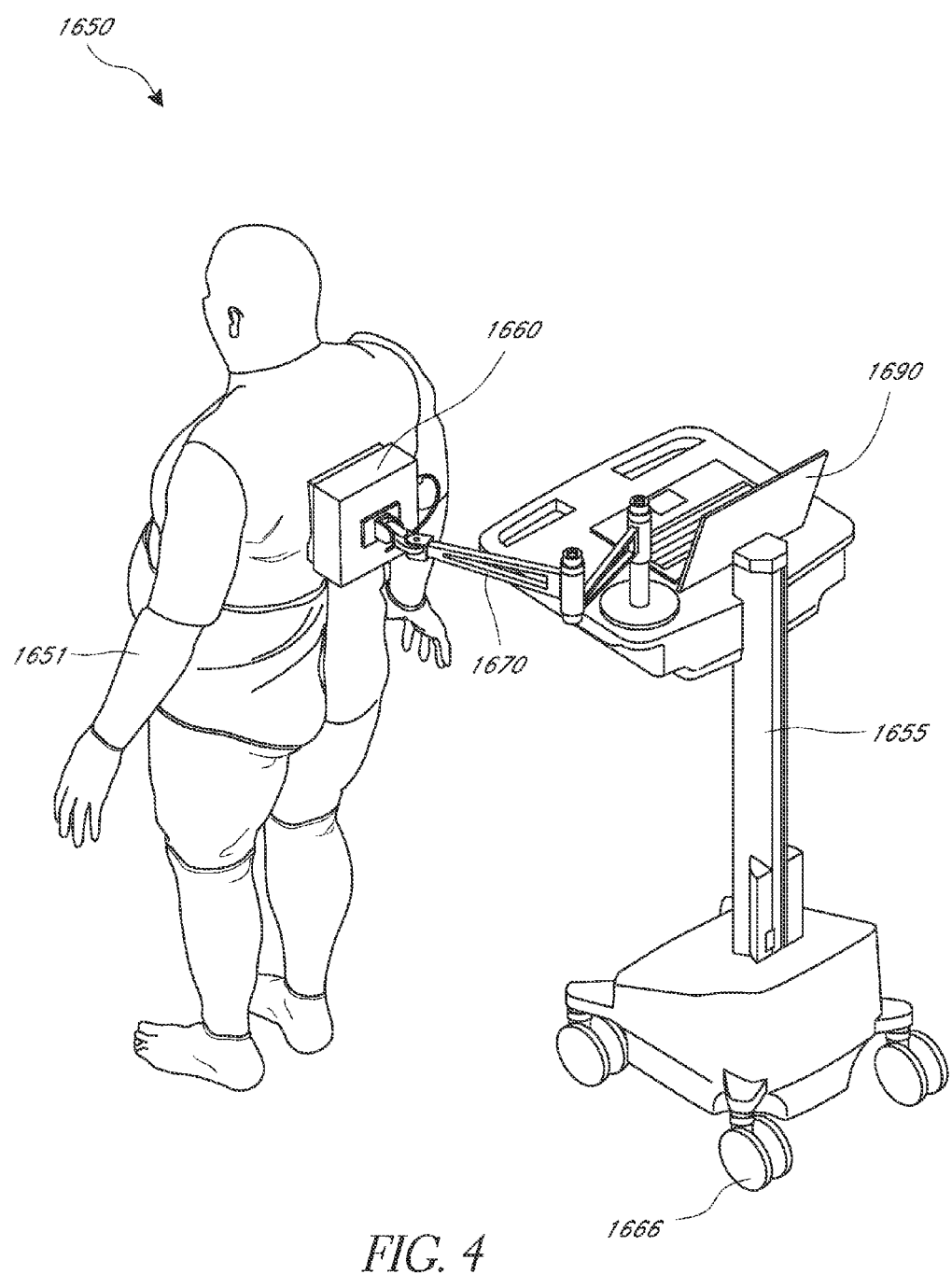
FIG. 4 depicts an embodiment of an electromagnetic tracking system on a support that uses a sensor to locate an intragastric device inside the body of a human patient.

The planar field generator 1510 may have a mounting point 1509 designed to attach the field generator 1510 to a mounting arm, described in further detail herein, for example with respect to FIG. 4. The field generator 1510 may have one or more mounting holes 1511 that allow the field generator 1510 to be attached firmly to a fixture. As shown, the two mounting holes 1511 are M8 tapped holes (thread pitch 1.25 mm, depth 13 mm)×4, 2 per side. However, there may be fewer or more than two mounting holes 1511 and in a variety of shapes and sizes.

The field generator 1510 may also be a tabletop field generator (not shown). The tabletop field generator may be designed to be placed on a patient table in between the patient and the table. The tabletop field generator incorporates a thin barrier that minimizes any tracking distortions caused by conductive or ferromagnetic materials located below the tabletop field generator. The tabletop field generator contains a number of large coils that generate known electromagnetic fields. The volume may be projected outwards from the tabletop field generator's front face, offset by 120 mm from the tabletop field generator. The tabletop field generator may include any or all features and functionalities as the planar field generator described above.

The field generator 1510 is connected to the system control unit 1535. The generator 1510 may be connected to the system control unit 1535 by the cable 1514 allowing for communication of signals therebetween. The system control unit 1535 may include a power cable 1505 and an auxiliary cable 1504, for example a USB cable or Serial RS-232 cable, for example to connect to a computer or other component. The system control unit 1535 may provide power to the field generator 1510.

The system control unit 1535 is connected to the sensor interface unit 1530. The system control unit 1535 may be connected to the sensor interface unit 1530 by a cable 1534. There may be more than one system interface unit 1530 connected to the system control unit 1535 via multiple cables 1534. The cables 1534 allow for electronic communication of signals between the system control unit 1535 and the one or more sensor interface units 1530.

The system control unit 1535 may control the operation of the system 1500. In some embodiments, the system control unit 1535 provides an interface between components of the system 1500. The system control unit 1535 may also supply power to the field generator 1510 and/or control the field generator's 1510 electromagnetic output. The system control unit 1535 may also collect sensor data (via the sensor interface unit 1530) and calculates sensor positions and orientations. The system control unit 1535 then sends the position and orientation data to a host computer (see FIG. 2). Therefore, the system control unit 1535 may also interface with the computer. The system control unit 1535 may also provide visual status indications.

The sensor interface unit 1530 is connected to the catheter 1503. The catheter 1503 includes a sensor 1521 at the distal end of the catheter 1503. In some embodiments, the sensor 1521 may be integrated with an intragastric device. The sensor 1521 is an electromagnetic sensor. In some embodiments, the sensor 1521 may be an ultrasound or voltage sensor or marker. Use of a voltage sensor is discussed in further detail herein, for example with respect to FIG. 10C. The sensor 1521, which may be embedded in tools, are connected to the sensor interface unit 1530 via the one or more system interface units 1530. If the electromagnetic sensor 1521 is placed inside the measurement volume, a voltage will be induced in the sensors 1521, caused by the varying magnetic fields produced by the field generator 1510. The characteristics of the induced voltage depend on a combination of the sensor 1521 position and orientation in the measurement volume, and the strength and phase of the varying magnetic fields.

Figure 2:
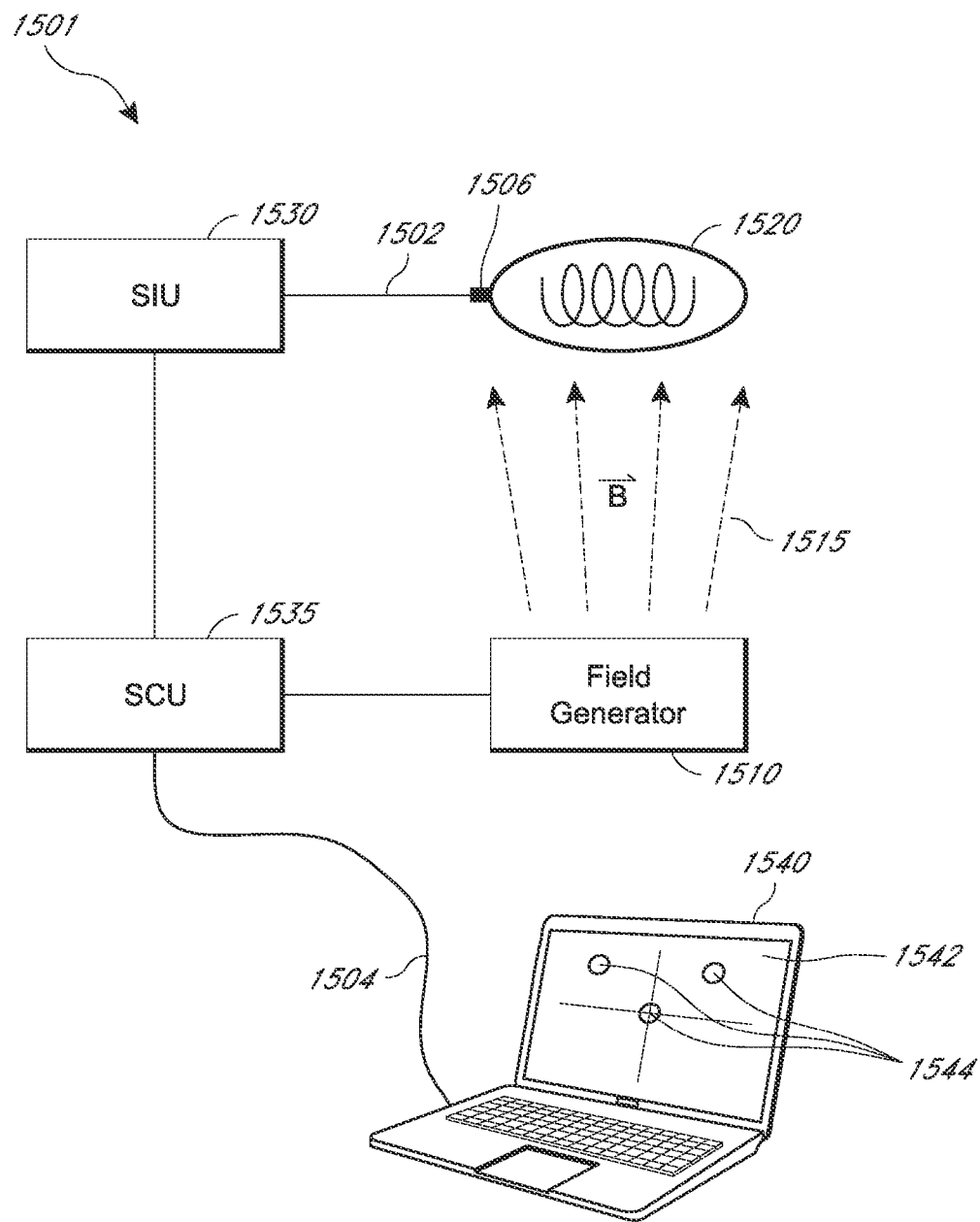
FIG. 2 depicts an embodiment of an electromagnetic tracking system that uses a sensor for locating an intragastric device.

FIG. 2 depicts an embodiment of an electromagnetic tracking system 1501 with an electromagnetic sensor 1506 for locating an intragastric device 1520. The system 1501 includes the intragastric device 1520 coupled with a catheter 1502 that includes one or more sensors 1506. The system 1501 further includes the sensor interface unit 1530, the system control unit 1535 and the field generator 1510 in electrical communication with a computer 1540.

As shown, the system 1501 includes an intragastric device 1520 that is non-toxic, does not cause sensitization, and is non-irritating. The intragastric device 1520 may be any of the balloons or other intragastric devices as described herein.

The intragastric device 1520 is connected to a catheter 1502. The catheter 1502 includes the electromagnetic sensor 1506 at the distal end of the catheter 1502 near the intragastric device 1520. In some embodiments, the sensor 1506 may be embedded with other features of the system 1501, such as an intermediate connector between the catheter 1503 and the intragastric device 1520. The catheter 1502 may be a small 2 Fr diameter catheter. The catheter 1502 may include the sensor 1506 as one or more small inductive sensors. In addition, external reference sensors 1622 (see FIG. 3A) may be placed on the patient, such as on the skin. The external reference sensors 1622 are intended to provide an anatomical frame of reference between the field generator 1510 and the patient. The catheter sensors 1506 will provide location data as they travel through the esophagus across the gastroesophageal (GE) junction and into the stomach. Data collected by the reference sensors 1622 and the catheter sensors 1506 are then displayed on a laptop computer. The electromagnetic sensor can be characterized for five or six degrees of freedom.

The catheter 1502 is connected to a sensor interface unit 1530. In some embodiments, the catheter 1502 is connected directly to the sensor interface unit 1530. In other embodiments, the catheter 1502 is connected indirectly to the sensor interface unit 1530 via an intermediate jumper cable, as described in further detail herein, for example with respect to FIG. 3A. The sensor interface units 1530 amplify and digitize the electrical signals from the sensors 1506. The sensor interface units 1530 also provide an increased distance between the system control unit 1535 and sensors 1506, while minimizing the potential for data noise.

The system 1501 includes the system control unit 1535. The system control unit 1535 is connected to the system interface unit 1530 by a cable allowing for electrical communication therebetween. The system control unit 1535 collects information from the system interface unit 1530 and calculates the position and orientation of each sensor 1506 and interfaces with the computer 1540.

The system control unit 1535 is connected to the field generator 1510 by a cable allowing electrical communication there between. The field generator 1510 generates a magnetic field 1515. The magnetic field 1515 encompasses the intragastric device 1520 and the sensor 1506 located near the intragastric device 1520 in the catheter 1502. The interaction of the magnetic field 1515 with the sensor 1506 creates an electrical signal that is detected and transmitted to the system interface unit 1530, which transmits a signal to the system control unit 1535, which transmits a signal to the computer 1540.

The computer 1540 is connected to the system control unit 1535 by a cable 1504. The cable 1504 allows for electronic communication between the computer 1540 and the system control unit 1535. The computer 1540 includes a display 1542. The display 1542 shows identifiers 1544. The identifiers 1544 indicate the locations of the various sensors located with the intragastric device 1520 and the catheter 1502. As shown, there are multiple identifiers 1544 corresponding to the location of the sensor 1506 on the intragastric device 1520 as well as the location of other reference anatomical sensors, discussed in further herein, for example with respect to FIG. 3

The system 1501 can power on and detect the presence, motion, and changes in orientation of the catheter sensors 1506. In some embodiments, the sensors 1506 are detected when placed at a range of 30 cm from the center point of the field generator 1510. In some embodiments, the range of detection for the sensors 1506 is greater than 45 cm at the center point of the field generator 1510. In some embodiments, the system 1501 can locate with the distal sensor 1506 the two lower corners of the field generator 1510 within a ±2 cm boundary in the X-direction when placed at a range of 30 cm from the center point of the field generator 1510.

Figure 3A:
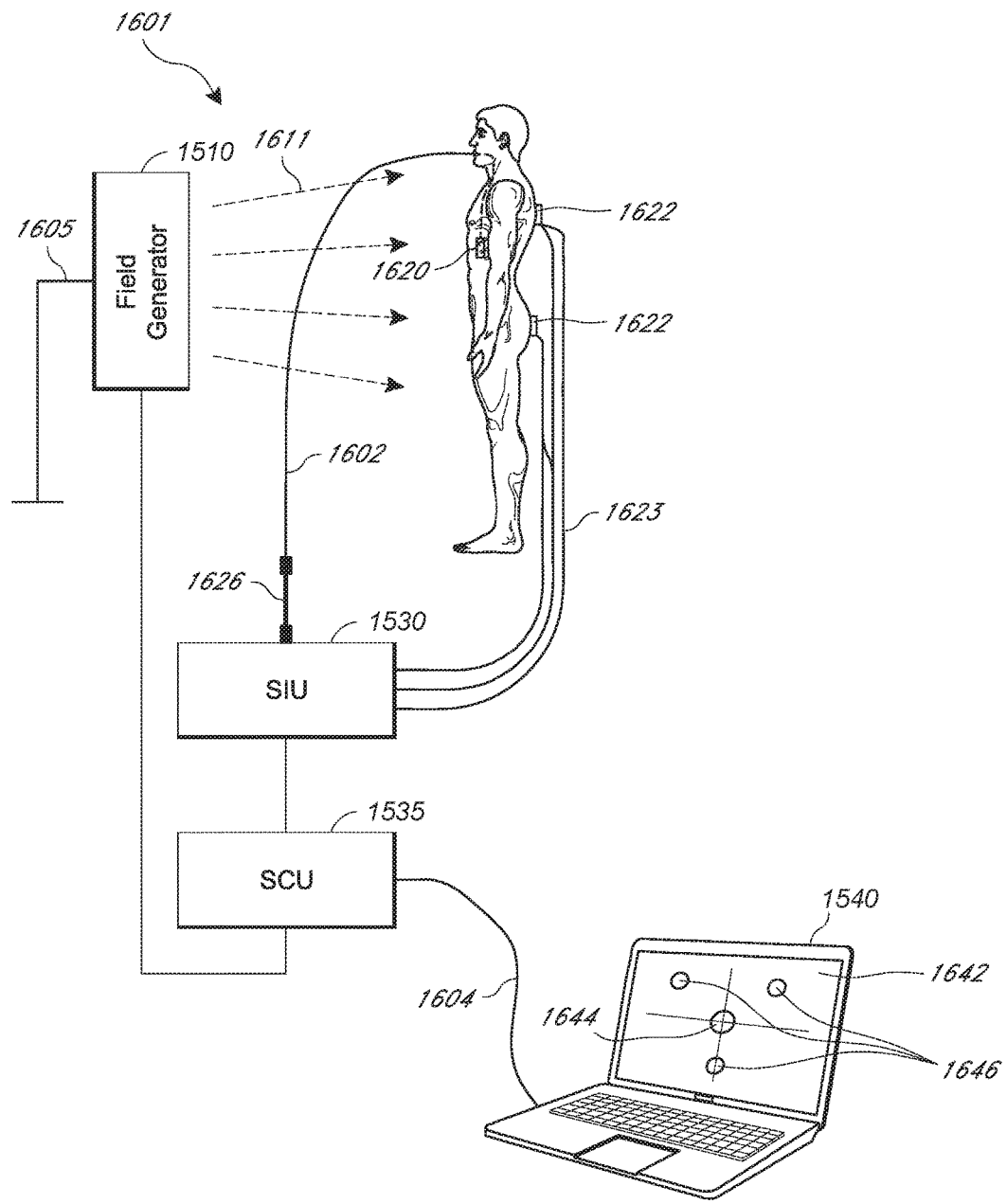
FIG. 3A depicts an embodiment of an electromagnetic tracking system for using a sensor to locate an intragastric device inside the body of a human patient.

FIG. 3A depicts an embodiment of an electromagnetic tracking system 1601 for using a sensor to locate an intragastric device 1620 inside the body of a human patient. The system 1601 includes a field generator 1510 mounted on a support 1605. The support 1605 may be a supporting structure formed from metal, plastic or other suitable materials. The support 1605 may be adjustable in order to adjust the location of the field generator 1510 relative to the location of a patient. In some embodiments, the support 1605 can move up and down to accommodate varying heights of patients. In this manner, the field generator 1510 may be positioned so that a magnetic field is generated on a region of interest, for example the patient's upper body and abdomen.

As shown, the patient may stand in front of the field generator 1510, which may be the field generator 1510. The patient has ingested the intragastric device 1620, which may be the intragastric device 1520, and is now inside the patient's body. The intragastric device 1620 is connected to a catheter 1602, which may be the catheter 1502. The catheter 1602 includes the electromagnetic sensor (not shown) at its distal and located near the intragastric device 1620. Therefore, the field generator 1510 will generate a magnetic field that interacts with the electromagnetic sensor. The electromagnetic sensor is in electrical communication with a sensor interface unit 1530. Electrical communication is provided by wiring connected to the sensor that extends through the catheter 1602 to the sensor interface unit 1530. Electrical signals generated by the electromagnetic sensor due to the presence of the magnetic field are transmitted to the sensor interface unit 1530.

The system 1601 also includes external anatomical reference sensors 1622. The external reference sensors 1622 may provide an anatomical frame of reference between the field generator 1510 and the patient. Small inductive currents are generated by the sensors 1622 while they are inside the tracking volume. As illustrated, three anatomical reference sensors 1622 are included but only two are shown in FIG. 3A. In some embodiments, may be more or fewer than three anatomical reference sensors 1622. The sensors 1622 are connected to the sensor interface unit 1530 by electronic cables 1623. The sensors 1622 are responsive to the magnetic field 1611 generated by the field generator 1510. In the presence of the magnetic field, the sensors 1622 generate a current or other signal that is transmitted to the sensor interface unit 1530.

The system 1601 also includes a jumper cable 1626. The jumper cable 1626 contains an SROM chip which provides electrical continuity from the catheter 1602 to the sensor interface unit 1530. The jumper cable 1626 may provide a connector gender changer to prevent misconnection between the sensor interface unit 1530 and the catheter 1602. Further detail of the jumper cable 1626 is described herein, for example with respect to FIG. 12.

The system control unit 1535 is connected to the computer 1540 by a cable 1604. The cable 1604 allows for electronic communication between the system control unit 1535 and the computer 1540. The computer includes a display 1642. The display 1642 shows the location of a sensor identifier 1644 as well as the locations of three anatomical identifiers 1646. The sensor identifier 1644 indicates the location of the sensor and the distal end of the catheter 1602. The anatomical identifiers 1646 indicate the locations of the anatomical reference sensors 1622.

The anatomical reference sensors 1622 are fixed on the patient and provide a frame of reference by which to locate the electromagnetic sensor. By having a fixed and known location, the anatomical reference sensors 1622 may be used to accurately locate the electromagnetic sensor, and thus the intragastric device 1620. The locations of the reference sensors 1622 shows up on the display 1642 as anatomical identifiers 1646 while the electromagnetic sensor shows up on the display 1642 as the sensor identifier 1644. By knowing the location of the sensors 1622 on the patient's body, and the relative location of the sensor identifier 1644 relative to the anatomical identifier 1646, the location of the electromagnetic sensor, and thus of the intragastric device 1620, inside the body can be determined.

The computer 1540, which may be a laptop computer, contains a system specific software program designed to provide the end user with a "real time" display of the catheter's 1602 location, as well as the location of the reference sensors 1622. The system 1601 may be calibrated prior to each use. The sensor takes a background measurement of the ambient magnetic field during a calibration cycle and when the catheter 1602 is brought within range, the sensor detects the change in the magnetic field and communicates the data to the software program residing in the computer 1540. The software analyses the data and presents the location of the various sensors on the computer display 1642. In some embodiments, no or little magnetic energy is generated by the sensor or the computer 1540.

The intragastric device 1620 is administered via a patient swallow of the balloon capsule that is adhered to the swallowable catheter 1602. The administration of the catheter can be done while visualizing the catheter as it traverses the esophagus past the GE junction into the stomach. Instructions for use (not shown) may be provided with the system 1601. The instructions may provide information on how to administer the catheter 1602, what the patient should expect during and after administration, and how to retrieve the catheter 1602 after completion of the procedure.

The intragastric device 1620 connected to the catheter 1602 is designed to be swallowed and tracked by the various sensors as it traverses to the stomach past the GE junction. The device 1620 is designed to start outer capsule separation after being swallowed. In some embodiments, the device 1620 starts outer capsule separation after being swallowed in approximately 2 minutes. Full placement and removal of the catheter 1602 may take approximately 10 minutes for each swallow procedure. In some embodiments, patients may swallow three catheters, and therefore the total time of the swallow procedure for these subjects is approximately 30 minutes. After completion of each swallow procedure, the catheter 1602 is removed by simply pulling it back through the mouth.

The system 1601 may be controlled using an application program interface (API) (not shown). The API is a set of commands that allow configuration and requesting information from the system 1601. The system 1601 may return information only when requested by the computer 1540. In some embodiments, the system 1601 may return information automatically, for instance at set intervals or continuously.

When the system 1601 is tracking the device 1620, it returns information about the sensors to the computer 1540. The system 1601 may return the position of each sensor's origin, given in mm, in the coordinate system of the field generator 1510. The system 1601 may return the orientation of each sensor, given in quaternion format. The quaternion values are rounded off, so the returned values may not be normalized. The system 1601 may return an error indicator value, between 0 and 9.9 (where 0 is the absence of error and 9.9 is the highest indication of error). The system 1601 may return the status of each sensor, indicating whether the sensor is out of the electromagnetic field volume, partially out of the volume, or missing. The system 1601 may return the frame number for each sensor transformation. The frame counter starts as soon as the system 1601 is powered on, and can be reset using API commands. The frame number returned with a transformation corresponds to the frame in which the data used to calculate thattransformation was collected. The system 1601 may return the system 1601 status, which may include system errors.

The various sensors may be five degrees of freedom (5DOF) or six degrees of freedom (6DOF). Five degrees of freedom provides information on the three translation values on the x, y and z-axes and any two of the three rotation values—roll, pitch and yaw. Six degrees of freedom provides information on the three translation values on the x, y and z-axes and the three rotation values roll, pitch and yaw. In embodiments with only one sensor incorporated, the rotation around the sensor's longitudinal axis cannot be determined. As such, only five degrees of freedom (5DOF) can be determined for single sensor embodiments. For example, how much a needle physically rolls is not as important as where it is pointing and where the tip is located. As such, a needle can be a 5DOF tool, with only one sensor incorporated into its design.

In embodiments that incorporate two sensors fixed relative to each other and ideally orthogonal, the system can determine six degrees of freedom (6DOF). First, the system determines 5DOF information for each sensor. Next, the system combines and compares this information, applies the fixed location data, and determines six degrees of freedom (6DOF).

For example, an ultrasound technician needs to know the location of the ultrasound probe as it moves over a subject, in order to match its findings to actual physical locations on that subject. Incorporating two sensors into the ultrasound probe produces 6DOF measurements and ensures that all translation and rotation values of the probe are captured.

The field generator 1510 may use a coordinate system with the origin located approximately on the surface of the field generator 1510. This global coordinate system may be defined during manufacture. The system 1601 may report the transformations in the global coordinate system. However, in some embodiments that use a reference tool (not shown), software can calculate and report transformations in the local coordinate system of the reference tool.

Each sensor has its own local coordinate system that is defined by an origin and three axes. Local coordinate systems are part of the measurement process. In some embodiments, there may be a single sensor. The single sensor's local coordinate system is based directly on that of the sensor. By default, the system assigns the z-axis along the sensor's length, with an origin at the sensor's center. It is possible to move the origin along the z-axis. The x and y axes are not fixed, due to the inability to determine rotation about the z-axis.

In some embodiments, there may be dual sensors having 5DOF. A dual 5DOF sensor is essentially two single sensors joined to the same sensor body connector. As such, the sensor actually has two local coordinate systems, each based on one of the sensors incorporated into its design. These local coordinate systems are determined in the same way as that of a single sensor.

In some embodiments, the system 1601 has metal objects, such as tables, tools, braces, and the like. This may create problems when using an electromagnetic sensor, and thus the system 1601 may therefore be resistant to certain metals. The problems caused by placing metal near an electromagnetic measurement system relate to eddy currents. An eddy current is caused when a conductive material is exposed to a dynamic magnetic field. The changing magnetic field induces a circulating flow of electrons within the conductive material, resulting in an electric current. These circulating currents (sometimes known as eddy currents) produce an electromagnetic effect of their own, creating magnetic fields that oppose the original, external magnetic field. The greater the electrical conductivity of the conductor, the greater the eddy current developed (and the greater the opposing magnetic field produced).

If a conductive metal intersects the electromagnetic field 1611, the opposing magnetic field created by resulting eddy currents disrupts that field and affects the transformation data produced. One method of reducing this effect is to adjust the placement of both the sensor being measured and the object producing the eddy currents. Moving the sensor so that the distance between the sensor and the field generator 1510 is smaller than its proximity to the object creating eddy currents may decrease the effects of the eddy currents on sensor measurements.

Another situation to consider is the effect of eddy currents in metallic loops. Loops may occur in structures like metallic table frames, or concrete reinforcement bars. Cutting the loops will reduce the effect of eddy currents. If cutting the loops is not an option, then locate the system 1601 to minimize the effects of the loops. In some embodiments, the system 1601 uses special technology to take into account such effects as eddy currents. The following metal alloys work well with the system 1601 when applied in amounts similar to that used in medical tool construction: cobalt-chrome alloy, steel DIN 1.441, titanium (TiAl16V4) and 300 series stainless steel.

Further, ferromagnetic material generally has little or no net magnetic property. However, if it is placed in the magnetic field 1611, its domains will re-orient in parallel with that field, and may even remain re-oriented when the field 1611 is turned off. Even metals with only small amounts of ferrous material in them may have these reactions.

The magnetic field produced in a ferromagnetic object attracts the external magnetic field 1611, resulting in the external magnetic field 1611 bending towards the object itself. As such, introducing a ferromagnetic object into the system's 1601 electromagnetic field 1611 will cause a distortion that can affect the transformation data produced.

Figure 3B:
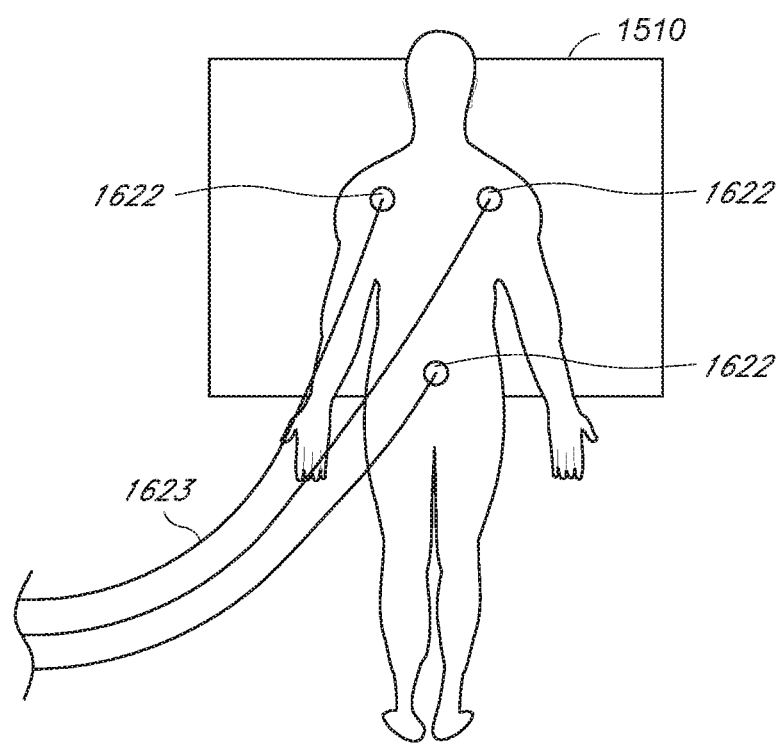
FIG. 3B is a rear view of the patient of FIG. 3A showing an embodiment of external reference sensors for an anatomical frame of reference.

FIG. 3B is a rear view of the patient from system 1601 shown in FIG. 3A. As shown in FIG. 3B, the patient has three external anatomical reference sensors 1622 attached to the backside of the patient. The sensors 1622 are arranged in a generally triangular configuration. In some embodiments, the sensors 1622 may be arranged in different configurations, such as rectangular, circular, or others. The sensors 1622 are connected by the cable 1623 to other components of the system 1601, such as the sensor interface unit 1530. In some embodiments, the sensors 1622 may be wirelessly connected to other components of the system 1601. As further shown, the patient is standing directly in front of the field generator 1510. In some embodiments, the patient need not be standing directly in front of the generator 1510.

FIG. 4 depicts an embodiment of an electromagnetic tracking system 1650 that includes a support 1655 and that uses a sensor (not shown) to locate an intragastric device (not shown) inside the body of a human patient 1651. The system 1650 includes the patient 1651 standing in front of a field generator 1660, which may be the field generator 1510, described herein. The generator 1660 is coupled with an arm 1670 that is adjustable. The arm 1670 may be adjusted such that the field generator 1660 is located next to the patient 1651. The arm 1670 may also adjust the field generator 1660 such that it produces a magnetic field in the vicinity of the patient's 1651 stomach. The arm 1670 may adjust the field generator 1660 vertically as well as horizontally. The arm 1670 can also rotate the field generator 1660, for example to accommodate patients who are lying down.

The system 1650 includes the support 1655 which supports a computer 1690. The support 1655 is adjustable in the vertical direction. In some embodiments, the support 1655 may be adjustable in other directions, for example it may adjust in the horizontal direction, rotate, etc. The support 1655 includes a surface upon which the computer 1690 and other components of the system 1650 may be placed or mounted. The support 1655 also includes four wheels 1666 that allow the support 1655 to be rolled around. In some embodiments, the support 1655 may include fewer or more than four wheels 1666.

The support 1655 may be designed to avoid tipping over. In some embodiments, the support 1655 may withstand 10° incline from a horizontal plane in any X or Y direction without tipping over. In some embodiments, the support 1655 may withstand a load equal to 25% of total weight in any X or Y direction without tipping over.

Figure 5:
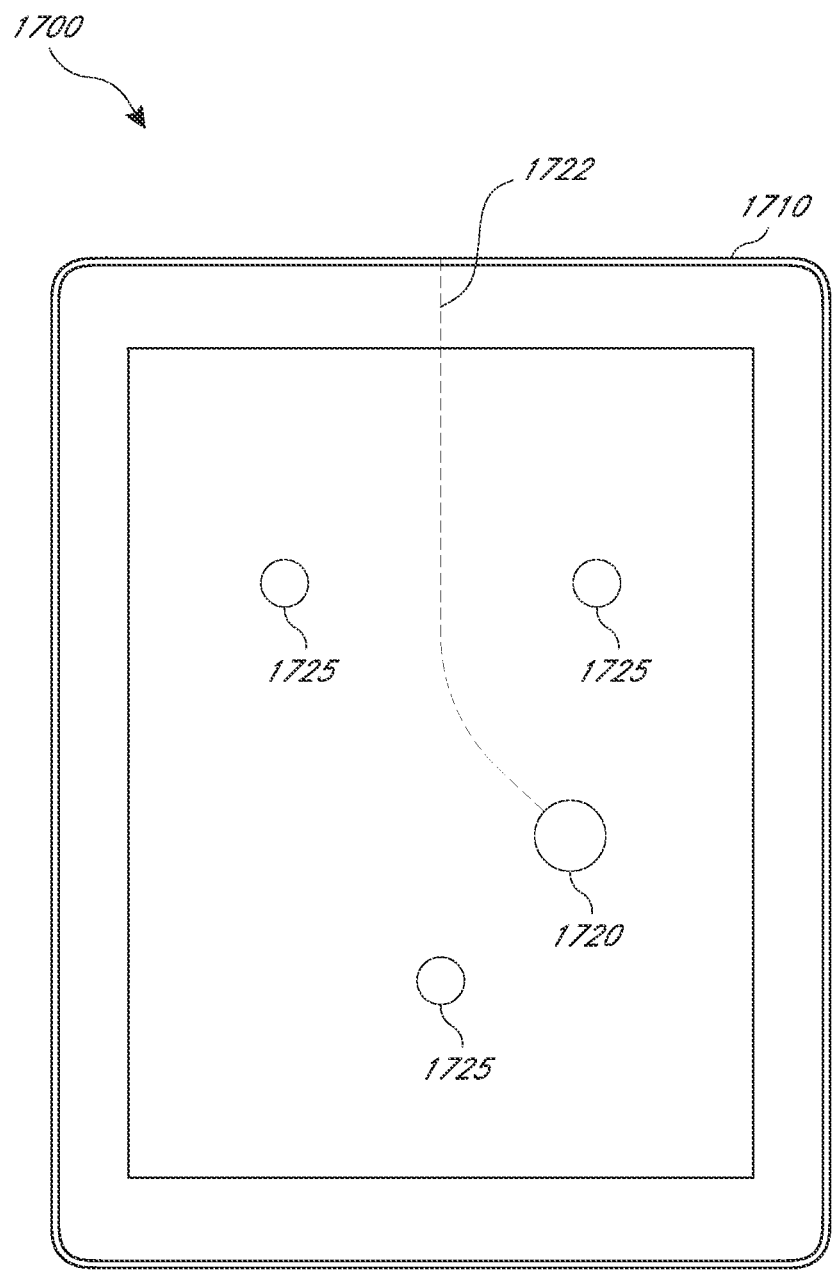
FIG. 5 depicts an embodiment of a display that can be used with the systems of FIGS. 2-4.

FIG. 5 depicts an embodiment of a display that can be used with the systems of FIGS. 2-4. The display 1700 includes a screen 1710. The screen 1710 displays the locations of the various identifiers corresponding to the various sensors. The screen 1710 may be a display on a computer. The screen 1710 may also be on a variety of other machines.

As shown, the display 1700 includes the locations of the identifiers 1720 and 1725. The identifier 1720 corresponds to the location of the sensor coupled with the catheter. For example, the identifier 1720 may correspond to the location of the electromagnetic sensor 1506 and the catheter 1502. The identifier 1720 may also correspond to the location of the sensor coupled with the intragastric device 1620 and the catheter 1602.

The display 1700 may also include a trace 1722. The trace 1722 may indicate the path that the identifier 1720 has traveled over time. Therefore, the trace 1722 may indicate the path that the sensor has traveled inside the patient's body. As shown, the trace 1722 may have a vertical section followed by a bend near the bottom of the trace 1722 as illustrated. In some embodiments, the bend in the trace 1722 is indicative of the path of a sensor traveling through into the stomach of a patient. Therefore, the path of the trace 1722 may be indicative of the location of the sensor and therefore of the intragastric device.

The identifiers 1725 may correspond to the locations of external anatomical reference sensors. For example, the identifiers 1725 may correspond to the locations of the three anatomical reference sensors 1622. As shown, the identifiers 1725 form a generally triangular shape. This may correspond, for example, to a generally triangular configuration of the sensors 1622 located on the back of the patient. By knowing the location of the identifiers 1725 relative to the patient, and the relative location of the identifier 1720 relative to the identifiers of 1725, the location of the sensor and therefore the intragastric device inside the body may be determined. As shown in FIG. 5, the location of the identifier 1720 may be indicative of an intragastric device being success successfully placed inside the stomach. The display 1700 shown is merely one example and other suitable displays may be implemented. In some embodiments, the screen 1710 may include markings or other reference points to facilitate locating the various identifiers.

Figure 6:
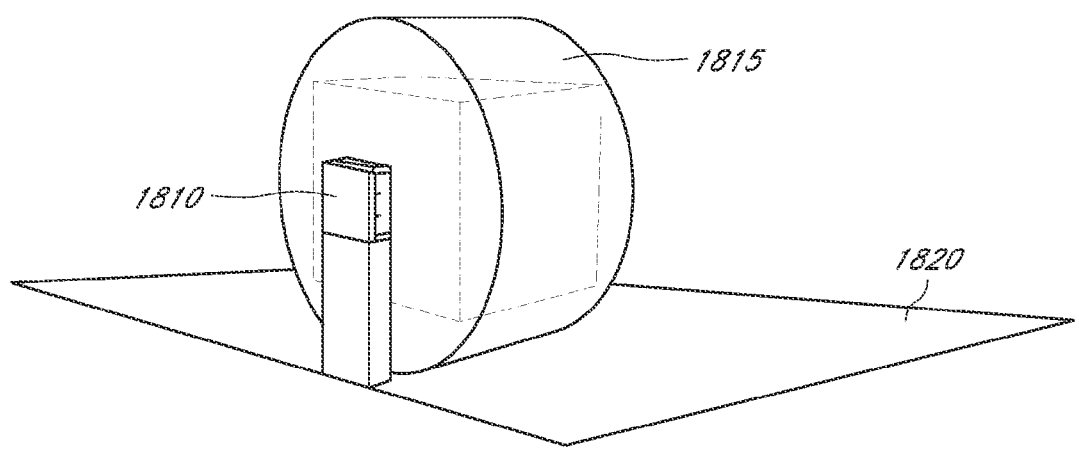
FIG. 6 depicts an embodiment a field generator and corresponding magnetic field envelope that may be used with the systems of FIGS. 2-4.

FIG. 6 depicts an embodiment a field generator and corresponding magnetic field envelope that may be used with the systems of FIGS. 2-4. The envelope 1815 represents the volume in which the sensors may interact with the generated magnetic field from the field generator 1810. The envelope 1815 is shown in a generally cylindrical shape. In some embodiments, the envelope 1815 may have a variety of shapes.

Figure 7:
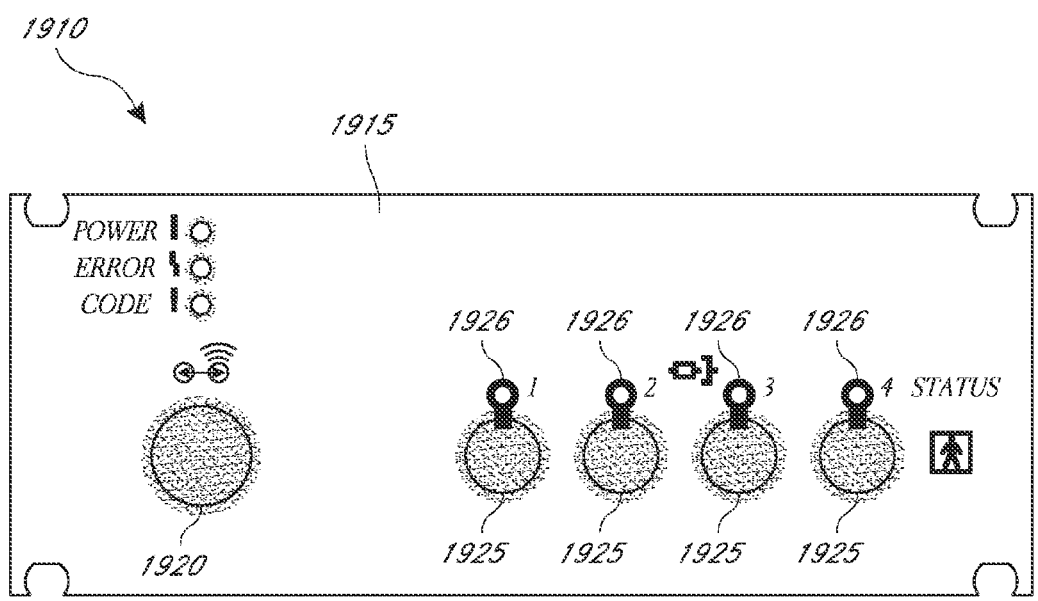
FIG. 7 depicts an embodiment of a control panel on a system control unit that may be implemented with the systems of FIGS. 2-4.

FIG. 7 depicts an embodiment of a control panel 1915 on a system control unit 1910 that may be implemented with the systems of FIGS. 2-4. The panel 1915 may be on the back side of the system control unit 1910.

The panel 1915 includes a field generator port 1920 and multiple sensor interface unit ports 1925 and status lights 1926. The port 1920 may be used to synchronize the system control unit 1910 to other equipment. The sensor interface unit ports 1925 connect the sensor interface units to the system control unit, allowing for communication with the connected sensors. For example, the ports 1925 may be used to connect the sensor interface unit 1530 to the system control unit 1535 to enable communication with the sensors 1506. The status lights 1926 may indicate whether the corresponding port 1925 is connected with a sensor or catheter.

Figure 8:
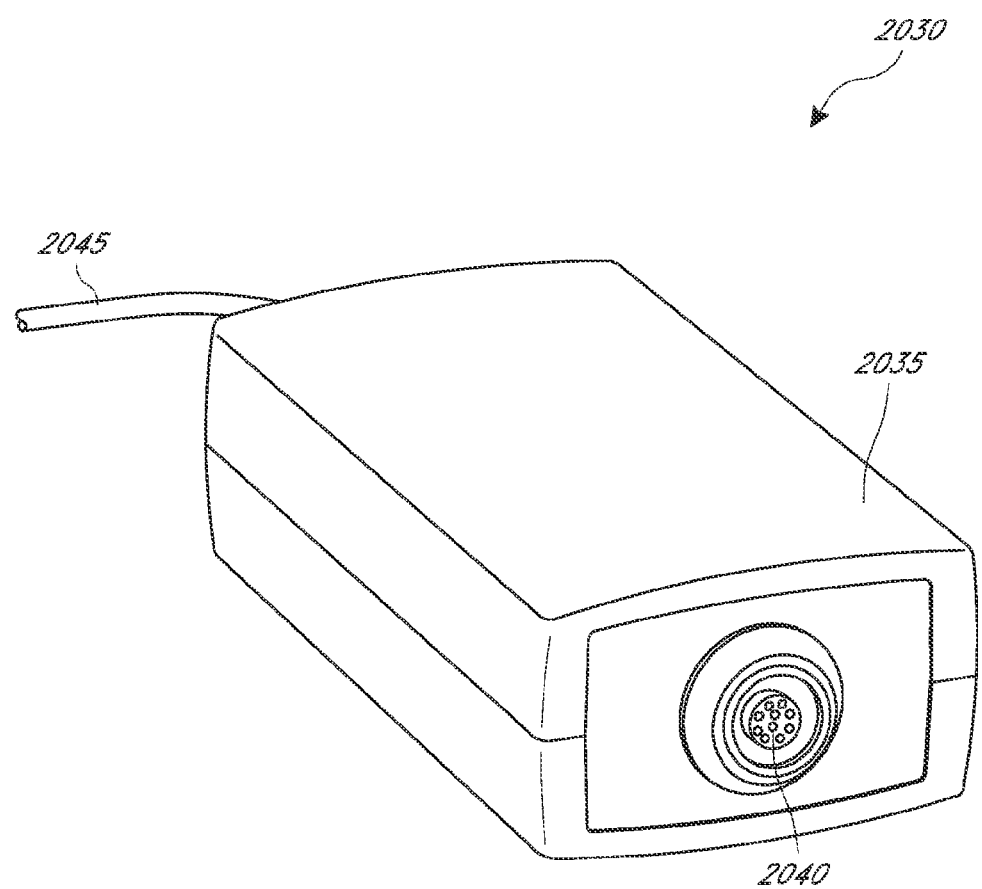
FIG. 8 depicts an embodiment of a sensor control unit that may be implemented with the systems of FIGS. 2-4.

FIG. 8 depicts an embodiment of a sensor interface unit 2030 that may be implemented with the systems of FIGS. 2-4. The sensor interface unit 2030 is the interface between the sensors and the system control unit, such as the system control unit 1535. The main function of the sensor interface unit 2030 is to convert the analog signals, produced by the sensors, to digital signals. The digital signals are sent to the system control unit for processing. Another function of the sensor interface unit 2030 is to increase the distance between the system control unit and the sensors, removing the requirement for a long tool cable and keeping bulky system components away from the application space. In addition, the shorter the tool cable, the less noise will appear on the signal from the sensors. In some embodiments, each sensor interface unit 2030 can support up to two 5DOF sensors, or one 6DOF sensor.

The sensor interface unit 2030 includes a sensor port 2040 and cable 2045. The sensor port 2040 connects the sensor interface unit 2030 to sensors, such as the sensor 1506. The sensor port 2040 may be a 10-pin circular plastic connector. The cable 204 electrically connects the sensor interface unit 2030 to the system control unit, such as the system control unit 1535.

Figure 9:
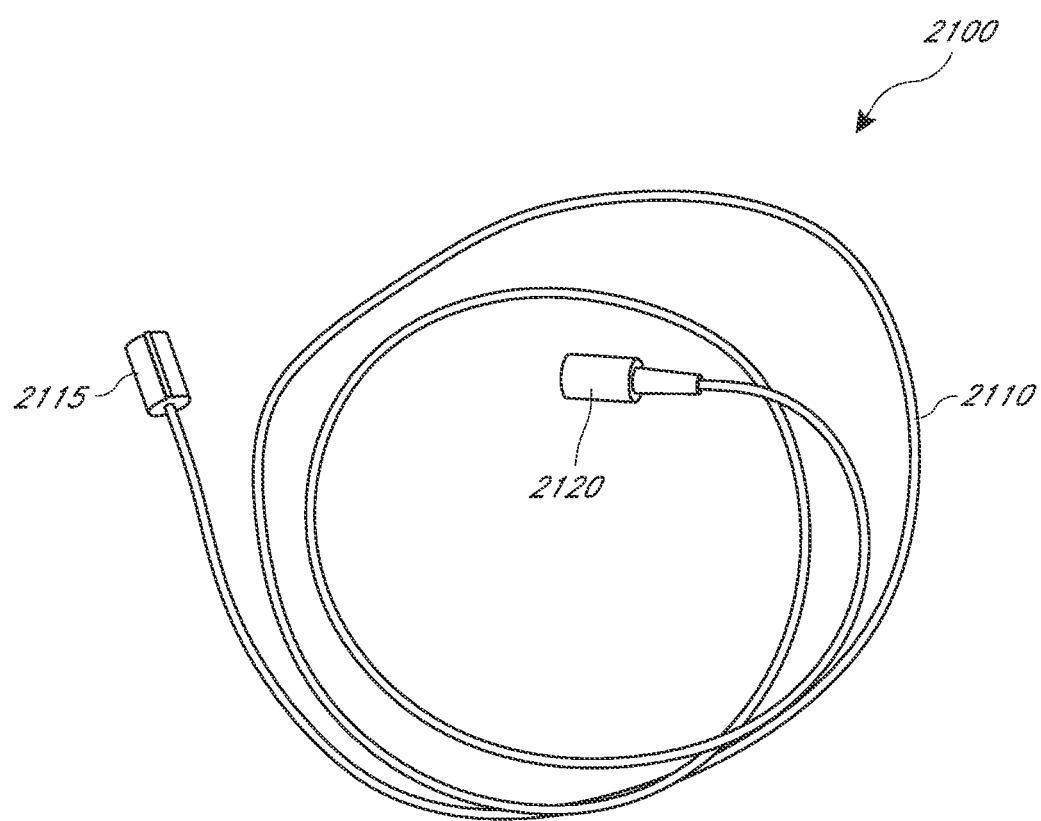
FIG. 9 depicts an embodiment of a catheter with integrated sensor that may be used with the systems of FIGS. 2-4.

FIG. 9 depicts an embodiment of a catheter 2100 with an integrated sensor 2115 that may be used with the systems of FIGS. 2-4. The catheter 2100 includes a shaft 2110 that extends along the length of the catheter 2100. The shaft 2110 forms a hollow channel through which electrical wires may be extended to attach to the sensor 2115. The catheter 2100 may include a plug 2120 on the opposite end as the sensor 2115. The plug 2120 may couple with the sensor interface unit, such as the sensor interface unit 1530. In some embodiments, the plug 2120 couples with a jumper cable that is attached to the system control unit.

Figure 10A:
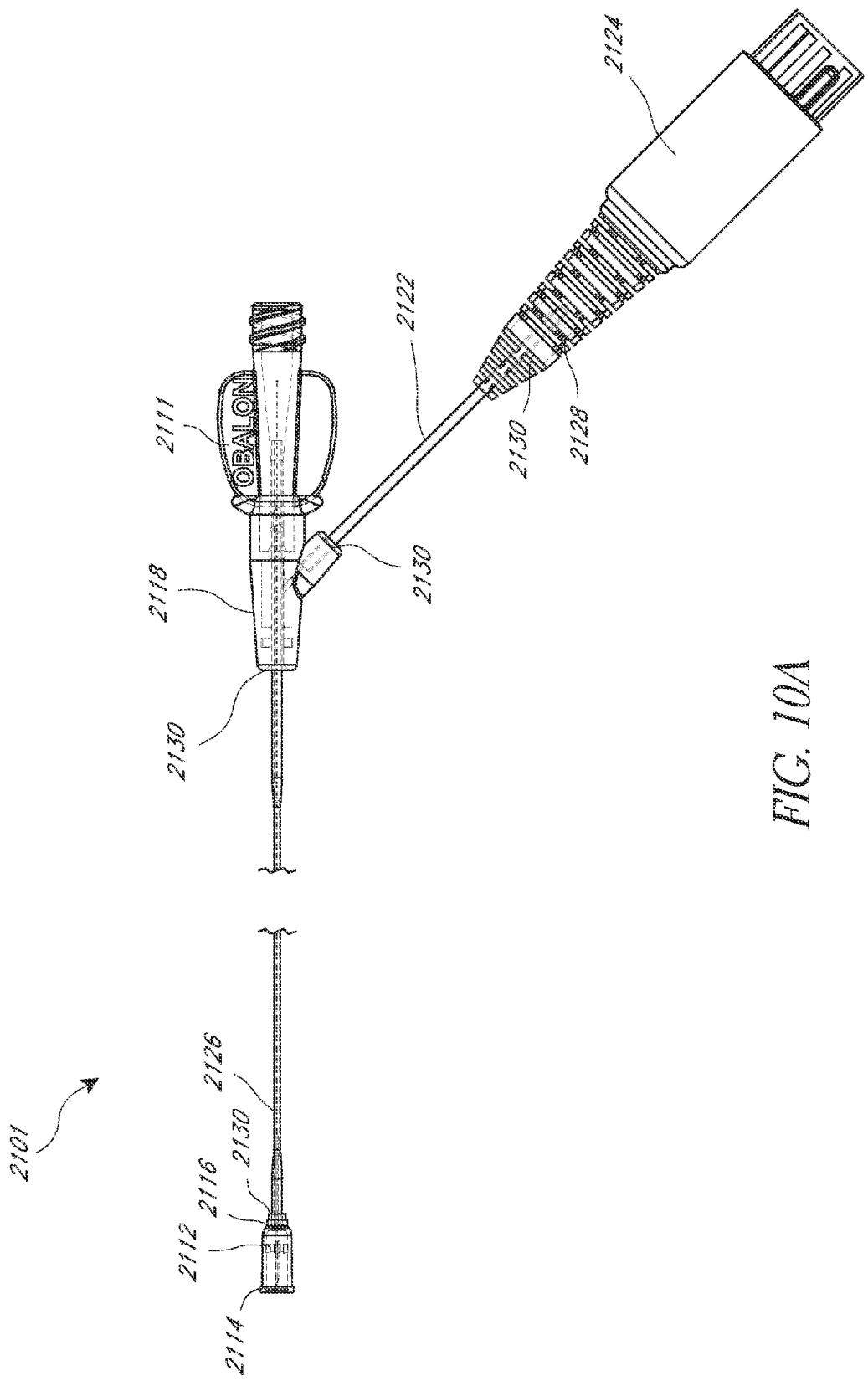
FIG. 10A depicts another embodiment of a catheter and sensor that may be used with the systems of FIGS. 2-4.

FIG. 10A depicts another embodiment of a catheter 2101 and sensor 2114 that may be used with the system of FIGS. 2-4. The catheter is a flexible, hydrophilic coated, 2-Fr catheter which contains a swallowable catheter (approximately 30 inches) which is bonded to approximately 40 inches of pellethane extension tubing to allow connection to the sensor interface unit. The distal end of the catheter contains two small inductive sensors, one at the distal end and the second approximately 6 inches from the distal tip. As the sensors within the catheter 2101 move through the esophageal tract into the stomach through the GE junction the sensors provide electrical signals to the sensor interface unit. The characteristics of these electrical signals are dependent of the distance and angle between a sensor and the field generator.

In some embodiments, the distal end of the various catheters, such as the catheter 2100 or 2101, is sealed with an adhesive plug. Attached to the distal end of the catheter is a 31×12.41 mm pharmaceutical grade porcine gelatin capsule with a hydrophilic coating containing food-grade sugar. The catheter 2101 may include a 2 Fr catheter shaft formed from Pebax® (Polyether Block Amids) and Polyvinylpyrrolidone to provide a swallowable catheter with a hydrophilic coating to provide lubricity. The catheter may include sensors that include a copper coil encased in epoxy to provide electrical signals for tracking the catheter. The catheter may include an outer capsule formed from a USP-grade hard porcine gelatin capsule supplied by Torpac, Inc. (New Jersey, USA) containing food grade sugar to mimic food bolus weight for swallowing. The outer capsule may have a polyvinylpyrrolidone hydrophilic coating to provide lubricity. The catheter may include a distal strain relief formed from a thermoplastic polyurethane elastomer to provide strength to hold the gelatin capsule on the catheter shaft. The catheter may include an extension tube formed from a thermoplastic polyurethane elastomer to extend the length of the catheter for attachment to the sensor interface unit. The catheter may include a markerband formed from 316 stainless steel to provides visibility to the tip of the catheter during visualization. The catheter may include adhesive that is UV curable for joining extruded components of the catheter together and to seal the sensors from fluid contact. The catheter may include a 4-Pin connector to provide communication between the catheter and the sensor interface unit. The connector may be formed from a PBT-Steel-Brass material. The catheter may include a heat shrink-connector to provide a strain relief for attaching the 4-Pin connector to the extension tube. The heat shrink-connector may be formed from a fluoropolymer.

As shown in FIG. 10A, the catheter 2101 may include a proximal luer hub 2111. The luer hub 211 may allow for attaching peripheral components or for grasping the catheter 2101. The catheter 2101 may also include a catheter inner assembly 2112 that includes a catheter needle, a monofilament thread, and a needle holder. The catheter 2101 may also include a needle sleeve 2114 that surrounds and protects the needle assembly 2112. The catheter 2101 is shown with a sensor 2116. In some embodiments, the sensor 2116 is a 0.3×13 mm 5DOF sensor manufactured by Northern Digital Inc. in Ontario, Canada. However, other sensors may be implemented.

The catheter 2101 may also include a Y-port 2118. The Y-port 2118 may be a splitter that connects various features of the catheter 2101 together. In some embodiments, the Y-port 2118 connects the luer hub 2111 and a strain relief tubing 2122 with a catheter bump tubing 2126. The strain relief tubing 2122 may extend off-axis from the Y-port 2118 and connect with a connector 2124. The connector 2124 may include a connector spacer 2128 and UV cure adhesive 2130. The adhesive 2130 may also be used in other locations of the catheter 2101, for example at the interface of the sensor 2116 and the catheter bump tubing 2126, and elsewhere as shown.

The catheter 2101 may have robust mechanical properties. In some embodiments, the catheter 2101 can bend 180° over a 0.5 cm radius mandrel without kinking at the center portion of a Peebax catheter shaft. The intragastric device may separate from the catheter 2101 when submerged in 37° C. water. The adhesive 2130 bond between a capsule and the catheter 2101 fails at more than 150 grams when preconditioned for twenty seconds in room temperature water. The adhesive 2130 bond between the strain relief tube 2122 and the catheter tubing 2126 fails at more than one foot-pound. The bond between the catheter 2101 and the marker band fails at more than one foot pound. The bond between the extension tube and the catheter tubing 2126 fails at more than one foot pound.

Figure 10B:
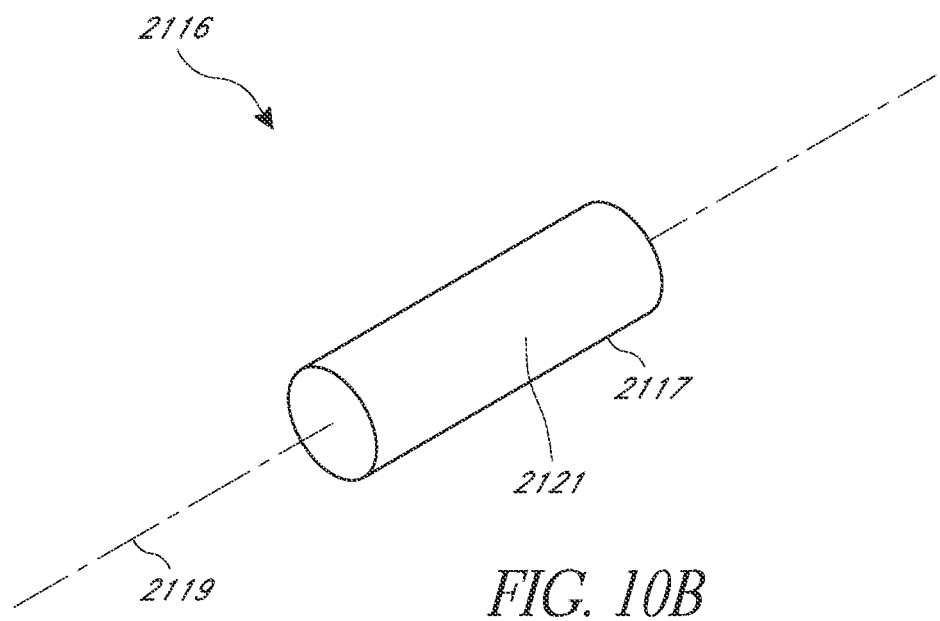
FIG. 10B depicts an embodiment of an electromagnetic sensor that may be implemented with the catheter of FIG. 10A.

FIG. 10B depicts an embodiment of the electromagnetic sensor 2116 that may be implemented with the catheter of FIG. 10A. The sensor 2116 includes a sensor body 2117. The body 2117 is elongated and generally cylindrical. However, the body 2117 may have a variety of shapes. The body 2117 is formed from a metal or other material that is responsive to an electromagnetic field. The body 2117 is symmetric about a longitudinal axis 2119. The body 2117 includes a geometric center 2121.

The sensor 2116 has its own local coordinate system that is defined by the geometric center 2121 and the longitudinal axis 2119. The remaining two axes are orthogonal to the longitudinal axis 2119 and intersect the center 2121. In some embodiments, the z-axis extends along the sensor's length and thus corresponds with the longitudinal axis 2119 as illustrated, with an origin at the sensor's center 2121. However, it is possible to move the origin along the z-axis. With a 5DOF sensor 2116, the orthogonal X and Y axes are not fixed, due to the inability to determine rotation about the z-axis.

With a 5DOF sensor 2116, information may be provided on the three translation values on the x, y and z-axes and any two of the three rotation values—roll, pitch and yaw. However, the rotation around the sensor's longitudinal axis 2119 cannot be determined. As such, only five degrees of freedom (5DOF) can be determined for single sensor embodiments.

Figure 10C:
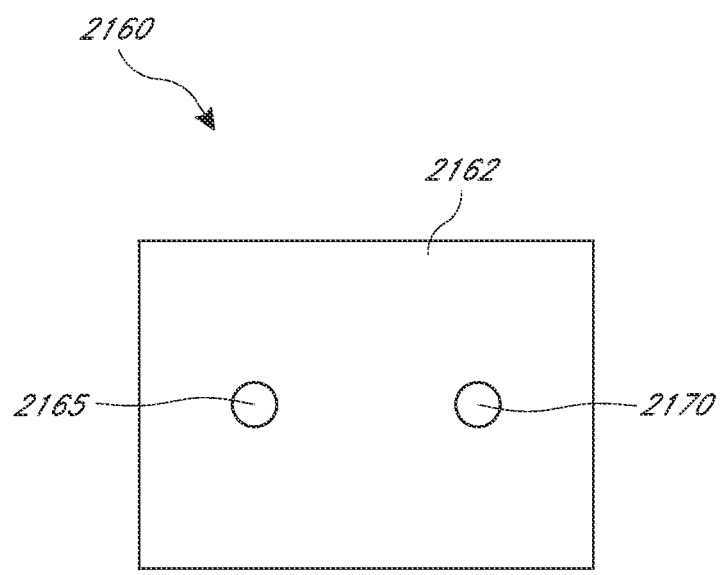
FIG. 10C depicts an embodiment of a voltage sensor that may be implemented with the catheter of FIG. 10A.

FIG. 10C depicts an embodiment of a voltage sensor 2160 that may be implemented with the catheter of FIG. 10A. In some embodiments, the voltage sensor 2160 may incorporate a micro sized integrated circuit (IC) as developed for an ingestible event marker by Proteus Digital Health, of Redwood, Calif. A micro size integrated circuit (IC) is embedded inside the swallowable balloon capsule. When the circuit is exposed to stomach fluid it provides an electrolyte to the circuit that powers a battery constructed on the surface of the circuit. The IC then powers up and communicates with a body mounted receiver. The receiver then communicates with an external device like a smart phone or tablet computer to provide information to the health care provider about when the capsule has reached the gastric fluid of the patient.

In some embodiments, the IC is coupled with the intragastric device, such as the device 1520 or 1620, of the electromagnetic tracking system. Once the device has reached the stomach it is provided the electrolyte to power the battery and communicate with its receiver indicating that the device is inside the stomach. The IC would then separate from the balloon capsule and pass naturally through the digestive tract.

An alternate embodiment includes creating a voltage potential near the intragastric device by embedding an anode 2165 and a cathode 2170 into the sensor 2160 as shown in FIG. 10C. In some embodiments, the anode 2165 and cathode 2170 is embedded in a catheter, such as the catheter 2101. The anode 2165 and cathode 2170 create a voltage potential between electrodes when in the presence of an electrolyte (such as stomach fluid). This generated voltage is passed through the catheter using miniature magnet wire and connected to a system that analyzes the voltage and reports confirmation of a threshold voltage level that would be sufficient to be confident that the catheter has entered the stomach. Once confirmation of threshold voltage is received, the catheter with attached electrodes would be withdrawn from the body after inflating the balloon, thus removing any potential risk of ingesting the anode/cathode materials.

The advantage of the voltage sensor 2160, with either the IC system or the anode/cathode configuration, is that the voltage sensor 2160 would only provide confirmation of position when it is in the presence of gastric fluid—thus preventing the doctor from prematurely inflating the balloon outside the stomach.

Another advantage of the catheter electrode system is that no foreign materials would be left inside the patient's body after balloon deployment (other than the balloon system itself).

Another embodiment includes the use of specific coatings on the intragastric device or catheter that could control the timing of when the electrodes are exposed to the stomach fluid, thus controlling the timing of voltage generation. These coatings could be hydrophilic to speed up exposure time, only soluble at low pH values (less than 5.0), or enteric coated to delay the exposure time.

Figure 11:
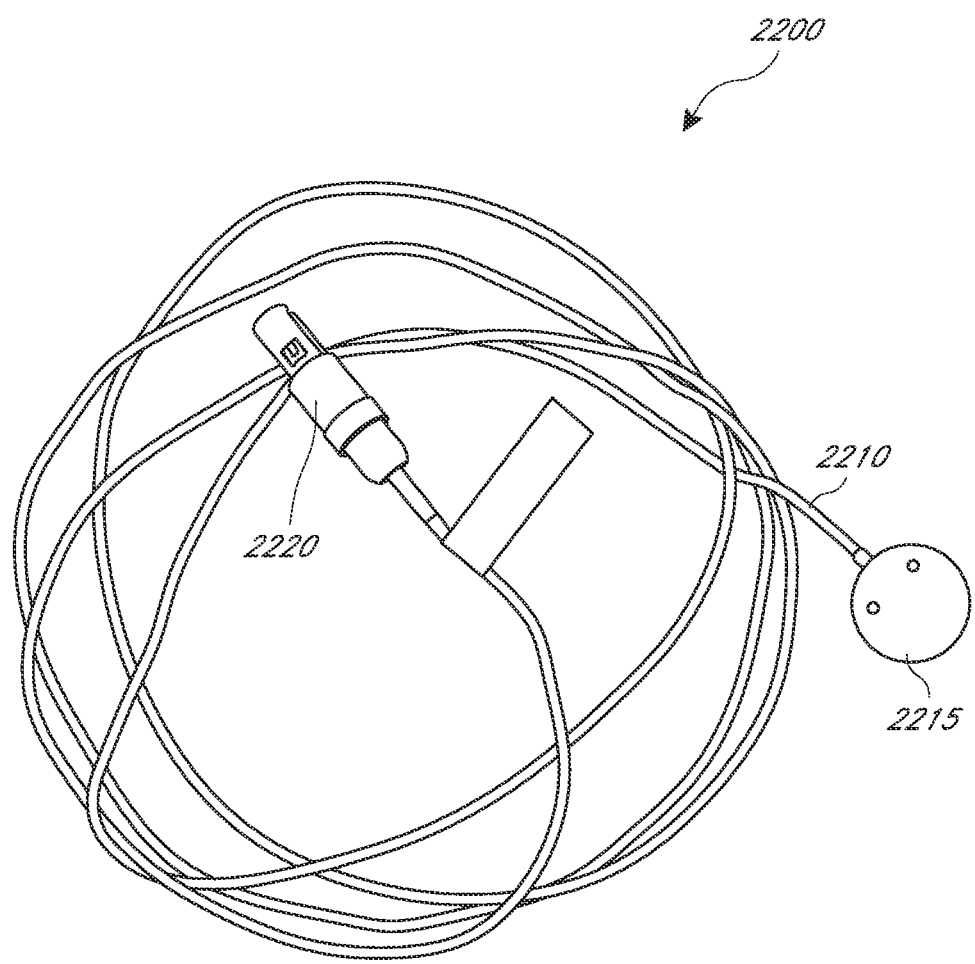
FIG. 11 depicts an embodiment of an external reference sensor that may be used as anatomical reference markers with the systems of FIGS. 2-4.

FIG. 11 depicts an embodiment of an external reference sensor assembly 2200 that may be used as anatomical reference sensors with the systems of FIGS. 2-4. The assembly 2200 includes a sensor 2215 connected to a cable 2210. On the opposite end of the cable 2210 is a connector 220 for connecting the assembly 2200 to the system control unit, such as the system control unit 1535. The sensor 2215 may attach to the back side of a patient and be fixed. The sensor 2215 may be fixed to the patient with mechanical or other suitable means, for instance adhesive or clips for attachment to clothing.

Figure 12:
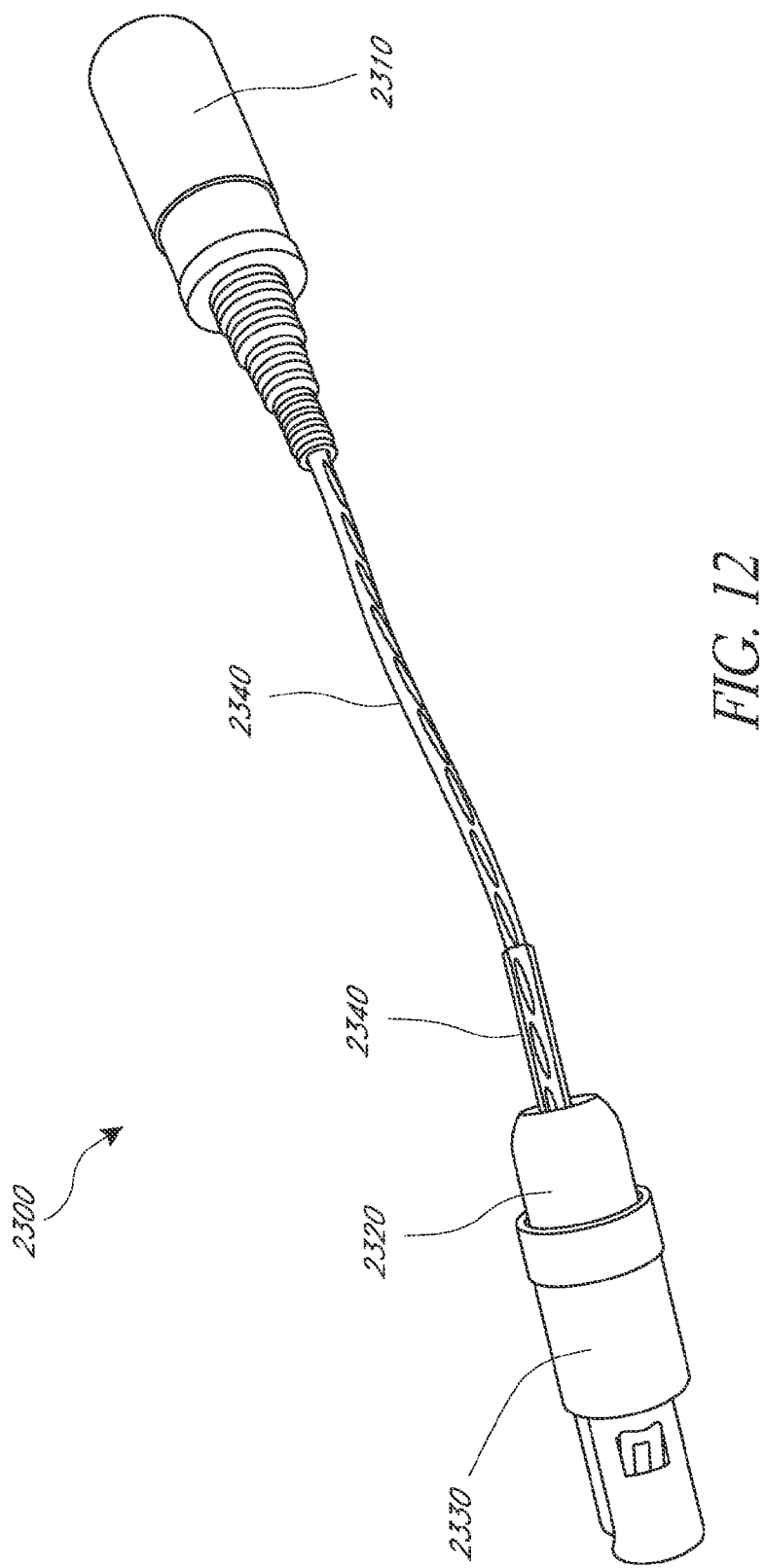
FIG. 12 depicts an embodiment of a jumper cable that may be used with the systems of FIGS. 2-4.

FIG. 12 depicts an embodiment of a jumper cable 2300 that may be used with the systems of FIGS. 2-4. The jumper cable 2300 may provide a connector gender changer to prevent misconnection between the sensor interface unit and the catheter, for instance between the sensor interface unit 1530 and the catheter 1602 in the system 1601 of FIG. 3A

The cable 2300 includes a connector 2310. The connector 2310 may be a four-pin female connector, but other connector types may also be used. The cable 2300 further includes heat shrink tubing 2340 along the length of the cable 2300. On the opposite end as the connector 2310 is a second connector 2330 with an EPROM chip 2320. The second connector 2330 may be a ten-pin male connector, but other connector types may also be used.

Magnetic Real-Time Confirmation of Placement

In certain embodiments, a magnetic tracking technology as is commercially available is employed. Suitable systems include, but are not limited to, the magnetic sensor system as developed by Lucent Medical Systems, Inc. of Kirkland, Wash. It is noted that embodiments using an electromagnetic-based system, such as embodiments incorporating the Aurora system from NDI, Inc., described above, employ active electromagnetic sensors, as described above. This is in contrast to embodiments that employ passive magnetic sensors, such as embodiments that incorporate the Lucent System, and which embodiments are described in further detail below.

The Lucent System

The Lucent Medical Systems technology is described in U.S. Pat. Nos. 5,879,297, 6,129,668, 6,216,028, and 6,263,230, the contents of which are hereby incorporated by reference in their entirety. The Lucent technology is generally directed to a system and method for detecting the location of an intragastric device within the body of a patient and, more specifically, to a detection apparatus which senses magnetic field strength generated by a magnet associated with the intragastric device.

The Lucent system can be employed to locate the intragastric device, e.g., the intragastric balloon, or one or more portions of a catheter employed to place, inflate, deflate, and/or remove the intragastric balloon. The location of the intragastric device is determined by sensing the magnetic field produced by a permanent magnet associated with the intragastric device. As used herein, the term "associated with" means permanently fixed, removably attached, or in close proximity with, the intragastric device. In one embodiment, the magnet is associated with a catheter at a location above the intragastric balloon. In another embodiment, the magnet is associated with the intragastric balloon itself. The magnet can be a small, cylindrical, rotatably attached, rare-Earth magnet. Suitable magnets include rare Earth magnets such as samarium cobalt and neodymium iron boron, both of which generate high field strengths per unit volume. While magnets which generate a high field strength for their size are preferred, weaker magnets such as Alnico, ceramic, or ferric magnets may also be utilized.

Since the magnet is permanent, it requires no power source. Accordingly, the magnet maintains its magnetic field indefinitely, which allows long-term positioning and detection of the intragastric device without the disadvantages associated with an internal or external power source. In particular, by avoiding the use of a power source, the undesirable electrical connections necessary for the use of a power source are avoided. Thus, there is no risk of electric shock to (or possible electrocution of) the patient. Furthermore, the magnet's static magnetic field passes unattenuated through body tissue and bone. This property allows the use of the device to detect the intragastric device at any location within the patient's body.

One known technique for locating a medical tube in the body of a patient is described in U.S. Pat. No. 5,425,382, which is incorporated herein by reference in its entirety. A tube with a permanent magnet located in its tip is inserted into the patient, e.g., a feeding tube that is inserted into the patient's nose, down the esophagus, and into the stomach. A detection apparatus is used to sense the magnet's static magnetic field strength at two different distances and while immersed in the Earth's ambient magnetic field. By measuring the static magnetic field strength at two different distances, the detection apparatus determines the magnetic field gradient. As the detection apparatus is moved about the patient's body, greater and lesser magnetic field gradients are indicated. The tube is located by moving the detection apparatus until the greatest magnitude is indicated by the detection apparatus.

The detection apparatus described in U.S. Pat. No. 5,425,382, incorporated herein by reference in its entirety, utilizes first and second magnetic sensors. The magnetic sensors may each comprise flux-gate toroidal sensors to detect the magnetic field gradient. An alternative magnetic field gradient detector system is described in U.S. Pat. No. 5,622,169, which is incorporated herein by reference in its entirety. The magnetic sensors each comprise three orthogonally arranged flux-gate toroidal sensor elements. The magnetic sensor comprises magnetic sensor elements that are orthogonally arranged to measure magnetic field strength in three orthogonal directions. Similarly, the magnetic sensor comprises magnetic sensor elements to measure magnetic field strength in the x, y, and z directions, respectively. Using the sensors, the magnetic field gradient may be determined in the x, y, and z directions. With measurements of magnetic field gradient in three directions, the location of the magnet may be readily determined using conventional vector mathematics. The mathematical sign of the magnetic gradient is indicative of the direction of the magnetic field dipole of the magnet. The magnet, and hence the intragastric device, is detected using a known detection apparatus that contains at least two static magnetic field strength sensors configured geometrically to null detection of ambient, homogeneous magnetic fields (e.g., the Earth's field), while still detecting the magnetic field strength gradient produced by the magnet. The magnet detection apparatus detects the location of the magnet based on the difference in magnetic field strength at the two sensors. However, it is possible to construct a magnetic field detection apparatus with different sensor configurations to provide additional data related to the position and orientation of the magnet. The various embodiments are directed to a technique for detection of a magnet using a multisensor array and a convergence algorithm that can accurately locate the position of the magnet in three dimensions.

Figure 13:
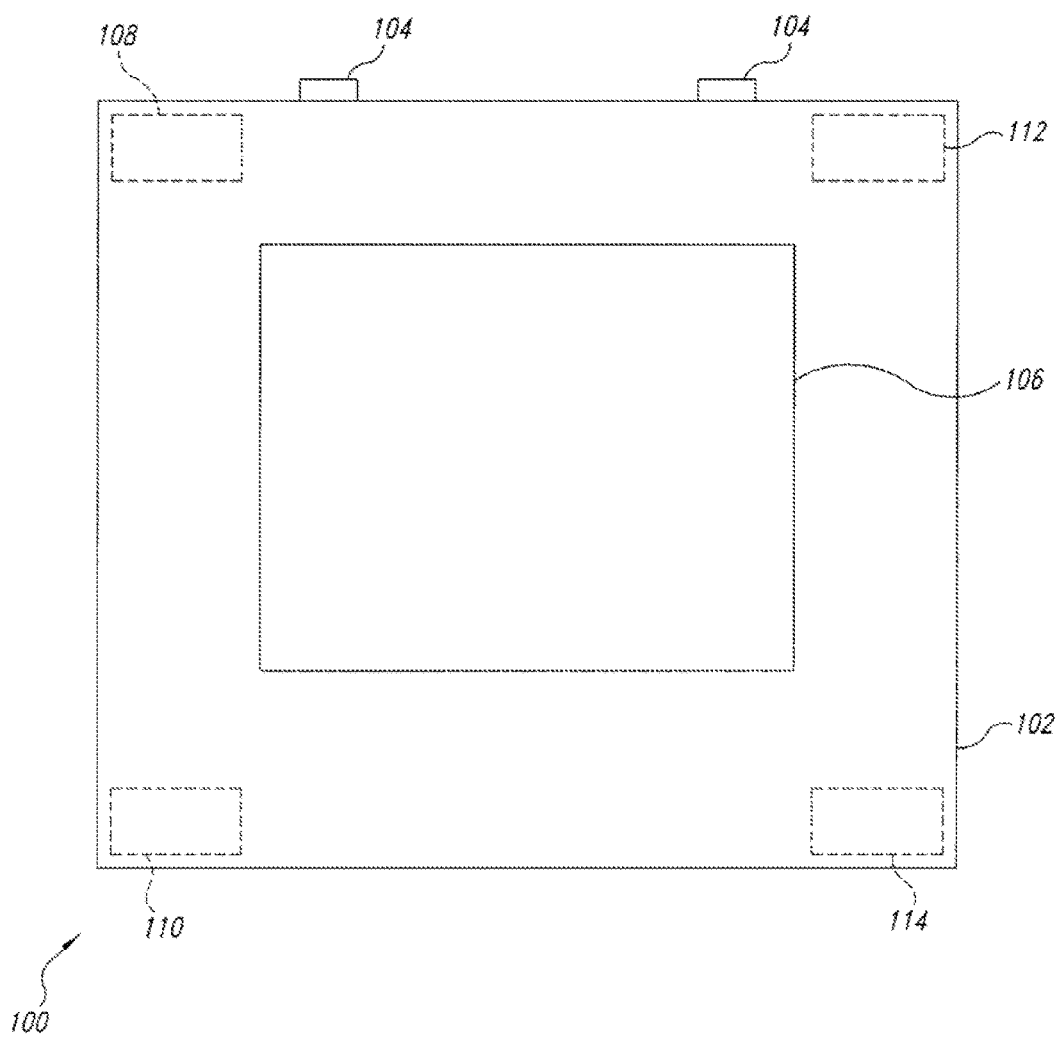
FIG. 13 is a top plan view of an embodiment of a detector illustrating one possible arrangement of magnetic sensors.

One embodiment of a passive magnetic detector is shown in FIG. 13. The detector system 100 includes a housing 102, control switches 104 such as a power switch and a reset switch, and a display 106. In an exemplary embodiment, the display 106 is a two-dimensional liquid crystal display. The display 106 may have an opaque background, or have a transparent area which allows the caregiver to view the skin below the surface of the detector system 100. The ability to view external patient landmarks significantly aids in the placement of catheters using the detector system 100. Alternatively, the display 106 may be an external display such as a video monitor.

Also mounted within the housing 102 are first, second, third, and fourth magnetic sensors 108, 110, 112, and 114, respectively. In a preferred embodiment, the static magnetic sensors 108-112 are spaced to provide maximal separation within the housing 102. In an exemplary embodiment, the magnetic sensors 108-112 are arranged in a substantially planar fashion within the housing 102 and located proximate the corners of the housing.

Figure 14:
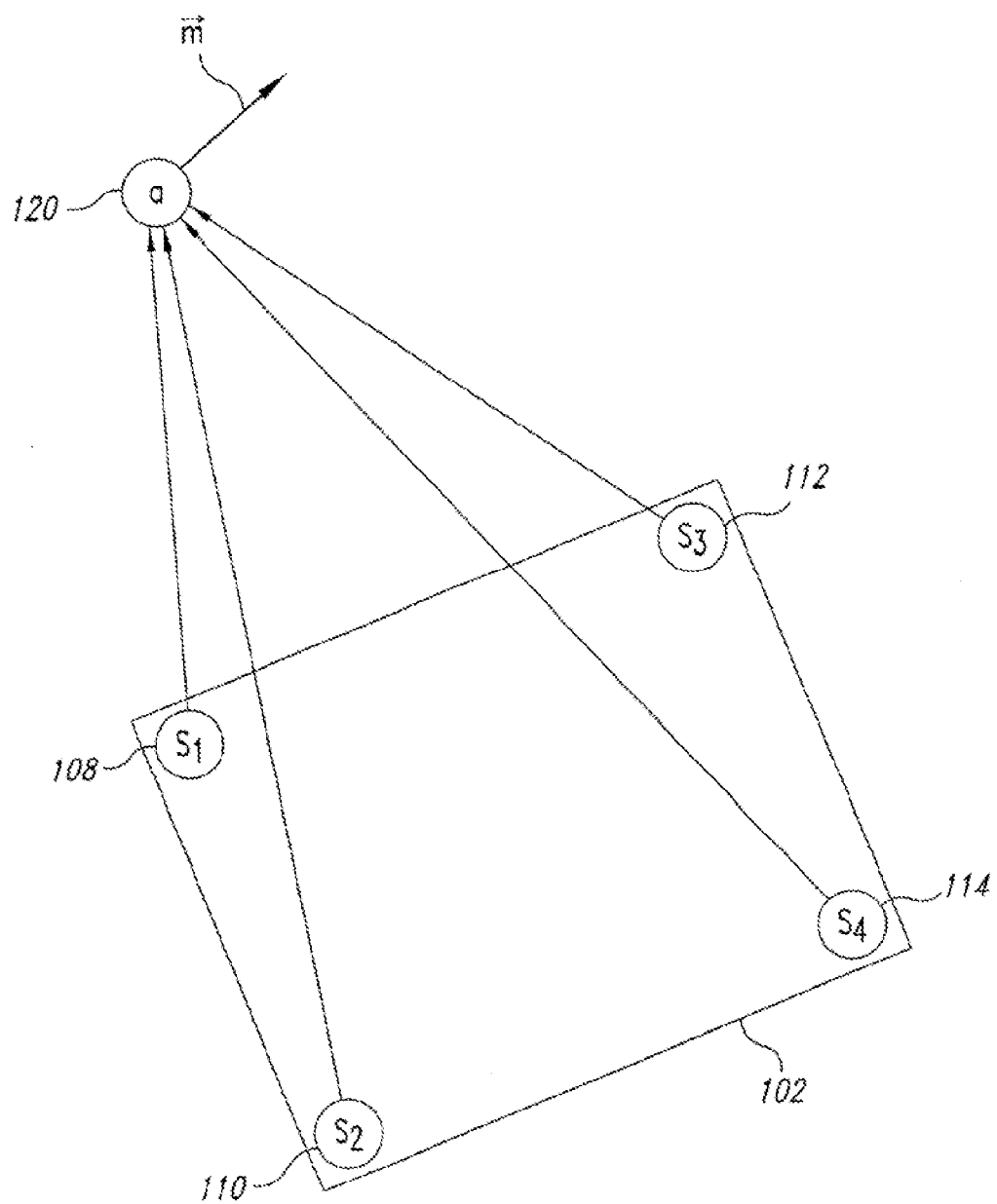
FIG. 14 illustrates the generation of magnetic field strength vectors using the magnetic sensor configuration of FIG. 3 to determine the location of a magnet.

The orientation of the magnetic sensors 108-114 is illustrated in FIG. 14 where the magnetic sensors 108-114 are positioned at locations $S_1$ to $S_4$, respectively, near the corners of the housing 102. Although the system 100 described in FIGS. 13 and 14 illustrates a rectangular configuration for the magnetic sensors 108-114, the principles of are readily applicable to any multisensor array. Accordingly, the system is not limited by the specific physical arrangement of the magnetic sensors.

In an exemplary embodiment, each of the magnetic sensors 108-114 comprise three independent magnetic sensing elements orthogonally arranged to provide three-dimensional measurement in the x, y, and z directions. The sensing elements of the magnetic sensors 108-114 are aligned with respect to a common origin such that each magnetic sensor senses the static magnetic field in the same x, y, and z directions. This permits the detection of magnetic field strength in a three-dimensional space by each of the magnetic sensors 108-114. The arrangement of the magnetic sensors 108-114 permits the detection of a magnet in a three-dimensional space within the patient. That is, in addition to locating the magnet within the patient, the detector system 100 provides depth information.

The configuration of the magnetic sensors 108-114 can be readily changed for specialized application. For example, a plurality of magnetic sensors may be configured in a spherical arrangement around a patient's waist to detect the location of the magnet 120 in the stomach. Furthermore, the magnetic sensing elements need not be orthogonally arranged. For example, the magnetic sensing elements may be configured in a planar array or other convenient configuration suited to the particular application (e.g., the spherical arrangement). The detector system must have at least as many sensing elements to provide data as there are unknowns in the equations to be solved and that the location and orientation of the magnetic sensing elements be known.

It is desirable to detect the position and orientation of the magnet 120 in three dimensional space. This results in five unknown parameters, that may conveniently be considered as x, y, z, θ, and φ where x, y, and z represent coordinates of the magnet 120 in three dimensional space relative to an origin such as the center of the housing 102, θ is the angular orientation of the magnet in the YZ plane and φ is the angular orientation of the magnet in the XY plane. In addition, the contribution of the Earth's magnetic field in the x, y, and z directions is unknown. Thus, the model used by the detector system 100 has eight unknown parameters that require eight independent measurements. In an exemplary embodiment of the detector system 100 described herein, a set of twelve magnetic sensing elements is used to provide over sampling. This results in greater reliability and accuracy while maintaining the computational requirements at a reasonable level.

The mathematical description provided below may be most easily understood with respect to a Cartesian coordinate system using magnetic sensing elements orthogonally arranged in the x, y, and z directions. However, it should be clearly understood that the embodiments not limited to such an arrangement. Any alignment of the magnetic sensing elements may be used with the detector system 100 so long as the location and orientation of the magnetic sensors 108-114 are known. Therefore, the system is not limited by the specific configuration of magnetic sensing elements.

As illustrated in FIG. 14, a magnet 120 is positioned at a location α. As is known in the art, the magnet 120 has a magnetic dipole that is represented by the vector m. The vector m represents the strength and orientation of the magnetic dipole. Under ideal conditions, the magnetic sensors 108-114 can measure the static magnetic field generated by the magnet 120 and determine the location of the magnet at location α with a single measurement. However, the presence of the Earth's magnetic field, stray magnetic fields that may be present near the vicinity of the magnet 120, internal noise from the magnet sensors 108-114, internal noise generated by electronics associated with the magnetic sensors, such as amplifiers and the like, make it virtually impossible to perform a measurement under "ideal" conditions. To provide accurate positional information for the magnet 120 in the presence of various forms of noise, the detector system 100 uses known formulas for magnetic field strength, plus actual sensor measurements as inputs to an estimation algorithm that converges to provide an accurate reading of the location and orientation of the magnet 120.

Figure 15A:
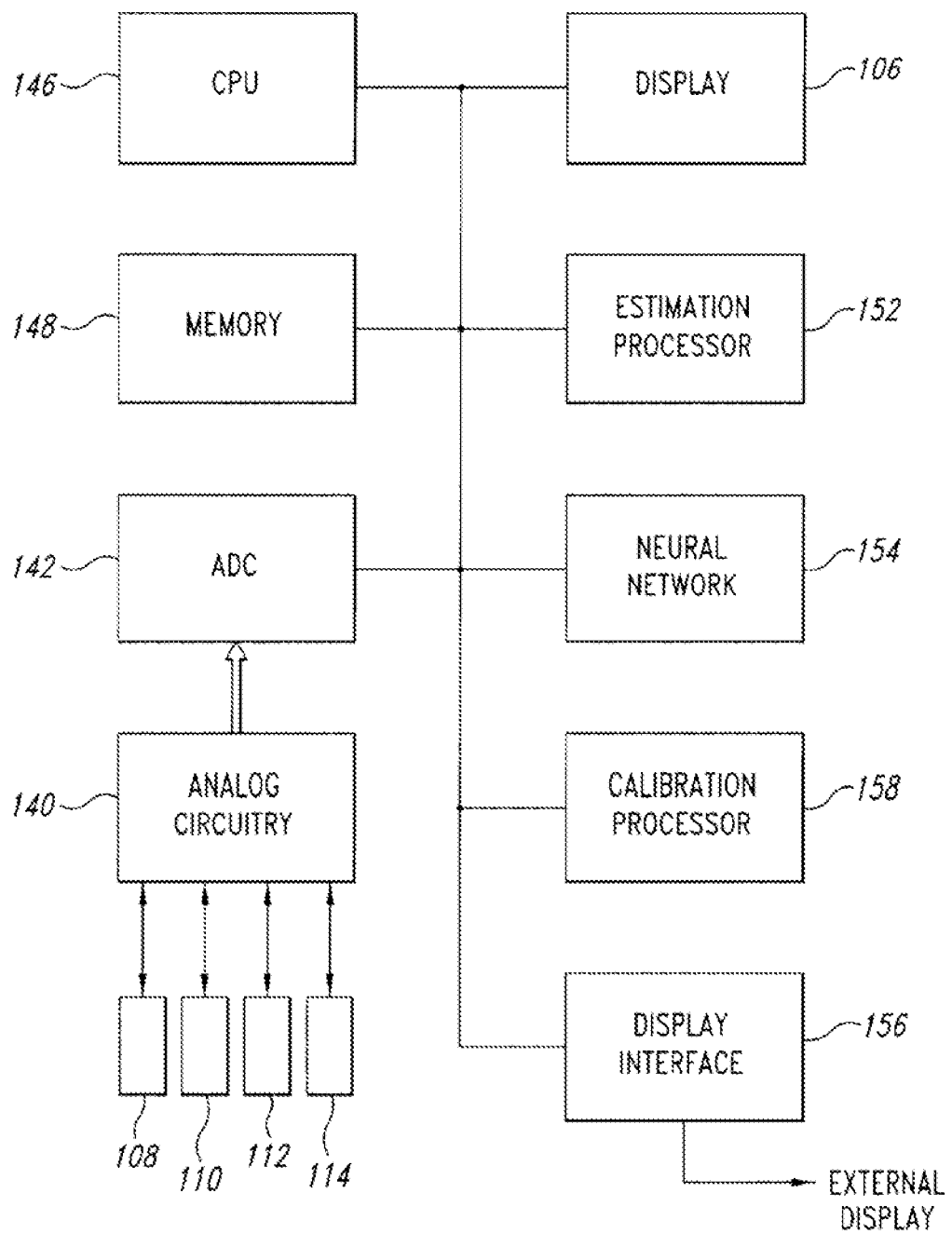
FIG. 15A is a functional block diagram of an exemplary embodiment of a system configured to determine the location of a magnet.

The elements used to process data from the magnetic sensor 108-114 are illustrated in a functional block diagram of FIG. 15A where the magnetic sensors 108-114 are coupled to analog circuitry 140. The specific form of the analog circuitry 140 depends on the specific form of the magnetic sensors 108-114. For example, if the magnetic sensors 108-114 are orthogonally positioned flux-gate toroidal sensors, similar to those illustrated in FIG. 14, the analog circuitry 140 may include amplifiers and integrators such as discussed in U.S. Pat. Nos. 5,425,382 and 5,622,669, the contents of which are hereby incorporated by reference in their entirety. In another exemplary embodiment, the magnetic sensors 108-114 comprise magneto-resistive elements whose resistance varies with the strength of a magnetic field. Each magnetic sensor 108-114 comprises three orthogonally arranged magneto-resistive sensing elements to sense the static magnetic field in the x, y, and z directions, respectively.

However, the magnetic sensors 108-114 may be any form of magnetic sensor. Several different types of magnetic sensors may be used in the practice of the methods of embodiments, including, but not limited to, Hall-effect, flux-gate, wound-core inductive, squid, magneto-resistive, nuclear precession sensors, and the like, as described elsewhere herein. Commercial magnetic field gradient sensors in the form of an integrated circuit can also be used with the detector system 100. Furthermore, the magnetic sensors 108-114 need not be identical types of sensors. For example, the magnetic sensors 108-112 may be one type of sensor while the magnetic sensor 114 may be a different type.

The analog circuitry 140 is designed to operate with the specific form of the magnetic sensors 108-114.

The output of the analog circuitry 140 is coupled to an analog-to-digital converter (ADC) 142. The ADC 142 converts the analog output signals from the analog circuitry 140 to a digital form. The operation of the ADC 142 is well known to those of ordinary skill in the art and will not be described in detail herein. The detector system 100 also includes a central processing unit (CPU) 146 and a memory 148. In an exemplary embodiment, the CPU 146 is a microprocessor, such as a Pentium™ or the like. The memory 148 may include both read-only memory and random access memory. The various components, such as the ADC 142, CPU 146, memory 148, and display 106 are coupled together by a bus system 150. As can be appreciated by those of ordinary skill in the art, the bus system 150 illustrates a typical computer bus system and may carry power and control signals in addition to data.

Also illustrated in the functional block diagram of FIG. 15A is an estimation processor 152. The estimation processor 152 performs an iterative comparison between an estimated position of the magnet 120 and a measured position of the magnet 120 based on data derived from the magnetic sensors 108-114. The iterative process continues until the estimated position and the measured position converge, resulting in an accurate measurement of the location α (see FIG. 14) of the magnet 120. It should be noted that the estimation processor 152 is preferably implemented by computer instructions stored in the memory 148 and executed by the CPU 146. However, for the sake of clarity, the functional block diagram of FIG. 15A illustrates the estimation processor 152 as an independent block since it performs an independent function. Alternatively, the estimation processor 152 can be implemented by other conventional computer components, such as a digital signal processor (not shown).

The detector system 100 assumes that the magnetic sensors 108-114 are sufficiently far from the location α of the magnet 120 that the magnet may be treated as a point dipole source. In addition, it is assumed that the spatial variation of any extraneous magnetic fields, such as the Earth's magnetic field, is small compared to the inhomogeneity produced by the presence of the point dipole source. However, under some circumstances, perturbations in the Earth's magnetic field may be caused by extraneous sources such as nearby electrical equipment, metallic building structural elements, and the like. The detector system 100 can be readily calibrated to compensate for such perturbations.

The equations used by the estimation processor 152 are readily derived from the fundamental laws of physics related to electricity and magnetism. A static magnetic field B produced by the magnetic dipole of a strength m, and situated at a location α, and measured at a location s is given by the following:

$$B(s) = \frac{3((s-a) \cdot m)(s-a) - \|s-a\|^2 m}{\|s-a\|^5} \quad (1)$$

where $\|s-\alpha\|^5$ all is a modulus value well known in matrix mathematics (e.g., $\|s-\alpha\|^2$ is a square modulus). It should be noted that the values α, m, s, and B are all vector values. The term "static magnetic field" is intended to describe the magnetic field generated by the magnet 120, as opposed to a time varying electromagnetic field or an alternating magnetic field. The magnet 120 generates a fixed, constant (i.e., static) magnetic field. The strength of the magnetic field detected by the detector system 100 depends on the distance between the magnet 120 and the magnetic sensors 108-114. Those skilled in the art can appreciate that the detected magnetic field strength may vary as the magnet 120 is moved within the patient or as the detector system 100 is moved with respect to the magnet. However, relative movement between the detector system 100 and the magnet 120 is not essential. The detector system 100 can readily determine the location and orientation of the magnet 120 in three-dimensional space even when the detector system and the magnet are not moving with respect to each other.

The values from the magnetic sensors 108-114 can be used in equation (1) to determine the strength of the magnetic field B at locations $S_1$-$S_4$, respectively. Changes in the magnetic field B over distance is defined as a gradient G(s) of B, which is a derivative of B with respect to s. The gradient G(s) can be represented by a 3×3 matrix derived from equation (1) and expressed in the following form:

$$G(s) = \frac{\begin{aligned}&-(15((s-a) \cdot m))(s-a)(s-a)^T + \\ &3\|s-a\|^2((s-a)m^T + m(s-a)^T + ((s-a) \cdot m)I)\end{aligned}}{\|s-a\|^7} \quad (2)$$

where T is a matrix transpose and I is a 3×3 identity matrix having the following form:

$$I = \begin{bmatrix} 1 & 0 & 0 \\ 0 & 1 & 0 \\ 0 & 0 & 1 \end{bmatrix}$$

It should be noted that equation (1) could be solved directly for the value α given the values B, m, and s. However, such a calculation can be difficult to solve and may require significant computing power. The iterative estimation process described below determines the location α and orientation of the magnet 120 by estimating the location α and comparing a predicted or estimated magnetic field that would result from the magnet 120 being located at the estimated location with the actual measured magnetic field as measured by the magnetic sensors 108-114. The iterative process varies the estimated location in a controlled manner until the predicted magnetic field closely matches the measured magnetic field. At that point, the estimated location and orientation matches the actual location α and orientation of the magnet 120. Such an iterative process can be performed very quickly by the detector system 100 without the need for extensive computational calculations required to solve for the location α directly using equation (1). The difference between the predicted magnetic field and the actual measured magnetic field is an error, or error function, that may be used to quantitatively determine the location α of the magnet 120. The error function is used in the iterative process to refine the estimated location of the magnet 120. Equation (2), indicating the gradient G(s) is used by the estimation processor 152 (see FIG. 3A) to determine the magnitude and a direction of error in the estimated location. Thus, equation (1) is used to generate predicted values and equation (2) uses the error results to determine how to alter the estimated position of the magnet 120.

The magnetic field strength B is measured at each of the locations $S_1$-$S_4$ by the magnetic sensors 108-114, respectively. While only four magnetic sensors are illustrated in FIG. 13 to FIG. 15A, the measurement may be generalized to n sensors such that each of the magnetic sensors provides a measurement of $B(s_i)$ at points $s_1$, where i=1 to n. The estimation processor 152 calculates quantities $\Delta_{ij}$ (measured)=$B(s_i)$−$B(s_j)$. This calculation provides a measure of the gradient from magnetic sensor i to magnetic sensor j and also cancels out the effects of the Earth's magnetic field, which is constant (i.e., gradient=0) at the magnetic sensor i and the magnetic sensor j. The estimation processor 152 also calculates predicted values $\Delta_{ij}$ (predicted) from equation (1). The estimate for the value α is adjusted until the measured values $\Delta_{ij}$ (measured) and predicted values $\Delta_{ij}$ (predicted) match as closely as possible. For example, the detector system 100 may initially assume that the location α of the magnet 120 is centered under the housing 102. Based on this estimated location, the estimation processor 152 calculates the predicted values for magnetic field strength at each of the magnetic sensors 108-114 that would result if the magnet 120 were actually at the estimated location. In an exemplary embodiment, the sensing elements of each of the magnetic sensors 108-114 provide a measure of the magnetic field B in three orthogonal directions resulting in magnetic field strength values $B_{xi}$, $B_{yi}$, and $B_{zi}$ where i equals 1 to n. Similarly, the gradient G(s) is also calculated for each of the three orthogonal directions.

The estimation processor 152 also uses measured magnetic field strength values from each of the magnetic sensors 108-114 and compares A (predicted) with $\Delta_{ij}$ (measured). Based on the difference between $\Delta_{ij}$ (predicted) and $\Delta_{ij}$ (measured), the estimation processor 152 generates a new estimated location for the magnet 120 (see FIG. 14) and iterates the prediction process until $\Delta_{ij}$ (predicted) closely matches $\Delta_{ij}$ (measured).

The degree of match between $\Delta_{ij}$ (predicted) and $\Delta_{ij}$ (measured) may be measured by a cost function comprising the sum of the squares of the difference between $\Delta_{ij}$ (predicted) and $\Delta_{ij}$ (measured) and then using non-linear iterative optimization algorithms to minimize the value of the cost function. The required gradients of the cost function are calculated using equation (2) above. Many different, well-known cost functions and/or optimization techniques, such as quasi-Newton, may be used by the estimation processor 152 to achieve the desired degree of match between $\Delta_{ij}$ (predicted) and $\Delta_{ij}$ (measured).

The iterative measuring process performed by the estimation processor 152 can be done in a short period of time. A typical measurement cycle is performed in fractions of a second. As the tube and associated magnet 120 are moved within the patient, the position and orientation of the magnet will change. However, because the measurement cycle is very short, the change in position and orientation of the magnet will be very small during any given measurement cycle, thus facilitating real-time tracking of the magnet as the magnet is moved inside the patient or as the housing 102 is moved on the surface of the patient.

As discussed above, the estimation processor performs an iterative comparison between an estimated position of the magnet and a measured position of the magnet. The initial estimated location may be derived by a number of possible techniques, such as random selection, a location under the sensor element 108-114 having the strongest initial reading, or, by way of example, the detector system 100 may initially estimate the location α of the magnet 120 is centered under the housing 102. However, it is possible to provide a more accurate initial estimation of the location α of the magnet 120 using a neural network 154, shown in FIG. 15A. It should be noted that the neural network 154 is preferably implemented by computer instructions stored in the memory 148 and executed by the CPU 146. However, for the sake of clarity, the functional block diagram of FIG. 15A illustrates the neural network 154 as an independent block since it performs an independent function. Alternatively, the neural network 154 can be implemented by other conventional computer components, such as a digital signal processor (not shown). Neural networks, by virtue of a learning process, are capable of receiving and processing large amounts of data in order to generate solutions to problems with many variables. The operation of a neural network is generally known in the art, and thus will be described herein only with respect to the specific application. That is, the operation of the neural network 154 to generate an initial position estimate will be discussed.

The neural network 154 has a learn mode and an operational mode. In the learn mode, the neural network 154 is provided with actual measurement data from the magnetic sensors 108-114. Since each of the magnetic sensors 108-114 have three different sensing elements, a total of 12 parameters are provided as inputs to the neural network 154. Based on the 12 parameters, the neural network 154 estimates the location and orientation of the magnet 120. The neural network 154 is then provided with data indicating the actual location and orientation of the magnet 120. This process is repeated a large number of times such that the neural network 154 "learns" to accurately estimate the location and orientation of the magnet 120 based on the 12 parameters. In the present case, the learning process described above (e.g., providing 12 parameters, estimating the location, and providing the actual location) was repeated 1,000 times. The neural network 154 learns the best estimated position for a set of 12 parameters. It should be noted that the user of the detector system 100 need not operate the neural network 154 in the learn mode. Rather, data from the learn mode process is provided along with the detector system 100. In normal operation, the neural network 154 is utilized only in the operational mode.

In the operational mode, the 12 parameters from the magnetic sensors 108-114 are given to the neural network 154, which generates an initial estimate of the location and orientation of the magnet 120. Based on experiments performed by the inventors, the neural network 154 can provide an initial estimate of the location of the magnet 120 within approximately ±2 cm. Such an accurate initial estimate reduces the number of iterations required by the estimation processor 152 to accurately determine the location α of the magnet 120. It should be noted that if the location α of the magnet 120 is sufficiently far from the detector system 100, the magnetic sensors 108-114 will provide very low signal levels. Accordingly, the neural network 154 will not generate an initial estimate until the parameters (i.e., the 12 input signals from the magnetic sensors 108-114) are above a minimum threshold and can therefore provide a reliable signal.

Given an accurate initial estimate, the estimation processor 152 can perform the iteration process described above and determine the location α of the magnet 120 within ±1 mm.

The detector system 100 also includes a display interface 156, shown in FIG. 15A, to permit the magnet image to be displayed on an external display (not shown). As those skilled in the art will appreciate, many of the components of the detector system 100, such as the CPU 146 and the memory 148 are conventional computer components. Similarly, the display interface 156 may be a conventional interface that allows the detector system image to be shown on a PC display or other monitor, such as a live image monitor 168 (see FIG. 15B).

One advantage of an external display is that the housing 102 may remain in a fixed position with respect to the patient. In this embodiment, the four magnetic sensors 108-114 may be replaced with a large number of sensors (e.g., sixteen sensors) uniformly distributed throughout the housing 102 to form an array of magnetic sensors (see FIG. 16). As the magnet 120 is moved relative to the housing 102, the movement is detected by three or more of the magnetic sensors and the position of the magnet calculated and shown on the external display. In this embodiment, the user need not reposition the housing, but simply views the external display where the array of magnetic sensors can track the position of the magnet 120.

Figure 15B:
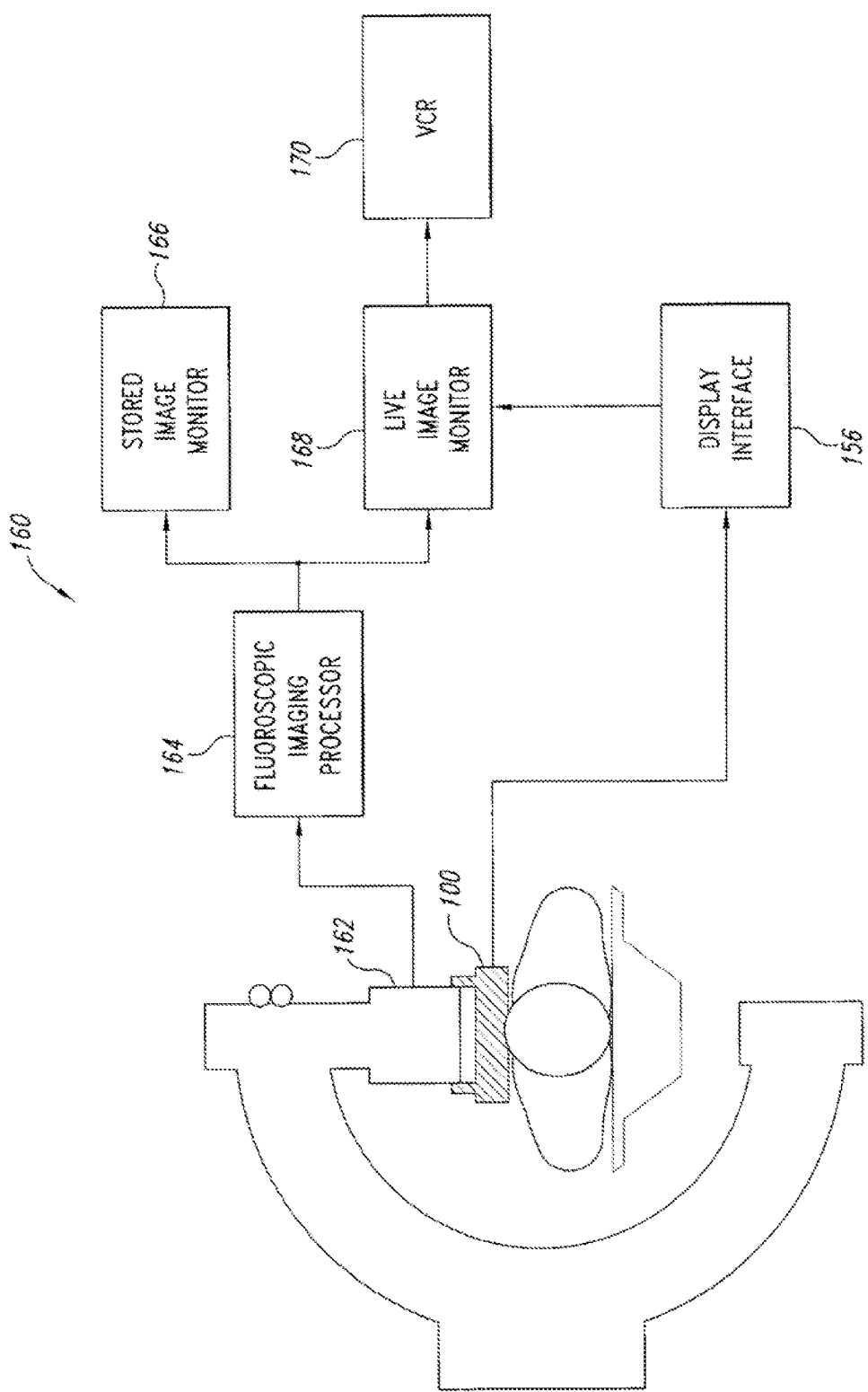
FIG. 15B is a functional block diagram illustrating the operation of the system of FIG. 15A to display the location of a magnet in conjunction with a conventional imaging system.

Another advantage of an external video display is the ability to combine the image generated by the detector system 100 with image data generated by conventional techniques. For example, FIG. 15B illustrates the operation of the detector system 100 in conjunction with a fluoroscope system 160. The fluoroscope system 160 is a conventional system that includes a fluoroscopic head 162, a fluoroscopic image processor 164, and an image storage system that includes a stored image monitor 166 and the live image monitor 168. In addition, a conventional video cassette recorder 170 or other recording device (computer memory, DVD, etc.) can record the images generated by the fluoroscope system 160 and images generated by the detector system 100. The operation of the fluoroscope system 160 is known in the art.

The detector system 100 is fixedly attached to the fluoroscopic head 162 in a known spatial relationship. A single "snapshot" image of the patient can be obtained using the fluoroscopic system 160 and displayed, by way of example, on the live image monitor 168. As a catheter containing the magnet 120 (see FIG. 14) is inserted in the patient, the detector system 100 detects the location α of the magnet 120 in the manner described above and can project the image of the magnet on the live image monitor 168 along with the snapshot image of the patient. In this manner, the user may advantageously utilize the snapshot fluoroscope image provided by the fluoroscope system 160 combined with the live image data provided by the detector system 100.

For satisfactory operation, it is preferred to have proper alignment between the fluoroscope system 160 and the detector system 100. This alignment or "registration" may be accomplished by placing a radio-opaque marker on the chest of the patient where the radio-opaque marker is aligned with the corners of the detector system 100. When the fluoroscope system 160 generates the snapshot image, the corners of the detector system 100 are indicated on the live image monitor 168 by virtue of the radio-opaque markers. The advantage of the image overlay using the detector system 100 is that the patient is only momentarily exposed to radiation from the fluoroscope system 160. Thereafter, the snapshot image is displayed with data from the detector system 100 overlaid on top of the snapshot image. Although this process has been described with respect to the fluoroscope system 160, those skilled in the art can appreciate that the system is applicable to any image-guided surgical process using X-ray, magnetic resonance imaging (MRI), positron emission tomography (PET), and the like.

The Earth's magnetic field is also detected by the magnetic sensors 108-114. However, assuming the Earth's magnetic field to be constant across the housing 102, the contribution of the Earth's magnetic field to the readings from the magnetic sensors 108-114 will be the same. By generating a differential signal between any two of the magnetic sensors 108-114, the effects of the Earth's magnetic field may be effectively canceled. However, as discussed above, there may be perturbations or inhomogeneity in the Earth's magnetic field caused by metallic elements, such as equipment, hospital bed rails, metal building structural elements, and the like. Because of the unpredictable nature of such interfering elements, proper operation of the detector system 100 requires calibration. The detector system 100 may be readily calibrated to compensate for localized perturbations in the Earth's magnetic field using a calibration processor 158, shown in FIG. 15A. It should be noted that the calibration processor 158 is preferably implemented by computer instructions stored in the memory 148 and executed by the CPU 146. However, for the sake of clarity, the functional block diagram of FIG. 15A illustrates the calibration processor 158 as an independent block since it performs an independent function. Alternatively, the calibration processor 158 can be implemented by other conventional computer components, such as a digital signal processor (not shown).

An initial calibration is performed before the magnet 120 is introduced into the patient. Thus, initial calibration occurs outside the presence of the magnetic field generated by the magnet 120. A measurement is performed using the detector system 100. Under ideal conditions, with no localized perturbations in the Earth's magnetic field, the signals generated by the magnetic sensors 108-114 will be the same. That is, each of the sensing elements oriented in the x direction will have identical readings, while each of the sensing elements oriented in the y direction will have identical readings and each of the elements oriented in the z direction will have identical readings. However, under normal operating conditions, localized perturbations in the Earth's magnetic field will exist. Under these circumstances, the signals generated by each sensor element of the magnetic sensors 108-114 all have some different value based on the detection of the Earth's magnetic field. The readings of any two of the magnetic sensors 108-114 may be differentially combined which, theoretically, will cancel out the Earth's magnetic field. However, due to localized perturbations in the Earth's magnetic field, there may be an offset value associated with the reading.

The calibration processor 158 determines the offset values associated with each of the magnetic sensors and compensates for the offset values during the measurement cycle. That is, the offset value for each of the magnetic sensors 108-114 is subtracted from the reading generated by the ADC 142 (see FIG. 15A). Thus, the differential reading between any two of the magnetic sensors 108-114 will be zero before the magnet 120 is introduced. Thereafter, as the magnet 120 is introduced, the differential readings from the magnetic sensors 108-114 will have nonzero values due to the static magnetic field generated by the magnet 120. If the detector system 100 is stationary, as illustrated in FIG. 15B, a single calibration process is sufficient to cancel out the effects of the Earth's magnetic field, including localized perturbations caused by external objects, such as metallic equipment, building structural elements, and the like.

Figure 15C:
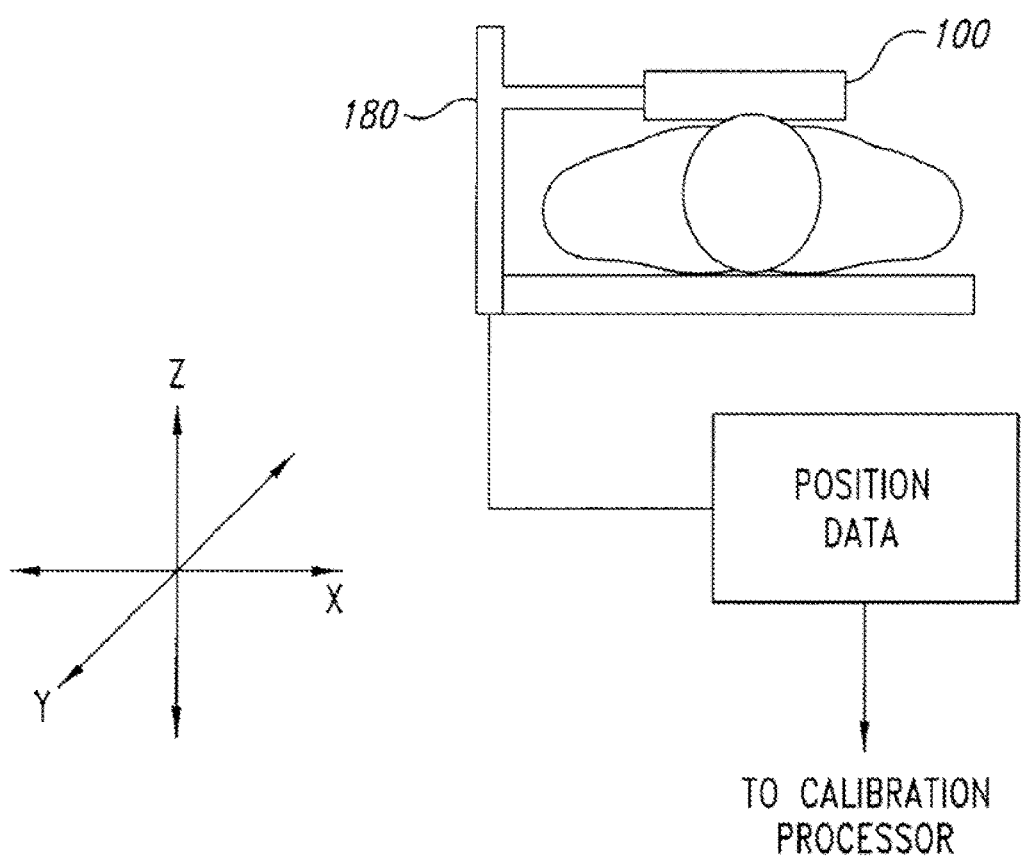
FIG. 15C illustrates an embodiment of the system of FIG. 15A to monitor the location of the detector system.

However, in certain embodiments, it is desirable to move the detector system 100 over the surface of the patient. As the detector system 100 is moved to a new position on the patient, the localized perturbations in the Earth's magnetic field may cause a degradation in the accuracy of the detector system 100 since the effects of the localized perturbations may no longer be completely canceled. However, the calibration processor 158 allows a continuous automatic recalibration of the detector system 100, even in the presence of the magnet 120. This is illustrated in FIG. 15C, where the detector system 100 is fixedly attached to a digitizing arm 180. The digitizing arm 180 is a conventional component that allows three-dimensional movement. The digitizing arm 180 may be conveniently attached to the patient bedside. In a preferred embodiment, the detector system 100 is attached to the digitizing arm and oriented such that the three dimensions of movement of the digitizing arm correspond to the x axis, y axis, and z axis, respectively, of the detector system 100. As the user moves the detector system 100, the digitizing arm accurately tracks the position of the detector system and generates data indicative of the position. The detector system 100 utilizes this position data to calculate the change in the measured magnetic field caused by the magnet 120 as the detector system 100 is moved. In this manner, the localized effects of the magnet 120 may be removed, with the resultant measurement being indicative of the localized perturbations of the Earth's magnetic field at the new position of the detector system 100.

The automatic recalibration process is particularly useful in a situation, such as a peripherally inserted central catheter (PICC), which may typically be inserted in the patient's arm and threaded through the venous system into the heart. Using conventional technology, the surgeon would typically place marks on the chest of the patient to mark the expected route over which the catheter will be inserted. Without the use of location sensing technology, the surgeon must blindly insert the catheter and verify its location using, by way of example, fluoroscopy. However, the detector system 100 permits the surgeon to track the placement of the PICC.

In the example above, the detector system 100 may be located over the arm of the patient where the PICC will be initially inserted. Following the initial calibration (in the absence of the magnet 120) the detector system 100 is calibrated and will compensate for the effects of the Earth's magnetic field including any localized perturbations. When the magnet 120 is introduced, the detector system 100 detects and displays the location α of the magnet in the manner previously described. As the surgeon inserts the PICC (with the attached magnet 120), it may be desirable to relocate the detector system to thereby track the progress of the PICC. Using the digitizing arm 180, the surgeon relocates the detector system 100 to a new location. For example, assume that the detector system 100 is moved six inches in the y direction, three inches in the x direction, and has not moved in the z direction. Based on the new location of the detector system 100, and using the technology described above, the estimation processor 152 (see FIG. 15A) can calculate the magnetic field at the new location due to the magnet 120. Given the contribution to magnetic field at the new location that results from the magnet 120, it is possible to subtract out the effects of the magnet 120. In the absence of the magnetic field from the magnet 120, any remaining or "residual" magnetic field is assumed to be the result of the Earth's magnetic field. The residual reading is processed in the manner described above for an initial calibration to thereby rezero or recalibrate the detector system 100 to compensate for the Earth's magnetic field, including localized perturbations, at the new location. Following this recalibration process, a measurement cycle may be initiated with the resultant measurement of the magnetic field being due solely to the presence of the magnet 120.

The user may manually recalibrate the detector system 100 at any point in time. However, the advantage of the technique described above is that the detector system 100 may be automatically recalibrated on a continuous basis as the detector system 100 is used. The digitizing arm 180 provides a continuous reading of the position of the detector system 100 and thus makes it possible to accurately track the location of the detector system. As the detector system 100 moves, it is constantly recalibrated to recompensate for the Earth's magnetic field. In the example above, the detector system 100 may be moved at will to follow the movement of the PICC as it is inserted into the heart without concern that external influences, such as a hospital bed rail, will cause a degradation in the accuracy of the measurement. Although the recalibration system has been described above with respect to the digitizing arm 180, it can be appreciated that other position sensing systems may also be readily utilized.

For example, commercial tracking systems are manufactured by Ascension Technology and Polhemus. The system manufactured by Ascension Technology, known as the "Bird Tracker" comprises an array of sensors that measure six degrees of freedom and provide accurate measurements within one-half inch at a distance of five feet and provide rotational information within one-half degree at a distance of five feet. The sensing elements used in the Bird Tracker may be attached to the housing 102 and the position of the housing tracked using the commercial system. Similarly, the Polhemus device, known as the "3-D Tracker," provides similar location measurements without the need of the digitizing arm 180.

Figure 17A:
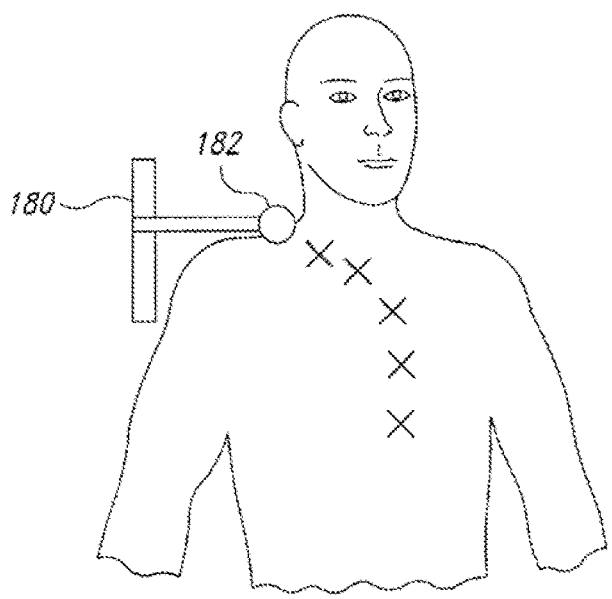
FIG. 17A illustrates the use of the system of FIG. 15C to select landmark locations on a patient.

Another application of position tracking, using, by way of example, the digitizing arm 180 permits the surgeon to provide digitized landmarks that will be shown on the display. A common surgical technique to assist in insertion of a catheter is to place landmarks on the surface of the patient that approximate the route that will be taken by the catheter. For example, with conventional technology the surgeon may place a series of x's on the patient's chest with a marker pen as landmarks to assist in insertion of electrical pacemaker leads. With the principles described herein, the digitizing arm 180 may be used to electronically record landmarks specified by the surgeon. This aspect is illustrated in FIG. 17A, when a computer input stylus 182 or other electronic input device is mounted to the digitizing arm 180. The computer stylus 182 may be attached to the detector system 100 or attached to the digitizing arm 180 in a position corresponding to, by way of example the center of the detector system. Prior to insertion of the catheter with the magnet 120, the surgeon may utilize the digitizing arm 180 and the computer stylus 182 to electronically generate landmarks, illustrated in FIG. 17A by a series of x's. It should be noted that the computer stylus 182 electronically "marks" the patient, but need not place any actual marks on the patient. In the example above, where heart pacemaking leads will be inserted, the surgeon may place a series of electronic landmarks from the neck to the heart along the route in which the pacemaker leads will be inserted. At each landmark, the digitizing arm 180 records the position marked by the surgeon. In subsequent operation, when the catheter with the magnet 120 is inserted into the patient, the digitizing arm 180 notes the location of the magnet 120 with respect to the landmarks previously marked by the surgeon. The landmarks are shown on an external display 184, shown in FIG. 17B, along with the position of the magnet 120, which is indicated by an arrow. As the surgeon inserts the magnet 120, the progress is shown on the external display 184 such that the magnet 120 passes along from landmark 1 to landmark 2 to landmark 3, and so forth. With this technique, the surgeon can readily detect divergence from the expected route. For example, if the catheter and magnet 120 are inadvertently diverted into a different vein, the surgeon will readily note the divergence from the marked pathway and quickly identify the problem. The catheter and magnet 120 may be withdrawn and reinserted to follow the landmarked pathway.

Figure 18A:
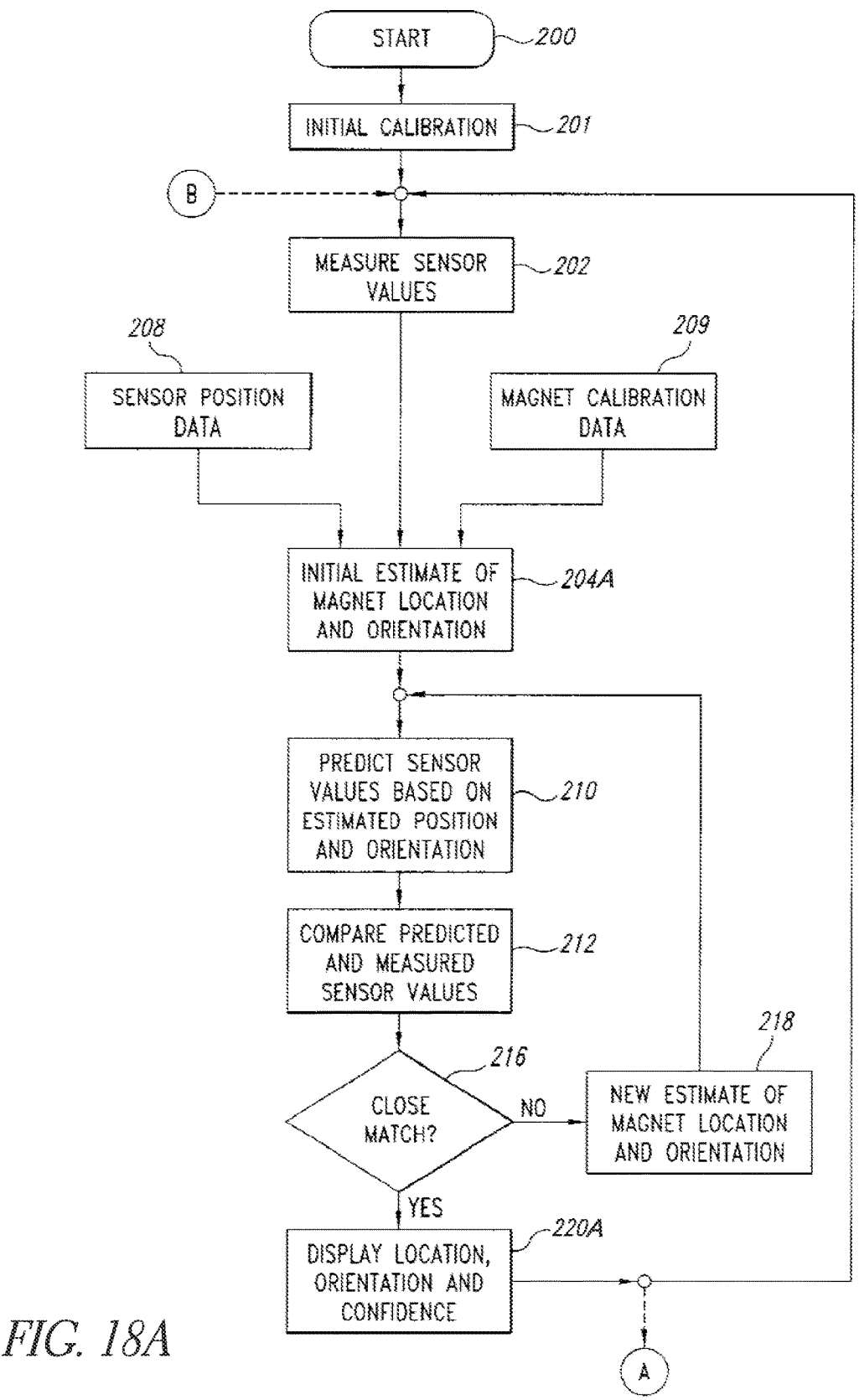
FIG. 18A is a flowchart used by the system of FIG. 15A to determine the location of a magnet.

The general operation of the detector system 100 is illustrated in the flowchart of FIG. 18A. At a start 200 the magnet 120 (see FIG. 14) has been inserted into the patient. In step 201, the system undergoes an initial calibration. In an exemplary embodiment, the initial calibration is performed before the magnet 120 is introduced. Thus, the system 100 compensates for the effects of the Earth's magnetic field, including localized perturbations, in the absence of any contribution from the magnet 120. Alternatively, the magnet 120 may be positioned in a known location with respect to the housing 102 such that the effects of the magnetic field caused by the magnet 120 are known and can be canceled in the manner described above with respect to the automatic recalibration process. That is, the contribution to the measured magnetic field caused by the magnet 120 in the known location can be subtracted from the measured readings with the resultant residual value being caused only by the Earth's magnetic field. Following the initial calibration, in step 202, the detector system 100 measures sensor values from the magnetic sensors 108-114. In step 204A, the estimation processor 152 (see FIG. 15A) calculates an initial estimate of the location α and orientation of the magnet 120. The initial estimate includes sensor position data from step 208 and magnet calibration data from step 209. The sensor position data calculated in step 208 provides data relating the position of each of the magnetic sensors 108-114 relative to a selected origin. For example, one magnetic sensor (e.g., magnetic sensor 108) may be arbitrarily selected as the mathematical origin for purposes of determining the relative positions of the other magnetic sensors (e.g., magnetic sensors 110-114). The common origin provides a frame of reference for purposes of the mathematical calculations. As previously discussed, the magnetic sensors 108-114 are aligned with respect to the common origin so that each magnetic sensor measures the magnetic field in the same x, y, and z directions. As those of ordinary skill in the art can appreciate, any selected origin can be used satisfactorily with the detector system 100.

The magnetic calibration data derived in step 209 is typically provided by the magnet manufacturer and includes data related to the strength of the magnetic dipole m (see FIG. 14), as well as the size and shape of the magnet 120. The measured sensor values, sensor position data, and magnet calibration data are provided as inputs to the estimation processor 152 (see FIG. 15A) in step 204A.

In an exemplary embodiment, the initial estimate of the location α is provided by the neural network 154 (see FIG. 15A) based on the measured sensor values derived in step 202. As previously discussed, the neural network 154 may require minimum values from the magnetic sensors 108-114 to assure a reliable initial estimate. The neural network 154 provides the initial estimate of magnet location and orientation.

In step 210, the estimation processor 152 (see FIG. 15A) calculates predicted sensor values. As described above, this requires a measurement $\Delta_{ij}$ (predicted) for each combination of the magnetic sensors 108-114 in each of the three orthogonal directions x, y, and z. In step 212, the estimation processor 152 compares the predicted sensor values (i.e., $\Delta_{ij}$ (predicted)) with the measured sensor values (i.e., $\Delta_{ij}$ (measured)). In decision 216, the estimation processor 152 determines whether the predicted and measured sensor values match within a desired degree of tolerance. If the predicted sensor values and the measured sensor values are not a close match, the result of decision 216 is NO. In that event, the estimation processor 152 calculates a new estimate of the magnet location α and orientation in step 218. Following the calculation of a new estimated location α of the magnet 120, the estimation processor 152 returns to step 210 to calculate a new set of predicted sensor values using the new estimate of magnet location and orientation. The estimation processor 152 continues this iterative process of adjusting the estimated location α of the magnet 120 and orientation and comparing predicted sensor values with measured sensor values until a close match is achieved. When a close match between the predicted sensor values and the measured sensor values is achieved, the result of decision 216 is YES. In that event, in step 220A the detector system 100 displays the magnet location α and orientation on the display 106 (see FIGS. 15A, 15B, and 16). In addition, the detector system 100 may display a confidence value indicative of a degree of confidence with which the location α and orientation of the magnet 120 have been determined. The calculation of a confidence value based on statistical data is well known in the art and need not be described in detail herein. Following the display of location and orientation data in step 220A, the detector system 100 returns to step 202 and repeats the process on a new set of measured sensor values. If cost function is too high, a close match may not be achieved in decision 216. Such conditions may occur, for example, in the presence of extraneous magnetic fields. In practice, it has been determined that close matches have a cost function in the range of 1-2 while the minimum cost function for an inaccurate local minimal are orders of magnitude greater. If a close match cannot be achieved (i.e., the cost function is too great), the detector system 100 can start the measurement process anew with a new estimated location or generate an error message indicating an unacceptably high cost function.

Figure 18B:
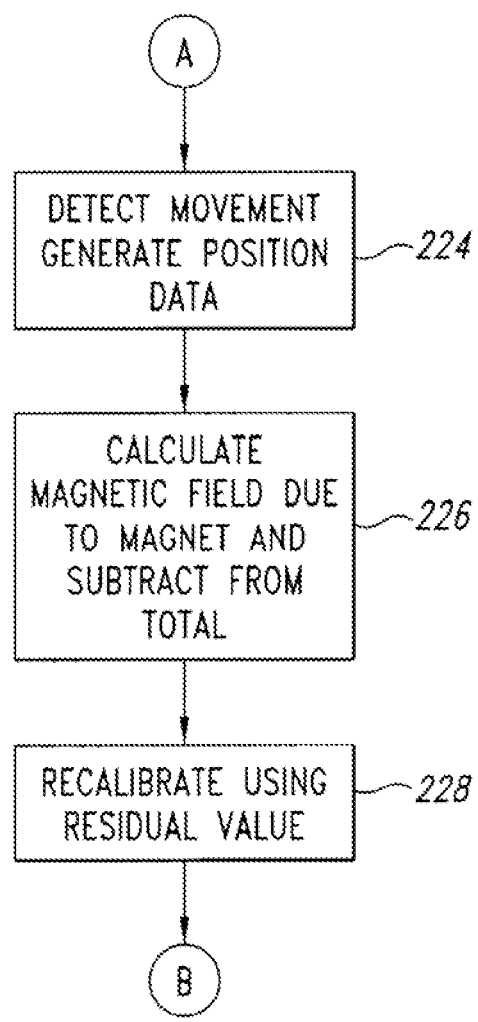
FIG. 18B is a flowchart illustrating the automatic calibration function of the system of FIG. 15A.

The flowchart of FIG. 18B illustrates the steps performed by the calibration processor 158 if automatic recalibration is implemented within the detector system 100. In this implementation, following the completion of step 220A, the system 100 may optionally move to step 224, illustrated in FIG. 18B, wherein the calibration processor 158 obtains the position data from the digitizing arm 180 (see FIG. 15C) indicating the present location of the detector system 100. Given the new location of the detector system 100 and the known location α of the magnet 120, the calibration processor 158 calculates the magnetic field resulting from the magnet and subtracts the effects of the magnet from the current measurements in step 226. As a result of this process, the remaining residual values measured by the magnetic sensors 108-114 (see FIG. 15A) are due to the effects of the Earth's magnetic field, including localized perturbations.

In step 228, this residual value is used to rezero the detector system 100 to compensate for the effects of the Earth's magnetic field at the new location. Following the recalibration process, the detector system 100 returns to step 202, shown in FIG. 18A, to perform additional measurement cycles with the detector system 100 at the new location and recalibrated for operation at the new location.

It should be noted that the automatic recalibration process illustrated in the flowchart of FIG. 18A automatically and continuously recalibrates the detector system 100.

However, in an alternative embodiment, the calibration processor 158 will perform the recalibration process only if the detector system 100 has been moved by a predetermined amount. This prevents the unnecessary recalibration when the detector system 100 has not been moved.

The iterative estimation process is described above using the difference in magnetic strength B provided by different pairs of magnetic sensors 108-114. Alternatively, the detector system 100 can use the measured field gradient values G. In this embodiment, equation (2) may be fit to the measured values, in a manner as described above with respect to the iterative process to fit the measurements of B. With respect to the flowchart of FIG. 18A, the step 202 provides gradient values with respect to pairs of the magnetic sensors 108-114. For example, a magnetic gradient measurement can be calculated using the magnetic field B measured by the magnetic sensor 114 with respect to the magnetic field measured by each of the remaining magnetic sensors 108-

112, respectively. In step 204A, the estimation processor 152 determines an initial estimate of the magnet location and orientation, and, in step 210, calculates predicted sensor values using equation (2). In step 212, the measured sensor values are compared with the predicted sensor values using conventional techniques, such as the cost functions described above. The iterative process continues until the measured sensor values and the predicted sensor values match within the predetermined degree of tolerance.

In yet another alternative technique, the detector system 100 utilizes the measurement data and solves equation (2) for a directly. The direct solution approach utilizes the fact that G is a symmetric matrix with positive eigenvalues. The eigenvalues and eigenvectors of the matrix G may be calculated and used algebraically to solve for the location $\alpha$ and m directly. This assumes that the magnitude, but not the direction, of m is known. In practice, the magnitude m is known because magnet calibration data is provided by the manufacturer. It should be noted that this technique requires an additional magnetic sensor to determine the orientation of the magnetic dipole. Mathematically, the orientation of the magnetic dipole is indicated by a + or − sign. The additional magnetic sensor, which need only measure the magnetic field strength B, is used to determine the sign of the mathematical function. In addition, combinations of these various techniques may be used by the detector system 100 to determine the location $\alpha$ of the magnet 120.

In yet another alternative, a Kalman filter may be used with equations (1) and (2) above to track the position of the magnetic dipole m with respect to the multi-detector array formed by the magnetic sensors 108-114. As is known to those of ordinary skill in the art, Kalman filters are statistical predictive filters that use statistical signal processing and optimal estimation. Numerous textbooks, such as "Tracking And Data Association," by Y. Bar-Shalom and R. E. Fortmann, Academic Press, Boston, 1988, provide details on the theory and operation of Kalman filters. In addition to the individual techniques described above, it is possible to use any or all of these techniques in a combination, such as a sum of cost functions for each sensor type. For example, the differences between $\Delta ij$ (predicted) and $\Delta ij$ (measured) can be required to match within a certain tolerance. If the multiple mathematical techniques are unable to identify a solution for which all difference values meet that tolerance, then an error can be signaled to the operator using the display 106 (see FIG. 15A). Assuming the errors in each sensor measurement are independent and small, the uncertainty in the estimate of the location $\alpha$ can be calculated using, for example, Cramer-Rao bounds. Thus, a degree of redundancy between measurement techniques can be advantageously implemented by the detector system 100. Such redundancy is highly desirable for biomedical applications.

FIG. 13 illustrates the operation of the detector system 100 for a specific configuration of the magnetic sensors 108-114. However, the techniques described above may be generalized to virtually any fixed configuration of sensors. A minimum of one gradient sensor or eight magnetic field sensors is required to measure G(s) and B(s), respectively, assuming that the strength of the magnetic dipole m is known. The magnetic sensors can be configured relatively arbitrarily and thus may be readily positioned at locations within the housing 102 (see FIG. 13) based on instrument design and/or other signal or noise considerations.

The magnetic sensors 108-114 may be calibrated using the known strength of the Earth's magnetic field. In the absence of any inhomogeneous fields (i.e., away from any strong magnetic dipoles) the X sensor element of all sensors 108-114 can be read at the same time. Similarly, all Y sensor elements and Z sensor elements can be read at the same time. In any configuration, the sum of the squares of the average readings of the magnetic field strength for each orthogonal direction (i.e., $B_x$, $B_y$, and $B_z$) should be constant. The constant value of the Earth's magnetic field can be used to determine the appropriate calibration factors for each magnetic sensor using conventional algebraic and least squares fitting methods.

An alternative calibration technique uses a small magnet of known strength placed in one or more locations relative to the magnetic sensors 108-114. Measurements are performed at each of the one or more locations to determine the appropriate calibration factors for each magnetic sensor. Other techniques, such as the use of an electromagnetic cage, Helmholtz cage, or the like, may also be used to calibrate the magnetic sensors 108-114.

The display 106 (see FIG. 13) provides graphical display of the position of the magnet 120 with respect to the housing 102. FIGS. 19A to 19D illustrate some of the different techniques used by the detector system 100 to indicate the location $\alpha$ of the magnet 120 (see FIG. 14). In the embodiment illustrated in FIG. 19A, the display 106 uses a circle 250 and a pair of orthogonal lines 252a and 252b to indicate the location $\alpha$ of the magnet 120 relative to the housing 102. The orthogonal lines 252a and 252b provide a visual indicator to the caregiver to assist in determining when the magnet 120 is centered under the detector system 100.

Figure 19A:
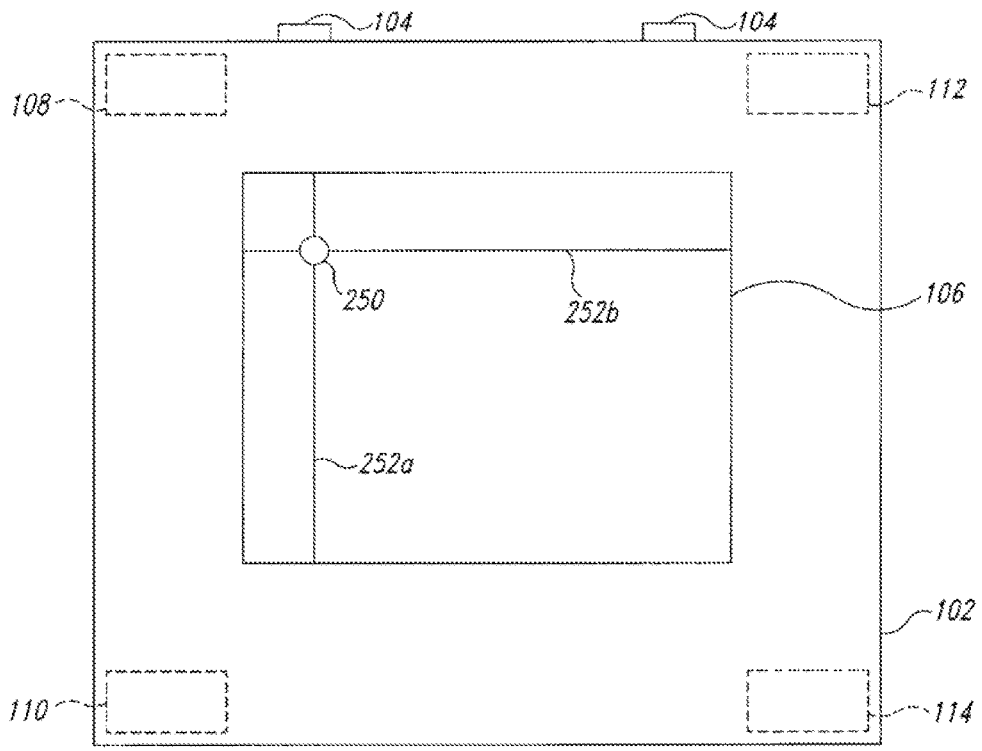
FIG. 19A illustrates one embodiment of the visual display used by the detector of FIG. 13.
Figure 19B:
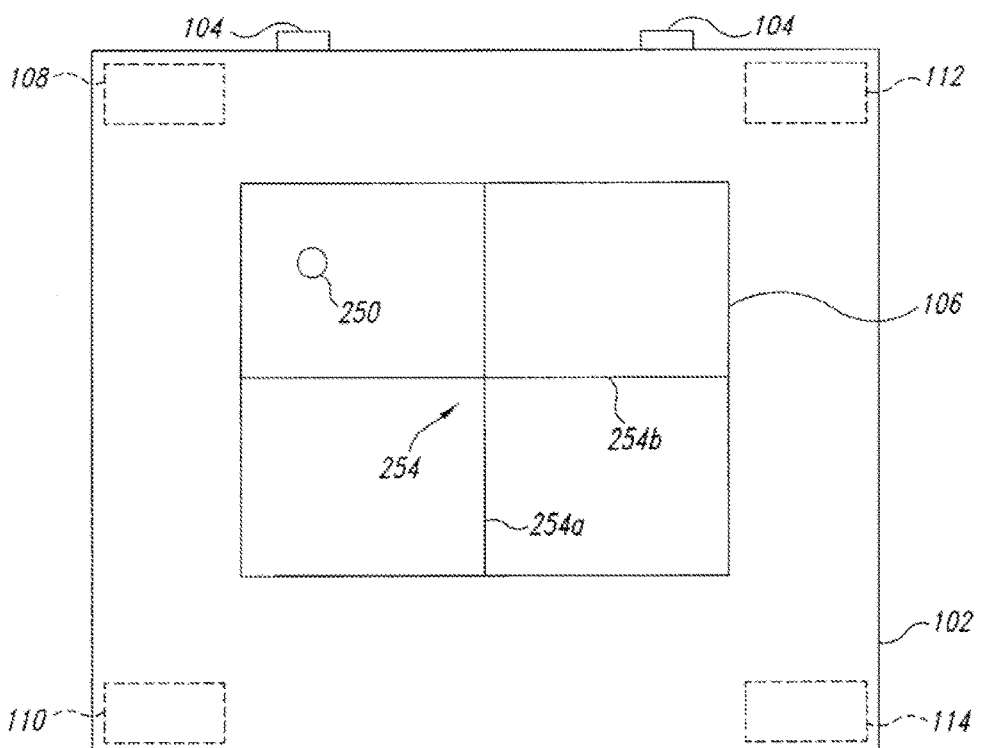
FIG. 19B is an alternative embodiment of the indicator used with the detector of FIG. 13.

In an alternative embodiment, illustrated in FIG. 19B, a fixed indicator 254, such as orthogonal lines 254a and 254b, form cross-hairs over the center of the display 106. The circle 250, or other indicator, is used to provide a visual indication of the location $\alpha$ of the magnet 120 relative to the housing 102. The circle 250 is centered in the cross-hairs in the center of the display 106 when the magnet 120 is centered directly beneath the detector system 100.

Figure 19C:
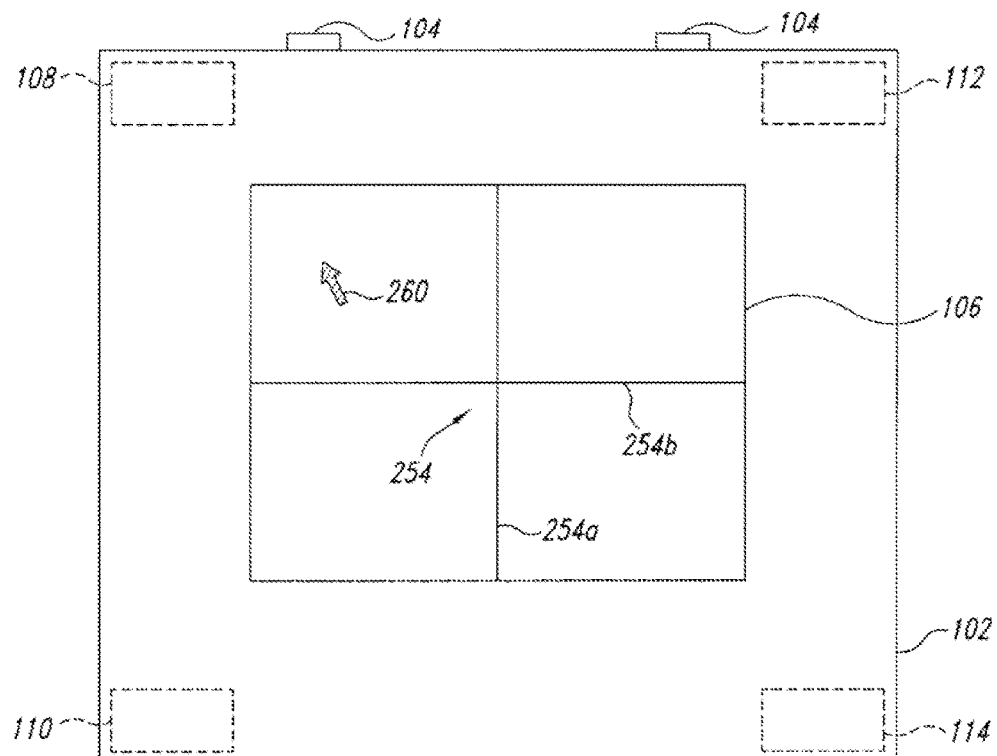
FIG. 19C is yet another alternative embodiment of the display used with the detector of FIG. 13.

In yet another embodiment, shown in FIG. 19C, the display 106 provides a different indicator, such as an arrow 260, to provide a visual indication of the location $\alpha$ of the magnet 120. The arrow 260 may also be used to indicate the orientation of the magnet 120.

Figure 19D:
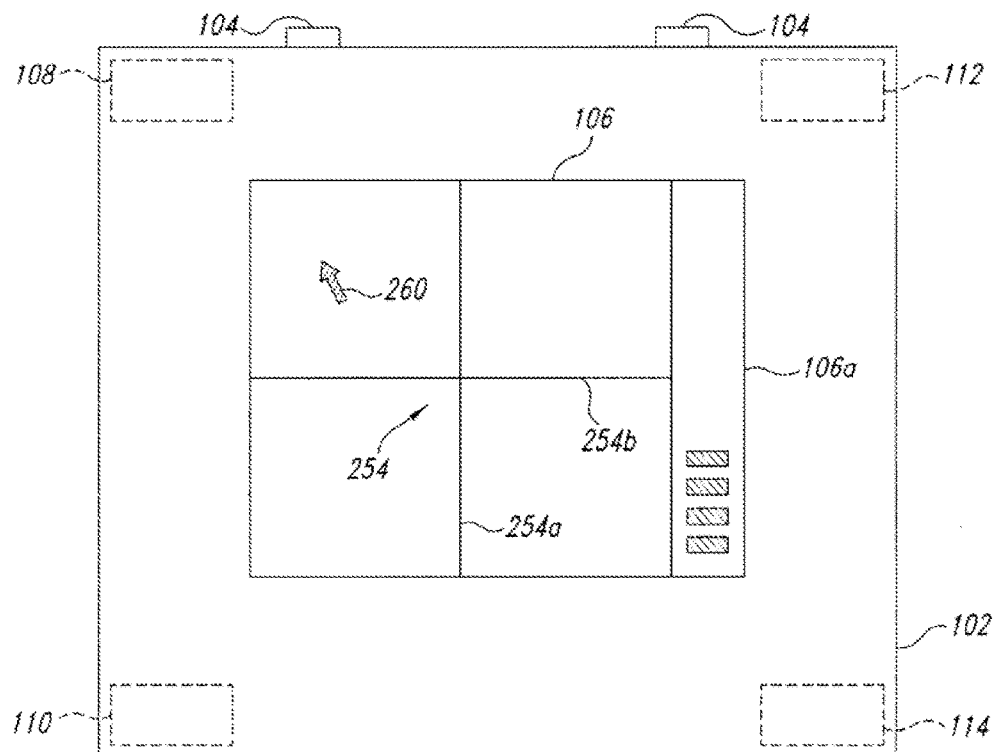
FIG. 19D is yet another alternative embodiment of the display of the detector of FIG. 13 with a depth indicator indicating the distance of the magnet from the detector.

The depth of the magnet 120 beneath the surface of the patient can be indicated on the display 106 in a variety of fashions. For example, a portion 106a of the display 106 can provide a visual indication of the depth of the magnet 120 using a bar graph, such as illustrated in FIG. 19D. However, the depth indicator portion 106a of the display 106 can also provide a numerical read-out of the depth of the magnet 120 in absolute units, such as centimeters, or in relative units.

Although the internal display 106 and external display are two-dimensional display devices, it is possible to display the magnet 120 with shading and graphical features to create the appearance of a three-dimensional object. Conventional display technology used in video games and other computer applications may be readily applied to the system 100 so that the magnet 120 appears like a three-dimensional arrow to show the location and direction of the magnetic dipole or a donut to simulate the shape of the magnet with an arrow extending therefrom. Techniques used for such three-dimensional graphic representations are well known in the art and need not be described in greater detail.

Figure 17B:
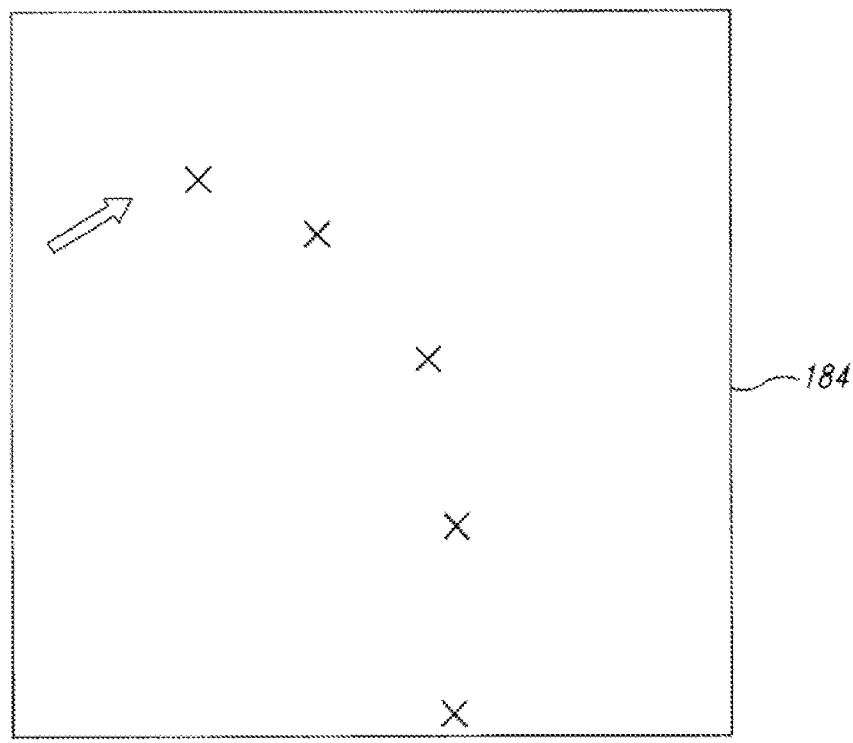
FIG. 17B illustrates the display of the selected locations and the location of a magnet.

In addition to displaying the magnet 120 as a three-dimensional graphic image, the system 100 can display the magnet from any perspective. For example, FIG. 17B illustrates the location of the magnet as viewed from the top surface of the patient, thus illustrating the location of the magnet in the X-Y plane. However, in some circumstances, it is desirable to view the magnet from a different perspective, such as the Y-Z plane. This perspective allows the user to see movement of the magnet 120 as it moves up and down (i.e., movement on the Z axis) within the patient. The user-selectable display perspective is particularly useful in applications, such as image-guided surgery, where the user must be able to visualize the movement of the intragastric device in any plane. For example, it is important to see directional movement in all three dimensions when inserting a cardiac catheter. There are known technologies to permit the display of the magnet 120 from any perspective. For example, MICROSOFT® WINDOWS® includes functions that allow the user to select the display perspective using a mouse, keyboard or other input device.

Thus, the detector system 100 determines the location α of the magnet 120 in a three-dimensional space and provides an easy-to-read visual indication of the location of the magnet, including a depth indication, as well as the orientation of the magnetic dipole. While the housing 102 is illustrated as a rectangular housing, with the magnetic sensors 108-114 distributed equidistantly within the housing 102, the rectangular shape was chosen for its ease in grasping by the caregiver. However, the housing 102 can have any shape or size. Furthermore, the display 106, while illustrated as a liquid crystal display, can be any convenient two-dimensional display, such as a dot matrix display or the like. Thus, the embodiments are not limited by the specific size or shape of the housing 102 or by the specific type of display 102. In addition, the detector system 100 can operate satisfactorily with a variety of different magnetic sensors. Thus, the system is not limited by the specific number or type of magnetic sensors employed in the detector system 100.

Figure 20:
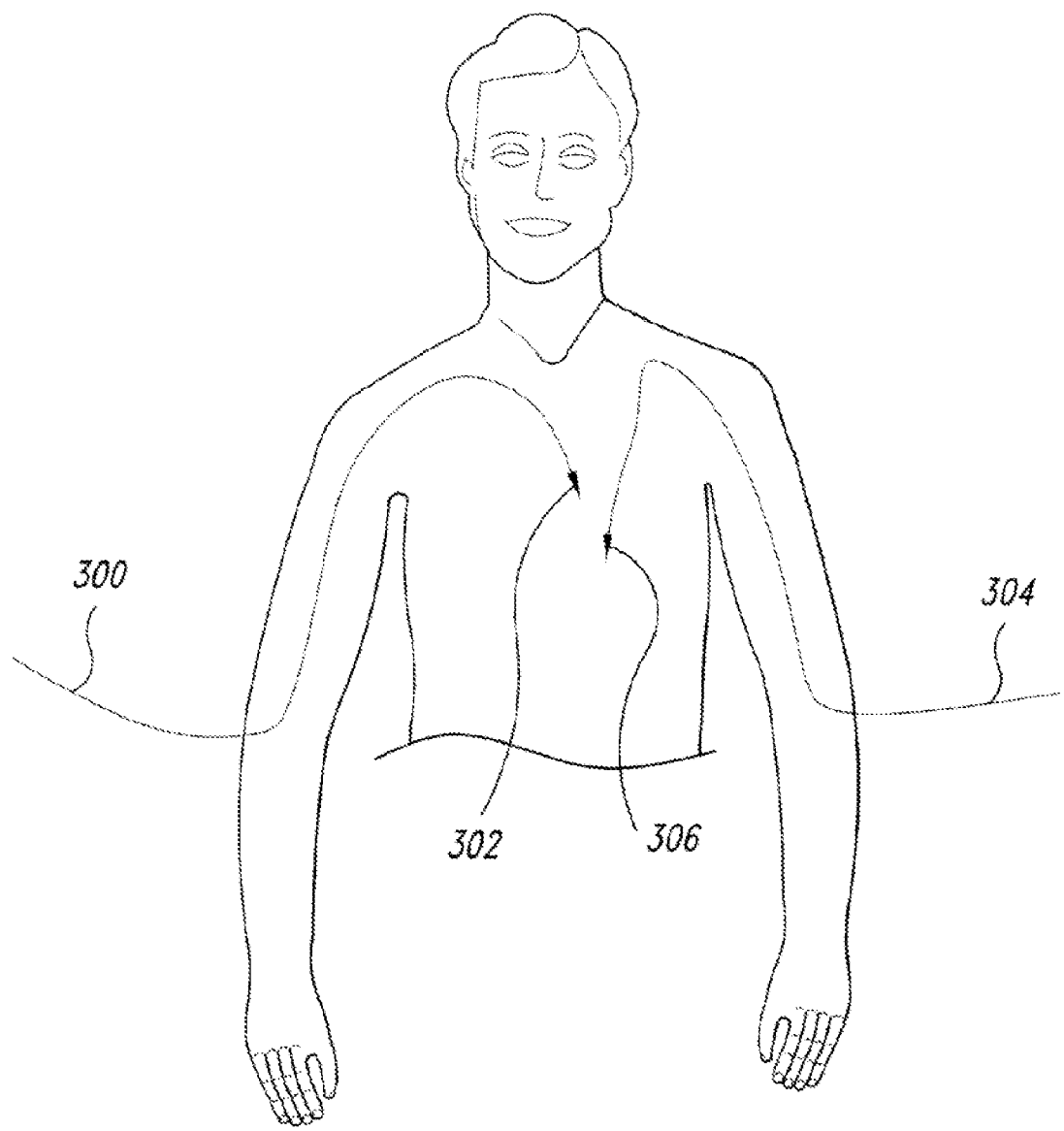
FIG. 20 illustrates the location of multiple magnets fixed to the ends of medical tubes positioned within the body of a human patient.

Various techniques have been described above to detect the three dimensional position and angular orientation of a single magnet. However, the principles of the embodiments may be extended to the detection of multiple magnets. The system 100 can detect the position of two intragastric devices, such as illustrated in FIG. 20, where a first peripherally inserted central catheter (PICC) 300 is inserted in one arm of the patient and has a magnet 302 associated with a terminal portion thereof. A second PICC 304 is inserted through another arm of the patient and includes a magnet 306 associated with a terminal portion thereof. Those skilled in the art will recognize that FIG. 20 serves only to illustrate the use of multiple tubes with multiple magnets. Any combination of known intragastric devices may be located using the techniques described herein. Accordingly, the embodiments are not limited by the specific type of medical tube (e.g., catheter) or device.

As previously described, the position and orientation of a single magnet may be described in three dimensional space by five parameters. Similarly, the position and orientation of the magnet 306 are also characterized by the same five parameters, although corresponding parameters will likely have different values. Thus, the position and orientation of the magnets 302 and 306 may be characterized by a total of ten unknown parameters. In addition, the contribution of the Earth's magnetic field in the x, y, and z, directions is unknown. Thus, the model used by the detector system 100 for two magnets has thirteen unknowns and requires thirteen independent measurements. In an exemplary embodiment of the detector system, illustrated in FIG. 21, five magnetic sensors, located at positions $S_1$-$S_5$, each having three orthogonally oriented sensing elements, provide a set of fifteen magnetic sensing elements. This is sufficient to detect the position and orientation of the magnets 302 and 306.

Figure 21:
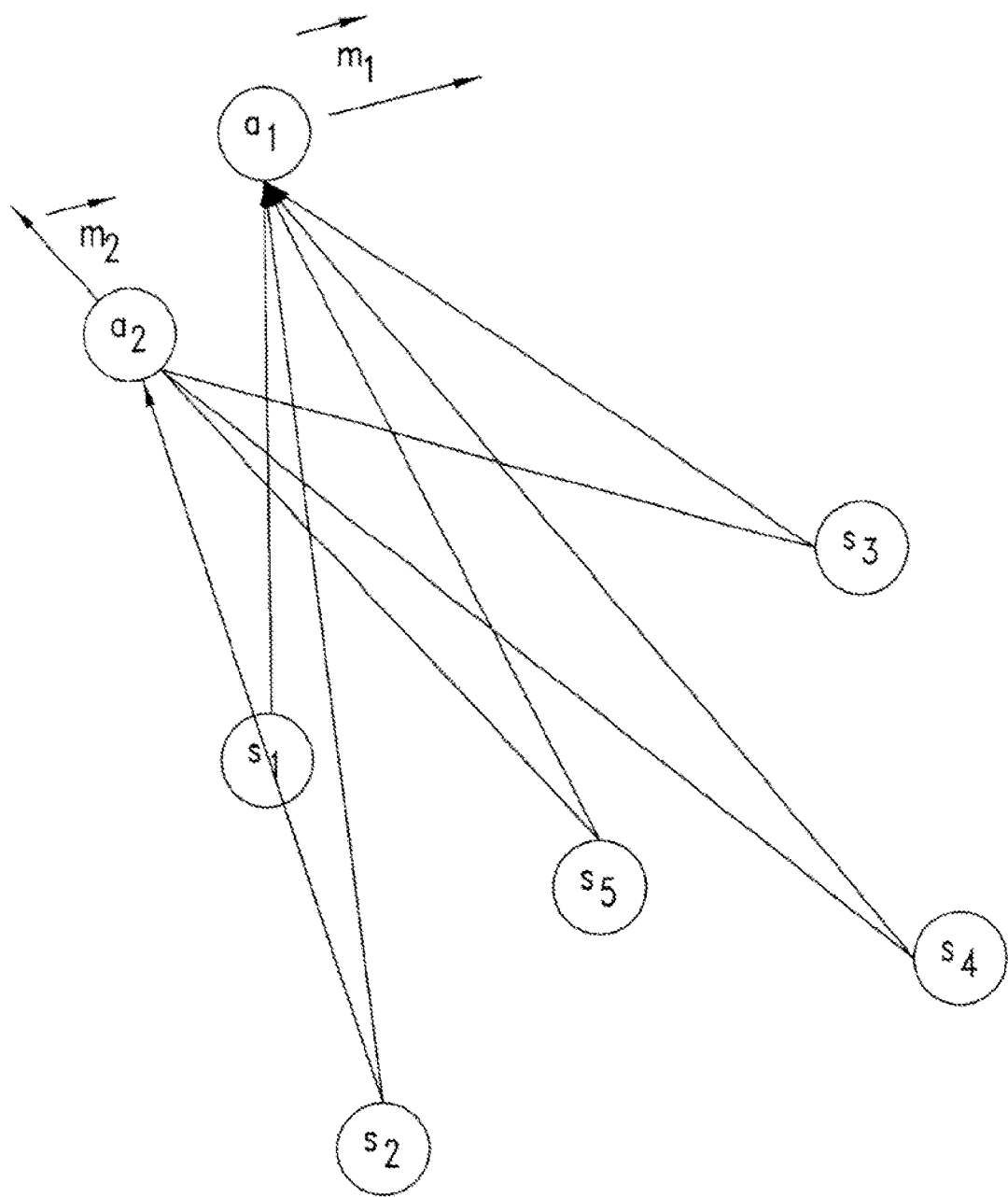
FIG. 21 illustrates the generation of magnet field strength vectors using an arbitrary magnetic sensor configuration to determine the location of multiple magnets.

As illustrated in FIG. 21, the magnet 302 is positioned at a location $α_1$. As is known in the art, the magnet 302 has a magnetic dipole that is represented by the vector $m_1$. Similarly, the magnet 306 is positioned at a location $α_2$ and has a magnetic dipole that is represented by the vector $m_2$. The vectors $m_1$ and $m_2$ represent the strength and orientation of the magnetic dipoles of the magnets 302 and 306, respectively.

The magnetic sensors, positioned at locations $S_1$-$S_5$ will detect the total magnetic field generated by both the magnet 302 and the magnet 306. Thus, the vector sensed at each of the magnetic sensors at locations $S_1$-$S_5$ will be the vector combination of the magnetic dipoles $m_1$ and $m_2$. However, the system 100 knows the strength of the magnetic dipoles $m_1$ and $m_2$ as well as the position and orientation of each of the sensors at locations $S_1$-$S_5$. Given this information, as well as the 15 separate measurements, the system can accurately detect the location and orientation of the magnets 302 and 306. The measurement techniques, using the equations described above, can be applied to two magnets. Although the process described herein can locate two magnets, the principles of can be further extended to more magnets. In the example above, thirteen parameters characterize the Earth's magnetic field (three parameters) and the two magnets 302 and 306 (five parameters each). A third magnet (not shown) can be characterized by the same five parameters discussed above. Thus, eighteen independent sensors are needed to characterize three magnets, twenty-three sensors are required to characterize four magnets and so forth.

The initial estimated location of the magnets 302 and 306 may also be determined using the neural network 154 (see FIG. 15A) or other techniques described herein. As will be described in greater detail below, the system 100 can include an array of magnetic sensors (see FIG. 16). In this embodiment, the estimation processor 152 can select a subset of sensors having measured magnetic field strength values above a predetermined threshold. The initial position of the magnets may be based on the values from the magnetic sensors whose readings are above the predetermined threshold.

In addition, the system 100 may perform an iterative process, as described above, to determine the location and orientation of the magnets 302 and 306. The process of optimization for minimizing the error (or cost) function for multiple magnets may be readily ascertained based on the foregoing description. For the sake of brevity, that description will not be repeated herein.

If a single magnet is associated with an intragastric device, it is possible to determine the position and angular orientation of the magnet and thus the intragastric device in the manner described above. The techniques described above are adequate to detect five degrees of freedom of the magnet and the intragastric device associated therewith. However, those skilled in the art will appreciate that a dipole magnet is symmetrical about its axis of magnetization. Thus, the intragastric device may be rotated along the axis of magnetization and the magnet will produce the same magnetic field. Thus, the system described above cannot determine the angular rotation of the intragastric device.

Figure 22:
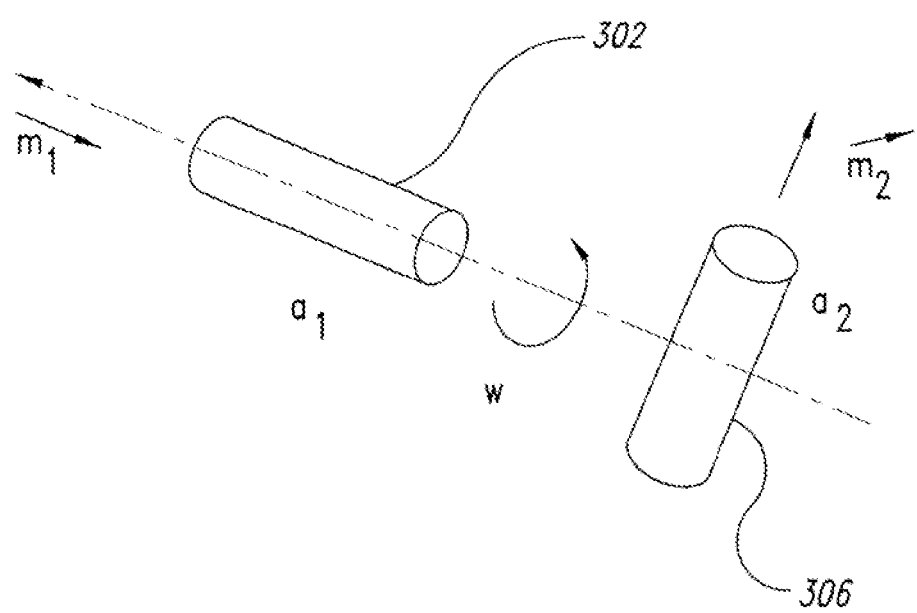
FIG. 22 illustrates the orientation of two magnets on a single tube to detect the rotational angle of the tube.

In another embodiment, the magnets 302 and 306 are both associated with a single intragastric device. As illustrated in FIG. 22, the magnets 302 and 306 are oriented such that their axes of magnetization are not aligned with each other. In the example illustrated in FIG. 22, the axis of magnetization of the magnet 302 is orthogonal to the axis of magnetization of the magnet 306. Given the knowledge of the strength of the magnetic dipoles $m_1$ and $m_2$, and the orientation of the axis of magnetization and the physical location of the magnet 302 with respect to the magnet 306, the system 100 can thereby detect a sixth degree of freedom of the intragastric device. This is illustrated in FIG. 22 as a rotational displacement ω. The techniques to determine the location and orientation of the magnets 302 and 306 are identical to that described above. However, given the additional knowledge of the fixed orientation of the axes of magnetization and the physical position of the magnet 302 with respect to the magnet 306, it is possible to detect rotational displacement 10 of the intragastric device. For example, the intragastric device may be an endoscope that may be guided by the image shown on the display 106 (see FIG. 15A) or on an external display. The system 100 can advantageously calculate six degrees of freedom (x, y, z, θ, φ, and ω) of the intragastric device associated with the magnets 302 and 306.

Figure 16:
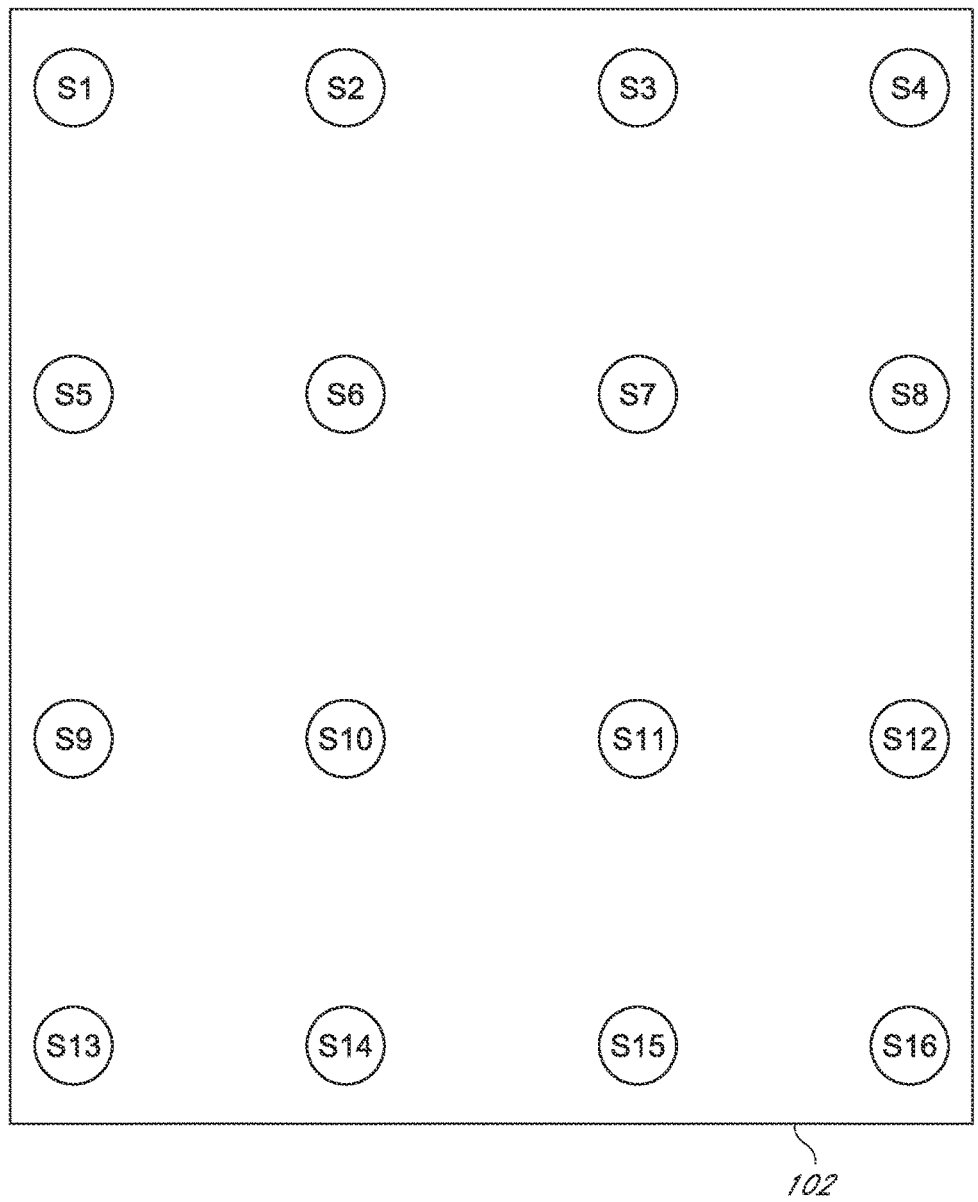
FIG. 16 illustrates a large number of magnetic sensors disposed within a predefined area to form a sensor array.

As previously described, a large number of magnetic sensors may be disposed to form a sensor array, as illustrated in FIG. 16. The housing 102 may be sufficiently large (e.g., 9 inches×12 inches). In this embodiment, the housing 102 may remain fixed in a stationary position on the measurement surface of the patient. As the magnet 120 (see FIG. 14) or the magnets 302 and 306 (see FIG. 20) are positioned in proximity with the housing 102, one or more of the sensors will detect the presence of the magnetic field. As described above, a sufficient number of magnetic sensors must detect the magnetic field and provide data in order to accurately characterize the location and orientation of the magnet. As described above, a sufficient number of magnetic sensors must detect the magnetic field and provide data in order to accurately characterize the location and orientation of the magnet.

FIG. 16 illustrates an array of sixteen magnetic sensors uniformly distributed within the housing at locations $S_1$-$S_{16}$. As previously described, each of the magnetic sensors may comprise individual magnetic sensing elements positioned in three orthogonal dimensions, which may conveniently be characterized as x, y, and z. The orientation of sensors along x, y, and z axes provides a convenient means for which to describe the magnetic sensors. However, the principles of the embodiments do not require a specific orientation of any of the sensors at the locations $S_1$-$S_{16}$ nor, indeed, do the sensors need to be uniformly distributed at the locations $S_1$-$S_{16}$. However, proper operation of the system 100 does require that the position and orientation of each of the magnetic sensors and magnetic sensing elements be known.

As described above, a small detector array may be moved with respect to the patient so as to track the insertion of an intragastric device in the associated magnet. As the magnetic sensors are moved, the effects of the Earth's magnetic field may change. Thus, recalibration is required as the sensors are moved with respect to the patient. The advantage of the large array illustrated in FIG. 16 is that the housing 102 need not be moved with respect to the patient. Thus, the effects of the Earth's magnetic field need only be measured and compensated for a single time.

As previously described, the initial position of a magnet may be determined using the sensor array of FIG. 16 using the detected magnetic field from four sensors that have the largest values or values above a predetermined threshold. For example, assume that the initial position of the magnet is unknown, that the magnetic sensors at locations $S_5$, $S_6$, $S_9$, and $S_{10}$ all have detected values above a predetermined threshold or have values greater than those detected by the sensors at other locations. As an initial estimate, the estimation processor 152 (see FIG. 15A) may assume that the magnet 120 (see FIG. 14) is located in a position equidistant from the magnetic sensors at the locations $S_5$, $S_6$, $S_9$, and $S_{10}$. Alternatively, the position within the boundaries defined by these locations $S_5$, $S_6$, $S_9$, and $S_{10}$ may be weighted based on the value detected by each of the sensors at those locations. For example, the sensor at location $S$ $S_6$ may have the highest value of the sensors at locations $S_5$, $S_6$, $S_9$, and $S_{10}$. Accordingly, the estimation processor 152 may calculate an initial position for the magnet 120 that is closer to the location $S$ $S_6$ rather than equidistant from each of the locations $S_5$, $S_6$, $S_9$, and $S_{10}$. Other weighting functions may also be used by the estimation processor 152.

In yet another alternative embodiment, the values detected by the sensors at locations $S_5$, $S_6$, $S_9$, and $S_{10}$ may be provided to the neural network 154 and processed in a manner described above. Thus, the system 100 offers a variety of techniques to determine the initial estimated location of the magnet 120. Through the iterative process described above, the location and orientation of one or more magnets may readily be detected and tracked by the system 100.

EXAMPLES

Component Integration into Device

Figure 23:
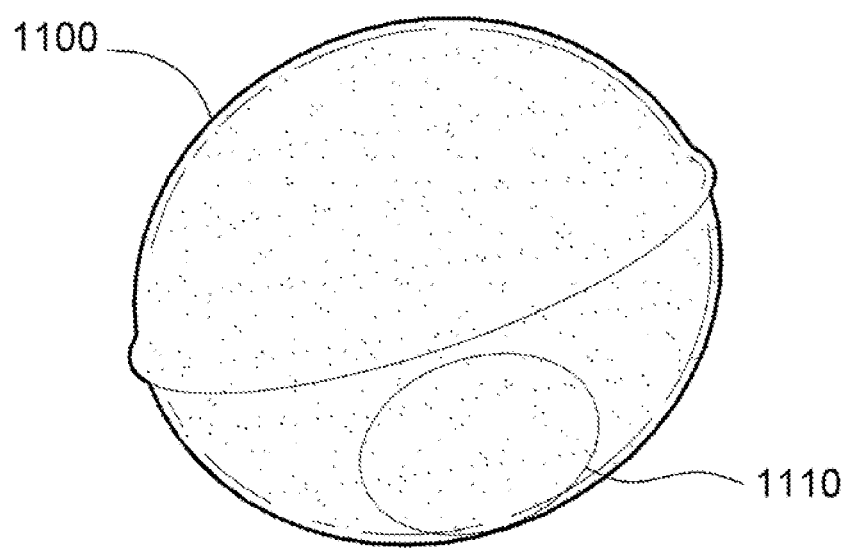
FIG. 23 depicts a balloon of one embodiment incorporating an electromagnetic, magnetic or magnetizable pellet in an enclosed volume of the intragastric balloon. The pellet can be loose or attached to a wall of the intragastric balloon.
Figure 24:
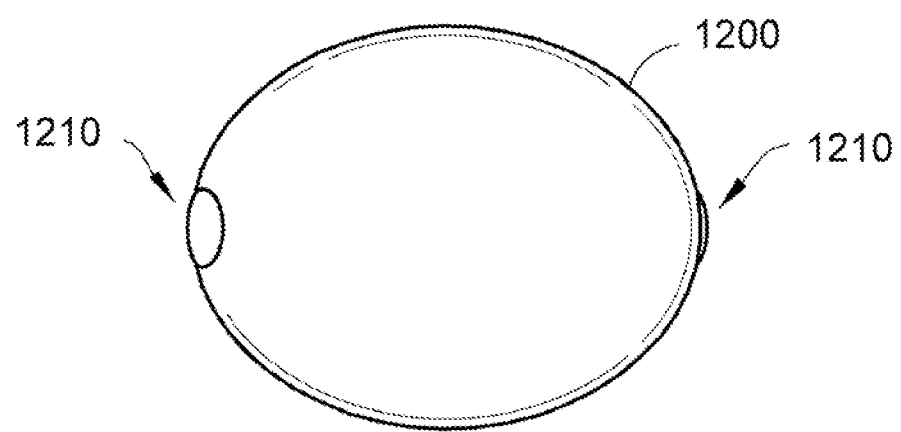
FIG. 24 depicts a balloon of one embodiment incorporating electromagnetic, magnetic or magnetizable buttons attached to opposite sides of the intragastric balloon.
Figure 25A:
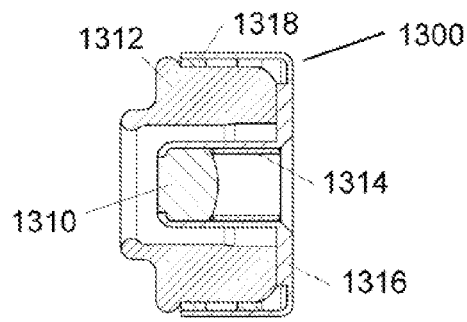
FIG. 25A depicts a cross section of a valve system including a septum plug, head unit, ring stop, tube septum, and an electromagnetic or magnetized retaining ring.
Figure 25B:
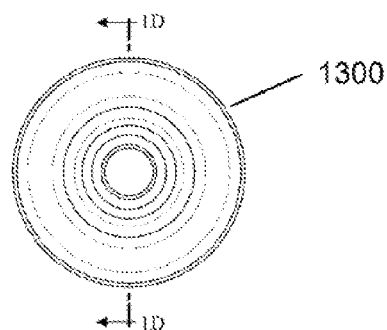
FIG. 25B is a top view of the valve system, depicted in cross-section along line 1D-1D in FIG. 25A.
Figure 25C:
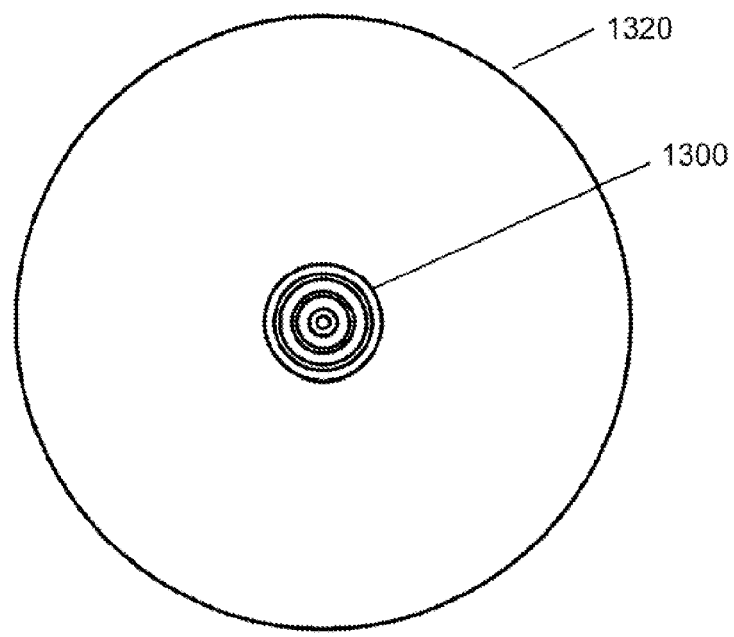
FIG. 25C is a top view of the valve system of FIGS. 25A and 25B incorporated into the wall of an intragastric balloon.
Figure 26:
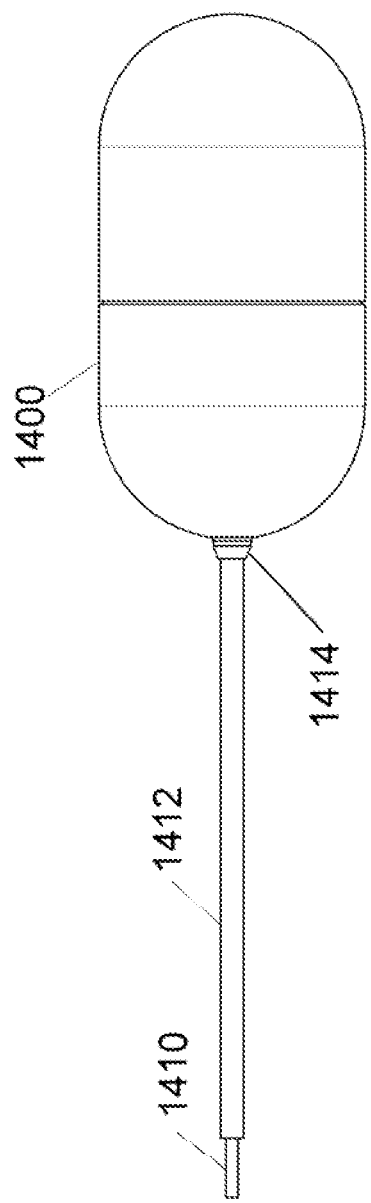
FIG. 26 depicts a gel cap 1400 containing an intragastric balloon of FIGS. 25A-C in uninflated form. The gel cap containing the uninflated balloon is engaged via the valve system of the intragastric balloon to a dual catheter system comprising a 2FR tube and a 4FR tube via a press-fit connecting structure incorporating an electromagnetic, magnetic, or magnetized component.

FIG. 23 depicts a balloon 1100 of one embodiment incorporating a pellet 1110 in an enclosed volume of the intragastric balloon. The pellet 1110 may be an electromagnetic sensor, a magnetic sensor, an acoustic sensor, a voltaic sensor, a pH sensor, and/or other sensors or markers described herein. The pellet 1110 can be loose or attached to a wall of the intragastric balloon. FIG. 24 depicts a balloon 1200 of one embodiment incorporating buttons 1210 attached to opposite sides of the intragastric balloon. The buttons 1210 may be electromagnetic, emagnetic, acoustic, voltaic, pH, and/or other buttons, sensors or markers described herein. FIG. 25A depicts a cross section of a valve system 1300 including a septum plug 1310, head unit 1312, ring stop 1314, tube septum 1316, and retaining ring 1318. The retaining ring may include electromagnetic, magnetic, acoustic, voltaic, pH, and/or other sensors or markers. FIG. 25B is a top view of the valve system, depicted in cross-section along line 1D-1D in FIG. 13A. FIG. 25C is a top view of the valve system of FIGS. 13A and 13B incorporated into the wall of an intragastric balloon 1320. FIG. 26 depicts a gel cap 1400 containing an intragastric balloon of FIGS. 25A-C in uninflated form. The gel cap containing the uninflated balloon is engaged via the valve system of the intragastric balloon to a dual catheter system comprising a 2FR tube 1410 and a 4FR tube 1412 via a press-fit connecting structure 1414 incorporating a magnetized component, e.g., a needle (not depicted).

Acoustic Tracking and Visualization Subcomponent

Various embodiments may implement acoustic tracking and visualization functionality into devices and systems described above. As used herein, "visualization" is used broadly to refer to locating, characterizing, or otherwise identifying an item of interest in the body in a number of ways, including by ultrasonic and other acoustic wave data such as wave strength, wave orientation, temporal characteristics of the wave, the effects of the wave on a sensor, and other attributes of an ultrasound or acoustic wave that may be used to facilitate tracking, locating, identifying, and characterizing an item of interest, as well as audio, visual, tactile, or other output based on the ultrasound data that characterizes the item of interest. As used herein, "acoustic" refers to using mechanical waves in gases, liquids or solids and covers the use of such techniques as vibrations, sounds, ultrasounds and infrasounds. While the acoustic embodiments are described primarily in the context of ultrasounds, it is understood that the embodiments may also be implemented with other acoustic techniques, such as those mentioned above, and others not explicitly mentioned. Thus, the ultrasound techniques described herein may also be implemented in other acoustic type embodiments. Due to the non-invasive nature of an acoustic-based device, physicians may desire to determine, or confirm, the location and orientation of the device prior to inflation or during the course of treatment. Thus, acoustic-related devices and methods for determining and confirming the location, orientation and/or state of an intragastric device at all phases of administration are disclosed. Such acoustic-based devices and techniques include ultrasound-related means, which include but are not limited to ultrasonography or ultrasonic imaging, "very directional" Doppler systems, Doppler imaging systems, and systems related to intravascular ultrasound techniques.

Ultrasound is an oscillating sound pressure wave with a frequency greater than the upper limit of the human hearing range. Ultrasound is thus not separated from 'normal' (audible) sound by differences in physical properties, only by the fact that humans cannot hear it. Although this limit varies from person to person, it is approximately 20 kilohertz (20,000 hertz) in healthy, young adults. Ultrasound devices operate with frequencies from 20 kHz up to several gigahertz.

Diagnostic sonography (ultrasonography) is an ultrasound-based diagnostic imaging technique used for visualizing internal body structures including tendons, muscles, joints, vessels and internal organs for possible pathology or lesions. The practice of examining pregnant women using ultrasound is called obstetric sonography, and is widely used. In physics, 'ultrasound' refers to sound waves with a frequency too high for humans to hear. Ultrasound images (sonograms) are made by sending a pulse of ultrasound into tissue using an ultrasound transducer (probe). The sound reflects and echoes off parts of the tissue; this echo is recorded and displayed as an image to the operator. The techniques employed for imaging tissue and organs using ultrasound can be adapted for imaging the intragastric device or devices of the embodiments Many different types of images can be formed using ultrasound. The most well-known type is a B-mode image, which displays a two-dimensional cross-section of the tissue being imaged. Other types of image can display a three-dimensional region, enabling precise location of the intragastric device within the gastric system. In certain embodiments, application of ultrasound can also be used to rupture the device, facilitating passage of the deflated device out of the body at the end of its useful life.

Compared to other prominent methods of medical imaging, ultrasonography has several advantages. It provides images in real-time (rather than after an acquisition or processing delay), it is portable and can be brought to a sick patient's bedside, it is substantially lower in cost, and it does not use harmful ionizing radiation. Each of these features is particularly advantageous for locating or tracking an intragastric device.

Typical diagnostic sonographic scanners operate in the frequency range of 2 to 18 megahertz, though frequencies up to 50-100 megahertz have been used in biomicroscopy. The choice of frequency is a trade-off between spatial resolution of the image and imaging depth: lower frequencies produce less resolution but image deeper into the body. Higher frequency sound waves have a smaller wavelength and thus are capable of reflecting or scattering from smaller structures. Higher frequency sound waves also have a larger attenuation coefficient and thus are more readily absorbed in tissue, limiting the depth of penetration of the sound wave into the body. Different frequencies can be employed, depending upon the condition of the intragastric device at the time of imaging. For example, an uninflated intragastric device in compacted form may benefit from use of a higher imaging wavelength (e.g., 7-18 MHz) due to the smaller cross section, especially when imaging in the region of the throat, wherein the device would be expected to be close to the surface of the body, while a lower imaging wavelength (e.g., 1-6 MHz) may be desirable for the intragastric device in a larger inflated form in the stomach, where the distance to the surface of the skin may be further, wherein a lower axial and lateral resolution but greater penetration is observed.

Ultrasonography can use a hand-held probe (called a transducer) that is placed directly on and moved over the patient. Sonography is effective for imaging soft tissues of the body. Superficial structures such as muscles, tendons, testes, breast, thyroid and parathyroid glands, and the neonatal brain are imaged at a higher frequency (7-18 MHz), which provides better axial and lateral resolution. Deeper structures such as liver and kidney are imaged at a lower frequency 1-6 MHz with lower axial and lateral resolution but greater penetration.

In ultrasound, a sound wave is typically produced by a piezoelectric transducer or a capacitive micromachined transducer, encased in a housing which can take a number of forms. Strong, short electrical pulses from the ultrasound machine make the transducer ring at the desired frequency. The frequencies can be anywhere between 2 MHz or lower and 18 MHz or higher. The sound is focused either by the shape of the transducer, a lens in front of the transducer, or a complex set of control pulses from the ultrasound scanner machine (beamforming). This focusing produces an arc-shaped sound wave from the face of the transducer. The wave travels into the body and comes into focus at a desired depth.

Transducers focus their beam with physical lenses or use phased array techniques to enable the sonographic machine to change the direction and depth of focus. Almost all piezoelectric transducers are made of ceramic. Materials on the face of the transducer enable the sound to be transmitted efficiently into the body (e.g., a rubbery coating, a form of impedance matching). In addition, a water-based gel is typically placed between the patient's skin and the probe. The techniques of the embodiments can be applied to administration of the gastric device to a patient with an empty stomach, or to a patient with a stomach partially filled with liquid and/or solid gastric contents.

The sound wave is partially reflected from the layers between different tissues, or from the interface between the device in compacted form and the surrounding tissue, or the interface between the device in inflated form and the surrounding tissue or gastric fluids or content. Specifically, sound is reflected anywhere there are density changes, such that some of the reflections return to the transducer. The return of the sound wave to the transducer results in the same process that it took to send the sound wave, except in reverse. The return sound wave vibrates the transducer, the transducer turns the vibrations into electrical pulses that travel to the ultrasonic scanner where they are processed and transformed into a digital image. The sonographic scanner determines from each received echo how long it took the echo to be received from when the sound was transmitted, and how strong the echo was. The focal length for the phased array can also be determined, enabling a sharp image of that echo at that depth. The ultrasonic imaging energy is delivered as a pulse with a specific carrier frequency. Moving objects change this frequency on reflection, so that it is only a matter of electronics to have simultaneous Doppler sonography enabling movement to be imaged. The received image is then digitally displayed.

Ultrasonography (sonography) uses a probe containing multiple acoustic transducers to send pulses of sound into a material. Whenever a sound wave encounters a material with a different density (acoustical impedance), as in a compact or inflated intragastric device, part of the sound wave is reflected back to the probe and is detected as an echo. The time it takes for the echo to travel back to the probe is measured and used to calculate the depth of the tissue interface causing the echo. The greater the difference between acoustic impedances, the larger the echo is. If the pulse hits gases or solids, the density difference is so great that most of the acoustic energy is reflected and it becomes impossible to see deeper. This feature is advantageous in the imaging of an inflated intragastric device.

The frequencies used for imaging are generally in the range of 1 to 18 MHz. Higher frequencies have a correspondingly smaller wavelength, and can be used to make sonograms with smaller details. However, the attenuation of the sound wave is increased at higher frequencies, so in order to have better penetration of deeper tissues, a lower frequency (3-5 MHz) is used.

Seeing deep into the body with sonography is very difficult. Some acoustic energy is lost every time an echo is formed, but most of it (approximately) is lost from acoustic absorption. The speed of sound varies as it travels through different materials, and is dependent on the acoustical impedance of the material. However, the sonographic instrument assumes that the acoustic velocity is constant at 1540 m/s. An effect of this assumption is that in a real body with non-uniform tissues, the beam becomes somewhat de-focused and image resolution is reduced. However, in the various embodiments, the profile of the device in its different forms (compacted, undergoing inflation, inflated, undergoing deflation, deflated) is generally readily ascertained despite the lower image resolution.

To generate a two-dimensional (2D) image, the ultrasonic beam is swept. A transducer may be swept mechanically by rotating or swinging. Or a one dimensional phased array transducer may be used to sweep the beam electronically. The received data is processed and used to construct the image. The image is then a 2D representation of the slice into the body. A 2D image may be acceptable for determining the passage of the device longitudinally through the gastrointestinal tract. Once in place, it may be desirable to image the device in the stomach in three dimensions. 3D images can be generated by acquiring a series of adjacent 2D images. A 2D phased array transducer that can sweep the beam in 3D can be employed, as is commonly used in cardiac imaging. Doppler ultrasonography is used to image motion. The different detected speeds are represented in color for ease of interpretation. Colors may alternatively be used to represent the amplitudes of the received echoes. Such ultrasonography can be advantageously employed to image the device as it moves down the esophagus.

Several modes of ultrasound used in medical imaging can be employed in various embodiments. A-mode (amplitude mode) is the simplest type of ultrasound. A single transducer scans a line through the body with the echoes plotted on screen as a function of depth. A-mode ultrasound also allows for pinpoint accurate focus of a destructive wave energy, e.g., for use in deflating an inflated intragastric device. In B-mode (brightness mode) ultrasound, a linear array of transducers simultaneously scans a plane through the body that can be viewed as a two-dimensional image on screen. This mode is more commonly known as 2D mode now. A C-mode image is formed in a plane normal to a B-mode image. A gate that selects data from a specific depth from an A-mode line is used; then the transducer is moved in the 2D plane to sample the entire region at this fixed depth. When the transducer traverses the area in a spiral, an area of 100 cm2 can be scanned in around 10 seconds. In M-mode (motion mode) ultrasound, pulses are emitted in quick succession—each time, either an A-mode or B-mode image is taken. Over time, this is analogous to recording a video in ultrasound. As the boundaries of the intragastric device produce reflections move relative to the probe, this can be used to determine the velocity of the intragastric device. Doppler mode makes use of the Doppler effect in measuring and visualizing moving objects such as the intragastric device. Velocity information can be presented as a color-coded overlay on top of a B-mode image. Doppler information can be continuously sampled along a line through the body, and all velocities detected at each time point are presented (on a time line). In pulsed wave (PW) Doppler, Doppler information is sampled from only a small sample volume (defined in 2D image), and presented on a timeline. Duplex mode is used to refer to the simultaneous presentation of 2D and (usually) PW Doppler information. Color Doppler can be referred to as Triplex mode. In the pulse inversion mode, two successive pulses with opposite sign are emitted and then subtracted from each other. This means that any linearly responding constituent will disappear while gases with non-linear compressibility stand out. Pulse inversion may also be used in a similar manner as in harmonic mode, wherein a deep penetrating fundamental frequency is emitted into the body and a harmonic overtone is detected. This way noise and artifacts due to reverberation and aberration are greatly reduced. Penetration depth can be gained with improved lateral resolution. An additional expansion or additional technique of ultrasound is biplanar ultrasound, in which the probe has two 2D planes that are perpendicular to each other, providing more efficient localization and detection. An omniplane probe is one that can rotate 180° to obtain multiple images. In 3D ultrasound, many 2D planes are digitally added together to create a 3-dimensional image of the object.

In contrast-enhanced ultrasound, microbubble contrast agents enhance the ultrasound waves, resulting in increased contrast. In a similar fashion, the intragastric device can advantageously be completely or partially filled with a heavy gas such as perfluorocarbon or nitrogen to enhance contrast. Heavy gases suitable for use include but are not limited to nitrogen, argon, $SF_6$, and halocarbons such as $C_2F_6$, $C_3F_8$, $C_4F_{10}$, $C_4F_8$, $C_3F_6$, $CF_4$, and $CClF_2$—$CF_3$.

Sonography can be enhanced with Doppler measurements, which employ the Doppler Effect to assess whether structures such as the intragastric device are moving towards or away from the probe, and the structure's relative velocity. By calculating the frequency shift of a particular sample volume, for example flow in an artery or a jet of blood flow over a heart valve, its speed and direction can be determined and visualized. This is particularly useful in cardiovascular studies (sonography of the vascular system and heart) and essential in many areas such as determining reverse blood flow in the liver vasculature in portal hypertension. The Doppler information is displayed graphically using spectral Doppler, or as an image using color Doppler (directional Doppler) or power Doppler (non-directional Doppler). This Doppler shift falls in the audible range and is often presented audibly using stereo speakers: this produces a very distinctive, although synthetic, pulsating sound. Most modern sonographic machines use pulsed Doppler to measure velocity. Pulsed wave machines transmit and receive series of pulses. The frequency shift of each pulse is ignored; however the relative phase changes of the pulses are used to obtain the frequency shift (since frequency is the rate of change of phase). The major advantages of pulsed Doppler over continuous wave is that distance information is obtained (the time between the transmitted and received pulses can be converted into a distance with knowledge of the speed of sound) and gain correction is applied. The disadvantage of pulsed Doppler is that the measurements can suffer from aliasing. The terminology "Doppler ultrasound" or "Doppler sonography" has been accepted to apply to both pulsed and continuous Doppler systems despite the different mechanisms by which the velocity is measured. There are no standards for the display of color Doppler. A common convention is to use red to indicate flow toward the transducer and blue away from the transducer, or to display a red shift representing longer waves of echoes (scattered) from the target.

Ultrasonography offers a number of advantages for imaging the intragastric device in vivo. Ultrasonography images solid surfaces very well and is particularly useful for delineating the interfaces between solid and fluid-filled spaces, enabling the imaging of the device in both a solid, compacted form as well as an inflated form or even a deflated form. The method enables live images to be obtained, showing motion as well as position of the intragastric device. The method has no known long-term side effects and rarely causes any discomfort to the patient. The equipment is widely available and comparatively flexible. Small, easily carried scanners are available such that examinations can be performed in a physician's office or in a clinic setting. The technology is also relatively inexpensive compared to other methods, such as CAT imaging or magnetic resonance imaging. Spatial resolution is better in high frequency ultrasound transducers than it is in most other imaging modalities, enabling accurate tracking of the intragastric device.

It is known that there might be difficulties imaging tissue structures deep in the body, especially in obese patients, using ultrasound. Body habitus has a large influence on image quality. Image quality and accuracy of diagnosis is limited with obese patients, overlying subcutaneous fat attenuates the sound beam and a lower frequency transducer is required (with lower resolution). However, the device in solid, compacted form provides satisfactory imaging contrast. The device in inflated form, especially when containing nitrogen, SF6, or other halocarbons, exhibits excellent contrast, unlike tissue structures in vivo, enabling ease of imaging even in the morbidly obese.

In some embodiments, an ultrasound sensor comprises a non-contact sensor. An ultrasonic level or sensor or sensing system requires no contact with the target. In the medical industries this is an advantage over inline sensors that may contaminate or otherwise interfere with the marker or item of interest. In some embodiments, the sensor is a microphone.

In some embodiments, a pulsed wave system is used. The principle behind a pulsed-ultrasonic technology is that the transmit signal consists of short bursts of ultrasonic energy. After each burst, the sensor electronics looks for a return signal within a small window of time corresponding to the time it takes for the energy to pass through the medium of interest. Only a signal received during this window will qualify for additional signal processing. In some embodiments a continuous wave system is used. In the pulsed, continuous, or other wave systems, the sensor may be a microphone that receives the return wave signal.

In some embodiments, a marker may transmit ultrasound signals. For instance, Ultrasound Identification (USID) may be used to automatically track and identify the location of intragastric devices in real time using simple, inexpensive nodes (badges/tags) attached to or embedded in the ultrasound devices, which then transmit an ultrasound signal to communicate their location to ultrasound sensors, such as microphones.

A computing system may be implemented in the ultrasound locating system. The computing system comprises hardware and software that receives data from the ultrasound sensor and calculates information related to the location, orientation, and/or state of an intragastric device according to certain algorithms. In some embodiments, the hardware may comprise a central processing unit, memory, an analog to digital converter, analog circuitry, a display. In some embodiments, the software proceeds through a number of steps including calibration, initialization, prediction, estimation, measuring magnetic sensor data, calculating various desired outputs including location, orientation, size, configuration, etc. in accordance with the techniques discussed herein.

The processor's output relating to the location, orientation and/or state of an intragastric device may be communicated to a user in a number of manners. In some embodiments, the output is shown visually on a display.

In some embodiments, the processor's output related to an intragastric device's location, orientation, and/or state is audibly communicated to a user through a speaker.

In some embodiments, the processor's output related to an intragastric device's location, orientation, and/or state is communicated to a user through a combination of methods. For instance, the system may employ a visual graphical display with audible alerts sent through speakers.

In some embodiments, the ultrasound locating system is calibrated before use. The ultrasound marker and the sensor are positioned in pre-planned locations and orientations to verify the output signal is within an expected range. In some embodiments, the ultrasound locating systems are calibrated or otherwise verified using a human patient simulator, or dummy, to test the ultrasound locating system as an ultrasound marker travels through the simulator. In some embodiments, the ultrasound locating system is checked for stray signals from nearby acoustic interferences.

The ultrasound sensor may be used in conjunction with the marker or markers in a variety of embodiments to locate or otherwise characterize an ingested intragastric device. In some embodiments, an off-the-shelf intragastric device, such as a swallowable, inflatable balloon, may be used without modification with any ultrasound markers. With that device, an ultrasound sensor that pulses sound waves and senses their return signal with a microphone may be used outside the body. The device could be swallowed in a deflated state and would then inflate or be inflated once inside the stomach. The ultrasound sensor may be used to locate or otherwise characterize the device by pulsing the device and receiving the return signals, in accordance with the techniques discussed above.

The devices once ingested may be located using the ultrasound intragastric locating system. In some embodiments, the sensor may locate the device by pulsing in various locations and analyzing the return signal. For instance, a return signal corresponding to a body organ without the device may be pre-determined by correlating a return wave signal to a location on the body before the device is swallowed. This could produce an ultrasound map of the organ or body without any device. Then, after swallowing the device, and by running the sensor over the body, if a different signal is returned for a corresponding location in the body, then the location of the device is thus identified. This may be implemented in accordance with the techniques discussed above.

The orientation of the devices once ingested may be ascertained using the ultrasound intragastric locating system. In some embodiments, the sensor may identify the orientation of the intragastric device by pulsing and sensing at various locations of the device and analyzing the return signals. For instance, before ingestion by a patient, the device may be pulsed at various orientations such that a pre-determined database exists of known correlations between return wave signatures and orientation of the device. This may be done for the device in the deflated, inflated, or other states. Then, after ingestion, the device may be pulsed and the return signals compared to the pre-determined database to determine the orientation of the device in accordance with the techniques discussed above.

Further, the various sizes and configurations of the devices once ingested may be characterized using the ultrasound intragastric locating system in accordance with the techniques discussed above. For instance, inflation of a balloon, or the inflation or configuration of multiple balloons, may be characterized and assessed. In some embodiments, the sensor may characterize the device or devices by pulsing and sensing at various locations of the device and analyzing the return signals. For instance, the deflated device would return a different pulsed signature than the inflated device. In such a manner, the device may be characterized as either inflated, deflated, or in some other state. The inflated device could further be characterized before ingestion by a patient such that the return signal signature is pre-determined and serves as a guidepost for assessing the state of the device. In some embodiments, the ultrasound locating system may be used in conjunction with a deflating system to characterize the deflation process.

The timing and other attributes of the various methods of administration can be characterized using the disclosed ultrasound intragastric locating system and techniques. Whether the device is administered using endoscopic techniques or orally, the progress of the device as it makes its way to the stomach can be tracked with the ultrasound locating system. For instance, the effects of swallowing the device with hard gelatin or water or other consumables may be characterized by tracking the location and orientation as it is ingested. In some embodiments, the endoscope employed to deliver the intragastric device incorporates an ultrasound emitting device at a preselected distance from the intragastric device to be deployed. The ultrasound transmittal can enable precise positioning of the intragastric balloon, as well as monitoring of the inflation process by changes in the emitted ultrasound due to proximal inflation of the intragastric device.

In some embodiments, the ultrasound locating system may characterize an intragastric device that has a circular or elliptical cross-section. Two ultrasonic modules placed in the device allow the system to measure the size and composition of the device using time of flight ultrasound technology.

Using the speed of sound, a distance can be computed from the time between transmission and reception. The time between transmission of the ultrasonic pulse and reception of the echo is given by: $t=2d/U$, or $d=Ut/2$, (53) where U is the speed of sound in the medium of interest, and d is the diameter of the device. If transmission occurs in two orthogonal directions, two dimensions of the intragastric device can be determined, and thus the area of the device can be computed. Assuming the device is an ellipse, the equation for the area of an ellipse using the major (a) and minor (b) axes is as follows:

$$A = \pi \cdot a \cdot b = (\pi \cdot U^2 \cdot t_1 \cdot t_2)/16$$

If the interior of an inflated device is clear, a clear echo signal is obtained and the time of flight of the ultrasound pulse is obtained in the clear area to determine device area. To detect the presence of matter, foreign or otherwise, in the device, two methods may be used. First, the orthogonal signal, that is the amplitude of the scattered ultrasonic pulse in the orthogonal direction, is compared with the original pulse echo return. And second, the amount of false return in the original pulse echo may even determine the ratio of solid to liquid matter in the analyzed cross section of the device.

The intragastric device may include two orthogonal ultrasonic transmitter/receiver ("transceiver") modules. One transceiver is an anterior/posterior (a/p) ultrasonic module, and the other transceiver is a lateral ultrasonic module. The device further includes a microprocessor that measures the time of flight from each transceiver module. The microprocessor is capable of distinguishing between device echoes and the empty device interior. The microprocessor is also capable of preparing a signal for transmission. The microprocessor is in electrical communication with a computer. In some embodiments, the computer and the microprocessor are incorporated into the same component. In at least one embodiment, the computer may be a look up table, capable of determining the semi-major axis, the semi-minor axis, and the scatter associated with the device.

The intragastric device may also include a transmitter capable of transmitting the signals from the device to a location outside of the body. The transmitter can include an antenna for transmission, or an antenna in the band (not shown) can be in electrical communication with the transmitter. The device may also include a module either containing a battery or capable of powering the intragastric device electronics inductively. External to the patient may be an antenna for receiving the transmitted signals and a receiver in operative communication with the antenna. A computer may be included that has software capable of decoding and processing the signals transmitted by the transmitter and received by the receiver. The computer software is capable of measuring the time of flight of horizontal and vertical ultrasonic pulses to determine the length and width of the intragastric device, and combining the length and width to find the area. It should be noted that from the scatter of the horizontal into the vertical receiver and the scatter of the vertical into the horizontal receiver, the presence of any material in the device can be determined.

The various ultrasound markers and their acoustic properties may be implemented in the ultrasound intragastric device locating system with ultrasound sensors or detectors. The ultrasound markers comprise any substance, material, or object, to which the ultrasound sensors or detectors are responsive. As mentioned, an ultrasound "marker" as used herein therefore includes the intragastric device itself, such that an off-the-shelf, unmodified intragastric device may already contain materials that are responsive to or otherwise may be used with the ultrasound locating system disclosed herein.

In some embodiments, the marker is a node attached to and/or embedded in and/or otherwise coupled to the intragastric device. Such a node may be, for example, a badge or tag that is responsive to applied ultrasound energy. The node may also emit or transmit an ultrasound signal to communicate its location to microphone sensors. The node may be incorporated with the intragastric device in various arrangements.

Acoustic Location

Figure 27:
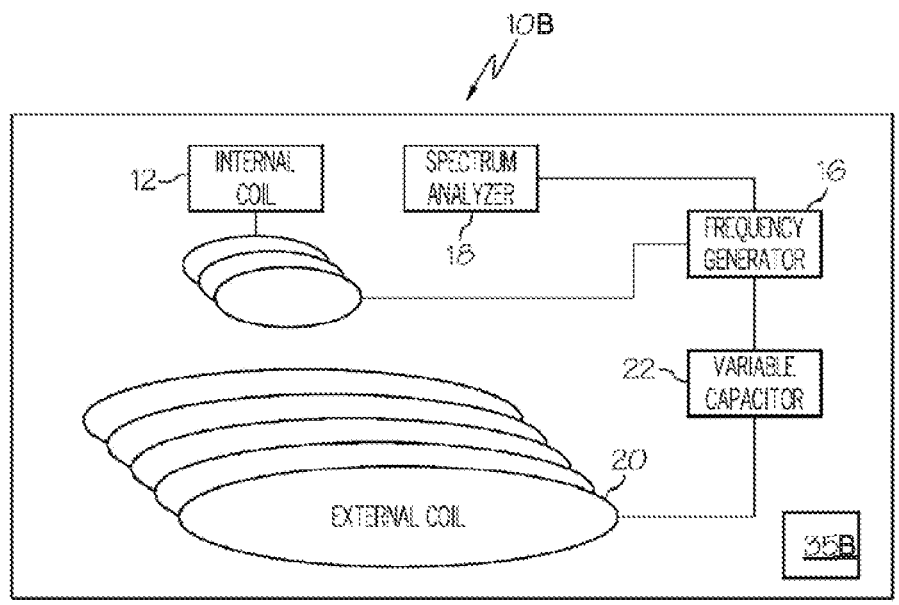
FIGS. 27-28 depict an embodiment of a system for locating or otherwise characterizing an intragastric device using ultrasound.
Figure 28:
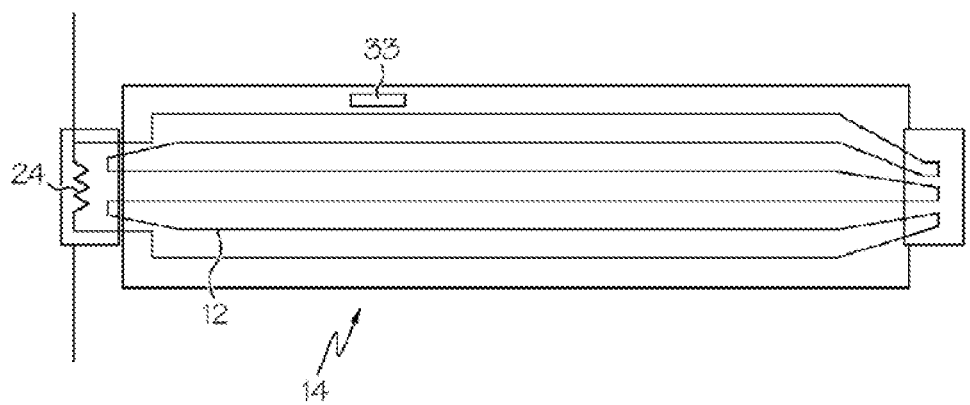

Referring now to FIGS. 27 and 28, a system for locating or otherwise characterizing an intragastric device using ultrasound is illustrated in accordance with at least one embodiment of the present invention. The system 10B of FIG. 27 is used for measuring a characteristic of the device, such as size, using an external tuned circuit and a passive coil embedded in or on the device. The system 10B includes a first coiled conductor 12 (or internal coil) positioned within an intragastric device 14 (shown in more detail in FIG. 28). The phrases "internal coil" and "inner coil" are also used herein to denote the first coiled conductor 12. The system further includes a circuit external to the device and patient that includes a tunable frequency generator 16, a spectrum analyzer 18, and a second coiled conductor 20. The phrases "external coil" and "outer coil" are also used herein to denote the second coiled conductor 20. The frequency generator may be a variable frequency oscillator, for example. The phrase "frequency generator" is used to denote any type of electrical or electronic device that produces repetitive electrical or electronic signals. For example, the frequency generator may be an electronic device capable of generating repeating sine waves. The phrase "spectrum analyzer" is used to denote any electrical or electronic device capable of measuring the frequency and amplitude of a signal.

The system further includes appropriate capacitance, inductance, and resistance to allow resonance both when a patient is absent and when the patient is present, as will be described in detail below. For example, the system shown in FIG. 27 includes a variable capacitor 22 that can be tuned to achieve resonance. Rather than providing a variable capacitor, in some embodiments, the capacitor can be of fixed value and a variable inductor can be included.

The system 10B may also include a device 24 for controlling heating within the interior coil 12, shown in FIG. 28. As seen in FIG. 28, the device 24, for example a resistor, is in electrical communication with the internal coil. In some embodiments, two electrical leads attached to the two-terminal resistor can be extended out from the intragastric device, thereby allowing a measurement to be taken. That is, the first terminal of the resistor can be in electrical communication with a first end of a first electrical lead, and the second terminal of the resistor can be in electrical communication with a first end of a second electrical lead. The second ends of the first and second electrical leads can extend outward, external to the intragastric device 14.

Figure 29:
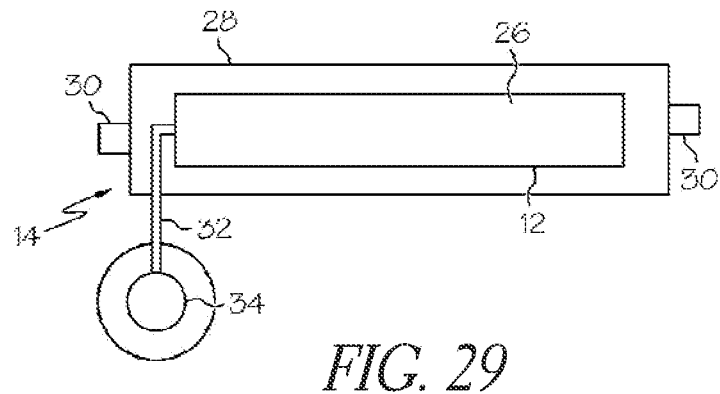
FIG. 29 depicts an embodiment of an intragastric device for use in the system of FIGS. 27-28, where the device has an internal coil, having an inflatable section a solid substrate, and placement tabs.

In at least one embodiment, the electrical leads are accessible via an access port on the patient's body, as seen in FIG. 29. FIG. 29 depicts the intragastric device 14 with internal coil 12, having an inflatable section 26, a solid substrate 28, and placement tabs 30. As seen, electrical leads 32 extend from the injection port 34 to the internal coil 12 to allow measurement of the current in the coil. In some embodiments, these leads can be conductively connected to the external circuit such that the external circuit includes the intragastric device 14 and its internal coil in the tuned circuit.

It should be noted that in the above-described embodiments, no battery or radiofrequency (RF) module is needed because the current in the intragastric device 14 is a result of induction.

The system may further include a computer 35B, depicted in FIG. 27, having software capable of performing calculations based on the current in the first coiled conductor and the resonant frequency in the external circuit in order to determine the size of the intragastric device 14. The derivations, calculations, and theory of operation of the system are presented below.

Figure 30A:
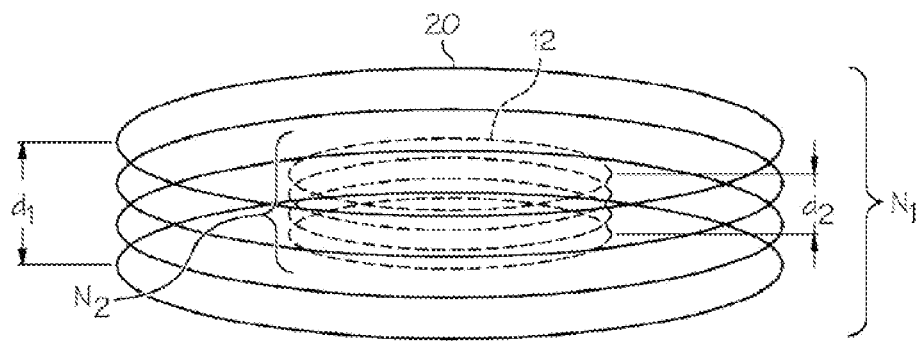
FIG. 30A depicts an embodiment of an ultrasound sensing mechanism using induction showing an inner coil and an outer coil placed concentrically and coaxially relative to one another.

Two embodiments of the present invention utilize induction to calculate the size, orientation or other characteristic of the intragastric device 14. The first embodiment using induction to be considered is when the inner coil and the outer coil are placed concentrically and coaxially relative one another, as shown schematically in FIG. 30A. Such an embodiment occurs when the external coil is placed around the patient's body such that the inner coil in or on the intragastric device 14 is concentric with the external coil. The number of turns N of each solenoid is equal to the number of turns per unit length (n)*the length (d) of the solenoid. So, the number of turns of the outer solenoid in FIG. 30A is given by the equation $N_1 = n_1 \cdot d_1$. It is assumed that the external coil is excited with the following current:

$$I = I_0 \sin \omega t, \quad (1)$$

where $\omega$ = the angular frequency of the current source and $I_0$ is the maximum current of the current source. Then, the magnetic field B for a relatively long coil is given by the relation:

$$B = \mu \cdot N_1 I_0 \cdot \sin(\omega \cdot t)/d_1, \quad (2)$$

where $N_1$ is the number of turns in the coil, and $d_1$ is the length of the coil. The magnetic flux from the larger external coil subtended by the intragastric device 14 is:

$$\Phi = A_2 \cdot B = A_2 \mu \cdot N_1 \cdot I_0 \sin(\omega \cdot t)/d_1, \quad (3)$$

where $\mu$ is the magnetic susceptibility of the material contained within the area $A_2$ of the inner coil, B is the magnetic field density, and $N_1$ is the number of turns in the coil. The electromotive force (emf) generated by coil 1 in coil 2 is given by the relation:

$$E = -d\Phi/dt = -A_2 \cdot B = A_2 \mu \cdot N_1 \cdot \omega_1 \cdot I_0 \cdot (\cos \omega t)/d_1 \quad (4)$$

The voltage induced in the entire intragastric device 14 is given by the relation:

$$E_T = N_2 \cdot E = -A_2 \mu \cdot N_1 \cdot N_2 \cdot \omega_1 \cdot I_0 \cos(\omega \cdot t)/d_1 \quad (5)$$

The self inductance (L) of a coil is defined as:

$$L = N \cdot \Phi/i = N \cdot A \cdot \mu \cdot N/1 = N^2 \cdot A \cdot \mu/d_1 \quad (6)$$

The self induced emf in the coil is then $$V = -L dI/dt = -\omega \cdot N^2 \cdot A \cdot \mu \cdot I_0 \cdot \cos(\omega t)/d_1 \quad (7)$$

The mutual inductance (M) of the two coils is defined as $$M_{21} = N_2 \cdot \Phi_{21} i_1, \quad (8)$$

where the current in coil 1 generates a flux in coil 2.

$$N_2 \cdot \Phi_{21} = N_2 \cdot B_1 \cdot \pi \cdot R_2^2, \quad (9)$$

and also $$N_2 \cdot \Phi_{21} = N_2 \cdot N_1 \cdot \pi \cdot \mu_0 \cdot R_{21}^2/2 \cdot R_1, \quad (10)$$

Thus the mutual inductance for the device and the external coil can be given by $$M_{21} = N_2 \cdot N_1 \cdot \pi \cdot \mu_0 \cdot R_{21}^2 / 2 \cdot R_1 \tag{11}$$

It should be noted that although the magnetic field generated by the larger coil is essentially constant through the smaller coil, this is not true of the field induced by the smaller coil in the larger. But the mutual inductance of the larger coil upon the smaller is equal to that of the smaller coil upon the larger.

Continuing with the derivation, the voltage of a circuit is the sum of the voltages resulting from the resistance (VR), capacitance (VC), and inductance (VL) such that $$V = V_R + V_C + V_L, \tag{12}$$

or as a function of time in integro-differential form, $$v(t) = I_1 \cdot R + L_1 \cdot dI_1/dt + 1/C \cdot \int I_1 \, dt, \tag{13}$$

or expressed completely as a differential equation (14):

$$\frac{1}{L_1} \cdot \frac{dv(t)}{dt} = \frac{d^2 I_1}{dt^2} + \frac{R}{L_1} \cdot \frac{dI_1}{dt} + \frac{1}{L_1 \cdot C} \cdot I_1. \tag{14}$$

If the variable frequency oscillator applies an excitation of $$v(t) = V_0 \sin(\omega t) \tag{15}$$

to the external coil and associated resistor and capacitor, then equation (14) can be written as $$\frac{V_0 \omega}{L_1} \cdot \frac{dv(t)}{dt} = \frac{d^2 I_1}{dt^2} + \left(\frac{1}{\tau_0}\right) \frac{dI_1}{dt} \cdot R + \omega_0^2 \cdot I_1, \text{ where} \tag{16}$$

$$\tau_0 = \frac{L_1}{R} \tag{17}$$

The tuned (or resonant) circuit including the external loop has a natural frequency given by:

$$\omega_n = \sqrt{1/(L \cdot C)} \tag{18}$$

The quality factor, or Q, of a resonant circuit is given by:

$$Q = \omega_n \cdot L/R = \sqrt{1/(L \cdot C)} \cdot L/R = 1/R \sqrt{L/C} \tag{19}$$

The bandwidth ($\omega 2-\omega 1$) of the frequency plot (i.e. the width at half maximum response as measured by the spectrum analyzer) is given by:

$$\omega_2 - \omega_1 = \omega_n/Q = R/L_1 = 1/\tau 0 \tag{20}$$

If the induced emf in the LAGB coil is known, then $$V = N_2 \cdot -A_2 \cdot B = A_2 \cdot \mu \cdot N_1 \cdot I_0 \cdot \omega / d_1 (\cos \omega t) \tag{21}$$

Considering the external tuned circuit without the LAGB included, then:

$$dV/dt = L \cdot d^2 I/dt^2 + R \cdot dI/dt + 1/C \cdot I, \tag{22}$$

which is the general equation for a series RLC circuit. So, $$1/L \cdot dV/dt = d^2 I/dt^2 + (1/\tau) \cdot dI/dt + \omega_0^2 \cdot I, \tag{23}$$

where $$\tau = L/R, \tag{24}$$

and $$\omega_n = \sqrt{1/(L \cdot C)} \tag{25}$$

The proportional half power frequencies are given by the relationship $$\Delta \omega_0 / \omega_n = 1/2Q = 1/\tau \cdot \omega) = R/L \sqrt{1/LC} = R \sqrt{C/L} \tag{26}$$

Now, an inductive circuit (which is a single conductive loop with no other resistance) is included in the external circuit that includes the intragastric device 14 or marker. If the external coil is circuit 1 and the intragastric device 14 or marker is circuit 2, then:

$$V_1 = L_1 \cdot d^2 I_1/dt^2 + M \cdot d^2 I_2/dt^2 + I_1 \cdot R_1 + 1/C \cdot \int I_1 \cdot dt \tag{27}$$

and because there is applied voltage in the device, and because the resistance is small in the device, $$V_2 = 0 = L_2 \cdot d^2 I_2/dt^2 + M \cdot d^2 I_1/dt^2 \tag{28}$$

Because we observe only the current parameters in the external coil circuit, the current in the LAGB can be eliminated, leaving:

$$d^2 I_2/dt^2 = -M/L_2 \cdot d^2 I_1/dt^2, \tag{29}$$

then substituting into equation (27) gives $$V_1 = L_1 \cdot d^2 I_1/dt^2 + M \cdot -M/L_2 \cdot d^2 I_1/dt^2 + I_1 \cdot R_1 + 1/C \cdot \int I_1 \cdot dt. \tag{30}$$

Taking the derivative of equation (30):

$$\frac{dV}{dt} = \left(\frac{(L_1 \cdot L_2 - M^2)}{L^2}\right) \cdot \frac{d^2 I}{dt^2} + R \cdot \frac{dI}{dt} + 1/C \cdot I, \tag{31}$$

which equals $$\frac{L_2}{(L_1 \cdot L_2 - M^2)} \cdot \frac{dV}{dt} = \tag{32}$$

$$\frac{d^2 I_1}{dt^2} + \frac{R \cdot L_2}{(L_1 \cdot L_2 - M^2)} \cdot \frac{dI_1}{dt} \cdot \frac{L_2}{C \cdot (L_1 \cdot L_2 - M^2)} \cdot I_1,$$

which equals $$L_2/(L_1 \cdot L_2 - M^2) \cdot dV/dt = d^2 I/dt^2 + (1/\tau) \cdot dI/dt + \omega_0^2 \cdot I. \tag{33}$$

The resonance frequency of the external coil changes in the presence of the LAGB, as does the bandwidth of the frequency, as shown below:

$$\omega_0^2 L_2/C \cdot (L_1 \cdot L_2 - M^2), \tag{34}$$

and where $$\tau = (L_1 \cdot L_2 - M^2)/R \cdot L_2 \tag{35}$$

Comparing the square of resonance frequency of the external coil in isolation and when concentric to the LAGB, the following ratio is obtained:

$$\frac{\omega_{no\_lap\_band}^2}{\omega_{lap\_band}^2} = \frac{\frac{1}{L_1} \cdot C}{\frac{L_2}{C \cdot (L_1 \cdot L_2 - M^2)}} \tag{36}$$

$$= \frac{(L_1 \cdot L_2 - M^2)}{(L_1 \cdot L_2)}$$

$$= 1 - \frac{M^2}{(L_1 \cdot L_2)}$$

where $\omega_{no\_lap\_band}$ is the natural frequency with no lap band or intragastric device 14 coil in the circuit and $\omega_{lap\_band}$ is the natural frequency with the lap band or intragastric device 14 coil in the circuit. Equation (36) assumes that the orientation of the external coil in relation to the LAGB is such that the resonance frequency is less in the presence of the LAGB. The ratio of the bandwidth is given by $$Q = \omega_n \cdot L/R = \sqrt{1/(L \cdot C)} \cdot L/R = 1/R \sqrt{L/C} \qquad (37)$$

The values of $L_1$, $L_2$, and M depend on the geometry of the coils. As stated above, the first embodiment is directed toward a configuration in which the inner coil and the outer coil are placed concentrically and coaxially, as in FIG. 4A. In such an embodiment, $$M = \pi \mu N_1 N_2 R_2^2 / 2R_1 = \mu N_1 N_2 A_2 / 2R_1, \qquad (38)$$

$$L_1 = N_1^2 \cdot A_1 \cdot \mu/d_1, \qquad (39)$$

and $$L_2 = N_2^2 \cdot A_2 \cdot \mu/d_2, \qquad (40)$$

where $R_1$ and $R_2$ are the radii of the two coils, $d_1$ and $d_2$ are the lengths of the two coils, and $A_1$ and $A_2$ are the respective areas enclosed by the coils.

Based on equations (38)-(40) for M, L1, L2, $$M^2/L_1 L_2 = \pi \cdot \mu^2 \cdot N_1^2 \cdot N_2^2 \cdot A_2^2 \cdot d_1 \cdot d_2 / 4 \cdot N_1^2 \cdot N_2^2 \cdot A_1^2 \cdot A_2 \cdot \mu^2 = \pi \cdot A_2 \cdot d_1 \cdot d_2 / 4 \cdot A_1^2 \qquad (41)$$

Substituting into equation (36) results in $$\frac{\omega_{no\_lap\_band}^2}{\omega_{lap\_band}^2} = \frac{\frac{1}{L \cdot C}}{\frac{L_2}{C \cdot (L_1 \cdot L_2 - M^2)}} \qquad (42)$$

$$= \frac{(L_1 \cdot L_2 - M^2)}{(L_1 \cdot L_2)}$$

$$= 1 - \frac{\pi \cdot A_2 \cdot d_1 \cdot d_2}{4 \cdot A_1^2}$$

Solving for the area A2 of the inner coil results in $$A_2 = \left(1 - \frac{\omega_{no\_lap\_band}^2}{\omega_{lap\_band}^2}\right) \cdot \left(\frac{4 \cdot A_1^2}{\pi \cdot d_1 \cdot d_2}\right) \qquad (43)$$

Figure 30B:
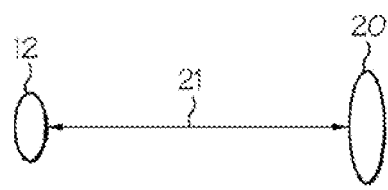
FIG. 30B depicts another embodiment of an ultrasound sensing mechanism using induction showing an inner coil and an outer coil placed in a coaxial non-concentric arrangement relative to one another.

The second embodiment using induction to be considered is when the inner coil 12 and the outer coil 20 are placed in a coaxial non-concentric arrangement relative to one another, as shown schematically in FIG. 30B. There is an impedance Z, shown at 21, between the coils. Such an embodiment occurs when the external coil is placed underneath or above, rather than around, the patient's body.

As stated earlier, the values of L1, L2, and M depend on the geometry of the coils. With the geometry of the second embodiment, namely of two coaxial non-concentric coils, L1, L2, and M are as follows:

$$M = \mu N_1 N_2 A_1 A_2 / 2\pi (R_1^2 + z^2)^{3/2}, \qquad (44)$$

and $$L_1 = N_1^2 \cdot A_1 \cdot \mu/d_1, \qquad (45)$$

and $$L_2 = N_2^2 \cdot A_2 \cdot \mu/d_2 \qquad (46)$$

Based on equations (44)-(46) for M, L1, L2, $$M^2/(L_1 \cdot L_2) = \mu^2 N_1^2 N_2^2 A_1^2 A_2^2 d_1 d_2 / 4_1 \pi^2 (R_1^2 + z^2)^3 N_1^2 N_2^2 A_1 A_2 \mu^2 = A_1 A_2 d_1 d_2 / 4\pi 2(R_1^2 + z^2)^3 \qquad (47)$$

Substituting into equation (36) results in $$\frac{\omega_{no\_lap\_band}^2}{\omega_{lap\_band}^2} = \frac{\frac{1}{L \cdot C}}{\frac{L_2}{C \cdot (L_1 \cdot L_2 - M^2)}} \qquad (48)$$

$$= \frac{(L_1 \cdot L_2 - M^2)}{(L_1 \cdot L_2)}$$

$$1 - \frac{A_1 A_2 d_1 d_2}{4\pi^2 (R_1^2 + z^2)^3}$$

Solving for the area A2 of the inner coil results in $$A_2 = \left(1 - \frac{\omega_{no\_lap\_band}^2}{\omega_{lap\_band}^2}\right) \cdot \left(\frac{4\pi^2 (R_1^2 + z^2)^3}{A_1 d_1 d_2}\right) \qquad (49)$$

The area of the concentric coaxial embodiment of equation (43) and the non-concentric coaxial embodiment of equation (49) can be summarized with the following equation:

$$A_2 = k \cdot \left(1 - \frac{\omega_{no\_lap\_band}^2}{\omega_{lap\_band}^2}\right), \qquad (50)$$

where k depends on the geometry of the coils. Thus, the area is proportional to the absolute value of one minus the ratio of the squares of the maximum resonant frequencies, as measured by the spectrum analyzer.

$$\Delta\omega_0/\omega_n = 1/2Q = 1/\tau \cdot \omega \qquad (51)$$

Thus, the change in resonance frequency peak and the change in bandwidth can both be used to determine the product of the area and the magnetic susceptibility of the intragastric device 14 or marker. In both embodiments of the induction method, the external coil can be adjusted in both height and orientation relative to the device coil to give maximum resonance frequency variation from isolation to insure proper relative position. The use of high magnetic susceptibility fluid in the device or marker ensures that only the device or marker area is measured rather than include the stomach tissue.

As stated earlier, the system may include a computer for calculating the area of the intragastric device 14 or marker. A person of ordinary skill in the art would readily understand how to write software that calculates the area of the inner coil, as presented in equations (43) and (49) above, based on the foregoing.

Figure 31A:
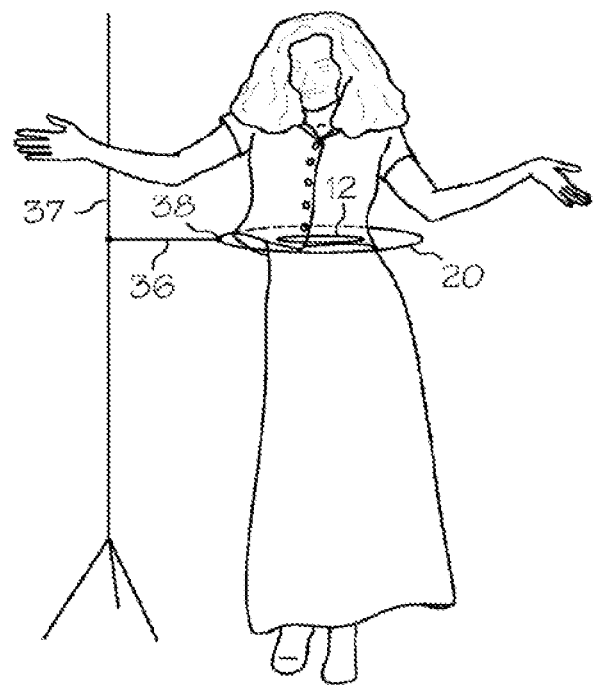
FIG. 31A depicts an embodiment of a coil holder that may use the concentric, coaxial induction sensing mechanism of FIG. 30A.

In order to adjust the external coil to produce a maximum resonance frequency, some embodiments of the present invention include a coil holder to which the external coil is secured. Referring now to FIG. 31A, one embodiment of a coil holder for a concentric, coaxial induction embodiment is shown. The coil holder is used for orienting the external coil with the internal coil. Because the above calculations are based on the orientation between the two coils, using a coil holder can simplify the setup of the system by making stationary the external coil. As seen in FIG. 31A, the coil holder 36 can simply be an arm moveably engaged to a vertical mount 37. It is important that the coil holder 36 can be raised and lowered vertically. It is also important that the coil holder 36 can be tilted, for example about a point 38 on the coil holder. In this manner, the external coil 20 can be placed concentrically and coaxially about the internal coil 12 within the patient. There are numerous other possible embodiments of the coil holder.

Figure 31B:
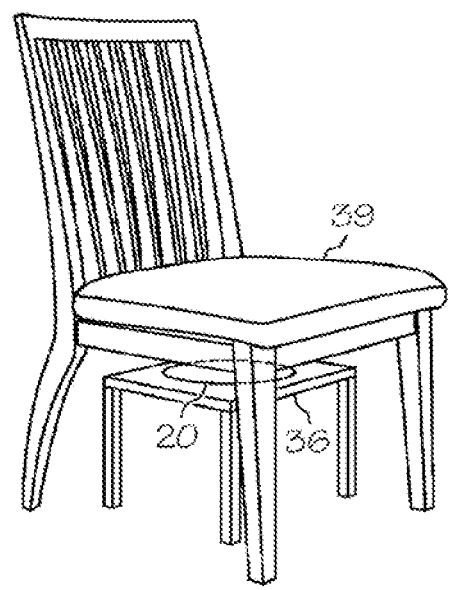
FIG. 31B depicts an embodiment of a coil holder that may use the non-concentric, coaxial induction sensing mechanism of FIG. 30B.

Referring now to FIG. 31B, another embodiment of a coil holder is shown. Specifically, FIG. 31B depicts a coil holder for a non-concentric, coaxial induction embodiment. As seen in FIG. 31B, the coil holder 36 can simply be a small table-like device placed under the seat of a chair 39. It is important that the coil holder 36 can be tilted, as before, thereby allowing the external coil 20 to be aligned with the internal coil within the patient to align. In such an embodiment, the patient sits down on a chair 39 and the coil holder 36 underneath the chair is oriented until the resonant frequency is achieved. There are numerous other possible embodiments of the coil holder. In some embodiments, the coil may be placed above the patient, rather than underneath (not depicted).

Figure 32:
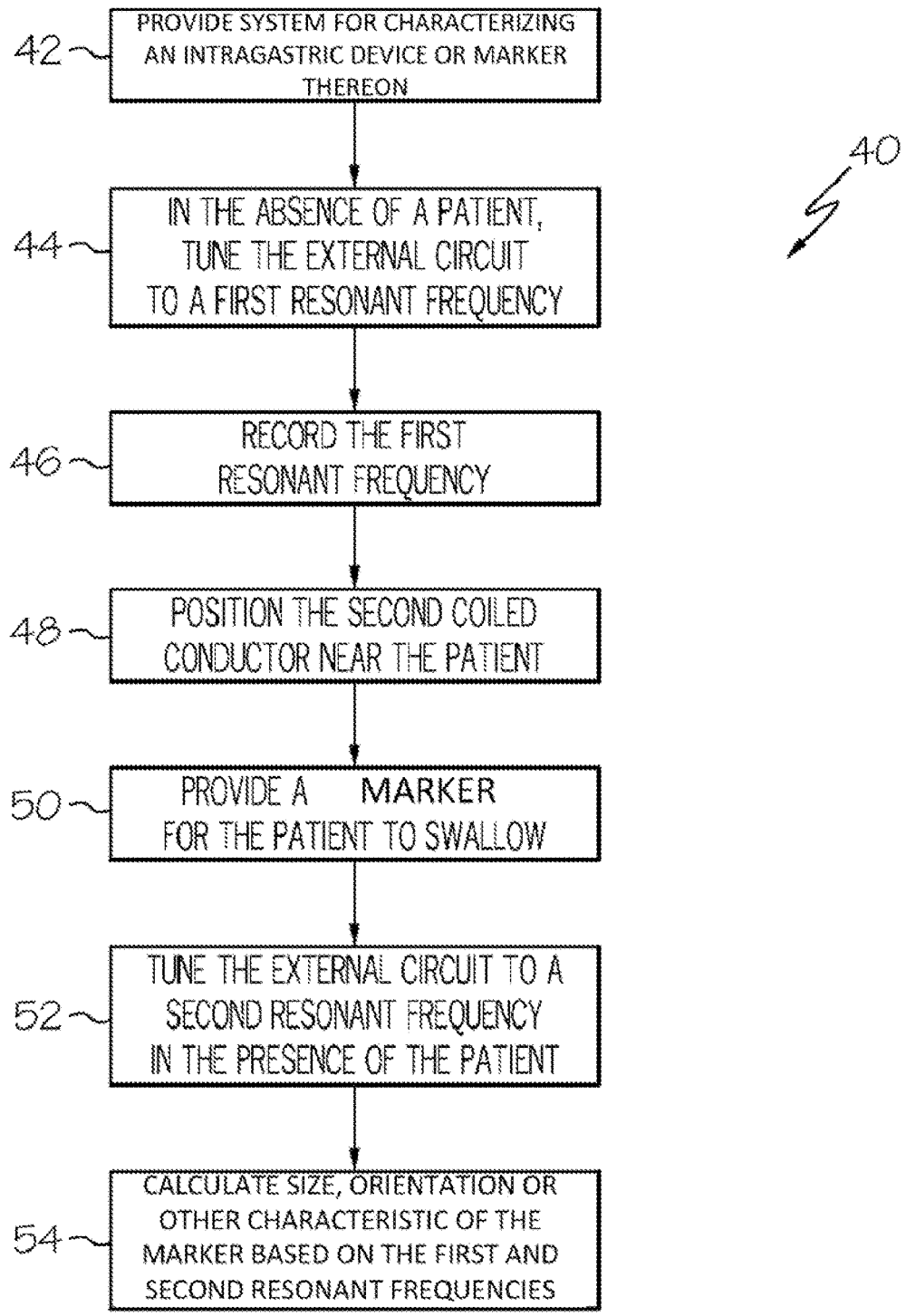
FIG. 32 depicts an embodiment of an ultrasound method for characterizing an intragastric device or marker thereon.

Referring now to FIG. 32, a method 40 of characterizing an intragastric device or marker thereon is shown, in accordance with at least one embodiment of the present invention. The method 40 includes the step 42 of providing a system for characterizing an intragastric device or marker thereon. Embodiments of such a system are described above. The method further includes the step 44 of tuning the circuit external to the device or marker to a first resonant frequency in the absence of a patient. This allows the practitioner to tune and measure the circuit without the effects of the coil in the marker. The first resonant frequency measured is recorded in step 46 of the method. The method further includes the step 48 of positioning the external coil near the patient. As described above, the external coil can be placed near the patient in two ways: concentrically and coaxially, and non-concentrically and coaxially. The coil is either placed around the patient at the approximate level of the device or marker, or underneath the patient. The method further includes the step 50 of providing a marker for the patient to swallow.

The measured characteristic of the device, such as the area, is based on the spike that occurs in the resonant frequency after the patient has swallowed the marker. The marker can be water with a solution of non-toxic paramagnetic material such as magnetic resonance imaging (MRI) contrast material. In some embodiments, the marker can simply be water. In many cases, the method is sensitive enough to detect the device or marker size or other characteristic without ingesting of the MRI contrast material or with a very dilute concentration. The method further includes the step 52 of tuning the circuit external to the device or marker to a second resonant frequency in the presence of the patient. In some embodiments of the method, the external coil can be moved so as to obtain the greatest change in resonance frequency of the external circuit. For example, the external coil can be moved up and down, side to side, and can be tilted so that it is aligned with the internal coil. Finally, the method includes the step 54 of calculating the size, orientation or other characteristic of the marker or device based on the difference between the first resonant frequency and the second resonant frequency. From the change of resonance frequency of the external tuned circuit, the area of the device or marker is calculated, knowing the magnetic susceptibility of the MRI contrast material.

Figure 33A:
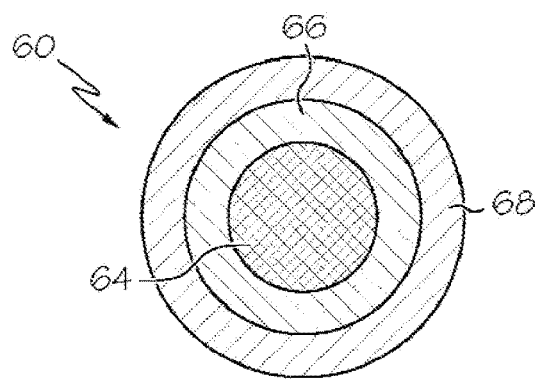
FIG. 33A is a top view of an embodiment of a system for equipment verification using a gastric magnetic susceptibility phantom.

Referring now to FIGS. 33A-36, a setup and method of equipment verification using a gastric magnetic susceptibility phantom. FIG. 33A depicts a top view of the basic setup of the phantom for equipment verification. The setup includes a peristaltic pump 60 with longitudinal axis 63 (shown in FIG. 33B), with a lumen 64, tissue 66, and three test laparoscopically adjustable gastric markers 68, such as gastric bands. It should be noted that more markers 68 could be used, depending on the accuracy desired.

Figure 33B:
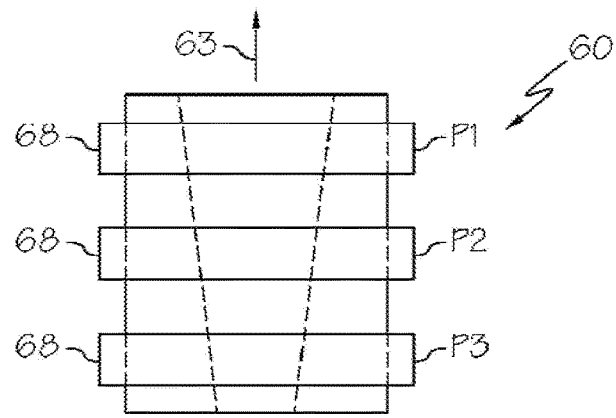
FIG. 33B is a side view of the system of FIG. 33A.

The peristaltic pump is filled with a magnetic contrast material and the pump is set to a speed consistent with the speed of human swallowing. As shown in FIG. 33B, a side view of the embodiment shown in FIG. 33A, the test laparoscopically adjustable gastric markers are positioned about the pump 60 at three positions, P1, P2, and P3. The first, second, and third markers are offset from one another along the longitudinal axis 63 of the pump.

Figure 34:
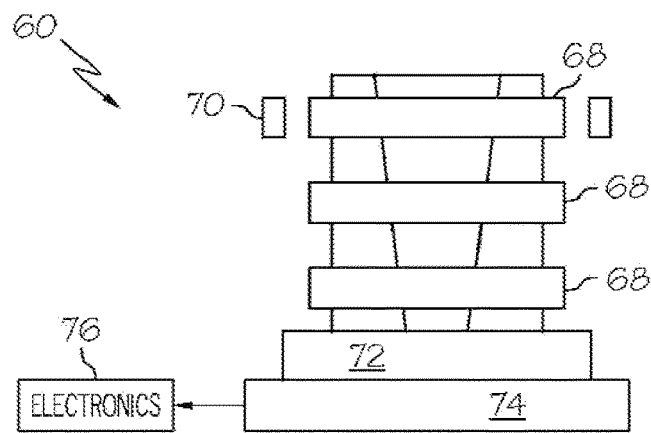
FIG. 34 is a side view of another embodiment of a system for equipment verification using a gastric magnetic susceptibility phantom showing movement of an adjustable outer coil.

Referring now to FIG. 34, the adjustable outer coil 70 is moved such that it is positioned about the markers 68. The resonance frequency of each of the markers 68 positioned about the pump is measured. The resonance frequencies are measured while the magnetic material passes through the phantom into the receptor 72 and back through the pump again. The values of the resonance frequencies are detected by the pickup coil 74 and transmitted to external electronics 76 for further calculations. The maximum deviation of the resonance frequency is determined from a spectrum analyzer.

Figure 35:
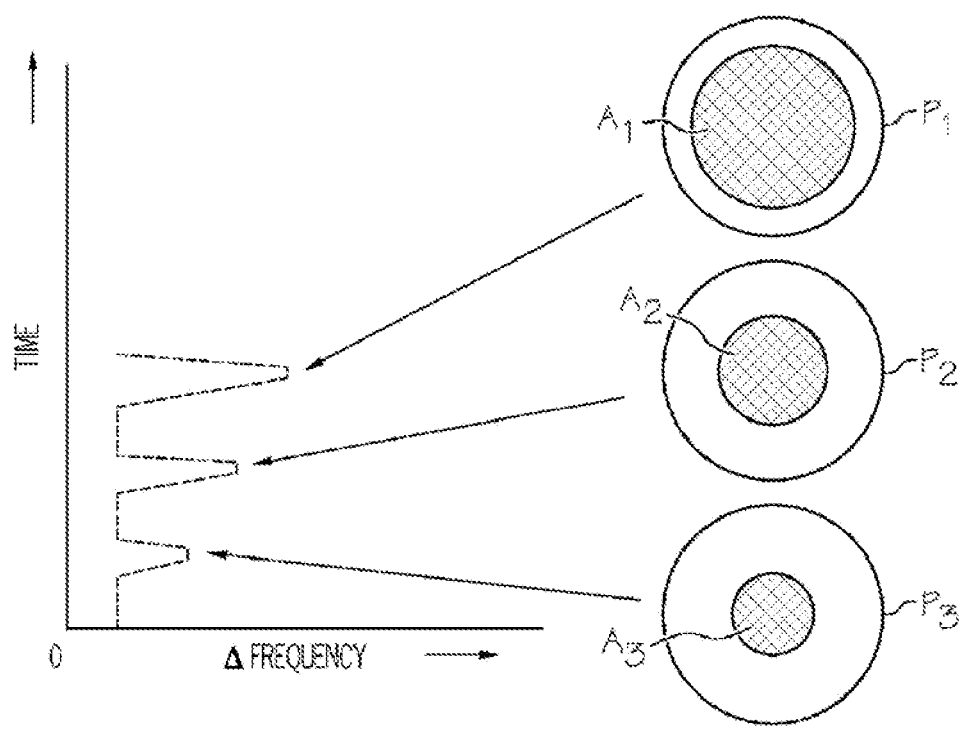
FIG. 35 is graph showing display of frequency data measured with the systems of FIGS. 33-34.

The above technique does not give an image of the intragastric device or surrounding anatomy inside the body. However, the data collected can be displayed graphically, as shown in FIG. 35. As seen in FIG. 35, the change in frequency can be graphically correlated to geometric characteristics, such as areas A1, A2, and A3 of the markers placed at positions P1, P2, and P3, respectively. As such, a practitioner can be assured that the external coil is working properly by comparing known good values of the A1, A2, and A3 versus the values that were measured during the verification procedure.

It should be noted that the external frequency generating apparatus described earlier can be modified to scan across the gastric lumen using appropriate radiofrequency excitation, thereby mimicking a rudimentary flow sensing magnetic resonance imaging apparatus. Such an apparatus would provide an image, using appropriate frequency domain software.

Figure 36:
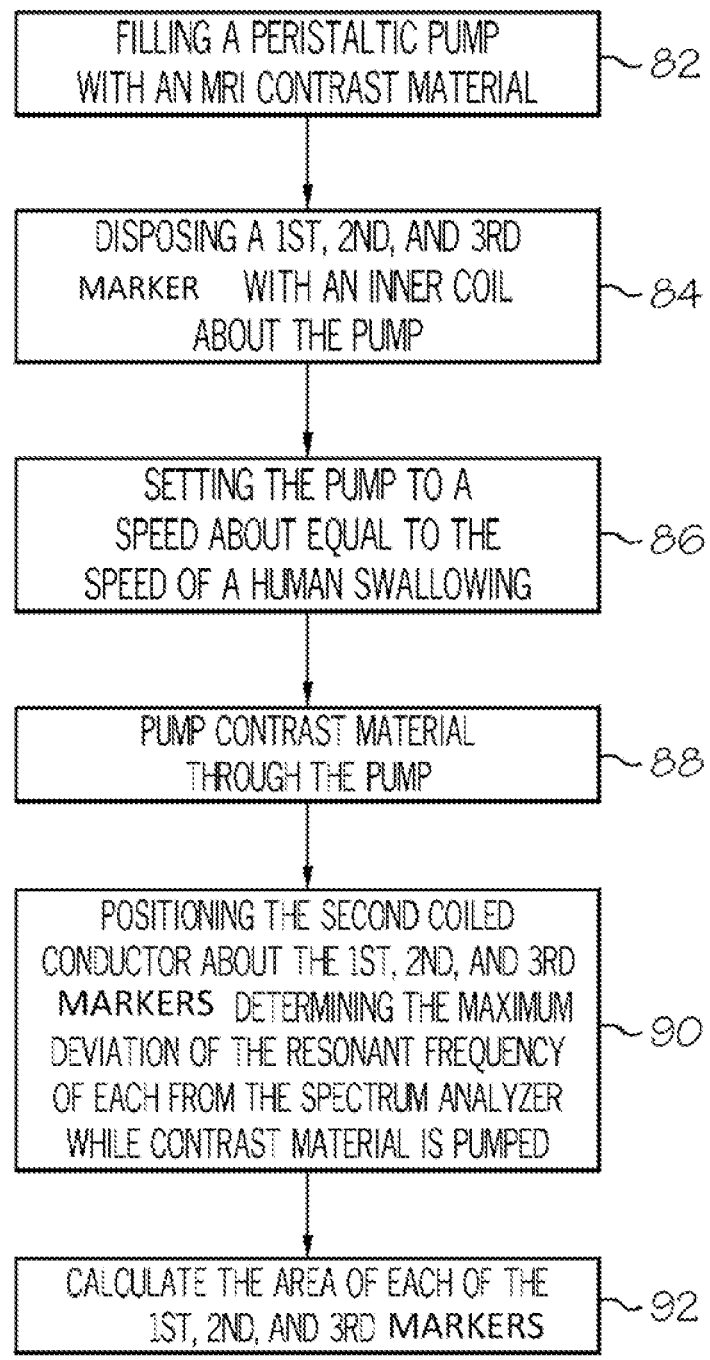
FIG. 36 is a flowchart showing an embodiment of a method for determining the size of a gastric lumen using the systems of FIGS. 33-34.

The method of determining the size of a gastric lumen using a gastric magnetic susceptibility phantom is shown in FIG. 36. The method includes the step 82 of filling a peristaltic pump with water or a water solution containing a magnetic resonance imaging contrast material. The method further includes the step 84 of disposing a first, second, and third marker or device, as described earlier with an internal coil, about the peristaltic pump. The first, second, and third markers are offset from one another along the longitudinal axis of the pump. The method further includes the step 86 of setting the pump to a speed approximately equal to the speed of human swallowing. The method further includes the step 88 of pumping the contrast material through the pump. The method further includes the step 90 of positioning the external coil 70 of FIG. 34 about the first, second, and third markers in turn and determining the maximum deviation of the resonant frequency of the each of the first, second, and third markers from the spectrum analyzer while contrast material is pumped through the pump. The method further includes the step 92 of calculating the area of each of the first, second, and third markers based on their resonant frequencies.

It should be noted that the steps in the method described in FIG. 36 need not be performed in the order shown, and as such, the method should not be limited to a particular order. Rather, a person of ordinary skill in the art will recognize that the method will perform equally well if, for example, the pump is set to a certain speed prior to filling it with the water solution.

Figure 37:
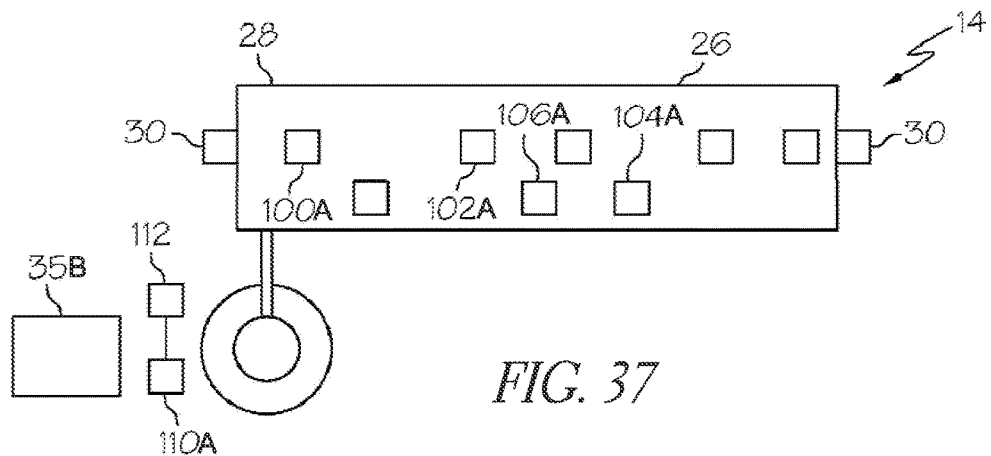
FIG. 37 depicts an embodiment of a system for characterizing an intragastric device, the system having two ultrasonic modules placed in the device that allow the system to measure the size and composition of the marker and/or device using time of flight ultrasound technology.

Referring now to FIGS. 37-40, a system for characterizing an intragastric device, such as measuring the the size of the device, is illustrated in accordance with at least one embodiment of the present invention. FIG. 37 is similar to FIG. 29. However, instead of an internal coil, the embodiment depicted in FIG. 37 has two ultrasonic modules placed in the device that allow the system to measure the size and composition of the marker and/or device using time of flight ultrasound technology.

The time between transmission of the ultrasonic pulse and reception of the echo is given by:

$$t = 2 \cdot d/U, \quad (52)$$

or $$d = U \cdot t/2, \quad (53)$$

where U is the speed of sound in the medium, typically water, and d is the diameter of the device or marker of interest.

If the speed of sound is known, a dimension can be computed from the time between transmission and reception. If transmission occurs in two orthogonal directions, two dimensions of the marker can be determined, and thus the area of the marker can be computed. Assuming the lumen is an ellipse, the equation for the area of an ellipse using the major (a) and minor (b) axes is as follows:

$$A = \pi \cdot a \cdot b = (\pi \cdot U^2 \cdot t_1 \cdot t_2)/16 \quad (54)$$

The marker may be differentiated from the gastric tissue by instructing the patient to drink water, thus flushing the gastric area. If the marker is clear, a clear echo signal is obtained and the time of flight of the ultrasound pulse is obtained in the clear area to determine marker area.

To detect the presence of persistent solid mater, two methods are used. First, the orthogonal signal, that is the amplitude of the scattered ultrasonic pulse in the orthogonal direction, is compared with the original pulse echo return. And second, the amount of false return in the original pulse echo may even determine the ratio of solid to liquid matter in the cross section of the area encompassed by the marker.

Referring now to FIG. 37, the intragastric device 14 includes two orthogonal ultrasonic transmitter/receiver ("transceiver) modules 100A, 102A. Transceiver 100A is an anterior/posterior (a/p) ultrasonic module, and transceiver 102A is a lateral ultrasonic module.

The device 14 further includes a microprocessor 104A that measures the time of flight from each transceiver module. The microprocessor is capable of distinguishing between tissue echoes and an empty marker. The microprocessor is also capable of preparing a signal for transmission. The microprocessor is in electrical communication with a computer 105. In some embodiments, the computer and the microprocessor are incorporated into the same component. In at least one embodiment, the computer may be a look up table, capable of determining the semi-major axis, the semi-minor axis, and the scatter associated with the lumen.

The intragastric device 14 also includes a transmitter 106A capable of transmitting the signals from the marker to a location outside of the body. The transmitter 106A can include an antenna for transmission, or an antenna in the band (not shown) can be in electrical communication with the transmitter. The device 14 also includes a module 108A either containing a battery or capable of powering the laparoscopically adjustable gastric band electronics inductively.

External to the patient is an antenna 110A for receiving the transmitted signals and a receiver 112 in operative communication with the antenna. As before, a computer 35B may be included that has software capable of decoding and processing the signals transmitted by the transmitter 106A and received by the receiver 112. The computer software is capable of measuring the time of flight of horizontal and vertical ultrasonic pulses to determine the length and width of the device 14 and/or marker, and combining the length and width to find the area. It should be noted that from the scatter of the horizontal into the vertical receiver and the scatter of the vertical into the horizontal receiver, the material in the area of interest can be determined.

Figure 38:
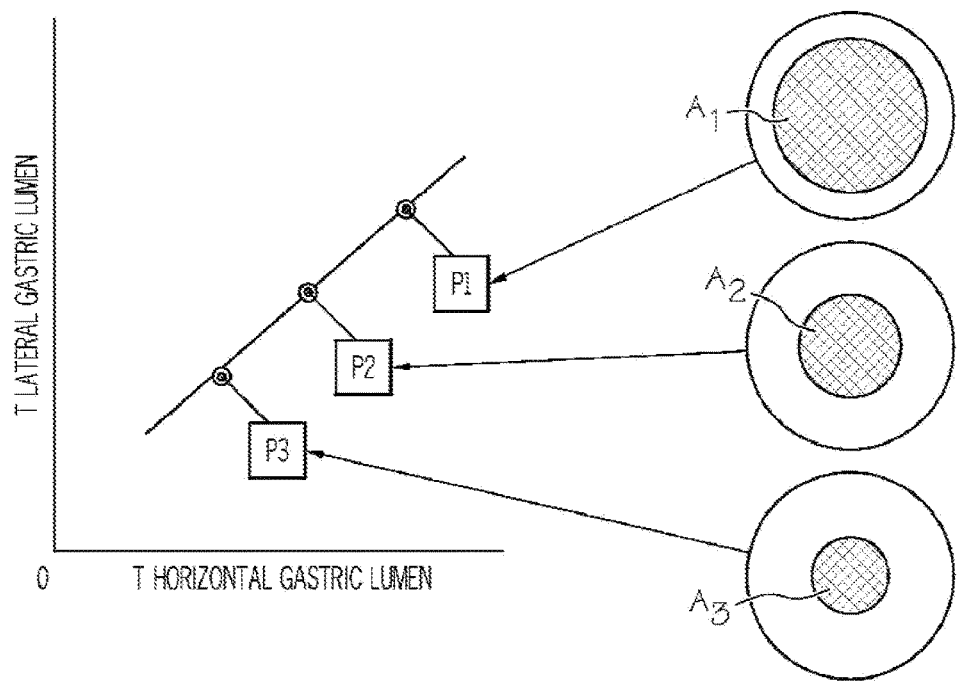
FIG. 38 is graph showing display of data measured with the system of FIG. 37.

The ultrasonic system can be calibrated in a manner similar to that described above with regards to FIGS. 33A-34. The above technique does not give an image of the device 14 or marker or internal anatomy. However, the data collected can be displayed in a graphical manner, as shown in FIG. 38. As seen in FIG. 38, the lateral and horizontal times of flight can be graphically correlated to the areas A1, A2, and A3 of the marker or device 14 placed at positions P1, P2, and P3, respectively.

In some embodiments, the device 14 or marker has an inner side and an outer side where the inner side is closer to the gastric lumen than the outer side, and the two ultrasonic modules are positioned on the outer side of the device, as in FIG. 37.

Figure 39:
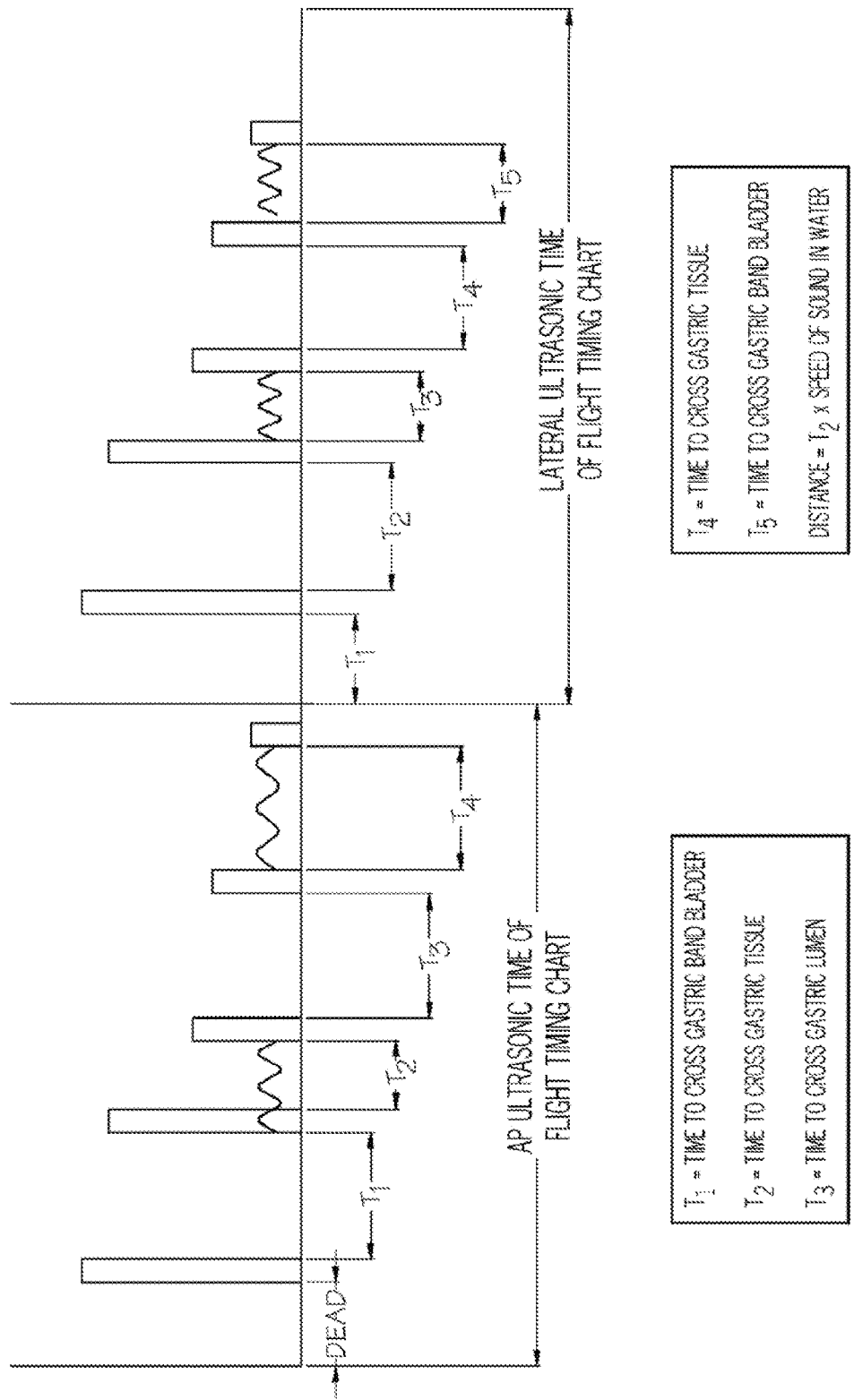
FIG. 39 depicts an embodiment of a pulse timing diagram depicting the time of flight using ultrasonic modules.

FIG. 39 depicts a pulse timing diagram depicting the time of flight using ultrasonic modules. Here, it is assumed that the device 14 or marker is a gastric band about a lumen. As seen in FIG. 39, the time of flight can be determined based on the time to cross the gastric band bladder, the time to cross the gastric tissue, and the time to cross the gastric lumen.

Figure 40:
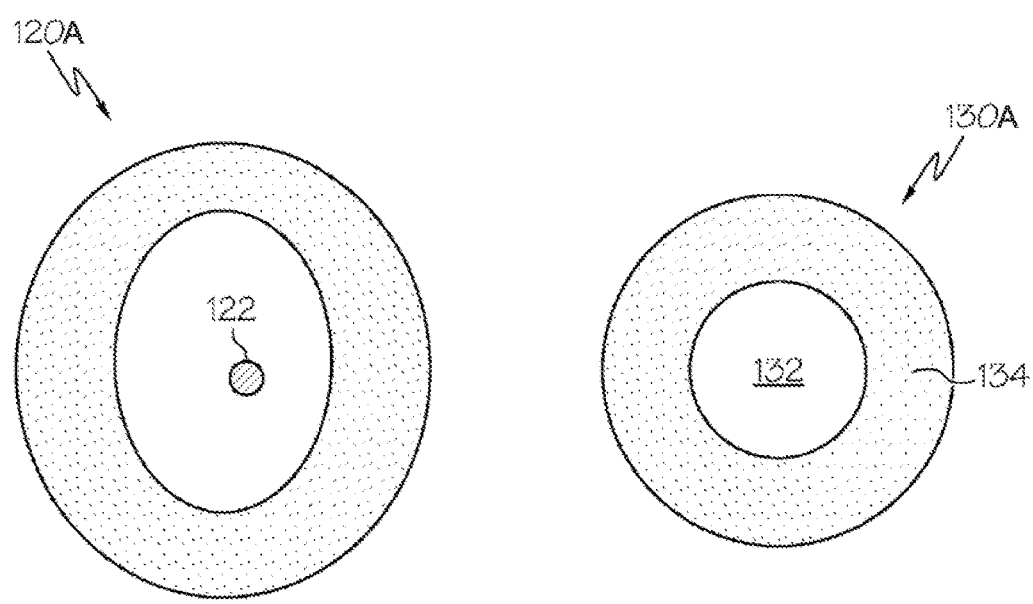
FIG. 40 shows embodiments of graphical representations of data collected with ultrasonic systems and induction systems of the present disclosure.

FIG. 40 is a graphical representation of the data collected for both the ultrasonic embodiment 120A and the induction embodiment 130A. The ultrasonic embodiment 120A is able to detect any solid mass 122 within the lumen. In the induction embodiment 130A, the area 132 from the induction embodiment is depicted as well as the area 134 from the adjustable gastric band tab circumference minus the area from the induction area.

In some embodiments the ultrasound marker is a liquid, solid, or combination thereof. The various materials may be contained in a sac in or on the intragastric device. The properties of the liquid may be tuned such that the acoustic signature is easily identified.

The above techniques may be used with an ultrasound marker and applied to the volume-occupying subcomponent when the volume-occupying subcomponent is in a creased or folded state such that when the volume-occupying subcomponent is in its deflated state the marker has a characteristic ultrasound visualization or signature, and when the volume-occupying subcomponent is inflated the marker has another characteristic ultrasound visualization or signature. Alternatively, the ultrasound marker may be applied or incorporated into the volume-occupying subcomponent so as to facilitate identification and location of the various subcomponents of the device, such as a valve, head, or weight. The ultrasound marker may be printed or painted onto a surface of the volume-occupying subcomponent or between layers of the material forming the volume-occupying subcomponent. Alternatively, an acoustically-responsive coating may be used as an ultrasound marker to assist with identifying and/or locating the volume-occupying subcomponent. Alternatively, the ultrasound marker may be applied to an elastomeric sleeve that covers all or part of the volume-occupying subcomponent.

In another embodiment, the volume-occupying subcomponent incorporates a subcomponent that changes mechanically upon inflation of the volume-occupying subcomponent, which mechanical change can be determined using the ultrasound visualization equipment. For example, a mechanical portion of the volume-occupying subcomponent containing an ultrasound visualization marker may elongate upon an increase in pressure in the volume-occupying subcomponent.

Alternatively, an ultrasound marker may be formed using a mesh, for example a metallic mesh, located between layers of the material from which the volume-occupying subcomponent is constructed. The pattern or patterns formed by the imbedded ultrasound marker will appear when the volume-occupying subcomponent is in an inflated, deployed state.

In some embodiments, an ultrasound sensor comprises a non-contact sensor. An ultrasonic level or sensor or sensing system requires no contact with the target. In the medical industries this is an advantage over inline sensors that may contaminate or otherwise interfere with the marker or item of interest. In some embodiments, the sensor is a microphone.

In some embodiments, a pulsed wave system is used. The principle behind a pulsed-ultrasonic technology is that the transmit signal consists of short bursts of ultrasonic energy. After each burst, the sensor electronics looks for a return signal within a small window of time corresponding to the time it takes for the energy to pass through the medium of interest. Only a signal received during this window will qualify for additional signal processing. In some embodiments a continuous wave system is used. In the pulsed, continuous, or other wave systems, the sensor may be a microphone that receives the return wave signal.

In some embodiments, a marker may transmit ultrasound signals. For instance, Ultrasound Identification (USID) may be used to automatically track and identify the location of intragastric devices in real time using simple, inexpensive nodes (badges/tags) attached to or embedded in the ultrasound devices, which then transmit an ultrasound signal to communicate their location to ultrasound sensors, such as microphones.

A computing system may be implemented in the ultrasound locating system. The computing system comprises hardware and software that receives data from the ultrasound sensor and calculates information related to the location, orientation, and/or state of an intragastric device according to certain algorithms. In some embodiments, the hardware may comprise a central processing unit, memory, an analog to digital converter, analog circuitry, a display. In some embodiments, the software proceeds through a number of steps including calibration, initialization, prediction, estimation, measuring magnetic sensor data, calculating various desired outputs including location, orientation, size, configuration, etc. in accordance with the techniques discussed herein.

The processor's output relating to the location, orientation and/or state of an intragastric device may be communicated to a user in a number of manners. In some embodiments, the output is shown visually on a display.

In some embodiments, the processor's output related to an intragastric device's location, orientation, and/or state is audibly communicated to a user through a speaker.

In some embodiments, the processor's output related to an intragastric device's location, orientation, and/or state is communicated to a user through a combination of methods. For instance, the system may employ a visual graphical display with audible alerts sent through speakers.

In some embodiments, the ultrasound locating system is calibrated before use. The ultrasound marker and the sensor are positioned in pre-planned locations and orientations to verify the output signal is within an expected range. In some embodiments, the ultrasound locating systems are calibrated or otherwise verified using a human patient simulator, or dummy, to test the ultrasound locating system as a ultrasound marker travels through the simulator. In some embodiments, the ultrasound locating system is checked for stray signals from nearby acoustic interferences.

The ultrasound sensor may be used in conjunction with the marker or markers in a variety of embodiments to locate or otherwise characterize an ingested intragastric device. In some embodiments, an off-the-shelf intragastric device, such as a swallowable, inflatable balloon, may be used without modification with any ultrasound markers. With that device, an ultrasound sensor that pulses sound waves and senses their return signal with a microphone may be used outside the body. The device could be swallowed in a deflated state and would then inflate once inside the stomach. The ultrasound sensor may be used to locate or otherwise characterize the device by pulsing the device and receiving the return signals, in accordance with the techniques discussed above.

The devices once ingested may be located using the ultrasound intragastric locating system. In some embodiments, the sensor may locate the device by pulsing in various locations and analyzing the return signal. For instance, a return signal corresponding to a body organ without the device may be pre-determined by correlating a return wave signal to a location on the body before the device is swallowed. This could produce an ultrasound map of the organ or body without any device. Then, after swallowing the device, and by running the sensor over the body, if a different signal is returned for a corresponding location in the body, then the location of the device is thus identified. This may be implemented in accordance with the techniques discussed above.

The orientation of the devices once ingested may be ascertained using the ultrasound intragastric locating system. In some embodiments, the sensor may identify the orientation of the intragastric device by pulsing and sensing at various locations of the device and analyzing the return signals. For instance, before ingestion by a patient, the device may be pulsed at various orientations such that a pre-determined database exists of known correlations between return wave signatures and orientation of the device. This may be done for the device in the deflated, inflated, or other states. Then, after ingestion, the device may be pulsed and the return signals compared to the pre-determined database to determine the orientation of the device in accordance with the techniques discussed above.

Further, the various sizes and configurations of the devices once ingested may be characterized using the ultrasound intragastric locating system in accordance with the techniques discussed above. For instance, inflation of a balloon, or the inflation or configuration of multiple balloons, may be characterized and assessed. In some embodiments, the sensor may characterize the device or devices by pulsing and sensing at various locations of the device and analyzing the return signals. For instance, the deflated device would return a different pulsed signature than the inflated device. In such a manner, the device may be characterized as either inflated, deflated, or in some other state. The inflated device could further be characterized before ingestion by a patient such that the return signal signature is pre-determined and serves as a guidepost for assessing the state of the device. In some embodiments, the ultrasound locating system may be used in conjunction with a deflating system to characterize the deflation process.

The timing and other attributes of the various methods of administration can be characterized using the disclosed ultrasound intragastric locating system and techniques. Whether the device is administered using endoscopic techniques or orally, the progress of the device as it makes its way to the stomach can be tracked with the ultrasound locating system. For instance, the effects of swallowing the device with hard gelatin or water or other consumables may be characterized by tracking the location and orientation as it is ingested.

In some embodiments, the ultrasound locating system may characterize an intragastric device that has a circular or elliptical cross-section. Two ultrasonic modules placed in the device allow the system to measure the size and composition of the device using time of flight ultrasound technology.

Using the speed of sound, a distance can be computed from the time between transmission and reception. The time between transmission of the ultrasonic pulse and reception of the echo is given by: $t=2d/U$, or $d=Ut/2$, (53) where U is the speed of sound in the medium of interest, and d is the diameter of the device. If transmission occurs in two orthogonal directions, two dimensions of the intragastric device can be determined, and thus the area of the device can be computed. Assuming the device is an ellipse, the equation for the area of an ellipse using the major (a) and minor (b) axes is as follows:

$$A = \pi \cdot a \cdot b = (\pi \cdot U^2 \cdot t_1 \cdot t_2)/16$$

If the interior of an inflated device is clear, a clear echo signal is obtained and the time of flight of the ultrasound pulse is obtained in the clear area to determine device area. To detect the presence of matter, foreign or otherwise, in the device, two methods may be used. First, the orthogonal signal, that is the amplitude of the scattered ultrasonic pulse in the orthogonal direction, is compared with the original pulse echo return. And second, the amount of false return in the original pulse echo may even determine the ratio of solid to liquid matter in the analyzed cross section of the device.

The intragastric device may include two orthogonal ultrasonic transmitter/receiver ("transceiver") modules. One transceiver is an anterior/posterior (a/p) ultrasonic module, and the other transceiver is a lateral ultrasonic module. The device further includes a microprocessor that measures the time of flight from each transceiver module. The microprocessor is capable of distinguishing between device echoes and the empty device interior. The microprocessor is also capable of preparing a signal for transmission. The microprocessor is in electrical communication with a computer. In some embodiments, the computer and the microprocessor are incorporated into the same component. In at least one embodiment, the computer may be a look up table, capable of determining the semi-major axis, the semi-minor axis, and the scatter associated with the device.

The intragastric device may also include a transmitter capable of transmitting the signals from the device to a location outside of the body. The transmitter can include an antenna for transmission, or an antenna in the band (not shown) can be in electrical communication with the transmitter. The device may also include a module either containing a battery or capable of powering the intragastric device electronics inductively. External to the patient may be an antenna for receiving the transmitted signals and a receiver in operative communication with the antenna. A computer may be included that has software capable of decoding and processing the signals transmitted by the transmitter and received by the receiver. The computer software is capable of measuring the time of flight of horizontal and vertical ultrasonic pulses to determine the length and width of the intragastric device, and combining the length and width to find the area. It should be noted that from the scatter of the horizontal into the vertical receiver and the scatter of the vertical into the horizontal receiver, the presence of any material in the device can be determined.

In some embodiments, the ultrasonic system can be calibrated. The data collected can be displayed in a graphical manner with the lateral and horizontal times of flight graphically correlated to various areas of the intragastric devices.

In some embodiments, the intragastric device has an inner side and an outer side where the inner side being closer to the intragastric device interior than the outer side, the two ultrasonic modules being positioned on the outer side of the intragastric device. The time of flight can be determined based on the time to cross the intragastric device.

Voltaic Tracking and Visualization Subcomponent

Tracking and visualization functionality can be incorporated into devices and systems described above. As used herein, "visualization" is used broadly to refer to identifying an item of interest in the body in a number of ways, including by providing a sensor or marker to produce a voltage in response to the gastric environment encountered by the voltage sensor or marker. Due to the non-invasive nature of the present device, physicians may desire to determine, or confirm, the location and orientation of the device prior to inflation, during the course of treatment, or after deflation. Accordingly, intragastric devices are provided that incorporate voltaic sensing components configured for enabling determining and confirming the location, orientation and/or state of an intragastric device at all phases of administration.

In some embodiments, a voltaic tracking and visualization subcomponent may be implemented in other embodiments described herein. For example, as described above, FIG. 10C depicts an embodiment of a voltage sensor that may be implemented with the catheter of FIG. 10A. This is merely one example and other embodiments may implement a voltaic sensor as well. Certain voltaic sensor embodiments are described below which may be implemented in or with the sensor of FIG. 10C or other systems described herein.

In some embodiments, an ingestible event marker (i.e., an IEM) and/or a personal signal receiver are implemented with an intragastric device. Embodiments of the IEM include an identifier, which may or may not be present in a physiologically acceptable carrier. The identifier is characterized by being activated upon contact with a target internal physiological site of a body (e.g., a specific target environment, including a target chemical environment, target physical environment etc.), such as digestive tract internal target site, including the stomach. The personal signal receiver is configured to be associated with a physiological location, e.g., inside of or on the body, and to receive a signal from the IEM. During use, the IEM broadcasts or otherwise communicates a signal which is received by the personal signal receiver and which may be indicative of the location of the sensor. For instance, the signal generated ma be indicative of the voltaic sensor being located in the stomach. Where desired, the signal receiver performs one or more subsequent operations, such as relaying the signal to a third external device, recording the signal, processing the recorded signal with additional data points, etc.

Embodiments include ingestible event marker compositions having an identifier stably associated therewith. The identifier of the IEM compositions is one that generates (i.e., emits) a detectable signal upon contact of the identifier with a target physiological sight. The identifiers of the present compositions may vary depending on the particular embodiment and intended application of the composition so long as they are activated (i.e., turned on) upon contact with a target physiological location, e.g., stomach. As such, the identifier may be an identifier that emits a signal when it contacts a target body (i.e., physiological) site. The identifier may be any component or device that is capable of providing a detectable signal following activation, e.g., upon contact with the target site. In certain embodiments, the identifier emits a signal once the composition comes into contact with a physiological target site, e.g., as summarized above.

Depending on the embodiment, the target physiological site or location may vary, where representative target physiological sites of interest include, but are not limited to: a location in the gastrointestinal tract, such as the mouth, esophagus, stomach, small intestine, large intestine, etc. In certain embodiments, the identifier is configured to be activated upon contact with fluid in the target site, regardless of the particular composition of the target site. In some embodiments, the identifier is configured to be activated only upon contact with a target site or region of interest, such as the stomach, in order to, for example, confirm the location of the intragastric device.

The signal obtained from the identifier may be a generic signal, e.g., a signal that merely identifies that the composition has contacted the target site, or a unique signal, e.g., a signal which in some way uniquely identifies that a particular ingestible event marker from a group or plurality of different markers in a batch has contacted a target physiological site. In yet other embodiments, the identifier emits a signal that uniquely identifies that particular identifier. Accordingly, in certain embodiments the identifier emits a unique signal that distinguishes one class of identifier from other types of identifiers. In certain embodiments, the identifier emits a unique signal that distinguishes that identifier from other identifiers. In certain embodiments, the identifier emits a signal that is unique, i.e., distinguishable, from a signal emitted by any other identifier ever produced, where such a signal may be viewed as a universally unique signal (e.g., analogous to a human fingerprint which is distinct from any other fingerprint of any other individual and therefore uniquely identifies an individual on a universal level). In one embodiment, the signal may either directly convey information about a given event, or provide an identifying code, which may be used to retrieve information about the event from a database, i.e., a database linking identifying codes with compositions.

The identifier may generate a variety of different types of signals, including but not limited to: voltaic, RF signals, magnetic signals, conductive (near field) signals, acoustic signals, etc. The transmission time of the identifier may vary, where in certain embodiments the transmission time may range from about 0.1 μsec to about 48 hours or longer, e.g., from about 0.1 μsec to about 24 hours or longer, such as from about 0.1 μsec to about 4 hours or longer, such as from about 1 sec to about 4 hours, including about 1 minute to about 10 minutes. Depending on the given embodiment, the identifier may transmit a signal once or transmit a signal two or more times, such that the signal may be viewed as a redundant signal.

In certain embodiments, the identifier is dimensioned to be orally ingestible, e.g., either by itself or upon combination with a physiologically acceptable carrier component of the composition, such as a swallowable catheter or balloon. As such, in certain embodiments, the identifier element is dimensioned to have a width ranging from about 0.05 to about 2 or more mm, e.g., from about 0.05 mm to about 1 mm, such as from about 0.1 mm to about 0.2 mm; a length ranging from about 0.05 to about 2 or more mm, e.g., from about 0.05 mm to about 1 mm, such as from about 0.1 mm to about 0.2 mm and a height ranging from about 0.05 to about 2 or more mm, e.g., from about 0.1 mm to about 1 mm, such as from about 0.05 mm to about 0.3 mm, including from about 0.1 mm to about 0.2 mm. In certain embodiments the identifier is 1 $mm^3$ or smaller, such as 0.1 $mm^3$ or smaller, including 0.2 $mm^3$ or smaller. The identifier element may take a variety of different configurations, such as but not limited to: a chip configuration, a cylinder configuration, a spherical configuration, a disc configuration, etc, where a particular configuration may be selected based on intended application, method of manufacture, etc.

In certain embodiments, the identifier may be one that is programmable following manufacture. For example, the signal generated by the identifier may be determined after the identifier is produced, where the identifier may be field programmable, mass programmable, fuse programmable, and even reprogrammable. Such embodiments are of interest where uncoded identifiers are first produced and following incorporation into a composition are then coded to emit an identifying signal for that composition. Any convenient programming technology may be employed. In certain embodiments, the programming technology employed is RFID technology. RFID smart tag technology of interest that may be employed in the subject identifiers includes, but is not limited to: that described in U.S. Pat. Nos. 7,035,877; 7,035,818; 7,032,822; 7,031,946, as well as published application no. 20050131281, and the like, the disclosures of which are herein incorporated by reference in their entirety. With RFID or other smart tag technology, a manufacturer/vendor may associate a unique ID code with a given identifier, even after the identifier has been incorporated into the composition. In certain embodiments, each individual or entity involved in the handling of the composition prior to use may introduce information into the identifier, e.g., in the form of programming with respect to the signal emitted by the identifier, e.g., as described in U.S. Pat. No. 7,031,946 the disclosure of which is herein incorporated by reference in its entirety.

The identifier of certain embodiments includes a memory element, where the memory element may vary with respect to its capacity. In certain embodiments, the memory element has a capacity ranging from about 1 bit to 1 gigabyte or more, such as 1 bit to 1 megabyte, including from about 1 bit to about 128 bit. The particular capacity employed may vary depending on the application, e.g., whether the signal is a generic signal or coded signal, and where the signal may or may not be annotated with some additional information, e.g., name of active agent associated with the identifier, etc.

Identifier components of some embodiments have: (a) an activation component; and (b) a signal generation component, where the signal generation component is activated by the activation component to produce an identifying signal, e.g., as described above.

The activation component is a component that activates the signal generation element of the identifier to provide a signal, e.g., by emission or upon interrogation, following contact of the composition with a target physiological site of interest, such as the stomach. Activation of the identifier may be achieved in a number of different ways, where such approaches include, but are not limited to: battery completion, battery connection, etc.

Embodiments of activation elements based on battery completion formats employ a battery that includes, when completed, a cathode, an anode, and an electrolyte, where the electrolyte is made up, at least in part, by fluid present at the target physiologic site (e.g. stomach fluid present in the stomach, where the stomach is the target physiological site). For example, when a stomach fluid activated IEM is ingested, it may travel, for instance with a swallowable catheter and/or an intragastric device, through the esophagus and proceed to enter the stomach. The cathode and anode provided on the IEM do not constitute a full battery. However, when the cathode and anode are exposed to stomach fluid, the stomach fluid acts as the electrolyte component of the battery and completes the battery. Therefore, as the IEM contacts the target site, a power source is provided which activates the identifier. The data signal is then transmitted.

In certain embodiments, the battery that is employed is one that comprises two dissimilar electrochemical materials which constitute the two electrodes (e.g., anode and cathode) of the battery. When the electrode materials are exposed and come in contact with the body fluid, such as stomach acid or other types of fluid, a potential difference (i.e., voltage), is generated between the electrodes as a result of the respective oxidation and reduction reactions that occur the two electrode materials. The two dissimilar materials in an electrolyte are at different potentials. As an example, copper and zinc when put into a cell have different potentials. Similarly, gold and magnesium have different potentials.

Materials for the anode include, but are not limited to metals such as Magnesium, Zinc, Sodium, Lithium, Iron, and alloys thereof. Materials for the cathode include, but are not limited to salts such as copper salts including iodide, chloride, bromide, sulfate, formate, (other anions possible); or $Fe^{3+}$ salts such as orthophosphate, pyrophosphate, (other anions possible); or Oxygen or hydrogen on platinum, gold or other catalytic surfaces. Intercalation compounds may also be used. For the anode, materials include graphite with Li, K, Ca, Na, Mg, and for the cathode materials include vanadium oxide and manganese oxide.

Certain high energy anode material such as Li, Na, and other alkali metals are unstable in their pure form in the presence of water or oxygen. These may however be used in an aqueous environment if stabilized. One example of this stabilization is the so-called "protected lithium anode" developed by Polyplus Corporation (Berkeley, Calif.), where a polymer film is deposited on the surface of lithium metal to protect it from rapid oxidation and allow its use in aqueous environment or air ambient. (Polyplus has IP pending on this). (.dagger..dagger.) Dissolved oxygen can also serve as a cathode. In this case, the dissolved oxygen in the bodily fluids would be reduced to OH— at a suitable catalytic surface such at Pt or gold. Other catalysts are also possible. Also of interest dissolved hydrogen in a hydrogen reduction reaction.

In certain embodiments, one or both of the metals may be doped with a non-metal, e.g., to enhance the voltage output of the battery. Non-metals that may be used as doping agents in certain embodiments include, but are not limited to: sulfur, iodine and the like.

In certain embodiments, the electrode materials are cuprous iodine (CuI) or cuprous chloride as the cathode and magnesium (Mg) metal or magnesium alloy as the anode. Embodiments of the present invention use electrode materials that are not harmful to the human body. In certain of these embodiments, the battery power source may be viewed as a power source that exploits electrochemical reaction in an ionic solution such as gastric fluid, blood, or other bodily fluids and some tissues.

Figure 41:
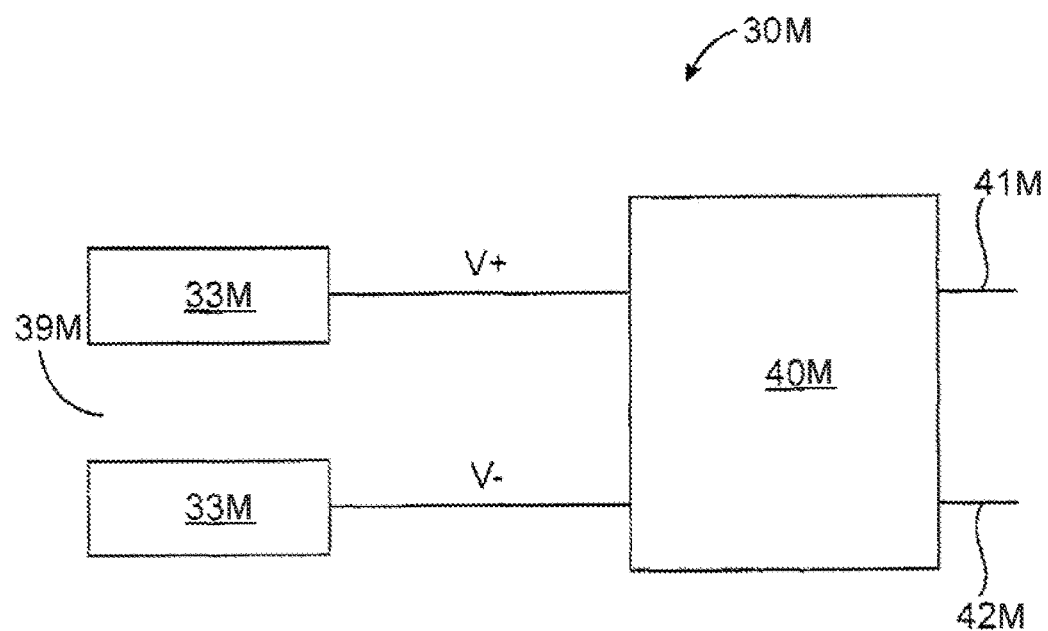
FIG. 41 depicts a diagrammatic representation of an embodiment of an identifier that may be used in a voltaic based intragastric locating system.

FIG. 41 provides a diagrammatic representation of an identifier 30M according to an embodiment of the invention. First and second electrode materials 32M and 33M are in an ionic solution 39M (e.g., stomach fluid). This configuration creates a low voltage (V−) and a high voltage (V+) as applied to an electronic circuit 40M. The two outputs of that electronic circuit 40M are electrodes 41M and 42M, which are the signal-transmission electrodes. In an alternate embodiment, the signal generation element 30M includes a single electrode. In an alternative embodiment, a coil for communication may be provided. In certain embodiments, a structure, e.g., membrane, larger than the chip which defines a path for the current to travel is provided.

Referring to FIG. 41, electrodes 32M and 33M can be made of any two materials appropriate to the environment in which the identifier 30M will be operating. The active materials are any pair of materials with different electrochemical potentials. For instance, in some embodiments where ionic solution 39M comprises stomach acids, electrodes 32M and 33M may be made of a noble metal (e.g., gold, silver, platinum, palladium or the like) so that they do not corrode prematurely. Alternatively, the electrodes can be fabricated of aluminum or any other conductive material whose survival time in the applicable ionic solution is long enough to allow identifier 30M to perform its intended function. Suitable materials are not restricted to metals, and in certain embodiments the paired materials are chosen from metals and non-metals, e.g., a pair made up of a metal (such as Mg) and a salt (such as CuI). With respect to the active electrode materials, any pairing of substances—metals, salts, or intercalation compounds—with suitably different electrochemical potentials (voltage) and low interfacial resistance are suitable.

In certain embodiments, the IEMs are characterized by including series battery structures, where these series battery structures may be configured to substantially reduce, if not eliminate, shorting between electrode elements of different battery structures of the series. As the batteries of the present invention are series batteries, the batteries include two or more individual battery structures or units, where the number of battery structures that may be present in a given series battery of the invention may be two or more, three or more, four or more, five or more, etc., as desired for a given application of the battery. Each individual battery structure includes at least one anode and at least one cathode, where the anode and the cathode are present on a surface of a solid support, where the support for each of the anode and cathode may be the same or different.

Aspects of the series batteries include configurations that substantially reduce, if not eliminate, shorting between two or more of the batteries of a given series. This elimination of shorting is provided despite the small area that is occupied by the two or more batteries of the series, e.g., where the battery units are present on the surface of a solid support. Embodiments of the subject series batteries include configurations in which the resistance between electrodes of two different battery structures of the series battery is much higher than the resistance between electrodes within a given battery structure. In certain embodiments, the ratio of the ionic resistance between electrodes of two different battery structures as compared to electrodes (i.e., anode and cathode) within a single battery structure is about 1.5× or more, such as about 5× or more, including about 10× or more.

Depending on a particular series battery configuration, shorting between batteries can be reduced, if not eliminated, using a variety of different approaches. Certain approaches that can be employed are reviewed in greater detail below, where the below approaches may or may not be used in combination, depending on the particular battery configuration of interest.

In certain embodiments, two or more battery structures are provided in series, where each battery structure includes a chamber having an anode and cathode positioned inside the chamber, e.g., on the same internal wall or different internal walls. The chamber has a volume that may vary, and in certain embodiments ranges from about $10^{-12}$ to about $10^{-5}$ L, such as from about $10^{-11}$ to about $10^{-7}$ L and including from about $10^{-10}$ to about $10^{-8}$ L. In certain embodiments, the chamber may include an amount of a dried conductive medium, e.g., as described in PCT Application Serial No. PCT/US07/82563, the disclosure of which is herein incorporated by reference in its entirety.

In certain embodiments, a given chamber includes at least one fluid entry port and at least one fluid exit port, so that liquid, e.g., stomach fluid, can enter the chamber when the composition in which the battery is present reaches the target site of interest and gas can exit the chamber upon entry of the liquid. While the dimensions of the fluid entry and exit ports may vary, in certain embodiments the ports have a diameter ranging from about 0.01 µm to about 2 mm, such as from about 5 µm to about 500 µm.

The ports of a given chamber are positioned relative to ports of other chambers to provide for efficient entry of fluid into and exit of gas from the chamber, and are also positioned to provide for substantially no, if any, shorting between two or more different chambers of the series battery. As such, location of the ports is chosen in view of both the battery structure itself and its physical relation to other battery structures of the series battery. Any configuration of fluid ports may be chosen, so long as the configuration provides the desired resistance ratio, e.g., as described above.

Figure 58:
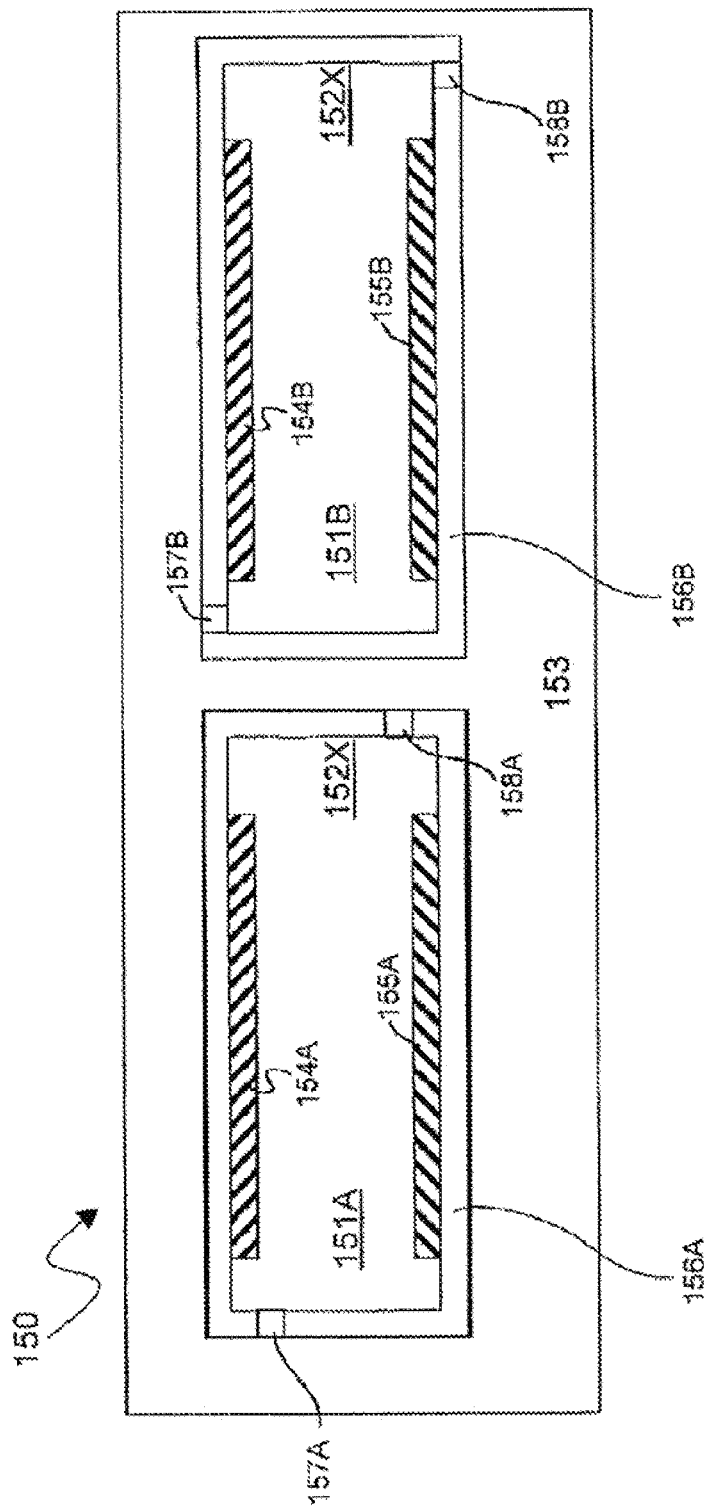
FIG. 58 depicts an embodiment of a series battery that may be incorporated with the voltaic sensor locating system.

FIG. 58 provides an overhead view of a series battery according to one embodiment. In FIG. 58, a series battery 150 is made up of two different battery structures 151A and 151B present on a surface 152X of a solid support 153. The battery structure 151A includes cathode 154A and anode 155A while the structure 151B includes cathode 154B and anode 155B. As illustrated, the cathodes and anodes of each battery structure are present in a chamber defined by boundary 156A and 156B. Present in the wall 156A of structure 151A are ports 157A and 158A, which provide for fluid entry and exit from the chamber. Ports 157A and 158A of structure 151A are positioned relative to ports 157B and 158B of structure 151B so that the potential for shorting between the electrodes of structures 151A and 151B is substantially, if not completely eliminated. In the configuration shown in FIG. 28, ports 157A and 158A are positioned on opposing walls of boundary 156A and ports 157B and 158B are positioned on opposing walls of boundary 156B. Furthermore, ports 157A and 158A are present on opposing walls of their boundary element 156A with respect to the positioning of ports 157B and 158B in boundary element 156B.

Figure 59:
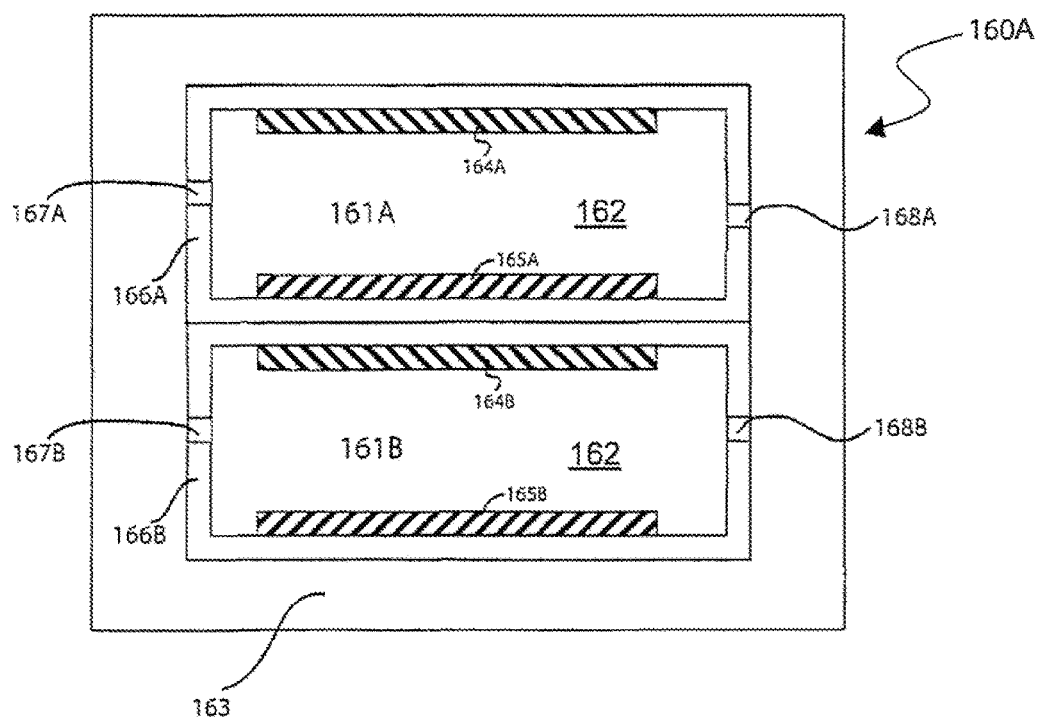
FIG. 59 depicts another embodiment of a series battery that may be incorporated with the voltaic sensor locating system.

FIG. 59 provides an overhead view of a series battery according to an embodiment. In FIG. 59, series battery 160A is made up of two different battery structures 161A and 161B present on surface 162 of solid support 163. Battery structure 161A includes cathode 164A and anode 165A while structure 161B includes cathode 164B and anode 165B. The structure illustrated in FIG. 59 differs from that shown in FIG. 58 as the battery structures are stacked next to each other. As illustrated, the cathodes and anodes of each battery structure are present in a chamber defined by boundary 166A and 166B. Present in the wall 166A of structure 161A are ports 167A and 168A, which provide for fluid entry and exit from the chamber. Ports 167A and 168A of structure 161A are positioned relative to ports 167B and 168B of structure 161B so that the potential for shorting between the electrodes of structures 161A and 161B is substantially, if not completely eliminated.

In addition to, or instead of, locating fluid ports to provide for the desired resistance ratio, the fluid ports may be modified to provide the desired resistance between battery structures. For example, the port may include a selective semi-permeable membrane. Any convenient semi-permeable membrane may be employed. The semi-permeable membrane may comprise ePTFE, Dacron®, polyurethane, silicone rubber, poly(lactide-co-glycolide) (PLGA), poly (caprolactone) (PCL), poly(ethylene glycol) (PEG), collagen, polypropylene, cellulose acetate, poly(vinylidene fluoride) (PVDF), nafion or other biocompatible material. The pore size of the membrane may vary depending on the particular configuration, where in certain embodiments the membrane have a pore size (MW cutoff of about 1000 d or less, such as about 500 d or less, including about 250 d or less, e.g., about 100 d or less, such as about 50 d or less). In certain embodiments, the membrane is a water only permeable membrane, such that water, but little if any other fluid constituents at the target site, pass through the membrane to reach to the dried conductive medium precursor of the identifier.

In certain embodiments, the solid support 153, 163 is a circuitry support element. The circuitry support element may take any convenient configuration, and in certain embodiments is an integrated circuit (IC) chip. The surface upon which the electrode elements are positioned may be the top surface, bottom surface or some other surface, e.g., side surface, as desired, where in certain embodiments the surface upon which the electrode elements are at least partially present is a top surface of an IC chip.

In certain embodiments, the series batteries have a small form factor. Batteries may be about 20 mm$^3$ or smaller, e.g., about 10 mm$^3$ or smaller, such as 1.0 mm$^3$ or smaller, including 0.1 mm$^3$ or smaller, including 0.02 mm$^3$ or smaller. In certain embodiments, the battery element is dimensioned to have a width ranging from about 0.01 mm to about 100 mm, e.g., from about 0.1 mm to about 20 mm, including from about 0.5 mm to about 2 mm; a length ranging from about 0.01 mm to about 100 mm, e.g., from about 0.1 mm to about 20 mm, including from about 0.5 mm to about 2 mm, and a height ranging from about 0.01 mm to about 10 mm, e.g., from about 0.05 mm to about 2 mm, including from about 0.1 mm to about 0.5 mm.

Series battery embodiments includes those further described in U.S. Provisional Application Ser. No. 60/889, 871, the disclosure of which is herein incorporated by reference in its entirety. The signal generation component of the identifier element is a structure that, upon activation by the activation component, emits a detectable signal, e.g., that can be received by a receiver, e.g., as described in greater detail below. The signal generation component of certain embodiments can be any convenient component or element that is capable of producing a detectable signal and/or modulating transduced broadcast power, upon activation by the activation component. Detectable signals of interest include, but are not limited to: conductive signals, acoustic signals, etc. The signals emitted by the signal generator may be generic or unique signals, where representative types of signals of interest include, but are not limited to: frequency shift coded signals; amplitude modulation signals; frequency modulation signals; etc.

In certain embodiments, the signal generation element includes circuitry which produces or generates the signal. The type of circuitry chosen may depend, at least in part, on the driving power that is supplied by the power source of the identifier. For example, where the driving power is 1.2 volts or above, standard CMOS circuitry may be employed. In other embodiments where the driving power ranges from about 0.7 to about 1.2 V, sub-threshold circuit designs may be employed. For driving powers of about 0.7 V or less, zero-threshold transistor designs may be employed. In some embodiments, the power source may be the voltage produced by contact of the voltaic sensor with the gastric environment, as discussed in further detail herein.

In certain embodiments, the signal generation component includes a voltage-controlled oscillator (VCO) that can generate a digital clock signal in response to activation by the activation component. The VCO can be controlled by a digital circuit, which is assigned an address and which can control the VCO with a control voltage. This digital control circuit can be embedded onto a chip that includes the activation component and oscillator. Using amplitude modulation or phase shift keying to encode the address, an identifying signal is transmitted.

The signal generation component may include a distinct transmitter component that serves to transmit the generated signal to a remote receiver, which may be internal or external to the patient. The transmitter component, when present, may take a number of different configurations, e.g., depending on the type of signal that is generated and is to be emitted. In certain embodiments, the transmitter component is made up of one or more electrodes. In certain embodiments, the transmitter component is made up of one or more wires, e.g., in the form of antenna(e). In certain embodiments, the transmitter component is made up of one or more coils. As such, the signal transmitter may include a variety of different transmitters, e.g., electrodes, antennas (e.g., in the form of wires) coils, etc. In certain embodiments, the signal is transmitted either by one or two electrodes or by one or two wires (a two-electrode transmitter is a dipole; a one electrode transmitter forms a monopole). In certain embodiments, the transmitter only requires one diode drop of power. In some embodiments, the transmitter unit uses an electric dipole or electric monopole antenna to transmit signals. In certain embodiments, the identifier employs a conductive near-field mode of communication in which the body itself is employed as a conductive medium. In such embodiments, the signal is not a magnetic signal or high frequency (RF) signal.

Figure 42:
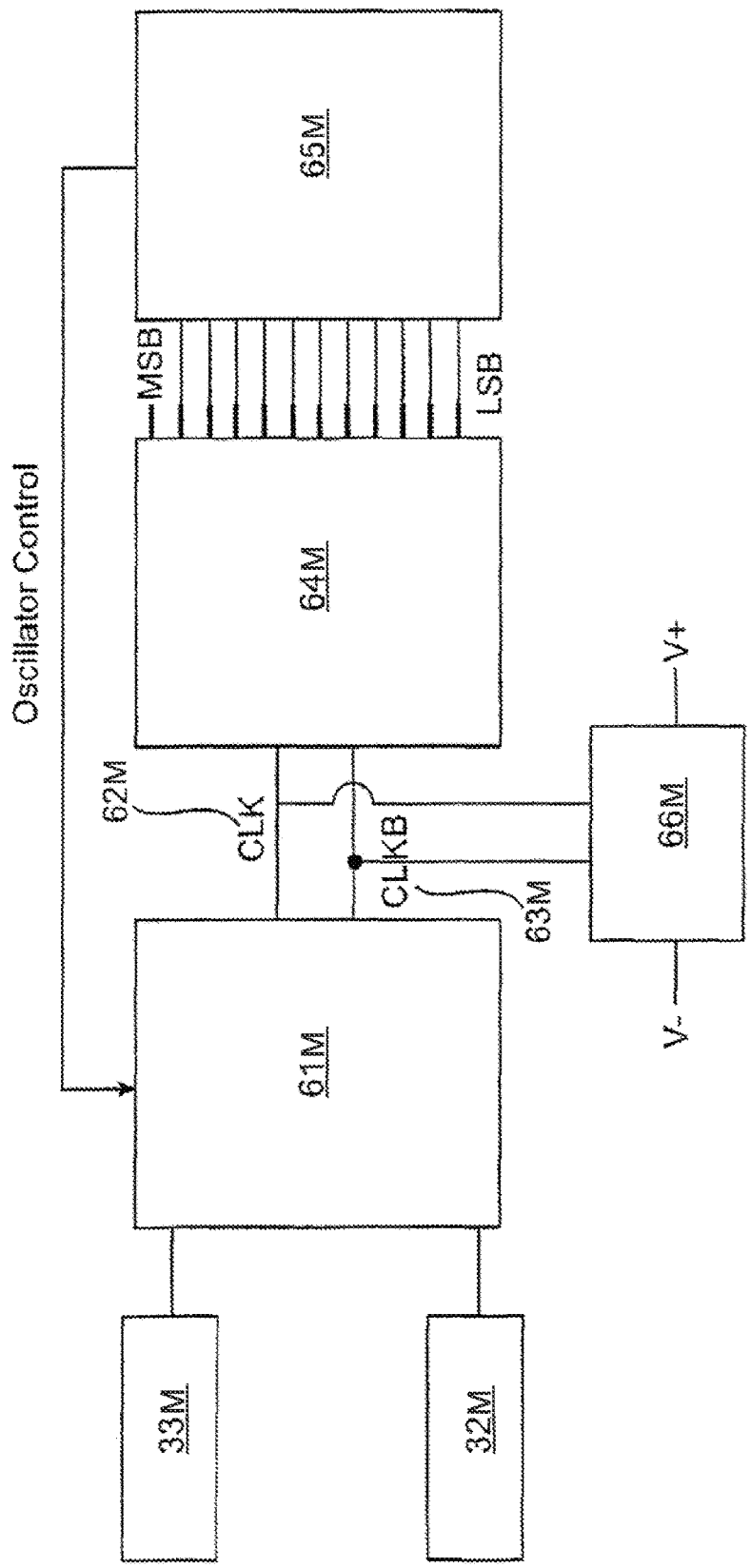
FIG. 42 provides detail of certain implementations of an electronic circuit of various embodiments of a voltaic sensor that may be used with a voltaic based intragastric locating system.

FIG. 42 shows the detail of one implementation of an electronic circuit that can be employed in an identifier according to some embodiments. On the left side are the two battery electrodes, a first metal 32M and a second metal 33M. These metals, when in contact with an electrolyte, form a battery that provides power to an oscillator 61M, in this case shown as a schematic. The metal 32M provides a low voltage, (ground) to the oscillator 61M. Metal 33M provides a high voltage (V-high) to the oscillator 61M. As the oscillator 61M becomes operative, it generates a clock signal 62M and an inverted clock signal 63M, which are opposites of each other. These two clock signals go into the counter 64M which simply counts the number of clock cycles and stores the count in a number of registers. In the example shown here, an 8 bit counter is employed. Thus, the output of counter 64M begins with a value of "00000000," changes to "00000001" at the first clock cycle, and continues up to "11111111." The 8-bit output of counter 64M is coupled to the input of an address multiplexer (mux) 65M. In one embodiment, mux 65M contains an address interpreter, which can be hard-wired in the circuit, and generates a control voltage to control the oscillator 61M. Mux 65M uses the output of counter 64M to reproduce the address in a serial bit stream, which is further fed to the signal-transmission driving circuit. Mux 65M can also be used to control the duty-cycle of the signal transmission. In one embodiment, mux 65M turns on signal transmission only one sixteenth of the time, using the clock counts generated by counter 64M. Such a low duty cycle conserves power and also allows other devices to transmit without jamming their signals. The address of a given chip can be 8 bits, 16 bits or 32 bits.

According to one embodiment, mux 65M produces a control voltage, which encodes the address serially and is used to vary the output frequency of oscillator 61M. By example, when the control voltage is low, that is, when the serial address bit is at a 0, a 1 megahertz signal is generated by the oscillator. When the control voltage is high, that is, when the address bit is a 1, a 2 megahertz signal is generated the oscillator. Alternately, this can be 10 megahertz and 20 megahertz, or a phase shift keying approach where the device is limited to modulating the phase. The purpose of mux 65M is to control the frequency of the oscillator or an AC alternative embodiment of the amplified signal of oscillation.

The outputs of mux 65M are coupled to electrode drive 66M which can drive the electrodes to impose a differential potential to the solution, drive an oscillating current through a coil to generate a magnetic signal, or drive a single electrode to push or pull charge to or from the solution.

In this manner, the device broadcasts the sequence of 0's and 1's which constitute the address stored in mux 65M. That address would be broadcast repeatedly, and would continue broadcasting until metal 32M or metal 33M is consumed and dissolved in the solution, when the battery no longer operates.

Other configurations for the signal generation component are of course possible. Other configurations of interest include, but are not limited to: those described in PCT application serial no. PCT/US2006/016370 and provisional application Ser. No. 60/807,060 filed on Jul. 11, 2006, the disclosure of each of which is herein incorporated by reference.

In certain embodiments, the activation component includes a power storage element. For example, a duty cycle configuration may be employed, e.g., where slow energy production from a battery is stored in a power storage element, e.g., in a capacitor, which then provides a burst of power that is deployed to the signal generation component. In certain embodiments, the activation component includes a timing element which modulates, e.g., delays, delivery of power to the signal generation element, e.g., so signals from different compositions, e.g., different IEMs, that are administered at substantially the same time are produced at different times and are therefore distinguishable.

In certain embodiments, the components or functional blocks of the identifiers of the ingestible event markers are present on integrated circuits, where the integrated circuits include a number of distinct functional blocks, i.e., modules. Within a given identifier, at least some of, e.g., two or more, up to an including all of, the functional blocks, e.g., power source, transmitter, etc., may be present in a single integrated circuit in the receiver. By single integrated circuit is meant a single circuit structure that includes all of the different functional blocks. As such, the integrated circuit is a monolithic integrated circuit (also known as IC, microcircuit, microchip, silicon chip, computer chip or chip) that is a miniaturized electronic circuit (which may include semiconductor devices, as well as passive components) that has been manufactured in the surface of a thin substrate of semiconductor material. The integrated circuits of certain embodiments of the present invention may be hybrid integrated circuits, which are miniaturized electronic circuits constructed of individual semiconductor devices, as well as passive components, bonded to a substrate or circuit board.

Embodiments of the present invention provide a low-power, miniature, ingestible marker that includes an integrated circuit (IC) which automatically activates itself after the marker contacts a patient's body fluid, transmits a predetermined signal based on locally generated power, and de-activates itself after a certain period of time. In these embodiments, as described above, the IEM uses the patient's body fluid, such as the stomach acid, to form a voltaic cell. Furthermore, the IEM uses a special circuit that changes the impedance of a closed circuit which forms the voltaic cell, thereby creating an external signal by modulating the amplitude and waveform of the current that flows through the patient's tissue and body fluid. As described in more detail below, such a circuit configuration allows the circuitry to operate at a low voltage while generating a signal that is sufficiently strong to be detected by a receiver in contact with the patient's body.

An IEM's IC can be packaged with an integrated voltaic cell which can be manufactured on the same substrate as the IC circuit. This wafer level integration significantly reduces the chip and simplifies the manufacturing process. As a result, each IEM's cost can be considerably lowered. In one embodiment, the anode and cathode electrode materials are fabricated on each side of the substrate, whereby the IC logic is situated between the two electrodes. In one embodiment, the logic circuit is situated in a location chosen to minimize the area overlapping vertically with the anode or cathode electrode.

Figure 43:
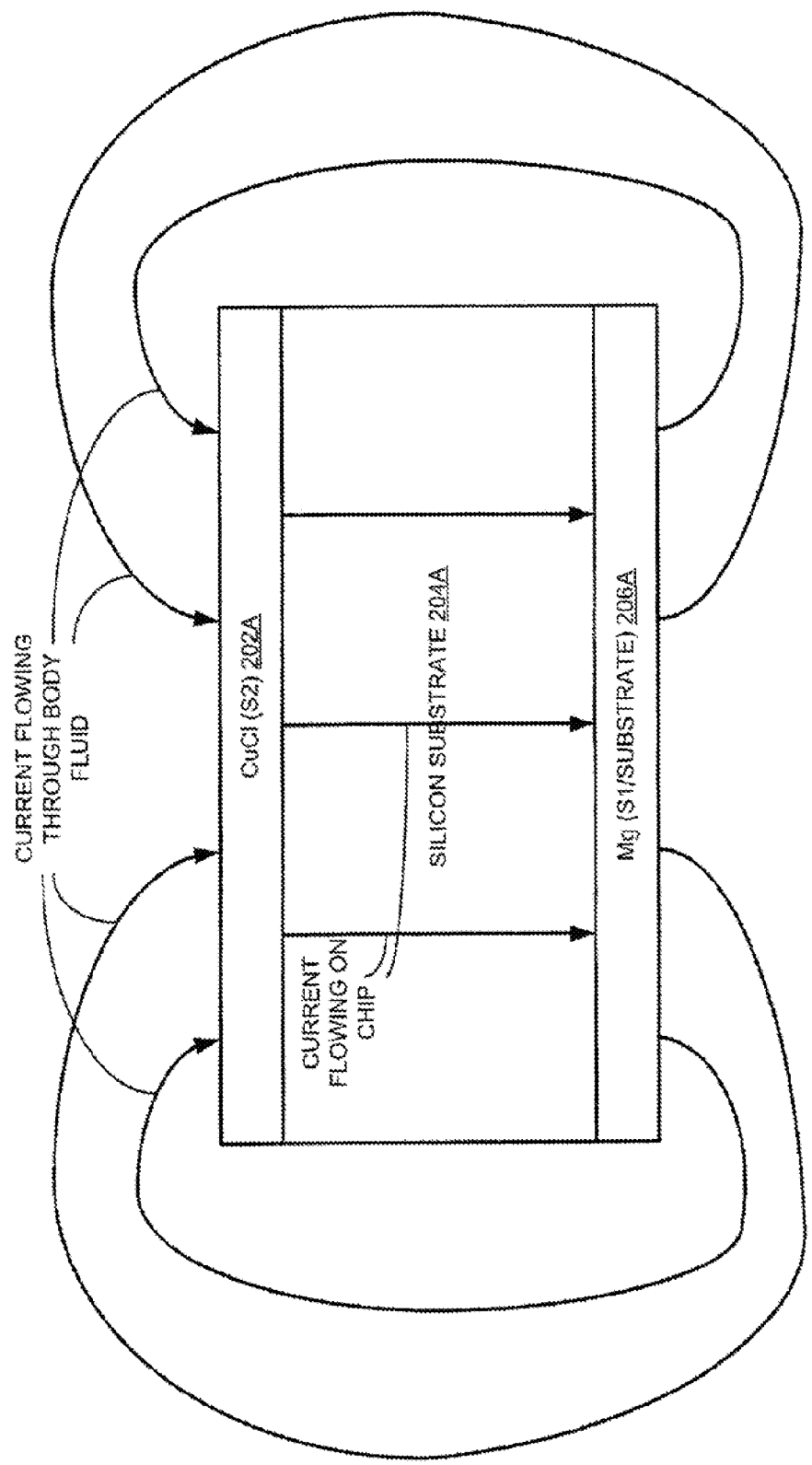
FIG. 43 illustrates an embodiment of a voltaic device configuration of an ingestible event marker (IEM) integrated circuit (IC) in accordance with one embodiment.

FIG. 43 illustrates an exemplary device configuration of the IEM IC in accordance with one embodiment. In one embodiment, the IC chip's substrate 204A is coupled to the anode (S1) of the voltaic cell, which can be a layer of Magnesium (Mg) 206A coated on the backside of substrate 204A. On the opposite side of substrate 204A is a layer of cathode (S2) material 202A, which in this example is Copper Chloride (CuCl). The electrodes 202A and 206A, and the body fluid which serves as an electrolyte fluid, form the voltaic cell. The IEM IC circuitry, which is fabricated on substrate 204A, is the "external" circuit that forms a return circuit for the voltaic cell. Essentially, the IEM IC changes the impedance of this "external" circuit, thereby changing the total amount of current flowing through the body fluid. A receiving circuit, e.g., on a personal health receiver as described in greater detail below, in contact with the body fluid can detect this current change and receive the encoded messages.

Note that the two electrodes S1 and S2 of the voltaic cell also serve as the transmission electrodes for the IC. This configuration significantly reduces the complexity of the IC chip. Furthermore, since a fluid-metal interface often exhibits high impedances, using a separate pair of electrodes which are different from the voltaic-cell electrodes can introduce additional high impedance to the circuit, thereby reducing the transmission efficiency and increasing power consumption. Therefore, using the voltaic-cell electrodes for transmission also improves the power-efficiency of the IC circuitry.

The IC of the IEM functions as an ingestible transmitter that transmits a unique identification code once powered on. This IC can be packaged within a pharmaceutically acceptable vehicle, e.g., as described above. When the IEM is swallowed and inside the stomach, the integrated voltaic cell, or battery, uses the stomach acid as the battery electrolyte to power up the main chip and commences broadcasting or otherwise electrically communicating thereafter. Furthermore, several pills can be ingested and transmit at the same time. During operation, a unique identification code, e.g., using BPSK modulation, is broadcasted. This broadcast can be received and demodulated by a receiver, e.g., a sensor interface unit. The receiver can decode and store the identification code with a time stamp.

In one embodiment, a IEM IC includes an impedance-detection circuitry. This circuitry is configured to detect the impedance between the anode and cathode electrodes. When the electrodes are not submerged in an electrolyte fluid, e.g., stomach acid, the impedance between the electrodes is high and the IC is not activated. When the electrodes are in contact with the electrolyte fluid and the impedance-detection circuit detects the drop in impedance, the IC is then activated.

Some embodiments allow the voltaic sensor to operate at low voltages. In general, the IC can operate with a power supply at 0.8-2 V. In one embodiment, the IC is configured to operate with a power supply at approximately 1.0-1.6 V. In addition, the voltaic cell exhibits an internal impedance of 200-10K Ohm. In one embodiment, the voltaic cell exhibits an internal impedance of approximately 500-5K Ohm. The IC also provides an ultra stable carrier clock frequency, thereby facilitating error-resistant communications.

In one embodiment, an IC includes three parts of circuitry. The first part is an impedance-detection circuitry that uses the battery as the power supply. The second part is the main circuit that broadcasts the messages. The impedance detection circuit can hold the main circuit at substantially zero power consumption before the battery detects an impedance lower than 10K Ohms. When the impedance drops to approximately 10K Ohms, the main circuit is activated and the impedance detection circuit can decouple itself from the battery. The third part is a watchdog circuitry designed to protect the patient's safety when hazardous situation occurs.

Figure 44:
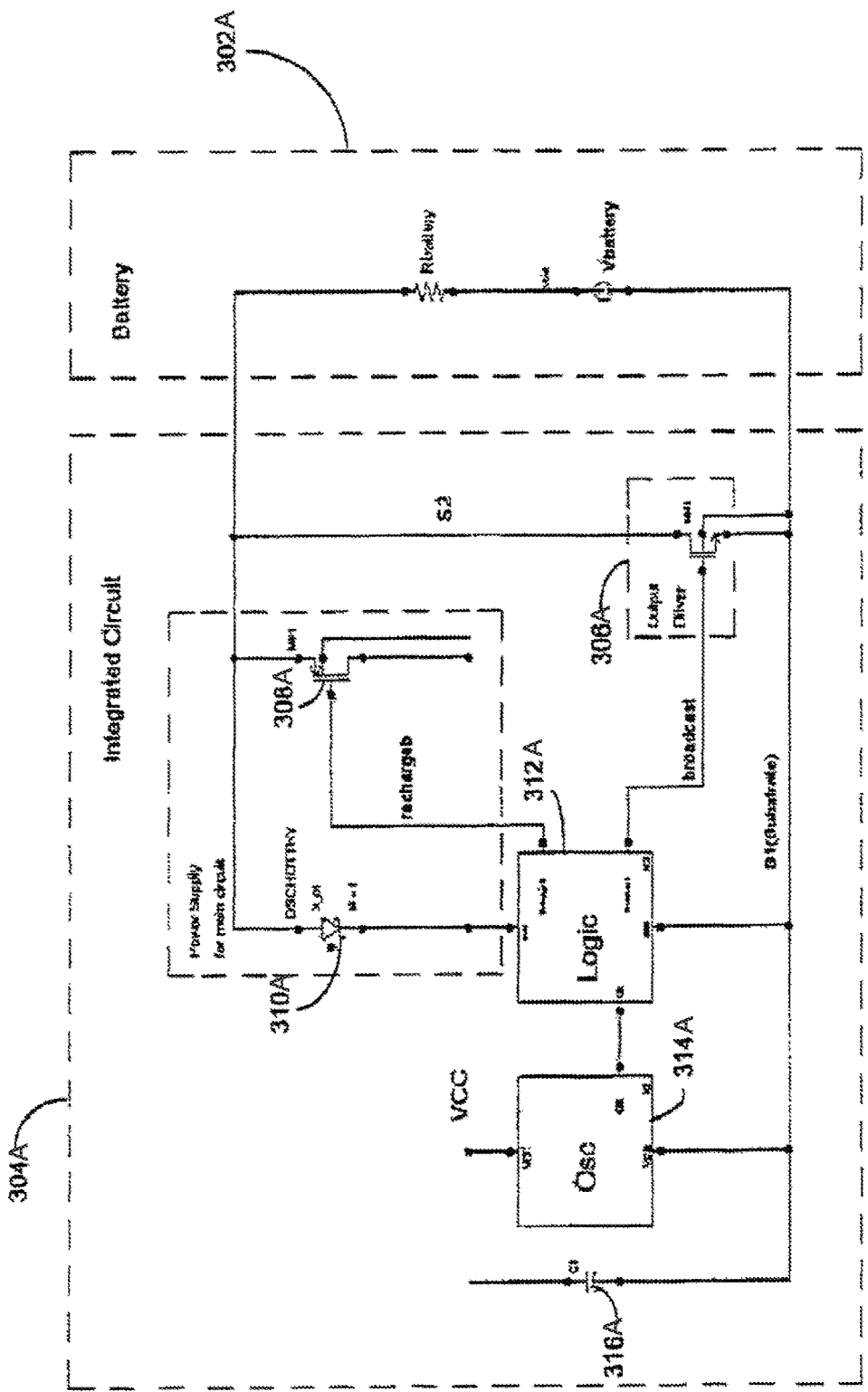
FIG. 44 is a schematic diagram illustrating an embodiment of a design for an IEM IC.

FIG. 44 presents an exemplary schematic diagram illustrating the design of a IEM IC in accordance with one embodiment of the present invention. In general, the IEM chip has a battery section 302A and an IC circuitry 304A. Battery section 302A includes the voltaic-cell electrodes, which when coupled with electrolyte fluid form a voltaic cell. The two battery electrodes are coupled to the high-voltage rail (VCC) and ground for the IC circuitry, respectively. IC circuitry 304A includes a transmission switch transistor 306A, a recharge transistor 308A, a recharge-protection diode 310A, a recharge capacitor 316A, a local oscillator 314A, and control logic 312A. Local oscillator 314A produces one or more carrier frequencies which is used by control logic 312A to issue a transmission command (labeled as "broadcast") to turn on and off transmission switch transistor 306A. For example, oscillator 316A can produce a 20 KHz signal, based on which control logic 312A can generate a binary-phase shift keying (BPSK)-encoded message. Control logic 312A then switches on and off transistor 306A to transmit these messages.

When transistor 312A is turned on, a low-impedance external return circuit is provided between the two voltaic-cell electrodes. Consequently, the current flowing through the patient's body is also increased. When transistor 312A is turned off, the external return circuit between the two voltaic-cell electrodes exhibits a high impedance. Correspondingly, the current flowing through the patient's body is significantly lower. Note that the current draw of the rest of the circuitry, e.g., the oscillator 314A and control logic 312A, is sufficiently low so that there is a significant difference in the body current between the broadcast period and the silence period.

When transistor 306A is turned on, the two voltaic-cell electrodes are effectively shorted. As a result, the voltage provided by the electrodes is significantly lower than when transistor 306A is turned off. To ensure that control logic 312A continues to operate properly, recharge capacitor 316A provides the necessary voltage (VCC) to control logic 312A. Note that recharge capacitor 316A is recharged when the IC chip is in a silence period, i.e., when transistor 306A remains off. When transistor 306A turns on which causes the voltage between the battery electrodes to drop, diode 310A prevents the charges stored in capacitor 316A from flowing back to the battery electrodes. In one embodiment, diode 310A is a Schottky diode to ensure a fast switching time.

It is possible that, during the transmission period, oscillator 314A and/or control logic 312A have depleted the charges stored in capacitor 316A, causing VCC to drop below a certain threshold. For example, the voltage provided by recharge capacitor 316A may drop below the voltage provided by the voltaic cell. The difference between these two voltages may not be large enough to turn on Schottky diode 310A. In this case, control logic 312A can issue a recharge signal to turn on recharge switching transistor 308A, which couples the battery voltage to capacitor 316A and recharges capacitor 316A.

In one embodiment, the communication between the IEM IC and the receiver is simplex. That is, the IEM IC only transmits signals without receiving any signals. The communication is performed via direct coupling between the IC electrodes and the receiver circuitry through the patient's body tissue and fluids. The transmission is performed at two frequencies, for example, one at 10 kHz and the other at 20 kHz. Other numbers of frequencies and frequency values are also possible. In general, different data-packet formats can be used with the present inventive system. In one embodiment, the transmitted data packet is 40-bit long, of which 16 bits are used as a synchronization/preamble pattern. The rest 24 bits carry a payload that encodes the IEM's identifier. In one embodiment, the payload can also include a forward error correction (FEC) code so that the transmission is more robust. In one embodiment, a data bit occupies 16 cycles of the carrier clock. The bits are BPSK encoded. Other encoding schemes are also possible. In a further embodiment, the 16-bit synchronization/preamble pattern include 12 bits for synchronization and 4 bits as a preamble.

Figure 45:
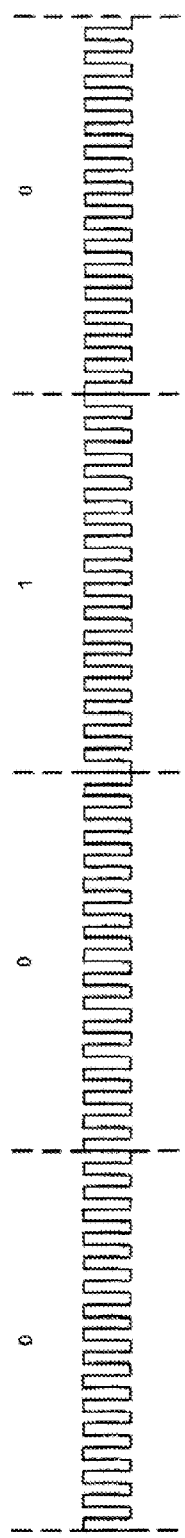
FIG. 45 illustrates an embodiment of a transmission sequence for a bit pattern of "0010" in accordance with one embodiment of the voltaic sensor.

FIG. 45 illustrates an exemplary transmission sequence for a bit pattern of "0010" in accordance with one embodiment of the present invention. Each bit is represented by 16 clock cycles. Depending on the battery configuration, it might be desirable to limit drive transistor 306A's duty cycle to maintain sufficient power to the oscillator. In one embodiment, the "on" state of drive transistor 306A is maintained to be substantially equal to or less than 25 μs. Thus, during the 20 kHz transmission where a clock cycle is 50 μs, the driver is on for 25 μs and off for 25 During the 10 kHz transmission, the driver is on for 25 μs and off for 75 μs. A logical "0" transmission begins with the rising edge of a data-clock cycle, and lasts for 16 clock cycles. Correspondingly, a logical "1" transmission begins with the falling edge of a data-clock cycle, and also lasts for 16 cycles. Note that other duty-cycle configuration and encoding schemes are also possible.

Figure 46:
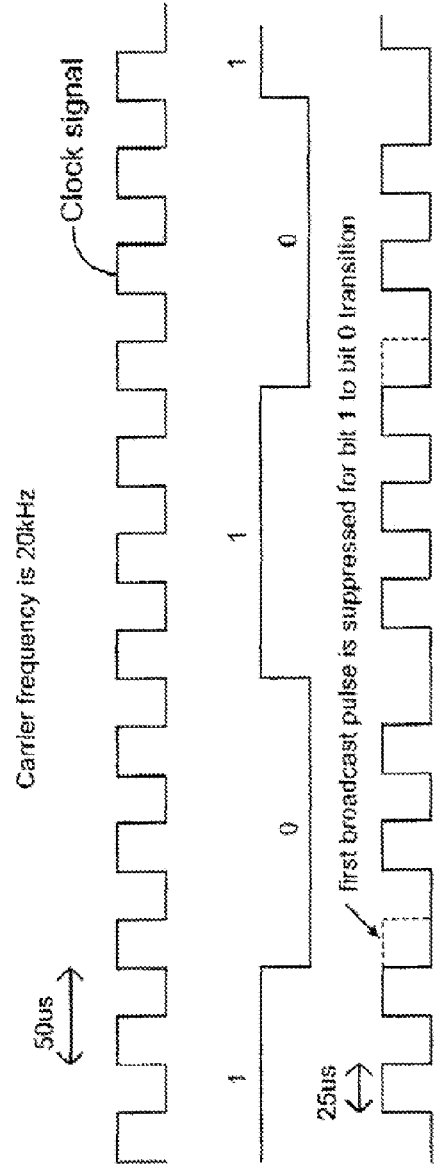
FIG. 46 illustrates an embodiment of a waveform for a 20 kHz transmission of a sequence "10101" in accordance with one embodiment of a voltaic sensor.
Figure 47:
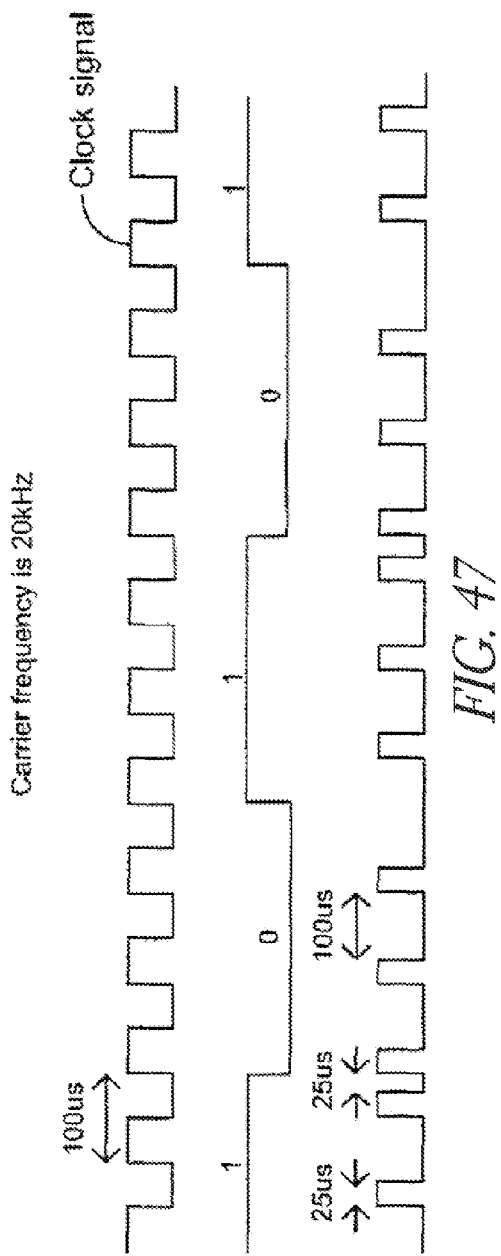
FIG. 47 illustrates an embodiment of a waveform of a 10 kHz transmission of a sequence "10101" in accordance with one embodiment of a voltaic sensor.

FIG. 46 presents an exemplary waveform for 20 kHz transmission of a sequence "10101" in accordance with one embodiment of the present invention. Note that for purposes of illustration, each logical bit occupies 3 clock cycles, instead of 16 cycles. FIG. 47 presents an exemplary waveform of 10 kHz transmission of a sequence "10101" in accordance with one embodiment of the present invention. Note that each logical bit is also shortened to 3 clock cycles.

In certain embodiments, the operation of the IEM can be divided into the following four periods: storage, holding period, broadcast period, and power down. During the storage period, the IC is turned off and typically consumes less than 5 mA. During the holding period, the IC is turned on. However, the broadcast is disabled for the oscillator clock signal to stabilize. In one embodiment, during the broadcast period, a packet is transmitted 256 times. During each transmission, the transmission driver transistor operates to transmit a packet and is then turned off for a period of time. When the transmitter driver transistor is off, the rest of the IEM IC remains powered on. In one embodiment, the average duty cycle during the entire broadcast period is maintained at approximately 3.9%. Other values of the average duty cycle are also possible. During the power-down period, the IEM IC is powered down gracefully. Broadcast is turned off completely.

Figure 48:
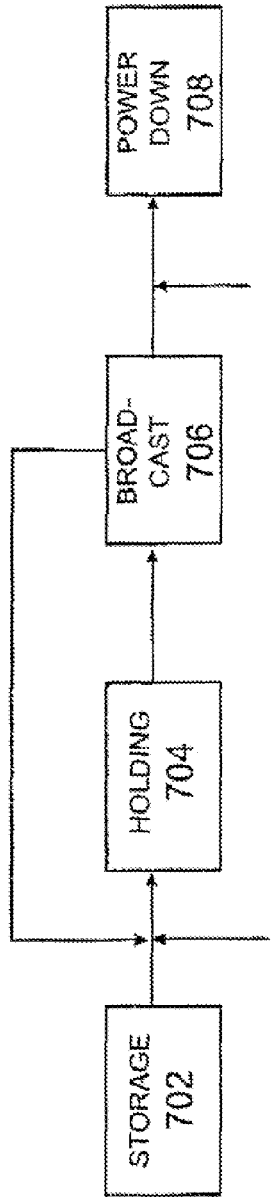
FIG. 48 is a state diagram illustrating the operation of an embodiment of an IEM IC in accordance with one embodiment of a voltaic sensor.

FIG. 48 presents an exemplary state diagram illustrating the operation of a IC in accordance with one embodiment. During operation, the system first enters a storage period 702, when an impedance detection circuit operates to detect the impedance between the two battery electrodes. Meantime, the IC is power-gated off. After the impedance detection circuit detects a low impedance, for example an impedance of approximately 10 kOhm, the circuit releases the IEM IC from the power-gated-off state. Correspondingly, the system enters a holding period 704. During holding period 704, the chip's broadcast function is disabled for approximately 10 seconds for the clock signal to stabilize. Next, the system enters a broadcast period 706. During this period, data packets are broadcasted twice in one cycle, one at 10 kHz and one at 20 kHz, with a cycle pattern of ON (10 KHz) for 32 ms-OFF for 768 ms-ON (20 KHz) for 64 ms-OFF for 1536 ms. Each cycle is approximately 2.4 seconds, and the system finishes 256 cycles in approximately 10 minutes. Note that, at each frequency, the chip's transmission duty cycle is maintained at approximately 3.9%. During the remaining 96.1% of the time, the recharge capacitor is recharged. Subsequently, the system enters a power-down state 708, when the oscillator is stopped and the chip is power-gated down. Note that if, for some reason, the chip keeps broadcasting continuously before the end of the 10-minute broadcast period, the system resets the chip's power supply and the broadcast process is started again. Such situation may occur when, for example, the stomach's conductivity suddenly drops so low that the oscillator and its generated clocks cannot function properly.

In some embodiments, operation parameters for an IC may be the following: the operating temperature may be from 20 to 45 degrees Celsius; the storage temperature may be from 0 to 60 degrees Celsiue; the storage humidity may be from 20% to 90% relative humidity; the human body conductivity/pH value may be from 0.01/4 to 1000/11 $S \cdot m^{-1}/pH$.

In some embodiments, an IEM circuit may have the following DC parameters: the power supply for the main chip ("Vcc") except the impedance detection circuit, and the output driver may be from 1.0-1.8 volts and typically about 1.6 volts; the DC current for the chip during recharging ("I(s2)") may be from 8-12 uA and typically about 1.6 uA; the battery voltage ("V(s2)") may be from 1.0-1.8 volts and typically 1.6 volts; the output driver's ON-resistance ("Zon") (function of "Vbattery") may be from 7-55 Ohms and typically 11 Ohms; the output driver's OFF-resistance ("Zoff") may be from about 75K-500k Ohms and typically 100K ohms; the Battery voltage when fully wetted ("Vbattery") may be from about 1.0-1.8 volts and typically about 1.6 volts; the solution's conductivity for the chip to function properly ("Rbattery") may be from about 500-5K ohms and typically about 1K-3K ohms.

In some embodiments, an IEM circuit may have the following AC parameters (note that for actual chip design the targeted value can have +/-5% to +/-10% over temperature, power supply voltage, and transistor's threshold voltage range): the oscillator's frequency ("f_osc") may be from 256-384 kHz and typically about 320 kHz; the low broadcast frequency ("f1_broadcast") may be from about 8-12 kHz and typically about 10 kHz; the high broadcast frequency ("f2_broadcast") may be from about 16-24 kHz and typically about 20 kHz; the holding time before enabling chip to do broadcasting at power-on ("T_brdcsten") may be from about 8-12 seconds and typically about 10 seconds; the time for broadcasting ("T_brdcstoff") may be from about 8-12 minutes and typically about 10 minutes.

An IEM chip's physical size can be between 0.1 $mm^2$ and 10 $mm^2$. Because of the special IC configuration, embodiments of the present invention can provide an IEM chip that is sufficiently small to be included to most types of pills. For example, a IEM IC chip can have a size less than 2×2 $mm^2$. In one embodiment, the IC chip can be 1×1 $mm^2$ or smaller. In one embodiment, the chip is 1 mm×1 mm. The bottom side of the chip's substrate serves as the S1 electrode, and the S2 is a pad fabricated on the top side of the substrate. The pad's size can be between 2500 $\mu m^2$ and 0.25 $mm^2$. In one embodiment, the pad is approximately 85 $\mu m \times 85$ $\mu m$.

Although the previous description discloses a chip configuration that uses the same electrodes for battery and signal transmission, in certain embodiments separate electrodes are employed for power generation and signal transmission.

Figure 49:
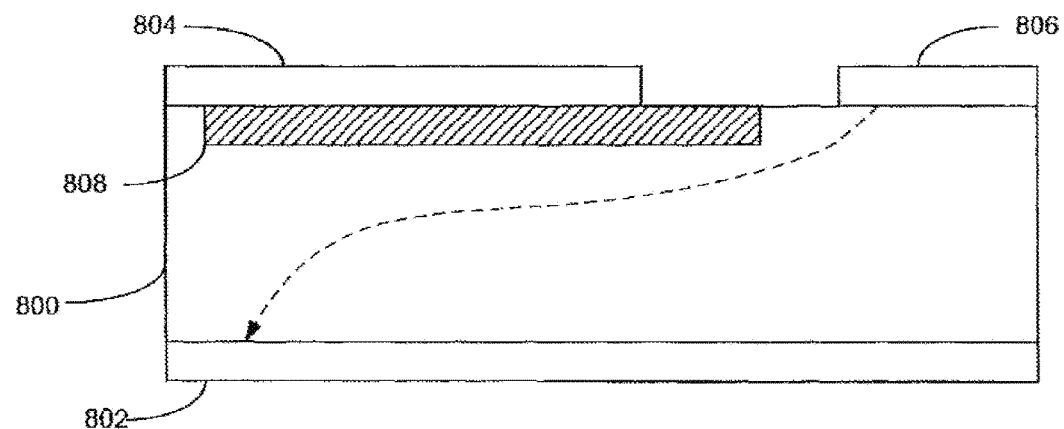
FIG. 49 illustrates an embodiment of an IEM chip configuration where two separate electrodes are used for battery and signal transmission, respectively, in a voltaic sensor.

FIG. 49 illustrates one exemplary IEM chip configuration where two separate electrodes are used for battery and signal transmission, respectively. A ground electrode 802 is fabricated on the bottom side of a substrate 800. On the top side of substrate 800 is a battery electrode 804 and a transmission electrode 806. Also fabricated on substrate 800 is a circuitry region 808. During operation, the battery formed by electrodes 802 and 804 provides a power supply to the circuitry within region 808. The circuitry drives transmission electrodes 806 and 802, and produces a current change in the patient's body. It is possible that the current flowing from transmission electrode 806 to ground electrode 802 may flow below the circuitry region 808, causing changes to the electrical potentials in the circuit elements. Such potential changes can cause undesirable latch-ups in the transistors within circuitry region 808.

One approach to avoid such latch-ups is to separate the transmission-electrode region and the circuitry regions so that there is minimum lateral current flow that would change the potential under the circuits. For example, the substrate contacts can be located in regions that can divert current flow from the circuitry area.

Figure 50:
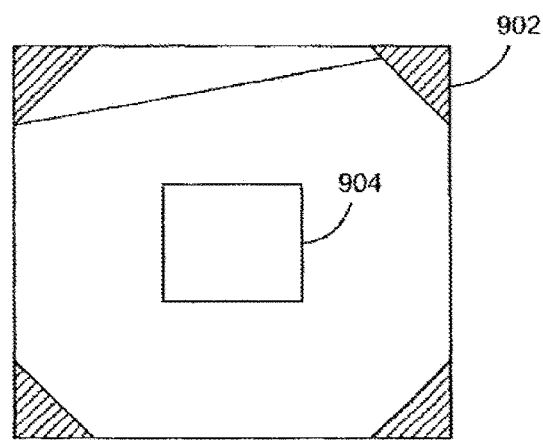
FIG. 50 illustrates an exemplary chip configuration that minimizes circuit latch-ups in accordance with one embodiment of a voltaic sensor.

FIG. 50 illustrates an exemplary chip configuration that minimizes circuit latch-ups in accordance with one embodiment of the present invention. As shown in FIG. 50, it is possible to place substrate contact regions at the four corners of the substrate. As a result, the electrode current flowing toward the substrate is diverted to the four corners, away from the circuitry region which is in the middle. Similarly, special layout design scan be used for the merged-electrode chip configurations.

Figure 51:
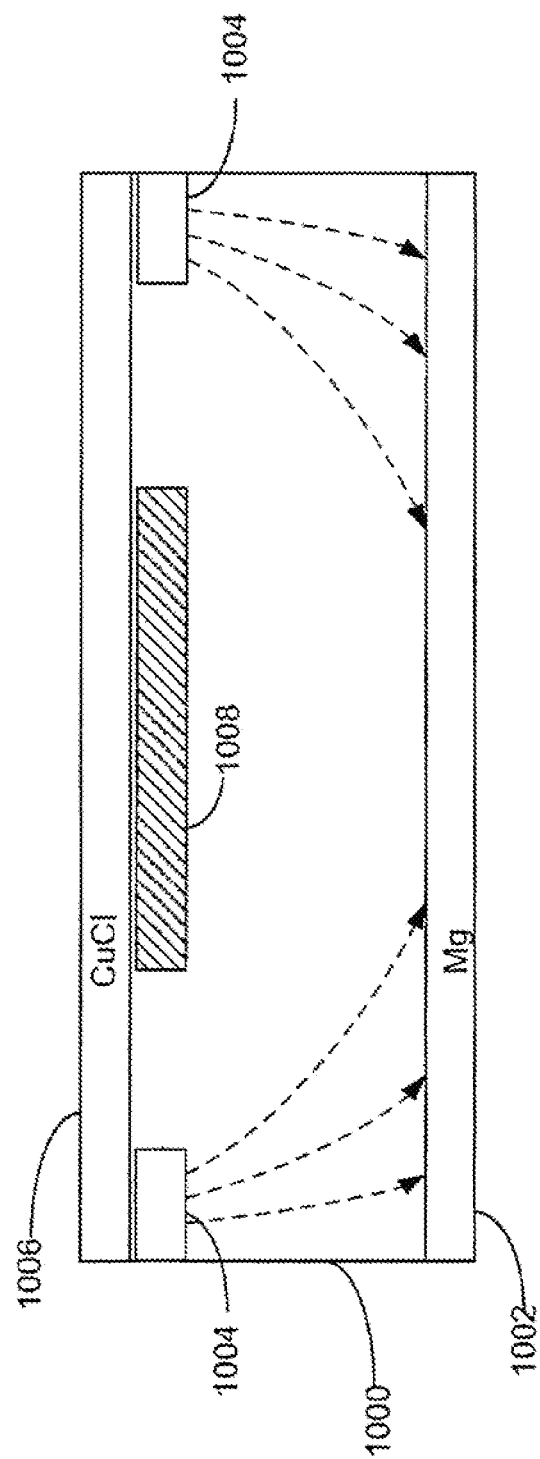
FIG. 51 illustrates an embodiment of a layout for an IEM chip that minimizes latch-ups in an IEM.

FIG. 51 illustrates an exemplary layout that minimizes latch-ups in a IEM chip. As shown in FIG. 51, on the bottom of a substrate 1000 is a Mg electrode 1002. On the top side of substrate 1000 is a CuCl electrode 1006. Electrodes 1002 and 1006 serve as both battery electrodes and transmission electrodes. Below CuCl electrode 1006 are a number of transmission driver circuitry regions 1004, which are located at the peripheral of the layout. A control-logic circuitry region 1008 is located at the center of the chip. This way, the current flowing from the transmission drivers toward the Mg electrode 1002 is diverted away from the control-logic circuitry region 1008, thereby avoiding any latch-ups in the transistors.

Figure 52:
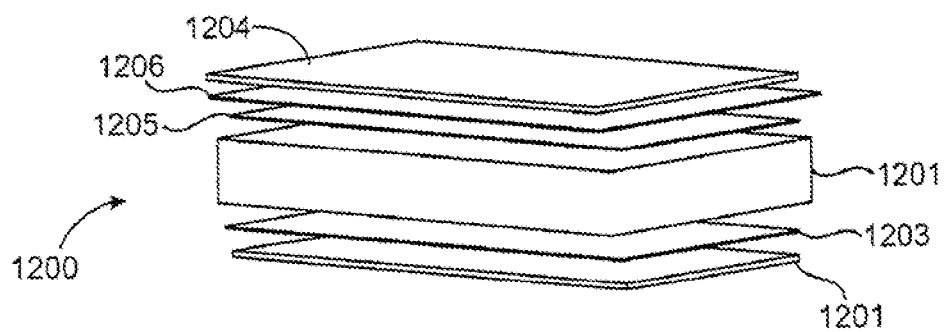
FIG. 52 is an exploded view of an embodiment of an IEM that may be used with a voltaic sensor.

FIG. 52 is an exploded view of an embodiment of an IEM that may be used with the voltaic sensor. In FIG. 52, an IEM 1200 includes silicon dioxide substrate 1201, e.g., having a thickness of 300 $\mu m$. On the bottom surface is an electrode layer of Magnesium 1202, e.g., having a thickness of 8 $\mu m$. Positioned between Mg electrode layer 1202 and bottom surface of substrate 1201 is titanium layer 1203, e.g., having a thickness of 1000 Angstroms. Positioned on upper surface of substrate 1201 is electrode layer (CuCl) 1204, e.g., having a thickness of 6 $\mu m$. Positioned between upper electrode layer 1204 and substrate 1201 is titanium layer 1205, e.g., having a thickness of 1000 Angstroms, and gold layer 1206, e.g., have a thickness of 5 $\mu m$.

While the signal generation and emission protocol above has been described in terms of activation and transmission occurring at substantially the same time, e.g., following contact with target site and/or environment, in certain embodiments the activation of the IEM and transmission of the signal can be separate events, i.e., that may occur at distinct times separated by some duration. For example, an IEM may include a conducting medium that provides for activation prior to ingestion. In certain embodiments, the IEM is encapsulated in a fluid, electrolyte sponge, or other conducting media such that it can be activated externally prior to digestion. In these embodiments, the receiver is configured to detect a transmitted signal only when the signal is transmitted from the target site of interest. For example, the system may be configured so that transmission will only occur upon contact with body tissue insuring proper event marking. For example, activation can occur with handling of the IEM. Pressure sensitive membranes that break with handling or contact may be employed, where braking causes electrolyte material to enable connection of the battery elements. Alternatively, degradation of the gel capsule in the stomach can also release stored electrolyte and activate the IEM. Encapsulating the IEM in a sponge (composed of conducting material which retains water close to the IEM) allows for activation to occur in the presence of small amounts of liquid. This configuration counteracts poor transmission performance in the absence of conducting fluids.

Note that other layout designs are also possible. In addition, silicon-over-insulator (SOI) fabrication techniques can be used to insulate the logic-control circuitry region from the conductive substrate, so that the transmission current cannot interfere with the control circuit.

In certain embodiments, the identifier compositions are disrupted upon administration to a subject. As such, in certain embodiments, the compositions are physically broken, e.g., dissolved, degraded, eroded, etc., following delivery to a body, e.g., via ingestion, injection, etc. The compositions of these embodiments are distinguished from devices that are configured to be ingested and survive transit through the gastrointestinal tract substantially, if not completely, intact.

In certain embodiments, the identifiers do not include an imaging system, e.g., camera or other visualization or imaging element, or components thereof, e.g., CCD element, illumination element, etc. In certain embodiments, the identifiers do not include a sensing element, e.g., for sensing a physiological parameter, beyond the activator which detects contact with the targeted physiological site. In certain embodiments, the identifiers do not include a propulsion element. In certain embodiments, the identifiers do not include a sampling element, such as a fluid retrieval element. In certain embodiments, the identifiers do not include an actuatable active agent delivery element, such as an element that retains an active agent with the composition until a signal is received that causes the delivery element to release the active agent.

The identifiers may be fabricated using any convenient processing technology. In certain embodiments, planar processing protocols are employed to fabricate power sources having surface electrodes, where the surface electrodes include at least an anode and cathode at least partially on the same surface of a circuitry support element. In certain embodiments, planar processing protocols are employed in a wafer bonding protocol to produce a battery source. Planar processing techniques, such as Micro-Electro-Mechanical Systems (MEMS) fabrication techniques, including surface micromachining and bulk micromachining techniques, may be employed. Deposition techniques that may be employed in certain embodiments of fabricating the structures include, but are not limited to: electrodeposition (e.g., electroplating), cathodic arc deposition, plasma spray, sputtering, e-beam evaporation, physical vapor deposition, chemical vapor deposition, plasma enhanced chemical vapor deposition, etc. Material removal techniques include, but are not limited to: reactive ion etching, anisotropic chemical etching, isotropic chemical etching, planarization, e.g., via chemical mechanical polishing, laser ablation, electronic discharge machining (EDM), etc. Also of interest are lithographic protocols. Of interest in certain embodiments is the use of planar processing protocols, in which structures are built up and/or removed from a surface or surfaces of an initially planar substrate using a variety of different material removal and deposition protocols applied to the substrate in a sequential manner. Illustrative fabrication methods of interest are described in greater detail in PCT application serial no. PCT/US2006/016370, the disclosure of which is herein incorporated by reference in its entirety.

In certain fabrication protocols, a sacrificial layer is used. For example, in certain three-dimensional embodiments, such as ones described in greater detail below, where gaps or spaces are desired, sacrificial layers may be employed during fabrication, where such layers are removed in whole or in part prior to use of the battery. Sacrificial layer materials of interest include, but are not limited to, photoresists which can be hard baked to make them stable processing. The photoresist sacrificial layer can be removed using any convenient protocol, e.g., with acetone, once the deposition of the top electrode is complete. Other materials that can be used as a sacrificial layer include, but are not limited to, a silicon nitride, silicon dioxide, benzocyclobutene or tungsten. Other methods of removing the sacrificial layer include but are not limited to gas phase removal, dry etch removal and hydrogen peroxide.

In some embodiments, planar processing, e.g., MEMS, fabrication protocols are employed to fabricate batteries that include an anode and cathode that are at least partially present on the same surface of a circuitry support element. By "at least partially present on the same surface of a circuitry support element" is meant that at least a portion of a cathode and at least a portion of anode are present on the same surface of a circuitry support element, where both electrodes may be entirely present on the surface of the circuitry support element, one electrode may be wholly present on a surface and the other electrode only partially present on surface, e.g., where the other electrode includes a portion that is present on a different surface than the surface on which the first electrode is positioned, and where both electrodes are partially present on the same surface and then partially present on different surfaces. The implantable on-chip battery can be deposited on the chip in a variety of ways. The circuitry support element may take any convenient configuration, and in certain embodiments is an integrated circuit (IC) chip. The surface upon which the electrode elements are positioned may be the top surface, bottom surface or some other surface, e.g., side surface, as desired, where in certain embodiments the surface upon which the electrode elements are at least partially present is a top surface of an IC chip.

Using MEMS fabrication techniques, batteries of some embodiments can be manufactured to be a very small size, e.g., as reviewed above. The electrodes of the batteries can be deposited in a variety of thicknesses, e.g., ranging from about 0.001 to about 1000 µm, such as from about 0.5 to about 10 µm. Where gaps are present between electrodes, the gaps may have a width ranging from about 0.001 to about 1000 µm, such as from about 1 to about 10 µm.

Figure 60:
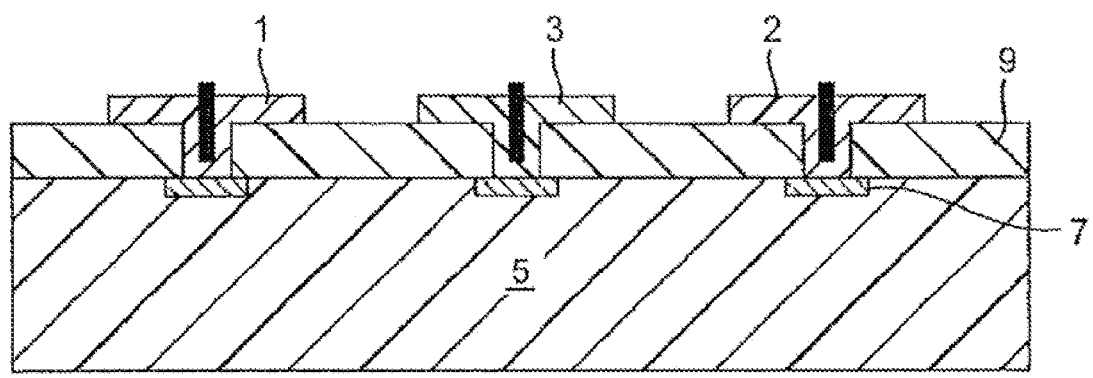
FIG. 60 shows an embodiment of a planar or interdigitated battery for an on-chip battery with two cathodes and one anode that may be incorporated with the voltaic sensor locating system.

In one embodiment two cathodes are deposited on the surface of a chip with an anode separating the two cathodes. A dielectric layer is deposited in between the electrodes and the circuit chip with circuit contacts penetrating the chip surface. This configuration allows multiple batteries to be put into series which provides for a greater voltage to be applied to the circuit chip upon activation of the battery by contact with the target site. FIG. 60 shows a planar, interdigitated battery layout. The dielectric material 9 is deposited on the circuit chip 5 which contains the circuit contacts 7. The anode 3 separates the first cathode 1 from the second cathode 2. Embodiments employing this configuration include ones in which batteries are in series (e.g., as described above), which provides for higher voltages that may be used by the circuit upon contact with the target physiological site. In certain embodiments, this configuration also provides for low battery impedance because the electrodes are placed so closely together. This embodiment is characterized in that both the cathode and anode elements are wholly present on the same surface of the chip.

In some embodiments, at least one of the anode and cathode elements is partially present on the same surface as the other electrode, but also partially present on another surface, e.g., side, bottom, etc., of the chip. For example, the anode may be present on a small portion of one side of the surface of the circuit chip and wrap around that side to cover the bottom of the circuit chip. The cathode is present on the remainder of the top surface of the circuit chip, and a small gap is provided between the cathode and the anode. In one aspect, a large cathode plate covers a majority of the top surface of the circuit chip while the anode covers the bottom surface of the circuit chip and wraps around the side to the top surface. Both electrodes, e.g., plates, can be connected to the circuit chip via a circuit contact through the dielectric layer on the top surface of the chip.

Figure 61:
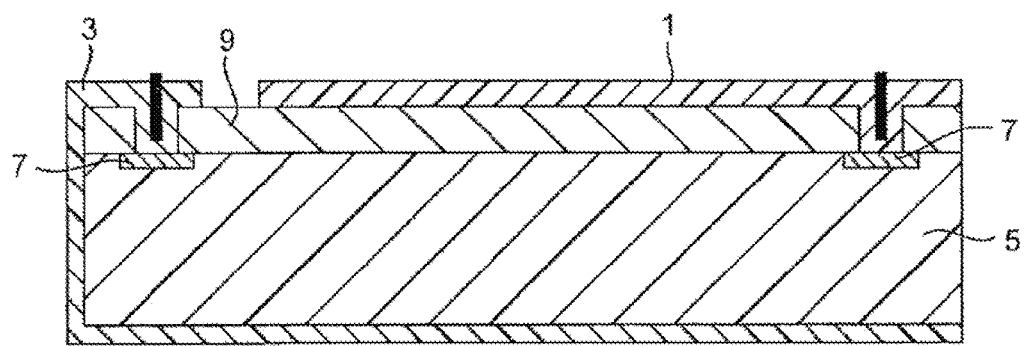
FIG. 61 shows an embodiment of a large plate configuration for an on-chip battery that may be incorporated with the voltaic sensor locating system.

FIG. 61 shows the dielectric material 9 covering the circuit chip 5. Cathode 1 is deposited over a majority of the top surface of the dielectric material 9. The anode 3 is deposited over the remainder of the top surface as well as the side and bottom surfaces of the circuit chip 5 saving a separation between the cathode 1 and anode 3 on the top. In certain embodiments, the separation ranges from about 0.001 to about 1000 μm, such as from about 0.1 to about 100 μm, e.g., about 2.0 μm. In certain embodiments, the circuit chip 5 may be flipped during fabrication in order to deposit the anode 3 on the bottom surface of the chip 5. Circuit contacts 7 for both the anode 3 and cathode 1 are provided on the top surface of the circuit chip 5, traveling down through the dielectric 9. This configuration provides a very large electrode area since it utilizes both the top and bottom of the circuit chip 5 as well as one of the sides.

In another embodiment, a cathode is positioned on a top surface of a circuit chip, e.g., present as a layer that has been deposited over a dielectric on the top surface of the circuit chip. During fabrication, a sacrificial layer is then deposited on top of the cathode layer. An anode layer is then deposited on top of the sacrificial layer. The sacrificial layer can then be removed leaving a gap which provides an area for target site fluids, e.g., electrolytic stomach fluids, to contact the anode and cathode. Using this embodiment, additional electrode layers can be stacked on top of one another after depositing another sacrificial layer on top of the anode. In doing so, the implantable on-chip battery can be put into series, e.g., where a vertical series configuration is desired.

Figure 62:
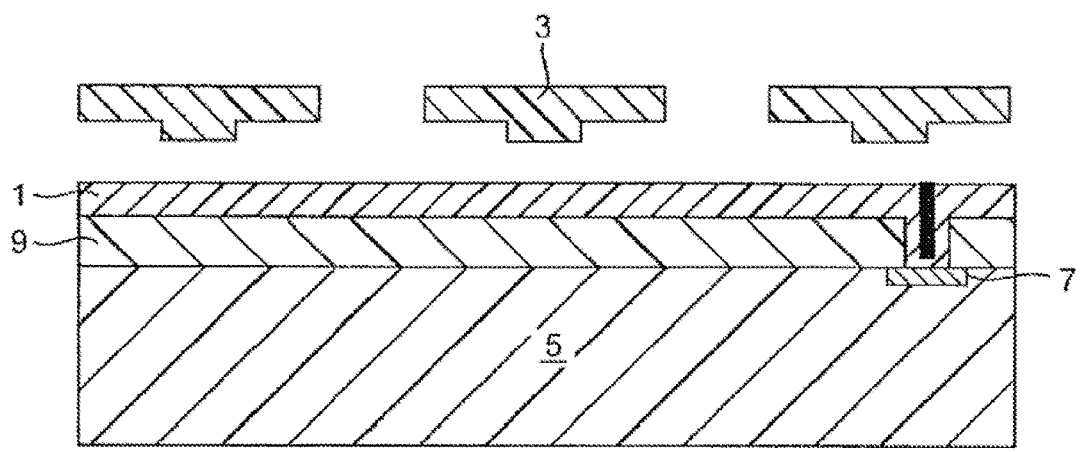
FIG. 62 shows an embodiment of a 3-d configuration of an on-chip battery with three anodes bridged over the cathode that may be incorporated with the voltaic sensor locating system.

FIG. 62 shows dielectric layer 9 disposed on top of circuit chip 5. The cathode 1 is deposited on top of dielectric layer 9 and through to the circuit contact 7. A sacrificial layer (not shown) is deposited on top of the cathode 1 to provide a base for the anodes 3 to be deposited. Once the sacrificial layer is deposited, its surface can be etched to provide a rougher surface. Therefore, when the anodes 3 are deposited onto the sacrificial layer, the bottom of the anodes 3 will conform to a rough surface. The sacrificial layer could also be deposited using cathodic arc, which would deposit it in a rough and porous manner. Multiple anodes 3 can be deposited in multiple sizes to provide multiple voltages to the chip circuit 5. Once the anodes 3 are deposited, the sacrificial layer can be removed to create a gap, where in certain embodiments the gap ranges from about 0.001 to about 1000 μm, such as from about 0.1 to about 100 μm, and including from about 1 to about 10 μm. In certain embodiments, the gab between the anodes 3 and the cathode 1 is chosen to provide a battery with desired impedances and different currents. The areas of the anodes 3 can also be manufactured to provide different voltages to the circuit chip 5, as desired. Therefore, the anodes 3 can be manufactured to provide multiple voltages with multiple impedances and currents for the same chip, with minimal use of chip space.

Figure 63:
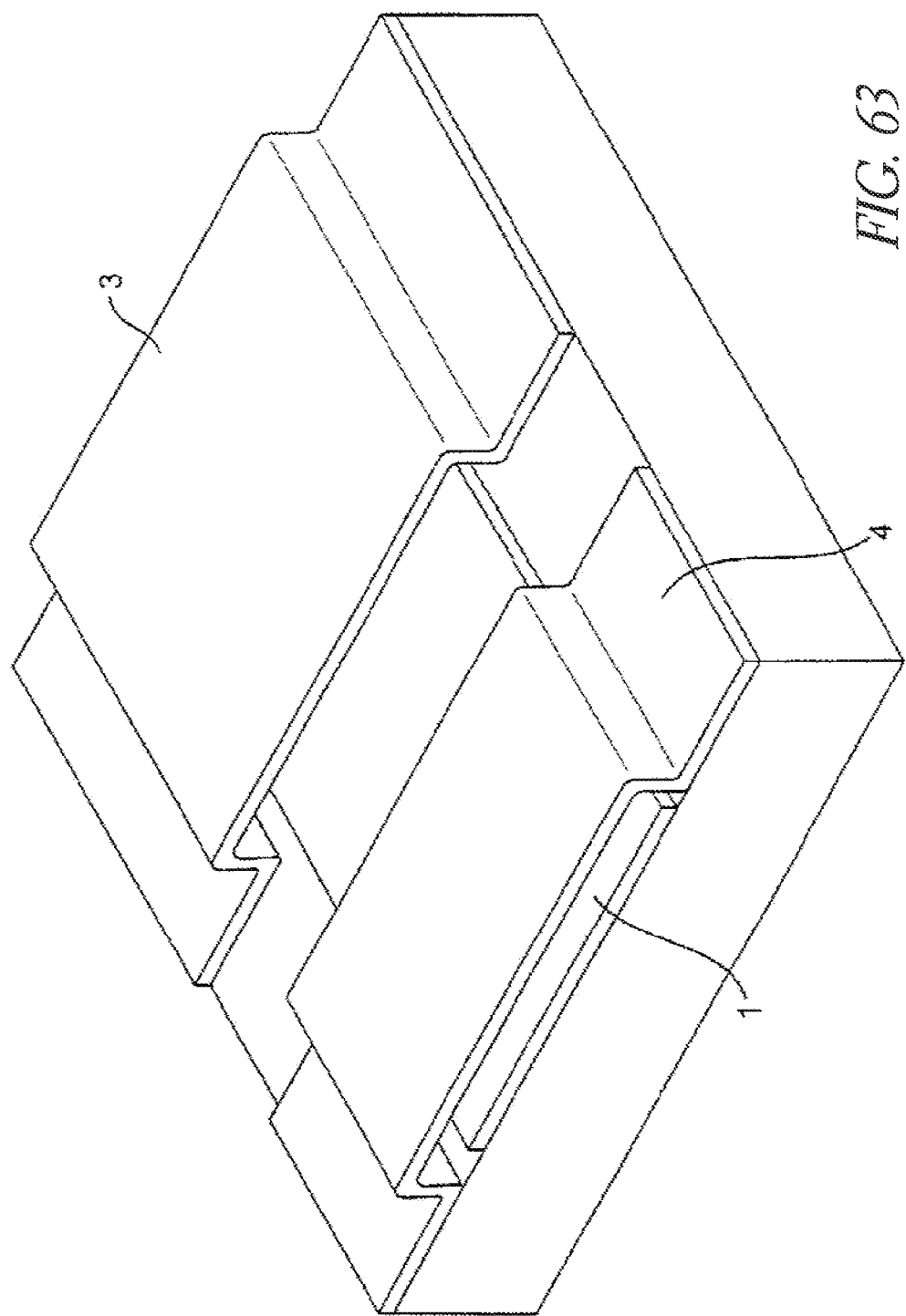
FIG. 63 is a perspective view of a 3-d configuration of an on-chip battery that may be incorporated with the voltaic sensor locating system.

In some embodiments, a cathode layer is deposited over the dielectric on the surface of the chip, and multiple anodes are deposited over different areas of the cathode. A sacrificial layer is deposited to separate the anodes from the cathode during fabrication, and upon removal produces a gap between the common cathode and two or more anodes positioned over the cathode. As shown in FIG. 63, the anode 3 may be anchored to the outer area of the circuit chip 5. It is at that point 4 where the circuit contact for the anode 3 may be placed. FIG. 63 differs from FIG. 62 in that only two anodes 3 are deposited above the cathode 1. The two anodes 3 are also different sizes, and therefore provide different surface areas. The anodes 3 can be manufactured to meet the requirements of the application. If multiple voltages are desired, the anodes 3 can be manufactured out of different materials. If multiple currents are desired, the anodes 3 can be deposited in multiple sizes. If multiple impedances are desired, the anodes 3 can be deposited with different sized gaps between the anodes 3 and the cathode 1.

Figure 64:
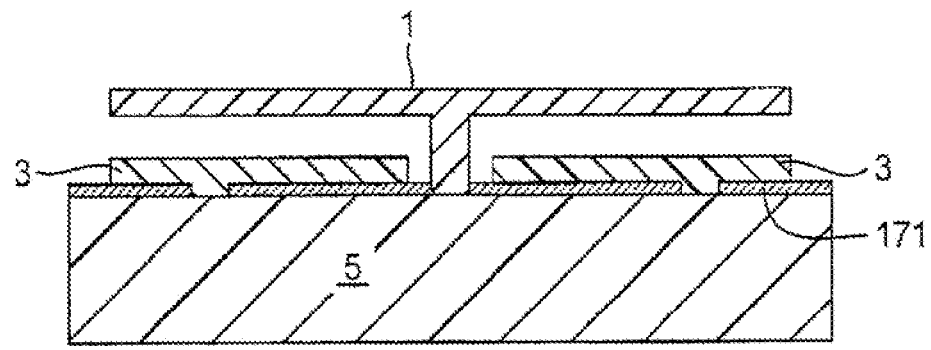
FIG. 64 depicts another embodiment of an on-chip battery that may be incorporated with the voltaic sensor locating system.

In some embodiments, two anode plates are present on the surface of the circuit chip with a cathode circuit contact deposited in the middle of the surface. The cathode is then attached to the circuit contact in a way such that it hangs over the anodes, thereby forming a gap between the cathode and anode. FIG. 64 shows another embodiment of the implantable on-chip capacitor that utilizes the space above the circuit chip 5. An insulating layer 171 is formed on the surface of the circuit chip 5. The circuit contact for the cathode 1 is formed at the center of the chip with anodes 3 formed at either side leaving a gap between the circuit contact and the anodes 3. During fabrication, a sacrificial layer is then deposited on top of the anodes 3 to form a base for the cathode 1. Once the cathode 1 is deposited, the sacrificial layer is removed providing a space for the liquid to enter.

Figure 65:
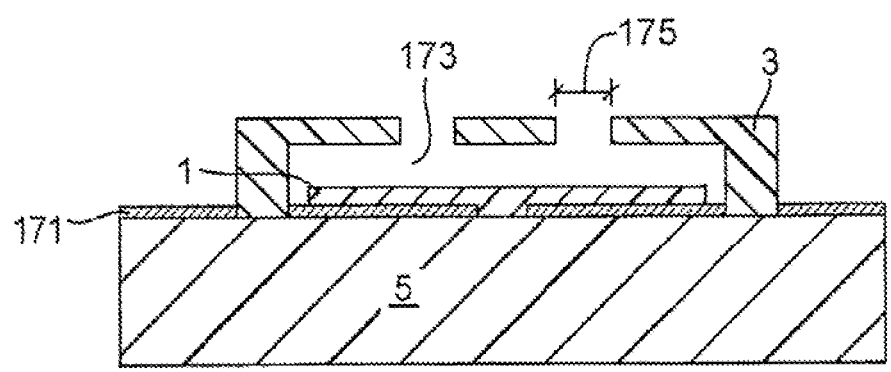
FIG. 65 depicts another embodiment of an on-chip battery that may be incorporated with the voltaic sensor locating system.

In some embodiments, a cathode is present on the surface of the circuit chip with an anode positioned in a manner sufficient to provide an open chamber above and at least partially around the cathode. Openings are provided that allow electrolytic fluid to flow into the chamber, which produces a current path between the anode and the cathode. Multiple openings may be provided as desired, e.g., in order to ensure that no air gets trapped inside of the chamber. In FIG. 65, the anode 3 surrounds the cathode 1 creating a chamber 173 into which an electrolytic fluid will enter. An insulating layer 11 separates the cathode 1 from the circuit chip 5. Upon contact with the target site, the electrolytic fluid will enter the chamber 173 through the openings 175. The openings 175 may be situated in opposite corners of the chamber 173 to make sure that no air gets trapped inside. The configuration of FIG. 65 may be desirable in certain instances. For instances when there may not be an abundant amount of electrolytic fluid present in the stomach, the implantable on-chip battery can be fabricated to contain the fluid it comes in contact with around the electrodes, e.g., as shown in FIG. 65. By doing so the battery would be assured of having a continuous reaction whereas, if it were open, the fluid may enter and exit the reaction area and cause the battery to stop.

Where a given battery unit includes a chamber, e.g., as shown in FIG. 65, surface coating to modulate fluid flow into and out of the chamber may be employed, as desired. In certain embodiments, the surface of a portion of the chamber, e.g., an interior surface of the chamber, may be modified to provide for desired fluid flow properties. For example, the surface energy of one or more surfaces of the chamber and fluid ports may be modified to provide for enhanced fluid flow into the chamber. For example, the surface energy of one or more surfaces of the chamber may be increased, such that the surface becomes more hydrophilic. A variety of different surface energy modification protocols may be employed, where the particular protocol chosen may depend on the particular composition of the barrier and the desired surface energy properties. For example, if one wishes to increase the surface energy of a given surface, the surface may be subjected to plasma treatment, contacted with a surface energy modification such as surface modifying polymer solutions described in, e.g., U.S. Pat. Nos. 5,948,227 and 6,042,710, the disclosure of each of which is incorporated herein in its entirety for all purposes. In certain embodiments, a hydrophilic substance may be employed to attract and retain the electrolytic fluid within the chamber, e.g., as described in PCT application serial no. PCT/US07/82563, the disclosure of which is herein incorporated by reference in its entirety.

In certain embodiments, one or more surfaces of the battery, e.g., interior surfaces of a chamber, are modified to modulate gas bubble formation and positioning on the surface. For example, activation of a battery may result in bubble production, e.g., hydrogen gas bubble production. Surface modification may be employed so that bubbles produced during activation, e.g., on the active cathode, are drawn from the cathode to another location, e.g., away from the cathode, outside of the chamber, etc.

The above embodiments are examples of planar processing protocol produced batteries in which at least one anode and at least one cathode are present on the same surface of a circuitry support element. The above description is in no way limiting, as other embodiments may be produced which have the above common characteristic.

In some embodiments, planar processing protocols are employed in a wafer bonding protocol to produce a battery source. In certain of such embodiments, a dielectric can be deposited on a circuit chip. A cathode layer can then be deposited on top of the dielectric. An anode can be deposited on a separate support wafer. The anode may then be bonded to the bottom of the circuit chip at which point the support wafer can be etched out to allow the anode surface to come in contact with the electrolytic fluid. As such, another fabrication technique that can be used in making the implantable on-chip battery is wafer bonding.

Figure 66:
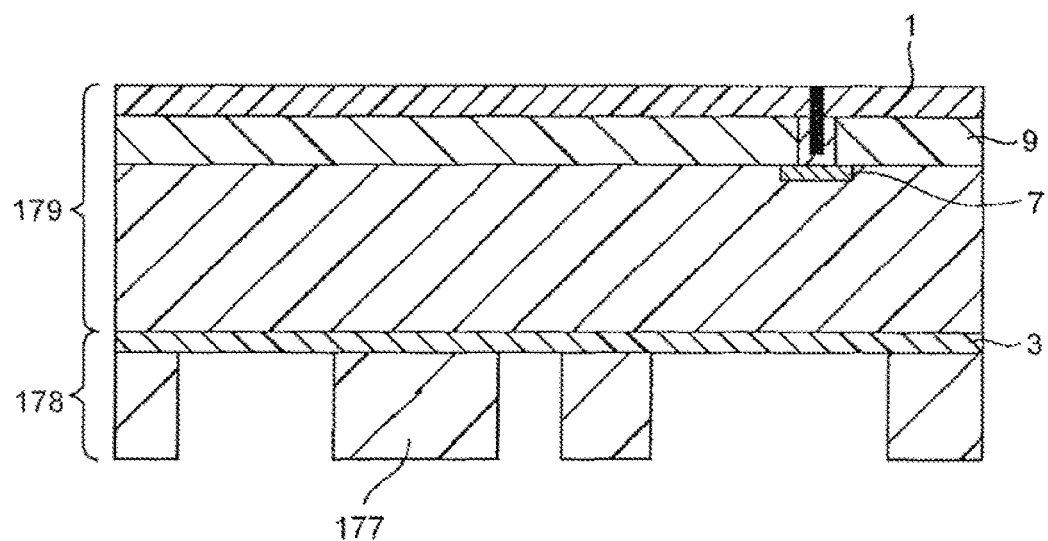
FIG. 66 depicts another embodiment of an on-chip battery that uses wafer bonding that may be incorporated with the voltaic sensor locating system.

The implantable on-chip battery can be manufactured using two wafers, such as in the embodiment of FIG. 66. The circuit chip 5 provides the base for the cathode 1, which is deposited on top of a dielectric 9. This composes the first wafer assembly 179. The second wafer assembly 178 is comprised of a support wafer 177 and the anode 3. The anode 3 is deposited on the surface of the support wafer 177. The anode 3 is then bonded to the circuit chip 5 and the bulk support wafer 177 is etched away exposing areas of the anode 3. The amount of the support wafer 177 that is etched away is dependent on the areas that are desired for the anode 3. This fabrication method can be useful for the implantable on-chip battery because if more circuitry is desired it can be placed in the support wafer 177.

These embodiments discussed above and others can be altered to switch a cathode with an anode and vice versa, providing yet additional disclosed configurations of the invention. Additional planar process fabricated embodiments of interest include those described in U.S. Provisional Application Ser. No. 60/889,868; the disclosure of which is herein incorporated by reference in its entirety.

In addition to the identifier component described above, the ingestible event markers may be present in (i.e., combined with) a physiologically acceptable carrier component, e.g., a composition or vehicle that aids in ingestion of the identifier and/or protects the identifier until it reaches the target site of interest. By "physiologically acceptable carrier component" it is meant a composition, which may be a solid or fluid (e.g., liquid), which is ingestible. Such markers may be incorporated into an intragastric locating system in any of the manners described herein, for example by incorporation into a catheter, with the intragastric device such as the balloon, with an intermediate device coupling the catheter to the intragastric device, or others. The markers may be configured to release from any structure of the intragastric locating system, for example after location has been confirmed. Such markers may be implemented in a physiologically acceptable carrier component to assist in passage, disposal, etc. of the marker.

Common carriers and excipients, such as corn starch or gelatin, lactose, dextrose, sucrose, microcrystalline cellulose, kaolin, mannitol, dicalcium phosphate, sodium chloride, and alginic acid are of interest. Disintegrators commonly used in the formulations of the invention include croscarmellose, microcrystalline cellulose, corn starch, sodium starch glycolate and alginic acid.

A liquid composition may comprise a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder. For example, a powder containing active compound, suspending agent, sucrose and a sweetener can be reconstituted with water to form a suspension; and a syrup can be prepared from a powder containing active ingredient, sucrose and a sweetener.

A composition in the form of a tablet or pill can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

"Controlled release", "sustained release", and similar terms are used to denote a mode of active agent delivery that occurs when the active agent is released from the delivery vehicle at an ascertainable and controllable rate over a period of time, rather than dispersed immediately upon application or injection. Controlled or sustained release may extend for hours, days or months, and may vary as a function of numerous factors. For the pharmaceutical composition of the present invention, the rate of release will depend on the type of the excipient selected and the concentration of the excipient in the composition. Another determinant of the rate of release is the rate of hydrolysis of the linkages between and within the units of the polyorthoester. The rate of hydrolysis in turn may be controlled by the composition of the polyorthoester and the number of hydrolysable bonds in the polyorthoester. Other factors determining the rate of release of an active agent from the present pharmaceutical composition include particle size, acidity of the medium (either internal or external to the matrix) and physical and chemical properties of the active agent in the matrix.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example, liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methyl-cellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product. These may be similar to the flavoring agents used in some embodiments to signal to a user that the intragastric balloon has deflated, as described herein.

Other components suitable for use in the formulations of the present invention can be found in Remington's Pharmaceutical Sciences, Mace Publishing Company, Philadelphia, Pa., 17th ed. (1985).

The locating systems may include signal receivers configured to receive a signal from the identifier of the IEM, i.e., to receive a signal emitted by the IEM upon contact of the IEM with the target physiological site following ingestion of the IEM. The signal receiver may vary significantly depending on the nature of the signal that is generated by the signal generation element, e.g., as reviewed below. As such, the signal receiver may be configured to receive a variety of different types of signals, including but not limited to: RF signals, magnetic signals, conductive (near field) signals, acoustic signals, etc., as indicated above.

In certain embodiments, the receiver is configured to receive a signal conductively from another component, e.g., the identifier of an IEM, such that the two components use the body of the patient as a communication medium. As such, the signal that is transferred between identifier of the IEM and the receiver travels through the body, and requires the body as the conduction medium. The identifier emitted signal may be transmitted through and received from the skin and other body tissues of the subject body in the form of electrical alternating current (a.c.) voltage signals that are conducted through the body tissues. As a result, such embodiments do not require any additional cable or hard wire connection, or even a radio link connection for transmitting the sensor data from the autonomous sensor units to the central transmitting and receiving unit and other components of the system, since the sensor data are directly exchanged via the skin and other body tissues of the subject. This communication protocol has the advantage that the receivers may be adaptably arranged at any desired location on the body of the subject, whereby the receivers are automatically connected to the required electrical conductor for achieving the signal transmission, i.e., the signal transmission is carried out through the electrical conductor provided by the skin and other body tissues of the subject. Where the receivers include sensing elements (see below), one may have a plurality of receiver/sensor elements distributed throughout the body and communicating with each other via this body conductive medium protocol. Such a body-based data transmission additionally has the advantage that the transmitting power required therefore is extremely small. This avoids the generation of interference in the electrical operation of other devices, and also helps to prevent the unintended interception or tapping and surveillance of the sensitive medical data. The resulting very low power consumption is additionally advantageous for achieving the goal of a long-term monitoring, especially in applications having a limited power supply.

The signal receiver is configured to receive a signal from an identification element of an IEM. As such, the signal receiver is configured so that it can recognize a signal emitted from an identifier of an IEM. In certain embodiments, the signal detection component is one that is activated upon detection of a signal emitted from an identifier. In certain embodiments, the signal receiver is capable of (i.e., configured to) simultaneously detecting multiple pharma-informatics enabled compositions, e.g., 2 or more, 5 or more, 10 or more, etc.

The signal receiver may include a variety of different types of signal receiver elements, where the nature of the receiver element necessarily varies depending on the nature of the signal produced by the signal generation element. In certain embodiments, the signal receiver may include one or more electrodes (e.g., 2 or more electrodes, 3 or more electrodes, includes multiple, e.g., 2 or more, 3 or more, 4 or more pairs of electrodes, etc.) for detecting signal emitted by the signal generation element. In certain embodiments, the receiver device will be provided with two electrodes that are dispersed at a distance, e.g., a distance that allows the electrodes to detect a differential voltage. This distance may vary, and in certain embodiments ranges from about 0.1 to about 5 cm, such as from about 0.5 to about 2.5 cm, e.g., about 1 cm. In certain embodiments, the first electrode is in contact with an electrically conductive body element, e.g., blood, and the second electrode is in contact with an electrically insulative body element relative to said conductive body element, e.g., adipose tissue (fat). In an alternative embodiment, a receiver that utilizes a single electrode is employed. In certain embodiments, the signal detection component may include one or more coils for detecting signal emitted by the signal generation element. In certain embodiments, the signal detection component includes an acoustic detection element for detecting signal emitted by the signal generation element. In certain embodiments, multiple pairs of electrodes (e.g., as reviewed above) are provided, for example to increase detection probability of the signal.

The signal receivers of interest include both external and implantable signal receivers. In external embodiments, the signal receiver is ex vivo, by which is meant that the receiver is present outside of the body during use. Where the receiver is implanted, the signal receiver is in vivo. The signal receiver is configured to be stably associated with the body, e.g., either in vivo or ex vivo, at least during the time that it receives the emitted signal from the IEM.

In the broadest sense, receivers of the invention may be either mobile or immobile relative to the patient for which they are configured to operate. Mobile embodiments of the signal receiver include ones that are sized to be stably associated with a living subject in a manner that does not substantially impact movement of the living subject. As such, embodiments the signal receiver have dimensions that, when employed with a subject, such as a human subject, will not cause the subject to experience any difference in its ability to move. In these embodiments, the receiver is dimensioned such that its size does not hinder the ability of the subject to physically move.

In certain embodiments, the signal receivers can be configured to have a very small size. Where the signal receiver has a small size, in certain embodiments the signal receiver occupies a volume of space of about 5 cm$^3$ or less, such as about 3 cm$^3$ or less, including about 1 cm$^3$ or less. In certain embodiments, the desired functionality of the signal receiver is achieved with one rechargeable battery.

In addition to receiving a signal from an identifier of an ingestible event marker, the signal receiver may further include one or more distinct physiological parameter sensing abilities. By physiological parameter sensing ability is meant a capability of sensing a physiological parameter or biomarker, such as, but not limited to: chemical composition of fluid, In certain embodiments, the signal receiver includes a set of 2 or more electrodes that provide for dual functions of signal receiving and sensing. For example, in addition to receiving signal, the electrodes can also serve additional sensing functions.

In certain embodiments, a signal receiver that may be viewed as an autonomous sensor unit is included. In certain of these embodiments, the sensor unit includes a sensor and a pair of transmit/receive electrodes that are adapted to be arranged on the skin or body surface of the subject. The receiver may further include a central transmitting and receiving unit which is adapted to be arranged on the body of the subject, and a portable data recording unit. The autonomous sensor units are adapted to acquire sensor data from the body of the subject that may be indicative of the location of the marker, i.e., medical and/or physical data such as one or more of pulse rate, blood oxygen content, blood glucose content, other blood composition data, blood pressure data, electrocardiogram data, electroencephalogram data, respiration rate data, perspiration data, body temperature data, activity, motion, electrode impedance, and the like. In addition, the component includes the ability to receive a signal from an internal device, e.g., the identifier of an IEM. The transmit/receive electrodes of each autonomous sensor unit are adapted to transmit the acquired sensor data into the body of the subject, so that these sensor data are transmitted via the skin and/or other body tissues of the subject to a central transmitting and receiving unit, such as the sensor interface units described above with respect to the electromagnetic locating systems. Other signals, such as monitoring signals and polling signals can be transmitted from the central transmitting and receiving unit through the body tissues of the subject to the sensor unit, where these signals are picked up by the transmit/receive electrodes of the respective sensor unit.

Additional elements that may be present in the signal receiver include, but are not limited to: a signal demodulator, e.g., for decoding the signal emitted from ingestible event marker; a signal transmitter, e.g., for sending a signal from the signal receiver to an external location; a data storage element, e.g., for storing data regarding a received signal, physiological parameter data, medical record data, etc.; a clock element, e.g., for associated a specific time with an event, such as receipt of a signal; a pre-amplifier; a microprocessor, e.g., for coordinating one or more of the different functionalities of the signal receiver.

Aspects of implantable versions of the signal receiver will have a biologically compatible enclosure, two or more sense electrodes, a power source, which could either be a primary cell or rechargeable battery, or one that is powered by broadcast inductively to a coil. The signal receiver may also have circuitry that includes a demodulator to decode the transmitted signal, some storage to record events, a clock, and a way to transmit outside the body. The clock and transmit functionality may, in certain embodiments, be omitted. The transmitter could be an RF link or conductive link to transfer information from local data storage to an external data storage device.

The demodulator component, when present, may be any convenient demodulator configured to demodulate the signal emitted from the identifier of the pharma-informatics enabled pharmaceutical composition. In certain embodiments, the demodulator is an in-vivo transmission decoder that allows for accurate signal decoding of a low-level signal, even in the presence of significant noise, using a small-scale chip which consumes very low power. In one embodiment, the in-vivo transmission decoder is designed to decode signals which were modulated using binary phase shift keying (BPSK). The signal can then be demodulated using a Costas loop. The binary code is recovered by applying a symbol recovery technique to the Costas loop output. In some embodiments, the in-vivo transmission decoder can include an automatic gain control (AGC) block. The AGC block can determine the strongest frequency component and signal power of the incoming signal. The strongest frequency of the signal can be used to adjust filters and voltage-controlled oscillators in other parts of the algorithm. This can help the receiver to actively adjust to variations of the incoming signal frequency and drift of the incoming signal frequency. By measuring the signal power, the AGC block can then calculate and apply the gain necessary to normalize the signal power to a predetermined value. This gain can further be adjusted by reading the signal power at the Costas loop. In one embodiment, the in-vivo transmission decoder can actively adjust the sampling rate of the incoming signal to adjust to conditions such as the amount of noise present. For example, if the signal to noise ratio (SNR) is sufficient, the sampling rate can be maintained at a low value. If the SNR decreases below a set threshold during the decoding process, the sampling rate can be increased. In this manner, the sampling rate can be kept as low as possible without compromising the accuracy of the recovered signal. By actively adjusting the sampling rate to be as low as possible, the algorithm saves power. Further aspects of such in-vivo transmission decoders are provided in U.S. Provisional Application Ser. No. 60/866,581 titled "In-Vivo Transmission Decoder," the disclosure of which application is herein incorporated by reference in its entirety.

In certain embodiments, the components or functional blocks of the present receivers are present on integrated circuits, where the integrated circuits include a number of distinct functional blocks, i.e., modules. Within a given receiver, at least some of, e.g., two or more, up to an including all of, the functional blocks may be present in a single integrated circuit in the receiver. By single integrated circuit is meant a single circuit structure that includes all of the different functional blocks. As such, the integrated circuit is a monolithic integrated circuit (also known as IC, microcircuit, microchip, silicon chip, computer chip or chip) that is a miniaturized electronic circuit (which may include semiconductor devices, as well as passive components) that has been manufactured in the surface of a thin substrate of semiconductor material. The integrated circuits of certain embodiments of the present invention may be hybrid integrated circuits, which are miniaturized electronic circuits constructed of individual semiconductor devices, as well as passive components, bonded to a substrate or circuit board.

Figure 53:
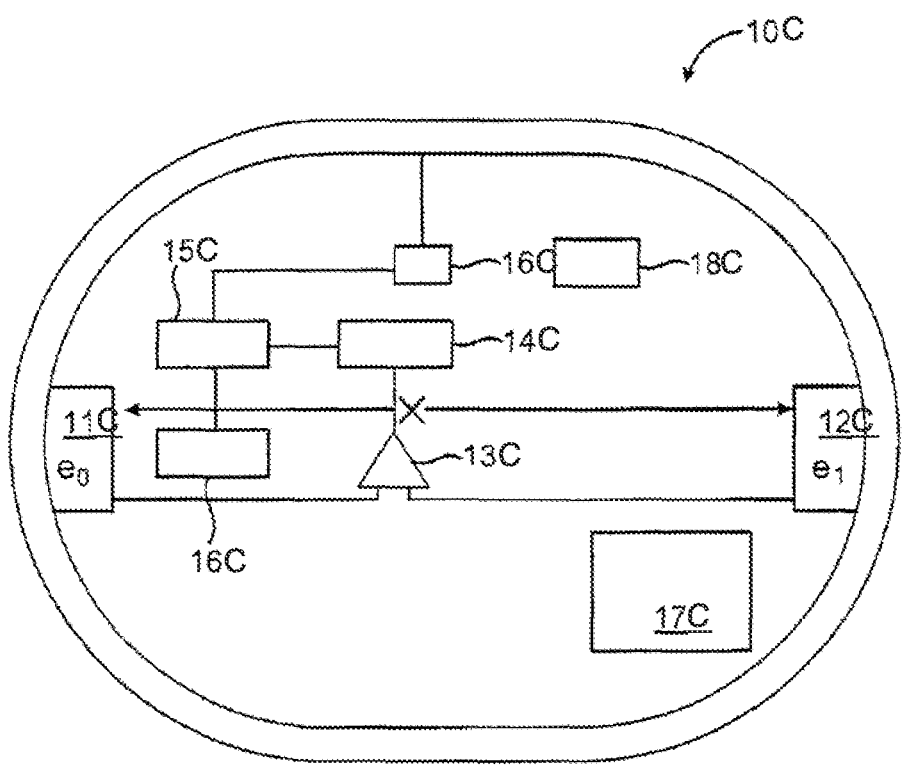
FIG. 53 is a diagram showing an embodiment of a signal receiver that may be incorporated with a voltaic sensor.

FIG. 53 provides a schematic representation of a functional block diagram according to an embodiment of the invention. In FIG. 53, a receiver 10C includes first and second electrodes 11C & 12C respectively, which are separated by distance X and serve as an antenna to receive a signal generated by an identifier. The distance X may vary, and in certain embodiments ranges from about 0.5 to about 5 cm, such as from about 0.5 to about 1.5 cm, e.g., about 1 cm. Amplifier 13C detects the differential signal across the electrodes. The detected signal then goes into the demodulator 14C. Also shown is memory 15C to store the demodulated data. Clock 16C which writes to that memory which time-stamps the events. Transmit circuit (Tx) (16) transfers data from the memory out to the external receiver (not shown). There is also a power source 17C which powers all the microelectronics. In the embodiment depicted, also present is a microprocessor 18C, which coordinates the function between all these blocks. Finally, a coil 19C wound around the perimeter provides for RF transmission out. As summarized above, all of the different functional blocks shown in the embodiment of FIG. 53 could be on the same integrated circuit.

Figure 54:
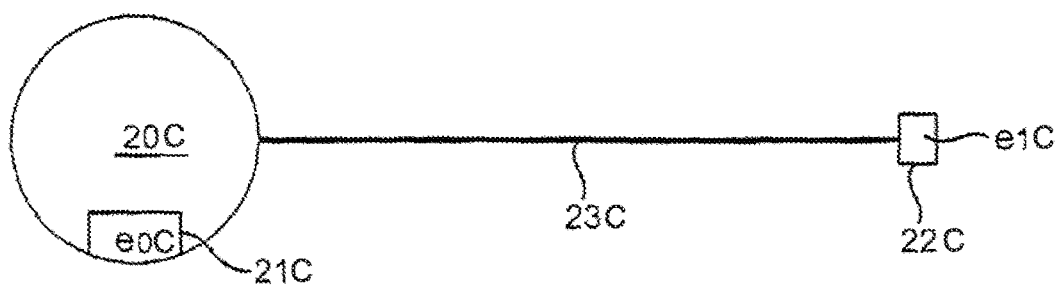
FIG. 54 is a diagram of an embodiment of a signal receiver that may be incorporated with a voltaic sensor.

Another embodiment is depicted in FIG. 54. In FIG. 54, the main portion of the receiver 20C includes all of the functionalities listed above and electrode 21C. Also shown is electrode 22C which is at the end of wire 23C. This configuration provides for sufficient distance between $e_0$ and $e_1$ to serve as an effective receiver and yet minimizes the overall size of the receiver 20C.

In some embodiments, the signal receivers may be external. Where the signal receivers are external, they may be configured in any convenient manner. External configuration may include any of the elements described above with respect to implantable embodiments, as desired. As such, external receivers may include circuits as depicted in FIG. 53, and described above. Accordingly, elements as described above, such as signal receivers, transmitters, memory, processors, demodulators, etc., may be present in external receivers of the invention, as desired. For example, functional diagrams of circuitry that may be present in external receivers of the invention are shown in FIGS. 55A and 55B.

Figure 55A:
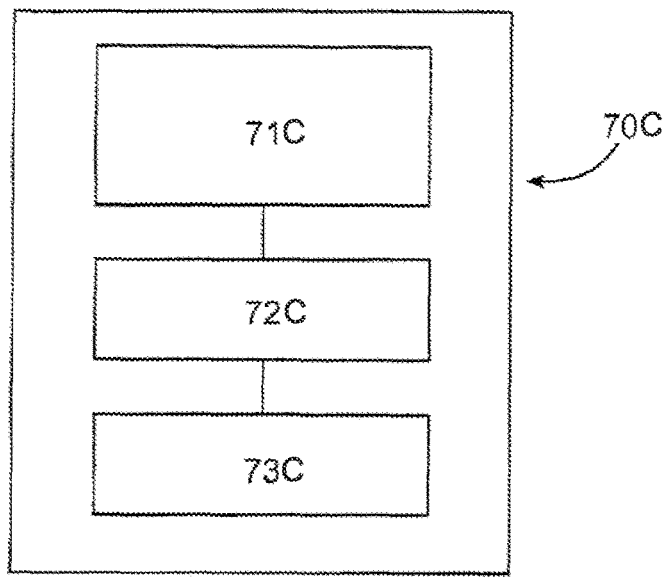
FIGS. 55A and 55B provide additional information about various aspects of embodiments of external receivers according to embodiments of the voltaic sensor.
Figure 55B:
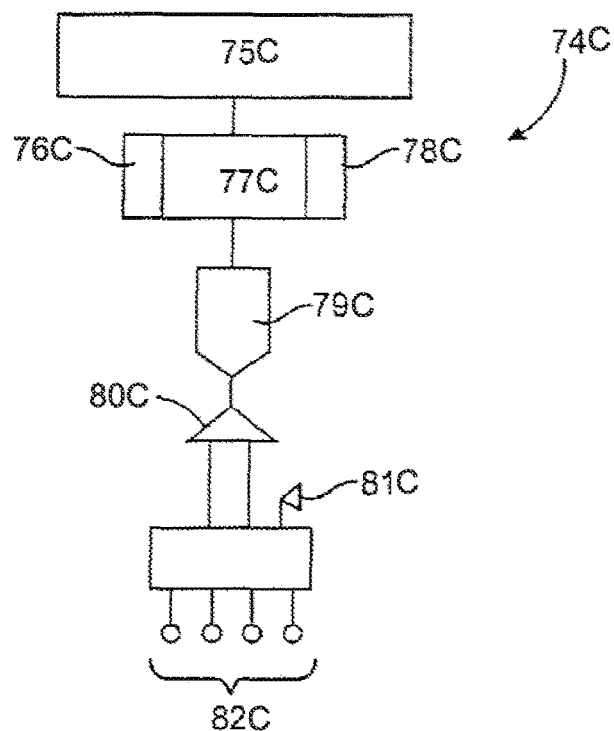

FIG. 55A provides a functional block diagram of a receiver 70C according to one embodiment, where the receiver includes an external interface block 71C, where the external interface block may include a wireless communication element (e.g., antenna), serial port, conductive interface, etc. Also present is signal receiver circuitry block 72C. Also present is receiver electrodes functional block 73C. FIG. 55B provides a view of a circuit 74C found in a receiver according to an embodiment of the invention. Circuit 74C includes external interface 75C, memory 76C, digital signal processor (DSP) 77C and real time clock (RTC) 78C. Also shown is analog to digital converter (ADC) 79C, pre-amplifier 80C, optional reference (common mode cancellation circuit) 81C and electrodes 82C.

In certain external embodiments, the receiver may be configured to be in contact with or associated with a patient only temporarily, i.e., transiently, for example while the ingestible event marker is actually being ingested. For example, the receiver may be configured as an external device having two finger electrodes or handgrips. Upon ingestion of the IEM, the patient or a healthcare provider touches the electrodes or grabs the handgrips completely to produce a conductive circuit with the receiver. Upon emission of the signal from the IEM, e.g., when the IEM contacts the stomach, the signal emitted by the identifier of the IEM is picked up by the receiver. At this point, the receiver may provide an indication to the patient or healthcare provider, e.g., in the form of an audible or visual signal, that the signal from the IEM has been received. As indicated above, in certain external embodiments, the receiver is configured to be in contact with or associated with a patient only temporarily, i.e., transiently, for example while the intragastric device, ingestible marker, etc., is actually being ingested.

In some embodiments, the marker may be ingested by the subject using any convenient means capable of producing the desired result, where the administration route depends, at least in part, on the particular format of the composition, e.g., as reviewed above, and involves ingesting the ingestible event marker, e.g., by swallowing the IEM composition along with an intragastric device and/or the swallowable catheter. Depending on the particular application, the methods may include ingesting an event marker by itself or in conjunction with another composition of matter such as an intragastric device. Once the ingestible event marker reaches the target physiological site, the identifier of the IEM emits a detectable signal, e.g., as reviewed above. A signal receiver may handle received data (e.g., in the form of a signal emitted from an ingestible event marker) in various ways. In some embodiments, the signal receiver simply retransmits the data to an external device (e.g., using wires that extend through the catheter, by using conventional RF communications, or others), e.g., immediately or following some period of time, in which case the data is stored in a storage element of the receiver. Accordingly, in certain embodiments, the signal receiver stores the received data for subsequent retransmission to an external device or for use in processing of subsequent data (e.g., detecting a change in some parameter over time). For instance, an implanted collector may include conventional RF circuitry (operating, e.g., in the 405 MHz medical device band) with which a practitioner can communicate, e.g., using a data retrieval device, such as a wand as is known in the art. In other embodiments, the signal receiver processes the received data to determine whether to take some action such as operating an effector that is under its control, activating a visible or audible alarm, transmitting a control signal to an effector located elsewhere in the body, or the like. The signal receivers may perform any combination of these and/or other operations using received data.

FIG. 56 is a side view of an embodiment of an intragastric system 5600 having a balloon capsule 5610 attached to a delivery/inflation catheter 5620 where the balloon has a voltaic sensor 5630 therein. The capsule 5610 and catheter 5620 may be any of the embodiments described herein. The sensor 5630 may be any of the embodiments of an ingestible event marker as described herein. The sensor 5630 is shown located at the end of the capsule 5610 opposite from the coupling with the catheter 5620. However, this is merely one example and the sensor 630 may be in a any suitable location, either inside or outside the capsule 5610.

FIG. 57 is a side view of an embodiment of an intragastric balloon system 5700 including a balloon 5710 and catheter 5720 with an anode 5750 and a cathode 5740 having specific pH coatings 5760. The pH coatings 5760 may be chosen so as to control the exposure of the anode and cathode to the gastric environment, such as the gastric fluid. The catheter 5720 may have wires 5720 to communicate electrical signals received by the system, such as voltage. The wires 5720 may, for example, electrically couple with the sensor interface units, as described herein.

Figure 67:
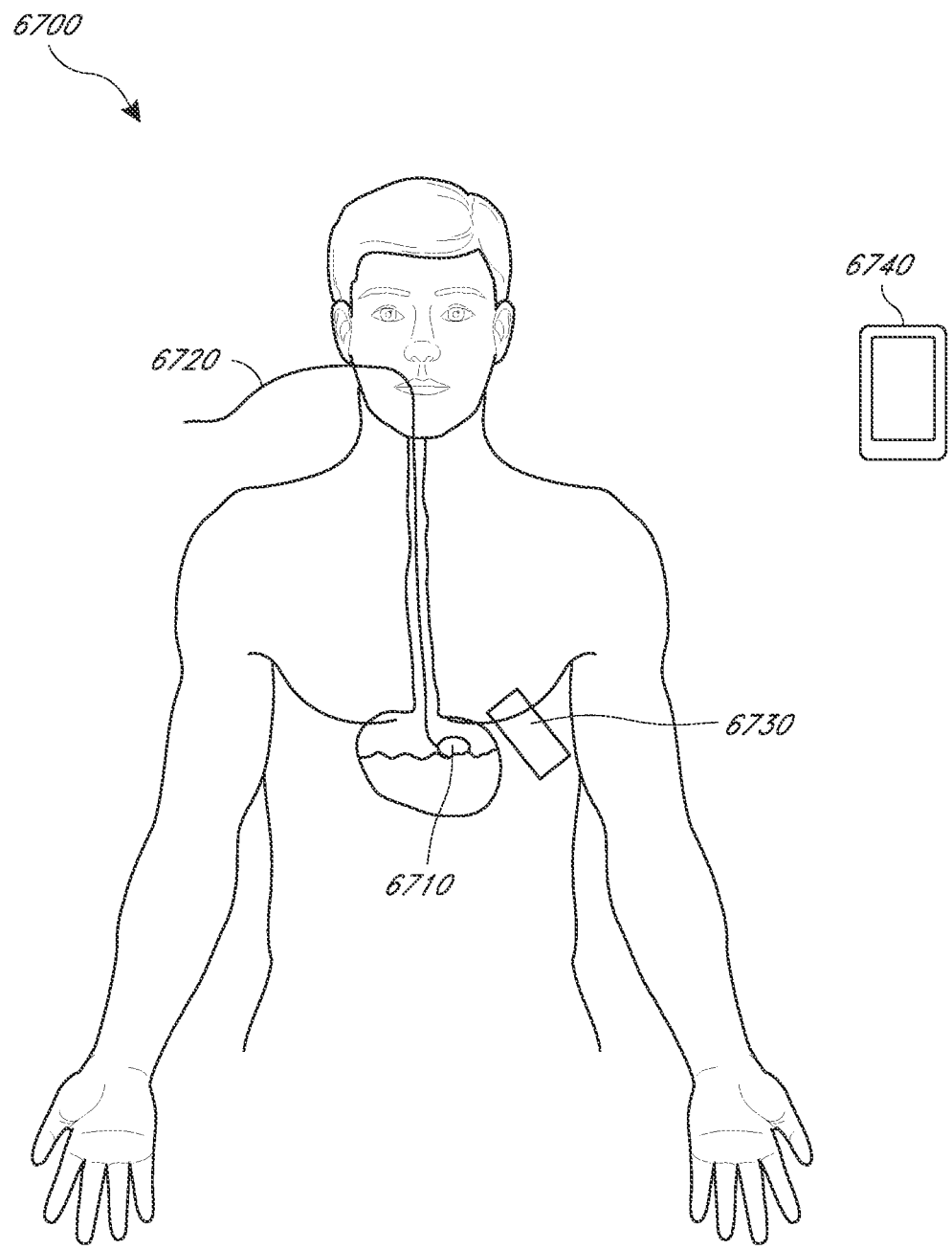
FIG. 67 illustrates use with a patient of an embodiment of a voltaic locating system having an event marker.

FIG. 67 illustrates use with a patient of an embodiment of a voltaic locating system 6700 having an event marker. The system 6700 includes a balloon capsule 6710 exposed to gastric fluid inside the stomach of the patient. The capsule 6710 may be ingested in any of the manners described herein. The capsule 6710 is coupled with a balloon catheter 6720. In some embodiments, the catheter 6720 is coupled with the ingestible event marker. In some embodiments, the capsule 6710 is coupled with the marker. In some embodiments, the balloon system 5600 of FIG. 56 may be implemented with the system 6700 shown in FIG. 67. As further shown in FIG. 67, the system 6700 may further include a signal receiver 6730, which may be external to the patient's body. In some embodiments, the receiver 6730 is located near the patient's stomach. The system 6700 may also include a mobile device 6740, such as a smartphone or tablet, that communicates with the receiver 6730.

Figure 68:
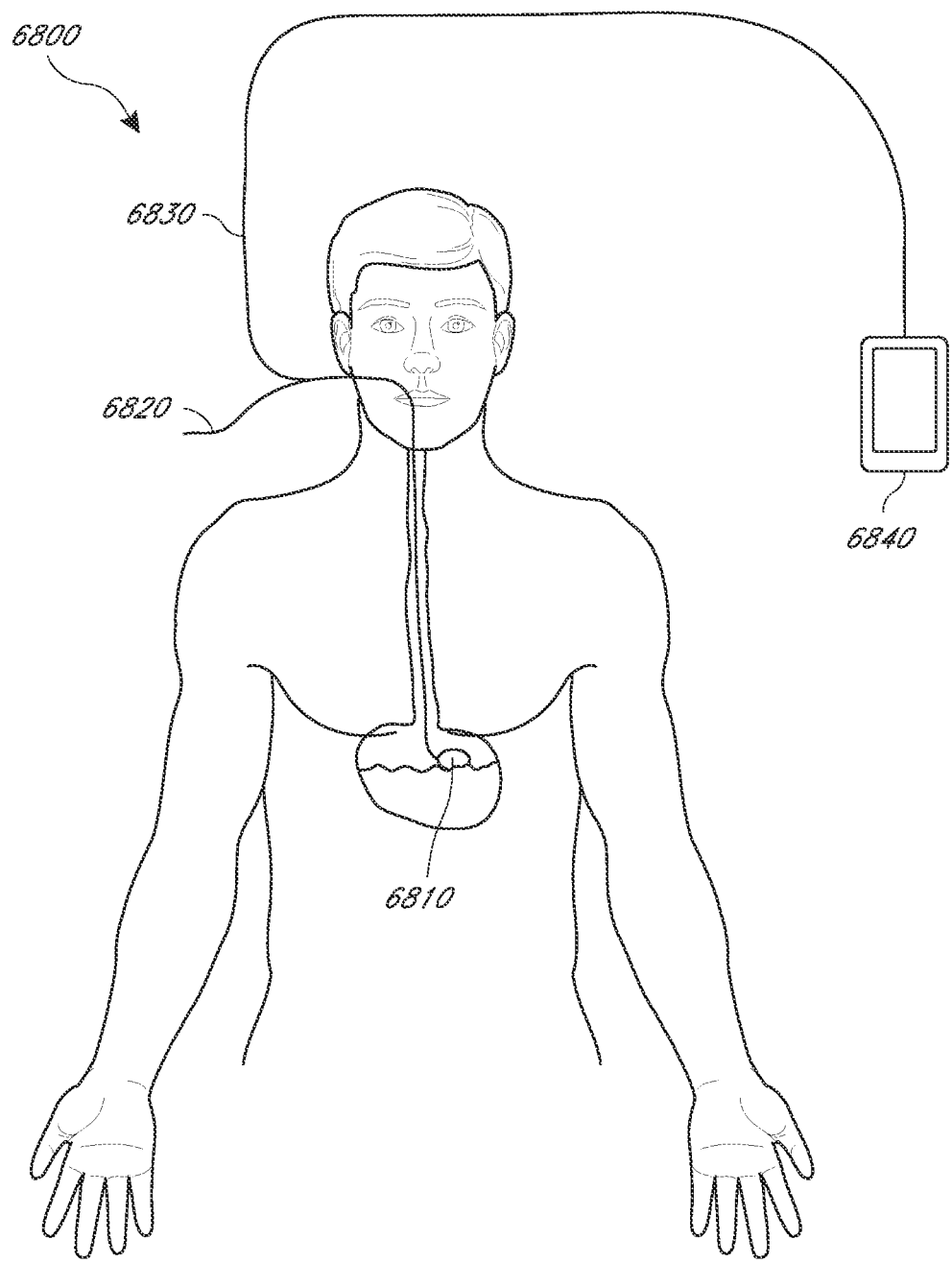
FIG. 68 illustrates use with a patient of an embodiment of a voltaic locating system having an anode and cathode.

FIG. 68 illustrates use with a patient of an embodiment of a voltaic locating system 6800 having an anode and cathode. The system 6800 may include a balloon capsule 6810 exposed to gastric fluid in the stomach of the patient. The capsule 6810 may be ingested in any of the manners described herein. The capsule 6810 is electrically coupled with wires inside of a balloon catheter 6820. In some embodiments, the catheter 6820 includes an anode and cathode at its distal end near the balloon 6810. The anode and cathode may provide the voltage signal to confirm placement in the stomach once the anode and cathode contact the gastric fluid, as described herein. The system 6800 may also include a voltage lead 6830 in electrical communication with the cathode and anode. The voltage lead may couple the anode and cathode to a signal receiver 6840 that measures the voltage. The receiver 6840 may report to a user of the system 6800 when the voltage level has reached a predetermined threshold, for example a voltage level indicative of the gastric environment of the stomach.

pH Based Tracking and Visualization Subcomponent

Tracking and visualization functionality can be incorporated into devices and systems described above. As used herein, "visualization" is used broadly to refer to identifying an item of interest in the body in a number of ways, including by measuring the pH levels encountered by the intragastric device or by portions thereof. Due to the non-invasive nature of the present device, physicians may desire to determine, or confirm, the location and orientation of the device prior to inflation, during the course of treatment, or after deflation. Accordingly, intragastric devices are provided that incorporate pH sensing components configured for enabling determining and confirming the location, orientation and/or state of an intragastric device at all phases of administration.

Figure 69A:
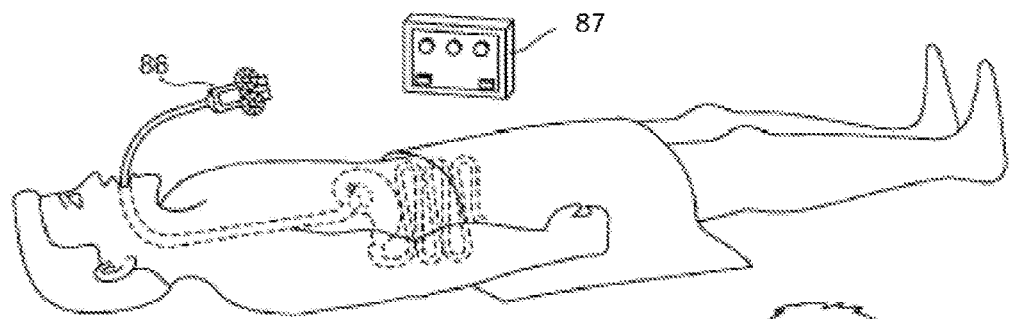
FIG. 69A depicts an embodiment of the present disclosure with an integrated controller and display, as well as a separate controller unit option, demonstrated during use with a patient.

A variety of pH measuring systems may be used to indicate the pH level along the alimentary canal encountered by an intragastric device. FIG. 69A depicts an embodiment of an intragastric device 10A (shown in FIG. 69B) inside a patient with an external controller 86, as well as a separate display unit 87 option, demonstrated during use with a patient. As shown, the external controller 86 may be integrated with the device. FIG. 69A also shows an embodiment where the controller 86 may plug into a separate display unit 87 for a larger or more sophisticated display.

Figure 69B:
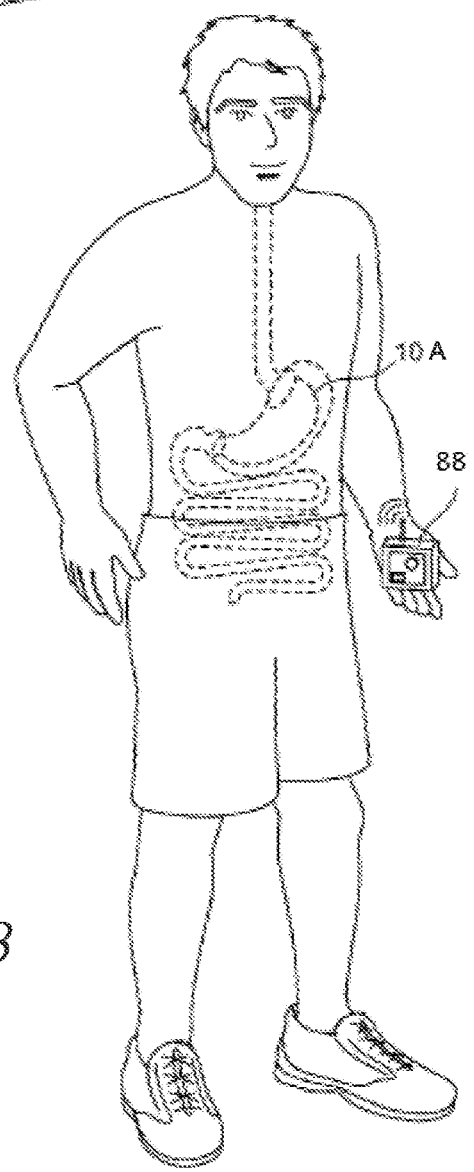
FIG. 69B depicts an embodiment of the present disclosure with a wireless external controller used near the patient.

FIG. 69B depicts an embodiment of the intragastric device 10A with a wireless external display 88. As shown, the external display 88 could be used with the intragastric device 10A or accessory therewith where wireless communication is being utilized. While monitoring the data, the physician could alter the orientation, location, etc. of the intragastric device, to ensure it is within an ideal position and orientation, etc. The device 10A could have the ability to collect and analyze the data with an algorithm to determine whether the device was in the ideal position, orientation, etc.

Figure 69C:
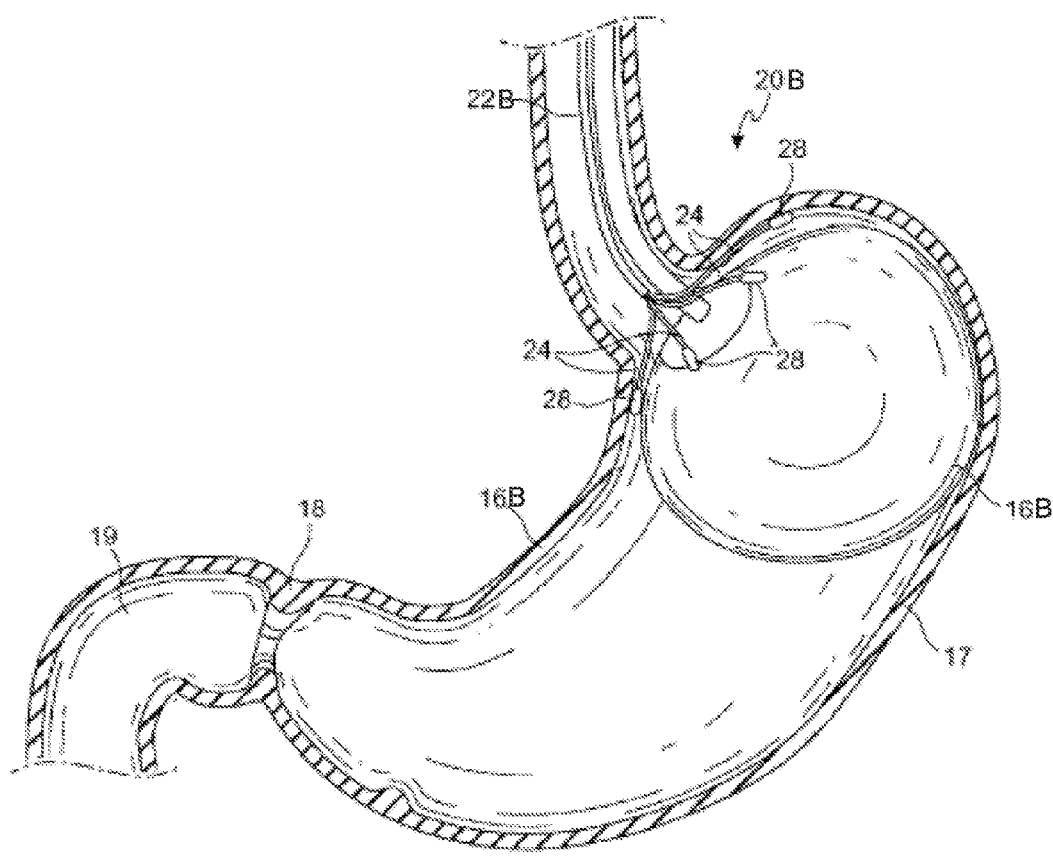
FIG. 69C depicts a side view of an embodiment of pH sensors of the present disclosure located on an intragastric device within a cross-section of a stomach.

In some embodiments, the intragastric device and/or accessories therewith includes a sensor or sensors to be used with the intragastric device or procedure to monitor one or more parameters, such as pH, inside the alimentary canal, including the esophagus, stomach and/or intestines. FIG. 69C depicts a side view of an embodiment of pH sensors 28B of an intragastric system 20B located on an intragastric device 16B, such as a balloon, within a cross-section of a stomach. In some embodiments, the sensors 28B would be adapted to accurately monitor pH with fine resolution, low hysteresis and would be adapted for tissue contact. The sensors could have a very small surface contact area or could have a wider surface contact area.

The system 20B may include an instrument that is separate from the intragastric device 16B and may be constructed with a shaft for placement down the esophagus and possibly an arm for manipulation. The system may further include an accessory that is attached to or contacting the intragastric device 16B and may be removed after the device is placed.

In some embodiments, the sensors 28B are used as a guide during placement of the intragastric device 16B to monitor placement, performance, adjustments or other data as needed. The sensor 28B is used when placing the intragastric device or performing a bariatric surgical procedure that induces weight loss by a variety of weight loss mechanisms. The sensors could be used to ensure that the intragastric device is placed in the proper location. The weight loss mechanism may include space occupying devices such as an inflatable intragastric balloon, as shown in FIG. 69C, or other similar devices described herein, where the sensors may be used, for example, to ensure proper fill volumes are achieved to lose weight. The intragastric device 16B equipped with sensors 28B may also gather placement or adjustment data to customize the placement and/or fit to the patient for improved long term performance.

Whether a wired or wireless sensor 28B is used, the external display may have the capability to gather and record data regarding the ambient pH level surrounding the intragastric device 16B. In some embodiments, the external display may be on the controller 86, the external display 87 and/or the wireless external display 88 shown in FIGS. 69A-B. The external display may also contain the ability to perform analysis of the collected data for further diagnostic capabilities. The external display may have the capability to gather the data and display it in a variety of presentations. It may display raw data, averages, or it could analyze the data and diagnose a generalized state as being appropriate or inappropriate. For example, an inappropriate state might be displayed with a red light while an appropriate state might be indicated with a green light. Similarly, the external display could be shown in a lighted bar graph where a more appropriate state is indicated by more bars and a less appropriate state is indicated by less bars. Where a wired sensor is used, the external display 87 (FIG. 69A) could be connected and integrated into the system 20B for reading the parametric data. Where a wireless sensor is used, the wireless external display 88 (FIG. 69B) could be wirelessly connected to the system 20B.

In some embodiments, the intragastric device 16B or portions thereof could contain an array of the sensors 28B that are positioned on top of or integrated into a thin, flexible sheet or element. This element could take a variety of shapes including a strip, disk, frusto-cone, sphere, a portion of any of these or other. Where an array of sensors 28B is used, the display may show a 2D or 3D color plot or graphical representation of the pH mapping across the sensor array. A variety of visual displays could be used to represent the state of the device 16B condition.

In some embodiments, multiple sensor arrays could be located on a single arm 24 or multiple arms 24. The single arm 24 could take the form of a loop, a curved wire, a spiral, cylinder, cone or multiples of these, or other shapes and multiples, to cover a region of interest. The arm or arms 24 could articulate to allow for manipulation for ideal positioning of the device 16B during the introduction into the body. In some embodiments, the sensors 28B may be incorporated with an instrument with a narrow cross-section to allow it to fit down the working channel of a gastroscope. Alternatively, it may require a larger sizing for additional features such as articulating arms, but could be sized small enough to fit down the esophagus next to the gastroscope, and long enough for proper manipulation outside the body. Where there are expanding or articulating features, the device 16B or accessory may have adequate ability to collapse into a long narrow profile to facilitate placement down the esophagus. The device 16B may also be smooth and contoured to reduce the potential for tissue irritation.

The sensor 28B could be in indirect contact with the patient such as being outside of a sizing balloon or outside of a tube where the alimentary canal contacts the balloon or tube. The sensors 28B or device 16B could be reusable or disposable. After the device 16B placement, adjustment, or procedure was completed, the sensors 28B or instrument used to place the device 16B, such as a catheter, could be removed.

An instrument or accessory used to place the device 16B could be made of many different materials or combinations of materials. For an instrument, the materials would be acid resistant for transient contact with the stomach for single or repeat use. For a device accessory that is intended to remain on the device 16B, the accessory may need more acid resistant properties. Elements of the device 16B could be made of Nitinol, shape memory plastics, shape memory gels, stainless steel, superalloys, titanium, silicone, elastomers, teflons, polyurethanes, polynorborenes, styrene butadiene co-polymers, cross-linked polyethylenes, cross-linked polycyclooctenes, polyethers, polyacrylates, polyamides, polysiloxanes, polyether amides, polyether esters, and urethane-butadiene co-polymers, other polymers, or combinations of the above, or other suitable materials or materials as described elsewhere herein.

In some embodiments, the system 20B could contain wireless or wired sensors 28B. Where wired sensors 28B are used on the instrument 20, the wires used to transmit data could be contained inside a shaft 22B, and data could be sent directly from the sensor 28B to the display, for example a small display on the controller 86 or larger display unit 87 in FIG. 69A, for monitoring, or to a microprocessor for analysis and then to the display. The microprocessor or external display could be integrated directly into the system 20B, or the system 20B could plug into a separate and larger external display 87 (shown in FIG. 69A).

Where wireless sensors 28B are used with the system 20B, an external display, such as wireless external display 88 shown in FIG. 69B, may be used to remotely send and receive signals via telemetry from the sensor 28B. The external display 88 may display the data for monitoring or could contain a microprocessor for analysis and then display the data.

In one embodiment, a wireless or wired sensor 28B may be used on the system 20B to communicate with a separate external display unit, whether a small display on the controller 86, the larger wired display 87, or the wireless display 88. It may be desirable to control the sensor 28B from the external display unit. The external display unit may send a command to the sensor 28B to query it to start gathering data. The external display unit may also send a separate or simultaneous command to send data. The sensor 28B may receive the command from the external display unit and then transmit or respond to collect and/or send data. When sufficient data was received, a command may be sent from the external display unit to the sensor 28B to tell the sensor 28B to stop gathering and/or sending data.

In addition, the sensor 28B and or memory module of the system 20B may be communicatively coupled with a transmitter, a receiver, or both, to allow communication of data or other information with outside receivers and transmitters. The transmitter may transmit signals received from the sensor, or signal data stored in the memory module.

In some embodiments, the sensors 28B may assist with placing the intragastric device 16B. The device 16B may be placed down the esophagus and then filled through a fill tube with saline, air or other fluid or method as described herein to the appropriate volume. With this system 20B, the sensor 28B could be placed between the balloon 16 and the surrounding anatomy to measure the pH level. The system 20B could be used for adjusting the device 16B at a later time, by filling or removing fluid in the device 16B to customize the fit for each patient over time. In some cases, it may be necessary to increase the device 16B fill volume to increase weight loss. It may also be necessary to remove fluid from the device 16B to reduce intolerance where a balloon, for example, was overfilled at the time of placement. Since the device 16B is free to move and rotate within the stomach, it could be monitoring orientation as well.

The sensors 28B could be used to gather important patient data to understand performance, positioning, patient status or whether an adjustment needs to be performed for the adjustable intragastric device 16B, or whether the device 16B needs to be replaced or resized. The sensed pH could detect whether the device was not in an ideal condition, and display this information to the external display 86.

Appropriate algorithm(s) may determine and/or control ideal parameter condition(s), or such condition(s) could be based on a parameter range. For example, the data could be collected from the sensor 28B for a fixed time period. A microprocessor in the external controller 86 or display 87, 88 could then calculate the average over time, the minimum, the maximum, the standard deviation or the variation in standard deviation over time, or other suitable analysis. Based on the analysis, the microprocessor may determine whether the intragastric device 16B was in the ideal position or adjustment state.

Figure 70A:
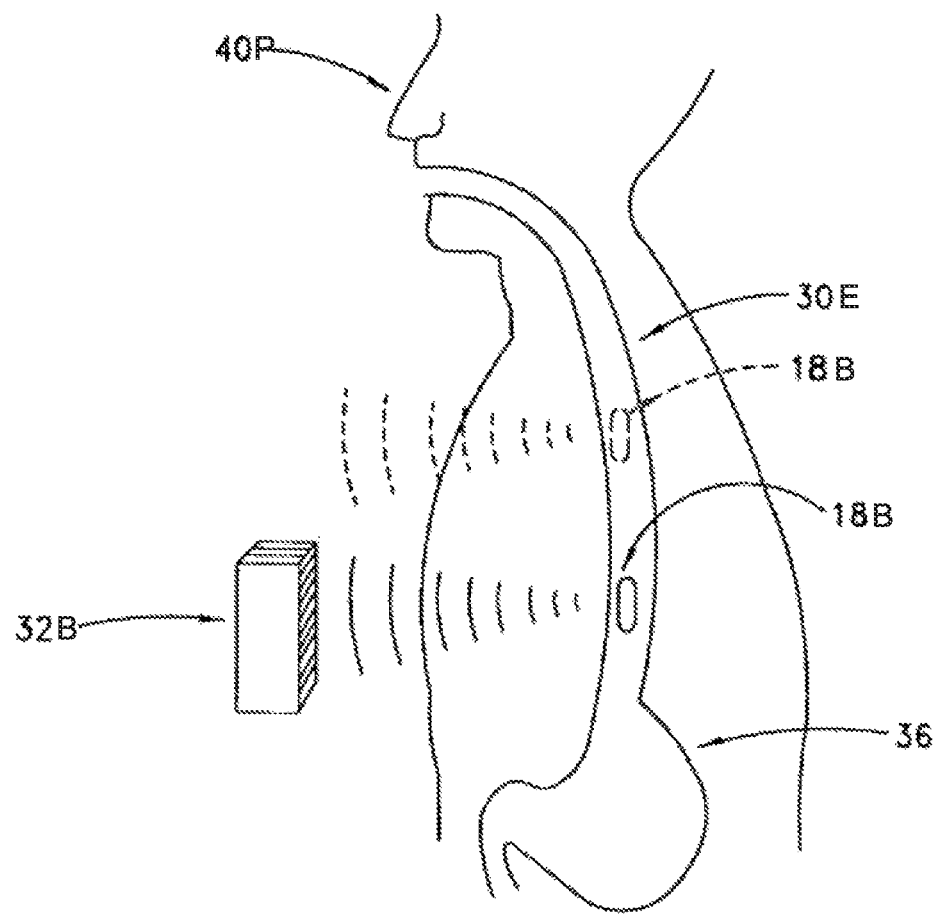
FIG. 70A is a schematic side view of a person with a pH monitor which may be incorporated with an intragastric device within the esophagus.

FIG. 70A is a schematic side view of a person with a pH monitor 18B which may be incorporated with an intragastric device within the esophagus. FIG. 70A illustrates how physiological parameter data such as pH can be relayed by the monitor 18B, which is positioned within the esophagus 30E, to a radiofrequency receiver or radioreceiver 32B located outside the body of a person 40P. As is illustrated in FIG. 70A, more than one monitor 18B can be incorporated with an intragastric device (not shown in FIG. 70A) so that data can be obtained from a plurality of locations. Further, the monitor 18B may be any pH sensor discussed herein, for example sensor 28B with respect to FIGS. 69A-69C.

In certain embodiments, this transmission of data is accomplished via radio telemetry in real time. The radioreceiver 32B receives physiological parameter data within 12 seconds after it is measured by the monitor 18B. After reception of this data, the radioreceiver 32B apparatus can record, manipulate, interpret and/or display the data, using technology well known to those skilled in the art. In certain embodiments, the patient can wear the receiver 32 and recorder on, for example, a belt, bracelet, arm or leg band, or necklace during the period of pH analysis.

In certain embodiments, the monitor 18B can record and compress physiological parameter data, such as pH level, as it is gathered, rather than transmit the data in real time. Following an assessment period, or at intervals therein, an external transceiver can be used to download pulses of condensed data. Transmission of data can be initiated at predetermined intervals or by an activation signal sent from the external transceiver or other activating device to the monitor 18B, as will be understood by those of skill in the art. In this manner, a tabletop transceiver can be utilized, either at the patient's home, or in the physician's office or other clinical site.

In other embodiments, the monitor 18B can record, compress, and store physiological parameter data as it is gathered, using a memory chip and microprocessor. The person 40P can excrete the monitor 18B in his or her stool, and the monitor 18B can be retrieved. Subsequently, data stored in the monitor 18B can be downloaded into an external data retrieval device, which can be a computer or other analysis machine located outside the patient's body. This downloading can be accomplished by IR or RF transmission in response to an activation signal, using magnetic field or radiofrequency technology well known to those skilled in the art.

Figure 70B:
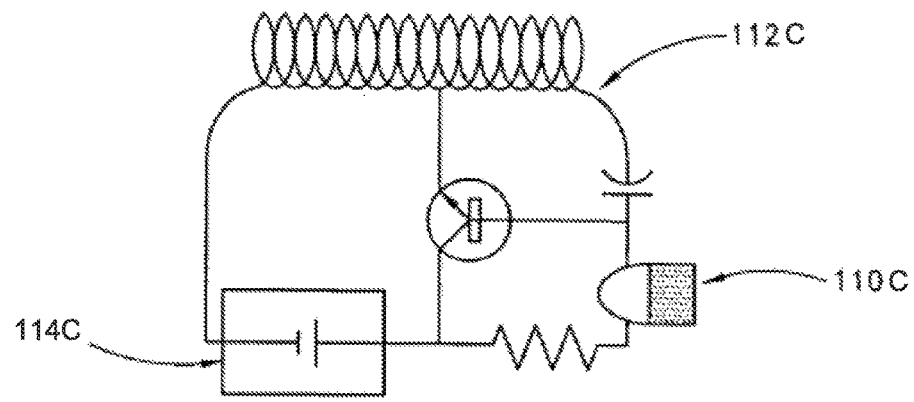
FIG. 70B is a schematic view of one embodiment of an electrical circuit for the pH monitor of FIG. 70A.

FIG. 70B is a schematic view of one embodiment of an electrical circuit for the pH monitor 18B. FIG. 70B illustrates a simplified circuit for the monitor 18B of a physiological parameter such as pH level. This monitor 18B may also be referred to as a "probe" or "pill" and may be incorporated with the intragastric devices described herein. In the particular embodiment illustrated in FIG. 70B, pH is the physiological parameter to be sensed, and it is detected by a transducer 110C, which comprises a pH sensor and preferably also a reference sensor. In the present invention, a monitoring transducer can be any transducer that senses a physiological parameter and furnishes a signal one of whose electrical characteristics, such as current or voltage, is proportional to the measured physiological parameter.

Although a pH sensor is described here, those skilled in the art will appreciate that a sensor of any of a variety of other physiological parameters, such as pressure or temperature, can be detected and monitored. Sometimes, temperature and/or pressure will be sensed and transduced together with pH, in order to adjust or calibrate the pH readings and make them more accurate, or to supply additional data helpful in the analysis of the patient's condition. In addition, the concentration of ions or other solutes present in body fluids can be detected and analyzed using this invention. For example, ions such as sodium, potassium, calcium, magnesium, chloride, bicarbonate, or phosphate may be measured. Other solutes whose concentrations in body fluids are of importance and may be measured by the present invention include, among others, glucose, bilirubin (total, conjugated, or unconjugated), creatinine, blood urea nitrogen, urinary nitrogen, renin, and angiotensin. Any combination of two or more of the preceding parameters may be sensed by the transducer 110C. For any physiological parameter sensed and transduced by means of a transducer, a reference sensor may or may not be required.

FIG. 70B also illustrates a radiofrequency transmitter circuit 112C and a power source 114C. The radiofrequency transmitter circuit 112C can comprise an antenna (or antenna coil), and the antenna can be at least in part external to the monitor 18B. Alternatively, the antenna, if present, can be entirely self-contained within the monitor 18B. As an alternative to RF transmission, a signal which is indicative of the monitored parameter can be propagated through the patient's tissue from an electrical contact on the probe to a conductive dermal electrode or other conductor in contact with the patient.

When located within the monitor 18B, the power source 114C can be a battery or capacitor or any other device that is capable of storing an electrical charge at least temporarily. In a battery powered embodiment, battery life can be extended by disconnecting the battery from other circuit components thereby limiting parasitic current drain. This can be accomplished in a variety of ways, such as by including a magnetically activated switch in the monitor 18B. This switch can be used to connect or disconnect the battery as needed. By packaging the monitor 18B with an adjacent permanent magnet, the switch can be opened thereby disconnecting the battery and the shelf life of the device can thus be extended. Removing the monitor 18B from the packaging (and the adjacent permanent magnet) closes the switch and causes the battery to become connected and supply power to the monitor 18B.

In some embodiments, the source of power to the monitor 18B can be external to the monitor 18B. For example, the monitor 18B can derive power from an external electromagnetic radiofrequency (RF) source, as occurs with passive RF telemetry techniques, such as RF coupling, that are well known to those skilled in the art. The monitor 18B can be energized by a time-varying RF wave that is transmitted by an external transceiver 32, also known as an "interrogator," which can also serve as a reader of data from the monitor 18B. When the RF field passes through an antenna coil located within the monitor 18B, an AC voltage is induced across the coil. This voltage is rectified to supply power to the monitor 18B. The physiological parameter data stored in the monitor 18B is transmitted back to the interrogator 32 (FIG. 70A), in a process often referred to as "backscattering." By detecting the backscattering signal, the data stored in the monitor 18B can be fully transferred.

Other possible sources of power for the monitor 18B include light, body heat, and the potential difference in voltage that can be generated in body fluids and detected by electrodes made of varying materials. The harnessing of such power sources for biotelemetry purposes is well described in R. Stuart Mackay: *Bio-Medical Telemetry, Sensing and Transmitting Biological Information from Animals and Man,* 2d ed., IEEE Press, New York, 1993, whose section entitled "Electronics: Power Sources" is hereby incorporated herein by reference in its entirety.

Figure 70C:
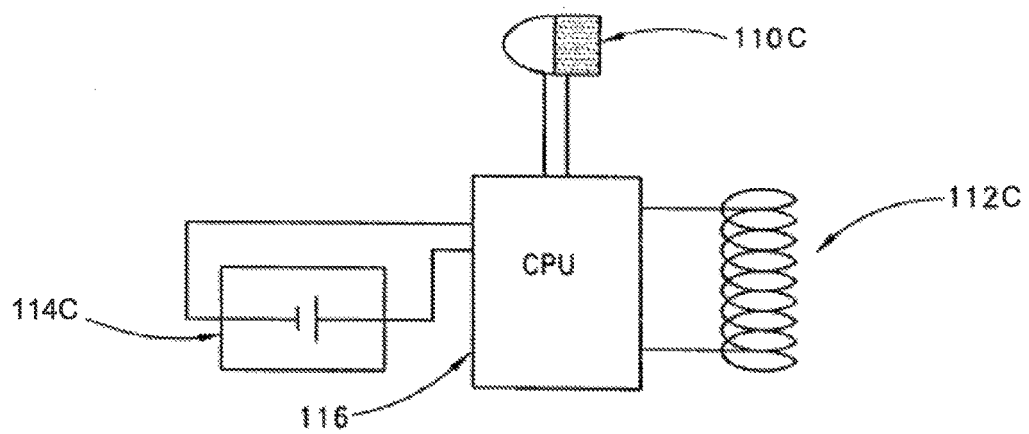
FIG. 70C is a schematic view of an embodiment of a pH monitor circuit, wherein the circuit also includes a microprocessor.

FIG. 70C is a schematic view of an embodiment of a pH monitor circuit, wherein the circuit also includes a microprocessor 116. In some embodiments, the microprocessor 116 can perform one or more functions, including temporary storage or memory of data, reception of input signal from the transducer, and transformation between analog and digital signals, among other functions that will be apparent to those skilled in the art. The transducer 110C, radiofrequency transmitter 112C, and power source 114C are also present.

Many other circuitry components that can help to generate, amplify, modify, or clarify the electrical signal can be used in other embodiments of the monitor. Such components include buffers, amplifiers, signal offset controls, signal gain controls, low pass filters, output voltage clamps, and analog-to-digital converters, among others. Numerous possible circuitry features of a portable pH monitoring device, all of which can be used in the present invention, are well described in U.S. Pat. No. 4,748,562 by Miller, et al., the disclosure of which is incorporated herein by reference in its entirety.

In certain embodiments, the monitor 18B further comprises a digital recorder or memory chip (not illustrated), which records the transduced physiological parameter data. This recorder or memory chip will allow temporary storage of this data accumulated over time.

Shown in FIGS. 71A-71H are various views of various embodiments of intragastric systems and apparatuses that use a chemical-property indicating medium to detect pH level. In some embodiments, an intragastric apparatus may comprise a detection indicator and a housing. The detection indicator may be configured to change from a first visual indication to a second visual indication upon contact with a fluid based on a characteristic of the fluid, such as acidity. The housing may comprise an interior chamber configured to receive the fluid and to provide contact between the fluid and the detection indicator. The housing may further be configured to removably engage a lumen inserted into a patient to receive the fluid from the patient through the lumen. In some embodiments, a first opening of the removable housing is engaged to a proximal end of a lumen inserted into a patient. A transfer of a fluid sample from a distal end of the lumen, through the lumen, and into the removable housing through the first opening may be caused such that the fluid sample contacts a detection indicator coupled with the removable housing. A visual comparison of the detection indicator with a reference indicator, coupled to the removable housing, may then be performed to determine a characteristic of the fluid sample. The first opening of the removable housing, may be removed from the proximal end of the lumen.

In some embodiments, the intragastric tube or the guide element may incorporate a chemical-property indicating medium to facilitate verification that the intragastric tube and/or intragastric devices thereon have been inserted properly into the patient's stomach. The fluids present in a patient's stomach have an acidic pH below 5.0. By exposing the indicating medium to the fluids surrounding the distal end of the intragastric tube, the indicating medium enables the user to verify that the pH of those fluids is below 5.0, thus confirming correct insertion of the intragastric tube in the proper location, orientation, state, etc. If the indicating medium is incorporated in the intragastric tube, the fluids surrounding the distal end of the tube may be aspirated through the tube and into contact with the medium, the condition of which may then be observed by the user. If the indicating medium is incorporated in the guide element, the fluids surrounding the distal end of the tube will come in contact with the medium without additional overt action by the user, although the guide element must subsequently be withdrawn from the patient so that the condition of the medium may be observed. The indicator may generally be used to obtain a measurement of the gastric pH.

Shown in FIG. 71A is a side view of an example embodiment of an intragastric tube 810 in which a chemical-property indicating medium is incorporated near the proximal end section 114D thereof. FIG. 71B is a cross section view of the example embodiment tube 810 taken along section lines 44-44 of FIG. 71A.

As shown in FIGS. 71A-71B, the intragastric tube 810 may comprise a generally tubular proximal end section 114D having an interior wall 814 forming at least one lumen 146D. If plural lumina are provided in tube 810, the lumen 146D may be the one adapted for use in aspirating fluid near the distal end of the tube. The intragastric tube 810 may include a section 812 for housing a chemical property indicating medium 820. Section 812 may be enlarged, compared to the diameter of other sections of the intragastric tube. A channel 822 is preferably provided in which the chemical property indicating medium 820 is captured. Several openings 816 are preferably provided between the main bore of lumen 146D and the channel 822 to allow communication of fluid between the lumen 146D and the channel 822. The openings 816, channel 822, and medium 820 are preferably adapted such that when fluid is present in lumen 146D, it inundates channel 822 and exposes medium 820.

In some embodiments, the medium 820 furnishes a visual indication of a chemical property, such as pH, which may, for example, be manifested as a change in color, reflectivity, or the like. Section 812 may be clear or translucent to allow the medium 820 to be viewed externally. The shape of section 812 may act as a magnifying lens to allow a small medium to be easily viewed. Any appropriate chemical-property indicating medium, including but not limited to litmus. pH indicating strips, paper, cloth, or any other substrate impregnated with or hearing a pH indicator, or the like, may be used to implement medium 820. The position and size of section 812 is preferably selected such that the condition of the indicator strip is visually apparent when fluids are initially aspirated through lumen 146D so that the user need not take any additional steps in order to confirm correct insertion of the intragastric tube in the patient's stomach.

Shown in FIG. 71C a side view of an additional example embodiment of an intragastric tube 830 in which a chemical-property indicating medium is incorporated near the proximal end section 114D thereof. There is shown in FIG. 71D a side view of an additional example embodiment of an intragastric tube 840 in which a chemical-property indicating medium is incorporated near the proximal end section 114D thereof. FIG. 71E is a cross section view of the embodiment 830 taken along the section lines 47-47 thereof. FIG. 71F is a cross section view of the embodiment 840 taken along the section lines 48-48 thereof.

As shown in FIGS. 71C-71F, in some embodiments each of intragastric tubes 830 and 840 comprises a generally tubular proximal end section 114D having an interior wall 814 forming at least one lumen 146D. If plural lumina are provided in tube 830 or 840, the lumen 146D may be the one adapted for use in aspirating fluid near the distal end of the tube. Intragastric tube 830 may comprise a chemical-property indicating medium applied to the interior wall 814 in the form of a plurality of indicating elements 832 spaced circumferentially along the interior wall 814. Intragastric tube 840 may comprise a chemical-property indicating medium applied to the interior wall 814 in the form of an indicating element 842 that covers the circumference of the interior wall 814. These particular configurations of the indicating elements 832 and 842 are examples. Other configurations could also be used.

In some embodiments, the indicating elements 832 and 842 may be formed using any suitable chemical-property indicating medium or substance, including but not limited to a coating, litmus, pH-indicating strips, paper, cloth, or the like. For example, the medium may be formed as a coating or gelatin bearing phenolphthalein. The term medium is also intended to refer to any indicating substance, regardless of whether or not the indicating chemical or component is carried in or on a substrate, matrix, or similar carrier. Other indicating media could also be used. If the medium is integrated with a substrate such as a paper strip, such substrate may be applied to the interior wall 814 using an appropriate adhesive or fastening technology, which may include infrared or ultrasonic bonding. The positions and sizes of the indicating elements 832 and 842 are preferably selected such that the condition of the indicating elements is visually apparent when fluids are initially aspirated through lumen 146D, so that the user need not take any additional steps in order to confirm correct insertion of the intragastric tube in the patient's stomach. In some applications, aspirated fluid that contacts the indicating medium may be reintroduced into the patient or may otherwise come in contact with the patient.

In some embodiments, the indicating medium is attached or adherent to the interior wall 814, to prevent particles or fragments of the indicating medium itself from being inadvertently introduced into the patient through the intragastric tube or otherwise contacting the patient. In some embodiments, an indicating medium is preferably selected for bio-compatibility to avoid any potentially toxic effects.

Figures 71G, 71H:
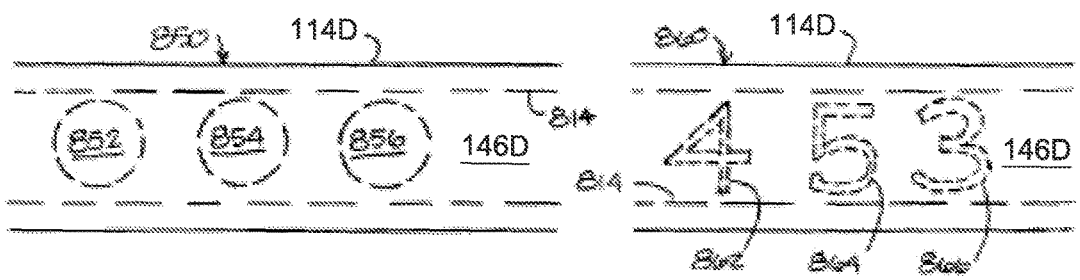
FIG. 71G is a side view of a further embodiment of an intragastric tube, showing a chemical-property indicating medium thereof for pH level detection in a third example configuration.
FIG. 71H is a side view of a further alternate embodiment of an intragastric tube, showing a chemical-property indicating medium thereof for pH level detection in a fourth example configuration.

Shown in FIG. 71G is a side view of an additional example embodiment of a intragastric tube 850 in which a chemical-property indicating medium is incorporated near the proximal end section 114D thereof. As shown in FIG. 71G, a plurality of distinct indicating elements, such as 852, 854, and 856 are provided, each having a medium for visually and distinctly indicating a different chemical property or a different value of a chemical property. The indicating elements 852, 854, and 856 may, for example, change appearance to indicate different pH thresholds have been sensed, or may change appearance to indicate the presence or absence of specific chemicals, proteins, or other detectable components in the fluid aspirated from the vicinity of the distal end of the intragastric tube. This would give a measurement of gastric pH, as well as verify proper placement, orientation, state, etc. of the intragastric tube and/or device. The activated appearance of each of the indicating elements 852, 854, 856 may be visually distinctive. For example, they may appear as distinguishably different colors, thereby minimizing ambiguity as to which indicators are activated. Although the indicating elements are shown in the shape of dots, any suitable shape could also be used, and the elements may be provided in any practical size and number. Any suitable indicating media could be used to implement the indicating elements 852, 854, and 856, such as those described in connection with the embodiments 830 and 840 of FIGS. 71C-71D.

Shown in FIG. 71H is a side view of an additional example embodiment of a intragastric tube 860 in which a chemical-property indicating medium is incorporated near the proximal end section 114D thereof. As shown in FIG. 71H, a plurality of distinct indicating elements, such as 862, 864, and 866 are provided, each having a medium for visually and distinctly indicating a different chemical property or a different value of a chemical property, and each having a different shape, size, or other characteristic so that there is no ambiguity as to which indicators are activated. The indicating elements 862, 864, and 866 may, for example, change appearance to indicate different pH thresholds have been sensed, or may change appearance to indicate the presence or absence of specific chemicals, proteins, or other detectable components in the fluid aspirated from the vicinity of the distal end of the intragastric tube. The shape, size, or other characteristics of the indicating elements may be selected to correspond to the property indicated. In some embodiments, the indicating elements 862, 864, and 866 may be designed to change appearance when fluid pH crosses specific pH thresholds of 4.0, 5.0, and 3.0, respectively, and the indicating elements may be formed as recognizable characters, symbols, or glyphs corresponding to these thresholds. Other distinctive shapes and forms and other schemes defining correspondence between the visual distinctiveness of the indicating element and the property being sensed could also be used. The activated appearance of each of the indicating elements 862, 864, 866 may be visually distinctive in ways in addition to their shape, for example, they may appear as distinguishably different colors, to further minimize ambiguity as to which indicators are activated. Any suitable indicating media could be used to implement the indicating elements 862, 864, and 866, such as those described in connection with the embodiments 830 and 840 of FIGS. 71C and 71D, respectively.

Figure 72:
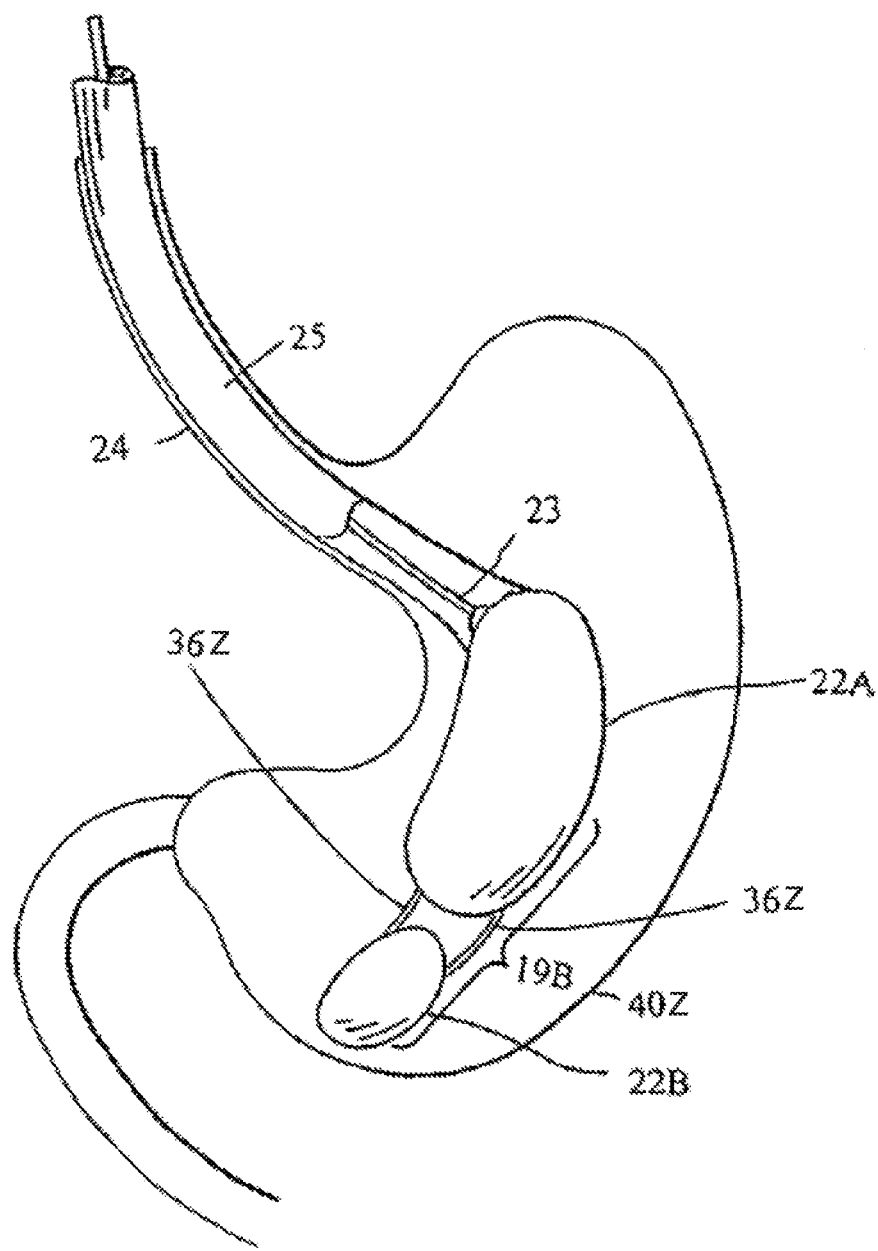
FIG. 72 shows an embodiment of an intragastric device having a pH sensor connected in tandem with a space filler.

FIG. 72 shows a further embodiment of an intragastric device 19B with a space filler 22A and a sensor 22C, such as a pH sensor, with delivery means for implanting and retrieving the device and sensor. In some embodiments, the sensor 22C comprises a pH sensor element for sensing a pH of a stomach of the patient, wherein the pH sensor element may further comprise a transmitter for wirelessly transmitting the sensed pH to a receiver outside a body of the patient. The sensed pH or the change of the sensed pH may be analyzed for assessing the intragastric device 19B location, orientation, state, performance, etc. FIG. 72 depicts an embodiment of the intragastric device 19B with the space filler 22A secured to and in tandem to the sensor 22C. In some embodiments, the space filler 22A is secured to and in parallel with the sensor 22C. In some embodiments, the space filler 22A and the sensor 22C of the intragastric device 19B are configured to be in tandem inside a stomach pouch.

In some embodiments, there may be two or more space fillers 22A. In some embodiments, the sensor 22C may also be a second space filler. In some embodiments, the two or more space fillers are in tandem to each other. In some embodiments, the two or more space fillers are parallel to each other. In some embodiments, the second space filler is enclosed entirely or partially within the first space filler 22A.

In some embodiments, at least a portion of one or both of two space fillers is made of a biodegradable material and one or both have a sensor 22C for measuring the property of the content surrounding, in or near the space filler or fillers, wherein the property includes pH. In some embodiments, more than two space fillers 22A and/or sensors 22C are incorporated in, on, or otherwise with, the intragastric device 19B.

In some embodiments, a catheter sheath 25 or delivery device for the intragastric device 19B passes through the esophagus 24 and cardiac notch into the stomach 40Z of a patient. Once it is delivered to the stomach, the space filler or fillers 22A and/or sensor 22C are inflated. As shown in FIG. 72, in some embodiments the intragastric device 19B comprises a plurality of connecting members 36Z between the first space filler 22A and the second space filler or sensor 22C, wherein the first space filler 22A is connected to an infusing tubing 23 via a sealed inlet.

Figure 73A:
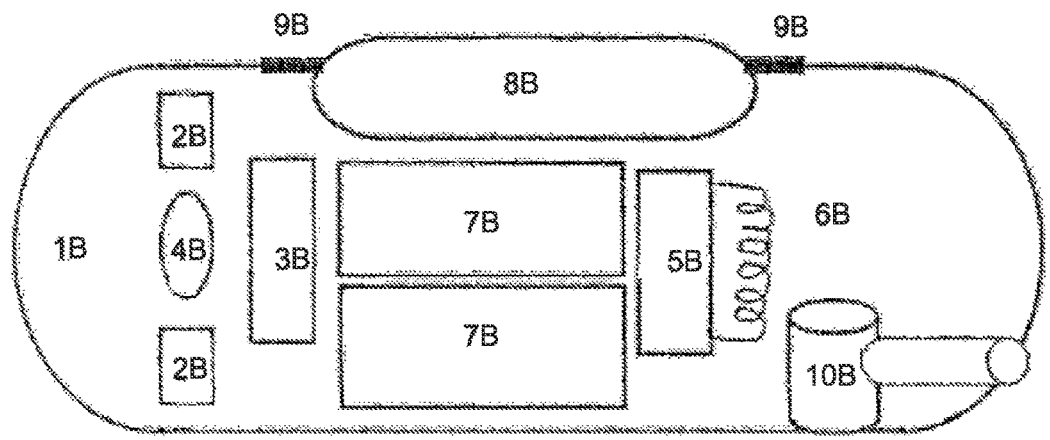
FIG. 73A is a schematic illustration of a capsule device that may be incorporated with an intragastric device to detect pH level.
Figure 73B:
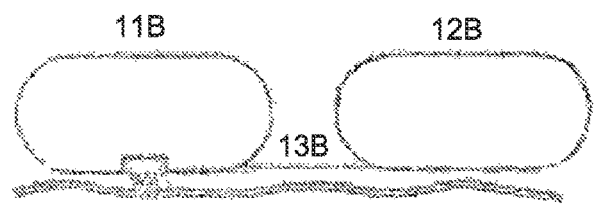
FIG. 73B is a schematic illustration of a system that may be incorporated with an intragastric device for measuring pH having two capsules connected to each other.

In some embodiments, capsule technology may be incorporated with the intragastric device to sense pH level. FIG. 73A is a schematic illustration of an embodiment of a capsule device that may be incorporated with an intragastric device to sense pH level. FIG. 73B is a schematic illustration of a system that may be incorporated with an intragastric device for measuring pH having two capsules connected to each other.

Referring to FIG. 73A, an embodiment of a capsule device and its components are illustrated. As shown, the capsule device comprises a pH electrode 8B which is positioned at the capsule device to allow direct contact with the environment surrounding the capsule device. The pH electrode 8B is further in electrical contact with a reference electrode 9B. Additionally, the capsule device comprises a means which can be connected with the transmitter 5B for transmitting the pH measurement data to a recording and/or analyzing unit.

In some embodiments, the capsule device contains a fixing means 10B which preferably comprises an evacuable well and a pin. The device may be fixed to an intragastric device via the fixing means, which may be mechanical, chemical or other means for attaching and fixing the capsule to the device.

In some embodiments, the capsule device may have a pH sensor used in conjunction with an imaging system. The pH level may indicate a likely position, orientation, location, etc. and the imaging system may be used to confirm or provide verification of the position, etc. In some embodiments, the capsule device may comprise an optical window 1B and an imaging system for obtaining images from inside of the esophagus. The imaging system may include an illumination source 2B, such as a white LED, an imaging camera 3B, which detects the images and an optical system 4B which focuses the images onto the imaging camera 3B. The illumination source 2B may illuminate the inner portions of the esophagus through the optical window 1B. The capsule device further includes a transmitter 5B and an antenna 6B for transmitting the video signal of the image camera 3B, and a power source 7B, such as a battery, that provides power to the electrical elements of the capsule device.

Reference is now made to FIG. 73B which schematically illustrates a plurality of connected capsules 11B and 12B in accordance with an embodiment of the invention. The plurality of capsules may be connected by, for example, a thread, tube, cable, wire or flexible narrow shaft 13B. According to some embodiments more than one connecting wire or shaft may be used to connect two or more capsules. The connecting wire 13B may physically and/or electrically connect the two or more capsules and may be of any suitable lengths from a few millimeters to a centimeter or more. The flexible connection between the two capsules may make the capsules more flyable and maneuverable in an esophagus than would be a single rigid or partially flexible capsule device of the same size or mass. In some embodiments, the first capsule 11B may contain the components necessary for pH measurement and the component for fixing the capsule device to, in or on the intragastric device, wherein the second capsule 12B may also contain components necessary for pH measurement and/or the component for fixing the capsule device to, in or on the intragastric device. In some embodiments, more than two capsules are used, where each may be used for pH sensing and/or fixation. In some embodiments, the first capsule 11B may contain the components necessary for pH measurement and a component for fixing the capsule device to the mural surface of the stomach, wherein the second capsule 12B may contain the components necessary for imaging the stomach and/or intragastric device.

Figure 74:
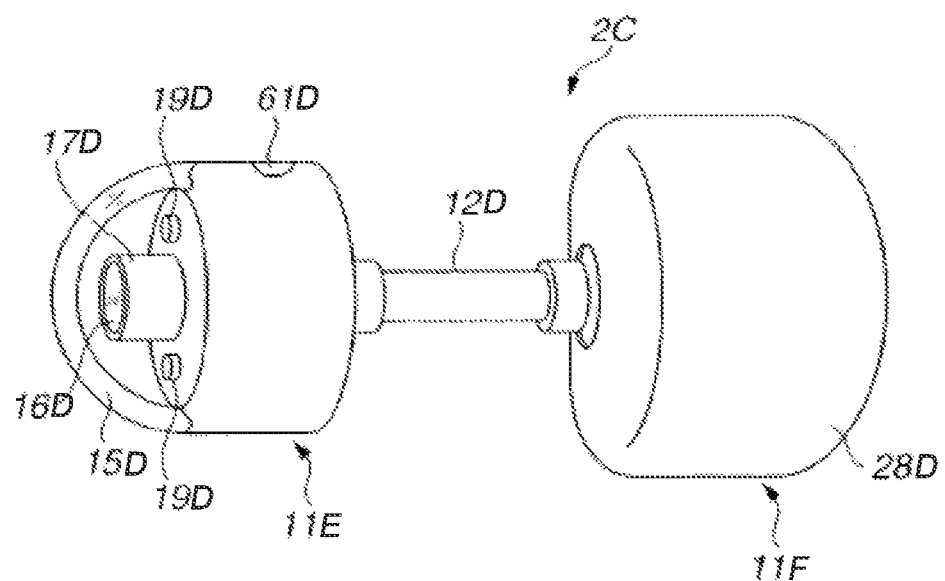
FIG. 74 illustrates an embodiment of a capsule system with one or more pH sensors, for incorporation with an intragastric device, having two hard capsule-like units and a soft flexible tube connecting the capsule units.

FIG. 74 illustrates an embodiment of a capsule system 2C with one or more pH sensors 61D, for incorporation with an intragastric device, having two hard capsule-like units 11E, 11F and a soft flexible tube 12D connecting the capsule units. The capsule-type system 2C comprises a first capsule 11E and a second capsule 11F as two capsule-like hard units of different diameters and a soft flexible tube 12D connecting the capsules and having a diameter less than the diameter of the two capsules 11E, 11F, and has a structure in which the two capsules 11E, 11F are connected by the tube.

The capsule-type system 2C may have a structure in which one or more sensors 61D, such as a pH sensor, are provided, for example, in the first capsule 11E. The sensor or sensors 61D are secured to the outer member of the capsule, such as the transparent cover 15D, so that a sensing zone of the sensor 61D is exposed to the outside, and the inside of the capsule is maintained in a water-tight state.

Data such as chemical parameters (e.g., pH value) of body fluids are obtained from the sensing zones. The data obtained are temporarily accumulated in a memory (not shown in the figures) located inside the capsule and then transmitted by a transmission-receiving circuit and antenna to a receiver such as an external unit located outside the body.

In some embodiments, a pH sensor 61D may be used in conjunction with an imaging system. For example, in the first capsule 11E, the cylindrical peripheral portion of the hard capsule frame may be water-tight sealed with a dome-like hard transparent cover 15D via a seal member. An image pickup device and an illumination device may be housed inside the first capsule. In some embodiments, an objective lens 16D constituting the image pickup device may be mounted on a light-shielding lens frame 17D and disposed opposite the transparent cover 15D in the central portion of the internal space covered with the dome-like transparent cover 15D. An image pickup element, for example, a CMOS image pickup device, may be disposed in the image forming position of the objective lens. In some embodiments, white LEDs 19D are disposed as illumination devices in a plurality of places around the lens frame 17D, and the light emitted by the white LEDs 19D passes through the transparent cover 15D and illuminates the space outside thereof. An elastic resin cover 28D may be on an external part of the second capsule 11F. In some embodiments, the image pickup device may be used to verify the location, orientation, state, etc. of an intragastric device after the pH sensor 61D indicates a particular pH level.

The pH Sensor may be integrated with the intragastric locating system in a number of manners. For example, as shown in FIG. 23, the balloon 1100 may incorporate a pellet 1110 that is a pH sensor pellet. The pellet can be loose or attached to a wall of the intragastric balloon 1100. As another example, as shown in FIG. 24, the balloon 1200 of one embodiment may incorporate buttons 1210 as pH sensor buttons that are attached to opposite sides of the intragastric balloon 1200. As another example, as shown in cross-section in FIG. 25A, the valve system 1300 may include the retaining ring 1318 containing a pH sensor. FIG. 25B is a top view of the valve system 1300 that may contain the pH sensor, depicted in cross-section along line 1D-1D in FIG. 25A. FIG. 25C is a top view of the valve system of FIGS. 25A and 25B incorporated into the wall of an intragastric balloon 1320 that may contain the pH sensor. As another example, FIG. 26 depicts a gel cap 1400 containing the intragastric balloon of FIGS. 25A-C in uninflated form that may contain the pH sensor. The gel cap containing the uninflated balloon is engaged via the valve system of the intragastric balloon to a dual catheter system comprising a 2FR tube 1410 and a 4FR tube 1412 via a press-fit connecting structure 1414 which may incorporate a pH sensor, e.g., a needle (not depicted).

Figure 75:
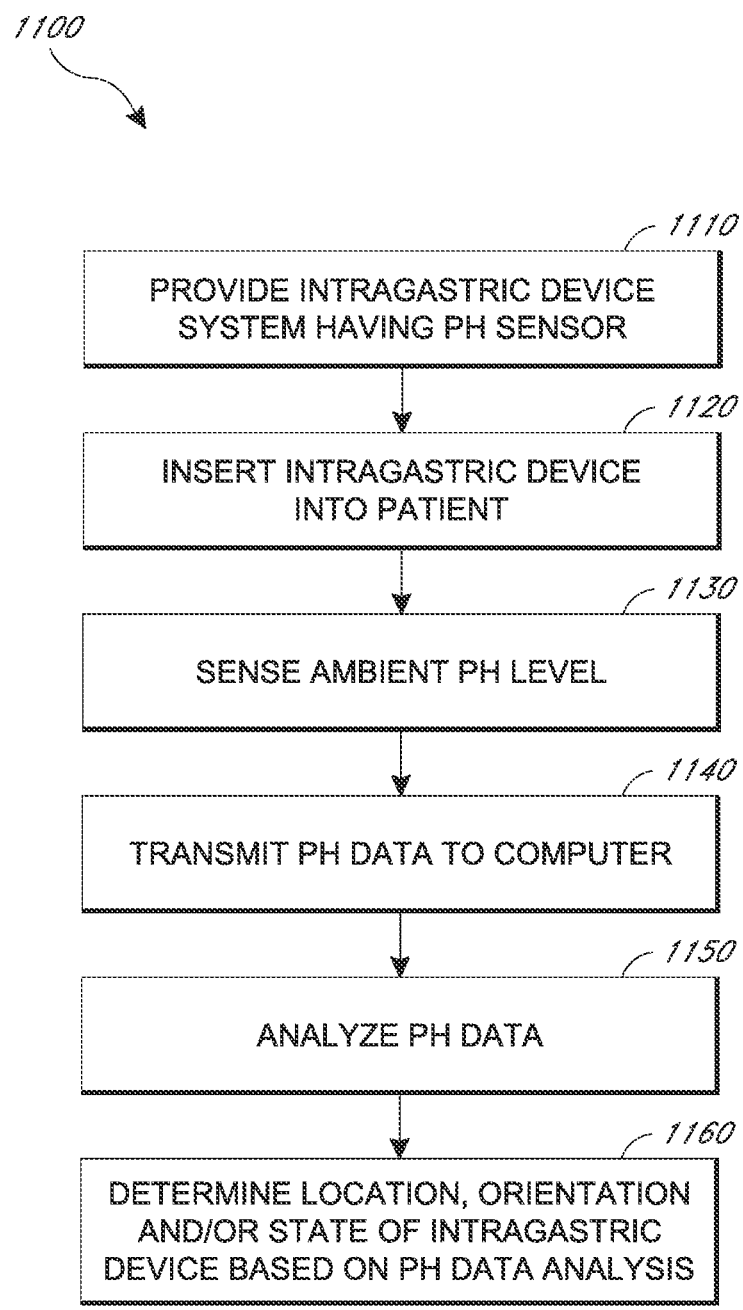
FIG. 75 is a flowchart of an embodiment of a method for using a pH sensor with an intragastric device to determine the location, orientation, and/or state of the intragastric device. The method may be used with other systems, including electromagnetic, magnetic, voltaic, and ultrasound systems.

The preceding examples, and/or any other embodiments of the device, may be used in a variety of manners. FIG. 75 is a flowchart of an embodiment of a method 1100 for using pH detection to locate and/or characterize an intragastric device. The method 1100 may include block 1110 where an intragastric device system having a pH sensor is provided. The intragastric device system having a pH sensor may be any of the examples or embodiments described herein, for example with respect to FIGS. 1A-10. The method 1100 may further include block 1120 where the intragastric device is inserted into a patient. The intragastric device may be inserted into a patient in any of the manners described herein, for instance by swallowing a balloon, by inserting a catheter with a balloon, etc.

The method 1100 may further include block 1130 where the ambient pH level is sensed. The ambient pH level may be the pH level of the surrounding fluids in the alimentary canal encountered by the device. For instance, the pH level of the esophagus and/or stomach may be sensed as the device travels through the respective portions of the canal. The method may further include block 1140 where the data relating to the pH level is transmitted to a computer. By computer it is meant to include any device that receives the signal that includes the data, for instance a receiver. In some embodiments, the data is sent wirelessly to a receiver. In some embodiments, the data is sent by wire from a wired sensor to a connected computer or receiver. Any of the examples and/or embodiments discussed herein may also be used in block 1140 to transmit the pH data.

The method 1100 may further include block 1150 where the pH data is analyzed. The pH data may be analyzed by any of the methods discussed herein, for instance by visual reading on a display, by numerical analysis, and/or others. In some embodiments, the pH data is analyzed by a computer. In some embodiments, the pH data is analyzed by a doctor or technician.

Finally, the method 1100 may further include block 1160 where the location, orientation, state, etc. of the intragastric device is determined based on the pH data. In some embodiments, analysis of the pH data indicates a likely location, orientation, state, etc. of the device. For instance, a lower pH level may indicate that the device is in the stomach and a higher pH level may indicate that the device is in the esophagus. Such information may be useful, for example, in determining whether to inflate a balloon.

Commercial Systems

In some embodiments, commercial systems may be incorporated into the present disclosure to provide pH sensing. One such commercial system is the BRAVO® pH Monitoring System by Given Imaging. The BRAVO® pH monitoring system is a catheter-free ambulatory pH test that utilizes a small pH capsule to transmit pH data up to 96 hours. While the system is useful for pH measurement and monitoring of gastric reflux to assist clinicians diagnose gastroesophageal reflux disease (GERD), the system may also be incorporated into embodiments of the present disclosure for verifying the location, orientation, state, etc. of an intragastric device inside the body.

In some embodiments, a system using two main components for pH sensing is implemented. The first main component is a small pH capsule about the size of a gelcap that is incorporated in, on, or otherwise with, the intragastric device, and transmits data to a receiver. The second main component is the pager-sized receiver that receives pH data from the capsule. Data from the receiver may be uploaded to pH analysis software using infrared technology. The capsule may be integrated with the intragastric device in a number of ways. Further, multiple capsules may be incorporated with the intragastric device in various locations. In some embodiments, capsules are placed on opposing sides of the intragastric device, such as top/bottom, front/back, and left/right. Individual readings from each sensor can provide indications of the orientation of the device, in addition to location, state, etc.

Another commercial system which may be incorporated into some embodiments is the VersaFlex™ System from Sierra Scientific Instruments in Los Angeles, Calif. The system has a probe, such as a pH sensor, inserted into the gastric lumen and connected to a pH recording device, such as the Digitrapper from Sierra Scientific Instruments, Los Angeles, Calif. The probes are small and flexible to ensure maximum comfort for the patient. The probes are available in single or dual channel configurations. The tubing may be 1.5 mm (4 Fr) diameter tubing with smooth surfaces to eliminate the large "bump" typically found at the sensor tip. They may further have optimal stiffness for easier intubation that softens at body temperature for greater patient comfort. The dual channel configuration features two sensors spaced 5 cm apart. Because pH probes must be soaked and calibrated prior to any procedure, a calibration kit is provided containing disposable tubes with pH buffers, providing a convenient solution to streamline pre-procedure tasks. The calibration kit can contain, for example, pH7 and pH4 buffers as well as deionized water for rinsing.

Figure 76:
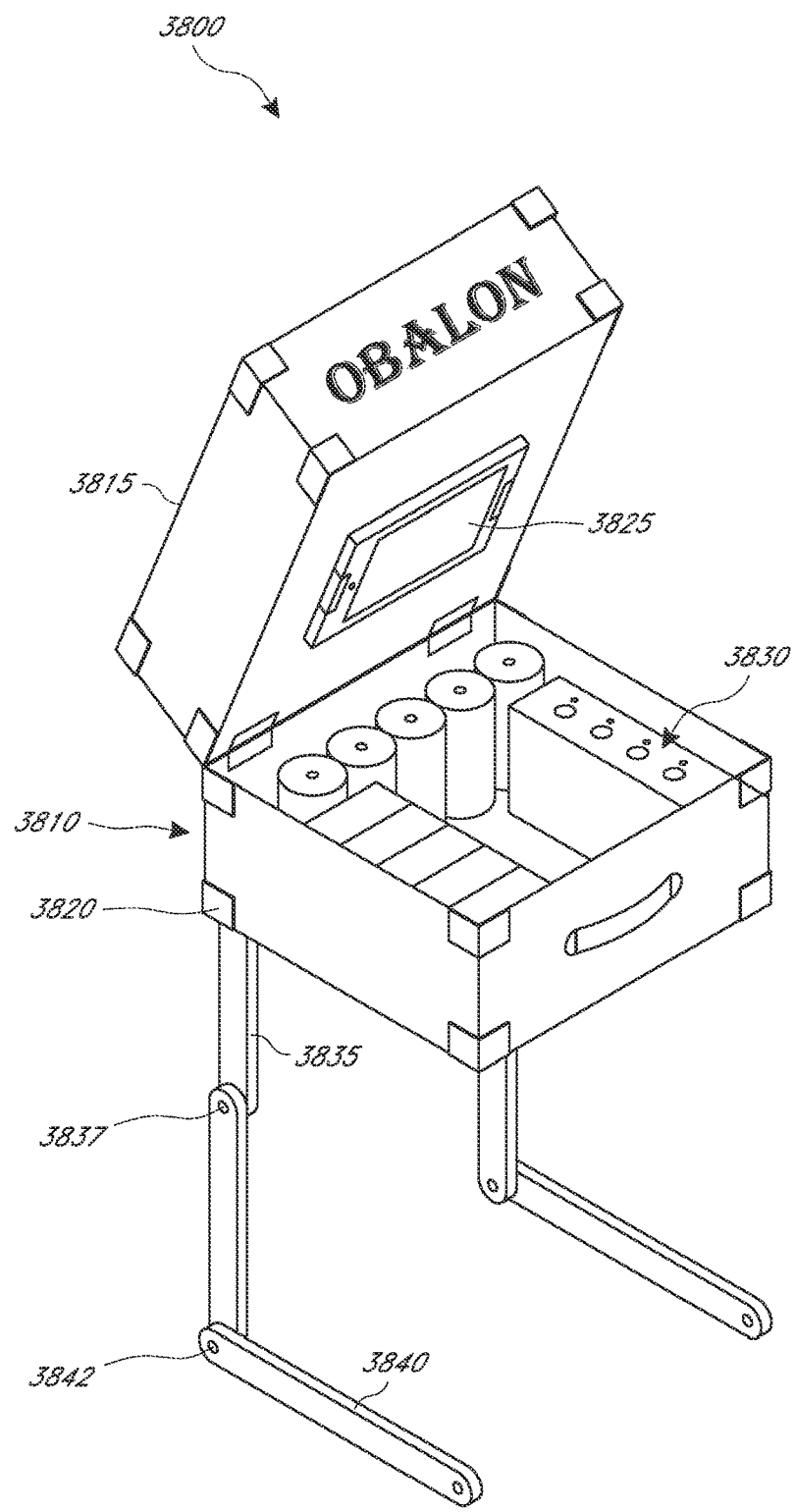
FIG. 76 is a perspective view of a suitcase embodiment of the intragastric locating systems of the present disclosure.

FIG. 76 is a perspective view of an embodiment of a suitcase kit 3800 for the intragastric locating systems of the present disclosure. The kit 3800 may include any of the tracking systems discussed herein, for example the system 1501 or 1601. The kit 3800 provides a collapsible and portable assembly for transporting the various systems. The kit 3800 includes a case 3810. The case 3810 may be similar to a standard suitcase with a handle for easy carrying. The case 3810 includes a top portion 3815 and a bottom portion 3820. The top portion 3815 is rotatably attached to the bottom portion 3820 such that the top portion 3815 may rotate to open and close. The top portion 3815 includes a display 3825 that may be electrically connected with other features of the system.

The bottom portion 3820 may define a cavity 3830 therein. The cavity 3820 may include space for storing the various components of the various systems. For instance, the components of the systems 1501 or 1601 may be stored in the cavity 3820. By closing the top portion 3815, the contents of the cavity 3830 may be protected from theft or the elements. The bottom portion 3820 may further include a set of vertical supports 3835 and horizontal supports 3840. The supports 3835, 3840 may be coupled together to allow them to rotate relative to each other and stow with the bottom portion 3820. As shown, the supports 3835, 3840 are extended such that the case 3810 is elevated. The supports 3835, 3840 may be rotatably coupled at joints 3842, which may be a pin or bushing to allow rotation.

Figure 77:
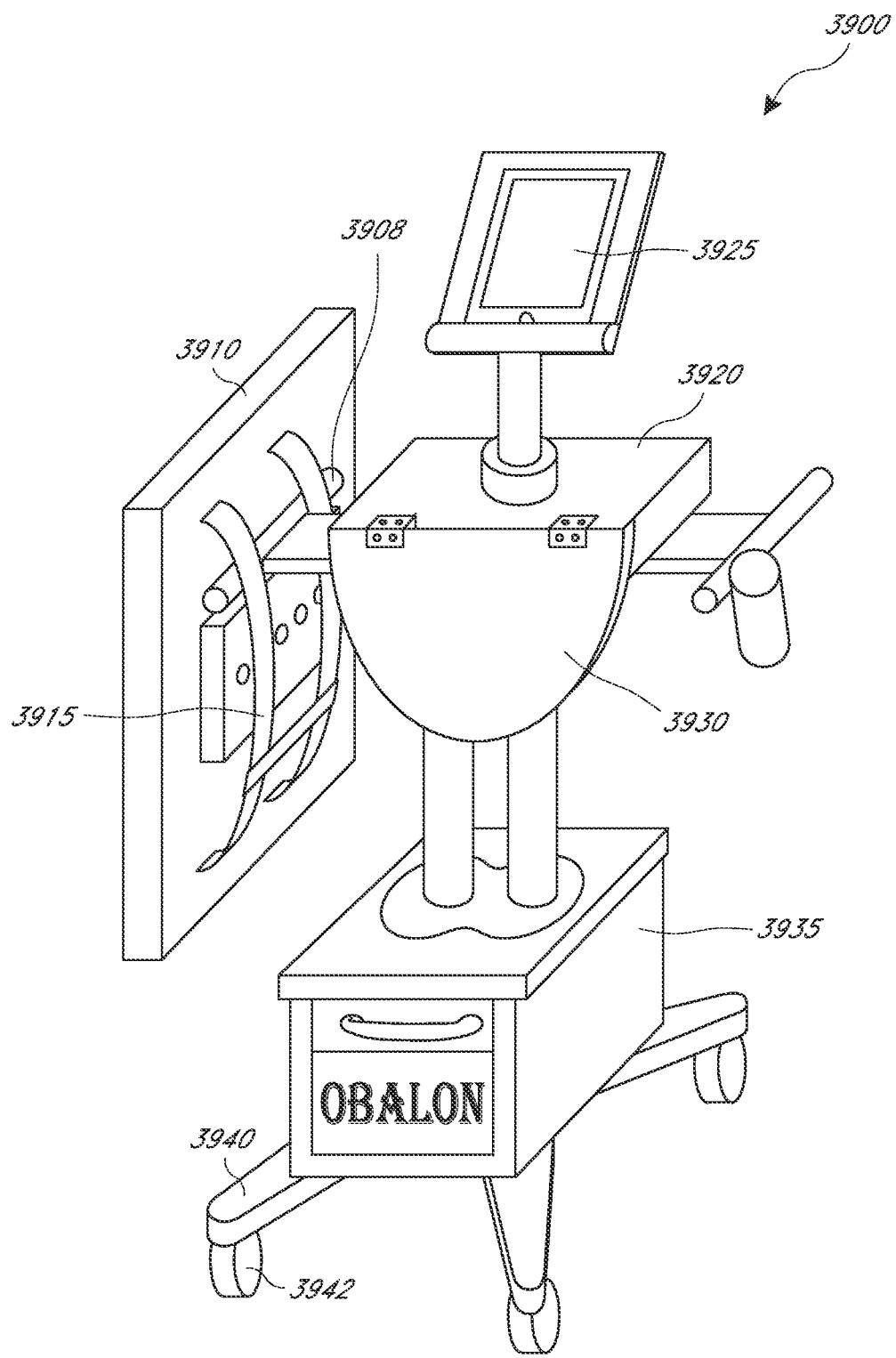
FIG. 77 is a perspective view of a backpack embodiment of the intragastric locating systems of the present disclosure.
Figure 78:
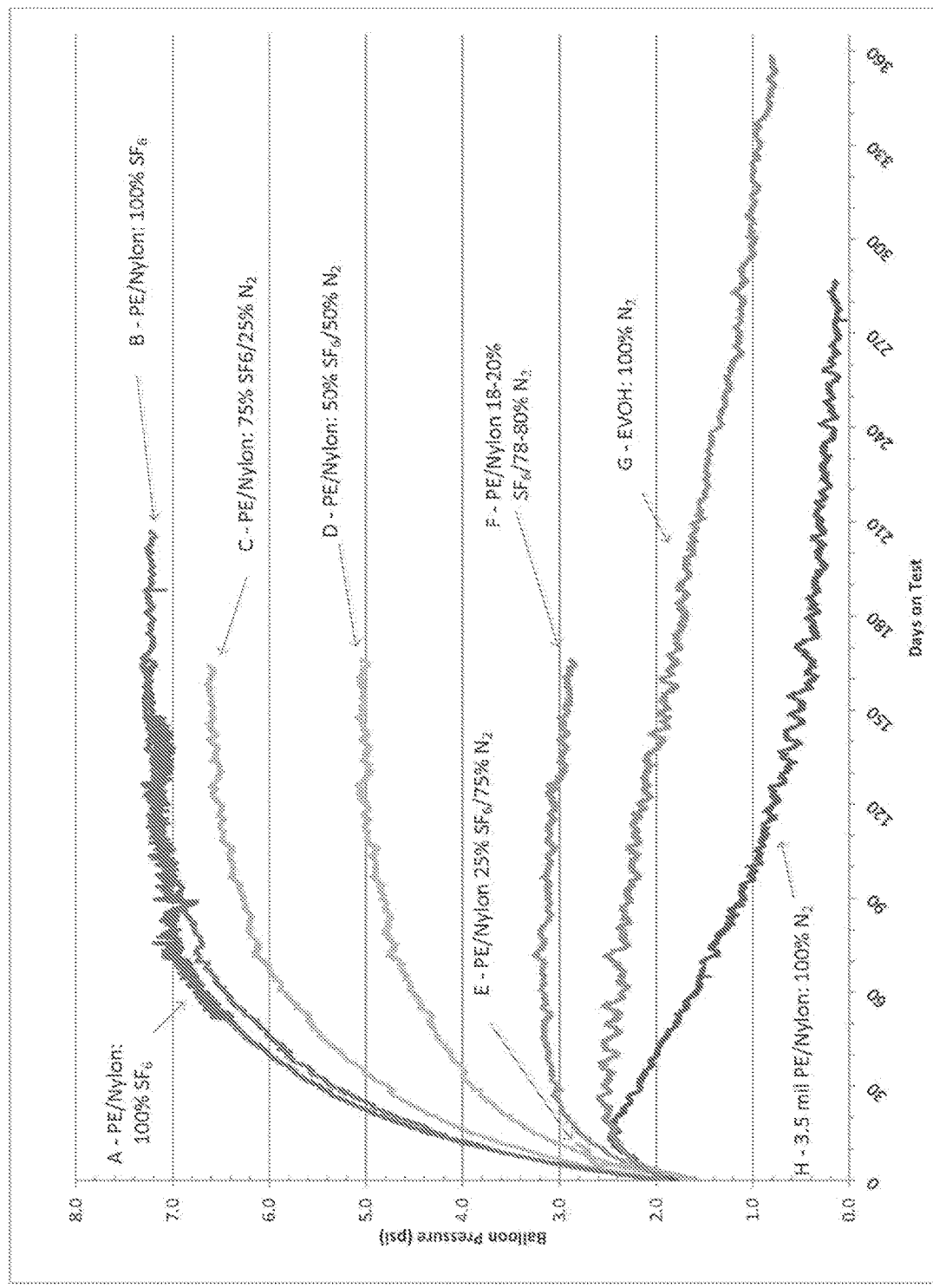
FIG. 78 provides experimental data for pressure in various intragastric balloons over time for various concentrations of $SF_6$ and/or $N_2$ as a fill gas. Line A refers to a first balloon having a wall comprising a layer of polyethylene and a layer of nylon (PE/Nylon) and filled with 100% $SF_6$. Line B refers to a second balloon having a wall comprising a layer of polyethylene and a layer of nylon (PE/Nylon) and filled with 100% $SF_6$. Line C refers to a balloon having a wall comprising a layer of polyethylene and a layer of nylon (PE/Nylon) and filled with 75% $SF_6$/25% $N_2$. Line D refers to a balloon having a wall comprising a layer of polyethylene and a layer of nylon (PE/Nylon) and filled with 50% $SF_6$/50% $N_2$. Line E refers to a balloon having a wall comprising a layer of polyethylene and a layer of nylon (PE/Nylon) and filled with 25% $SF_6$/75% $N_2$. Line F refers to a balloon having a wall comprising a layer of polyethylene and a layer of nylon (PE/Nylon) and filled with 18-20% $SF_6$/78-80% $N_2$. Line G refers to a balloon having a wall comprising a layer of ethylene vinyl alcohol (EVOH) and filled with 100% $N_2$. Line H refers to a balloon having a wall comprising a layer of 3.5 mil polyethylene and a layer of nylon (PE/Nylon) and filled with 100% $N_2$.

FIG. 77 is a perspective view of an embodiment of a backpack kit 3900 for the intragastric locating systems of the present disclosure. The kit 3900 may include any of the tracking systems discussed herein, for example the system 1501 or 1601. As shown, the kit 390 includes a case 3910. The case 3910 may store various components of the various systems and allow for easy movement of those components to and from different kits 3900. The case 3910 is shown hanging on a support member 3908 by straps 3915. The straps 3915 may allow for securing the case 3910 to the member 3908. The straps 3915 may also be sued to carry the case 3910 like a typical backpack.

The support members 3908 are coupled with a support surface 3920. The surface 3920 provides an elevated platform on which to place items while performing procedures with the systems. The surface 3920 supports a display 3925. The display 3925 may be used to show the identifiers indicating the locations of the various sensors. The surface 3920 also includes a foldable end portion 3930. The end portion 3930 is shown in the down position. It may also rotate up to provide more area for the surface 3920. The surface 3920 and end portion 3920 are supported on a frame 3935. The frame 3935 may include compartments for storing items, such as patient records or components for the system such as disposable catheters. In some embodiments, the frame 3935 includes a drawer for storing items. The frame 3935 is supported by a mount 3940 having wheels 3942 that allow the kit 3900 to be easily moved by rolling on the wheels 3942.

Film Permeability

A variety of different composite films were tested for permeability of gases as measured by $CO_2$ diffusion at 37° C., and for suitability for use as materials for wall or other components of the intragastric devices of various embodiments. As shown in the data of Table 3, the permeability of varying composite wall constructions were evaluated and determined by their resistance to $CO_2$ diffusion rates, where the smaller the permeability test result, the higher barrier to gas diffusion the film provides. As noted, the permeability of the film and degree of barrier the film provides to gas diffusion was derived using $CO_2$ at 37° C., one of the most permeable gasses. This can be used as a surrogate to other gas diffusion rates where generally $CO_2$ is 3 to 5 times faster in diffusion across a membrane than oxygen, and nitrogen is 0.2 to 0.4 times faster than the oxygen transmission rate when these are evaluated at 25° C. As Table 3 indicates, permeability of the film is also affected by orientation of the film (which layer is exposed to the $CO_2$ gas first), and Relative Humidity. The walls were tested under conditions of low relative humidity (0%, representative of conditions inside the balloon upon fill) and high relative humidity (100%, representative of in vivo conditions). In certain embodiments, a composite wall having a permeability of <10 cc/m²/day is generally preferred; however, depending upon the desired effect of inflation and re-inflation by in vivo gasses such as $CO_2$, a higher permeability of >10 cc/m²/day in in vivo conditions can be desirable. For example, each of the films in the table can be suitable for use in various selected embodiments, such that the resulting balloon wall has a permeability to $CO_2$ of even greater than >10 cc/m²/day, e.g., >50 cc/m²/day, >100 cc/m²/day, >200 cc/m²/day, >300 cc/m²/day, >400 cc/m²/day, >500 cc/m²/day, >750 cc/m²/day, >1000 cc/m²/day, >1500 cc/m²/day, >2000 cc/m²/day, >2500 cc/m²/day, >3000 cc/m²/day, >3500 cc/m²/day, or even >4000 cc/m²/day. In selected embodiments, it is generally preferred to have a permeability of from about 1, 2, 3, 4, 5, 6, 7, 8, 9, or 10 cc/m²/day to about 15, 20, 25, 30, 35, 40, 45, 50, 60, 70, 80, 90, 100, 110, 120, 130, 140 or 150 cc/m²/day. In Table 3 and elswhere herein, various films are listed. When the film comprises two or more layers, a "/" is used to indicate a layer of one material adjacent to another layer, optionally with intervening layers or materials. For example, "A/B/C" would refer to a film comprising a layer of A adjacent to a layer of B, and the layer of B adjacent to a layer of C on an opposite side of layer B from the side adjacent to layer A, with or without intervening layers or materials (e.g., tie layers, adhesives, surface preparations, surface treatments, or the like). Referring to the first entry of Table 3, "PE/EVOH/PE" refers to a film comprising a first layer of polyethylene adjacent to a layer of ethylene vinyl alcohol, and the layer of ethylene vinyl alcohol adjacent to a second layer of polyethylene on an opposite side of the ethylene vinyl alcohol to that adjacent to the first layer of polyethylene.

TABLE 3

| Film | Film Thickness (in) | Innermost Layer ($CO_2$ Exposed Layer) | RH % | Permeability Test Results (cc/m2/day) (1 ATM/ 37° C.) |
|---|---|---|---|---|
| PE/EVOH/PE | 0.002 ± 0.001 | PE | 0 | 10.8 |
| 70% Nylon 6.66, 30% MXD6/ EVOH/PVDC/ 70% Nylon 6.66, 30% MXD6/ LLDPE + LDPE | 0.003 | Nylon 6.66 | 0 | 2.4 |
| 70% Nylon 6.66, 30% MXD6/ EVOH/PVDC/ 70% Nylon 6.66, 30% MXD6/ LLDPE + LDPE | 0.003 | Nylon 6.66 | 95 ± 5 | 51.0 |
| 70% Nylon 6.66, 30% MXD6/ EVOH/PVDC/ 70% Nylon 6.66, 30% MXD6/ LLDPE + LDPE | 0.003 | LDPE | 95 ± 5 | 3.3 |
| 70% Nylon 6.66, 30% MXD6/PVDC/ 70% Nylon 6.66, 30% MXD6/ LLDPE + LDPE | 0.002 | LDPE | 0 | 43.0 |
| 70% Nylon 6.66, 30% MXD6/PVDC/ 70% Nylon 6.66, 30% MXD6/ LLDPE + LDPE | 0.003 | LDPE | 0 | 50.0 |
| 70% Nylon 6.66, 30% MXD6/PVDC/ 70% Nylon 6.66, 30% MXD6/ LLDPE + LDPE | 0.002 | LDPE | 95 ± 5 | 41.0 |
| 70% Nylon 6.66, 30% MXD6/PVDC/ 70% Nylon 6.66, 30% MXD6/ LLDPE + LDPE | 0.003 | LDPE | 95 ± 5 | 49.0 |
| Bi-axially Oriented PP/EVOH/PE | 0.00125 | LDPE | 0 | 15.4 |
| Bi-axially Oriented PP/EVOH/PE | 0.00175 | PE | 0 | 8.2 |
| Bi-axially Oriented PP/EVOH/PE | 0.00125 | PE | 95 ± 5 | 282.6 |
| Bi-axially Oriented PP/EVOH/PE | 0.00125 | PE | 95 ± 5 | 1088.0 |
| Bi-axially Oriented PP/EVOH/PE | 0.00175 | PE | 95 ± 5 | 235.4 |
| Cast PP | 0.002 ± 0.001 | NA | 0 | 772.0 |
| Cast PP/PE/EVOH/PE | 0.0025 | PE | 0 | 7.2 |
| Cast PP/PE/EVOH/PE | 0.0025 | PE | 0 | 10.1 |
| Cast PP/PE/EVOH/PE | 0.0025 | PE | 95 ± 5 | 169.3 |
| Cast PP/PE/EVOH/PE | 0.0025 | PE | 95 ± 5 | 18.5 |
| Coextruded PE/EVOH/PE | 0.00125 | PE | 0 | 8.1 |
| Coextruded PE/EVOH/PE | 0.0015 | PE | 0 | 4.9 |
| Coextruded PET/SiOx/PE | 0.002 ± 0.001 | PE | 0 | 12.4 |
| CoExtrude-LLDPE/HDPE/ EVOH/HDPE | 0.0025 | HDPE | 0 | 1.7 |
| HDPE/HDPE/PVdC/ EVOH/HDPE/ LLDPE + LDPE | 0.003 | HDPE | 0 | 5.0 |

TABLE 3-continued

| Film | Film Thickness (in) | Innermost Layer (CO₂ Exposed Layer) | RH % | Permeability Test Results (cc/m2/day) (1 ATM/ 37° C.) |
|---|---|---|---|---|
| HDPE/HDPE/PVdC/EVOH/HDPE/LLDPE + LDPE | 0.003 | HDPE | 95 ± 5 | 6.8 |
| HDPE/HDPE/PVdC/EVOH/HDPE/LLDPE + LDPE | 0.003 | LDPE | 0 | 4.4 |
| HDPE/HDPE/PVdC/EVOH/HDPE/LLDPE + LDPE | 0.003 | LDPE | 95 ± 5 | 52.0 |
| HDPE/HDPE/PVdC/HDPE/HDPE/LLDPE + LDPE | 0.003 | LDPE | 0 | 74.0 |
| HDPE/HDPE/PVdC/HDPE/HDPE/LLDPE + LDPE | 0.003 | LDPE | 0 | 47.0 |
| HDPE/HDPE/PVdC/HDPE/HDPE/LLDPE + LDPE | 0.003 | LDPE | 95 ± 5 | 68.0 |
| HDPE/HDPE/PVdC/HDPE/HDPE/LLDPE + LDPE | 0.003 | LDPE | 95 ± 5 | 44.0 |
| Kurarister ™ C, 3 mil | 0.003 | UNK | 0 | 3.2 |
| Nylon12/PvDC/Nylon 12/LLDPE + LDPE | 0.003 | LLDPE + LDPE | 0 | 52.0 |
| Nylon12/PvDC/Nylon 12/LLDPE + LDPE | 0.003 | LLDPE + LDPE | 95 ± 5 | 56.0 |
| MPI Supernyl LLDPE 40 μm | 0.0022 | LLDPE | 0 | 3.3 |
| MPI Supernyl LLDPE 40 μm | 0.0022 | LLDPE | 95 ± 5 | 5.8 |
| MPI Supernyl LLDPE 50 μm | 0.0026 | LLDPE | 0 | 4.2 |
| MPI Supernyl LLDPE 50 μm | 0.0026 | LLDPE | 95 ± 5 | 7.5 |
| Nylon12/PvDC/Nylon 12/LLDPE + LDPE | 0.003 | LLDPE + LDPE | 0 | 59.3 |
| Nylon12/PVDC/Nylon12/LLDPE + LDPE | 0.003 | LLDPE + LDPE | 95 ± 5 | 29.5 |
| Nylon12/PVDC/Nylon12/LLDPE + LDPE-Thermoformed | 0.003 | LLDPE + LDPE | 0 | 73.2 |
| Nylon12/PVDC/Nylon12/LLDPE + LDPE | 0.0024 | LLDPE + LDPE | 0 | 77.0 |
| Nylon12/PVDC/Nylon12/LLDPE + LDPE | 0.0024 | LLDPE + LDPE | 95 ± 5 | 68.0 |
| Nylon12/PVdC/Nylon12/LDPE-Cast | 0.003 | LDPE | 0 | 58.0 |
| Nylon12/Nylon Tie/EVA/PVdC/Adhesive/Nylon12/Nylon Tie/LDPE-Cast | 0.003 | LDPE | 95 ± 5 | 54.0 |
| Nylon12/PVdC/Nylon12/LDPE | 0.0035 | LDPE | 0 | 14.9 |
| Nylon12/PVdC/Nylon12/LDPE | 0.004 | LDPE | 0 | 34.0 |
| Nylon12/PVdC/Nylonl2/LDPE | 0.0035 | LDPE | 95 ± 5 | 24.9 |
| Nylon12/PVdC/Nylon12/LDPE | 0.0035 | LDPE | 95 ± 5 | 41.3 |
| Nylon12/PVdC/Nylon12/LDPE | 0.004 | LDPE | 95 ± 5 | 31.7 |
| Nylon 6.66/PVDC/Nylon 6.66/LLDPE + LDPE | 0.0024 | LDPE | 0 | 54.0 |
| Nylon 6.66/PVDC/Nylon 6.66/LLDPE + LDPE | 0.0024 | LDPE | 95 ± 5 | 56.0 |
| Nylon 6.66/EVOH/PVDC/Nylon 6.66/LDPE | 0.0032 | LDPE | 0 | 5.5 |
| Nylon 6.66/EVOH/PVDC/Nylon 6.66/LDPE | 0.0032 | LDPE | 95 ± 5 | 6.4 |
| Nylon 6.66/EVOH/PVDC/Nylon 6.66/LDPE | 0.0032 | Nylon 6.66 | 95 ± 5 | 49.9 |
| Nylon 6.66/PVDC/Nylon 6.66/LLDPE + LDPE | 0.0027 | LDPE | 0 | 57.0 |
| Nylon 6.66/PVDC/Nylon 6.66/LLDPE + LDPE | 0.003 | LDPE | 0 | 41.0 |
| Nylon 6.66/PVDC/Nylon 6.66/LLDPE + LDPE | 0.0027 | LDPE | 95 ± 5 | 55.0 |
| Nylon 6.66/PVDC/Nylon 6.66/LLDPE + LDPE | 0.003 | LDPE | 95 ± 5 | 46.0 |
| Multi-layer Nylon 12/LLDPE + LDPE | 0.0035 | LDPE | 0 | 3203.5 |
| Multi-layer Nylon 12/LLDPE + LDPE | 0.004 | LDPE | 0 | 2725.5 |
| Multi-layer Nylon 12/LLDPE + LDPE | 0.0045 | LDPE | 0 | 2553.6 |
| Multi-layer Nylon 12/LLDPE + LDPE | 0.0035 | LDPE | 95 ± 5 | 2539.3 |
| Multi-layer Nylon 12/LLDPE + LDPE | 0.004 | LDPE | 95 ± 5 | 2527.8 |
| Multi-layer Nylon 12/LLDPE + LDPE + Parylene | 0.0045 | LDPE | 0 | 1522.6 |
| Multi-layer Nylon 12/LLDPE + LDPE + Parylene | 0.0045 | LDPE | 95 ± 5 | 1275.5 |
| NYLON-SIOX/HDPE/LLDPE | 0.003 | LLDPE | 95 ± 5 | 83.0 |
| NYLON-SIOX/HDPE/LLDPE | 0.003 | LLDPE | 0 | 70.0 |
| Nylon-SIOX/LLDPE | 0.0015 | LLDPE | 0 | 134.0 |
| Nylon-SIOX/LLDPE | 0.0015 | LLDPE | 95 ± 5 | 82.0 |
| OPP Co-extrude with mPE/EVOH/mPE | 0.002 | mPE | 0 | 5.9 |
| OPP Laminated to mPE/EVOH/mPE | 0.0025 | mPE | 0 | 4.7 |
| OPP Laminated to mPE/EVOH/mPE | 0.003 | mPE | 0 | 3.4 |
| OPP Laminated to mPE/EVOH/mPE | 0.0025 | mPE | 95 ± 5 | 294.3 |
| OPP SIOX/LLDPE | 0.002 | LLDPE | 0 | 540.5 |
| OPP SIOX/LLDPE | 0.002 | LLDPE | 0 | 1081.0 |
| OPP SIOX/LLDPE | 0.002 | LLDPE | 95 ± 5 | 565.0 |
| OPP SIOX/LLDPE | 0.002 | LLDPE | 95 ± 5 | 594.5 |
| OPP/mPE/EVOH/mPE | 0.0021 | mPE | 0 | 5.0 |
| OPP/mPE/EVOH/mPE | 0.0021 | mPE | 95 ± 5 | 437.1 |
| OPP/PE/EVOH/PE | 0.0025 | OPP | 0 | 8.5 |
| OPP/PE/EVOH/PE | 0.0025 | OPP | 95 ± 5 | 11.6 |
| OPP/PE/EVOH/PE | 0.00175 | PE | 0 | 8.1 |
| OPP/PE/EVOH/PE | 0.0025 | PE | 0 | 8.9 |

TABLE 3-continued

| Film | Film Thickness (in) | Innermost Layer ($CO_2$ Exposed Layer) | RH % | Permeability Test Results (cc/m2/day) (1 ATM/ 37° C.) |
|---|---|---|---|---|
| OPP/PE/ EVOH/PE | 0.0025 | PE | 0 | 18.6 |
| OPP/PE/ EVOH/PE | 0.0025 | PE | 95 ± 5 | 259.0 |
| OPP/PE/ EVOH/PE | 0.0025 | PE | 95 ± 5 | 556.1 |
| OPP/PVDC/mPE | 0.0017 | mPE | 0 | 74.2 |
| OPP/PVDC/mPE | 0.0017 | mPE | 95 ± 5 | 84.6 |
| OPP-SIOX/LLDPE | 0.002 ± 0.001 | LLDPE | 95 ± 5 | 1159.7 |
| Oriented PA | 0.002 ± 0.001 | NA | 0 | 750.9 |
| Oriented PP | 0.002 ± 0.001 | NA | 0 | 726.0 |
| PA/EVOH/ PA/LLDPE | 0.0022 | LLDPE | 0 | 5.0 |
| PA/EVOH/ PA/LLDPE | 0.0022 | LLDPE | 0 | 3.1 |
| PA/EVOH/ PA/LLDPE | 0.0022 | LLDPE | 95 ± 5 | 10.8 |
| PE/EVOH/PE | 0.002 ± 0.001 | PE | 0 | 9.2 |

Animal Studies

Two different composite walls were tested: a material (Nylon12/PvDC/Nylon 12/LLDPE+LDPE) with high barrier material characteristics and a material with low barrier characteristics (multi-layer Nylon12/LLDPE+LDPE). A series of experiments were performed using a mixture of 75% $N_2$ and 25% $CO_2$ as the balloon initial fill. As shown in the data of Table 4, each of the balloons maintained pressure over the duration tested, but gained substantially in volume. Considering the composite walls studied are not a metal canister (volume and pressure change due to material stretch) there was a significant change in the number of overall gas molecules inside the balloon from the initial gas fill. Since the internal balloon environment started with $CO_2$ and nitrogen, most likely additional $CO_2$ entered due to the environment the balloon was subjected to ($N_2$ and $CO_2$ headspace) but also most likely other gases available in the air as well as water vapor also diffused within the balloon wall.

TABLE 4

| Pig # | Balloon #, Wall Composition | Starting implant pressure (PSI) | Estd. Volume at implant | Explant Volume (cc) | Explant Pressure (PSI) | % $CO_2$ in balloon (meas. w/ $CO_2$ meter) | Measured % $CO_2$ in stomach gas (%) | Final Vol. | % gas gain (calc.) |
|---|---|---|---|---|---|---|---|---|---|
| 1 | 1, Barrier Material (Nylon/Saran) | 1.0 | 277 | 360 | 1.1 | 22% | 10% | 385 | 23.5 |
| 1 | 2, Barrier Material (Nylon/Saran) | 1.09 | 282 | 340 | 0.7 | 19.63% | 10% | 358 | 15 |
| 2 | 3, Non-Barrier Material (Nylon) | 1.15 | 283 | 330 | 1.2 | 26.57% | 8% | 320 | 14.5 |
| 2 | 4, Non-Barrier Material (Nylon) | 1.07 | 281 | 323 | 0.96 | 31% | 8% | 316 | 12.4 |

TABLE 3-continued

| Film | Film Thickness (in) | Innermost Layer ($CO_2$ Exposed Layer) | RH % | Permeability Test Results (cc/m2/day) (1 ATM/ 37° C.) |
|---|---|---|---|---|
| PET | 0.001 | PE | 0 | 524.7 |
| SiOx-PET/EVOH/PE | 0.002 | PE | 0 | 1.4 |
| SiOx-PET/MPE/ EVOH/mPE | 0.0016 | mPE | 0 | 1.0 |
| Si-Ox-PET/PE/ EVOH/PE | 0.00125 | PE | 0 | 1.7 |
| Si-Ox-PET/PE/ EVOH/PE | 0.0015 | PE | 0 | 1.6 |
| Si-Ox-PET/PE/ EVOH/PE | 0.0015 | PE | 0 | 5.4 |
| Si-Ox-PET/PE/ EVOH/PE | 0.002 | PE | 0 | 1.5 |
| Si-Ox-PET/PE/ EVOH/PE | 0.002 | PE | 0 | 1.8 |
| Si-Ox-PET/PE/ EVOH/PE | 0.002 | PE | 95 ± 5 | 22.6 |

Volume gains were higher for the barrier material composite walls than for the non-barrier walls. An analysis of gas in the balloons after explants (Tables 5a and 5b) showed gains in oxygen, hydrogen, and argon in addition to the nitrogen and carbon dioxide that was already present in the balloon at initial inflation. The balloons, both with a good barrier composite wall (table 5a) and a poor barrier composite wall (table 5b) both gained in overall volume while maintaining pressure after 30 days in vivo. Explant results of the balloon with a composite wall containing a good barrier material (#2, table 5a) showed a slightly higher increase in carbon dioxide than the wall without a barrier material (#3, table 5b). It is unlikely that nitrogen diffused in or out of the balloon due to its inertness as well as the external gastric environment most likely matched the internal concentration of nitrogen such that there was no (or an insignificant) diffusion gradient for the nitrogen gas.

TABLE 5a

| Gas | % v/v, by MS | Detection Limit |
|---|---|---|
| Nitrogen | 64.04 | 0.01 |
| Oxygen | 7.63 | 0.01 |

TABLE 5a-continued

| Gas | % v/v, by MS | Detection Limit |
| --- | --- | --- |
| Argon | 0.60 | 0.01 |
| Carbon Dioxide | 19.63 | 0.01 |
| Hydrogen | 8.10 | 0.01 |
| Helium | not detected | 0.01 |
| Methane | not detected | 0.01 |

TABLE 5b

| Gas | % v/v, by MS | Detection Limit |
| --- | --- | --- |
| Nitrogen | 62.33 | 0.01 |
| Oxygen | 9.27 | 0.01 |
| Argon | 0.7 | 0.01 |
| Carbon Dioxide | 26.57 | 0.01 |
| Hydrogen | 1.13 | 0.01 |
| Helium | not detected | 0.01 |
| Methane | not detected | 0.01 |

The data show that when it is desirable to minimize volume gain over the useful life of the device, a non-barrier composite wall material may be more desirable than a barrier wall. This observation is contrary to conventional wisdom that seeks to maintain the initial fill of gas in the balloon by maximizing barrier properties of the intragastric balloon wall.

Simulated Gastric Environment

Balloons constructed with non-barrier film composite walls were tested (multi-layer Nylon 12/LLDPE+LDPE) in a simulated gastric environment (tank containing a 1.2 pH HCl solution with NaCl and pepsin at 40° C. with a variable $N_2/CO_2$ headspace; samples were taken at peak $CO_2$ at 50% and trough $CO_2$ at 0% in the tank). The balloons were initially filled with either pure $N_2$ or a mixture of $N_2$ (75%) and $CO_2$ (25%), and pressure, volume, and gas gain were monitored over time. The balloon filled with pure nitrogen exhibited significantly higher gain of $CO_2$ when compared to the balloon filled with the $N_2/CO_2$ mixture. When a volume gain (as manifested in a gain of $CO_2$ gas) is desired, pure nitrogen as the initial fill gas in connection with a non-barrier film is desirable. Data for the experiments is provided in Table 6.

TABLE 6

| Experiment # | Material | Sample # | Balloon Internal Gas | Pressure (Day 0) T = 0 (psi) | Volume (Day 0) T = 0 (cc) | Volume (Day 1) T = 1 (cc) | Volume (Day 2) 50% CO₂ T = 2 (cc) | Pressure (Day 2) 50% CO₂ T = 2 (psi) | (Day 2) 9:00 AM % Gas Gain T = 2 (%) | Volume (Day 5) 9:00 am 50% CO₂ T = 5 (cc) | Volume (Day 5) 7:00 PM 50% CO₂ T = 5 (cc) | Volume (Day 5) 7:00 PM 0% CO₂ T = 5 (cc) | Pressure (Day 5) 7:00 PM 0% CO₂ T = 5 (psi) | (Day 5) 7:00 PM % Gas Gain T = 5 (%) |
|---|---|---|---|---|---|---|---|---|---|---|---|---|---|---|
| 1 | Non-Barrier Film | 1 | N₂ | 1.12 | 304 | 312 | 314 | 1.84 | 7.4% | 323 | 319 | 319 | 2.50 | 12.3% |
|   |   | 3 |   | 1.12 | 300 | 310 | 313 | 1.81 | 8.2% | 319 | 314 | 314 | 2.53 | 12.3% |
|   |   | 4 |   | 1.09 | 294 | 309 | 311 | 1.79 | 9.5% | 321 | 313 | 313 | 2.56 | 14.1% |
|   |   | 5 |   | 1.10 | 300 | 312 | 314 | 1.82 | 8.6% | 324 | 318 | 318 | 2.70 | 14.3% |
|   |   | 6 |   | 1.10 | 309 | 317 | 320 | 1.68 | 6.9% | 329 | 328 | 328 | 2.58 | 13.9% |
|   |   | avg. |   | 1.11 | 301 | 312 | 314 | 1.79 | 8.1% | 323 | 318 | 318 | 2.57 | 13.4% |
| 2 |   | 1B | N₂/CO₂ (75%/25%) | 1.10 | 318 | 328 | 326 | 1.15 | 2.1% | 302 | 324 | 324 | 1.37 | 2.6% |
|   |   | 2B |   | 1.00 | 295 | 301 | 299 | 1.04 | 1.2% | 299 | 297 | 297 | 1.28 | 1.8% |
|   |   | 4B |   | 1.10 | 292 | 300 | 295 | 1.18 | 1.1% | 305 | 293 | 293 | 1.25 | 1.0% |
|   |   | 5B |   | 1.08 | 294 | 306 | 303 | 1.22 | 2.9% | 298 | 302 | 302 | 1.16 | 2.4% |
|   |   | 6B |   | 1.07 | 293 | 300 | 293 | 1.18 | 0.5% | 307 | 295 | 295 | 1.26 | 1.4% |
|   |   | avg. |   | 1.07 | 298 | 307 | 303 | 1.15 | 1.6% | — | — | — | 1.26 | 1.8% |

| Experiment # | Material | Sample # | Balloon Internal Gas | Volume (Day 6) 8:00 AM 50% CO₂ T = 6 (cc) | Pressure (Day 6) 8:00 AM 50% CO₂ T = 6 (psi) | (Day 6) 8:00 AM % Gas Gain* T = 6 (%) | Volume (Day 6) 7:00 PM 0% CO₂ T = 6 (cc) | Pressure (Day 6) 7:00 PM 0% CO₂ T = 6 (psi) | (Day 6) 7:00 PM % Gas Gain T = 6 (%) | Volume (Day 7) 8:00 AM 50% CO₂ T = 7 (cc) | Pressure (Day 7) 8:00 AM 50% CO₂ T = 7 (psi) | CO₂ % (Day 7) 8:00 AM % Gas Gain* T = 7 (%) | Volume (Day 7) 7:00 PM 0% CO₂ T = 7 (cc) |
|---|---|---|---|---|---|---|---|---|---|---|---|---|---|
| 1 | Non-Barrier Film | 1 | N₂ | 323 | 3.03 | 16.0% | 318 | 2.84 | 14.9% | 322 | 3.02 | 16.8% | 319 |
|   |   | 3 |   | 320 | 3.01 | 16.3% | 321 | 2.87 | 17.7% | 322 | 3.05 | 18.8% | 320 |
|   |   | 4 |   | 322 | 3.04 | 18.7% | 322 | 2.98 | 16.7% | 325 | 3.15 | 18.3% | 323 |
|   |   | 5 |   | 322 | 3.19 | 17.7% | 329 | 2.89 | 15.6% | 331 | 3.08 | 17.0% | 329 |
|   |   | 6 |   | 330 | 3.12 | 17.0% | 323 | 2.90 | 16.2% | 325 | 3.08 | 17.7% | 323 |
|   |   | avg. |   | 323 | 3.08 | 17.1% |   |   |   | balloon cut during test |   |   |   |
| 2 |   | 1B | N₂/CO₂ (75%/25%) | 329 | 1.82 | 5.7% | 329 | 1.48 | 4.2% | 327 | 1.63 | 4.4% | 326 |
|   |   | 2B |   | 300 | 1.61 | 4.0% | 301 | 1.38 | 3.2% | 300 | 1.57 | 3.8% | 299 |
|   |   | 4B |   | 299 | 1.64 | 4.2% | 298 | 1.46 | 3.1% | 299 | 1.61 | 4.0% | 296 |
|   |   | 5B |   | 304 | 1.55 | 4.6% | 306 | 1.33 | 4.1% | 303 | 1.45 | 3.9% | 303 |
|   |   | 6B |   | 299 | 1.62 | 4.0% | 298 | 1.41 | 2.8% | 300 | 1.60 | 4.1% | 297 |
|   |   | avg. |   | 306 | 1.65 | 4.5% | 306 | 1.41 | 3.5% | 306 | 1.57 | 4.1% | 304 |

TABLE 6-continued

| Experiment # | Material | Sample # | Balloon Internal Gas | Pressure (Day 7) 7:00 PM T = 7 (psi) | CO₂ % (Day 7) 7:00 PM T = 7 (%) | Volume (Day 8) 8:00 AM T = 8 (cc) | Pressure (Day 8) 8:00 AM T = 8 (psi) | CO₂ % (Day 8) 8:00 AM T = 8 (%) | Volume (Day 8) 7:00 PM T = 8 (cc) | Pressure (Day 8) 7:00 PM T = 8 (psi) | CO₂ % (Day 8) 7:00 PM T = 8 (%) | Volume (Day 9) 8:00 AM T = 9 (cc) | Pressure (Day 9) 8:00 AM T = 9 (psi) |
|---|---|---|---|---|---|---|---|---|---|---|---|---|---|
| | | | | | End of Cycle → | | 50% CO₂ % Gas Gain | 50% CO₂ % Gas Gain | 0% CO₂ % Gas Gain | 0% CO₂ % Gas Gain | 0% CO₂ % Gas Gain | 50% CO₂ % Gas Gain | 50% CO₂ |
| 1 | Non-Barrier Film | 1 | N₂ | 2.90 | 15.5% | 322 | 3.01 | 16.8% | 318 | 2.88 | 15.1% | 323 | 2.96 |
| | | 3 | | 2.92 | 17.7% | 323 | 2.99 | 18.8% | 322 | 2.87 | 17.9% | 323 | 3.00 |
| | | 4 | | 2.91 | 16.7% | 325 | 3.07 | 17.9% | 325 | 2.96 | 17.4% | 323 | 3.01 |
| | | 5 | | 2.88 | 15.6% | 332 | 3.03 | 17.1% | 330 | 2.88 | 15.8% | 332 | 2.91 |
| | | 6 | | 2.90 | 16.3% | 326 | 3.03 | 17.6% | 324 | 2.90 | 16.6% | 325 | 2.97 |
| | | avg. | | | | | | | | | | | |
| 2 | | 1B | N₂/CO₂ (75%/25%) | 1.42 | 3.3% | 329 | 1.43 | 4.0% | 325 | 1.30 | 2.5% | 327 | 1.28 |
| | | 2B | | 1.37 | 2.7% | 301 | 1.42 | 3.4% | 314 | 1.28 | 5.8% | 301 | 1.35 |
| | | 4B | | 1.37 | 2.3% | 299 | 1.29 | 2.6% | 300 | 1.32 | 3.0% | 298 | 1.45 |
| | | 5B | | 1.23 | 2.9% | 306 | 1.32 | 4.0% | 304 | 1.23 | 3.2% | 307 | 1.35 |
| | | 6B | | 1.42 | 2.6% | 299 | 1.43 | 3.1% | 299 | 1.34 | 2.7% | 299 | 1.39 |
| | | avg. | | 1.36 | 2.8% | 307 | 1.38 | 3.4% | 308 | 1.29 | 3.4% | 306 | 1.36 |

| Experiment # | Material | Sample # | Balloon Internal Gas | T = 9 (%) | Volume (Day 12) 8:00 AM T = 8 (cc) | Pressure (Day 12) 8:00 AM T = 8 (psi) | % Gas Gain* T = 8 (%) | Volume (Day 13) 8:00 AM T = 9 (cc) | Pressure (Day 13) 8:00 AM T = 9 (psi) | % Gas Gain* T = 9 (%) | Volume (Day 14) 8:00 AM T = 10 (cc) | Pressure (Day 14) 8:00 AM T = 10 (psi) | % Gas Gain* T = 10 (%) |
|---|---|---|---|---|---|---|---|---|---|---|---|---|---|
| | | | | End of Cycle → | | | | | 50% CO2 | 50% CO2 | 50% CO2 | 50% CO2 | 50% CO2 |
| 1 | Non-Barrier Film | 1 | N₂ | 16.8% | 323 | 3.00 | 17.0% | 325 | 3.37 | 19.2% | 323 | 3.25 | 18.1% |
| | | 3 | | 18.8% | 322 | 3.25 | 19.7% | 326 | 3.36 | 21.2% | 327 | 3.21 | 20.7% |
| | | 4 | | 17.1% | 325 | 3.27 | 18.8% | 327 | 3.38 | 19.8% | 326 | 3.36 | 19.5% |
| | | 5 | | 16.5% | 330 | 3.25 | 17.6% | 333 | 3.30 | 18.5% | 334 | 3.30 | 18.8% |
| | | 6 | | 17.3% | 325 | 3.19 | 18.3% | 328 | 3.35 | 19.7% | 328 | 3.28 | 19.3% |
| | | avg. | | | | | | | | | | | |
| 2 | | 1B | N₂/CO₂ (75%/25%) | 2.9% | 326 | 1.62 | 4.2% | 330 | 1.68 | 5.3% | 329 | 1.68 | 5.1% |
| | | 2B | | 3.1% | 302 | 1.42 | 4.5% | 304 | 1.69 | 5.3% | 302 | 1.48 | 3.9% |
| | | 4B | | 3.1% | 298 | 1.66 | 3.0% | 300 | 1.56 | 4.1% | 299 | 1.43 | 3.3% |
| | | 5B | | 4.4% | 305 | 1.62 | 5.3% | 309 | 1.69 | 6.3% | 307 | 1.57 | 5.3% |
| | | 6B | | 3.0% | 298 | 1.58 | 3.6% | 298 | 1.70 | 4.1% | 300 | 1.66 | 4.4% |
| | | avg. | | 3.3% | 306 | 1.58 | 4.1% | 308 | 1.66 | 5.0% | 307 | 1.56 | 4.4% |

Balloons constructed with various composite walls, a barrier material Nylon12/PvDC/Nylon12/LLDPE+LDPE) and a non-barrier material (multi-layer Nylon12/LLDPE+LDPE) were tested in a simulated gastric environment (tank containing a 1.2 pH HCl solution with NaCl and pepsin at 40° C. with a variable $N_2/CO_2$ headspace (75%/25% to 100%/0%)). The balloons were initially filled with a mixture of $N_2$ (75%) and $CO_2$ (25%). Pressure for the balloons fabricated from $CO_2$ barrier materials maintained pressure and volume over the time period tested, whereas the balloons fabricated from $CO_2$ non-barrier materials exhibited substantial pressure gain over the same time period, with a smaller volume gain. Results are presented in Table 7 stimulated gastric environment. The simulated gastric environment comprised a tank containing a 1.2 pH HCl solution with NaCl and pepsin at 40° C. The headspace in the tank was cycled from a gas mixture comprising 75% $N_2$/25% $CO_2$ headspace to one comprising 100% $N_2$/0% $CO_2$. The balloons were initially filled with various mixtures of $N_2$ and $CO_2$, and volume was monitored. Data regarding volume changes are provided in Table 8. The balloons constructed using walls having a higher permeability to $CO_2$ gained substantially in volume compared to those with high $CO_2$ barrier properties. For the balloons constructed using walls having a higher permeability to $CO_2$, those with higher ratios of $N_2$ to $CO_2$ as initial fill gas gained less volume than

TABLE 7

| Exp. | Material | Sample | Balloon Internal Gas | Volume (Day 0) (cc) | Pressure (Day 0) (psi) | Volume (Day 1) (cc) | Pressure (Day 1) (psi) | Volume (Day 2) (cc) | Pressure (Day 2) (psi) | Volume (Day 3) (cc) | Pressure (Day 3) (psi) | Volume (Day 4) (cc) | Pressure (Day 4) (psi) | Volume (Day 5) (cc) | Pressure (Day 5) (psi) |
|---|---|---|---|---|---|---|---|---|---|---|---|---|---|---|---|
| 1 | Barrier | 1 | $N_2/CO_2$ | | | 280 | 1.05 | | | 286 | 1.05 | 289 | 1.08 | 292 | 1.07 |
| | | 2 | (75%/25%) | | | 279 | 1.03 | | | 284 | 1.01 | 287 | 1.03 | 292 | 1.04 |
| | | avg. | | | | 280 | 1.04 | | | 285 | 1.03 | 288 | 1.06 | 292 | 1.06 |
| 2 | Barrier | 1 | $N_2/CO_2$ | | | 279 | 1.06 | | | 283 | 0.97 | 284 | 1.14 | 287 | 1.01 |
| | | 2 | (75%/25%) | | | 278 | 1.07 | | | 282 | 1.04 | 286 | 1.13 | 287 | 1.02 |
| | | avg. | | | | 279 | 1.07 | | | 283 | 1.01 | 285 | 1.14 | 287 | 1.02 |
| 3 | Barrier | 1 | $N_2/CO_2$ | | | 280 | 1.05 | | | 287 | 1.05 | 285 | 1.09 | 287 | 1.05 |
| | | 2 | (75%/25%) | | | 278 | 1.02 | | | 280 | 0.97 | 285 | 1.05 | 286 | 1.00 |
| | | avg. | | | | 279 | 1.04 | | | 284 | 1.01 | 285 | 1.07 | 287 | 1.03 |
| 4 | Barrier | 1 | $N_2/CO_2$ | 296 | 1.14 | | | | | 303 | 1.28 | 308 | 1.35 | 309 | 1.36 |
| | | 2 | (75%/25%) | 295 | 1.05 | | | | | 303 | 1.18 | 306 | 1.39 | 306 | 1.29 |
| | | avg. | | 296 | 1.10 | | | | | 303 | 1.23 | 307 | 1.37 | 308 | 1.33 |
| 5 | Non-Barrier | 1 | $N_2/CO_2$ | 304 | 1.12 | | | | | 313 | 2.26 | 320 | 2.44 | 322 | 2.51 |
| | | 2 | (75%/25%) | 292 | 1.11 | | | | | 312 | 2.37 | 315 | 2.59 | 315 | 2.58 |
| | | avg. | | 298 | 1.12 | | | | | 313 | 2.32 | 318 | 2.52 | 319 | 2.55 |
| 6 | Non-Barrier | 1 | $N_2/CO_2$ | 298 | 1.15 | | | | | 308 | 2.34 | 311 | 2.48 | 312 | 2.59 |
| | | 2 | (75%/25%) | 294 | 1.14 | | | | | 301 | 2.15 | 306 | 2.39 | 308 | 2.51 |
| | | avg. | | 296 | 1.15 | | | | | 305 | 2.25 | 309 | 2.44 | 310 | 2.55 |
| 7 | Non-Barrier | 1 | $N_2/CO_2$ | 297 | 1.14 | | | | | 307 | 2.17 | 310 | 2.43 | 308 | 2.45 |
| | | 2 | (75%/25%) | 302 | 1.15 | | | | | 312 | 2.22 | 315 | 2.43 | 316 | 2.54 |
| | | avg. | | 300 | 1.15 | | | | | 310 | 2.20 | 313 | 2.43 | 312 | 2.50 |
| 8 | Barrier | 1 | $N_2/CO_2$ | 298 | 1.11 | | | | | 303 | 1.28 | 305 | 1.39 | 305 | 1.36 |
| | | 2 | (75%/25%) | 302 | 1.12 | | | | | 303 | 1.28 | 303 | 1.34 | 306 | 1.31 |
| | | avg. | | 300 | 1.12 | | | | | 303 | 1.28 | 304 | 1.37 | 306 | 1.34 |
| 9 | Barrier | 1 | $N_2/CO_2$ | 294 | 1.18 | | | | | 301 | 1.24 | 303 | 1.30 | 304 | 1.29 |
| | | 2 | (75%/25%) | 291 | 1.13 | | | | | 298 | 1.24 | 298 | 1.35 | 299 | 1.33 |
| | | avg. | | 293 | 1.16 | | | | | 300 | 1.24 | 301 | 1.33 | 302 | 1.31 |

Balloons constructed with composite walls with high $CO_2$ barrier properties (Experiments 1, 2, and 3) (Nylon12/PvDC/Nylon 12/LLDPE+LDPE) and walls having a higher permeability to $CO_2$ (Experiments 4, 5, and 6) consisting of multi-layer Nylon12/LLDPE+LDPE were exposed to a those with lower ratios of $N_2$ to $CO_2$. The data demonstrate that permeation of $CO_2$ into balloons fabricated with walls having a higher permeability to $CO_2$ occurs quickly in the gastric environment, and that this process can be employed to assist with inflation in the early stages of implant.

TABLE 8

| Experiment | Material | Sample | Balloon Internal Gas | Volume (Day 1) 5:00 PM (cc) | Pressure (Day 1) 5:00 PM (psi) | Volume (Day 2) 8:00 AM (cc) | Pressure (Day 2) 8:00 AM (psi) | Volume (Day 2) 8:30 PM (cc) | Pressure (Day 2) 8:30 PM (psi) | Volume (Day 3) 8 AM (cc) | Pressure (Day 3) 8 AM (psi) |
|---|---|---|---|---|---|---|---|---|---|---|---|
| 1 | Barrier | 1 | N2/CO2 | 298 | 1.07 | 301 | 1.08 | 301 | 1.11 | 301 | 1.13 |
| | | 2 | (92%/8%) | 293 | 1.02 | 293 | 1.06 | 295 | 1.06 | 302 | 1.10 |
| | | 3 | | 285 | 1.00 | 287 | 1.05 | 284 | 1.03 | 289 | 1.07 |
| | | avg. | | 296 | 1.05 | 297 | 1.07 | 298 | 1.09 | 302 | 1.12 |
| 2 | Barrier | 1 | N2/CO2 | 286 | 1.09 | 287 | 1.09 | 287 | 1.13 | 287 | 1.12 |
| | | 2 | (90%/10%) | 291 | 1.09 | 294 | 1.14 | 294 | 1.13 | 296 | 1.17 |
| | | 3 | | 293 | 1.08 | 298 | 1.13 | 297 | 1.15 | 300 | 1.19 |
| | | avg. | | 290 | 1.09 | 304 | 1.20 | 293 | 1.14 | 294 | 1.16 |
| 3 | Barrier | 1 | N2/CO2 | 290 | 1.10 | 295 | 1.15 | 294 | 1.17 | 297 | 1.21 |
| | | 2 | (85%/15%) | 290 | 1.02 | 290 | 1.03 | 290 | 1.08 | 294 | 1.10 |
| | | 3 | | 299 | 1.16 | 304 | 1.20 | 302 | 1.27 | 308 | 1.27 |
| | | avg. | | 293 | 1.09 | 293 | 1.09 | 295 | 1.17 | 300 | 1.19 |

TABLE 8-continued

| Experiment | Material | Sample | Balloon Internal Gas | Volume (Day 1) 5:00 PM (cc) | Pressure (Day 1) 5:00 PM (psi) | Volume (Day 2) 8:00 AM (cc) | Pressure (Day 2) 8:00 AM (psi) | Volume (Day 2) 8:30 PM (cc) | Pressure (Day 2) 8:30 PM (psi) | Volume (Day 3) 8 AM (cc) | Pressure (Day 3) 8 AM (psi) |
|---|---|---|---|---|---|---|---|---|---|---|---|
| 4 | Non-Barrier | 1 | N2/CO2 (92%/8%) | 290 | 1.04 | 298 | 1.54 | 296 | 1.48 | 297 | 1.72 |
|   |   | 2 |   | 292 | 1.07 | 300 | 1.60 | 298 | 1.55 | 302 | 1.81 |
|   |   | 3 |   | 291 | 1.09 | 301 | 1.68 | 296 | 1.65 | 301 | 1.80 |
|   |   | avg. |   | 291 | 1.07 | 299 | 1.57 | 297 | 1.56 | 300 | 1.78 |
| 5 | Non-Barrier | 1 | N2/CO2 (90%/10%) | 283 | 1.07 | 293 | 1.64 | 291 | 1.56 | 294 | 1.80 |
|   |   | 2 |   | 287 | 1.05 | 295 | 1.60 | 295 | 1.50 | 295 | 1.67 |
|   |   | 3 |   | 290 | 1.00 | 300 | 1.48 | 298 | 1.44 | 301 | 1.65 |
|   |   | avg. |   | 287 | 1.04 | 294 | 1.62 | 293 | 1.53 | 297 | 1.71 |
| 6 | Non-Barrier | 1 | N2/CO2 (85%/15%) | 287 | 1.06 | 297 | 1.76 | 295 | 1.76 | 300 | 1.99 |
|   |   | 2 |   | 298 | 1.07 | 307 | 1.66 | 305 | 1.69 | 312 | 1.93 |
|   |   | 3 |   | 290 | 1.13 | 304 | 1.78 | 302 | 1.80 | 305 | 2.03 |
|   |   | avg. |   | 292 | 1.09 | 302 | 1.71 | 300 | 1.73 | 306 | 1.98 |

Human Gastric Environment

Balloons constructed with non-barrier film composite walls were tested in vivo in 10 patients in a clinical study for 30 days. The balloon wall comprised multi-layer Nylon 12/LLDPE+LDPE. One balloon per patient was administered. Balloons were filled with a mixed gas to approximately 245 cc with an average starting balloon pressure of 1.01 psi above atmosphere. The initial fill gas was 95% Nitrogen and 5% $CO_2$. At the end of 30 days, balloons remained full and firm, although ending pressure and volumes could not be discerned visually/endoscopically. Of the 10 balloons retrieved, 10 balloons had internal gas samples obtained, and 8 provided meaningful data. Table 9 provides the data retrieved from the balloons. The end gas samples are reflective of the gastric environment and are averaged as follows: 82.4% $N_2$, 10.6% $O_2$, 5.9% $CO_2$, and 0.84% Ar. Thus, the internal balloon environment reflects that of the average gastric environment gas concentrations. Data for the experiments is provided in Table 9.

TABLE 9

| Patient # | Starting Balloon Gas Concentration | | Ending Balloon Gas Concentration (% v/v, by MS) | | | |
|---|---|---|---|---|---|---|
| Patient # | [N2] | [CO2] | [N2] | [O2] | [CO2] | [Ar] |
| 1 | 95.00 | 5.00 | 81.19 | 10.20 | 7.60 | 0.86 |
| 2 | 95.00 | 5.00 | 81.24 | 12.90 | 4.85 | 0.86 |
| 3 | 95.00 | 5.00 | 82.41 | 10.80 | 5.65 | 0.85 |
| 4 | 95.00 | 5.00 | 82.07 | 11.20 | 5.70 | 0.82 |
| 5 | 95.00 | 5.00 | 82.87 | 10.05 | 6.00 | 0.82 |
| 6 | 95.00 | 5.00 | 82.54 | 11.50 | 4.80 | 0.88 |
| 7 | 95.00 | 5.00 | Erroneous Sample | | | |
| 8 | 95.00 | 5.00 | 81.76 | 10.20 | 7.00 | 0.82 |
| 9 | 95.00 | 5.00 | Erroneous Sample | | | |
| 10 | 95.00 | 5.00 | 84.95 | 8.20 | 5.80 | 0.81 |
| Avg. |  |  | 82.38 | 10.63 | 5.93 | 0.84 |
| Std Dev |  |  | 1.20 | 1.36 | 0.97 | 0.03 |
| Max |  |  | 84.95 | 12.90 | 7.60 | 0.88 |
| Min |  |  | 81.19 | 8.20 | 4.80 | 0.81 |

In certain embodiments wherein it is desirable to maintain the starting pressure and volume of the device, this can be accomplished by matching the internal balloon environment at implant (i.e., the fill gases) closely to the gastric environment. In such embodiments, the balloon can be inflated with an initial gas fill gas comprising approximately 80-85% nitrogen, 8-12% oxygen, and 4-8% carbon dioxide. The concentration of argon and other in vivo gases can be considered inconsequential to the total volume/pressure, and may be omitted for convenience or included as desirable. To encourage inflation of the balloon in vivo, the starting concentrations of oxygen and/or carbon dioxide can be reduced.

Experiments were conducted to determine pressure in various balloons over time for different initial fill gases. In reference to FIG. 43, the initial fill gases included the following (vol. %): 100% $SF_6$; 100% $N_2$; 50% $SF_6$ in combination with 50% $N_2$; 25% $SF_6$ in combination with 75% $N_2$; and 18-20% $SF_6$ in combination with 78-80% $N_2$. One type of balloon tested included a composite polymeric wall including a layer of 3.5 mil polyethylene and a layer of nylon. Another type of balloon tested included an ethylene vinyl alcohol layer in the composite polymeric wall. As shown by the data presented in FIG. 43, the balloons including 100% $N_2$ as the fill gas exhibited slight increass in pressure over approximately the first 2-4 weeks of the test, followed by a loss of pressure over time. The balloon including an ethylene vinyl alcohol layer was able to maintain pressure at a level equal to or greater than to the initial fill pressure for approximately four months, while the balloon including a polyethylene/nylon wall was able to maintain such a pressure for approximately 1 month. Balloons including 100% $SF_6$ exhibited substantial increase in pressure over the first approx. 2 to 3 months, at which time the pressure tended to level off for the duration of the test. By adding $N_2$ to the $SF_6$, the pressure at which leveling occurred was lowered. A mixture of approx. 18-20% $SF_6$ with the remainder $N_2$ exhibited a modest rise in pressure over approx. one month followed by substantially level maintenance of pressure over an approx. 4 month period of time.

The present invention has been described above with reference to specific embodiments. However, other embodiments than the above described are equally possible within the scope of the invention. Different method steps than those described above may be provided within the scope of the invention. The different features and steps of the invention may be combined in other combinations than those described. The scope of the invention is only limited by the appended patent claims.

All references cited herein are incorporated herein by reference in their entirety. To the extent publications and patents or patent applications incorporated by reference contradict the disclosure contained in the specification, the specification is intended to supersede and/or take precedence over any such contradictory material.

To the extent publications and patents or patent applications incorporated by reference herein contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, unless otherwise expressly stated, should be construed as open ended as opposed to limiting. As examples of the foregoing, the term 'including' should be read to mean 'including, without limitation' or the like; the term 'comprising' as used herein is synonymous with 'including,' 'containing,' or 'characterized by,' and is inclusive or open-ended and does not exclude additional, unrecited elements or method steps; the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise. In addition, as used in this application, the articles 'a' and 'an' should be construed as referring to one or more than one (i.e., to at least one) of the grammatical objects of the article. By way of example, 'an element' means one element or more than one element.

The presence in some instances of broadening words and phrases such as 'one or more', 'at least', 'but not limited to', or other like phrases shall not be read to mean that the narrower case is intended or required in instances where such broadening phrases may be absent.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches. Where a range of values is provided, it is understood that the upper and lower limit, and each intervening value between the upper and lower limit of the range is encompassed within the embodiments.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A system for locating an intragastric device inside the body, the system comprising:
    a volume occupying intragastric device comprising a swallowable balloon capsule comprising an intragastric balloon with a polymeric wall defining a balloon lumen and a self-sealing valve system attached to the polymeric wall, wherein the valve system is configured for introducing a fill fluid into the balloon lumen in an in vivo gastric environment;
    a swallowable catheter configured to releasably couple with the valve system of the intragastric balloon at a distal end of the swallowable catheter;
    an electromagnetic field generator configured to generate an electromagnetic field;
    a swallowable electromagnetic sensor configured to produce an electric current when exposed to the electromagnetic field and integrated with the catheter, so as to provide a location of the intragastric balloon or the swallowable catheter in vivo, wherein the catheter comprises the swallowable electromagnetic sensor, wherein the swallowable electromagnetic sensor is situated at the distal end of the swallowable catheter, and is adapted to be characterized for five or six degrees of freedom when coupled to the valve system of the intragastric balloon;
    at least one external reference sensor configured to be placed on the body and to produce an electric current when exposed to the electromagnetic field,
    a sensor interface configured to electrically communicate with the electromagnetic sensor and the at least one external reference sensor, the sensor interface comprising a sensor port adapted to connect the sensor interface to the electromagnetic sensor and the at least one external reference sensor, the sensor interface further comprising an analog to digital converter to convert analog signals produced by the electromagnetic sensor and the at least one external reference sensor to digital signals for transmission;
    a system controller configured to electrically communicate with the sensor interface and with the electromagnetic field generator, wherein the digital signals are transmitted to the system controller for processing via a cable, wherein the system controller calculates sensor position and orientation to generate position and orientation data using hardware, wherein the hardware comprises at least one component selected from the group consisting of a central processing unit, a memory, an analog to digital converter, an analog circuitry, and a display; and
    a computer configured to electrically communicate with the system controller to obtain the position and orientation data through a cable, to display an identifier indicating the location of the electromagnetic sensor inside the body and to display at least one second identifier indicating the location of the at least one external reference sensor;
    wherein the sensor interface, the system controller, and the electromagnetic field generator are configured to be in electrical communication with the computer, and wherein the sensor interface connects the electromagnetic sensor to the catheter.

2. The system of claim 1, wherein the electromagnetic sensor is configured to couple with a distal end of the swallowable catheter.

3. The system of claim 1, wherein the electromagnetic sensor is configured to couple with the intragastric device.

4. The system of claim 1, further comprising three external reference sensors configured to be placed outside the body and to produce an electric current when exposed to the magnetic field.

5. The system of claim 1, wherein the computer is further configured to display a trace indicating a path travelled by the electromagnetic sensor inside the body.

6. The system of claim 1, wherein the self-sealing valve system comprises the electromagnetic sensor.

7. The system of claim 1, wherein the magnetic field generator is configured to produce a series of varying magnetic fields.

8. The system of claim 1, wherein the sensor interface is configured to amplify the electric current produced by the electromagnetic sensor to the system controller, and further wherein the sensor interface is configured to amplify the electric current produced by the at least one external reference sensor to the system controller.

9. The system of claim 1, wherein the at least one external reference sensor is adapted to be located on a skin of the body.

10. The system of claim 1, wherein the swallowable catheter includes the swallowable electromagnetic sensor at the distal end of the swallowable catheter.

11. The system of claim 1, wherein the swallowable electromagnetic sensor is embedded with an intermediate connector between the swallowable catheter and the volume occupying intragastric device.

12. The system of claim 1, wherein the swallowable electromagnetic sensor is an inductive sensor.

13. The system of claim 1, wherein the swallowable electromagnetic sensor is adapted to provide location data as it travels through the esophagus and into the stomach.

14. The system of claim 1, wherein the catheter does not exceed 2.7 mm in diameter.

15. The system of claim 1, wherein the catheter is flexible and hydrophilic coated.

16. The system of claim 1, wherein the catheter comprises a second swallowable electromagnetic sensor approximately 6 inches from the distal end of the catheter.

17. The system of claim 1, wherein the catheter comprises a catheter inner assembly that comprises a catheter needle, a monofilament thread, a needle holder, and a needle sleeve that surrounds and protects the catheter needle, wherein the catheter needle is configured to pierce a septum of the self-sealing valve system to provide fluid communication between an interior of the catheter and the balloon lumen of the intragastric device.

18. The system of claim 1, wherein the catheter is adapted to bend 180° over a 0.5 cm radius mandrel without kinking at a center portion of a catheter shaft.

19. The system of claim 1, wherein the intragastric device is adapted to separate from the catheter when submerged in 37° C. water.

20. The system of claim 1, wherein an adhesive bond between the intragastric device and the catheter is adapted to fail at more than 150 grams when preconditioned for twenty seconds in room temperature water.

21. The system of claim 1, further comprising the fill fluid, wherein the polymeric wall is configured to have, under conditions of the in vivo gastric environment, a permeability to $CO_2$ of from 10 $cc/m^2/day$ to 50 $cc/m^2/day$, such that a rate and an amount of diffusion of $CO_2$ from the in vivo gastric environment into the balloon lumen through the polymeric wall is controlled, at least in part, by a concentration of an inert gas in the fill fluid.

22. The system of claim 21, wherein the polymeric wall comprises a $CO_2$ barrier material comprising an ethylene vinyl alcohol layer.

23. The system of claim 21, wherein the polymeric wall comprises a two layer $CO_2$ barrier material comprising a nylon layer and a polyethylene layer.

24. The system of claim 21, wherein the polymeric wall comprises a three layer $CO_2$ barrier material comprising a nylon layer, a polyvinylidene chloride layer, and a polyethylene layer.

25. The system of claim 21, wherein the polymeric wall comprises a three layer $CO_2$ barrier material comprising a nylon layer, an ethylene vinyl alcohol layer, and a polyethylene layer.

26. The system of claim 21, wherein the fill fluid consists essentially of gaseous $N_2$.

27. The system of claim 21, wherein the fill fluid consists essentially of gaseous $N_2$ and gaseous $CO_2$.

28. The system of claim 21, wherein the fill fluid consists essentially of gaseous $N_2$ and gaseous $CO_2$, and wherein the gaseous $N_2$ is excess in concentration to the gaseous $CO_2$ in the fill fluid.

29. The system of claim 21, wherein the fill fluid comprises $SF_6$ in one or more of liquid form, vapor form, or gaseous form.

30. The system of claim 21, wherein the fill fluid comprises gaseous $N_2$ and gaseous $SF_6$.

31. The system of claim 1, wherein the swallowable catheter comprises:
a needle sleeve configured to reversibly couple with the valve system;
tubing joined with the needle sleeve;
a luer hub joined with a proximal end of the tubing, wherein the luer hub, the tubing and the needle sleeve are configured for introducing the fill fluid into a lumen of the balloon; and
an electrical connector joined with a proximal end of the tubing, wherein the electrical connector is configured for releasably connecting with sensor interface, and wherein the electromagnetic sensor is located at the needle sleeve and electrically coupled with the electrical connector.

32. The system of claim 31, wherein the swallowable catheter further comprises a y-adapter joined with a proximal end of the tubing, wherein the luer hub is joined with a first proximal end of the y-adaptor and the electrical connector is joined with a second proximal end of the y-adaptor.

33. The system of claim 32, wherein the swallowable catheter further comprises a wire connecting the electrical connector with the electromagnetic sensor.

34. The system of claim 1, wherein the intragastric balloon comprises a deflation subcomponent configured to auto-deflate after a predetermined useful life in vivo.

35. The system of claim 34, wherein the predetermined useful life is between 30 days and 90 days.

36. The system of claim 34, wherein the predetermined useful life is 6-months.

37. The system of claim 1, further comprising at least one external reference sensor adapted to be placed on a skin of a patient, and adapted to provide an anatomical frame of reference between the electromagnetic field generator and the patient.

38. The system of claim 37, wherein the computer is adapted to display data collected by the external reference sensor and the swallowable electromagnetic sensor.

39. The system of claim 37, wherein the swallowable electromagnetic sensor includes a sensor body that is elongated and cylindrical, wherein the sensor body is formed from a metal or other material that is responsive to an electromagnetic field, wherein the sensor body is symmetric about a longitudinal axis and includes a geometric center, wherein the swallowable electromagnetic sensor has its own local coordinate system that is defined by the geometric center and the longitudinal axis, wherein the remaining two axes are orthogonal to the longitudinal axis and intersect the center, wherein the z-axis extends along the swallowable electromagnetic sensor's length and corresponds with the longitudinal axis with an origin along the z-axis, such that the swallowable electromagnetic sensor is adapted to provide information on the three translation values on the x, y and z-axes and any two of the three rotation values of roll, pitch and yaw, such that five degrees of freedom can be determined for the swallowable electromagnetic sensor.

40. A method for electromagnetically locating a volume occupying intragastric device inside the body of a patient, the method comprising:
   providing the electromagnetic system of claim 1;
   generating an electromagnetic field with the electromagnetic field generator situated outside of the body of the patient;
   introducing into the body of the patient, via swallowing, the intragastric device comprising an uninflated balloon releasably coupled with the catheter and coupled with the electromagnetic sensor, the electromagnetic sensor configured to produce an electrical current in the presence of the electromagnetic field generated by the field generator;
   sensing a current induced in the electromagnetic sensor by the electromagnetic field; and
   confirming a location of the uninflated gastric balloon inside the patient based on sensing the current induced in the electromagnetic sensor.

41. The method of claim 40, further comprising inflating the uninflated intragastric balloon, when the location of the uninflated intragastric balloon is the stomach of the patient.

\* \* \* \* \*

UNITED STATES PATENT AND TRADEMARK OFFICE
CERTIFICATE OF CORRECTION

PATENT NO. : 10,264,995 B2
APPLICATION NO. : 14/407923
DATED : April 23, 2019
INVENTOR(S) : Brister et al.

Page 1 of 4

It is certified that error appears in the above-identified patent and that said Letters Patent is hereby corrected as shown below:

On the Title Page

Item (72) Inventors at Line 1, Change "Carlsbad, CA" for Mark C. Brister to --Encinitas, CA--.

Item (72) Inventors at Line 2, Change "Carlsbad, CA" for Neil R. Drake to --San Diego, CA--.

Item (72) Inventors at Line 3, Change "Carlsbad, CA" for Sheldon Nelson to --Vista, CA--.

Item (72) Inventors at Line 4, Change "Carlsbad, CA" for Daniel J. Proctor to --San Diego, CA--.

In the Specification

In Column 11 at Line 50, Change "layer" to --layer.--.

In Column 17 at Line 41, Change "unit" to --unit.--.

In Column 23 at Line 43, Change "71A;" to --71A.--.

In Column 23 at Line 54, Change "71C;" to --71C.--.

In Column 23 at Line 57, Change "71D;" to --71D.--.

In Column 26 at Line 33, Change "radioopacity" to --radiopacity--.

In Column 27 at Line 4, Change "occupyable" to --occupiable--.

In Column 27 at Line 19, Change "is are" to --is--.

In Column 30 at Line 18, Change "occupyable" to --occupiable--.

Signed and Sealed this
Sixth Day of August, 2019

Andrei Iancu
*Director of the United States Patent and Trademark Office*

CERTIFICATE OF CORRECTION (continued)
U.S. Pat. No. 10,264,995 B2

In Column 30 at Line 19, Change "occupyable" to --occupiable--.

In Column 30 at Line 21, Change "occupyable" to --occupiable--.

In Column 33 at Line 41, Change "½r±¼ r" to --½ r±¼ r--.

In Column 36 at Line 38, Change "radioopaque" to --radiopaque--.

In Column 49 at Line 40, Change "105-120 105-120;" to --105-120;--.

In Column 52 at Line 6, Change "in2-" to --in 2- --.

In Column 54 at Line 59, Change "polyim ides" to --polyimides--.

In Column 62 at Line 59, Change "that that" to --that--.

In Column 66 at Line 20 (Approx.), Change "Biaxally" to --Biaxially--.

In Column 68 at Line 52, Change "half To" to --half. To--.

In Column 79 at Line 6, Change "state" to --state.--.

In Column 81 at Line 18, Change "etc.)" to --etc.).--.

In Column 86 at Line 48, Change "range" to --range.--.

In Column 86 at Line 52, Change "simulators" to --simulators.--.

In Column 92 at Line 31, Change "thattransformation" to --that transformation--.

In Column 94 at Line 23, Change "1510," to --1510--.

In Column 96 at Line 18, Change "system" to --systems--.

In Column 96 at Line 30, Change "of" to --on--.

In Column 96 at Line 38, Change "Amids)" to --Amides)--.

In Column 96 at Line 54, Change "markerband" to --marker band--.

In Column 97 at Line 26, Change "Peebax" to --Pebax--.

In Column 98 at Line 67, Change "3A" to --3A.--.

CERTIFICATE OF CORRECTION (continued)
U.S. Pat. No. 10,264,995 B2

In Column 100 at Line 51, Change "detector" to --detector system 100--.

In Column 112 at Lines 50-54, Delete "However, in an alternative embodiment, the calibration processor 158 will perform the recalibration process only if the detector system 100 has been moved by a predetermined amount. This prevents the unnecessary recalibration when the detector system 100 has not been moved." and insert the same on Column 112, Line 49 as the continuation of the same paragraph.

In Column 115 at Line 12, Change "MICROSOFT®" to --MICROSOFT®,--.

In Column 119 at Line 44, Change "embodiments" to --embodiments.--.

In Column 128 at Line 52 (Approx.), should read, --$E_T = N_2 \cdot E = -A_2 \cdot \mu \cdot N_1 \cdot N_2 \cdot \omega_1 \cdot I_0 \cdot \cos(\omega \cdot t)/d_1$--.

In Column 128 at Line 67 (Approx.), should read, --$N_2 \cdot \Phi_{21} = N_2 \cdot N_1 \cdot \pi \cdot \mu_0 \cdot R_2^2 \cdot i_{i1}/2 \cdot R_1$,--.

In Column 129 at Line 48 (Approx.), Change "$\omega_2 - \omega_1 = \omega_n/Q = R/L_1 - 1/\tau 0$" to --$\omega_2 - \omega_1 = \omega_n/Q = R/L_1 = 1/\tau_0$--.

In Column 129 at Line 67 (Approx.), Change "$\Delta\omega_0/\omega_n = 1/2Q = 1/\tau \cdot \omega) = R/L \cdot \sqrt{1/LC} = R\sqrt{C/L}$" to --$\Delta\omega_0/\omega_n = 1/2Q = 1/\tau \cdot \omega = R/L \cdot \sqrt{1/LC} = R\sqrt{C/L}$--.

In Column 131 at Lines 66-67 (Approx.), Change "$M^2/(L_1 \cdot L_2) = \mu^2 N_1^2 N_2^2 A_2^1 A_2^2 d_1 d_2/4_1\pi^2(R_1^2 + z^2)^3 N_1^2 N_2^2 A_1 A_2 \mu^2 = A_1 A_2 d_1 d_2/4\pi 2(R_1^2 + z^2)^3$" to --$M^2/(L_1 \cdot L_2) = \mu^2 N_1^2 N_2^2 A_1^2 A_2^2 d_1 d_2/4_1\pi^2 (R_1^2 + z^2)^3 N_1^2 N_2^2 A_1 A_2 \mu^2 = A_1 A_2 d_1 d_2/4\pi^2(R_1^2 + z^2)^3$--.

In Column 135 at Line 5, Change "the the" to --the--.

In Column 140 at Line 66, Change "ma" to --may--.

In Column 143 at Line 63, Change "at" to --as--.

In Column 149 at Line 60, Change "(CuCI)." to --(CuCl).--.

In Column 152 at Line 10, Change "25 During" to --25 µs. During--.

In Column 153 at Line 9, Change "Celsiue;" to --Celsius;--.

In Column 157 at Line 65, Change "gab" to --gap--.

In Column 163 at Line 18, Change "fluid," to --fluid.--.

CERTIFICATE OF CORRECTION (continued)
U.S. Pat. No. 10,264,995 B2

In Column 169 at Line 46, Change "polynorborenes," to --polynorbornenes,--.

In Column 170 at Line 18, Change "and or" to --and/or--.

In Column 172 at Line 56, Change "2d" to --$2^{nd}$--.

In Column 174 at Line 29, Change "hearing" to --bearing--.

In Column 181 at Line 58 (Approx.), Change "elswhere" to --elsewhere--.

In Column 193 at Line 13, Change "Table 7" to --Table 7.--.

In Column 196 at Line 33 (Approx.), Change "increass" to --increase--.